United States Patent
Kotschy et al.

(10) Patent No.: US 10,654,849 B2
(45) Date of Patent: May 19, 2020

(54) (HETERO)ARYL-SUBSTITUTED-PIPERIDINYL DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: András Kotschy, Törökbálint (HU); Csaba Wéber, Pilisszentlászló (HU); Attila Vasas, Fót (HU); Balázs Molnár, Isaszeg (HU); árpád Kiss, Budapest (HU); Alba Macias, Cambridgeshire (GB); James Brooke Murray, Linton (GB); Elodie Lewkowicz, Paris (FR); Olivier Geneste, Rueil-Malmaison (FR); Mäia Chanrion, Issy les Moulineaux (FR); Didier Demarles, Checy (FR); Lisa Ivanschitz, Suresnes (FR)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 16/306,941

(22) PCT Filed: Jun. 9, 2017

(86) PCT No.: PCT/EP2017/064062
§ 371 (c)(1),
(2) Date: Dec. 4, 2018

(87) PCT Pub. No.: WO2017/212010
PCT Pub. Date: Dec. 14, 2017

(65) Prior Publication Data
US 2019/0144449 A1    May 16, 2019

(30) Foreign Application Priority Data

Jun. 10, 2016 (FR) ..................... 16 55387
Dec. 28, 2016 (FR) ..................... 16 63463

(51) Int. Cl.
| | | |
|---|---|---|
| C07D 471/04 | (2006.01) |
| C07D 487/04 | (2006.01) |
| C07D 495/04 | (2006.01) |
| A61P 35/00 | (2006.01) |
| A61K 31/519 | (2006.01) |
| A61K 31/522 | (2006.01) |

(52) U.S. Cl.
CPC .......... *C07D 471/04* (2013.01); *A61K 31/519* (2013.01); *A61K 31/522* (2013.01); *A61P 35/00* (2018.01); *C07D 487/04* (2013.01); *C07D 495/04* (2013.01)

(58) Field of Classification Search
CPC ................................................... C07D 471/04
USPC ........................................................ 514/218
See application file for complete search history.

(56) References Cited

U.S. PATENT DOCUMENTS

| | | |
|---|---|---|
| 9,546,150 B2 | 1/2017 | Colland et al. |
| 9,840,491 B2 | 12/2017 | Ioannidis et al. |
| 9,902,728 B2 | 2/2018 | Ioannidis et al. |
| 9,932,351 B2 | 4/2018 | Ioannidis et al. |
| 9,938,300 B2 | 4/2018 | Ioannidis et al. |
| 10,000,495 B2 | 6/2018 | Ioannidis et al. |

FOREIGN PATENT DOCUMENTS

| | | |
|---|---|---|
| WO | WO 2008108957 | 9/2008 |
| WO | WO 2013030218 | 3/2013 |

OTHER PUBLICATIONS

International Search Report for PCT/EP2017/064062 dated Jun. 6, 2017.

*Primary Examiner* — Kahsay Habte
(74) *Attorney, Agent, or Firm* — Hueschen and Sage

(57) ABSTRACT

Compounds of formula (I):

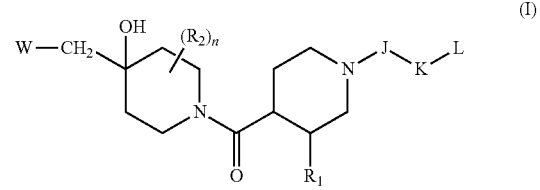

wherein $R_1$, $R_2$, J, K, L, n and W are as defined in the description.
Medicinal products containing the same which are useful in treating conditions requiring pro-apoptotic and/or anti-proliferative agents.

31 Claims, No Drawings

(HETERO)ARYL-SUBSTITUTED-PIPERIDINYL DERIVATIVES, A PROCESS FOR THEIR PREPARATION AND PHARMACEUTICAL COMPOSITIONS CONTAINING THEM

The present invention relates to new (hetero)aryl-substituted-piperidinyl derivatives, to a process for their preparation and to pharmaceutical compositions containing them.

The compounds of the present invention are new and have very valuable pharmacological characteristics in the field of apoptosis and oncology.

Ubiquitination is a process controlling essential cellular functions such as protein turnover and homeostasis, protein activation and localisation. Ubiquitin is a 76 amino acids polypeptide which is covalently attached to postranslationnaly modified protein substrates via an isopeptide bond. Deubiquinating enzymes (DUBs) are in majority cysteine proteases that cleave the ubiquitin-ubiquitin bond or ubiquitin-protein bond at the Cter glycine of Ubiquitin. Approximately 100 DUBs regulate the thousands ubiquitinated proteins and then some redundancy of deubiquitinase substrates regulation are observed.

Dysregulation of DUBs have been associated with several diseases such as neurodegenerative and infectious diseases (Edelman et al., *Expert Rev. Mol. Med.* 2011, 13, 1-17) and human malignancies (Pal et al., *Cancer Res.* 2014, 74, 4955-4966). Accordingly, overexpression of DUBs or increase of their activity have been associated to numerous types of cancers (Luise et al., *Plos One* 2011, 6, e15891; Rolen et al., *Mol. Carcinog.* 2006, 45, 260-269) and poor prognosis.

Ubiquitin Specific Protease 7 (USP7), also known as Herpes-virus-Associated Ubiquitin-Specific Protease (HAUSP), belongs to the deubiquitinating family. USP7 has been reported to stabilize numerous oncogenes involved in survival and proliferations via cell cycle progression, apoptosis, DNA repair, DNA replication and epigenetic factors regulation (Nicholson et al., *Cell Biochem. Biophys.* 2011, 60, 61-68). In addition, USP7 has been shown to regulate immune response via inflammation and Treg modulation (Van Loosdregt et al., *Immunity* 2013, 39, 259-27; Colleran et al., *Proc. Natl. Acad. Sci. USA* 2013, 110, 618-623). USP7 has also been implicated in other pathologic states such as neurodevelopmental disorder (Hao et al., *Mol. Cell* 2015, 59, 956-969) and viral infection (Holowaty et al., *Biochem. Soc. Trans.* 2004, 32, 731-732). USP7 overexpression has been associated with late stages of cancers and poor prognosis in lung, neuroblastoma, myeloma, prostate, colon and breast cancers. Although some inhibitors have been published in the literature, most of them were not selective and, to date, no USP7 inhibitors have entered the clinic (Kemp et al., *Progress in Medicinal Chemistry* 2016, 55, 149-192). There is, therefore, a therapeutic need for compounds that inhibit the activity of the protein USP7.

In addition to being new, the compounds of the present invention have pro-apoptotic and/or anti-proliferative properties making it possible to use them in pathologies involving a defect in apoptosis, such as, for example, in the treatment of cancer and of immune and auto-immune diseases.

The present invention relates more especially to compounds of formula (I):

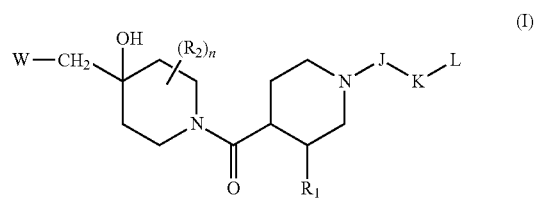

wherein:
  $R_1$ represents an aryl group or a heteroaryl group,
  $R_2$ represents a hydrogen atom or a halogen atom,
  n is an integer equal to 0, 1 or 2,
  J represents a —C(O)— group, a —CH($R_3$)— group, or a —SO$_2$— group,
  $R_3$ represents a hydrogen atom or a linear or branched ($C_1$-$C_6$)alkyl group,
  K represents a bond or a -Cy$_1$- group,
  L represents a -Cy$_2$ group or a —CH$_2$-Cy$_2$ group,
  W represents the group

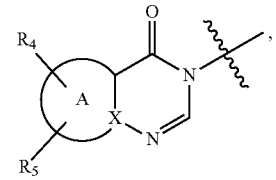

wherein:
  A represents a heteroaryl ring,
  X represents a carbon atom or a nitrogen atom,
  $R_4$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a —$Y_1$—NR$_6$R$_7$ group, a —$Y_1$—OR$_6$ group, a linear or branched halo($C_1$-$C_6$)alkyl group, an oxo group, a —$Y_1$-Cy$_3$ group, a -Cy$_3$-R$_7$ group, a -Cy$_3$-OR$_7$ group, or a —$Y_1$—NR$_6$—C(O)—R$_7$ group,
  $R_5$ represents a hydrogen atom, a halogen atom, or a linear or branched ($C_1$-$C_6$)alkyl group,
  $R_6$ represents a hydrogen atom or a linear or branched ($C_1$-$C_6$)alkyl group,
  $R_7$ represents a hydrogen atom, a linear or branched ($C_1$-$C_6$)alkyl group, or a —$Y_2$-Cy$_4$ group,
  $Y_1$ and $Y_2$ independently of one another represent a bond or a linear or branched ($C_1$-$C_4$)alkylene group,
  Cy$_1$ represents a cycloalkyl group, a heterocycloalkyl group, an aryl group, or a heteroaryl group, which is linked to the group J and to the group L,
  Cy$_2$, Cy$_3$ and Cy$_4$ independently of one another, represent a cycloalkyl group, a heterocycloalkyl group, an aryl group, or a heteroaryl group,
it being understood that:
  "aryl" means a phenyl, naphthyl, or indanyl group,
  "heteroaryl" means any mono- or fused bi-cyclic group composed of from 5 to 10 ring members, having at least one aromatic moiety and containing from 1 to 3 heteroatoms selected from oxygen, sulphur and nitrogen,
  "cycloalkyl" means any mono- or fused bi-cyclic non-aromatic carbocyclic group containing from 3 to 7 ring members,
  "heterocycloalkyl" means any non-aromatic mono- or fused bi-cyclic group containing from 3 to 10 ring members, and containing from 1 to 3 heteroatoms selected from oxygen, sulphur and nitrogen, it being possible for the aryl, heteroaryl, cycloalkyl and heterocycloalkyl groups so defined to be substituted by from 1 to 4 groups selected from linear or branched ($C_1$-$C_6$)alkyl, linear or branched ($C_2$-$C_6$)alkenyl, linear or branched ($C_2$-$C_6$)alkynyl, linear or branched halo($C_1$-$C_6$)alkyl, —$Y_1$—OR', —$Y_1$—NR'R", —$Y_1$—S(O)$_m$—R', oxo (or N-oxide where appropriate), nitro, cyano, —C(O)—R', —C(O)—OR', —O—C(O)—R', —C(O)—NR'R", —$Y_1$—NR'—C(O)—R", —$Y_1$—NR'—C(O)—OR", halogen, cyclopropyl, and pyridinyl which can be substituted by a linear or branched ($C_1$-$C_6$)alkyl group, it being understood that R' and R" independently of one another, represent a hydrogen atom, a linear or branched ($C_1$-$C_6$)alkyl group, a linear or branched ($C_2$-$C_6$)alkenyl group, a linear or branched ($C_1$-$C_6$)alkoxy group, a linear or branched halo($C_1$-$C_6$)alkyl, a linear or branched hydroxy ($C_1$-$C_6$)alkyl group, a linear or branched ($C_1$-$C_6$)alkoxy($C_1$-$C_6$)alkyl group, a phenyl group, a cyclopropylmethyl group, a tetrahydropyranyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen, it being understood that the second nitrogen in question may be substituted by from 1 to 2 groups representing a hydrogen atom, or a linear or branched ($C_1$-$C_6$)alkyl group, and it being understood that m is an integer equal to 0, 1 or 2, their enantiomers, diastereoisomers and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Among the heteroaryl groups there may be mentioned, without implying any limitation, pyrrolyl, furyl, thienyl, thiazolyl, isothiazolyl, oxazolyl, isoxazolyl, pyrazolyl, imidazolyl, pyridinyl (also known as pyridyl), pyrazinyl, pyridazinyl, pyrimidinyl, pyridinonyl, indolyl, dihydroindolyl, dihydroisoindolyl, indazolyl, dihydrocyclopentathienyl, benzothienyl, tetrahydrobenzothienyl, benzofuranyl, imidazopyridinyl, benzotriazolyl, benzodioxolyl, dihydrobenzodioxinyl, quinolinyl, isoquinolinyl, tetrahydroquinolinyl, tetrahydroisoquinolinyl, quinoxalinyl, dihydroquinoxalinyl, dihydrothienodioxinyl, quinazolinonyl, pyrrolopyridazinyl, dihydropyrrolizinyl, tetrahydroindolizinyl, etc.

Among the cycloalkyl groups there may be mentioned, without implying any limitation, cyclopropyl, cyclobutyl, cyclopentyl, cyclohexyl, etc.

Among the heterocycloalkyl groups there may be mentioned, without implying any limitation, pyrrolidinyl, tetrahydropyranyl, piperidinyl, piperazinyl, morpholinyl, etc.

In another embodiment of the invention, W advantageously represents the group

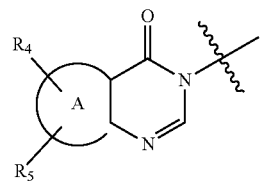

wherein $R_4$, $R_5$ and A are as defined for formula (I).

More especially,

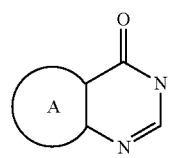

A represents,

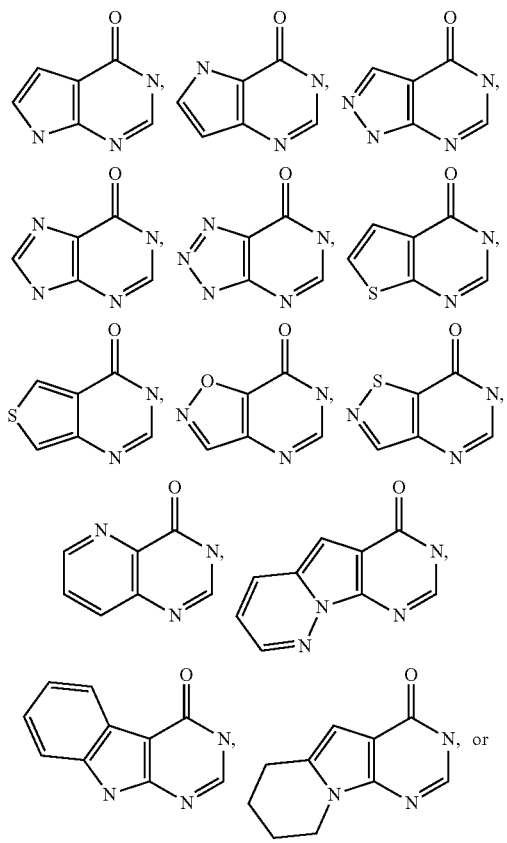

or

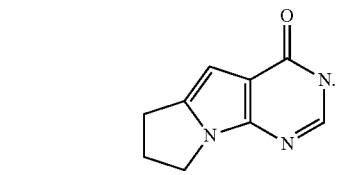

More particularly,

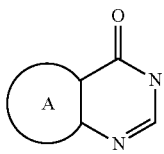

represents

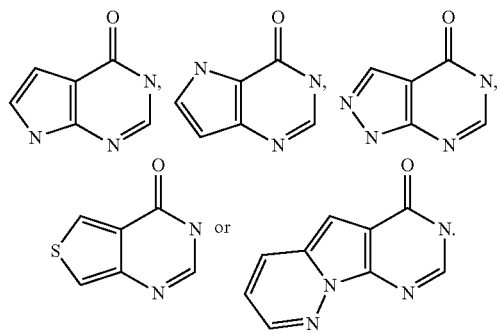

Advantageously,

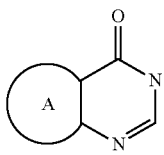

represents

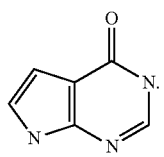

Preferably,

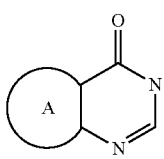

represents

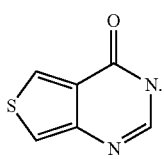

In another embodiment of the invention, W advantageously represents the group

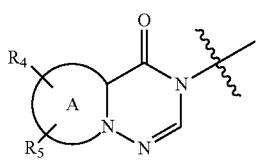

wherein $R_4$, $R_5$ and A are as defined for formula (I).
More especially,

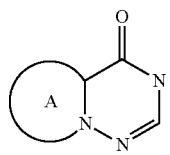

represents

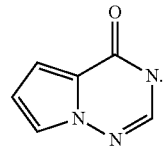

$R_1$ advantageously represents a phenyl group or a thienyl group. More preferably, $R_1$ represents a phenyl group.

Advantageously, the compounds of formula (I) display a trans configuration as follows:

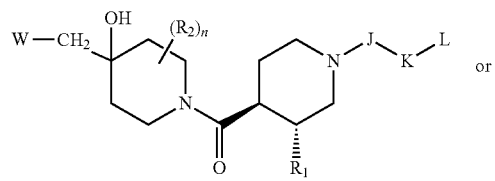

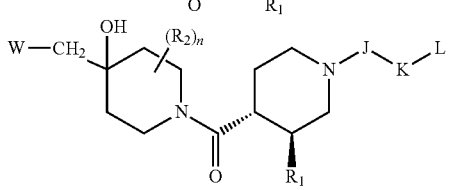

More preferably, the compounds of formula (I) display a trans configuration as follows:

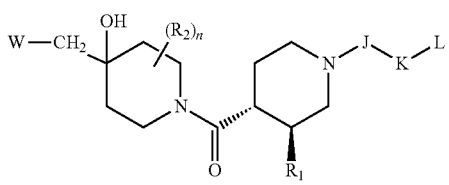

Preferably, $R_2$ represents a hydrogen atom or a fluorine atom. More preferably, $R_2$ represents a hydrogen atom. Advantageously, the —$(R_2)_n$ group represents a gem-difluoro group.

In some preferred embodiment of the invention, $R_3$ represents a hydrogen atom or a methyl group. More preferably, $R_3$ represents a hydrogen atom.

In the preferred compounds of the invention, J represents a —C(O)— group or a —CH$_2$— group. Preferably, J represents a —C(O)— group. Advantageously, J represents a —CH$_2$— group.

K preferably represents a bond or a -Cy$_1$- group selected from a phenyl group, a pyrrolyl group, a thienyl group, a thiazolyl group, a pyridinyl group, a tetrahydrobenzothienyl group, a dihydrothienodioxinyl group, a cyclopropyl group, a cyclobutyl group, or a pyrrolidinyl group. More preferably, K preferably represents a bond or a -Cy$_1$- group selected from a thienyl group, a thiazolyl group or a pyridinyl group.

Advantageously, L represents a -Cy$_2$ group. More preferably, Cy$_2$ represents a phenyl group, an indanyl group, a pyrrolyl group, a furyl group, a thienyl group, a thiazolyl group, an isothiazolyl group, an oxazolyl group, an isoxazolyl group, a pyrazolyl group, a pyridinyl group, a pyrazinyl group, a pyridazinyl group, a pyrimidinyl group, a pyridinonyl group, an indolyl group, a dihydroindolyl group, a dihydroisoindolyl group, an indazolyl group, a dihydrocyclopentathienyl group, a tetrahydrobenzothienyl group, a benzofuranyl group, an imidazopyridinyl group, a benzotriazolyl group, a benzodioxolyl group, a dihydrobenzodioxinyl group, a quinolinyl group, a tetrahydroquinolinyl group, a tetrahydroisoquinolinyl group, a quinoxalinyl group, a dihydroquinoxalinyl group, a quinazolinonyl group, or a pyrrolidinyl group. Even more preferably, Cy$_2$ represents a phenyl group, a pyrrolyl group, a furyl group, a thienyl group, a thiazolyl group, an oxazolyl group, an isoxazolyl group, a pyrazolyl group, a pyridinyl group, a pyrazinyl group, a pyridazinyl group, a pyrimidinyl group, or an imidazopyridinyl group.

Preferably, Cy$_2$ represents a cycloalkyl group, a heterocycloalkyl group, an aryl group, or a heteroaryl group which are substituted by 1 or 2 groups selected from linear or branched (C$_1$-C$_6$)alkyl, linear or branched halo(C$_1$-C$_6$)alkyl, —Y$_1$—OR', —Y$_1$—NR'R", N-oxide, cyano, —C(O)—OR', —C(O)—NR'R", halogen, in which R' and R" independently of one another represent a hydrogen atom, a linear or branched (C$_1$-C$_6$)alkyl group, a linear or branched (C$_1$-C$_6$) alkoxy group, a tetrahydropyranyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen, it being understood that the second nitrogen in question may be substituted by a linear or branched (C$_1$-C$_6$)alkyl group.

In some preferred embodiment of the invention, K represents a thienyl group, a thiazolyl group or a pyridinyl group and L represents a pyrrolyl group, a furyl group, a thienyl group, a pyrazolyl group, a pyridinyl group, a pyrimidinyl group, or an imidazopyridinyl group, each said heteroaryl group may be substituted by 1 or 2 groups selected from linear or branched (C$_1$-C$_6$)alkyl, linear or branched halo(C$_1$-C$_6$)alkyl, —Y$_1$—OR', —Y$_1$—NR'R", N-oxide, cyano, —C(O)—NR'R", halogen, in which R' and R" independently of one another represent a hydrogen atom, a linear or branched (C$_1$-C$_6$)alkyl group, a linear or branched (C$_1$-C$_6$)alkoxy group, a linear or branched (C$_1$-C$_6$)alkoxy (C$_1$-C$_6$)alkyl group, a tetrahydropyranyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen. More preferably, K represents a thiazolyl group and L represents a pyridinyl group.

Other compounds of the invention to which preference is given are those wherein K represents a bond and L represents a phenyl group, a thiazolyl group, an oxazolyl group, an isoxazolyl group, a pyrazolyl group, a pyridinyl group, a pyrazinyl group, a pyridazinyl group or a pyrimidinyl group, each said group may be substituted by 1 or 2 groups selected from linear or branched (C$_1$-C$_6$)alkyl, —Y$_1$—OR', —Y$_1$—NR'R", cyano, —C(O)—OR', halogen, it being understood that R' and R" independently of one another represent a hydrogen atom, a linear or branched (C$_1$-C$_6$)alkyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen, it being understood that the second nitrogen in question may be substituted by from 1 to 2 groups representing a hydrogen atom, or a linear or branched (C$_1$-C$_6$) alkyl group.

In a preferred embodiment, the -J-K-L group linked to the piperidinyl ring is defined such as J represents a —C(O)— group, K represents a -Cy$_1$- group and L represents a -Cy$_2$ group.

In another preferred embodiment, the -J-K-L group is defined such as J represents a —CH$_2$— group, K represents a bond and L represents a -Cy$_2$ group.

In another preferred embodiment, the -J-K-L group is defined such as J represents a —C(O)— group, K represents a bond and L represents a -Cy$_2$ group.

In another preferred embodiment, the -J-K-L group is defined such as J represents a —CH$_2$— group, K represents a -Cy$_1$- group and L represents a -Cy$_2$ group In the preferred compounds of the invention, $R_4$ represents a halogen atom, a linear or branched (C$_1$-C$_6$)alkyl group, or a —Y$_1$-Cy$_3$ group. Preferably, $R_4$ represents a bromine atom, a methyl group, or a -Cy$_3$ group.

Advantageously, Cy$_3$ represents a phenyl group, a naphthyl group, a pyrrolyl group, a furyl group, a thienyl group, a thiazolyl group, a pyrazolyl group, an imidazolyl group, a pyridinyl group, a pyrimidinyl group, a pyridinonyl group, an indolyl group, a benzodioxolyl group, a dihydrobenzodioxinyl group, a cyclopropyl group, a cyclobutyl group, a cyclopentyl group, a cyclohexyl group, a pyrrolidinyl group, a tetrahydropyranyl group, or a piperidinyl group.

Cy$_3$ preferably represents a cycloalkyl group, a heterocycloalkyl group, an aryl group, or a heteroaryl group which are substituted by from 1 to 3 groups selected from linear or branched (C$_1$-C$_6$)alkyl, linear or branched halo(C$_1$-C$_6$)alkyl, —Y$_1$—OR', —Y$_1$—NR'R", cyano, halogen, in which R' and R" independently of one another represent a hydrogen atom or a linear or branched (C$_1$-C$_6$)alkyl group, or the substituents of the pair (R', R") form together with the nitrogen atom carrying them a non-aromatic ring composed of from 5 to 7 ring members which may contain in addition to the nitrogen a second heteroatom selected from oxygen and nitrogen.

Advantageously, $R_5$ represents a hydrogen atom or a methyl group. More preferably, $R_5$ represents a hydrogen atom.

In the preferred compounds of the invention, $R_6$ represents a hydrogen atom or a methyl group.

$R_7$ preferably represents a hydrogen atom, a methyl group, or a —CH$_2$-Cy$_4$ group.

Preferably, Cy$_4$ represents a phenyl group or a dihydroindolyl group.

Preferred compounds of the invention are:
3-[(4-hydroxy-1-{[(3R,4R)-1-{[3-methyl-5-(pyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one;
3-[(1-{[(3R,4R)-1-{[5-(6-aminopyridin-3-yl)-3-fluorothiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one;
7-cyclopropyl-3-[(1-{[(3R,4R)-1-{[3-fluoro-5-(pyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;
3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;
3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(naphthalen-2-yl)-3,7-dihydro-4H-pyrrolo[2,3-d]pyrimidin-4-one;
7-(4-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methylphenyl)-3,7-dihydro-4H-pyrrolo[2,3-d]pyrimidin-4-one;
7-(3-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
7-(furan-3-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
7-(2-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
7-(2-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
7-[4-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(4-methylpiperazin-1-yl)phenyl]-3,7-dihydro-4H-pyrrolo[2,3-d]pyrimidin-4-one;
7-[3-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1H-pyrrol-1-yl)-3,7-dihydro-4H-pyrrolo[2,3-d]pyrimidin-4-one;
3-{[1-({(3R,4R)-1-[(2-bromo-4-methyl-1,3-thiazol-5-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;
5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}-4-methyl-1,3-thiazol-2-yl)pyridine-2-carbonitrile;
3-[(1-{[(3R,4R)-1-({2-[6-(dimethylamino)pyridin-3-yl]-4-methyl-1,3-thiazol-5-yl}carbonyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;
3-[(4-hydroxy-1-{[(3R,4R)-1-({4-methyl-2-[6-(trifluoromethyl)pyridin-3-yl]-1,3-thiazol-5-yl}carbonyl)-3-phenylpiperidin-4-yl]carbonyl}piperidin-4-yl)methyl]-7-phenyl-3,7-dihydro-4H-pyrrolo[2,3-d]pyrimidin-4-one;
3-[(4-hydroxy-1-{[(3R,4R)-1-{[2-(6-methoxypyridin-3-yl)-4-methyl-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;
3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;
7-(3-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
3-[(1-{[(3R,4R)-1-({2-[6-(dimethylamino)pyridin-3-yl]-1,3-thiazol-5-yl}methyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;
3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;
7-(4-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;
3-[(4-hydroxy-1-{[(3R,4R)-1-({2-[6-(morpholin-4-yl)pyridin-3-yl]-1,3-thiazol-5-yl}methyl)-3-phenylpiperidin-4- yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methylphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(1-{[(3R,4R)-1-({2-[6-(dimethylamino)pyridin-3-yl]-1,3-thiazol-5-yl}methyl)-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

7-(4-chlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(1-{[(3R,4R)-1-({2-[6-(dimethylamino)pyridin-3-yl]-1,3-thiazol-5-yl}methyl)-3-phenylpiperidin-4-yl]carbonyl}-4-hydroxypiperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-6,8-dimethylpyrimido[5',4':4,5]pyrrolo[1,2-b]pyridazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(morpholin-4-yl)phenyl]-3,7-dihydro-4H-pyrrolo[2,3-d]pyrimidin-4-one;

7-(3-chlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methyl-1-oxidopyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-({2-[6-(piperazin-1-yl)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-({2-[6-(trifluoromethyl)pyridin-3-yl]-1,3-thiazol-5-yl}methyl)piperidin-4-yl]carbonyl}piperidin-4-yl)methyl]-7-(4-methoxyphenyl)-3,7-dihydro-4H-pyrrolo[2,3-d]pyrimidin-4-one;

7-(3,4-dichlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carbonitrile;

3-[(4-hydroxy-1-{[(3R,4R)-1-{[2-(6-methylpyridin-3-yl)-1,3-thiazol-5-yl]methyl}-3-phenylpiperidin-4-yl]

carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-2-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

7-(3,4-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3,4-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one;

5-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-1-phenyl-1,5-dihydro-4H-pyrazolo[3,4-d]pyrimidin-4-one;

7-(3,5-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3,5-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

4-{3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-4-oxo-3,4-dihydro-7H-pyrrolo[2,3-d]pyrimidin-7-yl}benzonitrile;

3-[(4-hydroxy-1- {[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1-{[(3R,4R)-1- {[2-(6-methylpyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1- {[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one;

7-[3-(hydroxymethyl)phenyl]-3-[(4-hydroxy-1- {[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-fluorophenyl)-3-[(4-hydroxy-1-{[(3R,4R)-1-{[4-methyl-2-(6-methylpyridin-3-yl)-1,3-thiazol-5-yl]

carbonyl}-3-phenylpiperidin-4-yl]carbonyl}piperidin-4-yl)methyl]-3,7-dihydro-4H-pyrrolo[2,3-d]pyrimidin-4-one;

5-[(4-hydroxy-1- {[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-1-phenyl-1,5-dihydro-4H-pyrazolo[3,4-d]pyrimidin-4-one;

3-[(4-hydroxy-1- {[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one;

7-(4-fluorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(3-chloro-5-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3-chloro-5-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(4-chloro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(5-chlorothiophen-2-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(5-chlorothiophen-2-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-bromo-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]pyrrolo[2,1-f][1,2,4]triazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

7-[4-(hydroxymethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenylpyrrolo[2,1-f][1,2,4]triazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenylpyrrolo[2,1-f][1,2,4]triazin-4(3H)-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

3-[(4-hydroxy-1-{[(3R,4R)-1- {[2-(6-methoxypyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenylthieno[3,4-d]pyrimidin-4(3H)-one;

3-[(4-hydroxy-1-{[(3R,4R)-1- {[2-(6-methylpyridin-3-yl)-1,3-thiazol-5-yl]methyl}-3-phenylpiperidin-4-yl]carbonyl}piperidin-4-yl)methyl]-7-phenylthieno[3,4-d]pyrimidin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1- {[2-(6-methylpyridin-3-yl)-1,3-thiazol-5-yl]methyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1- {[2-(6-methoxypyridin-3-yl)-1,3-thiazol-5-yl]methyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1- {[2-(6-methoxypyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;

3-[(4-hydroxy-1-{[(3R,4R)-1- {[2-(6-methoxypyridin-3-yl)-1,3-thiazol-5-yl]methyl}-3-phenylpiperidin-4-yl]

carbonyl}piperidin-4-yl)methyl]-7-(4-methylphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;

3-[(4-hydroxy-1-{[[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-({2-[6-(hydroxymethyl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one;

3-[(4-hydroxy-1-{[[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one;

7-[4-(difluoromethyl)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-[4-(difluoromethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-[4-(difluoromethyl)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-[1-(difluoromethyl)-1H-pyrazol-4-yl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-[1-(difluoromethyl)-1H-pyrazol-4-yl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(3-methyl-3H-imidazo[4,5-b]pyridin-6-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

7-[3-(dimethylamino)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(1-{[(3R,4R)-1-{[2-(5-fluoro-6-hydroxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-3-carboxamide;

3-[(4-hydroxy-1-{[(3R,4R)-1-({2-[5-(hydroxymethyl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-({2-[6-(tetrahydro-2H-pyran-4-yloxy)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one;

3-[(1-{[(3R,4R)-1-{[2-(5-amino-6-methoxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one;

3-[(4-hydroxy-1-{[(3R,4R)-3-phenyl-1-{[2-(thiophen-2-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrazol-4-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;

7-(2,3-dihydro-1,4-benzodioxin-6-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(2,3-dihydro-1,4-benzodioxin-6-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one;

3-{[1-({(3R,4R)-1-[(2-bromopyridin-4-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-{[1-({(3R,4R)-1-[(5-bromopyridin-3-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

7-(3-chlorophenyl)-3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-3-phenyl-1-{[2-(thiophen-2-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrazol-4-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;

3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;

3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;

7-(2,3-dihydro-1,4-benzodioxin-6-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

7-(1,3-benzodioxol-5-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(1,3-benzodioxol-5-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(1,3-benzodioxol-5-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-{[1-({(3R,4R)-1-[(5-bromopyridin-3-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

3-[(4-hydroxy-1-{[(3R,4R)-3-phenyl-1-(pyridin-3-ylmethyl)piperidin-4-yl]carbonyl}piperidin-4-yl)methyl]-7-phenyl-3,7-dihydro-4H-pyrrolo[2,3-d]pyrimidin-4-one;

3-{[4-hydroxy-1-({(3R,4R)-1-[(6'-methyl-3,3'-bipyridin-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one;

3-[(4-hydroxy-1-{[(3R,4R)-3-phenyl-1-(pyridin-4-ylmethyl)piperidin-4-yl]carbonyl}piperidin-4-yl)methyl]-7-phenyl-3,7-dihydro-4H-pyrrolo[2,3-d]pyrimidin-4-one;

5-[5-({(3R,4R)-4-[(4-hydroxy-4-{[7-(3-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile;

5-[5-({(3R,4R)-4-[(4-{[7-(4-chlorophenyl)-4-oxo-4,7-dihydro-3H-pyrrolo[2,3-d]pyrimidin-3-yl]methyl}-4-hydroxypiperidin-1-yl)carbonyl]-3-phenylpiperidin-1-yl}methyl)-1,3-thiazol-2-yl]pyridine-2-carbonitrile;

5-[5-({(3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile;

3-[(4-hydroxy-1-{[(3R,4R)-1-{[4-methyl-2-(morpholin-4-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-({2-[6-(2-methoxyethoxy)
pyridin-3-yl]-1,3-thiazol-5-yl}methyl)-3-phenylpiperi-
din-4-yl]carbonyl}piperidin-4-yl)methyl]-7-phenyl-3,7-
dihydro-4H-pyrrolo[2,3-d]pyrimidin-4-one;
3-[(4-hydroxy-1-{[(3R,4R)-1-{[2-(4-methylpiperazin-1-yl)-
1,3-thiazol-5-yl]methyl}-3-phenylpiperidin-4-yl]
carbonyl}piperidin-4-yl)methyl]-7-phenyl-3,7-dihydro-
4H-pyrrolo[2,3-d]pyrimidin-4-one;
3-[(4-hydroxy-1-{[(3R,4R)-1-{[2-(6-hydroxypyridin-3-yl)-
1,3-thiazol-5-yl]methyl}-3-phenylpiperidin-4-yl]
carbonyl}piperidin-4-yl)methyl]-7-(3-hydroxyphenyl)-3,
7-dihydro-4H-pyrrolo[2,3-d]pyrimidin-4-one;
3-{[4-hydroxy-1-({(3R,4R)-1-[(4-methyl-1,3-thiazol-5-yl)
carbonyl]-3-phenylpiperidin-4-yl}carbonyl)piperidin-4-
yl]methyl}-7-phenyl-3,7-dihydro-4H-pyrrolo[2,3-d]py-
rimidin-4-one;
3-{[4-hydroxy-1-({(3R,4R)-1-[(2-methyl-1,3-thiazol-5-yl)
carbonyl]-3-phenylpiperidin-4-yl}carbonyl)piperidin-4-
yl]methyl}-7-phenyl-3,7-dihydro-4H-pyrrolo[2,3-d]py-
rimidin-4-one;
3-{[1-({(3R,4R)-1-[(2-chloro-1,3-thiazol-5-yl)carbonyl]-3-
phenylpiperidin-4-yl}carbonyl)-4-hydroxypiperidin-4-yl]
methyl}-7-phenyl-3,7-dihydro-4H-pyrrolo[2,3-d]pyrimi-
din-4-one;
3-[(4-hydroxy-1-{[(3R,4R)-3-phenyl-1-(pyrazin-2-ylm-
ethyl)piperidin-4-yl]carbonyl}piperidin-4-yl)methyl]-7-
phenyl-3,7-dihydro-4H-pyrrolo[2,3-d]pyrimidin-4-one;
3-[(4-hydroxy-1-{[(3R,4R)-3-phenyl-1-(1,3-thiazol-5-ylm-
ethyl)piperidin-4-yl]carbonyl}piperidin-4-yl)methyl]-7-
phenyl-3,7-dihydro-4H-pyrrolo[2,3-d]pyrimidin-4-one;
5-[5-({(3R,4R)-4-[(4-{[7-(4-fluorophenyl)-4-oxo-4,7-di-
hydro-3H-pyrrolo[2,3-d]pyrimidin-3-yl]methyl}-4-hy-
droxypiperidin-1-yl)carbonyl]-3-phenylpiperidin-1-
yl}methyl)-1,3-thiazol-2-yl]pyridine-2-carbonitrile;
methyl 3-{[(3R,4R)-4-({4-hydroxy-4-[(4-oxo-7-phenyl-4,7-
dihydro-3H-pyrrolo[2,3-d]pyrimidin-3-yl)methyl]piperi-
din-1-yl}carbonyl)-3-phenylpiperidin-1-yl]
carbonyl}benzoate;
5-[(4-hydroxy-1-{[(3R,4R)-1- {[2-(6-methylpyridin-3-yl)-
1,3-thiazol-5-yl]methyl}-3-phenylpiperidin-4-yl]
carbonyl}piperidin-4-yl)methyl]-1-(4-methoxyphenyl)-1,
5-dihydro-4H-pyrazolo[3,4-d]pyrimidin-4-one;
5-[(4-hydroxy-1- {[(3R,4R)-1-{[2-(6-methoxypyridin-3-
yl)-1,3-thiazol-5-yl]methyl}-3-phenylpiperidin-4-yl]
carbonyl}piperidin-4-yl)methyl]-1-(4-methoxyphenyl)-1,
5-dihydro-4H-pyrazolo[3,4-d]pyrimidin-4-one;
5-[(4-hydroxy-1-{[(3R,4R)-1-{[4-methyl-2-(6-methylpyri-
din-3-yl)-1,3-thiazol-5-yl]carbonyl}-3-phenylpiperidin-
4-yl]carbonyl}piperidin-4-yl)methyl]-1-(4-methoxyphe-
nyl)-1,5-dihydro-4H-pyrazolo[3,4-d]pyrimidin-4-one;
3-{[4-hydroxy-1-({(3R,4R)-1-[(2-{6-[(2-methoxyethyl)
amino]pyridin-3-yl}-1,3-thiazol-5-yl)methyl]-3-phe-
nylpiperidin-4-yl}carbonyl)piperidin-4-yl]methyl}-7-
phenyl-3,7-dihydro-4H-pyrrolo[2,3-d]pyrimidin-4-one;
3-{[4-hydroxy-1-({(3R,4R)-1-[(1-methyl-1H-pyrazol-4-yl)
methyl]-3-phenylpiperidin-4-yl}carbonyl)piperidin-4-yl]
methyl}-7-(4-methoxyphenyl)-3,7-dihydro-4H-pyrrolo
[2,3-d]pyrimidin-4-one;
3-[(4-hydroxy-1-{[(3R,4R)-3-phenyl-1-(pyrazin-2-ylm-
ethyl)piperidin-4-yl]carbonyl}piperidin-4-yl)methyl]-7-
(4-methoxyphenyl)-3,7-dihydro-4H-pyrrolo[2,3-d]py-
rimidin-4-one;
3-{[4-hydroxy-1-({(3R,4R)-1-[(5-methyl-1,3-thiazol-2-yl)
methyl]-3-phenylpiperidin-4-yl}carbonyl)piperidin-4-yl]
methyl}-7-(4-methoxyphenyl)-3,7-dihydro-4H-pyrrolo
[2,3-d]pyrimidin-4-one;
3-{[1-({(3R,4R)-1-[(5-bromopyridin-3-yl)methyl]-3-phe-
nylpiperidin-4-yl}carbonyl)-4-hydroxypiperidin-4-yl]
methyl}-7-(4-methoxyphenyl)-3,7-dihydro-4H-pyrrolo
[2,3-d]pyrimidin-4-one;
methyl 5-{[(3R,4R)-4-({4-hydroxy-4-[(4-oxo-7-phenyl-4,7-
dihydro-3H-pyrrolo[2,3-d]pyrimidin-3-yl)methyl]piperi-
din-1-yl}carbonyl)-3-phenylpiperidin-1-yl]
carbonyl}pyridine-3-carboxylate;
1-(2,3-dihydro-1,4-benzodioxin-6-yl)-5-[(4-hydroxy-1-
{[(3R,4R)-1-{[4-methyl-2-(6-methylpyridin-3-yl)-1,3-
thiazol-5-yl]carbonyl}-3-phenylpiperidin-4-yl]
carbonyl}piperidin-4-yl)methyl]-1,5-dihydro-4H-pyra-
zolo[3,4-d]pyrimidin-4-one;
1-(2,3-dihydro-1,4-benzodioxin-6-yl)-5-[(4-hydroxy-1-
{[(3R,4R)-1-{[2-(6-methylpyridin-3-yl)-1,3-thiazol-5-yl]
methyl}-3-phenylpiperidin-4-yl]carbonyl}piperidin-4-yl)
methyl]-1,5-dihydro-4H-pyrazolo[3,4-d]pyrimidin-4-
one;
3-{[4-hydroxy-1-({(3R,4R)-1-[(5-methyl-1,3-thiazol-2-yl)
methyl]-3-phenylpiperidin-4-yl}carbonyl)piperidin-4-yl]
methyl}-7-phenyl-3,7-dihydro-4H-pyrrolo[2,3-d]pyrimi-
din-4-one;
3-{[4-hydroxy-1-({(3R,4R)-1-[(3-methyl-1,2-oxazol-5-yl)
methyl]-3-phenylpiperidin-4-yl}carbonyl)piperidin-4-yl]
methyl}-7-phenyl-3,7-dihydro-4H-pyrrolo[2,3-d]pyrimi-
din-4-one;
3-{[1-({(3R,4R)-1-[(2,4-dimethyl-1,3-thiazol-5-yl)methyl]-
3-phenylpiperidin-4-yl}carbonyl)-4-hydroxypiperidin-4-
yl]methyl}-7-(4-methoxyphenyl)-3,7-dihydro-4H-pyr-
rolo[2,3-d]pyrimidin-4-one;
3-[(4-hydroxy-1-{[(3R,4R)-1-(1,3-oxazol-4-ylmethyl)-3-
phenylpiperidin-4-yl]carbonyl}piperidin-4-yl)methyl]-7-
(4-methoxyphenyl)-3,7-dihydro-4H-pyrrolo[2,3-d]py-
rimidin-4-one;
3-{[4-hydroxy-1-({(3R,4R)-1-[(5-methyl-1,3-oxazol-2-yl)
methyl]-3-phenylpiperidin-4-yl}carbonyl)piperidin-4-yl]
methyl}-7-(4-methoxyphenyl)-3,7-dihydro-4H-pyrrolo
[2,3-d]pyrimidin-4-one;
5-{[(3R,4R)-4-({4-hydroxy-4-[(4-oxo-7-phenyl-4,7-di-
hydro-3H-pyrrolo[2,3-d]pyrimidin-3-yl)methyl]piperi-
din-1-yl}carbonyl)-3-phenylpiperidin-1-yl]
methyl}pyridine-2-carbonitrile;
3-[[4-hydroxy-1-[(3R,4R)-1-[4-methyl-2-(6-methyl-3-
pyridyl)thiazole-5-carbonyl]-3-phenyl-piperidine-4-car-
bonyl]-4-piperidyl]methyl]-7-[4-(hydroxymethyl)phenyl]
pyrrolo[2,1-f][1,2,4]triazin-4-one;
3-[[4-hydroxy-1-[(3R,4R)-1-[4-methyl-2-(6-methyl-3-
pyridyl)thiazole-5-carbonyl]-3-phenyl-piperidine-4-car-
bonyl]-4-piperidyl]methyl]-7-[4-(hydroxymethyl)phenyl]
thieno[3,4-d]pyrimidin-4-one;
3-[[4-hydroxy-1-[(3R,4R)-1-[2-(6-methyl-3-pyridyl)thiaz-
ole-5-carbonyl]-3-phenyl-piperidine-4-carbonyl]-4-pip-
eridyl]methyl]-7-(3-methoxyphenyl)pyrrolo[2,3-d]py-
rimidin-4-one;
3-[[3,3-difluoro-4-hydroxy-1-[(3R,4R)-1-[4-methyl-2-(6-
methyl-3-pyridyl)thiazole-5-carbonyl]-3-phenyl-piperi-
dine-4-carbonyl]-4-piperidyl]methyl]-7-phenyl-pyrrolo
[2,3-d]pyrimidin-4-one;
3-[[3,3-difluoro-4-hydroxy-1-[(3R,4R)-1-[4-methyl-2-(6-
methyl-3-pyridyl)thiazole-5-carbonyl]-3-phenyl-piperi-
dine-4-carbonyl]-4-piperidyl]methyl]-7-(4-methoxyphe-
nyl)pyrrolo[2,3-d]pyrimidin-4-one;
3-[[4-hydroxy-1-[(3R,4R)-1-[(2-methoxypyrimidin-4-yl)
methyl]-3-phenyl-piperidine-4-carbonyl]-4-piperidyl]
methyl]-7-phenyl-pyrrolo[2,3-d]pyrimidin-4-one;

3-[[4-hydroxy-1-[(3R,4R)-1-[(2-methoxypyrimidin-4-yl)
methyl]-3-phenyl-piperidine-4-carbonyl]-4-piperidyl]
methyl]-7-(4-methoxyphenyl)pyrrolo[2,3-d]pyrimidin-4-
one;

3-[[4-hydroxy-1-[(3R,4R)-1-[(5-methylpyrazin-2-yl)
methyl]-3-phenyl-piperidine-4-carbonyl]-4-piperidyl]
methyl]-7-phenyl-pyrrolo[2,3-d]pyrimidin-4-one;

3-[[4-hydroxy-1-[(3R,4R)-1-[(5-methylpyrazin-2-yl)
methyl]-3-phenyl-piperidine-4-carbonyl]-4-piperidyl]
methyl]-7-(4-methoxyphenyl)pyrrolo[2,3-d]pyrimidin-4-
one;

3-[[4-hydroxy-1-[(3R,4R)-3-phenyl-1-(pyrimidin-2-ylm-
ethyl)piperidine-4-carbonyl]-4-piperidyl]methyl]-7-phe-
nyl-pyrrolo[2,3-d]pyrimidin-4-one;

3-[[4-hydroxy-1-[(3R,4R)-3-phenyl-1-(pyrimidin-2-ylm-
ethyl)piperidine-4-carbonyl]-4-piperidyl]methyl]-7-(4-
methoxyphenyl)pyrrolo[2,3-d]pyrimidin-4-one;

3-[[4-hydroxy-1-[(3R,4R)-1-[(2-methylpyrimidin-4-yl)
methyl]-3-phenyl-piperidine-4-carbonyl]-4-piperidyl]
methyl]-7-phenyl-pyrrolo[2,3-d]pyrimidin-4-one;

3-[[4-hydroxy-1-[(3R,4R)-1-[(2-methylpyrimidin-4-yl)
methyl]-3-phenyl-piperidine-4-carbonyl]-4-piperidyl]
methyl]-7-(4-methoxyphenyl)pyrrolo[2,3-d]pyrimidin-4-
one;

3-[[4-hydroxy-1-[(3R,4R)-1-[(6-methoxypyridazin-3-yl)
methyl]-3-phenyl-piperidine-4-carbonyl]-4-piperidyl]
methyl]-7-(4-methoxyphenyl)pyrrolo[2,3-d]pyrimidin-4-
one;

3-[[4-hydroxy-1-[(3R,4R)-1-[(5-methylpyrazin-2-yl)
methyl]-3-phenyl-piperidine-4-carbonyl]-4-piperidyl]
methyl]-7-phenyl-thieno[3,4-d]pyrimidin-4-one;

3-[[4-hydroxy-1-[(3R,4R)-1-[(2-methylpyrimidin-4-yl)
methyl]-3-phenyl-piperidine-4-carbonyl]-4-piperidyl]
methyl]-7-phenyl-thieno[3,4-d]pyrimidin-4-one.

The invention relates also to a process for the preparation of compounds of formula (I), which process is characterized in that there is used as starting material the compound of formula (II):

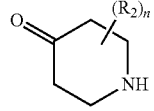

(II)

wherein $R_2$ and n are as defined for formula (I),
which is subjected to coupling with a compound of formula (III):

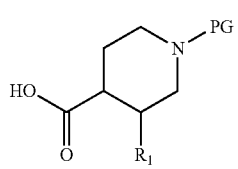

(III)

wherein $R_1$ is as defined for formula (I), and PG represents a protecting group of the amine function, to yield the compound of formula (IV):

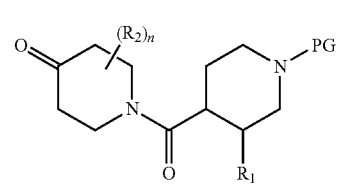

(IV)

wherein $R_1$, $R_2$, n and PG are as defined hereinbefore, compound of formula (IV) which is further converted to an epoxide compound of formula (V):

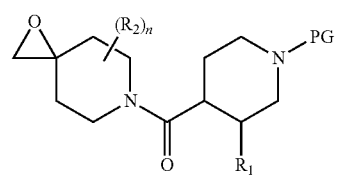

(V)

wherein $R_1$, $R_2$, n and PG are as defined hereinbefore, compound of formula (V) which is further subjected to coupling with compound of formula (VI):

(VI)

wherein W is as defined for formula (I),
to yield the compound of formula (VII):

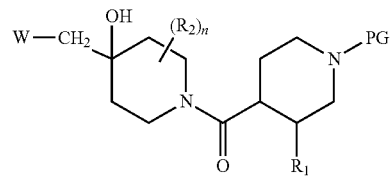

(VII)

wherein $R_1$, $R_2$, n, W and PG are as defined hereinbefore, compound of formula (VII) which, after a reaction removing the protecting group PG, is further subjected to:
either coupling with compound of formula (VIII):

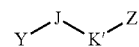

(VIII)

wherein J is as defined in formula (I), K' represents a -$Cy_1$- group, Y represents a hydroxy group or a halogen atom, and Z represents a halogen atom, to yield the compound of formula (IX):

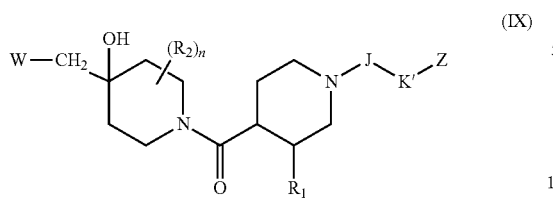

wherein $R_1$, $R_2$, J, K', n, W and Z are as defined hereinbefore, compound of formula (IX) which is further subjected to coupling with compound of formula (X):

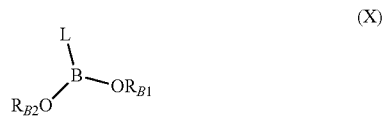

wherein L is as defined for formula (I), and $R_{B1}$ and $R_{B2}$ represent a hydrogen atom, a linear or branched ($C_1$-$C_6$) alkyl group, or $R_{B1}$ and $R_{B2}$ are linked together by a linear or branched ($C_2$-$C_6$)alkylene group, to yield the compound of formula (I-a), a particular case of the compounds of formula (I):

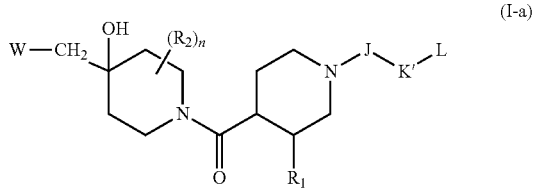

wherein $R_1$, $R_2$, J, K', L, n and W are as defined hereinbefore, or coupling with compound of formula (XI):

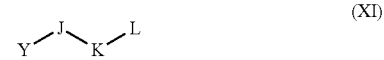

wherein J, K and L are as defined in formula (I), and Y represents a hydroxy group or a halogen atom, to yield the compound of formula (I), compound of formula (I) or compound of formula (I-a), which is a particular case of compound of formula (I), may then be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

In another embodiment of the invention, compounds of formula (I) may be obtained using an alternative process, which process is characterized in that there is used as starting material the compound of formula (XII):

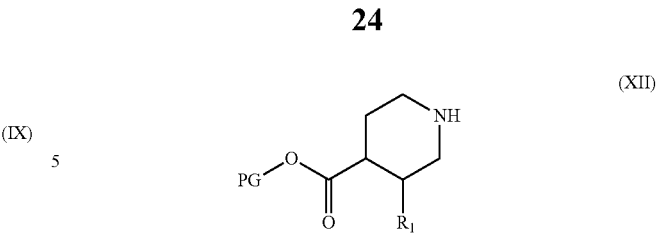

wherein $R_1$ is as defined for formula (I), and PG represents a protecting group of the carboxylic acid function, which is subjected to:
either coupling with compound of formula (VIII):

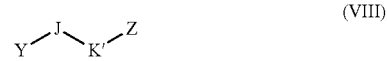

wherein J is as defined in formula (I), K' represents a -$Cy_1$- group, Y represents a hydroxy group or a halogen atom, and Z represents a halogen atom, to yield the compound of formula (XIII):

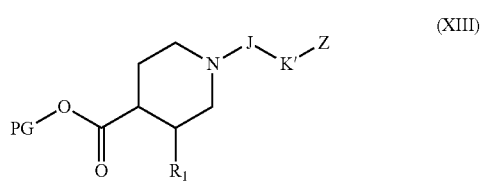

wherein $R_1$, J, K', Z and PG are as defined hereinbefore, compound of formula (XIII) which is further subjected to coupling with compound of formula (X):

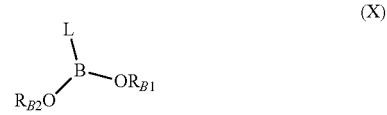

wherein L is as defined for formula (I), and $R_{B1}$ and $R_{B2}$ represent a hydrogen atom, a linear or branched ($C_1$-$C_6$) alkyl group, or $R_{B1}$ and $R_{B2}$ are linked together by a linear or branched ($C_2$-$C_6$)alkylene group, to yield the compound of formula (XIV):

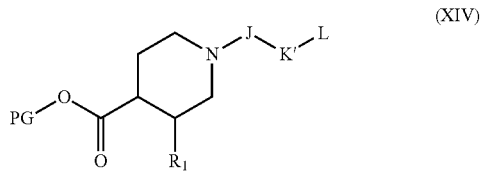

wherein $R_1$, J, K', L and PG are as defined hereinbefore, or coupling with compound of formula (XI):

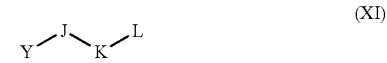

wherein J, K and L are as defined in formula (I), and Y represents a hydroxy group or a halogen atom,
to yield the compound of formula (XV),

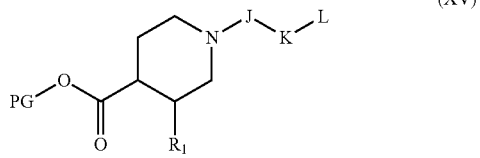
(XV)

wherein $R_1$, J, K, L and PG are as defined hereinbefore, compounds of formula (XIV) and (XV) which, after a reaction removing the protecting group PG, are further subjected to coupling with a compound of formula (II), to yield the compound of formula (XVI):

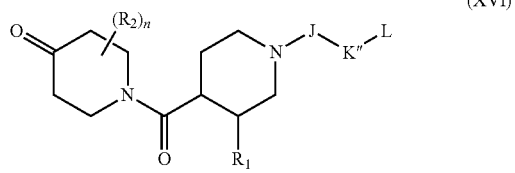
(XVI)

wherein $R_1$, $R_2$, J, L and n are as defined hereinbefore, and K" is either K' or K as defined hereinbefore,
compound of formula (XVI) which is further converted to an epoxide compound of formula (XVII):

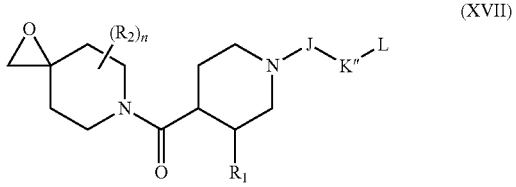
(XVII)

wherein $R_1$, $R_2$, J, K", L and n are as defined hereinbefore, compound of formula (XVII) which is further subjected to coupling with compound of formula (VI):

(VI)

wherein W is as defined for formula (I),
to yield the compound of formula (I), which may be purified according to a conventional separation technique, which is converted, if desired, into its addition salts with a pharmaceutically acceptable acid or base and which is optionally separated into its isomers according to a conventional separation technique,
it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II), (III), (VI), (VIII), (X), (XI) and (XII) are either commercially available or can be obtained by the person skilled in the art using conventional chemical reactions described in the literature.

Pharmacological studies of the compounds of the invention have shown pro-apoptotic and/or anti-proliferative properties. The ability to reactivate the apoptotic process in cancerous cells is of major therapeutic interest in the treatment of cancers and of immune and auto-immune system diseases.

Among the cancer treatments envisaged there may be mentioned, without implying any limitation, treatment of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer. More especially, the compounds according to the invention will be useful in the treatment of chemo-, targeted therapy- or radio-resistant cancers.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The pharmaceutical compositions according to the invention comprise one or more excipients or carriers selected from diluents, lubricants, binders, disintegration agents, stabilisers, preservatives, absorbents, colorants, sweeteners, flavourings etc.

By Way of Non-Limiting Example there May be Mentioned:
   as diluents: lactose, dextrose, sucrose, mannitol, sorbitol, cellulose, glycerol,
   as lubricants: silica, talc, stearic acid and its magnesium and calcium salts, polyethylene glycol,
   as binders: magnesium aluminium silicate, starch, gelatin, tragacanth, methylcellulose, sodium carboxymethylcellulose and polyvinylpyrrolidone,
   as disintegrants: agar, alginic acid and its sodium salt, effervescent mixtures.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies, and also to pharmaceutical compositions comprising that type of combination and their use in the manufacture of medicaments for use in the treatment of cancer.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may more-over be administered in the form of two separate pharmaceutical compositions, each containing one of the active ingredients, or in the form of a single pharmaceutical composition, in which the active ingredients are in admixture.

The compounds of formula (I) may also be used in combination with radiotherapy in the treatment of cancer.

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO Combi-Flash Rf 200i with pre-packed silica-gel cartridges (RediSep® $R_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an HANBON NP7000 Liquid Chromatography system with a Gemini-NX® 5 µM C18, 250 mm×50 mm i.d. column running at a flow rate of 99.9 mL min$^{-1}$ with UV diode array detection (210-400 nm) using 5 mM aqueous $NH_4HCO_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionization mode. Molecular weight scan range is 100 to 1350. Parallel UV detection was done at 210 nm and 254 nm. Samples were supplied as a 1 mM solution in MeCN, or in THF/$H_2O$ (1:1) with 5 µL loop injection. LCMS analyses were performed on two instruments, one of which was operated with basic, and the other with acidic eluents.

Basic LCMS: Gemini-NX, 3 µm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 µm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-$d_6$ or CDCl$_3$ as solvent. 1H NMR data is in the form of delta values, given in part per million (ppm), using the residual peak of the solvent (2.50 ppm for DMSO-$d_6$ and 7.26 ppm for CDCl$_3$) as internal standard. Splitting patterns are designated as: s (singlet), d (doublet), t (triplet), q (quartet), quint (quintet), sept (septet), m (multiplet), brs (broad singlet), brd (broad doublet), brt (broad triplet), brq (broad quartet), brm (broad multiplet), vbrs (very broad singlet), dd (doublet of doublets), td (triplet of doublets), dt (doublet of triplets), dq (doublet of quartet), ddd (doublet of doublet of doublets), dm (doublet of multiplets), tm (triplet of multiplets), qm (quartet of multiplets).

Combination gas chromatography and low resolution mass spectrometry were performed on Agilent 6850 gas chromatograph and Agilent 5975C mass spectrometer using 15 m×0.25 mm column with 0.25 µm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI+/−, ionization voltage: (+−)4.5 kV. Mass resolution min. 10000.

Elementary analyses were performed on a Thermo Flash EA 1112 Elemental Analyzer.

LIST OF ABBREVIATIONS

Abbreviation Name
abs. absolute
aq. aqueous
Ar argon
AtaPhos*PdCl$_2$ bis(di-tert-butyl(4-dimethylaminophenyl) phosphine) dichloropalladium(II)
Boc tert-butoxycarbonyl
cc. concentrated
DCM dichloromethane
DEE diethyl ether
DIPO diisopropyl oxide
disp. dispersion
DMEDA N,N-dimethylethylenediamine
DMF dimethylformamide
EDC.HCl N-(3-dimethylaminopropyl)-N-ethylcarbodiimide hydrochloride
EEO ethyl ethanoate
eq. equivalent
LC liquid chromatography
LDA lithium diisopropylamide
mCPBA meta-chloro-perbenzoic acid
MeCN acetonitrile
MSM methylsulfinylmethane
MTBE tert-butyl methylether
NMP N-methylpyrrolidone
PDO p-dioxane
r.t. room temperature
sat. saturated
SEM trimethylsilylethoxymethyl
TBAF tetrabutylammonium fluoride
TFA trifluoroacetic acid
THF tetrahydrofuran
TMP.MgCl.LiCl 2,2,6,6-tetramethylpiperidine-magnesium chloride-lithium chloride (1:1) complex General Procedure 1

Step 1:

To a stirred solution of 4-chloro-7H-pyrrolo[2,3-d]pyrimidine (Preparation R1a; 1.84 g, 12 mmol, 1 eq.) in abs. DMF (15 ml) sodium-hydride (720 mg, 60% disp. in mineral oil, 18 mmol, 1.5 eq.) was added, and stirred for 10 minutes at r.t. under Ar. Alkylating agent (13.18 mmol) was added to the reaction mixture and stirred for 1-6 hours at r.t. The mixture was poured into water (150 ml), then it was extracted with EEO (3×150 ml). The combined organic layers were washed with water, brine, dried over MgSO$_4$, and evaporated.

Step 2:

A part of the compound obtained in Step 1 above (1.36 mmol) and lithium-hydroxide monohydrate (571 mg, 13.62 mmol, 10 eq.) were stirred in PDO-water (40 ml, 1:1 v/v) mixture at 110° C. for 7-36 hours. The reaction mixture was neutralized with 1 N aq. HCl solution and the resulted precipitate was filtered off, washed with water and dried.

General Procedure 2
Step 1:
Preparation R1a (460 mg, 3 mmol, 1 eq.), heteroaryl/arylboronic acid (7.5 mmol) and copper(II)-acetate (817 mg, 4.5 mmol) were stirred in pyridine (10 ml) at 50-60° C. for 16-72 hours.
Work-Up 1:
The mixture was evaporated to Celite and purified by flash chromatography (heptane-EEO, gradient).
Work-Up 2:
The mixture was filtered and the resulted filtrate was purified by preparative LC (on C-18 Gemini-NX 5 μm column, 5 mM aqueous $NH_4HCO_3$-MeCN, gradient).
Step 2:
The resulted compound obtained in Step 1 above (1.36 mmol) and lithium-hydroxide monohydrate (571 mg, 13.62 mmol, 10 eq.) were stirred in PDO-water (40 ml, 1:1 v/v) mixture at 110° C. for 7-24 hours. The reaction mixture was neutralized with 1 N aq. HCl solution, the resulted precipitate was filtered off, washed with water, dried.

General Procedure 3
Step 1:
Preparation R1b (746 mg, 5 mmol, 1 eq.), heteroaryl/aryl-iodide (10 mmol), CuI (286 mg, 1.5 mmol, 0.3 eq.), R,R-diaminocyclohexane (171 mg, 1.5 mmol, 0.3 eq.), anhydrous $K_3PO_4$ (4.24 g, 20 mmol, 4 eq.) was stirred in diglyme (15 ml) for 6-16 hours at 120° C. under $N_2$ atmosphere.
Work-Up 1:
After the reaction completed, the mixture was diluted with water (200 ml) (or. 25% aq. $NH_3$) and cooled to r.t. The mixture was filtered, washed with water (3×30 ml), aq. $NH_3$ solution (40 ml, 25%), water (3×50 ml), heptane (50 then 30 ml) and dried in vacuum.
Work-Up 2:
The reaction mixture was evaporated to Celite and purified by flash chromatography (heptane:EEO, gradient).
Step 2:
The corresponding 4-methoxy-7-heteroaryl/aryl-pyrrolo[2,3-d]pyrimidine obtained in
Step 1 above (61.3 mmol, 1 eq.), cc. HCl aqueous solution (10 ml, ~12.2 M, 122.5 mmol, 2 eq.) and PDO (70 ml) was stirred at 100° C. for 0.5-2 hours. After the reaction completed, the mixture was partially evaporated. The formed suspension was filtered and the solid on the filter was washed with water and dried.

General Procedure 4
Step 1:
Preparation R1a (154 mg, 1 mmol, 1 eq.), di-tert-butyl-diazodicarboxylate (690 mg, 3 mmol, 3 eq.), triphenylphosphine (786 mg, 3 mmol, 3 eq.) and corresponding alcohol (3 mmol, 3 eq.) were stirred in abs. toluene (10 ml) under Ar atmosphere at 50° C. for 2 hours. The reaction mixture was evaporated, taken in THF and purified by preparative LC (on C-18 Gemini-NX 5 μm column, 5 mM aqueous $NH_4HCO_3$-MeCN, gradient).
Step 2:
A part of 4-chloro-7-aryl/alkyl-pyrrolo[2,3-d]pyrimidine obtained in Step 1 above (1.36 mmol) and lithium-hydroxide monohydrate (571 mg, 13.62 mmol) were stirred in PDO-water (40 ml, 1:1 v/v) mixture at 110° C. for 7-24 hours. The reaction mixture was neutralized with 1 N aq. HCl solution, the resulted precipitate was filtered off, washed with water and dried.

General Procedure 5
Step 1:
Pyrimidine-4-one derivative (1 mmol), epoxide compound Preparation R1f (1 mmol) and $K_2CO_3$ (276.4 mg, 2 mmol, 2 eq.) were stirred in DMF (5 ml) at 75° C. for 2-8 hours.
Work-Up 1:
The mixture was poured into ice-water mixture and the resulted precipitate was filtered off, washed with water and dried.
Work-Up 2:
The reaction mixture was filtered and the solid was washed with DMF. The resulted filtrate was purified by preparative LC (on C-18 Gemini-NX 5 μm column, 5 mM aqueous $NH_4HCO_3$-MeCN, gradient).
Step 2:
A part of the compound obtained in Step 1 above (1 mmol) was stirred in aq. HCl solution (1 N, 10 ml, 10 mmol, 10 eq.) and PDO (5 ml) for 1-3 hours at 75° C.
Work-Up 1:
The mixture was cooled to about 0-5° C. with ice bath and the white precipitate was filtered off and dried in vacuum (resulted HCl salt).
Work-Up 2:
The mixture was totally evaporated and was used to the further step (resulted HCl salt).
Work-Up 3:
The mixture was purified by preparative LC (on C-18 Gemini-NX 5 μm column, 5 mM aqueous $NH_4HCO_3$-MeCN, gradient, resulted free base).

General Procedure 6
Compound obtained in General Procedure 5 (1 mmol, 1 eq.), aryl/heteroaryl-$CH_2$—X (1 mmol, 1 eq.; wherein X represents a halogen atom) and $K_2CO_3$ (483 mg, 3.5 mmol, 3.5 eq.) were stirred in DMF (10 ml) at r.t. for 4-16 hours.
Work-Up 1:
The mixture was poured into ice-water mixture and the resulted precipitate was filtered off, washed with water and dried.
Work-Up 2:
The mixture was filtered and the filtrate was injected to preparative LC (on C-18 Gemini-NX 5 μm column, 5 mM aqueous $NH_4HCO_3$-MeCN, gradient).

General Procedure 7
Compound obtained in General Procedure 5 (2.7 mmol), EDC.HCl (1.183 g, 6.172 mmol) and corresponding carboxylic acid (2.7 mmol) were stirred in pyridine (25 ml) at r.t. for 16 hours.
Work-Up 1:
The reaction mixture was evaporated, the residue was taken in DMF and injected to preparative LC (on C-18 Gemini-NX 5 μm column, 5 mM aqueous $NH_4HCO_3$-MeCN, gradient).
Work-Up 2:
The reaction mixture was evaporated. The residue was triturated with water and the resulted solid was filtered off.

General Procedure 8
Compound obtained in General Procedure 5 (1 mmol, 1 eq.), corresponding sulfonyl chloride (2 mmol, 2 eq.) and $K_2CO_3$ (553 mg, 4 mmol, 4 eq.) were stirred in DMF (10 ml) at r.t. for 4-28 hours. The mixture was evaporated to Celite and purified by flash chromatography (eluent: DCM-MeOH).

General Procedure 9
The corresponding halogenated component (0.15 mmol, 1 eq.), corresponding boronic acid (0.375 mol, 2.5 eq.), ATAphos*$PdCl_2$ (10.6 mg, 0.015 mmol, 0.1 eq.), $Cs_2CO_3$ (171 mg, 0.525 mmol, 3.5 eq.) was diluted with THF (2.5 ml) and water (2.5 ml). The mixture was flushed with nitrogen and stirred in microwave reactor at 80° C. for 100-150 minutes. The reaction mixture was injected through syringe filter to preparative LC (on C-18 Gemini-NX 5 μm column, 5 mM aqueous $NH_4HCO_3$-MeCN, gradient).

General Procedure 10

To the stirred solution of the corresponding O-benzyl or O-methyl containing compound (0.17 mmol) in DCM (5 ml), boron-tribromide (0.3 ml, 440 mg, 1.7 mmol, 10 eq.) was added dropwise at r.t. After 3 hours of stirring, the reaction mixture was quenched with EtOH and evaporated. The residue was purified by preparative LC (on C-18 Gemini-NX 5 μm column, 5 mM aqueous $NH_4HCO_3$-MeCN, gradient).

General Procedure 11

The procedure is the same as described under General procedure 5 using Preparation R1m as epoxide component. The residue was purified by preparative LC (on C-18 Gemini-NX 5 μm column, 5 mM aqueous $NH_4HCO_3$-MeCN, gradient).

General Procedure 12

The mixture of the nitro compound (1.45 mmol), tin(II)-chloride dihydrate (1.64 g, 7.45 mmol, 5 eq.) in EtOH (30 ml) and HCl (1 N, 5 ml, aq.) was stirred for 20 hours at 80° C. To the reaction mixture sat. aqueous $NaHCO_3$ (50 ml) was added, then the mixture was evaporated to Celite and purified by flash chromatography (DCM-MeOH).

General Procedure 13

To a stirred mixture of amino/amide compound (0.105 mmol), $K_2CO_3$ (22 mg, 0.158 mmol, 1.5 eq.) in DMF (1 ml) iodomethane (10 μl) was added at r.t. After 18 hours of stirring the reaction mixture was filtered and injected to preparative LC (on C-18 Gemini-NX 5 μm column, 5 mM aqueous $NH_4HCO_3$-MeCN, gradient).

General Procedure 14

The N-Boc compound (0.1 mmol) was stirred in aq. HCl solution (1 N, 3 ml, 3 mmol, 30 eq.) and PDO (2 ml) for 2-5 hours at 75° C. The mixture was purified by preparative LC (on C-18 Gemini-NX 5 μm column, 5 mM aqueous $NH_4HCO_3$-MeCN, gradient, resulted as free amine base).

General Procedure 15

The mixture of the corresponding methoxy compound (0.44 mmol), cc. HCl (aq. 37%, 1.1 ml, 13 mmol, 30 eq.) and PDO (7 ml) was stirred at 100° C. for 3 hours. To the reaction mixture NaOH solution (aq. 2 M, 6.6 ml) was added. The solid compound was filtered off, then purified by preparative LC (on C-18 Gemini-NX 5 μm column, 5 mM aqueous $NH_4HCO_3$-MeCN, gradient).

Preparation R1b: 4-methoxy-7H-pyrrolo[2,3-d]pyrimidine

Preparation R1a (100 g, 0.651 mol, 1 eq.), NaOH (31.26 g, 0.781 mol, 1.2 eq.) and MeOH (400 ml) was stirred at 90° C. for 24 hours. The mixture was quenched with water (1200 ml) and cooled to r.t. with ice bath. The mixture is stirred for 30 minutes, and filtered through a glass filter. The precipitate was washed with water (3×100 ml) then dried and Preparation R1b was obtained as a white solid. HRMS calculated for $C_7H_7N_3O$: 149.0589; found 150.0667 [(M+H)$^+$ form].

$^1$H-NMR (400 MHz, MSM-d$_6$): δ=12.02 (vbrs, 1H), 8.37 (s, 1H), 7.35 (d, 1H), 6.47 (d, 1H), 4.02 (s, 3H).

$^{13}$C-NMR (100 MHz, MSM-d$_6$) δ ppm 162.6, 152.9, 150.8, 124.6, 104.8, 98.3, 53.7.

Preparation R1c: 5-[5-(chloromethyl)-1,3-thiazol-2-yl]-2-methylpyridine

Step 1: [2-(6-methylpyridin-3-yl)-1,3-thiazol-5-yl]methanol

2-Bromothiazole-5-methanol (20 g, 0.103 mol, 1 eq.), 2-methylpyridine-5-boronic acid (18.3 g, 0.134 mol, 1.3 eq.), ATAphos*PdCl$_2$ (3.65 g, 5.152 mmol, 0.05 eq.), Cs$_2$CO$_3$ (67.14 g, 0.206 mol, 2 eq.) were dissolved in THF (800 ml) and water (800 ml). The mixture was flushed with nitrogen and stirred at 80° C. for 3 hours. The mixture was cooled to r.t. and diluted with EEO (300 ml). The layers were separated, the aqueous layer was extracted with EEO (3×100 ml), the combined organic layer was dried over MgSO$_4$ and, after filtration, evaporated. The residue was crystallized from EEO/DIPO, filtered and dried in vacuum to give a brown solid. HRMS calculated for $C_{10}H_{10}N_2OS$: 206.0514; found 207.0591 [(M+H)$^+$ form].

$^1$H-NMR (500 MHz, MSM-d$_6$): δ=2.52 (s, 3H), 4.72 (d, J=10.4 Hz, 2H), 5.67 (t, J=11.0 Hz, 1H), 7.38 (d, J=16.3 Hz, 1H), 7.77 (s, 1H), 8.14 (dd, J=16.0, 4.8 Hz, 1H), 8.96 (d, J=4.5 Hz, 1H).

Step 2: Preparation R1c

[2-(6-Methyl-3-pyridyl)thiazol-5-yl]methanol (18.23 g, 88.38 mmol, 1 eq.) was dissolved in abs. DMF (1.37 ml, 1.29 g, 17.68 mmol, 0.2 eq.) and dry DCM (400 ml). SOCl$_2$ (8.36 ml, 13.67 g, 114.9 mmol, 1.3 eq.) was dropped to the mixture in DCM (50 ml) solution (~15 min) at r.t. The mixture was stirred at 50° C. for 2 hours. The mixture was cooled to r.t. Water (50 ml) was dropped slowly to the mixture, then it was neutralized with sat. NaHCO$_3$ solution (250 ml, pH 7-8). The layers were separated. The aqueous layer was extracted with DCM (4×50 ml). The combined organic layer was dried over MgSO$_4$, filtered. The solution was diluted with EEO (300 ml) and filtered through silica bed (~20 g). The mixture was evaporated to give Preparation R1c as a yellow solid. HRMS calculated for $C_{10}H_9ClN_2S$: 224.0175; found 225.0247 [(M+H)$^+$ form].

$^1$H NMR (500 MHz, MSM-d$_6$): δ=2.53 (s, 3H), 5.17 (s, 2H), 7.41 (d, J=16.5 Hz, 1H), 7.98 (s, 1H), 8.17 (dd, J=16.0, 5.0 Hz, 1H), 8.99 (d, J=5.0 Hz, 1H).

$^{13}$C-NMR (125 MHz, MSM-d$_6$): δ (ppm) 24.5, 38.4, 124.1, 134.4, 144.4, 146.7.

Preparation R1d: 4-methyl-2-(6-methylpyridin-3-yl)-1,3-thiazole-5-carboxylic Acid

Step 1: ethyl 4-methyl-2-(6-methylpyridin-3-yl)-1,3-thiazole-5-carboxylate

Ethyl 2-bromo-4-methylthiazole-5-carboxylate (26.9 g, 107.6 mmol, 1 eq.), 2-methylpyridine-5-boronic acid (19.2 g, 139.8 mmol, 1.3 eq.), ATAphos*PdCl$_2$ (3.05 g, 4.3 mmol, 0.04 eq.), Na$_2$CO$_3$ (34.2 g, 322.65 mmol, 3 eq.) were dissolved in THF (250 ml) and water (250 ml). The mixture was flushed with nitrogen and stirred at 80° C. for 2 hours. After the reaction ended, the mixture was cooled to r.t. and diluted with EEO (250 ml). The layers were separated and the aqueous layer was extracted with EEO (2×50 ml). The combined organic layer was dried over MgSO$_4$ and, after filtration, evaporated. The raw product was dissolved in DCM/EEO/heptane (1:1:1 v/v, 600 ml) and filtered through silica (~30 g) and washed with DCM/EEO/heptane (1:1:1 v/v, 100 ml). The mixture was evaporated. The residue was recrystallized from DIPO (100 ml) and dried in vacuum to give a beige solid. HRMS calculated for $C_{13}H_{14}N_2O_2S$: 262.0776; found 263.0852 [(M+H)$^+$ form].

$^1$H NMR (500 MHz, MSM-d$_6$): δ=1.31 (t, J=17.5 Hz, 3H), 2.54 (s, 3H), 2.70 (s, 3H), 4.30 (q, J=17.8 Hz, 2H), 7.42 (d, J=20.3 Hz, 1H), 8.24 (dd, J=20.4, 6.1 Hz, 1H), 9.04 (d, J=5.4 Hz, 1H).

Step 2: Preparation R1d

Ethyl 4-methyl-2-(6-methyl-3-pyridyl)thiazole-5-carboxylate (21.07 g, 80.33 mmol, 1 eq.) was dissolved in EtOH (40 ml). NaOH (4.82 g, 120.49 mmol, 1.5 eq.) was dissolved in water (80 ml). The aq. NaOH was added to the organic mixture and stirred at 80° C. for 45 minutes. After the reaction ended, the mixture was cooled to r.t. After 1 week, the black precipitate was sedimented. The mixture was filtered through a silica/Celite bed. The mixture was acidified with cc. HCl solution (to pH-1), and the resulting precipitate was filtered off, washed with water (50 ml) and dried in vacuum to give Preparation R1d as an off-white solid. HRMS calculated for $C_{11}H_{10}N_2O_2S$: 234.0463; found 235.0533 [(M+H)$^+$ form].

$^1$H NMR (500 MHz, MSM-d$_6$): δ=2.52 (s, 3H), 2.63 (s, 3H), 7.36 (d, J=16.2 Hz, 1H), 8.14 (dd, J=16.2, 4.8 Hz, 1H), 8.95 (d, J=4.8 Hz, 1H).

Preparation R1e: tert-butyl 1-oxa-6-azaspiro[2.5]octane-6-carboxylate

Trimethyl-sulfoxonium iodide (20.0 g, 150 mmol) was dissolved in abs. MSM (75 ml) then sodium-hydride dispersion (60% in mineral oil, 6 g, 150 mmol) was added sequentially and stirred for 20 minutes at r.t. N-Boc-piperidin-4-one (20.0 g, 100 mmol) solution in MSM (75 ml, abs.) was added to the mixture and stirred for 15 hours at r.t. The reaction mixture was poured into ice-water mixture (200 ml) and extracted with diethyl-ether (4×200 ml). The combined organic layer was washed with water, brine, then dried over MgSO$_4$ and evaporated to give Preparation R1e. HRMS calculated for $C_{11}H_{19}NO_3$: 213.1365; found 158.0811 [(M+H-tBu)$^+$ form].

$^1$H NMR (500 MHz, MSM-d$_6$): δ ppm 3.5/3.37 (brm+brm, 4H), 2.65 (s, 2H), 1.64/1.38 (m+m, 4H), 1.4 (s, 9H).

$^{13}$C NMR (125 MHz, MSM-d$_6$): δ ppm 154.3, 79.3, 57.4, 53.3, 42.7, 33, 28.5.

Preparation R1f: tert-butyl (3R,4R)-4-(1-oxa-6-azaspiro[2.5]oct-6-ylcarbonyl)-3-phenylpiperidine-1-carboxylate

Step 1: tert-butyl (3R,4R)-4-[(4-oxopiperidin-1-yl)carbonyl]-3-phenylpiperidine-1-carboxylate 4-piperidone hydrochloride hydrate (0.969 g, 6.3 mmol), EDC.HCl (3.623 g, 18.9 mmol) and (3R,4R)-1-tert-butoxycarbonyl-3-phenyl-piperidine-4-carboxylic acid (1.928 g, 6.3 mmol) were dissolved in pyridine (10 mL) and stirred at r.t. for 16 hours. The reaction mixture was evaporated to Celite and purified by flash chromatography (DCM:MeOH, gradient) to give the product of the title. HRMS calculated for $C_{22}H_{30}N_2O_4$: 386.2206; found 409.2093 [(M+Na)$^+$ form].

$^1$H-NMR (500 MHz, MSM-d$_6$): δ 1.42 (s, 9H), 4.14-1.50 (m, 16H), 7.32-7.15 (m, 5H).

Step 2: Preparation R1f tert-butyl (3R,4R)-4-[(4-oxopiperidin-1-yl)carbonyl]-3-phenylpiperidine-1-carboxylate (60 g, 155 mmol 1 eq.) and trimethylsulfoxonium-iodide (85.41 g, 388 mmol, 2.5 eq.) was charged into a round bottom flask and dissolved/suspended in MeCN (150 ml) and MTBE (150 ml). In parallel, NaOH (15.5 g, 388 mmol, 2.5 eq.) was dissolved in water (21.6 ml) (~40% solution). The aq. NaOH solution was added to the mixture and stirred at 60° C. for 2 hours. After the reaction completed, the mixture was cooled to r.t., filtered through a Celite bed and the filter cake was washed with MTBE (2×60 ml). Water (150 ml) was added to the organic layer and, after extraction, the layers were separated. The aq. layer was extracted with further MTBE (2×60 ml). The combined organic layers were dried over MgSO$_4$ and after filtration evaporated to give Preparation R1f as beige solid foam. HRMS calculated for $C_{23}H_{32}N_2O_4$: 400.2362; found 423.2247 [(M+Na)$^+$ form].

$^1$H-NMR (500 MHz, MSM-d$_6$): δ=1.41 (s, 9H), 1.79-0.86 (m, 6H), 2.61-2.51 (m, 2H), 4.16-2.73 (m, 10H), 7.33-7.18 (m, 5H).

Preparation R1g: 3-fluoro-5-iodo-thiophene-2-carboxylic Acid

Step 1: 3-fluoro-5-iodo-thiophene-2-carboxylate and methyl 3-fluoro-4,5-diiodo-thiophene-2-carboxylate To the solution of methyl 3-fluorothiophene-2-carboxylate (2.42 g, 15.1 mmol) in THF (10 ml) at TMP.MgCl.LiCl (1 N, in THF/toluene, 25 ml, 25 mmol) was added dropwise at −45° C. in 5 minutes. After 30 minutes of stirring iodine (4.04 mg, 15.9 mmol) was added in THF (10 ml) at −45° C. to the mixture. After warming up (1 hour) sat. NH$_4$Cl solution (50 ml, aq.) was added to the mixture while stirring. The mixture was extracted with EEO (5×10 ml). The combined organic layer was evaporated. The residue was purified by preparative LC (on C-18 Gemini-NX 5 μm column, 5 mM aqueous NH$_4$HCO$_3$-MeCN, gradient) to give 3-fluoro-5-iodo-thiophene-2-carboxylate and methyl 3-fluoro-4,5-diiodo-thiophene-2-carboxylate, separately.

Methyl 3-fluoro-5-iodo-thiophene-2-carboxylate

GC-MS calculated for $C_6H_4FIO_2S$: 285.8961; found 285.9 [(M, EI) form].

$^1$H NMR (500 MHz, MSM-d$_6$): δ ppm 7.52 (s, 1H), 3.78 (s, 3H).

$^{13}$C NMR (125 MHz, MSM-d$_6$): δ ppm 159.4, 158.8, 128.5, 117.2, 86.4, 52.8.

Methyl 3-fluoro-4,5-diiodo-thiophene-2-carboxylate

GC-MS calculated for $C_6H_4FIO_2S$: 411.7927; found 411.9 [(M, EI) form].

$^1$H NMR (500 MHz, MSM-d$_6$): δ ppm 3.8 (s, 3H).

$^{13}$C NMR (125 MHz, MSM-d$_6$): δ ppm 159, 158.2, 117.4, 96.1, 90.6, 53.1.

Step 2: Preparation R1g

Methyl 3-fluoro-5-iodo-thiophene-2-carboxylate (1.188 g, 4.135 mmol), lithium-hydroxide monohydrate (867 mg, 20.7 mmol) were stirred in methanol (10 ml) and water (10 ml) at 70° C. for 1 hour. The mixture was partially evaporated and the aqueous residue was acidified with 1 N HCl (25 ml, aq.). The resulted precipitate was filtered off, washed with water and dried to give Preparation R1g. GC-MS calculated for $C_5H_2FIO_2S$: 271.8804; found 271.9 [(M, EI) form].

$^1$H NMR (500 MHz, MSM-d$_6$): δ ppm 13.48 (brs), 7.74 (s, 1H).

$^{13}$C NMR (125 MHz, MSM-d$_6$): δ ppm 160.4, 158.3, 128.5, 119, 85.1.

Preparation R1h: 3-fluoro-4,5-diiodo-thiophene-2-carboxylic Acid

Methyl 3-fluoro-4,5-diiodo-thiophene-2-carboxylate (614 mg, 1.49 mmol), lithium-hydroxide monohydrate (256 mg, 6 mmol) were stirred in methanol (8 ml) and water (8 ml) at r.t. for 5 hours. The mixture was partially evaporated and the aqueous residue was acidified with 1 N HCl (10 ml, aq.). The resulted precipitate was filtered off, washed with water and dried to give Preparation R1h. HRMS calculated for $C_5HFI_2O_2S$: 397.7771; found 352.7798 [(M−H—$CO_2$)$^+$ form].
$^1$H NMR (500 MHz, MSM-$d_6$): δ ppm 13.72 (brs, 1H).
$^{13}$C NMR (125 MHz, MSM-$d_6$): δ ppm 160, 157.7, 119.1, 95.1, 90.5.

Preparation R1i: 3-fluoro-4-iodo-5-methyl-thiophene-2-carboxylic Acid

Step 1: methyl 3-fluoro-4-iodo-5-methyl-thiophene-2-carboxylate

To the solution of methyl 3-fluoro-5-iodo-thiophene-2-carboxylate Preparation R1g (286 mg, 1 mmol) in THF (3 ml) TMP.MgCl.LiCl (1 N, in THF/toluene, 1.5 ml, 1.5 mmol) was added dropwise at −45° C. in 5 minutes. After 60 minutes of stirring iodomethane (123 ml, 282 mg, 2 mmol) was added in THF (2 ml) at −45° C. to the mixture and stirred for 2 hours at −40° C. After warming up, sat. $NH_4Cl$ solution (5 ml, aq.) was added to the mixture while stirring. The mixture was extracted with EEO (4×10 ml). The combined organic layer was evaporated. The residue was purified by preparative LC (on C-18 Gemini-NX 5 μm column, 5 mM aqueous $NH_4HCO_3$-MeCN, gradient) to give the product of the title. HRMS calculated for $C_7H_6FIO_2S$: 299.9117; 300.9200 [(M+H)$^+$ form].
$^1$H NMR (500 MHz, MSM-$d_6$): δ ppm 3.8 (s, 3H), 2.43 (s, 3H).
$^{13}$C NMR (125 MHz, MSM-$d_6$): δ ppm 159.8, 158.5, 145.1, 109.6, 77.2, 52.8, 19.1.

Step 2: Preparation R1i

Methyl 3-fluoro-4-iodo-5-methyl-thiophene-2-carboxylate (40 mg, 0.133 mmol), lithium-hydroxide monohydrate (11 mg, 0.266 mmol) were stirred in methanol (1 ml) and water (1 ml) at r.t. for 3 hours. The mixture was partially evaporated and the aqueous residue was acidified with 1 N HCl (3 ml, aq.). The resulted precipitate was filtered off, washed with water and dried to give Preparation R1i. 1H NMR (500 MHz, MSM-$d_6$): δ ppm 13.41 (brs, 1H), 2.41 (s, 3H).
$^{13}$C NMR (125 MHz, MSM-$d_6$): δ ppm 160.8, 158, 144.2, 76.9, 19.1.

Preparation R1j: 3-chloro-5-iodo-thiophene-2-carboxylic Acid

Step 1: 3-chloro-5-iodothiophene-2-carboxylic acid methyl ester

To the solution of 3-chlorothiophene-2-carboxylic acid methyl ester (353 g, 2 mmol) in THF (5 ml) at TMP.MgCl.LiCl (1 N, in THF/toluene, 3 ml, 3 mmol) was added dropwise at −45° C. After 20 minutes of stirring iodine (507 mg, 4 mmol) was added in THF (2 ml) at −45° C. to the mixture. After warming up, sat.$NH_4Cl$ solution (5 ml, aq.) and $Na_2S_2O_3$ solution (5 ml, 10% aq.) was added to the mixture while stirring. The mixture was extracted with EEO (4×10 ml). The combined organic layer was evaporated. The residue was purified by preparative LC (on C-18 Gemini-NX 5 μm column, 5 mM aqueous $NH_4HCO_3$-MeCN, gradient) to give the product of the title. HRMS calculated for $C_6H_4ClIO_2S$: 301.8665; found 301.9000 [(M+H)$^+$ form].
$^1$H NMR (500 MHz, MSM-$d_6$): δ ppm 37.55 (s, 1H), 3.8 (s, 3H).
$^{13}$C NMR (125 MHz, MSM-$d_6$): δ ppm 159.5, 139.4, 130.9, 130.6, 86.8, 53.

Step 2: Preparation R1j 3-chloro-5-iodothiophene-2-carboxylic acid methyl ester (477 mg, 1.58 mmol), lithium-hydroxide monohydrate (132 mg, 3.16 mmol) were stirred in methanol (5 ml) and water (5 ml) at 50° C. for 2.5 hours. The mixture was partially evaporated and the aqueous residue was acidified with 1 N HCl solution (4 ml, aq.). The resulted precipitate was filtered off, washed with water and dried to give Preparation R1j. GC-MS calculated for $C_5H_2ClIO_2S$: 287.8509; found 243.8 [(M-$CO_2$, EI) form].
$^1$H NMR (500 MHz, MSM-$d_6$): δ ppm 13.6 (brs, 1H), 7.51 (s, 1H).
$^{13}$C NMR (125 MHz, MSM-$d_6$): δ ppm 160.6, 139.3, 132.4, 130.1, 85.8.

Preparation R1k: 5-chloro-3-fluoro-4-iodo-thiophene-2-carboxylic Acid

Step 1: methyl 5-chloro-3-fluoro-4-iodo-thiophene-2-carboxylate

To the solution of methyl 3-fluoro-5-iodo-thiophene-2-carboxylate (286 mg, 1 mmol) in THF (5 ml) at TMP.MgCl.LiCl (1 N, in THF/toluene, 1.5 ml, 1.5 mmol) was added dropwise at −45° C. in 5 minutes. After 30 minutes of stirring hexachloroethane (236 mg, 1 mmol) was added in THF (2 ml) at −45° C. to the mixture. After warming up, sat.$NH_4Cl$ solution (5 ml, aq.) was added to the mixture while stirring. The mixture was extracted with EEO (4×10 ml) and the combined organic layers were evaporated. The residue was purified by preparative LC (on C-18 Gemini-NX 5 μm column, 5 mM aqueous $NH_4HCO_3$-MeCN, gradient) to give the product of the title. GC-MS calculated for $C_6H_3ClFIO_2S$: 319.8571; found 319.9 [(M, EI) form].
$^1$H NMR (500 MHz, MSM-$d_6$): δ ppm 3.82 (s, 3H).
$^{13}$C NMR (125 MHz, MSM-$d_6$): δ ppm 159.1, 157.9, 135.9, 111.7, 81.1, 53.2.

Step 2: Preparation R1k

Methyl 5-chloro-3-fluoro-4-iodo-thiophene-2-carboxylate (76 mg, 0.237 mmol), lithium-hydroxide monohydrate (20 mg, 0.474 mmol) were stirred in methanol (4 ml) and water (4 ml) at r.t. for 2 hours. The mixture was partially evaporated and the aqueous residue was acidified with 1 N HCl (2 ml, aq.). The resulted precipitate was filtered off, washed with water and dried to give Preparation R1k. $^1$H NMR (400 MHz, MSM-$d_6$): δ ppm 13.88 (brs, 1H).
$^{19}$F NMR (376.5 MHz, MSM-$d_6$): δ ppm −101.7.
$^{13}$C NMR (100 MHz, MSM-$d_6$): δ ppm 157.4.

Preparation R1l: 5-chloro-3-fluoro-4-methyl-thiophene-2-carboxylic Acid

Step 1: methyl 5-chloro-3-fluoro-thiophene-2-carboxylate

To the solution of methyl 3-fluoro-thiophene-2-carboxylate (1826 mg, 11.4 mmol) in THF (5 ml) TMP.MgCl.LiCl (1 N, in THF/toluene, 21 ml, 21 mmol) was added dropwise at −45° C. in 5 minutes. After 30 minutes of stirring at −45° C., hexachloroethane (2.7g, 11.4 mmol) was added at −45° C. to the mixture and stirred for 1 hour at −40° C. After warming up, sat.NH$_4$Cl solution (10 ml, aq.) was added to the mixture while stirring. The mixture was extracted with EEO (4×10 ml) and the combined organic layers were evaporated. The residue was purified by preparative LC (on C-18 Gemini-NX 5 μm column, 5 mM aqueous NH$_4$HCO$_3$-MeCN, gradient) to give the product of the title. GC-MS calculated for $C_6H_4ClFO_2S$: 193.9604; found 193.9 [(M, EI) form].

$^1$H NMR (500 MHz, MSM-d$_6$): δ ppm 7.46 (s, 1H), 3.81 (s, 3H).
$^{13}$C NMR (125 MHz, MSM-d$_6$): δ ppm 159.5, 157.5, 135.3, 120.2, 111.5, 53.

Step 2: methyl 5-chloro-3-fluoro-4-methyl-thiophene-2-carboxylate

To the solution of methyl 5-chloro-3-fluoro-thiophene-2-carboxylate (579 mg, 3 mmol) in THF (3 ml) TMP.MgCl.LiCl (1 N, in THF/toluene, 6 ml, 6 mmol) was added dropwise at −45° C. in 5 minutes. After 60 minutes of stirring, iodomethane (1.3 ml, 2964 mg, 20.9 mmol) was added in THF (2 ml) at −45° C. to the mixture and stirred for 2 hours at −40° C. After warming up, sat.NH$_4$Cl solution (5 ml, aq.) was added to the mixture while stirring. The mixture was extracted with EEO (4×10 ml) and the combined organic layers were evaporated. The residue was purified by preparative LC (on C-18 Gemini-NX 5 μm column, 5 mM aqueous NH$_4$HCO$_3$-MeCN, gradient) to give the product of the title. GC-MS calculated for $C_7H_6ClFO_2S$: 207.9761; found 207.9 found [(M, EI) form].

$^1$H NMR (500 MHz, MSM-d$_6$): δ ppm 3.81 (s, 3H), 2.09 (s, 3H).
$^{13}$C NMR (125 MHz, MSM-d$_6$): δ ppm 159.7, 156.4, 130.8, 127, 109.6, 53, 10.5.

Step 3: Preparation R1l

Methyl 5-chloro-3-fluoro-4-methyl-thiophene-2-carboxylate (316 mg, 1.62 mmol), lithium-hydroxide monohydrate (271 mg, 6.46 mmol) were stirred in methanol (5 ml) and water (5 ml) at r.t. for 4 hours. The mixture was partially evaporated and the aqueous residue was acidified with 1 N HCl (2 ml, aq.). The resulted precipitate was filtered off, washed with water and dried to give Preparation R1l. $^1$H NMR (500 MHz, MSM-d$_6$): δ ppm 13.57 (brs, 1H), 2.07 (s, 3H)
$^{13}$C NMR (125 MHz, MSM-d$_6$): δ ppm 160.7, 155.9, 129.8, 126.9, 111.4, 10.5

Preparation R1m: [4-methyl-2-(6-methyl-3-pyridyl)thiazol-5-yl]-[(3R,4R)-4-(2-oxa-6-azaspiro[2.5]octane-6-carbonyl)-3-phenyl-1-piperidyl]methanone

Step 1: ethyl (3R,4R)-3-phenylpiperidine-4-carboxylate hydrochloride 1-tert-butyl 4-ethyl (3R,4R)-3-phenylpiperidine-1,4-dicarboxylate (10 g, 30 mmol) was stirred in the mixture of MeCN (100 ml) and cc. HCl solution (7.38 ml, 90 mmol, aq.) at 80° C. for 30 minutes. The reaction mixture was evaporated, and dried over vacuum to give the product of the title.

Step 2: ethyl (3R,4R)-1-[(2-bromo-4-methyl-1,3-thiazol-5-yl)carbonyl]-3-phenylpiperidine-4-carboxylate Ethyl (3R,4R)-3-phenylpiperidine-4-carboxylate hydrochloride (7.89 g, 29.9 mmol), 2-bromo-4-methyl-thiazole-5-carboxylic acid (6.64 g, 29.9 mmol) and EDC.HCl (17.2 g, 89.7 mmol) was dissolved in pyridine (200 ml) and stirred at r.t. for 23 hours. The reaction mixture was evaporated. To the residue, water (200 ml) was added and extracted with DCM (3×50 ml). The combined organic layer was dried over MgSO$_4$ and evaporated to give the product of the title. HRMS calculated for $C_{19}H_{21}BrN_2O_3S$: 436.0456; found 437.0546 [(M+H)$^+$ form].

$^1$H NMR (500 MHz, MSM-d$_6$): δ ppm 7.36-7.19 (m, 5H), 4.96-2.74 (vbrs, 4H), 3.82 (q, 2H), 3.03 (m, 1H), 2.87 (m, 1H), 2.34 (s, 3H), 1.98/1.62 (m+m, 2H), 0.86 (t, 3H).
$^{13}$C NMR (125 MHz, MSM-d$_6$): δ ppm 160.5, 151.6, 136.3, 129.2, 60.1, 47.3, 45.3, 29.2, 16.4, 14.2.

Step 3: ethyl (3R,4R)-1-{[4-methyl-2-(6-methyl-pyridin-3-yl)-1,3-thiazol-5-yl]carbonyl}-3-phenylpiperidine-4-carboxylate In 8 separated microwave tubes, ethyl (3R,4R)-1-[(2-bromo-4-methyl-1,3-thiazol-5-yl)carbonyl]-3-phenylpiperidine-4-carboxylate (8×1.87 g, 34.2 mmol), 2-methylpyridine-5-boronic acid (8×1.17 g, 68.4 mmol), ATAphos*PdCl$_2$ (8×303 mg, 3.4 mmol) and Cs$_2$CO$_3$ (8×4.18 g, 102.6 mmol) were dissolved in THF (8×25 ml) and water (8×15 ml). The 8 tubes were microwave irradiated at once at 80° C. for 2 hours (Anton-Paar Multiwave Pro). The organic layers of 8 tubes were combined, partially evaporated and purified by preparative LC (on C-18 Gemini-NX 5 μm column, 5 mM aqueous NH$_4$HCO$_3$-MeCN, gradient) to give the product of the title. HRMS calculated for $C_{25}H_{27}N_3O_3S$: 449.1773; found 450.1860[(M+H)$^+$ form].

$^1$H NMR (400 MHz, MSM-d$_6$): δ ppm 8.98 (d, 1H), 8.17 (dd, 1H), 7.4 (d, 1H), 7.36-7.16 (m, 5H), 5-2.75 (vbrs, 4H), 3.83 (q, 2H), 3.05 (m, 1H), 2.87 (m, 1H), 2.53 (s, 3H), 2.43 (s, 3H), 2.01/1.64 (dm+qm, 2H), 0.87 (t, 3H).
$^{13}$C NMR (100 MHz, MSM-d$_6$): δ ppm 146.7, 134.4, 124, 60.1, 47.3, 45.5, 29.2, 24.3, 16.5, 14.2.

Step 4: (3R,4R)-1-{[4-methyl-2-(6-methylpyridin-3-yl)-1,3-thiazol-5-yl]carbonyl}-3-phenylpiperidine-4-carboxylic acid Ethyl (3R,4R)-1-{[4-methyl-2-(6-methylpyridin-3-yl)-1,3-thiazol-5-yl]carbonyl}-3-phenyl piperidine-4-carboxylate (7.48 g, 16.64 mmol) and lithium-hydroxide hydrate (1.75 g, 41.6 mmol) were stirred in the mixture of EtOH (30 ml) and water (10 ml) at 75° C. for 3.5 hours. The reaction mixture was partially evaporated, to residue was acidified (to pH=4.5-5.5) with HCl solution (1 N, aq.) and the resulted suspension was filtered. The solid compound on the filter was washed with water and dried to give the product of the title. HRMS calculated for $C_{23}H_{23}N_3O_3S$: 421.146; found 422.1544 [(M+H)$^+$ form].

$^1$H NMR (400 MHz, MSM-d$_6$): δ ppm 11.82 (brs, 1H), 8.97 (d, 1H), 8.15 (dd, 1H), 7.39 (d, 1H), 7.35-7.18 (m, 5H), 4.34-4.05 (brm, 4H), 3.01-2.84 (m, 2H), 2.54 (s, 3H), 2.44 (s, 3H), 2.06/1.66 (m+m, 2H).

$^{13}$C NMR (100 MHz, MSM-d$_6$): δ ppm 146.8, 134.4, 123.8, 29.5, 24.3, 16.5.

Step 5: 1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-one (3R,4R)-1-{[4-methyl-2-(6-methylpyridin-3-yl)-1,3-thiazol-5-yl]carbonyl}-3-phenyl piperidine-4-carboxylic acid (3786 mg, 8.98 mmol), piperidin-4-one hydrate hydrochloride (1518 mg, 9.88 mmol) and EDC.HCl (5.16 g, 26.94 mmol) were stirred in pyridine (30 ml) at r.t. for 16 hours. The reaction mixture was evaporated, the residue was taken in MeOH (20 ml) and poured into water (120 ml) and extracted with DCM (3×60 ml). The combined organic layer was washed with water, brine, dried over MgSO$_4$ and evaporated to give the product of the title. HRMS calculated for C$_{23}$H$_{23}$N$_3$O$_3$S: 502.2039; found 503.2088 [(M+H)$^+$ form].

$^1$H NMR (400 MHz, MSM-d$_6$): δ ppm 8.98 (brs, 1H), 8.17 (dd, 1H), 7.4 (d, 1H), 7.36-7.13 (m, 5H), 4.92-2.76 (m, 10H), 2.53 (s, 3H), 2.45 (s, 3H), 2.25-1.52 (m, 6H).

Step 6: Preparation R1m

1-{[(3R,4R)-1-{[4-methyl-2-(6-methylpyridin-3-yl)-1,3-thiazol-5-yl]carbonyl}-3-phenyl piperidin-4-yl]carbonyl}piperidin-4-one (3.89 g, 7.74 mmol) and trimethylsulfoxonium-iodide (2.09 g, 9.3 mmol) was stirred in MeCN (19 ml) at r.t. and solution of NaOH (309 mg, 9.3 mmol) in water (0.4 ml) was added to the mixture. Then the reaction mixture was stirred at 70° C. for 2 hours. The reaction mixture was poured into water (200 ml) and neutralized with aqueous HCl solution (1 N, 9 ml) and extracted with DCM (3×80 ml). The combined organic layer was washed with water and brine and evaporated to give Preparation R1m as solid foam. HRMS calculated for C$_{29}$H$_{32}$N$_4$O$_3$S: 516.2195; found 517.2267 [(M+H)$^+$ form].

$^1$H NMR (500 MHz, MSM-d$_6$): δ ppm 8.98 (brs, 1H), 8.17 (dd, 1H), 7.4 (d, 1H), 7.37-7.15 (brs/brs, 5H), 3.82-0.88 (m, 14H), 3.53 (m, 1H), 2.97 (brm, 1H), 2.56 (m, 2H), 2.53 (s, 3H), 2.44 (s, 3H).

$^{13}$C NMR (125 MHz, MSM-d$_6$): δ ppm 164.1, 160.8, 152.4, 146.8, 134.5, 125.6, 124.1, 57.4/57.1, 53.4/53.1, 42.9/42.8, 24.5, 16.7.

Preparation R1n: 3-[[4-Hydroxy-1-[(3R,4R)-3-phenylpiperidine-4-carbonyl]-4-piperidyl]methyl]-7-(2-trimethylsilylethoxymethyl)pyrrolo[2,3-d]pyrimidin-4-one Step 1: 2-[(4-chloropyrrolo[2,3-d]pyrimidin-7-yl)methoxy]ethyl-trimethyl-silane Preparation R1a (2.81 g, 18.3 mmol) was dissolved in THF (25 ml) cooled to 0° C., and NaH (60% disp., 1.1 g, 27.4 mmol) was added to the mixture and stirred for 1 hour. Then SEM-Cl (8.1 ml, 45.76 mmol) was added to the mixture and allowed to warm up to r.t. After 2.5 hours, water (25 ml) was added to the reaction mixture and extracted with EEO (2×30 ml). The combined organic layer was dried over MgSO$_4$ and evaporated. The residue was purified by flash chromatography (220 g Silica Gold column, heptane-EEO gradient) to give the product of the title.

Step 2: 7-(2-Trimethylsilylethoxymethyl)-3H-pyrrolo[2,3-d]pyrimidin-4-one

2-[(4-chloropyrrolo[2,3-d]pyrimidin-7-yl)methoxy]ethyl-trimethyl-silane (3.5 g, 12.3 mmol) and lithium-hydroxide hydrate (5.17 g, 123 mmol) were stirred at 100° C. for 116 hours in the mixture of PDO (20 ml) and water (20 ml). The reaction mixture was filtered, the filtrate was acidified with aqueous HCl solution (1 N, 80 ml), and the resulted solid compound was filtered off, washed with water and dried to give the product of the title.

Step 3: tert-Butyl 4-hydroxy-4-[[4-oxo-7-(2-trimethylsilylethoxymethyl)pyrrolo[2,3-d]pyrimidin-3-yl]methyl]piperidine-1-carboxylate 7-(2-Trimethylsilylethoxymethyl)-3H-pyrrolo[2,3-d]pyrimidin-4-one (3.11g, 11.7 mmol), Preparation R1e (2.75 g, 2.9 mmol) and K$_2$CO$_3$ (1.78 g, 12.9 mmol) were stirred in DMF (70 ml) at 60° C. for 40 hours. To the reaction mixture water was added, the resulted solid compound was filtered off, washed with water to give the product of the title. HRMS calculated for C$_{23}$H$_{38}$N$_4$O$_5$Si: 478.2611; found 479.2694 [(M+H)$^+$ form].

Step 4: 3-[(4-Hydroxy-4-piperidyl)methyl]-7-(2-trimethylsilylethoxymethyl)pyrrolo[2,3-d]pyrimidin-4-one tert-Butyl 4-hydroxy-4-[[4-oxo-7-(2-trimethylsilylethoxymethyl)pyrrolo[2,3-d]pyrimidin-3-yl]methyl]piperidine-1-carboxylate (1.84 g, 3.86 mmol) was dissolved in DCM (50 ml) and formic acid (5 ml) and TFA (1317 mg, 0.885 ml, 11.58 mmol) were added then the mixture was stirred for 4 days at r.t. To the reaction mixture aqueous sodium-hydroxide solution (1 N, 100 ml) was added, then extracted with DCM (50 ml). The organic layer was dried over MgSO$_4$, filtered, evaporated to give the product of the title. HRMS calculated for C$_{18}$H$_{30}$N$_4$O$_3$Si: 378.2087; found 379.2176 [(M+H)$^+$ form].

Step 5: tert-Butyl (3R,4R)-4-[4-hydroxy-4-[[4-oxo-7-(2-trimethylsilylethoxymethyl) pyrrolo[2,3-d]pyrimidin-3-yl]methyl]piperidine-1-carbonyl]-3-phenyl-piperidine-1-carboxylate 3-[(4-hydroxy-4-piperidyl)methyl]-7-(2-trimethylsilylethoxymethyl)pyrrolo[2,3-d]pyrimidin-4-one (1.527 g, 3.77 mmol), (3R,4R)-1-tert-butoxycarbonyl-3-phenyl-piperidine-4-carboxylic acid (1.152 g, 3.77 mmol) and EDC.HCl (1.446 g, 7.54 mmol) were stirred in pyridine (15 ml) overnight at r.t. The reaction mixture was evaporated to Celite, and purified by flash chromatography (DCM-MeOH) to give the product of the title. HRMS calculated for C$_{35}$H$_{51}$N$_5$O$_6$Si: 665.3609; found 666.3696 [(M+H)$^+$ form].

Step 6: Preparation R1n

The solution of tert-butyl (3R,4R)-4-[4-hydroxy-4-[[4-oxo-7-(2-trimethylsilylethoxy methyl)pyrrolo[2,3-d]pyrimidin-3-yl]methyl]piperidine-1-carbonyl]-3-phenyl-piperidine-1-carboxylate (1.6 g, 2.4 mmol), formic acid (3 ml) and TFA (820 mg, 0.55 ml, 7.2 mmol) in DCM (30 ml) was stirred at r.t. for 4 days. To the reaction mixture potassium-carbonate (15 g) was added as aqueous solution and extracted with DCM. The organic layer was evaporated to give Preparation R1n. HRMS calculated for $C_{30}H_{43}N_5O_4Si$: 565.3084; found 566.3138 [(M+H)$^+$ form].

Preparation R1o: 5-bromo-4-(tert-butoxycarbonylamino)thiophene-2-carboxylic Acid 4-Amino-5-bromo-thiophene-2-carboxylic acid (500 mg, 2.25 mmol) was dissolved in the mixture of PDO (2 ml) and water (2 ml) and sodium-hydroxide (194 mg, 4.8 mmol) was added to the mixture at 0° C. Then di-tert-butyl dicarbonate (1768 mg, 8.1 mmol) was added to the mixture and stirred at 0° C. for 3 hours, then the reaction mixture was allowed to warm up to r.t. and stirred for 116 hours. The reaction mixture water was added and acidified by aqueous HCl solution (1 N, 4 ml). The resulted solid was filtered off washed with water and dried. The residue was purified by preparative LC (on C-18 Gemini-NX 5 µm column, 5 mM aqueous $NH_4HCO_3$-MeCN, gradient, resulted as ammonium salt) to give Preparation R1o. $^1$H NMR (500 MHz, MSM-$d_6$): δ ppm 8.71 (s, 1H), 7.44 (brs, 4H), 7.24 (s, 1H), 1.44 (s, 9H).
$^{13}$C NMR (125 MHz, MSM-$d_6$): δ ppm 125.8, 28.5.
$^{15}$N NMR (470.6 MHz, MSM-$d_6$): δ ppm 99.

Preparation R1p: 4-nitro-5-(4-pyridyl)thiophene-2-carboxylic acid

Using General Procedure 9 starting from methyl 5-chloro-4-nitro-thiophene-2-carboxylate and 4-(4,4,5,5-tetramethyl-1,3,2-dioxaborolan-2-yl)pyridine as reactant, the crude product (200 mg, 0.75 mmol) was stirred with lithium-hydroxide hydrate (60 mg, 1.5 mmol) in mixture of water (2 ml) and methanol (10 ml) at r.t. for 4 hours. The reaction mixture was neutralized with aqueous HCl solution (1 N, 1.5 ml). The resulted precipitate was filtered off, washed with water and dried to give Preparation R1p. 1H NMR (500 MHz, MSM-$d_6$): δ ppm 14.18 (vbrs, 1H), 8.74 (brs, 2H), 8.19 (s, 1H), 7.65 (m, 2H).
$^{13}$C NMR (125 MHz, MSM-$d_6$): δ ppm 161.8, 150.4, 145.9, 143.6, 138.2, 134.4, 129.2, 124.3.

Preparation R1q-(3S,4R): (3S,4R)-1-benzyl-3-(2-thienyl)piperidine-4-carboxylic Acid and Preparation R1q-(3R,4S): (3R,4S)-1-benzyl-3-(2-thienyl)piperidine-4-carboxylic Acid To a stirred suspension of sodium-hydride (60% disp., 1.4 g, 35.1 mmol) in abs. DEE (135 ml) ethyl 1-benzyl-3-oxo-piperidine-4-carboxylate hydrochloride (3.54 g, 11.9 mmol) was added at 0° C. After 30 minutes of stirring trifluoromethanesulfonic anhydride (3.88 g, 2.28 ml, 13.5 mmol) was added dropwise to the reaction mixture and stirred for 3 hours while temperature allowed to warm up to r.t. To the reaction mixture water (100 ml) was added, the layers were separated, the aqueous layer was washed with DEE. The DEE layer was dried over $MgSO_4$, and evaporated.

From a part of the prepared ethyl 1-benzyl-5-(trifluoromethylsulfonyloxy)-3,6-dihydro-2H-pyridine-4-carboxylate (2.184 g, 5.55 mmol), 2-thienylboronic acid (925 mg, 7.23 mmol), ATAphos*PdCl$_2$ (400 mg, 0.55 mmol), Cs$_2$CO$_3$ (3.63 g, 11.1 mol) was dissolved in THF (11 ml) and water (11 ml). The mixture was flushed with nitrogen and microwave irradiated at 82° C. for 140 minutes. The layers were separated, the organic layer was evaporated to Celite and purified by flash chromatography (Heptane-EEO, gradient).

The previously prepared ethyl 1-benzyl-5-(trifluoromethylsulfonyloxy)-3,6-dihydro-2H-pyridine-4-carboxylate (2.184 g, 5.55 mmol), 2-thienylboronic acid (925 mg, 7.23 mmol), ATAphos*PdCl$_2$ (400 mg, 0.55 mmol), and Cs$_2$CO$_3$ (3.63 g, 11.1 mol) were dissolved in the mixture of THF (11 ml) and water (11 ml). The mixture was flushed with nitrogen and microwave irradiated at 82° C. for 140 minutes. The layers were separated, the organic layer was evaporated to Celite and purified by flash chromatography (Heptane-EEO, gradient).

The resulted ethyl 1-benzyl-5-(2-thienyl)-3,6-dihydro-2H-pyridine-4-carboxylate (2.85 g, 8.7 mmol), Pd on carbon (3×1.5 g, 10%), HCl solution (1 N in ether, 8.7 ml, 8.7 mmol) and EtOH (65 ml) were added into an autoclave. The autoclave was closed, inertized, vacuumized and filled with hydrogen (8 bar) and the reaction mixture was stirred in autoclave at 90° C. for 420 hours. During the curse of reaction, the catalyst was filtered out and replaced twice by fresh one. The reaction mixture was removed from the autoclave and filtered through Celite and the filtrate was evaporated. The residue was purified by preparative LC (on C-18 Gemini-NX 5 µm column, 5 mM aqueous $NH_4HCO_3$-MeCN, gradient).

The resulted methyl cis-1-benzyl-3-(2-thienyl)piperidine-4-carboxylate (664 mg, 2 mmol) was dissolved in NaOEt solution (1 N, in EtOH, freshly prepared, 10 ml, 10 mmol) and stirred at 75° C. for 3 hours. Then water (5 ml) was added to the reaction mixture and continued stirring at 75° C. for 4 hours. The reaction mixture was partially evaporated, then neutralized by aqueous 1 N HCl solution, the solid was filtered off, washed with water and dried. The two enantiomers were separated by chiral LC to give Preparation R1q-(3S,4R) and Preparation R1q-(3R,4S). HRMS calculated for $C_{17}H_{19}NO_2S$: 301.1136; found 302.1217 [(M+H)$^+$ form].
$^1$H NMR (400 MHz, MSM-$d_6$): δ ppm 12.15 (brs, 1H), 7.37-7.19 (m, 5H), 7.32 (dd, 1H), 6.91 (dd, 1H), 6.88 (dd, 1H), 3.51 (s, 2H), 3.24 (tm, 1H), 2.9-2.05 (m, 4H), 2.39 (tm, 1H), 1.91-1.67 (dm/qm, 2H).

Preparation R1s: (4-methyl-2-phenyl-thiazol-5-yl)-[(3R,4R)-4-(2-oxa-6-azaspiro[2.5]octane-6-carbonyl)-3-phenyl-1-piperidyl]methanone Step 1: 1-[(3R,4R)-3-phenylpiperidine-4-carbonyl]piperidin-4-one hydrochloride tert-butyl (3R,4R)-4-(4-oxopiperidine-1-carbonyl)-3-phenylpiperidine-1-carboxylate (obtained in Step 1 of the Preparation R1f, 4.77 g, 12.34 mmol) was stirred in PDO (20 ml) and aqueous HCl solution (20 ml, 1 N) at 70° C. for 1 hour. The reaction mixture was evaporated and dried to give the product of the title. HRMS calculated for $C_{17}H_{22}N_2O_2$: 286.1681; found 287.1755 [(M+H)$^+$ form].
$^1$H NMR (400 MHz, MSM-$d_6$): δ ppm 9.68 (brd, 1H), 9.14 (brq, 1H), 7.40-7.18 (m, 5H), 3.73/3.31 (m/m, 2H), 3.73/3.31 (m/m, 2H), 3.56 (m, 1H), 3.33/3.10 (m/m, 2H), 3.31-3.13 (m, 2H), 3.26 (m, 1H), 2.17/1.56 (m/m, 2H), 2.15/1.81 (m/m, 2H), 2.03-1.87 (m, 2H).

Step 2: 1-[(3R,4R)-1-(4-methyl-2-phenyl-thiazole-5-carbonyl)-3-phenyl-piperidine-4-carbonyl]piperidin-4-one 1-[(3R,4R)-3-phenylpiperidine-4-carbonyl]piperidin-4-one hydrochloride (3.42 g, 10.6 mmol), EDC.HCl (6.64 g, 34.6 mmol) and 4-methyl-2-phenyl-thiazole-5-carboxylic acid (2.32 g, 10.6 mmol) were stirred in pyridine (60 ml) at r.t. for 20 hours. The reaction mixture was evaporated to Celite and purified by flash chromatography (DCM-MeOH/DCM, gradient) to give the product of the title. HRMS calculated for $C_{28}H_{29}N_3O_3S$: 487.1930; found 488.1991 [(M+H)$^+$ form].

$^1$H NMR (400 MHz, MSM-d$_6$): δ ppm 7.93/7.51 (brs/brs, 5H), 7.35/7.15 (brs/brs, 5H), 4.80-2.80 (brm, 4H), 3.74/3.63 (m/brm, 2H), 3.74/3.32 (m/m, 2H), 3.56 (td, 1H), 2.99 (td, 1H), 2.44 (s, 3H), 2.19/1.61 (m/m, 2H), 2.16/1.84 (m/m, 2H), 1.89/1.66 (brm/brm, 2H).

Step 3: Preparation R1s

To the stirred suspension of 1-[(3R,4R)-1-(4-methyl-2-phenyl-thiazole-5-carbonyl)-3-phenyl-piperidine-4-carbonyl]piperidin-4-one (4.5 g, 9.23 mmol) and trimethylsulfoxonium-iodide (2.44 g, 11.1 mmol) in MeCN (25 ml) aqueous sodium-hydroxide (40 w %, 443 mg NaOH/0.664 ml water) was added at r.t., stirred for 160 minutes. The reaction mixture was diluted with water (20 ml) and MeCN was evaporated. The residue was extracted with DCM and the organic layer was evaporated to give Preparation R1s. HRMS calculated for $C_{29}H_{31}N_3O_3S$: 501.2086; found 502.2160 [(M+H)$^+$ form].

$^1$H NMR (400 MHz, MSM-d$_6$): δ ppm 7.93 (m, 2H), 7.51 (m, 3H), 7.40-7.10 (brs/brs, 5H), 4.88-2.88 (brm, 4H), 3.82-2.97 (m, 4H), 3.54 (m, 1H), 2.97 (m, 1H), 2.56 (m, 2H), 2.43 (s, 3H), 1.83/1.63 (brd/brq, 2H), 1.45-0.86 (m, 2H).

Preparation R1t: 1-ethenyl-1H-indole-2-carboxylic Acid

The mixture of ethyl indole-2-carboxylate (2 g, 10.57 mmol), palladium(II)-acetate (119 mg, 0.53 mmol), copper (II)-bromide (2.37 g, 10.57 mmol), vinyl-acetate (20 ml, 248.7 mmol) and sodium-acetate (2.6 g, 31.7 mmol) was heated at 80° C. for 28 hours. The reaction mixture was evaporated to Celite and purified by flash chromatography (heptane-EEO, 0-5% gradient).

The mixture of the resulted ester (1.08 g, 5.017 mmol), lithium-hydroxide hydrate (1.05 g, 25.1 mmol) in ethanol and water (10-10 ml) was stirred at 80° C. for 90 minutes. The reaction mixture was acidified with aqueous HCl solution (1 N, 30 ml) at 0-5° C., the formed precipitate was filtered off, washed with water (5×20 ml) and dried to give Preparation R1t. 1H NMR (400 MHz, MSM-d6): δ ppm 13.22 (s, 1H), 7.75 (m, 3H), 7.51 (m, 1H), 7.22 (t, 1H), 5.48 (d, 1H), 5.28 (d, 1H)

Preparation R1u:
5-bromo-1-vinyl-pyrrole-2-carboxylic acid

The mixture of methyl 5-bromo-1H-pyrrole-2-carboxylate (1.2 g, 5.88 mmol), palladium(II)-acetate (132 mg, 0.588 mmol), copper(II)-bromide (2.63 g, 11.76 mmol), vinyl-acetate (27 ml, 294 mmol) and sodium-acetate (2.9 g, 35.3 mmol) was heated at 80° C. for 28 hours. The reaction mixture was evaporated to Celite and purified by flash chromatography (heptane-EEO, 0-25% gradient).

The mixture of the resulted ester (403 mg, 1.75 mmol), lithium-hydroxide hydrate (368 mg, 8.75 mmol) in ethanol and water (4-4 ml) was stirred at 80° C. for 60 minutes. The reaction mixture was acidified with aqueous HCl solution (1 N, 10 ml) at 0-5° C. The formed precipitate was filtered off, washed with water (5×20 ml) and dried to give Preparation R1u. $^1$H NMR (400 MHz, MSM-d6): δ ppm 12.63 (s, 1H), 7.11 (m, 1H), 6.94 (d, 1H), 6.45 (d, 1H), 5.42 (m, 2H)

Preparation R1v:
4-bromo-1-vinyl-pyrrole-2-carboxylic acid

The mixture of methyl 4-bromo-1H-pyrrole-2-carboxylate (1.2 g, 5.88 mmol), palladium(II)-acetate (132 mg, 0.588 mmol), copper(II)-bromide (2.63 g, 11.76 mmol), vinyl-acetate (27 ml, 294 mmol) and sodium-acetate (2.9 g, 35.3 mmol) was heated at 80° C. for 21 hours. The reaction mixture was evaporated to Celite and purified by flash chromatography (heptane-EEO, 0-5% gradient).

The mixture of the resulted ester (338 mg, 1.47 mmol), lithium-hydroxide hydrate (908 mg, 7.35 mmol) in ethanol and water (3.5-3.5 ml) was stirred at 80° C. for 105 minutes. The reaction mixture was acidified with aqueous HCl solution (1 N, 9 ml) at 0-5° C. The formed precipitate was filtered off, washed with water (2×5 ml) and dried to give Preparation R1v. $^1$H NMR (500 MHz, MSM-d6): δ ppm 12.93 (brs, 1H), 7.85 (d, 1H), 7.84 (dd, 1H), 6.94 (d, 1H), 5.5/4.9 (dd+dd, 2H).

$^{13}$C NMR (125 MHz, MSM-d6): δ ppm 131.4, 124.1, 123.4, 120.3, 102.8, 97.9

Preparation R1w:
4,5-dichloro-3-fluoro-thiophene-2-carboxylic Acid

Step 1: methyl 4,5-dichloro-3-fluoro-thiophene-2-carboxylate

To the solution of methyl 3-fluoro-thiophene-2-carboxylate (1826 mg, 11.4 mmol) in THF (5 ml) TMP.MgCl.LiCl (1 N, in THF/toluene, 21 ml, 21 mmol) was added dropwise at −45° C. in 5 minutes. After 30 minutes of stirring at −45° C., hexachloroethane (2.7g, 11.4 mmol) was added at −45° C. to the mixture and stirred for 1 hour at −40° C. After warming up, sat.NH$_4$Cl solution (10 ml, aq.) was added to the mixture while stirring. The mixture was extracted with EEO (4×10 ml). The combined organic layer was evaporated. The residue was purified by preparative LC (on C-18 Gemini-NX 5 μm column, 5 mM aqueous NH$_4$HCO$_3$-MeCN, gradient) to give the product of the title. GC-MS calculated for $C_6H_3Cl_2FO_2S$: 227.9215; found 227.9 found [(M, EI) form].

$^1$H NMR (500 MHz, MSM-d$_6$): δ ppm 3.85 (s, 3H).
$^{13}$C NMR (125 MHz, MSM-d$_6$): δ ppm 159, 152.8, 130.5, 115.5, 110.8, 53.4.

Step 2: Preparation R1w

Methyl 4,5-dichloro-3-fluoro-thiophene-2-carboxylate (130 mg, 0.567 mmol), lithium-hydroxide monohydrate (95 mg, 2.27 mmol) were stirred in methanol (3 ml) and water (3 ml) at r.t. for 3 hours. The mixture was partially evaporated and the aqueous residue was acidified with 1 N HCl (4 ml, aq.). The resulted precipitate was filtered off, washed with water and dried to give Preparation R1w. 13C NMR (125 MHz, MSM-d$_6$): δ ppm 160, 152.3, 129.5, 115.3, 112.8.

Preparation R1x:
2-(6-methyl-3-pyridyl)thiazole-5-carboxylic acid

Ethyl 2-(6-methyl-3-pyridyl)thiazole-5-carboxylate (745 mg, 3 mmol), lithium-hydroxide monohydrate (630 mg, 15 mmol) were stirred in ethanol (5 ml) and water (5 ml) at r.t.

for 8 hours. The mixture was partially evaporated and the aqueous residue was acidified with 1N HCl (15 ml, aq.). The resulted precipitate was filtered off, washed with water and dried to give Preparation R1x. HRMS calculated for $C_{10}H_8N_2O_2S$: 220.0307; found 221.0379 [(M+H)$^+$ form].

$^1$H NMR (500 MHz, MSM-d$_6$): δ ppm 13.69 (brs, 1H), 9.07 (d, 1H), 8.45 (s, 1H), 8.26 (dd, 1H), 7.44 (d, 1H), 2.55 (s, 3H). 13C NMR (125 MHz, MSM-d$_6$): δ ppm 149.3, 147.1, 134.9, 124.2, 24.5

Preparation R2b: 7-methyl-3H,4H,7H-pyrrolo[2,3-d]pyrimidin-4-one

Using General Procedure 1 starting from Preparation R1a and iodomethane as alkylating agent, Preparation R2b was obtained. HRMS calculated for $C_7H_7N_3O$: 149.0589; found 150.0668 [(M+H)$^+$ form].

$^1$H-NMR (500 MHz, MSM-d6): δ (ppm) 11.85 (brs, 1H), 7.88 (brs, 1H), 7.09 (d, 1H), 6.44 (d, 1H), 3.70 (m, 1H).
$^{13}$C-NMR (125 MHz, MSM-d6): δ (ppm) 158.7, 147.7, 143.8, 125.1, 108.1, 101.7, 31.8.

Preparation R2c: 7-ethyl-3H,4H,7H-pyrrolo[2,3-d]pyrimidin-4-one

Using General Procedure 1 starting from Preparation R1a and iodoethane as reagents, Preparation R2c was obtained. HRMS calculated for $C_8H_9N_3O$: 163.0746; found 164.0823 [(M+H)$^+$ form].

$^1$H-NMR (500 MHz, MSM-d6): δ (ppm) 11.38 (brs, 1H), 7.87 (d, J=2.0 Hz, 1H), 7.16 (d, J=3.4 Hz, 1H), 6.45 (d, J=3.4 Hz, 1H), 4.14 (q, J=7.1 Hz, 2H), 1.34 (t, J=7.1 Hz, 3H).

Preparation R2d: 7-(propan-2-yl)-3H,4H,7H-pyrrolo[2,3-d]pyrimidin-4-one

Using General Procedure 1 starting from Preparation R1a and 2-iodopropane as reagents, Preparation R2d was obtained. HRMS calculated for $C_9H_{11}N_3O$: 177.0902; found 178.0979 [(M+H)$^+$ form].

$^1$H-NMR (500 MHz, MSM-d6): δ (ppm) 11.83 (brs, 1H), 7.87 (s, 1H), 7.24 (d, 1H), 6.47 (d, 1H), 4.85 (sept., 1H), 1.42 (d, 6H).
$^{13}$C-NMR (125 MHz, MSM-d6): δ (ppm) 158.8, 146.8, 143.5, 120.7, 108.2, 102, 46.5, 23.
$^{15}$N-NMR (50.6 MHz, MSM-d6): δ (ppm) 168.

Preparation R2g: 7-cyclopropyl-3H,4H,7H-pyrrolo[2,3-d]pyrimidin-4-one

Using General Procedure 2 starting from Preparation R1a and cyclopropylboronic acid as reagents, Preparation R2g was obtained. HRMS calculated for $C_9H_9N_3O$: 175.0746; found 176.0819 [(M+H)$^+$ form].

$^1$H-NMR (500 MHz, MSM-d6): δ (ppm) 11.88 (brs, 1H), 7.89 (brs, 1H), 7.05 (d, 1H), 6.4 (d, 1H), 3.53 (m, 1H), 1.06-0.92 (m, 4H).
$^{13}$C-NMR (125 MHz, MSM-d6): δ (ppm) 158.7, 148.9, 143.8, 123.4, 108.8, 101.6, 27.5, 6.6.

Preparation R2h: 7-cyclobutyl-3H,4H,7H-pyrrolo[2,3-d]pyrimidin-4-one

Using General Procedure 1 starting from Preparation R1a and cyclobutyl bromide as reagents, Preparation R2h was obtained. HRMS calculated for $C_{10}H_{11}N_3O$: 189.0902; found 190.0974 [(M+H)$^+$ form].

$^1$H-NMR (500 MHz, MSM-d6): δ (ppm) 11.85 (brs, 1H), 7.88 (brs, 1H), 7.09 (d, 1H), 6.44 (d, 1H), 3.70 (m, 1H).
$^{13}$C-NMR (125 MHz, MSM-d6): δ (ppm) 158.7, 147.7, 143.8, 125.1, 108.1, 101.7, 31.8.

Preparation R2i: 7-cyclopentyl-3H,4H,7H-pyrrolo[2,3-d]pyrimidin-4-one

Using General Procedure 4 starting from Preparation R1a and cyclopentanol as reagents, Preparation R2i was obtained. HRMS calculated for $C_{11}H_{13}N_3O$: 203.1059; found 204.1139 [(M+H)$^+$ form].

$^1$H-NMR (400 MHz, MSM-d6): δ (ppm) 11.84 (brs, 1H), 7.87 (d, 1H), 7.21 (d, 1H), 6.46 (d, 1H), 4.97 (m, 1H), 2.16-1.57 (m, 8H).
$^{13}$C-NMR (100 MHz, MSM-d6): δ (ppm) 143.5, 121.3, 102, 55.6.

Preparation R2j: 7-cyclohexyl-3H,4H,7H-pyrrolo[2,3-d]pyrimidin-4-one

Using General Procedure 4 starting from Preparation R1a and cyclohexanol as reagents, Preparation R2j was obtained. HRMS calculated for $C_{12}H_{15}N_3O$: 217,1215; found 218.1293 [(M+H)$^+$ form].

$^1$H-NMR (400 MHz, MSM-d6): δ (ppm) 11.83 (brs, 1H), 7.86 (d, 1H), 7.23 (d, 1H), 6.46 (d, 1H), 4.45 (m, 1H), 1.97-1.13 (m, 10H).
$^{13}$C-NMR (100 MHz, MSM-d6): δ (ppm) 143.4, 121.1, 101.8, 53.8.

Preparation R2k: 7-(1-methylpiperidin-4-yl)-3H,4H,7H-pyrrolo[2,3-d]pyrimidin-4-one Using General Procedure 4 starting from Preparation R1a and 4-hydroxy-1-methylpiperidine as reagents, Preparation R2k was obtained. HRMS calculated for $C_{12}H_{16}N_4O$: 232.1324; found 233.1405 [(M+H)$^+$ form].

$^1$H-NMR (500 MHz, MSM-d6): δ (ppm) 11.82 (brs, 1H), 7.86 (d, 1H), 7.29 (d, 1H), 6.46 (d, 1H), 4.44 (m, 1H), 2.89/2.05 (m, 4H), 2.22 (s, 3H), 2.02/1.82 (m, 4H).
$^{13}$C-NMR (125 MHz, MSM-d6): δ (ppm) 143.9, 121.2, 102.1, 55.1, 52.1, 46.1, 32.3.

Preparation R2l: 7-(tetrahydro-2H-pyran-4-yl)-3,7-dihydro-4H-pyrrolo[2,3-d]pyrimidin-4-one Using General Procedure 4 starting from Preparation R1a and tetrahydro-4-pyranol as reagents, Preparation R2l was obtained. HRMS calculated for $C_{11}H_{13}N_3O_2$: 219.1008; found 220.1082 [(M+H)$^+$ form].

$^1$H-NMR (400 MHz, MSM-d6): δ (ppm) 11.88 (brs, 1H), 7.88 (d, 1H), 7.29 (d, 1H), 6.48 (d, 1H), 4.71 (m, 1H), 3.98/3.49 (m+m, 4H), 2.05/1.82 (m+m, 4H).
$^{13}$C-NMR (100 MHz, MSM-d6): δ (ppm) 143.5, 121.2, 102, 66.7, 51.3, 33.3.

Preparation R2m: 7-(prop-2-yn-1-yl)-3H,4H,7H-pyrrolo[2,3-d]pyrimidin-4-one

Using General Procedure 1 starting from Preparation R1b (instead of Preparation R1a) and 3-bromoprop-1-yne as reagents (without the hydrolysis step), the crude methoxy-pyrimidine product (400 mg, 2.3 mmol) was dissolved in PDO (4 ml) and aqueous HCl solution (37%, 0.18 ml) was added. The mixture was heated for 100° C. for 30 minutes in a Schlenk tube. After cooling DIPO (4 ml) was added to the reaction mixture, the resulted precipitate was filtered off and dried to give Preparation R2m. HRMS calculated for $C_9H_7N_3O$: 173.0589; found 174.0665 [(M+H)$^+$ form].

$^1$H-NMR (500 MHz, MSM-d6): δ (ppm) 11.98 (brs, 1H), 7.93 (s, 1H), 7.19 (d, 1H), 6.5 (d, 1H), 4.98 (d, 2H), 3.42 (t, 1H).

$^{13}$C-NMR (125 MHz, MSM-d6): δ (ppm) 158.6, 147.3, 144.3, 123.6, 102.5, 79.4, 76, 34.1.

Preparation R2n: 7-(2-methylpropyl)-3H,4H,7H-pyrrolo[2,3-d]pyrimidin-4-one

Using General Procedure 1 starting from Preparation R1a and 1-bromo-2-methylpropane as reagents, Preparation R2n was obtained. HRMS calculated for $C_{10}H_{13}N_3O$: 191.1059; found 192.1132 [(M+H)$^+$ form].

$^1$H-NMR (500 MHz, MSM-d6): δ (ppm) 11.84 (brs, 1H), 7.86 (s, 1H), 7.12 (d, 1H), 6.45 (d, 1H), 3.92 (d, 2H), 2.1 (sept., 1H), 0.82 (d, 6H).

$^{13}$C-NMR (125 MHz, MSM-d6): δ (ppm) 158.8, 147.7, 143.7, 124.5, 108, 101.6, 52, 29.6, 20.2.

Preparation R2o: 7-(2,2,2-trifluoroethyl)-3H,4H,7H-pyrrolo[2,3-d]pyrimidin-4-one Using General Procedure 1 starting from Preparation R1a and 2,2,2-trifluoroethyl trifluoromethanesulfonate as reagents, Preparation R2o was obtained. HRMS calculated for $C_8H_6N_3OF_3$: 217.0463; found 218.0543 [(M+H)$^+$ form].

$^1$H-NMR (500 MHz, MSM-d6): δ (ppm) 12.08 (brs, 1H), 7.97 (s, 1H), 7.19 (d, 1H), 6.57 (d, 1H), 5.06 (q, 2H).

$^{13}$C-NMR (125 MHz, MSM-d6): δ (ppm) 158.5, 148.4, 144.9, 124.7, 124.4, 108.8, 103.2, 45.1.

$^{19}$F-NMR (376.5 MHz, MSM-d6): δ (ppm) −70.3.

Preparation R2p: 7-(2,2-difluoroethyl)-3H,4H,7H-pyrrolo[2,3-d]pyrimidin-4-one

Using General Procedure 1 starting from Preparation R1a and 2-iodo-1,1-difluoroethane as reagents, Preparation R2p was obtained. HRMS calculated for $C_8H_7N_3OF_2$: 199.0557; found 200.0634 [(M+H)$^+$ form].

$^1$H-NMR (400 MHz, MSM-d6) δ ppm 11.99 (brs, 1H), 7.93 (s, 1H), 7.16 (d, 1H), 6.53 (d, 1H), 6.37 (tt, 1H), 4.6 (td, 2H).

$^{13}$C-NMR (400 MHz, MSM-d6) δ ppm 144.4, 124.8, 114.3, 102.5, 46.2.

Preparation R2q: 7-(cyclopropylmethyl)-3H,4H,7H-pyrrolo[2,3-d]pyrimidin-4-one

Using General Procedure 1 starting from Preparation R1a and cyclopropylmethyl bromide as reagents, Preparation R2q was obtained. HRMS calculated for $C_{10}H_{11}N_3O$: 189.0902; found 190.0980 [(M+H)$^+$ form].

$^1$H-NMR (500 MHz, MSM-d6): δ (ppm) 11.84 (s, 1H), 7.87 (s, 1H), 7.2 (d, 1H), 6.45 (d, 1H), 3.97 (d, 2H), 1.21 (m, 1H), 0.52-0.35 (m, 4H).

$^{13}$C-NMR (125 MHz, MSM-d6): δ (ppm) 158.7, 147.3, 143.7, 124, 108.1, 101.7, 49, 12.3, 4.07.

Preparation R2r: 7-(cyclobutylmethyl)-3H,4H,7H-pyrrolo[2,3-d]pyrimidin-4-one

Using General Procedure 1 starting from Preparation R1a and (bromomethyl)cyclobutane as reagents, Preparation R2r was obtained. HRMS calculated for $C_{11}H_{13}N_3O$: 203.1059; found 204.1134 [(M+H)$^+$ form].

$^1$H-NMR (500 MHz, MSM-d6): δ (ppm) 11.83 (brs, 1H), 7.87 (d, 1H), 7.12 (d, 1H), 6.43 (d, 1H), 4.13 (d, 2H), 2.72 (m, 1H), 1.92/1.74 (m+m, 4H), 1.82 (m, 2H).

$^{13}$C-NMR (125 MHz, MSM-d6): δ (ppm) 143.7, 124.2, 101.7, 49.6, 36, 25.6, 18.

Preparation R2s: 7-(buta-2,3-dien-1-yl)-3H,4H,7H-pyrrolo[2,3-d]pyrimidin-4-one

Using General Procedure 1 starting from Preparation R1b (instead of Preparation R1a) and 4-bromobuta-1,2-diene as reagents (without the hydrolysis step), the crude methoxypyrimidine product (300 mg, 1.65 mmol) was dissolved in PDO (4 ml) and aqueous HCl solution (37%, 0.18 ml) was added. The mixture was heated for 100° C. for 30 minutes in a Schlenk tube. After cooling, the reaction mixture was evaporated to give Preparation R2s. HRMS calculated for $C_{10}H_9N_3O$: 187.0745; found 188.0821 [(M+H)$^+$ form].

$^1$H-NMR (500 MHz, MSM-d6): δ (ppm) 11.91 (brs, 1H), 7.89 (s, 1H), 7.12 (d, 1H), 6.46 (d, 1H), 5.48 (m, 1H), 4.87 (m, 2H), 4.73 (m, 2H).

$^{13}$C-NMR (125 MHz, MSM-d6): δ (ppm) 208.3, 158.7, 147.4, 143.9, 123.9, 108.2, 102.1, 88.3, 78.1, 43.

Preparation R2t: 7-[3-(dimethylamino)propyl]-3H, 4H,7H-pyrrolo[2,3-d]pyrimidin-4-one Using General Procedure 1 starting from Preparation R1a and 3-dimethylaminopropyl chloride hydrochloride as reagents, Preparation R2t was obtained. HRMS calculated for $Cl_1H_{16}N_4O$: 220.1324; found 221.1401 [(M+H)$^+$ form].

$^1$H-NMR (500 MHz, MSM-d6): δ (ppm) 11.84 (brs, 1H), 7.88 (s, 1H), 7.13 (d, 1H), 6.44 (d, 1H), 4.12 (t, 2H), 2.15 (t, 2H), 2.1 (s, 6H), 1.85 (quint, 2H).

$^{13}$C-NMR (125 MHz, MSM-d6): δ (ppm) 158.8, 147.4, 143.8, 124.2, 108.2, 101.7, 56.4, 45.6, 43, 28.6.

Preparation R2u: 7-(2-fluoroethyl)-3H,4H,7H-pyrrolo[2,3-d]pyrimidin-4-one

Using General Procedure 1 starting from Preparation R1a and 1-fluoro-2-iodoethane as reagents, Preparation R2u was obtained. HRMS calculated for $C_8H_8NOF$: 181.0651; found 182.0728 [(M+H)$^+$ form].

$^1$H-NMR (400 MHz, MSM-d6) δ ppm 11.91 (brs, 1H), 7.9 (s, 1H), 7.17 (d, 1H), 6.49 (d, 1H), 4.74 (dt, 2H), 4.43 (dt, 2H).

$^{13}$C-NMR (100 MHz, MSM-d6) δ ppm 144, 124.3, 102, 83.1, 45.1.

Preparation R2v: 7-[2-(dimethylamino)ethyl]-3H, 4H,7H-pyrrolo[2,3-d]pyrimidin-4-one Using General Procedure 1 starting from Preparation R1a and 2-bromo-N,N-dimethylethylamine hydrobromide as reagents, Preparation R2v was obtained. HRMS calculated for $C_{10}H_{14}N_4O$: 206.1168; found 207.1242 [(M+H)$^+$ form].

$^1$H-NMR (500 MHz, MSM-d6): δ (ppm) 11.84 (brs, 1H), 7.88 (brd, 1H), 7.16 (d, 1H), 6.44 (d, 1H), 4.19 (t, 2H), 2.6 (t, 2H), 2.16 (s, 6H).

$^{13}$C-NMR (125 MHz, MSM-d6): δ (ppm) 158.7, 147.5, 143.7, 124.4, 108.1, 101.7, 59.2, 45.5, 42.6.

Preparation R2w: 7-(2-hydroxyethyl)-3H,4H,7H-pyrrolo[2,3-d]pyrimidin-4-one

Using General Procedure 1 starting from Preparation R1a and 2-chloroethanol as reagents, Preparation R2w was obtained. ¹H-NMR (400 MHz, MSM-d6): δ (ppm) 11.83 (brs, 1H), 7.86 (d, J=2.4 Hz, 1H), 7.12 (d, J=3.92 Hz, 1H), 6.43 (d, J=3.14 Hz, 1H), 4.92 (t, J=5.49 Hz, 1H), 4.15 (t, J=6.28 Hz, 2H), 3.68 (q, J=5.49 Hz, 2H).

Preparation R2x: 7-[(4-chlorophenyl)methyl]-3H, 4H,7H-pyrrolo[2,3-d]pyrimidin-4-one Using General Procedure 1 starting from Preparation R1a and 4-chlorobenzyl bromide as reagents, Preparation R2x was obtained. HRMS calculated for $C_{13}H_{10}ClN_3O$: 259.0512; found 260.0583 [(M+H)⁺ form].
¹H-NMR (400 MHz, MSM-d6): δ (ppm) 11.93 (s, 7.9 (s, 1H), 7.39 (m, 2H), 7.23 (m, 2H), 7.22 (d, 1H), 6.51 (d, 1H), 5.34 (s, 2H).
¹³C-NMR (100 MHz, MSM-d6): δ (ppm) 158.7, 147.4, 144.2, 137.5, 132.5, 129.5, 129, 124.2, 108.3, 102.4, 47.5.

Preparation R2y: 7-[(3-chlorophenyl)methyl]-3H, 4H,7H-pyrrolo[2,3-d]pyrimidin-4-one Using General Procedure 1 starting from Preparation R1a and 3-chlorobenzyl bromide as reagents, Preparation R2y was obtained. HRMS calculated for $C_{13}H_{10}ClN_3O$: 259.0512; found 260.0580 [(M+H)⁺ form].
¹H-NMR (500 MHz, MSM-d6): δ (ppm) 11.94 (brs, 1H), 7.92 (d, 1H), 7.35 (m, 1H), 7.35 (m, 1H), 7.28 (t, 1H), 7.25 (d, 1H), 7.16 (dm, 1H), 6.51 (d, 1H), 5.35 (s, 2H).
¹³C-NMR (125 MHz, MSM-d6): δ (ppm) 158.7, 147.6, 144.3, 140.9, 133.6, 131.1, 128, 127.5, 126.4, 124.3, 108.4, 102.4, 47.5.

Preparation R2z: 7-benzyl-3H,4H,7H-pyrrolo[2,3-d]pyrimidin-4-one

Using General Procedure 1 starting from Preparation R1a and benzyl bromide as reagents, Preparation R2z was obtained. HRMS calculated for $C_{13}H_{11}N_3O$: 225.0902; found 226.0986 [(M+H)⁺ form].
¹H-NMR (400 MHz, MSM-d6): δ (ppm) 11.91 (brs, 1H), 7.91 (s, 1H), 7.36-7.17 (m, 5H), 7.2 (d, 1H), 6.49 (d, 1H), 5.34 (s, 2H).
¹³C-NMR (100 MHz, MSM-d6): δ (ppm) 144.1, 124.3, 102.2, 48.1.

Preparation R2aa: 7-[(2-chlorophenyl)methyl]-3H, 4H,7H-pyrrolo[2,3-d]pyrimidin-4-one Using General Procedure 1 starting from Preparation R1a and 2-chlorobenzyl bromide as reagents, Preparation R2aa was obtained. HRMS calculated for $C_{13}H_{10}ClN_3O$: 2590512; found 260.0587 [(M+H)⁺ form].
¹H-NMR (400 MHz, MSM-d6): δ (ppm) 11.95 (brs, 1H), 7.89 (d, 1H), 7.5 (dm, 1H), 7.32 (m, 1H), 7.26 (m, 1H), 7.17 (d, 1H), 6.72 (dm, 1H), 6.55 (d, 1H), 5.44 (s, 2H).
¹³C-NMR (100 MHz, MSM-d6): δ (ppm) 144.3, 129.8, 129.8, 128.8, 128.1, 124.5, 102.5, 46.

Preparation R2ab: 7-(2-oxopyrrolidin-1-yl)-3,7-dihydro-4H-pyrrolo[2,3-d]pyrimidin-4-one Preparation R1b (1.74 g, 11.67 mmol) was dissolved in DMF (80 ml) and cooled to 0° C., sodium hydride (60% disp., 1.87 g, 46.67 mmol) was slowly added and stirred for 30 minutes at 0° C. Hydroxylamine-O-sulfonic acid (2.11 g, 18.67 mmol) was added to the reaction mixture and allowed to warm up to r.t. and stirred for 20 hours. Water (100 ml) was added to the reaction mixture and extracted with DCM (4×50 ml). The combined organic layer was washed with water and dried over $MgSO_4$ and evaporated. The residue was dissolved in MSM and purified by preparative LC (on C-18 Gemini-NX 5 μm column, 5 mM aqueous $NH_4HCO_3$-MeCN, gradient).

A part of the resulted N-amine compound (500 mg, 3.05 mmol) was dissolved in DCM (20 ml) and TEA (850 μl, 6.09 mmol, 2 eq.) and 4-chlorobutyryl chloride was (409 μl, 515 mg, 3.65 mmol, 1.2 eq.) added dropwise and stirred for 20 hours at r.t. Then the reaction mixture was evaporated, sat. $NaHCO_3$ solution (5 ml, aq.), MeCN (20 ml) and water (20 ml) were added to the residue and the mixture was stirred for 3 hours at 80° C. The reaction mixture was evaporated and water (50 ml) was added. The solution was extracted with DCM (3×10 ml) and the combined organic layers were evaporated. The residue was purified by preparative LC (on C-18 Gemini-NX 5 μm column, 5 mM aqueous $NH_4HCO_3$-MeCN, gradient).

The resulted pyrrolidone (200 mg, 0.862 mmol) was dissolved in HCl solution (4 ml, 1 N, aq.) and PDO (80 ml) and stirred at 60° C. for 6 hours. The reaction mixture was evaporated and the residue was purified by preparative LC (on C-18 Gemini-NX 5 μm column, 5 mM aqueous $NH_4HCO_3$-MeCN, gradient) gave Preparation R2ab. HRMS calculated for $C_{10}H_{10}N_4O_2$: 218.0804; found 219.0883 [(M+H)⁺ form].
¹H-NMR (500 MHz, MSM-d6): δ (ppm) 12.11 (brs, 1H), 7.91 (s, 1H), 7.2 (d, 1H), 6.53 (d, 1H), 3.77 (t, 2H), 2.47 (t, 2H), 2.17 (quint., 2H).
¹³C-NMR (125 MHz, MSM-d6): δ (ppm) 173.7, 158.4, 146.6, 145.2, 124.2, 107, 101.3, 49.8, 28.4, 16.9.

Preparation R2ac: 7-(3,4,5-trimethoxyphenyl)-3H, 4H,7H-pyrrolo[2,3-d]pyrimidin-4-one Using General Procedure 3 starting from Preparation R1b and 5-iodo-1,2,3-trimethoxybenzene as reagents, Preparation R2ac was obtained. HRMS calculated for $C_{15}H_{15}N_3O_4$: 301.1063; found 302.1138 [(M+H)⁺ form].
¹H-NMR (500 MHz, MSM-d6): δ (ppm) 12.07 (brs, 1H), 7.95 (d, 1H), 7.49 (d, 1H), 6.99 (s, 2H), 6.66 (d, 1H), 3.82 (s, 6H), 3.7 (s, 3H).
¹³C-NMR (125 MHz, MSM-d6): δ (ppm) 144.5, 124.6, 103.2, 103, 60.6, 56.6.

Preparation R2ad: 7-(3,5-dichlorophenyl)-3H,4H, 7H-pyrrolo[2,3-d]pyrimidin-4-one Using General Procedure 2 starting from Preparation R1a and 3,5-dichlorophenylboronic acid as reagents, Preparation R2ad was obtained. HRMS calculated for $C_{12}H_7Cl_2N_3O$: 278.9966; found 280.0040 [(M+H)⁺ form].
¹H-NMR (500 MHz, MSM-d6): δ (ppm) 12.03 (vbrs, 1H), 8.03 (s, 1H), 7.95 (d, 2H), 7.64 (t, 1H), 7.63 (d, 1H), 6.71 (d, 1H).
¹³C-NMR (125 MHz, MSM-d6): δ (ppm) 145.3, 126.7, 123.8, 122.7, 104.4.

Preparation R2ae: 7-(3-chloro-5-methoxyphenyl)-3H,4H,7H-pyrrolo[2,3-d]pyrimidin-4-one Using General Procedure 2 starting from Preparation R1a and 3-chloro-5-methoxyphenylboronic acid as reagents, Preparation R2ae was obtained. HRMS calculated for $C_{13}H_{10}ClN_3O_2$: 275.0461; found 276.0541 [(M+H)⁺ form].

¹H-NMR (400 MHz, MSM-d6): δ (ppm) 12.18 (s, 1H), 8 (d, 1H), 7.6 (d, 1H), 7.51 (t, 1H), 7.33 (t, 1H), 7.08 (t, 1H), 6.69 (d, 1H), 3.85 (s, 3H).
¹³C-NMR (100 MHz, MSM-d6): δ (ppm) 161, 158.7, 147.5, 145, 139.7, 134.5, 124, 116.3, 112.7, 110.2, 109.4, 104, 56.4

Preparation R2af: 7-(3,5-dimethoxyphenyl)-3H,4H, 7H-pyrrolo[2,3-d]pyrimidin-4-one Using General Procedure 2 starting from Preparation R1a and 2-(3,5-dimethoxy)-phenyl-4,4,5,5-tetramethyl-(1,3,2)-dioxaborolane as reagents, Preparation R2af was obtained. HRMS calculated for $C_{14}H_{13}N_3O_3$: 271.0957; found 272.1030 [(M+H)⁺ form].
¹H-NMR (500 MHz, MSM-d6): δ (ppm) 12.11 (s, 1H), 7.95 (d, 1H), 7.52 (d, 1H), 6.91 (d, 2H), 6.66 (d, 1H), 6.54 (t, 1H), 3.8 (s, 6H).
¹³C-NMR (125 MHz, MSM-d6): δ (ppm) 144.5, 124.2, 103.5, 103.1, 98.9.

Preparation R2ag: 7-(3,4-dichlorophenyl)-3H,4H, 7H-pyrrolo[2,3-d]pyrimidin-4-one Using General Procedure 3 starting from Preparation R1b and 3,4-dichlorophenylboronic acid as reagents, Preparation R2ag was obtained. HRMS calculated for $C_{12}H_7Cl_2N_3O$: 278.9966; found 280.003 [(M+H)⁺ form].
¹H-NMR (500 MHz, MSM-d6): δ (ppm) 12.21 (brs, 1H), 8.15 (t, 1H), 8.02 (brs, 1H), 7.82 (d, 1H), 7.82 (d, 1H), 7.61 (d, 1H), 6.72 (d, 1H).
¹³C-NMR (125 MHz, MSM-d6): δ (ppm) 145.1, 131.5, 125.9, 124.3, 123.8, 104.2.

Preparation R2ah: 7-(4-chloro-3-fluorophenyl)-3,7-dihydro-4H-pyrrolo[2,3-d]pyrimidin-4-one Using General Procedure 3 starting from Preparation R1b and 4-chloro-3-fluoroiodobenzene as reagents, Preparation R2ah was obtained. HRMS calculated for $C_{12}H_7ClFN_3O$: 263.0262; found 264.0339 [(M+H)⁺ form].
¹H-NMR (500 MHz, MSM-d6): δ (ppm) 12.21 (s, 1H), 8.02 (d, 1H), 7.97 (dd, 1H), 7.77 (dd, 1H), 7.72 (dd, 1H), 7.6 (d, 1H), 6.72 (d, 1H).
¹³C-NMR (125 MHz, MSM-d6): δ (ppm) 145.1, 131.5, 123.7, 121.5, 112.8, 104.2.

Preparation R2ai: 7-(4-chloro-3-methoxyphenyl)-3H,4H,7H-pyrrolo[2,3-d]pyrimidin-4-one Using General Procedure 3 starting from Preparation R1b and 2-chloro-5-iodoanisole as reagents, Preparation R2ai was obtained. HRMS calculated for $C_{13}H_{10}ClN_3O_2$: 275.0461; found 276.0537 [(M+H)⁺ form].
¹H-NMR (500 MHz, MSM-d6): δ (ppm) 12.15 (brs, 1H), 7.98 (brs, 1H), 7.58 (d, 1H), 7.57 (d, 1H), 7.49 (d, 1H), 7.36 (dd, 1H), 6.7 (d, 1H), 3.93 (s, 3H).
¹³C-NMR (125 MHz, MSM-d6): δ (ppm) 158.7, 155.3, 147.4, 144.8, 137.7, 130.5, 124.2, 119.8, 117.3, 110, 109.4, 103.7, 56.9.

Preparation R2aj: 7-(4-fluoro-3-methoxyphenyl)-3H,4H,7H-pyrrolo[2,3-d]pyrimidin-4-one Using General Procedure 3 starting from Preparation R1b and 1-fluoro-4-iodo-2-methoxybenzene as reagents, Preparation R2aj was obtained. HRMS calculated for $C_{13}H_{10}N_3O_2F$: 259.0757; found 260.0818 [(M+H)⁺ form].
¹H-NMR (500 MHz, MSM-d6): δ (ppm) 12.1 (s, 1H), 7.95 (s, 1H), 7.51 (d, 1H), 7.48 (dd, 1H), 7.38 (dd, 1H), 7.27 (ddd, 1H), 6.68 (d, 1H), 3.9 (s, 3H).
¹³C-NMR (125 MHz, MSM-d6): δ (ppm) 144.7, 124.5, 117, 116.5, 111, 103.4, 56.8.

Preparation R2ak: 7-(3,4-dimethoxyphenyl)-3H,4H, 7H-pyrrolo[2,3-d]pyrimidin-4-one Using General Procedure 3 starting from Preparation R1b and 3,4-dimethoxyphenylboronic acid pinacol ester as reagents, Preparation R2ak was obtained. HRMS calculated for $C_{14}H_{13}N_3O_3$: 271.0957; found 272.103 [(M+H)⁺ form].
¹H-NMR (500 MHz, MSM-d6): δ (ppm) 7.92 (d, 1H), 7.43 (d, 1H), 7.25 (d, 1H), 7.19 (dd, 1H), 7.08 (d, 1H), 6.65 (d, 1H), 3.8 (s, 6H).
¹³C-NMR (125 MHz, MSM-d6): δ (ppm) 144.5, 124.6, 116.9, 112.2, 109.3, 103.1, 56.3.

Preparation R2am: 7-(4-methylphenyl)-3H,4H,7H-pyrrolo[2,3-d]pyrimidin-4-one

Using General Procedure 3 starting from Preparation R1b and 4-iodotoluene as reagents, Preparation R2am was obtained. HRMS calculated for $C_{13}H_{11}N_3O$: 225.0902; found 226.0987 [(M+H)⁺ form].
¹H-NMR (500 MHz, MSM-d6): δ (ppm) 12.06 (brs, 1H), 7.93 (s, 1H), 7.58 (dm, 1H), 7.44 (d, 1H), 7.33 (dm, 1H), 6.66 (d, 1H), 2.37 (s, 3H).
¹³C-NMR (125 MHz, MSM-d6): δ (ppm) 158.8, 147.3, 144.5, 136.8, 135.4, 130.1, 124.5, 124.1, 109.6, 103.4, 21.

Preparation R2an: 4-{4-oxo-3H,4H,7H-pyrrolo[2,3-d]pyrimidin-7-yl}benzonitrile

Using General Procedure 3 starting from Preparation R1b and 4-iodobenzonitrile as reagents, Preparation R2an was obtained. HRMS calculated for $C_{13}H_8N_4O$: 236.0698; found 237.0775 [(M+H)⁺ form].
¹H-NMR (500 MHz, MSM-d6): δ (ppm) 12.25 (brs, 1H), 8.05 (m, 2H), 8.03 (m, 2H), 8.02 (brs, 1H), 7.66 (d, 1H), 6.75 (d, 1H).
¹³C-NMR (125 MHz, MSM-d6): δ (ppm) 147.6, 145.2, 141.5, 134, 124.6, 123.6, 119, 110.6, 109.4, 104.7.

Preparation R2ao: 7-[4-(trifluoromethyl)phenyl]-3H, 4H,7H-pyrrolo[2,3-d]pyrimidin-4-one Using General Procedure 3 starting from Preparation R1b and 4-iodobenzotrifluoride as reagents, Preparation R2ao was obtained. HRMS calculated for $C_{13}H_8F_3N_3O$: 279.0619; found 280.0691 [(M+H) form].
¹H-NMR (500 MHz, MSM-d6): δ (ppm) 12.23 (brs, 1H), 8.02 (m, 2H), 8.01 (d, 1H), 7.92 (m, 2H), 7.63 (d, 1H), 6.74 (d, 1H).
¹³C-NMR (125 MHz, MSM-d6): δ (ppm) 158.7, 147.6, 145.1, 126.9, 124.7, 123.8, 110.4, 104.5 ¹⁵N-NMR (50.6 MHz, MSM-d6): δ (ppm) 170.9.

Preparation R2ap: 7-[4-(difluoromethyl)phenyl]-3H, 4H,7H-pyrrolo[2,3-d]pyrimidin-4-one Using General Procedure 3 starting from Preparation R1b and 1-(difluoromethyl)-4-iodobenzene as reagents, Preparation R2ap was obtained. HRMS calculated for $C_{13}H_9F_2N_3O$: 261.0714; found 262.0784 [(M+H)$^+$ form].
$^1$H-NMR (500 MHz, MSM-d6): δ (ppm) 12.17 (brs, 1H), 7.99 (d, 1H), 7.91 (m, 2H), 7.75 (m, 2H), 7.58 (d, 1H), 7.12 (t, 1H), 6.72 (d, 1H).
$^{13}$C-NMR (125 MHz, MSM-d6): δ (ppm) 144.9, 127.2, 124.7, 123.9, 115.1, 104.1.

Preparation R2aq: 7-[4-(hydroxymethyl)phenyl]-3H,4H,7H-pyrrolo[2,3-d]pyrimidin-4-one Using General Procedure 3 starting from Preparation R1b and 4-iodobenzyl alcohol as reagents, Preparation R2aq was obtained. HRMS calculated for $C_{13}H_{11}N_3O_2$: 241.0851; found 242.0925 [(M+H)$^+$ form].
$^1$H-NMR (500 MHz, MSM-d6): δ (ppm) 12.07 (brs, 1H), 7.94 (s, 1H), 7.66 (m, 2H), 7.47 (m, 2H), 7.45 (d, 1H), 6.67 (d, 1H), 5.31 (t, 1H), 4.56 (d, 2H).
$^{13}$C-NMR (125 MHz, MSM-d6): δ (ppm) 158.9, 147.4, 144.6, 142.2, 136.6, 127.6, 124.3, 124.2, 109.9, 103.5, 62.8.

Preparation R2ar: 7-(4-chlorophenyl)-3H,4H,7H-pyrrolo[2,3-d]pyrimidin-4-one

Using General Procedure 3 starting from Preparation R1b and 1-chloro-4-iodobenzene as reagents, Preparation R2ar was obtained. HRMS calculated for $C_{12}H_8ClN_3O$: 245.0356; found 246.0427 [(M+H)$^+$ form].
$^1$H-NMR (500 MHz, MSM-d6): δ (ppm) 12.15 (brs, 1H), 7.97 (d, 1H), 7.78 (dm, 1H), 7.61 (dm, 1H), 7.53 (d, 1H), 6.7 (d, 1H).
$^{13}$C-NMR (125 MHz, MSM-d6): δ (ppm) 158.7, 147.3, 144.8, 136.7, 131.7, 129.6, 126.1, 123.9, 109.9, 103.9.

Preparation R2as: 7-(4-fluorophenyl)-3H,4H,7H-pyrrolo[2,3-d]pyrimidin-4-one

Using General Procedure 3 starting from Preparation R1b and 4-fluoroiodobenzene as reagents, Preparation R2as was obtained. HRMS calculated for $Cl_2H_8FN_3O$: 229.0651; found 230.0714 [(M+H)$^+$ form].
$^1$H-NMR (500 MHz, MSM-d6): δ (ppm) 12.12 (brs, 1H), 7.95 (d, 1H), 7.74 (m, 2H), 7.48 (d, 1H), 7.39 (m, 2H), 6.68 (d, 1H).
$^{13}$C-NMR (125 MHz, MSM-d6): δ (ppm) 144.7, 126.8, 124.2, 116.4, 103.5.

Preparation R2at: 7-[4-(dimethylamino)phenyl]-3H,4H,7H-pyrrolo[2,3-d]pyrimidin-4-one Using General Procedure 2 starting from Preparation R1a and 4-(dimethylamino)phenylboronic acid as reagents, Preparation R2at was obtained. HRMS calculated for $C_{14}H_{14}N_4O$: 254.1168; found 255.1243 [(M+H)$^+$ form].
$^1$H-NMR (400 MHz, MSM-d6): δ (ppm) 11.98 (brs, 1H), 7.89 (d, 1H), 7.43 (m, 2H), 7.33 (d, 1H), 6.82 (m, 2H), 6.61 (d, 1H), 2.94 (s, 6H).
$^{13}$C-NMR (100 MHz, MSM-d6): δ (ppm) 144.1, 125.6, 124.3, 112.7, 102.7, 40.6.

Preparation R2au: 7-[4-(4-methylpiperazin-1-yl)phenyl]-3H,4H,7H-pyrrolo[2,3-d]pyrimidin-4-one Using General Procedure 2 starting from Preparation R1a and 4-(4-methylpiperazin-1-yl)phenylboronic acid pinacol ester as reagents, Preparation R2au was obtained. HRMS calculated for $C_{17}H_{19}N_5O$: 309.1590; found 310.1674 [(M+H)$^+$ form].
$^1$H-NMR (400 MHz, MSM-d6): δ (ppm) 12.01 (brs, 1H), 7.9 (d, 1H), 7.49 (m, 2H), 7.37 (d, 1H), 7.06 (m, 2H), 6.63 (d, 1H), 3.2 (brm, 4H), 2.51 (brm, 4H), 2.27 (s, 3H).
$^{13}$C-NMR (100 MHz, MSM-d6): δ (ppm) 144.3, 125.4, 124.2, 115.9, 102.9, 54.8, 48.3, 45.9.

Preparation R2av: 7-[4-(morpholin-4-yl)phenyl]-3H,4H,7H-pyrrolo[2,3-d]pyrimidin-4-one Using General Procedure 2 starting from Preparation R1a and 4-morpholinophenylboronic acid as reagents, Preparation R2av was obtained. HRMS calculated for $C_{16}H_{16}N_4O_2$: 296.1273; found 297.1361 [(M+H)$^+$ form].
$^1$H-NMR (400 MHz, MSM-d6): δ (ppm) 12.01 (brs, 1H), 7.9 (s, 1H), 7.51 (m, 2H), 7.38 (d, 1H), 7.07 (m, 2H), 6.63 (d, 1H), 3.76 (m, 4H), 3.16 (m, 4H).
$^{13}$C-NMR (100 MHz, MSM-d6): δ (ppm) 484.8, 144.3, 125.4, 124.2, 115.7, 103, 66.5.

Preparation R2ax: 7-(4-methoxyphenyl)-3H,4H,7H-pyrrolo[2,3-d]pyrimidin-4-one

Using General Procedure 3 starting from Preparation R1b and 4-iodoanisole as reagents, Preparation R2ax was obtained. HRMS calculated for $C_{13}H_{11}N_3O_2$: 241.0851; found 242.0929 [(M+H)$^+$ form].
$^1$H-NMR (500 MHz, MSM-d6): δ (ppm) 12.04 (brs, 1H), 7.92 (d, 1H), 7.58 (dd, 1H), 7.4 (d, 1H), 7.08 (d, 1H), 6.65 (d, 1H), 3.81 (s, 3H).
$^{13}$C-NMR (125 MHz, MSM-d6): δ (ppm) 158.8, 158.8, 147.3, 144.4, 130.9, 126.1, 124.4, 114.8, 109.4, 103.1, 55.9.

Preparation R2ay: 7-[4-(trifluoromethoxy)phenyl]-3H,4H,7H-pyrrolo[2,3-d]pyrimidin-4-one Using General Procedure 3 starting from Preparation R1b and 1-iodo-4-(trifluoromethoxy)benzene as reagents, Preparation R2ay was obtained. HRMS calculated for $C_{13}H_8F_3N_3O_2$: 295.0569; found 296.0648 [(M+H)$^+$ form].
$^1$H-NMR (500 MHz, MSM-d6): δ (ppm) 12.15 (s, 1H), 7.97 (d, 1H), 7.86 (m, 2H), 7.56 (m, 2H), 7.54 (m, 1H), 6.71 (d, 1H).
$^{13}$C-NMR (125 MHz, MSM-d6): δ (ppm) 144.8, 126.4, 124.1, 122.5, 103.9.

Preparation R2az: 7-[4-(benzyloxy)phenyl]-3H,4H,7H-pyrrolo[2,3-d]pyrimidin-4-one Using General Procedure 3 starting from Preparation R1b and 4-benzyloxyiodobenzene as reagents, Preparation R2az was obtained. HRMS calculated for $C_{19}H_{15}N_3O_2$: 317.1164; found 318.1243 [(M+H)$^+$ form].
$^1$H-NMR (500 MHz, MSM-d6): δ (ppm) 12.05 (brs, 1H), 7.92 (d, 1H), 7.59 (dm, 2H), 7.48 (dm, 2H), 7.41 (d, 1H), 7.41 (tm, 2H), 7.35 (tm, 1H), 7.16 (dm, 2H), 6.65 (d, 1H), 5.18 (s, 2H).
$^{13}$C-NMR (125 MHz, MSM-d6): δ (ppm) 158.8, 157.6, 147.3, 144.4, 137.4, 131, 129, 128.4, 128.2, 126.1, 124.3, 115.7, 109.4, 103.1, 69.9.

Preparation R2ba: 7-(5-methylthiophen-2-yl)-3H,4H,7H-pyrrolo[2,3-d]pyrimidin-4-one Using General Procedure 3 starting from Preparation R1b and 2-iodo-5-methylthiophene as reagents, Preparation R2ba was obtained. HRMS calculated for $C_{11}H_9N_3OS$: 231.0466; found 232.0541 [(M+H)$^+$ form].
$^1$H-NMR (400 MHz, MSM-d6): δ (ppm) 12.17 (brs, 1H), 7.99 (d, 1H), 7.49 (d, 1H), 7.14 (d, 1H), 6.76 (dq, 1H), 6.67 (d, 1H), 2.46 (d, 3H).
$^{13}$C-NMR (100 MHz, MSM-d6): δ (ppm) 145, 124.2, 123.9, 119.4, 103.9, 15.4.

Preparation R2bb: 7-(5-chlorothiophen-2-yl)-3H,4H, 7H-pyrrolo[2,3-d]pyrimidin-4-one Using General Procedure 3 starting from Preparation R1b and 2-chloro-5-iodothiophene as reagents, Preparation R2bb was obtained. HRMS calculated for $C_{10}H_6N_3OSCl$: 250.9920; found 252.0005 [(M+H)$^+$ form].
$^1$H-NMR (500 MHz, MSM-d6) δ ppm 12.28 (brs, 1H), 8.07 (d, 1H), 7.67 (d, 1H), 7.3 (d, 1H), 7.13 (d, 1H), 6.72 (d, 1H)
$^{13}$C-NMR (125 MHz, MSM-d6) δ ppm 158.4, 146.8, 145.6, 136.4, 125.5, 124.6, 123.3, 117.5, 109.3, 104.6

Preparation R2bc: 7-(2,3-dihydro-1,4-benzodioxin-6-yl)-3,7-dihydro-4H-pyrrolo[2,3-d]pyrimidin-4-one Using General Procedure 2 starting from Preparation R1a and 1,4-benzodioxane-6-boronic acid as reagents, Preparation R2bc was obtained. HRMS calculated for $C_{14}H_{11}N_3O_3$: 269.0800; found 270.0881 [(M+H)$^+$ form].
$^1$H-NMR (500 MHz, MSM-d6): δ (ppm) 12.05 (brs, 1H), 7.92 (d, 1H), 7.4 (d, 1H), 7.22 (d, 1H), 7.13 (dd, 1H), 6.99 (d, 1H), 6.63 (d, 1H), 4.33-4.25 (m, 4H).
$^{13}$C-NMR (125 MHz, MSM-d6): δ (ppm) 144.4, 124.3, 117.7, 117.6, 113.8, 103.2.

Preparation R2bd: 7-(2H-1,3-benzodioxol-5-yl)-3H, 4H,7H-pyrrolo[2,3-d]pyrimidin-4-one Using General Procedure 2 starting from Preparation R1a and 3,4-methylenedioxyphenylboronic acid as reagents, Preparation R2bd was obtained. HRMS calculated for $C_{13}H_9N_3O_3$: 255.0644; found 256.0719 [(M+H)$^+$ form].
$^1$H-NMR (500 MHz, MSM-d6): δ (ppm) 12.05 (brs, 1H), 7.92 (d, 1H), 7.4 (d, 1H), 7.29 (d, 1H), 7.12 (dd, 1H), 7.05 (d, 1H), 6.63 (d, 1H), 6.11 (s, 2H).
$^{13}$C-NMR (125 MHz, MSM-d6): δ (ppm) 144.5, 124.5, 118.2, 108.7, 106.5, 103.1, 102.2.

Preparation R2be: 7-(naphthalen-2-yl)-3H,4H,7H-pyrrolo[2,3-d]pyrimidin-4-one

Using General Procedure 2 starting from Preparation R1a and 2-naphthaleneboronic acid as reagents, Preparation R2be was obtained. HRMS calculated for $C_{16}H_{11}N_3O$: 261.0902; found 262.0982 [(M+H)$^+$ form].
$^1$H-NMR (500 MHz, MSM-d6): δ (ppm) 12.14 (s, 1H), 8.25 (d, 1H), 8.09 (d, 1H), 8.01 (m, 1H), 8.01 (m, 1H), 8 (s, 1H), 7.91 (dd, 1H), 7.63 (d, 1H), 7.6 (tm, 1H), 7.57 (tm, 1H), 6.74 (d, 1H).
$^{13}$C-NMR (125 MHz, MSM-d6): δ (ppm) 158.8, 147.6, 144.8, 135.4, 133.4, 132, 129.4, 128.4, 128.2, 127.4, 126.9, 124.4, 123.5, 122.3, 109.9, 103.8.

Preparation R2bf: 7-(3-methylphenyl)-3H,4H,7H-pyrrolo[2,3-d]pyrimidin-4-one

Using General Procedure 3 starting from Preparation R1b and 3-iodotoluene as reagents, Preparation R2bf was obtained. HRMS calculated for $C_{13}H_{11}N_3O$: 225.0902; found 226.098 [(M+H)$^+$ form].
$^1$H-NMR (500 MHz, MSM-d6): δ (ppm) 12.08 (brs, 1H), 7.95 (d, 1H), 7.52 (brs, 1H), 7.49 (dm, 1H), 7.46 (d, 1H), 7.41 (t, 1H), 7.22 (brd, 1H), 6.67 (d, 1H), 2.39 (s, 3H).
$^{13}$C-NMR (125 MHz, MSM-d6): δ (ppm) 158.8, 147.3, 144.6, 139.2, 137.8, 129.5, 128.1, 125.2, 124.2, 121.8, 109.7, 103.5, 21.4.

Preparation R2bg: 7-[3-(trifluoromethyl)phenyl]-3H,4H,7H-pyrrolo[2,3-d]pyrimidin-4-one Using General Procedure 3 starting from Preparation R1b and 3-iodobenzotrifluoride as reagents, Preparation R2bg was obtained. HRMS calculated for $C_{13}H_8F_3N_3O$: 279.0620; found 280.0699 [(M+H)$^+$ form].
$^1$H-NMR (500 MHz, MSM-d6): δ (ppm) 12.19 (brs, 1H), 8.18 (brs, 1H), 8.07 (dm, 1H), 8.02 (d, 1H), 7.79 (t, 1H), 7.77 (dm, 1H), 7.65 (d, 1H), 6.73 (d, 1H).
$^{13}$C-NMR (125 MHz, MSM-d6): δ (ppm) 145.1, 131.1, 128.3, 124, 123.9, 121, 104.1.

Preparation R2bh: 7-{3-[(4-methylpiperazin-1-yl)methyl]phenyl}-3H,4H,7H-pyrrolo[2,3-d]pyrimidin-4-one Using General Procedure 3 starting from Preparation R1b and 3-(4-methyl-1-piperazinylmethyl)benzeneboronic acid pinacol ester as reagents, Preparation R2bh was obtained. HRMS calculated for $C_{18}H_{21}N_5O$: 323.1746; found 324.1828 [(M+H)$^+$ form].
$^1$H-NMR (500 MHz, MSM-d6): δ (ppm) 12.37/12.2/ 11.95 (brs, 3H), 8.04 (brs, 1H), 7.98 (s, 1H), 7.91 (dm, 1H), 7.67 (dm, 1H), 7.63 (d, 1H), 7.62 (t, 1H), 6.72 (d, 1H), 4.49 (brs, 2H), 3.8-3.3 (brm, 8H), 2.8 (brs, 3H).
$^{13}$C-NMR (125 MHz, MSM-d6): δ (ppm) 144.8, 130.3, 130, 127.3, 125.7, 124, 103.9, 58.7, 42.7.

Preparation R2bi: 7-[3-(hydroxymethyl)phenyl]-3H, 4H,7H-pyrrolo[2,3-d]pyrimidin-4-one Using General Procedure 3 starting from Preparation R1b and 3-iodobenzyl alcohol as reagents, Preparation R2bi was obtained. HRMS calculated for $C_{13}H_{11}N_3O_2$: 241.0851; found 242.0935 [(M+H)$^+$ form].
$^1$H-NMR (500 MHz, MSM-d6): δ (ppm) 12.11 (brs, 1H), 7.95 (d, 1H), 7.64 (brt, 1H), 7.55 (dm, 1H), 7.48 (t, 1H), 7.46 (d, 1H), 7.35 (dm, 1H), 6.68 (d, 1H), 4.58 (s, 2H).
$^{13}$C-NMR (125 MHz, MSM-d6): δ (ppm) 158.8, 147.4, 144.6, 144.4, 137.7, 129.4, 125.4, 124.2, 123, 122.5, 109.7, 103.5, 62.9.

Preparation R2bj: 7-(3-chlorophenyl)-3H,4H,7H-pyrrolo[2,3-d]pyrimidin-4-one

Using General Procedure 3 starting from Preparation R1b and 1-chloro-3-iodobenzene as reagents, Preparation R2bj was obtained. HRMS calculated for $C_{12}H_8ClN_3O$: 245.0356; found 246.0437 [(M+H)$^+$ form].
$^1$H-NMR (400 MHz, MSM-d6): δ (ppm) 12.17 (brs, 1H), 8 (d, 1H), 7.92 (m, 1H), 7.74 (dm, 1H), 7.58 (d, 1H), 7.57 (t, 1H), 7.47 (dm, 1H), 6.7 (d, 1H).
$^{13}$C-NMR (100 MHz, MSM-d6): δ (ppm) 145, 131.3, 127.2, 124.1, 123.9, 122.9, 104.

Preparation R2bk: 7-(3-fluorophenyl)-3H,4H,7H-pyrrolo[2,3-d]pyrimidin-4-one

Using General Procedure 3 starting from Preparation R1b and 1-fluoro-3-iodobenzene as reagents, Preparation R2bk was obtained. HRMS calculated for $C_{12}H_8N_3OF$: 229.0651; found 230.0729 [(M+H)$^+$ form].

$^1$H-NMR (400 MHz, MSM-d6): δ (ppm) 12.17 (brs, 1H), 7.99 (d, 1H), 7.72 (dm, 1H), 7.64 (m, 1H), 7.58 (d, 1H), 7.58 (m, 1H), 7.25 (m, 1H), 6.71 (d, 1H).

$^{13}$C-NMR (100 MHz, MSM-d6): δ (ppm) 144.9, 131.4, 130.9, 123.9, 120.2, 114, 111.6. $^{19}$F-NMR (376.5 MHz, MSM-d6): δ (ppm) −111.7.

Preparation R2bl: 7-[3-(dimethylamino)phenyl]-3H, 4H,7H-pyrrolo[2,3-d]pyrimidin-4-one Using General Procedure 2 starting from Preparation R1a and 3-(N,N-dimethylamino)phenylboronic acid as reagents, Preparation R2bl was obtained. HRMS calculated for $C_{14}H_{14}N_4O$: 254.1168; found 255.1229 [(M+H)$^+$ form].

$^1$H-NMR (500 MHz, MSM-d6): δ (ppm) 12.04 (brs, 1H), 7.92 (d, 1H), 7.45 (d, 1H), 7.3 (t, 1H), 6.94 (m, 1H), 6.93 (dm, 1H), 6.74 (dm, 1H), 6.65 (d, 1H), 2.95 (s, 6H).

$^{13}$C-NMR (125 MHz, MSM-d6): δ (ppm) 144.3, 129.9, 124.4, 112.4, 111.4, 108.6, 103.1, 40.5.

Preparation R2bm: 7-[3-(morpholin-4-yl)phenyl]-3H,4H,7H-pyrrolo[2,3-d]pyrimidin-4-one Using General Procedure 2 starting from Preparation R1a and 3-(morpholino)phenylboronic acid as reagents, Preparation R2bm was obtained. $^1$H-NMR (400 MHz, MSM-d6): δ (ppm) 12.05 (brs, 1H), 7.93 (s, 1H), 7.47 (d, J=3.53 Hz, 1H), 7.36 (t, J=8.13 Hz, 1H), 7.19 (t, J=2.20 Hz, 1H), 7.11 (dd, J=1.27, 7.93 Hz, 1H), 6.98 (dd, J=1.96, 8.49 Hz, 1H), 6.65 (d, J=3.5 Hz, 1H), 3.75 (t, J=4.61 Hz, 4H), 3.18 (t, J=4.61 Hz, 4H).

Preparation R2bo: 7-(3-methoxyphenyl)-3H,4H,7H-pyrrolo[2,3-d]pyrimidin-4-one

Using General Procedure 3 starting from Preparation R1b and 3-iodoanisole as reagents, Preparation R2bo was obtained. HRMS calculated for $C_{13}H_{11}N_3O_2$: 241.0851; found 242.0928 [(M+H)$^+$ form].

$^1$H-NMR (400 MHz, MSM-d6): δ (ppm) 12.1 (brs, 1H), 7.95 (d, 1H), 7.51 (d, 1H), 7.44 (t, 1H), 7.31 (m, 1H), 7.3 (m, 1H), 6.98 (dm, 1H), 6.67 (d, 1H), 3.82 (s, 3H).

$^{13}$C-NMR (100 MHz, MSM-d6): δ (ppm) 144.6, 130.4, 124.2, 116.7, 112.9, 110.5, 103.5.

Preparation R2bp: 7-[3-(trifluoromethoxy)phenyl]-3H,4H,7H-pyrrolo[2,3-d]pyrimidin-4-one Using General Procedure 3 starting from Preparation R1b and 3-(trifluoromethoxy)iodobenzene as reagents, Preparation R2bp was obtained. HRMS calculated for $C_{13}H_8F_3N_3O_2$: 295.0569; found 296.0651 [(M+H)$^+$ form].

$^1$H-NMR (500 MHz, MSM-d6): δ (ppm) 12.91 (s, 1H), 8 (s, 1H), 7.87 (t, 1H), 7.82 (ddd, 1H), 7.68 (t, 1H), 7.6 (d, 1H), 7.41 (ddd, 1H), 6.71 (d, 1H).

$^{13}$C-NMR (125 MHz, MSM-d6): δ (ppm) 145.1, 131.5, 123.9, 123.2, 119.5, 117.1, 104.1.

Preparation R2bq: 7-[3-(benzyloxy)phenyl]-3H,4H,7H-pyrrolo[2,3-d]pyrimidin-4-one Using General Procedure 3 starting from Preparation R1b and 1-benzyloxy-3-iodobenzene as reagents, Preparation R2bq was obtained. HRMS calculated for $C_{19}H_{15}N_3O_2$: 317.1164; found 318.1235 [(M+H)$^+$ form].

$^1$H-NMR (500 MHz, MSM-d6): δ (ppm) 12.1 (brs, 1H), 7.95 (d, 1H), 7.51 (d, 1H), 7.51-7.31 (m, 5H), 7.44 (t, 1H), 7.41 (m, 1H), 7.32 (dm, 1H), 7.05 (dm, 1H), 6.68 (d, 1H), 5.18 (s, 2H).

$^{13}$C-NMR (125 MHz, MSM-d6): δ (ppm) 144.6, 130.5, 124.1, 116.8, 113.6, 111.4, 103.6, 70.

Preparation R2br: 7-(6-methylpyridin-2-yl)-3H,4H, 7H-pyrrolo[2,3-d]pyrimidin-4-one Using General Procedure 3 starting from Preparation R1b and 2-iodo-6-methylpyridine as reagents, Preparation R2br was obtained. HRMS calculated for $C_{12}H_{10}N_4O$: 226.0855; found 227.0933 [(M+H)$^+$ form].

$^1$H-NMR (500 MHz, MSM-d6): δ (ppm) 12 (brs, 1H), 8.25 (dm, 1H), 8.05 (s, 1H), 7.9 (t, 1H), 7.88 (d, 1H), 7.25 (dm, 1H), 6.68 (d, 1H), 2.52 (s, 3H).

$^{13}$C-NMR (125 MHz, MSM-d6): δ (ppm) 144.9, 139.5, 122, 121.8, 113.8, 103.7, 24.4.

Preparation R2bs: 7-(6-methoxypyridin-2-yl)-3H, 4H,7H-pyrrolo[2,3-d]pyrimidin-4-one The mixture of Preparation R1a (1.0 g, 6.51 mmol), 2-iodo-6-methoxy-pyridine (2.35 g, 9.77 mmol, 1.5 eq.), copper(I)-iodide (125 mg, 0.65 mmol, 0.1 eq.), potassium-phosphate tribasic (2.76 g, 13 mmol, 2 eq.), (1R,2R)-(−)-1,2-diaminocyclohexane (74 mg, 0.65 mmol, 0.1 eq.) in PDO (50 ml) was stirred under inert atmosphere for 4 hours at 100° C. The inorganics were filtered off, the filtrate was evaporated, and the resulted residue was purified by flash chromatography (DCM).

The obtained arylated product (920 mg, 3.5 mmol) and lithium-hydroxide monohydrate (1.48 g, 35 mmol) were stirred in the mixture of PDO (15 ml) and water (15 ml) at 110° C. for 24 hours. The residue was acidified by aqueous HCl solution (1 N, 50 ml), the resulted precipitate was filtered off and dried to give Preparation R2bs.

HRMS calculated for $C_{12}H_{10}N_4O_2$: 242.0804; found 243.0884 [(M+H)$^+$ form].

$^1$H-NMR (500 MHz, MSM-d6): δ (ppm) 12.21 (brs, 1H), 8.08 (dd, 1H), 8.03 (s, 1H), 7.94 (d, 1H), 7.9 (t, 1H), 6.78 (dd, 1H), 6.7 (d, 1H), 3.94 (s, 3H).

$^{13}$C-NMR (125 MHz, MSM-d6): δ (ppm) 163.2, 158.5, 147.6, 147.4, 144.9, 141.9, 121.9, 111.2, 108.4, 108.4, 103.8, 53.9.

Preparation R2bt: 7-(naphthalen-1-yl)-3H,4H,7H-pyrrolo[2,3-d]pyrimidin-4-one

Using General Procedure 2 starting from Preparation R1a and 1-naphthaleneboronic acid as reagents, Preparation R2bt was obtained. HRMS calculated for $C_{16}H_{11}N_3O$: 261.0902; found 262.0984 [(M+H)$^+$ form].

$^1$H-NMR (500 MHz, MSM-d6): δ (ppm) 12.04 (s, 1H), 8.12 (d, 1H), 8.09 (d, 1H), 7.78 (d, 1H), 7.67 (t, 1H), 7.61 (dm, 1H), 7.6 (t, 1H), 7.51 (tm, 1H), 7.39 (d, 1H), 7.21 (t, 1H), 6.77 (d, 1H).

$^{13}$C-NMR (125 MHz, MSM-d6): δ (ppm) 158.9, 149.2, 144.6, 134.2, 134.1, 130.4, 129.5, 128.7, 127.8, 127.2, 126.4, 126.3, 126, 123, 108.7, 103.1 Preparation R2bu: 7-phenyl-3H,4H,7H-pyrrolo[2,3-d]pyrimidin-4-one Using General Procedure 3 starting from Preparation R1b and iodobenzene as reagents, Preparation R2bu was obtained. HRMS calculated for $C_{12}H_9N_3O$: 211.0746; found 212.083 [(M+H)$^+$ form].

¹H-NMR (500 MHz, MSM-d6): δ (ppm) 12.1 (brs, 1H), 7.95 (d, 1H), 7.71 (m, 2H), 7.54 (m, 2H), 7.5 (d, 1H), 7.4 (m, 1H), 6.69 (d, 1H).
¹³C-NMR (125 MHz, MSM-d6): δ (ppm) 158.8, 147.3, 144.6, 137.8, 129.7, 127.4, 124.6, 124.1, 109.8, 103.6.

Preparation R2bv: 7-(2-methylphenyl)-3H,4H,7H-pyrrolo[2,3-d]pyrimidin-4-one

Using General Procedure 2 starting from Preparation R1a and 2-methylphenylboronic acid as reagents, Preparation R2bv was obtained. HRMS calculated for $C_{13}H_{11}N_3O$: 225.0902; found 226.098 [(M+H)⁺ form].
¹H-NMR (500 MHz, MSM-d6): δ (ppm) 12 (brs, 1H), 7.83 (d, 1H), 7.41 (m, 1H), 7.41 (m, 1H), 7.35 (m, 1H), 7.3 (d, 1H), 7.21 (d, 1H), 6.66 (d, 1H), 2.01 (s, 3H).
¹³C-NMR (125 MHz, MSM-d6): δ (ppm) 158.9, 148.2, 144.4, 136.9, 135.6, 131.2, 129.2, 128.5, 127.1, 125.3, 108.6, 102.9, 17.9.

Preparation R2bw: 7-(2-chlorophenyl)-3H,4H,7H-pyrrolo[2,3-d]pyrimidin-4-one

Using General Procedure 2 starting from Preparation R1a and 2-chlorophenylboronic acid as reagents, Preparation R2bw was obtained. HRMS calculated for $C_{12}H_8ClN_3O$: 245.0356; found 246.0437 [(M+H)⁺ form].
¹H-NMR (400 MHz, MSM-d6): δ (ppm) 12.06 (brs, 1H), 7.86 (d, 1H), 7.73-7.48 (m, 4H), 7.27 (d, 1H), 6.68 (d, 1H).
¹³C-NMR (100 MHz, MSM-d6): δ (ppm) 144.7, 125.4, 102.2.

Preparation R2bx: 7-(2-fluorophenyl)-3H,4H,7H-pyrrolo[2,3-d]pyrimidin-4-one

Using General Procedure 2 starting from Preparation R1a and 2-fluorophenylboronic acid as reagents, Preparation R2bx was obtained. HRMS calculated for $C_{12}H_8N_3OF$: 229.0651; found 230.0730 [(M+H)⁺ form].
¹H-NMR (400 MHz, MSM-d6): δ (ppm) 12.09 (brs, 1H), 7.9 (d, 1H), 7.61 (m, 1H), 7.54 (m, 1H), 7.48 (m, 1H), 7.38 (m, 1H), 7.34 (dd, 1H), 6.7 (d, 1H).
¹³C-NMR (100 MHz, MSM-d6): δ (ppm) 144.8, 130.6, 129.6, 125.4, 125.3, 117, 103.5.

Preparation R2by: 7-[2-(dimethylamino)phenyl]-3H,4H,7H-pyrrolo[2,3-d]pyrimidin-4-one Using General Procedure 2 starting from Preparation R1a and dimethyl[2-(4,4,5,5-tetramethyl-1,3,2-dioxaborolan-2-yl)phenyl]amine as reagents, Preparation R2by was obtained. HRMS calculated for $C_{14}H_{14}N_4O$: 254.1168; found 255.1237 [(M+H)⁺ form].
¹H-NMR (500 MHz, MSM-d6): δ (ppm) 12 (brs, 1H), 7.85 (d, 1H), 7.36 (m, 1H), 7.24 (dm, 1H), 7.2 (d, 1H), 7.13 (dm, 1H), 7.02 (m, 1H), 6.64 (d, 1H), 2.36 (s, 6H).
¹³C-NMR (125 MHz, MSM-d6): δ (ppm) 144.4, 130.1, 129.4, 125.5, 121.1, 119, 102.9, 42.4.

Preparation R2bz: 7-(2-methoxyphenyl)-3H,4H,7H-pyrrolo[2,3-d]pyrimidin-4-one

Using General Procedure 2 starting from Preparation R1a and 2-methoxyphenylboronic acid as reagents, Preparation R2bz was obtained. HRMS calculated for $C_{13}H_{11}N_3O_2$: 241.0851; found 242.092 [(M+H)⁺ form].

¹H-NMR (400 MHz, MSM-d6): δ (ppm) 11.96 (brs, 1H), 7.82 (d, 1H), 7.46 (m, 1H), 7.37 (dm, 1H), 7.24 (dm, 1H), 7.18 (d, 1H), 7.08 (m, 1H), 6.6 (d, 1H), 3.74 (s, 3H).
¹³C-NMR (100 MHz, MSM-d6): δ (ppm) 144.2, 130.2, 129.3, 126, 120.8, 113.1, 102.4.

Preparation R2ca: 7-(pyridin-2-yl)-3H,4H,7H-pyrrolo[2,3-d]pyrimidin-4-one

Using General Procedure 3 starting from Preparation R1b and 2-iodopyridine as reagents, Preparation R2ca was obtained. HRMS calculated for $C_{11}H_8N_4O$: 212.0698; found 213.0774 [(M+H)⁺ form].
¹H-NMR (500 MHz, MSM-d6): δ (ppm) 12.29 (s, 1H), 8.55 (dd, 1H), 8.47 (dd, 1H), 8.06 (brs, 1H), 8.03 (t, 1H), 7.9 (d, 1H), 7.4 (t, 1H), 6.7 (d, 1H).
¹³C-NMR (125 MHz, MSM-d6): δ (ppm) 149.1, 145, 139.4, 122.5, 122, 116.9, 104. ¹⁵N-NMR (50.6 MHz, MSM-d6): δ (ppm) 171.2.

Preparation R2cb: 7-(pyridin-3-yl)-3H,4H,7H-pyrrolo[2,3-d]pyrimidin-4-one

Using General Procedure 2 starting from Preparation R1a and pyridine-3-boronic acid as reagents, Preparation R2cb was obtained. HRMS calculated for $C_{11}H_8N_4O$: 212.0698; found 213.0774 [(M+H)⁺ form].
¹H-NMR (500 MHz, MSM-d6): δ (ppm) 12.29 (s, 1H), 8.55 (dd, 1H), 8.47 (dd, 1H), 8.06 (brs, 1H), 8.03 (t, 1H), 7.9 (d, 1H), 7.4 (t, 1H), 6.7 (d, 1H).
¹³C-NMR (125 MHz, MSM-d6): δ (ppm) 149.1, 145, 139.4, 122.5, 122, 116.9, 104.
¹⁵N-NMR (50.6 MHz, MSM-d6): δ (ppm) 171.2.

Preparation R2cc: 7-(thiophen-2-yl)-3H,4H,7H-pyrrolo[2,3-d]pyrimidin-4-one

Using General Procedure 3 starting from Preparation R1b and 2-iodothiophene as reagents, Preparation R2cc was obtained. HRMS calculated for $C_{10}H_7N_3O\,S$: 217.0310; found 218.0384 [(M+H)⁺ form].
¹H-NMR (500 MHz, MSM-d6): δ (ppm) 12.2 (brs, 1H), 8.03 (s, 1H), 7.58 (d, 1H), 7.43 (dd, 1H), 7.39 (dd, 1H), 7.07 (dd, 1H), 6.69 (d, 1H).
¹³C-NMR (125 MHz, MSM-d6): δ (ppm) 158.5, 147.2, 145.3, 138.7, 126, 124.3, 122.8, 119.2, 109.4, 104.2.

Preparation R2cd: 7-(pyridin-4-yl)-3H,4H,7H-pyrrolo[2,3-d]pyrimidin-4-one

Using General Procedure 2 starting from Preparation R1a and pyridine-4-boronic acid pinacol ester as reagents, Preparation R2cd was obtained. HRMS calculated for $C_{11}H_8N_4O$: 212.0698; found 213.0773 [(M+H)⁺ form].
¹H-NMR (500 MHz, MSM-d6): δ ppm 12.31 (brs, 1H), 8.69 (m, 2H), 8.05 (s, 1H), 7.99 (m, 2H), 7.73 (d, 1H), 6.76 (d, 1H).
¹³C-NMR (125 MHz, MSM-d6): δ (ppm) 151.3, 145.6, 122.8, 117.3, 105.

Preparation R2ce: 7-(furan-3-yl)-3H,4H,7H-pyrrolo[2,3-d]pyrimidin-4-one

Using General Procedure 2 starting from Preparation R1a and 3-(4,4,5,5-tetramethyl-1,3,2-dioxaborolan-2-yl)furan as reagents, Preparation R2ce was obtained. HRMS calculated for $C_{10}H_7N_3O_2$: 201.0538; found 202.0617 [(M+H)⁺ form].

¹H-NMR (500 MHz, MSM-d6): δ (ppm) 12.13 (brs, 1H), 8.32 (dd, 1H), 8 (d, 1H), 7.8 (dd, 1H), 7.52 (d, 1H), 7.17 (dd, 1H), 6.66 (d, 1H).
¹³C-NMR (125 MHz, MSM-d6): δ (ppm) 158.6, 147.1, 145, 143.9, 133.8, 126, 123, 109.6, 106.5, 103.8.

Preparation R2cf: 7-(thiophen-3-yl)-3H,4H,7H-pyrrolo[2,3-d]pyrimidin-4-one

Using General Procedure 2 starting from Preparation R1a and thiophene-3-boronic acid pinacol ester as reagents, Preparation R2cf was obtained. HRMS calculated for $C_{10}H_7N_3OS$: 217.0310; found 218.0390 [(M+H)⁺ form].
¹H-NMR (500 MHz, MSM-d6): δ (ppm) 12.14 (s, 1H), 7.99 (d, 1H), 7.92 (dd, 1H), 7.71 (dd, 1H), 7.68 (dd, 1H), 7.57 (d, 1H), 6.66 (d, 1H).
¹³C-NMR (125 MHz, MSM-d6): δ (ppm) 158.6, 147, 144.8, 136.3, 127, 123.8, 123.3, 115.1, 109.5, 103.5.

Preparation R2cg: 7-(1-methyl-1H-imidazol-4-yl)-3H,4H,7H-pyrrolo[2,3-d]pyrimidin-4-one Using General Procedure 3 starting from Preparation R1b and 4-iodo-1-methyl-1H-imidazole as reagents, Preparation R2cg was obtained. HRMS calculated for $C_{10}H_9N_5O$: 215.0807; found 216.0879 [(M+H)⁺ form].
¹H-NMR (500 MHz, MSM-d6): δ (ppm) 9.24-7.3 (vbrs, 3H), 7.51 (d, 1H), 6.72 (brs, 1H), 3.77 (s, 3H).
¹³C-NMR (125 MHz, MSM-d6): δ (ppm) 121.7, 103.5, 35.
¹⁵N-NMR (50.6 MHz, MSM-d6): δ (ppm) 153.

Preparation R2ch: 7-(1-methyl-1H-pyrazol-4-yl)-3H,4H,7H-pyrrolo[2,3-d]pyrimidin-4-one Using General Procedure 3 starting from Preparation R1b and 4-iodo-1-methyl-1H-pyrazole as reagents, Preparation R2ch was obtained. HRMS calculated for $C_{10}H_9N_5O$: 215.0807; found 216.0889 [(M+H)⁺ form].
¹H-NMR (500 MHz, MSM-d6): δ (ppm) 12.12 (brs, 1H), 8.27 (s, 1H), 7.96 (s, 1H), 7.91 (d, 1H), 7.42 (d, 1H), 6.63 (d, 1H), 3.89 (s, 3H).
¹³C-NMR (125 MHz, MSM-d6): δ (ppm) 158.6, 146.9, 144.7, 132.1, 124.3, 123.4, 121.4, 109, 103.4, 38.5.

Preparation R2ci: 7-[1-(difluoromethyl)-1H-pyrazol-4-yl]-3H,4H,7H-pyrrolo[2,3-d]pyrimidin-4-one Using General Procedure 3 starting from Preparation R1b and 1-(difluoromethyl)-4-iodo-1H-pyrazole as reagents, Preparation R2ci was obtained. HRMS calculated for $C_{10}H_7F_2N_5O$: 251.0619; found 252.0682 [(M+H)⁺ form].
¹H-NMR (500 MHz, MSM-d6): δ (ppm) 11.88 (brs, 1H), 8.83 (d, 1H), 8.4 (d, 1H), 8.03 (s, 1H), 7.91 (t, 1H), 7.58 (d, 1H), 6.69 (d, 1H).
¹³C-NMR (125 MHz, MSM-d6): δ (ppm) 145.2, 136.2, 123.2, 121.3, 111, 104.

Preparation R2cj: 7-(pyrimidin-2-yl)-3H,4H,7H-pyrrolo[2,3-d]pyrimidin-4-one

Preparation R1b (300 mg, 2.011 mmol, 1 eq.), 2-chloropyrimidine (2.413 mmol, 1.2 eq.) and anhydrous $K_2CO_3$ (417 mg, 3.017 mmol, 1.5 eq.) was heated in DMF (10 ml) at 150° C. for 2 hours. The reaction mixture was filtered and purified by preparative LC (on C-18 Gemini-NX 5 μm column, 5 mM aqueous $NH_4HCO_3$-MCN, gradient) to give 4-methoxy-7-pyrimidin-2-yl-pyrrolo[2,3-d]pyrimidine.

Then the obtained product (0.633 mmol, 1 eq.), IM HCl aqueous solution (3 ml) and PDO (60 ml) were stirred at 100° C. for 1 hour. After the reaction completed, the mixture was evaporated and purified by preparative LC (on C-18 Gemini-NX 5 μm column, 5 mM aqueous $NH_4HCO_3$-MCN, gradient) to give Preparation R2cj. HRMS calculated for $C_{10}H_7N_5O$: 213.0651; found 214,0735 [(M+H)⁺ form].
¹H-NMR (500 MHz, MSM-d6): δ (ppm) 12.19 (brs, 1H), 8.94 (d, 1H), 8.01 (s, 1H), 7.78 (d, 1H), 7.54 (t, 1H), 6.71 (d, 1H).
¹³C-NMR (125 MHz, MSM-d6): δ (ppm) 159.7, 158.7, 156, 148.1, 145.2, 123.3, 120.1, 111.4, 104.5.

Preparation R2ck: 7-(1,3-thiazol-2-yl)-3H,4H,7H-pyrrolo[2,3-d]pyrimidin-4-one

Using General Procedure 3 starting from Preparation R1b and 2-iodothiazole as reagents, Preparation R2ck was obtained. HRMS calculated for $C_9H_6N_4OS$: 218.0262; found 219.0335 [(M+H)⁺ form].
¹H-NMR (500 MHz, MeCN-d3) δ ppm 8.5 (s, 1H), 7.62 (d, 1H), 7.52 (d, 1H), 7.22 (d, 1H), 6.51 (d, 1H).
¹³C-NMR (125 MHz, MeCN-d3) δ ppm 154.5, 137.9, 116.8, 114.8, 104.2.

Preparation R2cl: 7-(1H-indol-1-yl)-3H,4H,7H-pyrrolo[2,3-d]pyrimidin-4-one

Preparation R1b (1.74 g, 11.67 mmol) was dissolved in DMF (80 ml) and cooled to 0° C. Sodium hydride (60% disp., 1.87 g, 46.67 mmol) was slowly added and stirred for 30 minutes at 0° C. Hydroxylamine-O-sulfonic acid (2.11 g, 18.67 mmol) was added to the reaction mixture, allowed to warm up to r.t. and stirred for 20 hours. Water (100 ml) was added to the reaction mixture and extracted with DCM (4×50 ml). The combined organic layers were washed with water and dried over $MgSO_4$ and evaporated. The residue was dissolved in MSM and purified by preparative LC (on C-18 Gemini-NX 5 μm column, 5 mM aqueous $NH_4HCO_3$-MeCN, gradient).

A part of the resulted N-amino compound (500 mg, 3.05 mmol) was dissolved in PDO (5 ml) and 2,5-dimethoxytetrahydrofurane (454 ml, 462 mg, 3.5 mmol) was added. The mixture was stirred at 100° C. for 115 hours. The reaction mixture was diluted with aqueous HCl solution (5 N, 2 ml) and purified by preparative LC (on C-18 Gemini-NX 5 μm column, 5 mM aqueous $NH_4HCO_3$-MeCN, gradient) to give Preparation R2cl. HRMS calculated for $C_{14}H_{10}N_4O$: 250.0854; found 250.2000 [(M form)].
¹H-NMR (500 MHz, MSM-d6): δ (ppm) 12.22 (brs, 1H), 7.86 (s, 1H), 7.71 (d, 1H), 7.68 (m, 1H), 7.58 (d, 1H), 7.17 (m, 1H), 7.17 (m, 1H), 6.86 (m, 1H), 6.73 (m, 1H), 6.68 (dd, 1H).
¹³C-NMR (125 MHz, MSM-d6): δ (ppm) 158.5, 147.9, 145.9, 137, 129.7, 126.3, 125.4, 123.5, 121.5, 121.5, 109, 107, 102.3, 101.8.

Preparation R2 cm: 7-(1H-pyrrol-1-yl)-3H,4H,7H-pyrrolo[2,3-d]pyrimidin-4-one

Preparation R1b (1.74 g, 11.67 mmol) was dissolved in DMF (80 ml) and cooled to 0° C. Sodium hydride (60% disp., 1.87 g, 46.67 mmol) was slowly added and stirred for 30 minutes at 0° C. Hydroxylamine-O-sulfonic acid (2.11 g, 18.67 mmol) was added to the reaction mixture, allowed to warm up to r.t. and stirred for 20 hours. Water (100 ml) was added to the reaction mixture and extracted with DCM (4×50 ml). The combined organic layers were washed with water and dried over MgSO$_4$, evaporated. The residue was dissolved in MSM and purified by preparative LC (on C-18 Gemini-NX 5 μm column, 5 mM aqueous NH$_4$HCO$_3$-MeCN, gradient).

A part of the resulted N-amino compound (500 mg, 3.05 mmol) was dissolved in PDO (5 ml) and 2,5-dimethoxy-tetrahydrofurane (454 ml, 462 mg, 3.5 mmol) was added. The mixture was stirred at 100° C. for 115 hours. The reaction mixture was diluted with aqueous HCl solution (5 N, 2 ml) and purified by preparative LC (on C-18 Gemini-NX 5 μm column, 5 mM aqueous NH$_4$HCO$_3$-MeCN, gradient).

To a part of the resulted compound (63 mg, 0.294 mmol) PDO (25 ml) and aqueous HCl solution (1 N, 1.3 ml) was added and stirred at 60° C. for 5 hours. The reaction mixture was evaporated and the residue was purified by preparative LC (on C-18 Gemini-NX 5 μm column, 5 mM aqueous NH$_4$HCO$_3$-MeCN, gradient) to give Preparation R2 cm. HRMS calculated for C$_{10}$H$_8$N$_4$O: 200.0698; found 201.0770 [(M+H)$^+$ form].

$^1$H-NMR (500 MHz, MSM-d6): δ (ppm) 12.18 (brs, 1H), 7.92 (s, 1H), 7.46 (d, 1H), 7.12 (m, 2H), 6.61 (d, 1H), 6.21 (m, 2H).

$^{13}$C-NMR (125 MHz, MSM-d6): δ (ppm) 158.4, 147.4, 145.8, 125.1, 122.8, 108, 106.7, 101.1.

Preparation R2de: 6-methyl-7-phenyl-3H-pyrrolo[2,3-d]pyrimidin-4-one

Using General Procedure 3 starting from Preparation R1b and iodobenzene as reagents, 4-methoxy-7-phenyl-pyrrolo[2,3-d]pyrimidine was obtained (without hydrolysis). This crude product (450 mg, 2 mmol) was dissolved in THF (18 ml) stirred at −78° C., then LDA solution (1.8 M, 1.7 ml, 3 mmol) was added. After one hour of stirring at −78° C., iodomethane (190 μl, 3 mmol) solution in THF (5 ml) was added, and continued stirring for 90 minutes. Then the reaction mixture was diluted with brine (10 ml) and evaporated to Celite and purified by flash chromatography (Hexane-EEO=7-1).

The resulted crude product (400 mg, 1.6 mmol) was dissolved in cc. HCl aqueous solution (330 μl, ~12.2 M, 4 mmol) and PDO (5 ml) was stirred at 100° C. for 2 hours. After the reaction completed, the mixture was partially evaporated and the formed suspension was filtered. The solid on the filter was washed with water and dried to give Preparation R2de. HRMS calculated for C$_{13}$H$_{11}$N$_3$O: 225.0902; found 226.0985 [(M+H)$^+$ form].

$^1$H-NMR (500 MHz, MSM-d6): δ ppm 11.94 (s, 1H), 7.76 (d, 1H), 7.55 (tm, 2H), 7.49 (tm, 1H), 7.4 (dm, 2H), 6.41 (d, 1H), 2.17 (d, 3H).

$^{13}$C-NMR (125 MHz, MSM-d6): δ ppm 158.4, 143.6, 136.2, 132.6, 129.6, 128.7, 128.5, 100.9, 13.3.

Preparation R2df: 9-methyl-3H-pyrimido[4,5-b]indol-4-one

Preparation R1b (500 mg, 3.06 mmol) and 2,5-dimethoxytetrahydrofurane (810 mg, 6.13 mmol, d=1.02, 795 μl) in PDO (5 ml) were heated up to 100° C. for 102 hours, then 1 N aqueous HCl solution (5 ml) was added. The mixture was dissolved in DMF and purified by preparative LC (on C-18 Gemini-NX 5 μm column, 5 mM aqueous NH$_4$HCO$_3$-MeCN, gradient) to give Preparation R2df. HRMS calculated for C$_{11}$H$_9$N$_3$O: 199.0746; found 200.0827 [(M+H)$^+$ form].

$^1$H-NMR (500 MHz, MSM-d6): δ ppm 12.33 (brs, 1H), 8.21 (s, 1H), 7.63 (dm, 1H), 7.41 (ddd, 1H), 7.29 (td, 1H), 3.86 (s, 3H).

$^{13}$C-NMR (125 MHz, MSM-d6): δ ppm 158.5, 153.5, 148.1, 137, 124.6, 122, 121.8, 121, 110.7, 100.1, 28.5

Preparation R2dg: 6,8-dimethylpyrimido[5,4-b]indolizin-4(3H)-one

Preparation R1b (1.74 g, 11.67 mmol) was dissolved in DMF (80 ml) and cooled to 0° C. Sodium hydride (60% disp., 1.87 g, 46.67 mmol) was slowly added and stirred for 30 minutes at 0° C. Hydroxylamine-O-sulfonic acid (2.11 g, 18.67 mmol) was added to the reaction mixture, allowed to warm up to r.t. and stirred for 20 hours. Water (100 ml) was added to the reaction mixture and extracted with DCM (4×50 ml). The combined organic layers were washed with water, dried over MgSO$_4$ and evaporated.

A part of the resulted N-amino compound (300 mg, 1.83 mmol) and acetylacetone (206 μl, 201 mg 2.01 mmol,) were dissolved in 5 ml acetic acid and heated up to 120° C. for 2.5 hours, then TFA (5 ml) was added. The mixture was heated at 120° C. for 18 hours. Then water (1 ml) and methanol (10 ml) were added and the solution was evaporated. The residue was purified by preparative LC (on C-18 Gemini-NX 5 μm column, 5 mM aqueous NH$_4$HCO$_3$-MeCN, gradient), to give Preparation R2dg. HRMS calculated for C$_{11}$H$_{10}$N$_4$O: 214.0855; found 215.0935 [(M+H)$^+$ form].

$^1$H-NMR (500 MHz, MSM-d6) δ ppm 12.16 (s, 1H), 8 (s, 1H), 6.89 (s, 1H), 6.68 (d, 1H), 2.45 (d, 3H), 2.44 (s, 3H).

$^{13}$C-NMR (125 MHz, MSM-d6) δ ppm 159.7, 152.5, 143.4, 141.2, 138.9, 127.7, 115.5, 109.8, 91.2, 21.9, 17.4.

Preparation R2dh: 6-chloro-7-phenyl-3H-pyrrolo[2,3-d]pyrimidin-4-one

Using General Procedure 3 starting from Preparation R1b and iodobenzene as reagents, 4-methoxy-7-phenyl-pyrrolo[2,3-d]pyrimidine was obtained (without hydrolysis). The crude product (394 mg, 1.75 mmol) was dissolved in THF (14 ml) stirred at −78° C., then LDA solution (1.8 M, 1.2 ml, 2.16 mmol) was added. After one hour of stirring at −78° C., hexachloroethane (632 mg, 2.63 mmol) solution in THF (5 ml) was added, and continued stirring for 90 minutes. Then the reaction mixture was diluted with brine (10 ml), evaporated to Celite and purified by flash chromatography (Hexane-EEO=9-1).

The resulted crude product (110 mg, 0.42 mmol) was dissolved in cc. HCl aqueous solution (82 μl, ~12.2 M, 1 mmol) and PDO (5 ml) was stirred at 100° C. for 2 hours. After the reaction completed, the mixture was partially evaporated. The formed suspension was filtered and the solid on the filter was washed with water and dried to give Preparation R2dh. HRMS calculated for C$_{12}$H$_8$N$_3$OCl: 245.0356; found 246.043 [(M+H)$^+$ form].

$^1$H-NMR (500 MHz, MSM-d6) δ ppm 12.16 (s, 1H), 7.88 (s, 1H), 7.6-7.52 (m, 5H), 6.78 (s, 1H).

$^{13}$C-NMR (125 MHz, MSM-d6) δ ppm 157.6, 148.2, 145.3, 101.6.

Preparation R2di: 6-iodo-7-methyl-3H-pyrrolo[2,3-d]pyrimidin-4-one

To a stirred solution of Preparation R1a (8 g, 52.1 mmol) in abs. DMF (50 ml) was cooled down to 0° C., then sodium-hydride (3.13 g, 60% disp, in mineral oil, 78.2 mmol, 1.5 eq.) was added and stirred for 20 minutes at r.t. under Ar. Methyl iodide (8.2 g, 57.2 mmol, d=2.28, 3.6 ml) was added to the reaction mixture and stirred for 1.5 hours at r.t. The mixture was poured into water (50 ml) to give a solid compound which was filtered off.

A part of the resulted solid compound (500 mg, 2.98 mmol) was dissolved in 5 ml abs. THF and cooled down to −78° C. Then 2 M LDA (1.7 ml, 3.4 mmol) was added dropwise. The mixture was stirred at −78° C. for 1 hour, then iodide (757 mg, 2.98 mmol) was added. The solution was allowed to warm to r.t. and stirred for 22 hours. Finally, 5 ml water was added and a solid compound was formed, which was filtered off, to give Preparation R2di. HRMS calculated for $C_7H_{61}N_3O$: 274.9556; found 275.9634 [(M+H)$^+$ form].

$^1$H-NMR (500 MHz, MSM-d6) δ ppm 11.97 (s, 1H), 7.85 (s, 1H), 6.79 (s, 1H), 3.64 (s, 3H).

$^{13}$C-NMR (125 MHz, MSM-d6) δ ppm 157.3, 149.1, 144.2, 111.4, 110.3, 80.4, 33.2.

Preparation R2di: 5-fluoro-7-methyl-3H-pyrrolo[2,3-d]pyrimidin-4-one

Using General Procedure 1 starting from 4-chloro-5-fluoro-7H-pyrrolo[2,3-d]pyrimidine (instead of Preparation R1a) and iodomethane as alkylating agent, Preparation R2dj was obtained. HRMS calculated for $C_7H_6FN_3O$: 167.0495; found 168.0574 [(M+H)$^+$ form].

$^1$H-NMR (500 MHz, MSM-d6) δ ppm 11.97 (brs, 1H), 7.88 (s, 1H), 7.07 (s, 1H), 3.64 (s, 3H).

$^{13}$C-NMR (125 MHz, MSM-d6) δ ppm 156.9, 144.6, 144.4, 143.1, 108.1, 97.0, 31.6.

Preparation R2dk: 3,6,7,8-tetrahydro-4H-pyrimido[5,4-b]pyrrolizin-4-one

Step 1: 4-methoxy-7-((2-(trimethylsilyl)ethoxy)methyl)-7H-pyrrolo[2,3-d]pyrimidine To a preheated 100 ml two-necked sphere flask equipped with stirring bar and gas inlet, Preparation R1b (2.0 g, 11.4 mmol) was dissolved in abs. THF (45 ml). The solution was cooled to 0° C., and NaH (0.85 g, 3 eq.) was added. The mixture was stirred for 1 hour, then SEM-Cl (3.55 ml, 1.5 eq.) was added via syringe. Yellow solution and white precipitate formed. The mixture was allowed to warm to r.t., while the color faded away. After losing the color, the reaction was quenched with water (30 ml). The mixture was extracted with EEO (3×30 ml) and the collected organic layers were dried on $Na_2SO_4$. After filtration, solvent was evaporated and the crude product was purified with flash chromatography (hexane:EEO=20:1-9:1) to give the product of the title as a yellowish liquid.

Step 2: 6-iodo-4-methoxy-7-((2-(trimethylsilyl)ethoxy)methyl)-7H-pyrrolo[2,3-d]pyrimidine To a preheated 250 ml three-necked sphere flask equipped with a magnetic stirring bar and gas inlet, was added abs. THF (30 ml) and diisopropyl amine (2.7 ml, 1.5 eq.) under nitrogen atmosphere. The mixture was cooled to −78° C. and n-BuLi (8.0 ml, 1.5 equiv.) was added and stirred for 30 minutes. Then 4-methoxy-7-((2-(trimethylsilyl)ethoxy)methyl)-7H-pyrrolo[2,3-d]pyrimidine (3.64 g, 13.05 mmol, 1 eq.) dissolved in abs. THF (100 ml) was added slowly over 30 minutes and stirring was continued for 1 hour. Next, iodine (3.95 g, 1.2 eq.) dissolved in abs. THF (35 ml) was added slowly and stirred for an additional 3 hours. Then the cooling bath was removed and the reaction mixture was left to warm to r.t. Brine (500 ml) was added and the solution was extracted with EEO (150 ml) three times. The organic phases were dried, filtered evaporated and purified by flash chromatography (hexane:EEO—9:1) to give the product of the title as a yellowish white powder.

Step 3: 6-iodo-4-methoxy-7H-pyrrolo[2,3-d]pyrimidine

In a 100 ml Schlenk bomb, 6-iodo-4-methoxy-7-((2-(trimethylsilyl)ethoxy)methyl)-7H-pyrrolo[2,3-d]pyrimidine (4.72 g, 11.65 mmol) was dissolved in THF (50 ml). To the solution TBAF.3H$_2$O (11.34 g, 3 eq.) was added with 4 Å molecular sieves. The mixture was heated at 95° C. under nitrogen overnight. After cooling, the mixture was filtered through Celite, and the solvent was evaporated. To the resulting brown oil, water was added and an off-white powder precipitated. The precipitation was filtered, washed with water and MeCN (3×10 ml). After drying, the product of the title was obtained as an off-white powder.

Step 4: 7-allyl-6-iodo-4-methoxy-7H-pyrrolo[2,3-d]pyrimidine

In a preheated, two-necked 100 ml sphere-flask, equipped with a magnetic stirring bar and a gas inlet, 6-iodo-4-methoxy-7H-pyrrolo[2,3-d]pyrimidine (900 mg, 3.27 mmol) was dissolved in abs. THF (10 ml) under nitrogen. Then, triphenylphosphine (1.048 g, 1.2 eq.) was added. Then, with continuous stirring, allylic alcohol (232 mg, 1.2 eq.) was measured in via syringe. The mixture was cooled to 0° C. and diisopropyl-aza-dicarboxylate (808 mg, 1.2 eq.) was added dropwise via syringe. The mixture was allowed to warm to r.t., and monitored with TLC. After completion, solvent was evaporated, and the crude product was purified by flash chromatography (hexane:EEO=10:1) to give the product of the title as white crystals.

Step 5: 4-methoxy-7,8-dihydro-6H-pyrimido[5,4-b]pyrrolizine

In a preheated 100 ml Schlenk bomb, 7-allyl-6-iodo-4-methoxy-7H-pyrrolo[2,3-d]pyrimidine (1.60 g, 5.1 mmol) was measured in and dissolved in abs. THF (50 ml). 9-Borabicyclo[3.3.1]nonane (1.87 g, 3 eq.) was measured out in a double-manifold glovebox, dissolved in abs. THF (30 ml), and added into the Schlenk bomb via syringe at 0° C. The reaction was allowed to warm to r.t. and stirred overnight. Then [1,1'-Bis(diphenylphosphino)ferrocene]dichloropalladium(II) (366 mg, 0.1 eq.) and K$_2$CO$_3$ (4.93 g, 7 eq.) were measured in under nitrogen and added to the solution. The mixture was warmed to 85° C. for 4 hours. After completion, the solvent was evaporated and the crude product was purified by flash chromatography (hexane:EEO=3:1) to give the product of the title as a dark red solid.

Step 6: Preparation R2dk

The resulted methoxypyrrolizine obtained in Step 5 above (69.7 mg, 0.37 mmol) and lithium-hydroxide monohydrate (155 mg, 3.7 mmol) diluted in mixture of PDO (2 ml) and water (2 ml) and was stirred at 110° C. for 40 hours. After the reaction completed, the mixture was evaporated, purified by preparative LC (on C-18 Gemini-NX 5 µm column, 5 mM aqueous NH$_4$HCO$_3$-MeCN, gradient) to give Preparation R2dk. MS calculated for C$_9$H$_9$N$_3$O: 175.07; found 175.2 [(M+H)$^+$ EI form].

Preparation R2dl: 6,7,8,9-tetrahydro-3H-pyrimido[5,4-b]indolizin-4-one

Step 1: 7-(but-3-en-1-yl)-6-iodo-4-methoxy-7H-pyrrolo[2,3-d]pyrimidine

In a 100 ml sphere-flask, 6-iodo-4-methoxy-7H-pyrrolo[2,3-d]pyrimidine (obtained in Step 3 of Preparation R2dk, 1.99 g, 7.23 mmol) was dissolved in DMSO (70 ml), and KOH (690 mg, 1.7 eq.) was added. The mixture was sonicated for 10 minutes, then homoallyl bromide (2.15 ml, 3 eq.) was added at 0° C. After warming to r.t., the mixture was stirred until completion. After completion, water (50 ml) was added and the mixture as extracted with EEO (3×120 ml). The organic phases were collected, dried over sodium sulfate and evaporated. The crude product was purified by flash chromatography (hexane:EEO=20:1-5:1) to give the product of the title as a white solid.

Step 2: 4-methoxy-3,4,6,7,8,9-hexahydropyrimido[5,4-b]indolizine

7-But-3-enyl-6-iodo-4-methoxy-pyrrolo[2,3-d]pyrimidine (164 mg, 0.5 mmol) was dissolved in THF (2 ml) in a Schlenk tube under nitrogen atmosphere. The mixture was cooled to 0° C., and 9-borabicyclo[3.3.1]nonane (305 mg, 2.5 mmol) was added in THF (5 ml) solution via syringe and stirred overnight at r.t. [1,1'-Bis(diphenylphosphino)ferrocene]dichloropalladium(II) (75 mg, 0.1 mmol) and K$_2$CO$_3$ (967 mg, 7 mmol) were added to the reaction mixture and stirred for 3 hours at 80° C. Then the reaction mixture was evaporated to Celite and purified by flash chromatography (hexane-EEO=3-1).

Step 3: Preparation R2dl

The resulted methoxyindolizine obtained in Step 2 above (104 mg, 0.51 mmol) and lithium-hydroxide monohydrate (215 mg, 5.1 mmol) diluted in mixture of PDO (2 ml) and water (2 ml) and was stirred at 110° C. for 40 hours. After the reaction completed, the mixture was evaporated, purified by preparative LC (on C-18 Gemini-NX 5 µm column, 5 mM aqueous NH$_4$HCO$_3$-MeCN, gradient) to give Preparation R2dl. MS calculated for C$_{10}$H$_{11}$N$_3$O: 189.09; found 190 [(M+H)$^+$ EI form].

Preparation R3a: 3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from 3H,4H,7H-pyrrolo[2,3-d]pyrimidin-4-one as reagent, Preparation R3a was obtained. HRMS calculated for C$_{24}$H$_{29}$N$_5$O$_3$: 435.2270; found 436.2345 [(M+H)$^+$ form].
$^1$H-NMR (500 MHz, MSM-d6) δ ppm 11.91/11.9 (brs, 1H), 9.36/8.86 (brd+brq, 2H), 8.03/7.97 (s, 1H), 7.32-7.11 (m, 5H), 7.06/7.04 (dd, 1H), 6.47/6.43 (dd, 1H), 4.09-2.6 (m, 12H), 1.96-0.62 (m, 6H).

Preparation R3b: 3-({4-hydroxy-1-[(3R,4R)-3-phenylpiperidine-4-carbonyl]piperidin-4-yl}methyl)-7-methyl-3H,4H,7H-pyrrolo[2,3-d]pyrimidin-4-one Using General Procedure 5 starting from Preparation R2b as reagent, Preparation R3b was obtained as HCl salt. HRMS calculated for C$_{25}$H$_{31}$N$_5$O$_3$: 449.2427; found 450.2517 [(M+H)$^+$ form].
$^1$H-NMR (500 MHz, MSM-d6) δ ppm 9.16/8.72 (brd/brq, 2H), 8.02/8.07 (s, 1H), 7.34-7.11 (m, 5H), 7.11/7.13 (d, 1H), 6.45/6.48 (d, 1H), 4.01/3.73 (d/s, 1H), 4.00-0.58 (m, 16H), 3.89 (d, 2H), 3.71 (s, 3H).

Preparation R3c: 7-ethyl-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2c as reagent, Preparation R3c was obtained as HCl salt. HRMS calculated for C$_{26}$H$_{33}$N$_5$O$_3$: 463.2583; found 464.2654 [(M+H)$^+$ form].
$^1$H-NMR (500 MHz, MSM-d6) δ ppm 9.16/8.72 (brd/brq, 2H), 8.01/8.07 (s, 1H), 7.33-7.09 (m, 5H), 7.18/7.19 (d, 1H), 6.45/6.49 (d, 1H), 4.13/4.15 (q, 2H), 4.01/3.73 (d/s, 1H), 4.00-0.58 (m, 16H), 3.89 (d, 2H), 1.34/1.35 (t, 3H).

Preparation R3d: 3-({4-hydroxy-1-[(3R,4R)-3-phenylpiperidine-4-carbonyl]piperidin-4-yl}methyl)-7-(propan-2-yl)-3H,4H,7H-pyrrolo[2,3-d]pyrimidin-4-one Using General Procedure 5 starting from Preparation R2d as reagent, Preparation R3d was obtained. HRMS calculated for C$_{27}$H$_{35}$N$_5$O$_3$: 477.274; found 478.2819 [(M+H)$^+$ form].
$^1$H-NMR (500 MHz, MSM-d6) δ ppm 9.4/8.89 (brd+brq, 1+1 H), 8.08/8.03 (s/s, 1H), 7.32-7.09 (m, 5H), 7.27/7.25 (d/d, 1H), 6.51/6.47 (d/d, 1H), 4.84 (m, 1H), 4.05-0.6 (m, 16H), 3.48/3.43 (m/m, 1H), 3.22 (m, 1H), 1.43 (d, 6H).
$^{13}$C-NMR (125 MHz, MSM-d6) δ ppm 147.4, 121.1/121, 102.3/102.2, 46.4, 42.6/42.4, 41/40.6, 23.1.

Preparation R3e: 6-[3-({4-hydroxy-1-[(3R,4R)-3-phenylpiperidine-4-carbonyl]piperidin-4-yl}methyl)-4-oxo-3H,4H,7H-pyrrolo[2,3-d]pyrimidin-7-yl]-1,2-dihydropyridin-2-one Using General Procedure 15 starting from Preparation R3bs as reagent, Preparation R3e was obtained as free base. HRMS calculated for C$_{29}$H$_{32}$N$_6$O$_4$: 528.2485; found 529.2567 [(M+H)$^+$ form].
$^1$H-NMR (500 MHz, MSM-d6) δ ppm 8.17/8.13 (s/s, 1H), 7.87/7.86 (d/d, 1H), 7.83/7.8 (d/d, 1H), 7.82 (t, 1H), 7.26-6.99 (m, 5H), 6.71/6.68 (d/d, 1H), 6.6 (d, 1H), 4.85 (brs, 1H), 4.12-0.75 (m, 16H), 3.21/3.15 (t/t, 1H), 2.86 (m, 1H).
$^{13}$C-NMR (125 MHz, MSM-d6) δ ppm 148.4, 142, 122.2, 107.9, 107.1, 103.9/103.8, 46.4/46.3, 43.4/42.9.

Preparation R3g: 7-cyclopropyl-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2g as reagent, Preparation R3g was obtained as HCl salt. HRMS calculated for C$_{27}$H$_{33}$N$_5$O$_3$: 475.2583; found 476.2668 [(M+H)$^+$ form].
$^1$H-NMR (500 MHz, MSM-d6) δ ppm 9.26/8.78 (brd+brq, 2H), 8.12-6.38 (m, 8H), 4.05-0.62 (m, 23H).

Preparation R3h: 7-cyclobutyl-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2h as reagent, Preparation R3h was obtained. HRMS calculated for C$_{28}$H$_{35}$N$_5$O$_3$: 489.274; found 490.2796 [(M+H)$^+$ form].

¹H-NMR (500 MHz, MSM-d6) δ ppm 8.92 (vbrs, 2H), 8.06/8.01 (s/s, 1H), 7.43/7.4 (d/d, 1H), 7.34-7.08 (m, 5H), 6.53/6.49 (d/d, 1H), 5.09 (m, 1H), 4.85 (s, 1H), 4.08-0.55 (m, 16H), 3.47/3.42 (m/m, 1H), 3.21 (m, 1H), 2.5/2.38 (m+m, 4H), 1.82 (m, 2H)
¹³C-NMR (500 MHz, MSM-d6) δ ppm 147.6/147.5, 122/121.9, 102.5/102.4, 48.5, 42.6/42.5, 41/40.6, 31, 14.8

Preparation R3k: 3-({4-hydroxy-1-[(3R,4R)-3-phenylpiperidine-4-carbonyl]piperidin-4-yl}methyl)-7-(1-methylpiperidin-4-yl)-3H,4H,7H-pyrrolo[2,3-d]pyrimidin-4-one Using General Procedure 5 starting from Preparation R2k as reagent, Preparation R3k was obtained as HCl salt. HRMS calculated for $C_{30}H_{40}N_6O_3$: 532.3162; found 267.1658 [(M+2H)$^{2+}$ form].
¹H-NMR (500 MHz, MSM-d6) δ ppm 10.87/10.67 (brs, 1H), 9.29/8.8 (brq+brd, 2H), 8.13/8.08 (s, 1H), 7.35-7.11 (m, 5H), 7.14/7.12 (d, 1H), 6.57/6.53 (d, 1H), 4.82 (brs, 1H), 4.76 (m, 1H), 4.08-2.61 (m, 16H), 2.78 (d, 3H), 2.47-1.96 (m, 4H), 1.95-0.59 (m, 6H).

Preparation R3m: 3-({4-hydroxy-1-[(3R,4R)-3-phenylpiperidine-4-carbonyl]piperidin-4-yl}methyl)-7-(prop-2-yn-1-yl)-3H,4H,7H-pyrrolo[2,3-d]pyrimidin-4-one Using General Procedure 5 starting from Preparation R2m as reagent, Preparation R3m was obtained as HCl salt. HRMS calculated for $C_{27}H_{31}N_5O_3$: 473.2427; found 474.2502 [(M+H)$^+$ form].
¹H-NMR (500 MHz, MSM-d6) δ ppm 9.32/8.83 (brd+brq, 2H), 8.12/8.06 (s, 1H), 7.33-7.12 (m, 12H), 7.33-7.12 (m, 5H), 7.22/7.2 (d, 1H), 6.55/6.51 (d, 1H), 5/4.98 (d, 2H), 3.44/3.43 (t, 1H), 1.92-0.62 (m, 6H).

Preparation R3n: 3-({4-hydroxy-1-[(3R,4R)-3-phenylpiperidine-4-carbonyl]piperidin-4-yl}methyl)-7-(2-methylpropyl)-3H,4H,7H-pyrrolo[2,3-d]pyrimidin-4-one Using General Procedure 5 starting from Preparation R2n as reagent, Preparation R3n was obtained as HCl salt. HRMS calculated for $C_{28}H_{37}N_5O_3$: 491.2896; found 492.2963 [(M+H)$^+$ form].
¹H-NMR (500 MHz, MSM-d6) δ ppm 9.3/8.81 (brd+brq, 2H), 8.07/8.01 (s, 1H), 7.33-7.12 (m, 5H), 7.15/7.13 (d, 1H), 6.49/6.46 (d, 1H), 4.05-2.61 (m, 14H), 2.12 (m, 1H), 1.92-0.61 (m, 6H), 0.84/0.83 (d, 6H).

Preparation R3o: 3-({4-hydroxy-1-[(3R,4R)-3-phenylpiperidine-4-carbonyl]piperidin-4-yl}methyl)-7-(2,2,2-trifluoroethyl)-3H,4H,7H-pyrrolo[2,3-d]pyrimidin-4-one Using General Procedure 5 starting from Preparation R2o as reagent, Preparation R3o was obtained as HCl salt. HRMS calculated for $C_{26}H_{30}F_3N_5O_3$: 517.2301; found 518.2386 [(M+H)$^+$ form]. ¹H-NMR (500 MHz, MSM-d6) δ ppm 9.11/8.67 (brq+brd, 2H), 8.16-6.55 (m, 8H), 5.15-0.6 (m, 20H), 4.87 (brs, 1H).

Preparation R3p: 7-(2,2-difluoroethyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2p as reagent, Preparation R3p was obtained as HCl salt. HRMS calculated for $C_{26}H_{31}F_2N_5O_3$: 499.2395; found 500.2485 [(M+H)$^+$ form].
¹H-NMR (500 MHz, MSM-d6) δ ppm 9.28/8.8 (brd+brq., 2H), 8.12/8.07 (s/s, 1H), 7.36-7.11 (m, 5H), 7.18/7.17 (d/d, 1H), 6.57/6.53 (d/d, 1H), 6.39 (tm, 1H), 4.6 (m, 2H), 4.07-0.6 (m, 16H), 3.48/3.42 (m/m, 1H), 3.22 (m, 1H).
¹³C-NMR (125 MHz, MSM-d6) δ ppm 148.2/148.1, 125.2, 114.4, 102.9/102.8, 46.1, 42.6/42.4, 41/40.6.

Preparation R3q: 7-(cyclopropylmethyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2q as reagent, Preparation R3q was obtained as HCl salt. HRMS calculated for $C_{28}H_{35}N_5O_3$: 489.2740; found 490.2817 [(M+H)$^+$ form].
¹H-NMR (500 MHz, MSM-d6) δ ppm 9.11/8.68 (brq+brd, 2H), 8.06/8 (s, 1H), 7.34-7.1 (m, 5H), 7.23/7.21 (d, 1H), 6.5/6.46 (d, 1H), 4.07-2.6 (m, 14H), 1.92-0.63 (m, 7H), 0.54-0.35 (m, 4H).

Preparation R3r: 7-(cyclobutylmethyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2r as reagent, Preparation R3r was obtained as HCl salt. HRMS calculated for $C_{29}H_{37}N_5O_3$: 503.2896; found 504.2957 [(M+H)$^+$ form].
¹H-NMR (400 MHz, MSM-d6) δ ppm 9.45/8.92 (brq+brd), 8.09/8.03 (s, 1H), 7.34-7.08 (m, 5H), 7.15/7.13 (d, 1H), 6.47/6.44 (d, 1H), 4.19-2.59 (m, 15H), 2.02-0.56 (m, 12H).

Preparation R3s: 7-(buta-2,3-dien-1-yl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2s as reagent, Preparation R3s was obtained as HCl. HRMS calculated for $C_{28}H_{33}N_5O_3$: 487.2583; found 488.2657 [(M+H)$^+$ form].
¹H-NMR (500 MHz, MSM-d6) δ ppm 9.28/8.8 (brd+brq, 2H), 8.09/8.03 (s, 1H), 7.34-7.11 (m, 5H), 7.15/7.14 (d, 1H), 6.51/6.47 (d, 1H), 5.5 (m, 1H), 4.9 (m, 2H), 4.88 (s, 1H), 4.73 (m, 2H), 4.06-2.63 (m, 12H), 1.94-0.6 (m, 6H).

Preparation R3t: 7-[3-(dimethylamino)propyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2t as reagent, Preparation R3t was obtained as HCl salt. HRMS calculated for $C_{29}H_{40}N_6O_3$: 520.3162; found 261.1666 [(M+2H) form].
¹H-NMR (500 MHz, MSM-d6) δ ppm 10.53 (brs, 1H), 9.33/8.83 (brs+brm, 2H), 8.13/8.07 (s/s, 1H), 7.36-7.14 (m, 5H), 7.23/7.21 (d/d, 1H), 6.53/6.5 (d/d, 1H), 4.2 (m, 2H), 4.06-0.55 (m, 16H), 3.48/3.43 (m/m, 1H), 3.22 (m, 1H), 3.02 (m, 2H), 2.72/2.71 (s/s, 6H), 2.17 (m, 2H).
¹³C-NMR (125 MHz, MSM-d6) δ ppm 147.9/147.8, 124.4/124.3, 102.4, 54.4, 42.6/42.4, 42.5, 42, 41/40.6, 25.6.

Preparation R3u: 7-(2-fluoroethyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2u as reagent, Preparation R3u was obtained as HCl salt. HRMS calculated for $C_{25}H_{31}FN_5O_3$: 468.2411; found 482.2555 [(M+H)$^+$ form].
$^1$H-NMR (500 MHz, MSM-d6) δ ppm 9.16/8.71 (m+m, 2H), 8.08/8.03 (s, 1H), 7.34-7.11 (m, 5H), 7.2/7.18 (d, 1H), 6.53/6.49 (d, 1H), 4.82 (brs, 1H), 4.76 (dt, 2H), 4.44 (dt, 2H), 4.11-2.6 (m, 12H), 1.95-0.6 (m, 6H).

Preparation R3v: 7-[2-(dimethylamino)ethyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2v as reagent, Preparation R3v was obtained as HCl salt. HRMS calculated for $C_{28}H_{38}N_6O_3$: 506.3005; found 254.1581 [(M+2H)$^{2+}$ form].
$^1$H-NMR (500 MHz, MSM-d6) δ ppm 10.48 (brs, 1H), 9.27/8.8 (brs+brm, 2H), 8.16/8.11 (s/s, 1H), 7.37-7.16 (m, 5H), 7.25 (d, 1H), 6.57/6.54 (d/d, 1H), 4.9 (vbrs, 1H), 4.53 (m, 2H), 4.13-0.55 (m, 16H), 3.51 (m, 2H), 3.48/3.43 (brm/brm, 1H), 3.22 (m, 1H), 2.8/2.79 (d/d, 6H).
$^{13}$C-NMR (125 MHz, MSM-d6) δ ppm 148.1, 124.4, 103, 55.9, 42.9, 42.6/42.4, 41/40.6, 39.6.

Preparation R3w: 3-({4-hydroxy-1-[(3R,4R)-3-phenylpiperidine-4-carbonyl]piperidin-4-yl}methyl)-7-(2-hydroxyethyl)-3H,4H,7H-pyrrolo[2,3-d]pyrimidin-4-one Using General Procedure 5 starting from Preparation R2w as reagent, Preparation R3w was obtained.
$^1$H-NMR (400 MHz, MSM-d6) δ ppm 8.05/7.99 (s/s, 1H), 7.27-7.02 (m, 5H), 7.16/7.14 (d/d, 1H), 6.47/6.45 (d/d, 1H), 4.94/4.93 (t/t, 1H), 4.83/4.8 (s/s, 1H), 4.15 (m, 2H), 4.06-0.72 (m, 16H), 3.71 (m, 2H), 3.2/3.15 (m/m, 1H), 2.86 (m, 1H).
$^{13}$C-NMR (100 MHz, MSM-d6) δ ppm 147.4, 125.1, 101.8/101.7, 60.6, 47.3, 46.5/46.4, 43.4.

Preparation R3x: 7-[(4-chlorophenyl)methyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2x as reagent, Preparation R3x was obtained as HCl salt. HRMS calculated for $C_{31}H_{34}ClN_5O_3$: 559.2350; found 560.2418 [(M+H)$^+$ form].
$^1$H-NMR (500 MHz, MSM-d6) δ ppm 9.04/8.63 (brd+brq, 2H), 8.07/8.02 (s, 1H), 7.44-7.07 (m, 9H), 7.26/7.24 (d, 1H), 6.54/6.5 (d, 1H), 5.34/5.33 (s, 2H), 4.81 (brs, 1H), 4.04-2.61 (m, 12H), 1.92-0.61 (m, 6H).

Preparation R3y: 7-[(3-chlorophenyl)methyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2y as reagent, Preparation R3y was obtained as HCl salt. HRMS calculated for $C_{31}H_{34}ClN_5O_3$: 559.2350; found 560.2432 [(M+H)$^+$ form].
$^1$H-NMR (500 MHz, MSM-d6) δ ppm 9.1/8.67 (brd+brq, 2H), 8.09/8.03 (s, 1H), 7.4-7.08 (m, 9H), 7.29/7.27 (d, 1H), 6.55/6.52 (d, 1H), 5.35/5.34 (s, 2H), 4.83 (brs, 1H), 4.05-2.62 (m, 12H), 1.91-0.61 (m, 6H).

Preparation R3z: 7-benzyl-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2z as reagent, Preparation R3z was obtained as HCl salt. HRMS calculated for $C_{31}H_{35}N_5O_3$: 525.2740; found 526.2822 [(M+H) form].
$^1$H-NMR (500 MHz, MSM-d6) δ ppm 9.31/8.82 (brd+brq, 2H), 8.1/8.05 (s, 1H), 7.36-7.09 (m, 10H), 7.25/7.22 (d, 1H), 6.53/6.5 (d, 1H), 5.34/5.33 (s, 2H), 4.05-2.63 (m, 12H), 1.92-0.62 (m, 6H).

Preparation R3aa: 7-[(2-chlorophenyl)methyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2aa as reagent, Preparation R3aa was obtained as HCl salt. HRMS calculated for $C_{31}H_{34}ClN_5O_3$: 559.2350; found 560.2429 [(M+H)$^+$ form].
$^1$H-NMR (500 MHz, MSM-d6) δ ppm 9.12/8.68 (brd+brq, 2H), 8.07/8.01 (s, 1H), 7.54-6.76 (m, 9H), 7.2/7.18 (d, 1H), 6.56/6.55 (d, 1H), 5.44/5.43 (s, 2H), 4.86/4.85 (s, 1H), 4.06-2.61 (m, 12H), 1.91-0.62 (m, 6H).

Preparation R3ac: 3-({4-hydroxy-1-[(3R,4R)-3-phenylpiperidine-4-carbonyl]piperidin-4-yl}methyl)-7-(3,4,5-trimethoxyphenyl)-3H,4H,7H-pyrrolo[2,3-d]pyrimidin-4-one Using General Procedure 5 starting from Preparation R2ac as reagent, Preparation R3ac was obtained as HCl salt. HRMS calculated for $C_{33}H_{39}N_5O_6$: 601.2900; found 602.2960 [(M+H)$^+$ form].
$^1$H-NMR (500 MHz, MSM-d6) δ ppm 9.55/9.01 (brq+brd, 2H), 8.16/8.12 (s, 1H), 7.54/7.51 (d, 1H), 7.36-7.14 (m, 5H), 7.01/6.99 (s, 2H), 6.7/6.67 (d, 1H), 4.95 (brs, 1H), 4.1-2.61 (m, 12H), 3.83 (s, 6H), 3.7 (s, 3H), 1.98-0.62 (m, 6H).

Preparation R3ad: 7-(3,5-dichlorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ad as reagent, Preparation R3ad was obtained as HCl salt. HRMS calculated for $C_{30}H_{31}N_5O_3Cl_2$: 579.1804; found 580.1891 [(M+H)$^+$ form].
$^1$H-NMR (500 MHz, MSM-d6) δ ppm 9.06/8.65 (brd+brq, 2H), 8.18/8.14 (s, 1H), 7.98/7.97 (d, 2H), 7.71/7.68 (d, 1H), 7.67 (t, 1H), 7.34-7.14 (m, 5H), 6.77/6.73 (d, 1H), 4.88 (brs, 1H), 4.12-2.62 (m, 12H), 1.96-0.62 (m, 6H).

Preparation R3ae: 7-(3-chloro-5-methoxyphenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ae as reagent, Preparation R3ae was obtained as HCl salt. HRMS calculated for $C_{31}H_{34}ClN_5O_4$: 575.2299; found 576.2382 [(M+H)$^+$ form].

¹H-NMR (500 MHz, MSM-d6) δ ppm 8.83 (brs, 2H), 8.15/8.1 (s, 1H), 7.64/7.62 (d, 1H), 7.51/7.5 (t, 1H), 7.36/7.34 (t, 1H), 7.36-7.12 (m, 5H), 7.09 (t, 1H), 6.74/6.7 (d, 1H), 4.87 (s, 1H), 4.11-2.62 (m, 12H), 3.85 (s, 3H), 1.94-0.62 (m, 6H).

Preparation R3af: 7-(3,5-dimethoxyphenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2af as reagent, Preparation R3af was obtained as HCl salt. HRMS calculated for $C_{32}H_{37}N_5O_5$: 571.2795; found 572.2881 [(M+H)$^+$ form].

¹H-NMR (500 MHz, MSM-d6) δ ppm 9.11/8.68 (brq+brd, 2H), 8.12/8.07 (s, 1H), 7.57/7.55 (d, 1H), 7.34-7.13 (m, 5H), 6.93/6.91 (d, 2H), 6.71/6.67 (d, 1H), 6.56/6.55 (t, 1H), 4.86 (brs, 1H), 4.09-2.62 (m, 12H), 3.81 (s, 6H), 1.94-0.64 (m, 6H).

Preparation R3ag: 7-(3,4-dichlorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ag as reagent, Preparation R3ag was obtained as HCl salt. HRMS calculated for $C_{30}H_{31}Cl_2N_5O_3$: 579.18042; found 580.1870 [(M+H)$^+$ form].

¹H-NMR (500 MHz, MSM-d6) δ ppm 9.16/8.71 (brq+brd, 2H), 8.2-7.79 (m, 3H), 8.17/8.13 (s, 1H), 7.65/7.63 (d, 1H), 7.35-7.12 (m, 5H), 6.76/6.72 (d, 1H), 4.85 (brs, 1H), 4.11-2.61 (m, 12H), 1.95-0.6 (m, 6H).

Preparation R3ah: 7-(4-chloro-3-fluorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ah as reagent, Preparation R3ah was obtained as HCl salt. HRMS calculated for $C_{30}H_{31}N_5O_3FCl$: 563.2100; found 564.2181 [(M+H)$^+$ form].

¹H-NMR (500 MHz, MSM-d6) δ ppm 9.08/8.66 (brm/brm, 2H), 8.16/8.12 (s, 1H), 7.98/7.97 (dd, 1H), 7.82-7.72 (m, 1H), 7.78 (m, 1H), 7.65/7.63 (d, 1H), 7.33-7.26 (m, 2H), 7.26-7.2 (m, 2H), 7.17 (brt, 1H), 6.77/6.73 (d, 1H), 4.86 (vbrs, 1H), 4.12-0.58, (16H), 4.05/3.94/3.67 (d/s, 2H).

¹³C-NMR (125 MHz, MSM-d6) δ ppm 158.3, 157.7, 148.7/148.6, 146.7/146.6, 131.6, 129/128.9, 128.3/128.1, 127.7, 124.1, 121, 112.7, 109.3/109.2, 104.5, 69.4, 53.6/53.3.

Preparation R3ai: 7-(4-chloro-3-methoxyphenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ai as reagent, Preparation R3ai was obtained as HCl salt. HRMS calculated for $C_{31}H_{34}ClN_5O_4$: 575.2230; found 576.2382 [(M+H)$^+$ form].

¹H-NMR (400 MHz, MSM-d6) δ ppm 8.89 (brs, 2H), 8.14/8.06 (s, 1H), 7.62/7.6 (d, 1H), 7.6 (d, 1H), 7.51/7.5 (d, 1H), 7.38/7.36 (dd, 1H), 7.35-7.13 (m, 5H), 6.75/6.71 (d, 1H), 4.87 (s, 1H), 4.11-2.6 (m, 12H), 3.93 (s, 3H), 1.95-0.6 (m, 6H).

Preparation R3aj: 7-(4-fluoro-3-methoxyphenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2aj as reagent, Preparation R3aj was obtained as HCl salt. HRMS calculated for $C_{31}H_{34}FN_5O_4$: 559.2595; found 560.2638 [(M+H)$^+$ form].

¹H-NMR (500 MHz, MSM-d6) δ ppm 9.13/8.7 (brd+brq, 1+1 H), 8.12/8.07 (s/s, 1H), 7.55/7.53 (d/d, 1H), 7.49 (m, 2H), 7.39 (m, 2H), 7.35-7.14 (m, 5H), 7.28 (m, 2H), 6.73/6.69 (d/d, 1H), 4.65-0.6 (m, 16H), 3.91 (s, 3H), 3.48/3.42 (m/m, 1H), 3.22 (m, 1H).

¹³C-NMR (125 MHz, MSM-d6) δ ppm 148.4/148.3, 124.8/124.7, 116.8, 116.6, 110.8, 103.7, 56.8, 42.6/42.5, 41/40.6.

Preparation R3ak: 7-(3,4-dimethoxyphenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ak as reagent, Preparation R3ak was obtained as HCl salt. HRMS calculated for $C_{32}H_{37}N_5O_5$: 571.2795; found 572.2892 [(M+H)$^+$ form].

¹H-NMR (500 MHz, MSM-d6) δ ppm 9.11/8.69 (brd+brq, 2H), 8.09/8.04 (s, 1H), 7.48/7.46 (d, 1H), 7.35-7.06 (m, 8H), 6.69/6.68 (d, 1H), 4.86 (brs, 1H), 4.11-2.6 (m, 12H), 3.81 (s, 6H), 1.96-0.62 (m, 6H).

Preparation R3am: 3-({4-hydroxy-1-[(3R,4R)-3-phenylpiperidine-4-carbonyl]piperidin-4-yl}methyl)-7-(4-methylphenyl)-3H,4H,7H-pyrrolo[2,3-d]pyrimidin-4-one Using General Procedure 5 starting from Preparation R2am as reagent, Preparation R3am was obtained as HCl salt. HRMS calculated for $C_{31}H_{35}N_5O_3$: 525.2734; found 526.2816 [(M+H)$^+$ form].

¹H-NMR (500 MHz, MSM-d6) δ ppm 9.31/8.82 (brd+brq, 2H), 8.11/8.06 (s, 1H), 7.6/7.58 (m, 2H), 7.49/7.46 (d, 1H), 7.35/7.34 (m, 2H), 7.32-7.11 (m, 5H), 6.71/6.67 (d, 1H), 4.81 (brs, 1H), 4.11-2.61 (m, 12H), 2.37 (s, 3H), 1.94-0.61 (m, 6H).

Preparation R3an: 4-[3-({4-hydroxy-1-[(3R,4R)-3-phenylpiperidine-4-carbonyl]piperidin-4-yl}methyl)-4-oxo-3H,4H,7H-pyrrolo[2,3-d]pyrimidin-7-yl]benzonitrile Using General Procedure 5 starting from Preparation R2an as reagent, Preparation R3an was obtained as HCl salt. HRMS calculated for $C_{31}H_{32}N_6O_3$: 536.2536; found 537.2599 [(M+H)$^+$ form].

¹H-NMR (500 MHz, MSM-d6) δ ppm 9.19/8.73 (brd+brq, 2H), 8.18/8.14 (s/s, 1H), 8.12-8 (m, 4H), 7.71/7.69 (d/d, 1H), 7.35-7.13 (m, 5H), 6.8/6.76 (d/d, 1H), 4.85 (vbrs, 1H), 4.15-0.6 (m, 16H), 3.48/3.42 (m/m, 1H), 3.22 (m, 1H).

Preparation R3ao: 3-({4-hydroxy-1-[(3R,4R)-3-phenylpiperidine-4-carbonyl]piperidin-4-yl}methyl)-7-[4-(trifluoromethyl)phenyl]-3H,4H,7H-pyrrolo[2,3-d]pyrimidin-4-one Using General Procedure 5 starting from Preparation R2ao as reagent, Preparation R3ao was obtained as HCl salt. HRMS calculated for $C_{31}H_{32}N_5O_3F_3$: 579.2457; found 580.2529 [(M+H)$^+$ form].
$^1$H-NMR (500 MHz, MSM-d6) δ ppm 9.13/8.7 (brs+brs, 2H), 8.17/8.12 (s/s, 1H), 8.05/8.04 (d/d, 2H), 7.94/7.93 (d/d, 2H), 7.68/7.66 (d/d, 1H), 7.35-7.12 (m, 5H), 6.79/6.75 (d/d, 1H), 4.88 (s, 1H), 4.2-0.59 (m, 16H), 3.48/3.42 (m/m, 1H), 3.22 (m, 1H).

Preparation R3ap: 7-[4-(difluoromethyl)phenyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ap as reagent, Preparation R3ap was obtained as HCl salt. HRMS calculated for $C_{31}H_{33}F_2N_5O_3$: 561.2551; found 562.2636 [(M+H) form].
$^1$H-NMR (500 MHz, MSM-d6) δ ppm 9.11/8.68 (brd+brq, 2H), 8.14/8.09 (s, 1H), 7.93/7.91 (m, 2H), 7.76/7.75 (m, 2H), 7.62/7.6 (d, 1H), 7.34-7.12 (m, 5H), 7.13 (t, 1H), 6.77/6.73 (d, 1H), 4.87 (s, 1H), 4.11-2.61 (m, 12H), 1.93-0.64 (m, 6H).

Preparation R3aq: 3-({4-hydroxy-1-[(3R,4R)-3-phenylpiperidine-4-carbonyl]piperidin-4-yl}methyl)-7-[4-(hydroxymethyl)phenyl]-3H,4H,7H-pyrrolo[2,3-d]pyrimidin-4-one Using General Procedure 5 starting from Preparation R2aq as reagent, Preparation R3aq was obtained as HCl salt. HRMS calculated for $C_{31}H_{35}N_5O_4$: 541.2689; found 542.2787 [(M+H)$^+$ form].
$^1$H-NMR (500 MHz, MSM-d6) δ ppm 9.2/8.74 (brd+brq, 1+1 H), 8.11/8.06 (s/s, 1H), 7.67/7.65 (dm/dm, 2H), 7.51/7.48 (d/d, 1H), 7.47 (m, 2H), 7.34-7.1 (m, 5H), 6.72/6.68 (d/d, 1H), 4.56 (s, 2H), 4.08-0.61 (m, 16H), 3.48/3.43 (m/m, 1H), 3.21 (m, 1H).
$^{13}$C-NMR (125 MHz, MSM-d6) δ ppm 148.3/148.2, 127.8, 124.4, 124.2, 103.8, 62.8, 42.6/42.5, 41/40.6.

Preparation R3ar: 7-(4-chlorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ar as reagent, Preparation R3ar was obtained as HCl salt. HRMS calculated for $C_{30}H_{32}ClN_5O_3$: 545.2194; found 546.2288 [(M+H)$^+$ form].
$^1$H-NMR (500 MHz, MSM-d6) δ ppm 9.38/8.87 (brs, 2H), 8.24-6.62 (m, 12H), 4.13-0.58 (m, 18H).

Preparation R3as: 7-(4-fluorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2as as reagent, Preparation R3as was obtained as HCl salt. HRMS calculated for $C_{30}H_{32}N_5O_3F$: 529.2489; found 530.2563 [(M+H)$^+$ form].
$^1$H-NMR (500 MHz, MSM-d6) δ ppm 9.05/8.64 (brd+brq, 2H), 8.11/8.06 (s, 1H), 7.76/7.75 (m, 2H), 7.52/7.5 (d, 1H), 7.41/7.4 (m, 2H), 7.34-7.13 (m, 5H), 6.73/6.69 (d, 1H), 4.84 (brs, 1H), 4.1-2.65 (m, 12H), 1.95-0.63 (m, 6H).

Preparation R3at: 7-[4-(dimethylamino)phenyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2at as reagent, Preparation R3at was obtained as HCl salt. HRMS calculated for $C_{32}H_{38}N_6O_3$: 554.3005; found 555.3076 [(M+H)$^+$ form].
$^1$H-NMR (500 MHz, MSM-d6) δ ppm 9.15/8.71 (brd+brq, 2H), 8.07/8.02 (s, 1H), 7.52 (brm, 2H), 7.41/7.38 (d, 1H), 7.33-7.11 (m, 5H), 6.99 (brs, 2H), 6.68/6.64 (d, 1H), 4.07-2.62 (m, 12H), 2.99 (s, 6H), 1.93-0.64 (m, 6H).

Preparation R3ax: 3-({4-hydroxy-1-[(3R,4R)-3-phenylpiperidine-4-carbonyl]piperidin-4-yl}methyl)-7-(4-methoxyphenyl)-3H,4H,7H-pyrrolo[2,3-d]pyrimidin-4-one Using General Procedure 5 starting from Preparation R2ax as reagent, Preparation R3ax was obtained as HCl salt. HRMS calculated for $C_{31}H_{35}N_5O_4$: 541.2689; found 542.2782 [(M+H)$^+$ form].
$^1$H-NMR (500 MHz, MSM-d6) δ ppm 9.2/8.74 (brd+brq, 2H), 8.09/8.04 (s, 1H), 7.63-7.55 (m, 2H), 7.44/7.42 (d, 1H), 7.33-7.12 (m, 5H), 7.12-7.06 (m, 2H), 6.69/6.65 (d, 1H), 4.85 (brs, 1H), 4.07-2.63 (m, 12H), 3.82/3.75 (s, 3H), 1.95-0.61 (m, 6H).

Preparation R3ay: 3-({4-hydroxy-1-[(3R,4R)-3-phenylpiperidine-4-carbonyl]piperidin-4-yl}methyl)-7-[4-(trifluoromethoxy)phenyl]-3H,4H,7H-pyrrolo[2,3-d]pyrimidin-4-one Using General Procedure 5 starting from Preparation R2ay as reagent, Preparation R3ay was obtained as HCl salt. HRMS calculated for $C_{31}H_{32}N_5O_4F_3$: 595.2407; found 596.2494 [(M+H)$^+$ form].
$^1$H-NMR (400 MHz, MSM-d6) δ ppm 9.08/8.66 (brs, 2H), 8.13/8.08 (s, 1H), 7.93-7.53 (m, 4H), 7.59/7.57 (d, 1H), 7.36-7.12 (m, 5H), 6.75/6.72 (d, 1H), 4.86 (s, 1H), 4.14-2.59 (m, 12H), 1.95-0.63 (m, 6H).

Preparation R3az: 7-[4-(benzyloxy)phenyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2az as reagent, Preparation R3az was obtained as HCl salt. HRMS calculated for $C_{37}H_{39}N_5O_4$: 617.3002; found 618.3083 [(M+H)$^+$ form].
$^1$H-NMR (500 MHz, MSM-d6) δ ppm 9.12/8.68 (brs+brs, 2H), 8.08/8.03 (s, 1H), 7.6/7.58 (m, 2H), 7.51-7.11 (m, 10H), 7.45/7.42 (d, 1H), 7.17 (m, 2H), 6.69/6.65 (d, 1H), 5.18 (s, 2H), 4.85 (s, 1H), 4.1-2.6 (m, 12H), 1.95-0.61 (m, 6H).

Preparation R3ba: 3-({4-hydroxy-1-[(3R,4R)-3-phenylpiperidine-4-carbonyl]piperidin-4-yl}methyl)-7-(5-methylthiophen-2-yl)-3H,4H,7H-pyrrolo[2,3-d]pyrimidin-4-one Using General Procedure 5 starting from Preparation R2ba as reagent, Preparation R3ba was obtained as HCl salt. HRMS calculated for $C_{29}H_{33}N_5O_3S$: 531.2304; found 532.2361 [(M+H) form].

¹H-NMR (500 MHz, MSM-d6) δ ppm 9.05/8.68 (brs+brs, 2H), 8.14/8.1 (s, 1H), 7.53/7.51 (d, 1H), 7.33-7.11 (m, 5H), 7.16/7.15 (d, 1H), 6.77/6.76 (m, 1H), 6.71/6.67 (d, 1H), 4.88/4.87 (s, 1H), 4.09-2.62 (m, 12H), 2.46 (d, 3H), 1.92-0.62 (m, 6H).

Preparation R3bb: 7-(5-chlorothiophen-2-yl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bb as reagent, Preparation R3bb was obtained as HCl salt. HRMS calculated for $C_{28}H_{30}ClN_5O_3S$: 551.1758; found 552.1844 [(M+H)⁺ form].

¹H-NMR (500 MHz, MSM-d6) δ ppm 9.06/8.76 (brs+brs, 2H), 8.21/8.16 (s/s, 1H), 7.71/7.68 (d/d, 1H), 7.32/7.31 (d/d, 1H), 7.32-7.12 (m, 5H), 7.15/7.14 (d/d, 1H), 6.76/6.73 (d/d, 1H), 4.1-0.58 (m, 16H), 3.47/3.41 (m/m, 1H), 3.21 (m, 1H).

¹³C-NMR (125 MHz, MSM-d6) δ ppm 149.2/149.1, 125.6, 123.6, 117.6/117.5, 104.9, 42.6/42.5, 41/40.6.

Preparation R3bc: 7-(2,3-dihydro-1,4-benzodioxin-6-yl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bc as reagent, Preparation R3bc was obtained as HCl salt. HRMS calculated for $C_{32}H_{35}N_5O_5$: 569.2638; found 570.2709 [(M+H)⁺ form].

¹H-NMR (500 MHz, MSM-d6) δ ppm 9.42/8.89 (brd+brq, 2H), 8.11/8.06 (s, 1H), 7.44/7.41 (d, 1H), 7.33-7.11 (m, 5H), 7.23/7.22 (d, 1H), 7.15/7.13 (dd, 1H), 7/6.99 (d, 1H), 6.67/6.63 (d, 1H), 4.35-4.26 (m, 4H), 4.09-2.62 (m, 12H), 1.94-0.61 (m, 6H).

Preparation R3bd: 7-(2H-1,3-benzodioxol-5-yl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bd as reagent, Preparation R3bd was obtained as HCl salt. HRMS calculated for $C_{31}H_{33}N_5O_5$: 555.2482; found 570.2709 [(M+H)⁺ form].

¹H-NMR (500 MHz, MSM-d6) δ ppm 9.21/8.78 (brs+brs, 2H), 8.1/8.05 (s, 1H), 7.44/7.42 (d, 1H), 7.35-7.11 (m, 5H), 7.3/7.28 (d, 1H), 7.14/7.13 (dd, 1H), 7.07/7.06 (d, 1H), 6.68/6.64 (d, 1H), 6.12 (s, 2H), 4.87 (s, 1H), 4.09-2.62 (m, 12H), 1.95-0.62 (m, 6H).

Preparation R3be: 3-({4-hydroxy-1-[(3R,4R)-3-phenylpiperidine-4-carbonyl]piperidin-4-yl}methyl)-7-(naphthalen-2-yl)-3H,4H,7H-pyrrolo[2,3-d]pyrimidin-4-one Using General Procedure 5 starting from Preparation R2be as reagent, Preparation R3be was obtained as HCl salt. HRMS calculated for $C_{34}H_{35}N_5O_3$: 561.2740; found 562.2831 [(M+H)⁺ form].

¹H-NMR (500 MHz, MSM-d6) δ ppm 9.16/8.72 (brd+brq, 2H), 8.3-7.54 (m, 7H), 8.16/8.11 (s, 1H), 7.67/7.65 (d, 1H), 7.35-7.13 (m, 5H), 6.79/6.75 (d, 1H), 4.89 (brs, 1H), 4.12-2.65 (m, 12H), 1.96-0.65 (m, 6H).

Preparation R3bf: 3-({4-hydroxy-1-[(3R,4R)-3-phenylpiperidine-4-carbonyl]piperidin-4-yl}methyl)-7-(3-methylphenyl)-3H,4H,7H-pyrrolo[2,3-d]pyrimidin-4-one Using General Procedure 5 starting from Preparation R2bf as reagent, Preparation R3bf was obtained. HRMS calculated for $C_{31}H_{35}N_5O_3$: 525.2740; found 526.2825 [(M+H)⁺ form].

¹H-NMR (500 MHz, MSM-d6) δ ppm 9.13/8.69 (brq+brd, 2H), 8.11/8.06 (s, 1H), 7.57-7.11 (m, 10H), 6.71/6.67 (d, 1H), 4.2-2.62 (m, 12H), 1.94-0.59 (m, 6H).

Preparation R3bg: 3-({4-hydroxy-1-[(3R,4R)-3-phenylpiperidine-4-carbonyl]piperidin-4-yl}methyl)-7-[3-(trifluoromethyl)phenyl]-3H,4H,7H-pyrrolo[2,3-d]pyrimidin-4-one Using General Procedure 5 starting from Preparation R2bg as reagent, Preparation R3bg was obtained as HCl salt. HRMS calculated for $C_{31}H_{32}F_3N_5O_3$: 579.2457; found 580.2509 [(M+H)⁺ form].

¹H-NMR (400 MHz, MSM-d6) δ ppm 9.2/8.74 (brd+brq, 2H), 8.19/8.17 (m, 1H), 8.17/8.13 (s, 1H), 8.09/8.07 (dm, 1H), 7.86-7.74 (m, 2H), 7.7/7.67 (d, 1H), 7.35-7.11 (m, 5H), 6.78/6.74 (d, 1H), 4.78 (brs, 1H), 4.11-2.6 (m, 12H), 1.94-0.62 (m, 6H).

Preparation R3bh: 3-({4-hydroxy-1-[(3R,4R)-3-phenylpiperidine-4-carbonyl]piperidin-4-yl}methyl)-7-{3-[(4-methylpiperazin-1-yl)methyl]phenyl}-3H,4H,7H-pyrrolo[2,3-d]pyrimidin-4-one Using General Procedure 5 starting from Preparation R2bh as reagent, Preparation R3bh was obtained as HCl salt. HRMS calculated for $C_{36}H_{45}N_7O_3$: 623.3584; found 624.3656 [(M+H)⁺ form].

¹H-NMR (500 MHz, MSM-d6) δ ppm 12.37/11.6 (brs, 2H), 9.33/8.83 (brd+brq, 2H), 8.18/8.12 (s, 1H), 8.04-7.5 (m, 5H), 7.35-7.13 (m, 5H), 6.75/6.72 (d, 1H), 4.6-2.6 (m, 22H), 2.79 (s, 3H), 1.98-0.66 (m, 6H).

Preparation R3bi: 3-({4-hydroxy-1-[(3R,4R)-3-phenylpiperidine-4-carbonyl]piperidin-4-yl}methyl)-7-[3-(hydroxymethyl)phenyl]-3H,4H,7H-pyrrolo[2,3-d]pyrimidin-4-one Using General Procedure 5 starting from Preparation R2bi as reagent, Preparation R3bi was obtained as HCl salt. HRMS calculated for $C_{31}H_{35}N_5O_4$: 541.2689; found 542.2769 [(M+H)⁺ form].

¹H-NMR (500 MHz, MSM-d6) δ ppm 8.98/8.72 (brs+brs, 2H), 8.1/8.05 (s/s, 1H), 7.69-7.33 (m, 4H), 7.51/7.48 (d/d, 1H), 7.33-7.11 (m, 5H), 6.73/6.69 (d/d, 1H), 5.36 (t, 1H), 4.59 (d, 2H), 4.15-0.61 (m, 16H), 3.48/3.42 (m/m, 1H), 3.22 (m, 1H).

Preparation R3bj: 7-(3-chlorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bj as reagent, Preparation R3bj was obtained as HCl salt. HRMS calculated for $C_{30}H_{32}N_5O_3Cl$: 545.2194; found 546.2277 [(M+H)⁺ form].

¹H-NMR (500 MHz, MSM-d6) δ ppm 9.17/8.72 (brd+brq, 2H), 8.15/8.11 (s, 1H), 7.94-7.45 (m, 4H), 7.63/7.6 (d, 1H), 7.34-7.12 (m, 5H), 6.75/6.71 (d, 1H), 4.88 (brs, 1H), 4.13-2.62 (m, 12H), 1.95-0.62 (m, 6H).

Preparation R3bk: 7-(3-fluorophenyl)-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bk as reagent, Preparation R3bk was obtained. HRMS calculated for $C_{30}H_{32}FN_5O_3$: 529.2489; found 530.2571 [(M+H)⁺ form].

¹H-NMR (500 MHz, MSM-d6) δ ppm 9/8.61 (brd+brq, 1+1 H), 8.14/8.09 (s/s, 1H), 7.76-7.23 (m, 4H), 7.62/7.6 (d/d, 1H), 7.34-7.13 (m, 5H), 6.75/6.71 (d/d, 1H), 4.14-0.6 (m, 16 H), 3.47/3.42 (m/m, 1H), 3.2 (m, 1H).

¹³C-NMR (125 MHz, MSM-d6) δ ppm 148.6/148.5, 124.2, 104.3/104.2, 42.6/42.5, 41/40.6.

Preparation R3bl: 7-[3-(dimethylamino)phenyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bl as reagent, Preparation R3bl was obtained as HCl salt. HRMS calculated for $C_{32}H_{38}N_6O_3$: 554.3005; found 555.3086 [(M+H)⁺ form].

¹H-NMR (500 MHz, MSM-d6) δ ppm 9.23/8.76 (brd+brq, 1+1 H), 8.1/8.05 (s/s, 1H), 7.51/7.49 (d/d, 1H), 7.37 (brt, 1H), 7.33-7.13 (m, 5H), 7.18-6.76 (brd, 3H), 6.7/6.66 (d/d, 1H), 4.09-0.61 (m, 16H), 3.47/3.43 (m/m, 1H), 3.22 (m, 1H), 2.98 (s, 6H).

¹³C-NMR (125 MHz, MSM-d6) δ ppm 148.2/148.1, 130.2, 124.7, 103.6/103.5, 42.6/42.5, 41.1, 41/40.6.

Preparation R3bm: 3-({4-hydroxy-1-[(3R,4R)-3-phenylpiperidine-4-carbonyl]piperidin-4-yl}methyl)-7-[3-(morpholin-4-yl)phenyl]-3H,4H,7H-pyrrolo[2,3-d]pyrimidin-4-one Using General Procedure 5 starting from Preparation R2bm as reagent, Preparation R3bm was obtained as HCl salt. HRMS calculated for $C_{34}H_{40}N_6O_4$: 596.3111; found 597.3187 [(M+H)⁺ form].

¹H-NMR (500 MHz, MSM-d6) δ ppm 9.22/8.75 (brd+brq, 1+1 H), 8.1/8.06 (s/s, 1H), 7.52/7.49 (d/d, 1H), 7.38/7.37 (t/t, 1H), 7.33-7.13 (m, 5H), 7.23/7.21 (brs/brs, 1H), 7.14/7.12 (d/d, 1H), 7 (brd., 1H), 6.7/6.66 (d/d, 1H), 4.09-0.62 (m, 16H), 3.76 (m, 4H), 3.47/3.42 (m/m, 1H), 3.22 (m, 1H), 3.19 (m, 4H).

¹³C-NMR (125 MHz, MSM-d6) δ ppm 148.2/148.1, 130.1, 124.7/124.6, 115.3, 114.2, 111.3/111.2, 103.6/103.5, 66.5, 48.7, 42.6, 41/40.5.

Preparation R3bo: 3-({4-hydroxy-1-[(3R,4R)-3-phenylpiperidine-4-carbonyl]piperidin-4-yl}methyl)-7-(3-methoxyphenyl)-3H,4H,7H-pyrrolo[2,3-d]pyrimidin-4-one Using General Procedure 5 starting from Preparation R2bo as reagent, Preparation R3bo was obtained as HCl salt. HRMS calculated for $C_{31}H_{35}N_5O_4$: 541.2689; found 542.2762 [(M+H)⁺ form].

¹H-NMR (500 MHz, MSM-d6) δ ppm 9.21/8.75 (brd+brq, 2H), 8.12/8.01 (s, 1H), 7.56/7.54 (d, 1H), 7.49-6.96 (m, 9H), 6.72/6.68 (d, 1H), 4.84 (brs, 1H), 4.16-2.62 (m, 12H), 1.95-0.63 (m, 6H).

Preparation R3bp: 3-({4-hydroxy-1-[(3R,4R)-3-phenylpiperidine-4-carbonyl]piperidin-4-yl}methyl)-7-[3-(trifluoromethoxy)phenyl]-3H,4H,7H-pyrrolo[2,3-d]pyrimidin-4-one Using General Procedure 5 starting from Preparation R2bp as reagent, Preparation R3bp was obtained as HCl salt. HRMS calculated for $C_{31}H_{32}N_5O_4F_3$: 595.2407; found 596.2491 [(M+H)⁺ form].

¹H-NMR (400 MHz, MSM-d6) δ ppm 8.87 (brs, 2H), 8.16/8.11 (s, 1H), 7.9/7.88 (brs, 1H), 7.85/7.84 (dm, 1H), 7.7/7.69 (t, 1H), 7.66/7.63 (d, 1H), 7.43 (dm, 1H), 7.34-7.11 (m, 5H), 6.77/6.73 (d, 1H), 4.87/4.86 (s, 1H), 4.12-2.62 (m, 12H), 1.97-0.61 (m, 6H).

Preparation R3bq: 7-[3-(benzyloxy)phenyl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2bq as reagent, Preparation R3bq was obtained as HCl salt. HRMS calculated for $C_{37}H_{39}N_5O_4$: 617.3002; found 618.3051 [(M+H)⁺ form].

¹H-NMR (500 MHz, MSM-d6) δ ppm 9.24/8.77 (brd+brq, 2H), 8.12/8.08 (s, 1H), 7.56/7.53 (d, 1H), 7.51-7.03 (m, 14H), 6.72/6.68 (d, 1H), 5.18 (s, 2H), 4.09-2.63 (m, 12H), 1.94-0.62 (m, 6H).

Preparation R3br: 3-({4-hydroxy-1-[(3R,4R)-3-phenylpiperidine-4-carbonyl]piperidin-4-yl}methyl)-7-(6-methylpyridin-2-yl)-3H,4H,7H-pyrrolo[2,3-d]pyrimidin-4-one Using General Procedure 5 starting from Preparation R2br as reagent, Preparation R3br was obtained as HCl salt. HRMS calculated for $C_{30}H_{34}N_6O_3$: 526.2692; found 527.2764 [(M+H)⁺ form].

¹H-NMR (500 MHz, MSM-d6) δ ppm 9.43/8.91 (brq+brd, 2H), 8.26/8.25 (dm, 1H), 8.25/8.2 (s, 1H), 7.92/7.9 (d, 1H), 7.92 (m, 1H), 7.34-7.11 (m, 5H), 7.26 (m, 1H), 6.73/6.69 (d, 1H), 4.12-2.63 (m, 12H), 2.53/2.52 (s, 3H), 1.95-0.64 (m, 6H).

Preparation R3bs: 3-({4-hydroxy-1-[(3R,4R)-3-phenylpiperidine-4-carbonyl]piperidin-4-yl}methyl)-7-(6-methoxypyridin-2-yl)-3H,4H,7H-pyrrolo[2,3-d]pyrimidin-4-one Using General Procedure 5 starting from Preparation R2bs as reagent, Preparation R3bs was obtained as HCl salt. HRMS calculated for $C_{30}H_{34}N_6O_4$: 542.2642; found 543.2698 [(M+H)⁺ form].

¹H-NMR (500 MHz, MSM-d6) δ ppm 8.95 (brs, 2H), 8.8/6.81 (dd, 1H), 8.23/8.18 (s, 1H), 8.08/8.07 (dd, 1H), 8/7.98 (d, 1H), 7.93/7.92 (t, 1H), 7.35-7.1 (m, 5H), 6.75/6.72 (d, 1H), 4.14-2.62 (m, 12H), 3.95/3.94 (s, 3H), 1.96-0.62 (m, 6H).

Preparation R3bt: 3-({4-hydroxy-1-[(3R,4R)-3-phenylpiperidine-4-carbonyl]piperidin-4-yl}methyl)-7-(naphthalen-1-yl)-3H,4H,7H-pyrrolo[2,3-d]pyrimidin-4-one Using General Procedure 5 starting from Preparation R2bt as reagent, Preparation R3bt was obtained as HCl salt. HRMS calculated for $C_{34}H_{35}N_5O_3$: 561.2740; found 562.2827 [(M+H) form].
$^1$H-NMR (500 MHz, MSM-d6) δ ppm 9.28/8.8 (brq+brd, 2H), 8.17-6.74 (m, 15H), 4.82 (brs, 1H), 4.26-0.57 (m, 18H).

Preparation R3bu: 3-({4-hydroxy-1-[(3R,4R)-3-phenylpiperidine-4-carbonyl]piperidin-4-yl}methyl)-7-phenyl-3H,4H,7H-pyrrolo[2,3-d]pyrimidin-4-one Using General Procedure 5 starting from Preparation R2bu as reagent, Preparation R3bu was obtained as HCl salt. HRMS calculated for $C_{30}H_{33}N_5O_3$: 511.2583; found 512.2675 [(M+H) form].
$^1$H-NMR (500 MHz, MSM-d6) δ ppm 9.1/8.67 (brd+brd, 2H), 8.11/8.06 (s/s, 1H), 7.75-7.38 (m, 5H), 7.54/7.52 (d/d, 1H), 7.34-7.12 (m, 5H), 6.73/6.69 (d/d, 1H), 4.86 (s, 1H), 4.13-0.62 (m, 16H), 3.47/3.42 (m/m, 1H), 3.22 (m, 1H).
$^{13}$C-NMR (125 MHz, MSM-d6) δ ppm 148.3/148.2, 124.5/124.4, 103.9/103.8, 42.6/42.5, 41/40.6.

Preparation R3ca: 3-({4-hydroxy-1-[(3R,4R)-3-phenylpiperidine-4-carbonyl]piperidin-4-yl}methyl)-7-(pyridin-2-yl)-3H,4H,7H-pyrrolo[2,3-d]pyrimidin-4-one Using General Procedure 5 starting from Preparation R2ca as reagent, Preparation R3ca was obtained as HCl salt. HRMS calculated for $C_{29}H_{32}N_6O_3$: 512.2536; found 513.2612 [(M+H) form].
$^1$H-NMR (500 MHz, MSM-d6) δ ppm 9.07/8.65 (brd+brq, 2H), 8.56/8.55 (dm, 1H), 8.48/8.46 (dm, 1H), 8.22/8.17 (s, 1H), 8.05 (m, 1H), 7.94/7.92 (d, 1H), 7.41 (m, 1H), 7.33-7.12 (m, 5H), 6.75/6.71 (d, 1H), 4.9 (s, 1H), 4.15-2.63 (m, 12H), 1.92-0.65 (m, 6H).

Preparation R3cb: 3-({4-hydroxy-1-[(3R,4R)-3-phenylpiperidine-4-carbonyl]piperidin-4-yl}methyl)-7-(pyridin-3-yl)-3H,4H,7H-pyrrolo[2,3-d]pyrimidin-4-one Using General Procedure 5 starting from Preparation R2cb as reagent, Preparation R3cb was obtained. HRMS calculated for $C_{29}H_{32}N_6O_3$: 512.2536; found 513.261 [(M+H) form].
$^1$H-NMR (500 MHz, MSM-d6) δ ppm 9.35/8.85 (brd+brq, 1+1 H), 9.1/9.09 (d/d, 1H), 8.68 (dd, 1H), 8.39 (m, 1H), 8.2/8.15 (s/s, 1H), 7.75 (dd, 1H), 7.69/7.67 (d/d, 1H), 7.34-7.16 (m, 5H), 6.81/6.77 (d/d, 1H), 4.1-0.6 (m, 16H), 3.49/3.43 (m/m, 1H), 3.23 (m, 1H)
$^{13}$C-NMR (500 MHz, MSM-d6) δ ppm 148.9/148.8, 146.5, 143.4, 133.6/133.5, 125.4, 124, 104.8/104.7, 42.6/42.4, 41/40.6 Preparation R3cc: 3-({4-hydroxy-1-[(3R,4R)-3-phenylpiperidine-4-carbonyl]piperidin-4-yl}methyl)-7-(thiophen-2-yl)-3H,4H,7H-pyrrolo[2,3-d]pyrimidin-4-one
Using General Procedure 5 starting from Preparation R2cc as reagent, Preparation R3cc was obtained as HCl salt. HRMS calculated for $C_{28}H_{31}N_5O_3S$: 517.2148; found 518.2231 [(M+H)$^+$ form].
$^1$H-NMR (500 MHz, MSM-d6) δ ppm 9.15/8.7 (brd+brq, 1+1 H), 8.18/8.13 (s/s, 1H), 7.62/7.59 (d/d, 1H), 7.45/7.44 (dd, 1H), 7.4/7.39 (d/d, 1H), 7.32-7.11 (m, 5H), 7.09/7.08 (dd, 1H), 6.74/6.7 (d/d, 1H), 4.89 (brs, 1H), 4.1-0.6 (m, 16H), 3.47/3.42 (m/m, 1H), 3.21 (m, 1H).
$^{13}$C-NMR (125 MHz, MSM-d6) δ ppm 148.9/148.8, 126.1, 124.6, 122.9, 119.3/119.2, 104.5/104.4, 42.6/42.5, 41/40.6.

Preparation R3cd: 3-({4-hydroxy-1-[(3R,4R)-3-phenylpiperidine-4-carbonyl]piperidin-4-yl}methyl)-7-(pyridin-4-yl)-3H,4H,7H-pyrrolo[2,3-d]pyrimidin-4-one Using General Procedure 5 starting from Preparation R2cd as reagent, Preparation R3cd was obtained. HRMS calculated for $C_{29}H_{32}N_6O_3$: 512.2536; found 513.2609 [(M+H)$^+$ form].
$^1$H-NMR (500 MHz, MSM-d6) δ ppm 9.46/8.94 (brs+brq, 1+1 H), 9 (dm, 2H), 8.74 (m, 2H), 8.4/8.36 (s/s, 1H), 8.05/8.03 (d/d, 1H), 7.38-7.17 (m, 5H), 6.95/6.92 (d/d, 1H), 4.16-0.56 (m, 16H), 3.5/3.44 (m/m, 1H), 3.24 (m, 1H)
$^{13}$C-NMR (500 MHz, MSM-d6) δ ppm 149.8, 144.4, 123.2/123.1, 117.8, 107.4/107.3, 42.6/42.4, 41.1/40.6

Preparation R3cf: 3-({4-hydroxy-1-[(3R,4R)-3-phenylpiperidine-4-carbonyl]piperidin-4-yl}methyl)-7-(thiophen-3-yl)-3H,4H,7H-pyrrolo[2,3-d]pyrimidin-4-one Using General Procedure 5 starting from Preparation R2cf as reagent, Preparation R3cf was obtained as HCl salt. HRMS calculated for $C_{28}H_{31}N_5O_3S$: 517.2148; found 518.2233 [(M+H)$^+$ form].
$^1$H-NMR (500 MHz, MSM-d6) δ ppm 9.29/8.8 (brd+brq, 2H), 8.17/8.12 (s, 1H), 7.97-7.66 (m, 3H), 7.62/7.6 (d, 1H), 7.33-7.11 (m, 5H), 6.71/6.67 (d, 1H), 4.91 (brs, 1H), 4.12-2.63 (m, 12H), 1.94-0.63 (m, 6H).

Preparation R3cg: 3-({4-hydroxy-1-[(3R,4R)-3-phenylpiperidine-4-carbonyl]piperidin-4-yl}methyl)-7-(1-methyl-1H-imidazol-4-yl)-3H,4H,7H-pyrrolo[2,3-d]pyrimidin-4-one Using General Procedure 5 starting from Preparation R2cg as reagent, Preparation R3cg was obtained as HCl salt. HRMS calculated for $C_{28}H_{33}N_7O_3$: 515.2645; found 516.2728 [(M+H)$^+$ form].
$^1$H-NMR (500 MHz, MSM-d6) δ ppm 9.3/8.81 (brq+brd), 8.19/8.14 (s, 1H), 7.85 (brs, 1H), 7.68 (brs, 1H), 7.6/7.57 (d, 1H), 7.33-7.11 (m, 5H), 6.68/6.64 (brs, 1H), 4.14-2.63 (brs, 12H), 3.77 (s, 3H), 1.95-0.63 (m, 6H).

Preparation R3ch: 3-({4-hydroxy-1-[(3R,4R)-3-phenylpiperidine-4-carbonyl]piperidin-4-yl}methyl)-7-(1-methyl-1H-pyrazol-4-yl)-3H,4H,7H-pyrrolo[2,3-d]pyrimidin-4-one Using General Procedure 5 starting from Preparation R2ch as reagent, Preparation R3ch was obtained as HCl salt. HRMS calculated for $C_{28}H_{33}N_7O_3$: 515.2645; found 516.2716 [(M+H)$^+$ form].
$^1$H-NMR (500 MHz, MSM-d6) δ ppm 9.25/8.78 (brd+brq., 2H), 8.3/8.29 (s/s, 1H), 8.15/8.1 (s/s, 1H), 7.94/7.92 (d/d, 1H), 7.47/7.44 (d/d, 1H), 7.33-7.11 (m, 5H), 6.68/6.64 (d/d, 1H), 4.15-0.6 (m, 16H), 3.9 (s, 3H), 3.48/3.42 (m/m, 1H), 3.22 (m, 1H).

Preparation R3ci: 7-[1-(difluoromethyl)-1H-pyrazol-4-yl]-3-({4-hydroxy-1-[(3R,4R)-3-phenylpiperidine-4-carbonyl]piperidin-4-yl}methyl)-3H,4H,7H-pyrrolo[2,3-d]pyrimidin-4-one Using General Procedure 5 starting from Preparation R2ci as reagent, Preparation R3ci was obtained. HRMS calculated for $C_{28}H_{31}F_2N_7O_3$: 551.2457; found 552.254 [(M+H)$^+$ form].

$^1$H-NMR (500 MHz, MSM-d6) δ ppm 9.2/8.78 (brs+brs, 2H), 8.87/8.85 (d, 1H), 8.43/8.41 (d, 1H), 8.2/8.15 (s, 1H), 7.92 (t, 1H), 7.61/7.59 (d, 1H), 7.34-7.13 (m, 5H), 6.74/6.7 (d, 1H), 4.91 (s, 1H), 4.1-2.63 (m, 12H), 1.92-0.63 (m, 6H).

Preparation R3cj: 3-({4-hydroxy-1-[(3R,4R)-3-phenylpiperidine-4-carbonyl]piperidin-4-yl}methyl)-7-(pyrimidin-2-yl)-3H,4H,7H-pyrrolo[2,3-d]pyrimidin-4-one Using General Procedure 5 starting from Preparation R2cj as reagent, Preparation R3cj was obtained as HCl salt. HRMS calculated for $C_{28}H_{31}N_7O_3$: 513.2488; found 257.6326 [(M+2H)$^{2+}$ form].

$^1$H-NMR (500 MHz, MSM-d6) δ ppm 9.24/8.77 (brd+brq, 2H), 8.96/8.95 (brd, 1H), 8.18/8.13 (brs, 1H), 7.87/7.79 (d, 1H), 7.55 (t, 1H), 7.34-7.13 (m, 5H), 6.76/6.72 (d, 1H), 4.87 (brs, 1H), 4.13-2.61 (m, 12H), 1.93-0.63 (m, 6H).

Preparation R3ck: 3-({4-hydroxy-1-[(3R,4R)-3-phenylpiperidine-4-carbonyl]piperidin-4-yl}methyl)-7-(1,3-thiazol-2-yl)-3H,4H,7H-pyrrolo[2,3-d]pyrimidin-4-one Using General Procedure 5 starting from Preparation R2ck as reagent, Preparation R3ck was obtained as HCl salt. HRMS calculated for $C_{27}H_{30}N_6O_3S$: 518.2100; found 519.2181 [(M+H)$^+$ form].

$^1$H-NMR (500 MHz, MSM-d6) δ ppm 9.3/8.81 (brd/brq, 2H), 8.35/8.31 (s, 1H), 7.91/7.89 (d, 1H), 7.7/7.69 (d, 1H), 7.65/7.64 (d, 1H), 7.33-7.12 (m, 5H), 6.81/6.77 (d, 1H), 4.14-2.61 (m, 12H), 1.95-0.6 (m, 6H).

Preparation R3cn: 3-[[4-hydroxy-1-[(3S,4S)-3-phenylpiperidine-4-carbonyl]-4-piperidyl]methyl]pyrido[3,2-d]pyrimidin-4-one Using General Procedure 5 starting from 3H-pyrido[3,2-d]pyrimidin-4-one and tert-butyl (3S,4S)-4-(1-oxa-6-azaspiro[2.5]oct-6-ylcarbonyl)-3-phenylpiperidine-1-carboxylate (instead of Preparation R1f) as reagents, Preparation R3cn was obtained as HCl salt. HRMS calculated for $C_{25}H_{29}N_5O_3$: 447.227; found 448.2365 [(M+H)$^+$ form].

$^1$H-NMR (500 MHz, MSM-d6) δ ppm 9.34/8.83 (brs/brd, 2H), 8.83 (brm, 1H), 8.34/8.30 (s/s, 1H), 8.14/8.12 (d/d, 1H), 7.40-7.09 (m, 5H), aliphatic protons: 4.13-0.52 (8×CH$_2$), 3.49/3.42 (m, 1H), 3.21 (m, 1H).

$^{13}$C-NMR (500 MHz, MSM-d6) δ ppm 150.3/150.2, 149.8, 136.1, 129.3, 42.6/42.4, 41.0/40.5.

Preparation R3co: 3-[[4-hydroxy-1-[(3R,4R)-3-phenylpiperidine-4-carbonyl]-4-piperidyl]methyl]pyrido[3,2-d]pyrimidin-4-one Using General Procedure 5 starting from 3H-pyrido[3,2-d]pyrimidin-4-one as reagent, Preparation R3co was obtained as HCl salt. HRMS calculated for $C_{25}H_{29}N_5O_3$: 447.227; found 448.2365 [(M+H)$^+$ form].

$^1$H-NMR (500 MHz, MSM-d6) δ ppm 9.34, 8.83 (brs+brs, 2H), 8.83 (brs, 1H), 8.34/8.30 (s/s, 1H), 8.14/8.12 (d/d, 1H), 7.40-7.09 (m, 5H), aliphatic protons: 4.13-0.52 (8×CH$_2$), 3.49/3.42 (m, 1H), 3.21 (m, 1H).

$^{13}$C-NMR (500 MHz, MSM-d6) δ ppm 150.3/150.2, 149.8, 136.1, 129.3, 42.6/42.4, 41.0/40.5.

Preparation R3cp: 3-[[4-hydroxy-1-[(3R,4R)-3-phenylpiperidine-4-carbonyl]-4-piperidyl]methyl]thieno[2,3-d]pyrimidin-4-one Using General Procedure 5 starting from 3H-thieno[2,3-d]pyrimidin-4-one as reagent, Preparation R3cp was obtained as HCl salt. HRMS calculated for $C_{24}H_{28}N_4O_3S$: 452.1882; found 453.1933 [(M+H)$^+$ form].

$^1$H-NMR (500 MHz, MSM-d6) δ ppm 9.23/8.76 (brs/brm, 2H), 8.83 (brs, 1H), 8.26/8.21 (s/s, 1H), 7.61/7.59 (d/d, 1H), 7.43/7.39 (d/d, 1H) 7.34-7.15 (m, 5H) 4.93/4.92 (s/s, 1H) 4.04, 3.93/3.75 (d+d/s, 2H) 4.00-2.60 (m, 4H) 3.48/3.42 (m/m, 1H) 3.41-2.98 (m, 2H) 3.33-3.00 (m, 2H) 3.21 (m, 1H) 1.94-1.80 (m, 2H) 1.51-0.57 (m, 4H).

$^{13}$C-NMR (500 MHz, MSM-d6) δ ppm 124.8, 122.5/122.4, 47.7/47.2, 42.7, 42.6/42.5, 41.1/40.4, 26.6/26.4.

Preparation R3cq: 6-chloro-3-[[4-hydroxy-1-[(3R,4R)-3-phenylpiperidine-4-carbonyl]-4-piperidyl]methyl]pyrido[3,2-d]pyrimidin-4-one Using General Procedure 5 starting from 6-chloro-3H-pyrido[3,2-d]pyrimidin-4-one as reagent, Preparation R3cq was obtained as HCl salt. HRMS calculated for $C_{25}H_{28}ClN_5O_3$: 481.1881; found 482.1949 [(M+H)$^+$ form].

$^1$H-NMR (500 MHz, MSM-d6) δ ppm 9.13, 8.69 (brs+brm, 2H), 8.33/8.28 (s/s, 1H), 8.18/8.17 (d/d, 1H), 7.93/7.91 (d/d, 1H), 7.38-7.19 (m, 5H), 4.09 (brm, 1H), 4.05, 3.97/3.75 (d+d/s, 2H), 4.00-2.61 (m, 4H), 3.40-2.99 (brm, 4H), 3.48/3.40 (m/m, 1H), 3.22 (m, 1H) 1.95-1.80 (m, 2H), 1.52-0.52 (m, 4H).

$^{13}$C-NMR (125 MHz, MSM-d6) δ ppm 150.8/150.7, 139.9, 130.4, 42.6/42.5, 41.1/40.5.

Preparation R3cr: 3-[[4-hydroxy-1-[(3R,4R)-3-phenylpiperidine-4-carbonyl]-4-piperidyl]methyl]-6-methoxy-pyrido[3,2-d]pyrimidin-4-one and Preparation R3cs: 3-[[4-hydroxy-1-[(3R,4R)-3-phenylpiperidine-4-carbonyl]-4-piperidyl]methyl]-5H-pyrido[3,2-d]pyrimidine-4,6-dione Using General Procedure 5 starting from 6-methoxy-3H-pyrido[3,2-d]pyrimidin-4-one as reagent, Preparation R3cr and Preparation R3cs (byproduct) were obtained as HCl salt and separated by chromatography.

Preparation R3cr: HRMS calculated for $C_{26}H_{31}N_5O_4$: 477.2376; found 478.2458 [(M+H)$^+$ form].

$^1$H-NMR (500 MHz, MSM-d6) δ ppm 9.17, 8.72 (brs+brm, 2H) 8.22/8.17 (s/s, 1H) 8.02/8.00 (d/d, 1H), 7.35-7.15 (m, 5H), 7.31/7.29 (d/d, 1H), 4.06, 3.93/3.77, 3.74 (d+d/d+d, 2H), 4.00-2.60 (m, 4H), 3.99/3.96 (s/s, 3H), 3.48/3.42 (m, 1H), 3.34-2.98 (m, 4H), 3.21 (m, 1H), 1.94-1.80 (m, 2H), 1.52-0.57 (m, 4H).

$^{13}$C-NMR (125 MHz, MSM-d6) δ ppm 148.2/148.1, 139.5, 119.1, 54.2, 42.6/42.4, 41.1/40.5.

Preparation R3cs: HRMS calculated for $C_{25}H_{29}N_5O_4$: 463.222; found 464.2312 [(M+H)$^+$ form].

¹H-NMR (500 MHz, MSM-d6) δ ppm 11.67 (vbrs, 1H), 9.11, 8.68 (brs+brs, 2H), 8.08/8.04 (s/s, 1H), 7.75/7.73 (d/d, 1H), 6.83/6.81 (d/d, 1H), 7.36-7.18 (m, 5H), 4.89 (vbrs, 1H), 4.00-2-60 (m, 4H), 3.99, 3.93/3.74, 3.70 (d+d/d+d, 2H), 3.48/3.41 (m, 1H), 3.34-3.01 (m, 4H), 3.20 (m, 1H), 1.92-1.80 (m, 2H), 1.51-0.48 (m, 4H).
¹³C-NMR (125 MHz, MSM-d6) δ ppm 146.2/146.1, 140.3, 129.4, 42.6/42.5, 41.0/40.6.

Preparation R3ct: 6-(benzylamino)-3-[[4-hydroxy-1-[(3R,4R)-3-phenylpiperidine-4-carbonyl]-4-piperidyl]methyl]pyrido[3,2-d]pyrimidin-4-one Using General Procedure 5 starting from 6-chloro-3H-pyrido[3,2-d]pyrimidin-4-one as reagent without the deprotection step, the resulted crude Boc-protected compound (0.76 mmol) and $K_2CO_3$ (1.51 mmol) were stirred in benzylamine (5 ml) at 120° C. for 17 hours. The reaction mixture was purified by preparative LC (on C-18 Gemini-NX 5 μm column, 5 mM aqueous $NH_4HCO_3$-MeCN, gradient).
The resulted crude product (187 mg, 0.283 mmol) was stirred in aqueous HCl solution (1 N, 3 ml, 3 mmol) and PDO (3 ml) at 70° C. for 2 hours. The reaction mixture was purified by preparative LC (on C-18 Gemini-NX 5 μm column, 5 mM aqueous $NH_4HCO_3$-MeCN, gradient) to give Preparation R3ct as HCl salt. HRMS calculated for $C_{32}H_{36}N_6O_3$: 552.2849; found 277.1497 [(M+2H)$^{2+}$ form].
¹H-NMR (500 MHz, MSM-d6) δ ppm 9.37/8.86 (m/m, 2H), 8.31-7.12 (m, aromatic protons, 13H), 4.78-0.49 (m, aliphatic protons, 20H).

Preparation R3cu: 3-[[4-hydroxy-1-[(3R,4R)-3-phenylpiperidine-4-carbonyl]-4-piperidyl]methyl]-6-[(4-methoxyphenyl)methylamino]pyrido[3,2-d]pyrimidin-4-one Using General Procedure 5 starting from 6-chloro-3H-pyrido[3,2-d]pyrimidin-4-one as reagent without the deprotection step, the resulted crude Boc-protected compound (0.76 mmol) and $K_2CO_3$ (1.51 mmol) were stirred in benzylamine (5 ml) at 120° C. for 17 hours. The reaction mixture was purified by preparative LC (on C-18 Gemini-NX 5 μm column, 5 mM aqueous $NH_4HCO_3$-MeCN, gradient).
The resulted crude product (187 mg, 0.283 mmol) was stirred in aqueous HCl solution (1 N, 3 ml, 3 mmol) and PDO (3 ml) at 70° C. for 2 hours. The reaction mixture was purified by preparative LC (on C-18 Gemini-NX 5 μm column, 5 mM aqueous $NH_4HCO_3$-MeCN, gradient) to give Preparation R3cu as HCl salt. HRMS calculated for $C_{33}H_{38}N_6O_4$: 582.2955; found 292.1552 [(M+2H)$^{2+}$ form].
¹H-NMR (500 MHz, MSM-d6) δ ppm 9.33/8.83 (brt/brd, 2H), 8.23/8.18 (s/s, 1H), 7.91 (vbrs, 1H), 7.35-7.15 (m, 5H), 7.34 (d/d, 2H), 7.27 (brm, 1H), 6.92/6.91 (d/d, 2H), 4.62/4.59 (s/s, 2H), 4.08-0.54 (m, aliphatic protons, 8H), 3.73 (s, 3H), 3.48/3.42 (m/m, 1H), 3.21 (m, 1H).

Preparation R3cv: 6-[[4-hydroxy-1-[(3R,4R)-3-phenylpiperidine-4-carbonyl]-4-piperidyl]methyl]-3-phenyl-triazolo[4,5-d]pyrimidin-7-one Using General Procedure 5 starting from 3-phenyl-6H-triazolo[4,5-d]pyrimidin-7-one as reagent, Preparation R3cv was obtained as HCl salt. HRMS calculated for $C_{28}H_{31}N_7O_3$: 513.2488; found 514.2576 [(M+H)$^+$ form].

¹H-NMR (500 MHz, MSM-d6) δ ppm 9.28/8.79 (brd+brq, 2H), 8.5/8.47 (s, 1H), 8.06-7.54 (m, 5H), 7.4-7.19 (m, 5H), 4.98/4.96 (brs, 1H), 4.17-2.6 (m, 12H), 1.96-0.53 (m, 6H).

Preparation R3cw: 1-[[4-hydroxy-1-[(3R,4R)-3-phenylpiperidine-4-carbonyl]-4-piperidyl]methyl]-9-phenyl-purin-6-one Using General Procedure 5 starting from 9-phenyl-1H-purin-6-one as reagent, Preparation R3cw was obtained as HCl salt. HRMS calculated for $C_{29}H_{32}N_6O_3$: 512.2536; found 513.2616 [(M+H)$^+$ form].
¹H-NMR (500 MHz, MSM-d6) δ ppm 9.25/8.77 (brd+brq, 2H), 8.52/8.5 (s, 1H), 8.28/8.23 (s, 1H), 7.82-7.46 (m, 5H), 7.37-7.18 (s, 5H), 4.91 (brs, 1H), 4.14-2.63 (m, 12H), 1.96-0.58 (m, 6H).

Preparation R3cx: 5-[[4-hydroxy-1-[(3R,4R)-3-phenylpiperidine-4-carbonyl]-4-piperidyl]methyl]-1-phenyl-pyrazolo[3,4-d]pyrimidin-4-one Using General Procedure 5 starting from 1-phenyl-5H-pyrazolo[3,4-d]pyrimidin-4-one as reagent, Preparation R3cx was obtained as HCl salt. HRMS calculated for $C_{29}H_{32}N_6O_3$: 512.2536; found 513.2627 [(M+H)$^+$ form].
¹H-NMR (500 MHz, MSM-d6) δ ppm 9.22/8.76 (brs+brs, 2H), 8.39/8.36 (s, 1H), 8.34/8.3 (s, 1H), 8.09-7.38 (m, 5H), 7.36-7.16 (m, 5H), 4.94/4.93 (s, 1H), 4.12-2.59 (m, 12H), 1.95-0.58 (m, 6H).

Preparation R3cy: 7-bromo-3-[[4-hydroxy-1-[(3R,4R)-3-phenylpiperidine-4-carbonyl]-4-piperidyl]methyl]pyrrolo[2,1-f][1,2,4]triazin-4-one Using General Procedure 5 starting from 7-bromo-3H-pyrrolo[2,1-f][1,2,4]triazin-4-one as reagent, Preparation R3cy was obtained as HCl salt. HRMS calculated for $C_{24}H_{28}BrN_5O_3$: 513.1376; found 514.1462 [(M+H)$^+$ form].
¹H-NMR (500 MHz, MSM-d6) δ ppm 9.25/8.77 (brs+brs, 2H), 8.03/8 (s, 1H), 7.33-7.1 (m, 5H), 7.03/6.99/6.77/6.75 (d, 2H), 4.93/4.91 (s, 1H), 4.02-2.61 (m, 12H), 1.94-0.5 (m, 6H).
¹³C-NMR (125 MHz, MSM-d6) δ ppm 154, 120.9, 102.9.

Preparation R3cz: 6-[[4-hydroxy-1-[(3R,4R)-3-phenylpiperidine-4-carbonyl]-4-piperidyl]methyl]-3-phenyl-isothiazolo[4,5-d]pyrimidin-7-one Using General Procedure 5 starting from 3-phenyl-6H-isothiazolo[4,5-d]pyrimidin-7-one as reagent, Preparation R3cz was obtained as HCl salt. HRMS calculated for $C_{29}H_{31}N_5O_3S$: 529.2148; found 530.2223 [(M+H)$^+$ form].
¹H-NMR (400 MHz, MSM-d6) δ ppm 9.37/8.86 (brs+brs, 2H), 8.49/8.46 (s, 1H), 8.43 (m, 2H), 7.62-7.5 (m, 3H), 7.39-7.13 (m, 5H), 5.06/5.03 (s, 1H), 4.2-2.6 (m, 12H), 1.98-0.52 (m, 6H).

Preparation R3da: 3-[[4-hydroxy-1-[(3R,4R)-3-phenylpiperidine-4-carbonyl]-4-piperidyl]methyl]-7-phenyl-thieno[3,4-d]pyrimidin-4-one Using General Procedure 5 starting from 7-chloro-3H-thieno[3,4-d]pyrimidin-4-one as reagent, without the deprotection step, the resulted Boc-protected compound reacted with phenylboronic acid using General Procedure 9. The resulted phenylated crude product was deprotected according to Step 2 of General Procedure 5 to give Preparation R3da as HCl salt. HRMS calculated for $C_{30}H_{32}N_4O_3S$: 528.2195; found 529.2265 [(M+H)$^+$ form].

$^1$H-NMR (500 MHz, MSM-d6) δ ppm 9.14/8.7 (brq+brd, 2H), 8.51/8.47 (s, 1H), 8.05/8.04 (m, 2H), 8.03/7.98 (s, 1H), 7.52-7.33 (m, 3H), 7.32-7.1 (m, 5H), 4.9/4.88 (s, 1H), 4.02-2.61 (m, 12H), 1.93-0.58 (m, 6H).

$^{13}$C-NMR (125 MHz, MSM-d6) δ ppm 158, 143.5, 134, 127.4.

Preparation R3db: 3-[[4-hydroxy-1-[(3R,4R)-3-phenylpiperidine-4-carbonyl]-4-piperidyl]methyl]-7-phenyl-5H-pyrrolo[3,2-d]pyrimidin-4-one Using General Procedure 5 starting from 7-phenyl-3,5-dihydropyrrolo[3,2-d]pyrimidin-4-one as reagent, Preparation R3db was obtained as HCl salt. HRMS calculated for $C_{30}H_{33}N_5O_3$: 511.2583; found 512.2647 [(M+H)$^+$ form].

$^1$H-NMR (500 MHz, MSM-d6) δ ppm 12.35/12.3 (d, 1H), 9.26/8.79 (brs+brs, 2H), 8.1/8.05 (s, 1H), 8.1/8.08 (m, 2H), 7.92/7.9 (d, 1H), 7.43-7.08 (m, 8H), 4.92/4.91 (s, 1H), 4.07-2.62 (m, 12H), 1.97-0.63 (m, 6H).

Preparation R3dc: 7-chloro-3-[[4-hydroxy-1-[(3R,4R)-3-phenylpiperidine-4-carbonyl]-4-piperidyl]methyl]thieno[3,4-d]pyrimidin-4-one Using General Procedure 5 starting from 7-chloro-3H-thieno[3,4-d]pyrimidin-4-one as reagent, Preparation R3dc was obtained as HCl salt. HRMS calculated for $C_{24}H_{27}ClN_4O_3S$: 486.1492; found 487.1544 [(M+H)$^+$ form].

$^1$H-NMR (500 MHz, MSM-d6) δ ppm 9.16/8.71 (brd+brq, 2H), 8.44/8.4 (s, 1H), 8.01/7.96 (s, 1H), 7.34-7.15 (m, 5H), 4.87/4.85 (s, 1H), 4-2.59 (m, 12H), 1.93-0.52 (m, 6H).

Preparation R3dd: 6-[[4-hydroxy-1-[(3R,4R)-3-phenylpiperidine-4-carbonyl]-4-piperidyl]methyl]-3-phenyl-isoxazolo[4,5-d]pyrimidin-7-one Using General Procedure 5 starting from 3-phenyl-6H-isoxazolo[4,5-d]pyrimidin-7-one as reagent, Preparation R3dd was obtained as HCl salt. HRMS calculated for $C_{29}H_{31}N_5O_4$: 513.2376; found 514.2451 [(M+H)$^+$ form].

$^1$H-NMR (500 MHz, MSM-d6) δ ppm 9.13/8.76 (brs+brs, 2H), 8.44/8.4 (s, 1H), 8.33-8.26 (m, 2H), 7.67-7.59 (m, 3H), 7.39-7.18 (m, 5H), 4.99/4.97 (s, 1H), 4.19-2.62 (m, 12H), 1.95-0.52 (m, 6H).

Preparation R3de: 5-[[4-hydroxy-1-[(3R,4R)-3-phenylpiperidine-4-carbonyl]-4-piperidyl]methyl]-1-(4-methoxyphenyl)pyrazolo[3,4-d]pyrimidin-4-one Using General Procedure 5 starting from 1-(4-methoxyphenyl)-5H-pyrazolo[3,4-d]pyrimidin-4-one as reagent, Preparation R3de was obtained as HCl salt. HRMS calculated for $C_{30}H_{34}N_6O_4$: 542.2642; found 543.2711 [(M+H)$^+$ form].

$^1$H-NMR (500 MHz, MSM-d6) δ ppm 9.11/8.69 (brs+brm, 2H), 8.34/8.3 (s/s, 1H), 8.29/8.25 (s/s, 1H), 7.9/7.86 (dm/dm, 2H), 7.37-7.16 (m, 5H), 7.13/7.12 (m/m, 2H), 4.91 (brs, 1H), 4.13-0.53 (m, 16H), 3.81 (s, 3H), 3.48/3.42 (m/m, 1H), 3.22 (m, 1H).

$^{13}$C-NMR (125 MHz, MSM-d6) δ ppm 152.6/152.5, 136.3/136.2, 123.8, 114.9/114.8, 55.9, 42.6/42.5, 41.1/40.5.

Preparation R3df: 1-(2,3-dihydro-1,4-benzodioxin-6-yl)-5-[[4-hydroxy-1-[(3R,4R)-3-phenylpiperidine-4-carbonyl]-4-piperidyl]methyl]pyrazolo[3,4-d]pyrimidin-4-one Using General Procedure 5 starting from 1-(2,3-dihydro-1,4-benzodioxin-6-yl)-5H-pyrazolo[3,4-d]pyrimidin-4-one as reagent, Preparation R3df was obtained as HCl salt. HRMS calculated for $C_{31}H_{34}N_6O_5$: 570.2591; found 571.2663 [(M+H)$^+$ form].

$^1$H-NMR (500 MHz, MSM-d6): δ ppm 9.16/8.74 (brs+brs, 2H), 8.3/8.26 (s, 1H), 8.29/8.23 (s, 1H), 7.53/7.52 (d, 1H), 7.48/7.47 (dd, 1H), 7.36-7.15 (m, 5H), 7.04 (d, 1H), 4.92/4.9 (s, 1H), 4.35-4.26 (m, 4H), 4.1-2.6 (m, 12H), 1.94-0.58 (m, 6H).

Preparation R3dg: 6-chloro-7-(4-chloro-3-fluorophenyl)-3-[[4-hydroxy-1-[(3R,4R)-3-phenylpiperidine-4-carbonyl]-4-piperidyl]methyl]pyrrolo[2,3-d]pyrimidin-4-one Using General Procedure 5 starting from Preparation R2ah as reagent, Preparation R3dg was obtained as HCl salt. HRMS calculated for $C_{30}H_{30}N_5O_3FCl_2$: 597.171; found 598.1772 [(M+H)$^+$ form].

$^1$H-NMR (500 MHz, MSM-d6): δ ppm 8.07/8.03 (s, 1H), 7.85 (t, 1H), 7.75 (dd, 1H), 7.41 (dd, 1H), 7.3-7.09 (m, 5H), 6.87/6.84 (s, 1H), 4.81/4.79 (s, 1H), 4.06-2.51 (m, 12H), 1.68-0.74 (m, 6H).

Preparation R3dh: 3-[[4-hydroxy-1-[(3R,4R)-3-phenylpiperidine-4-carbonyl]-4-piperidyl]methyl]-6-methyl-7-phenyl-pyrrolo[2,3-d]pyrimidin-4-one Using General Procedure 5 starting from Preparation R2de as reagent, Preparation R3dh was obtained as HCl salt. HRMS calculated for $C_{31}H_{35}N_5O_3$: 525.274; found 526.2827 [(M+H)$^+$ form].

$^1$H-NMR (500 MHz, MSM-d6): δ ppm 9.14/8.69 (brs+brs, 2H), 7.95/7.9 (s, 1H), 7.61-7.37 (m, 5H), 7.36-7.15 (m, 5H), 6.45/6.42 (q, 1H), 4.84/4.83 (s, 1H), 4.06-2.61 (m, 12H), 2.19/2.17 (d, 3H), 1.95-0.6 (m, 6H).

Preparation R3di: 3-[[4-hydroxy-1-[(3R,4R)-3-phenylpiperidine-4-carbonyl]-4-piperidyl]methyl]-9-methyl-pyrimido[4,5-b]indol-4-one Using General Procedure 5 starting from Preparation R2df as reagent, Preparation R3di was obtained as HCl salt. HRMS calculated for $C_{29}H_{33}N_5O_3$: 499.2583; found 500.2677 [(M+H)$^+$ form].

$^1$H-NMR (500 MHz, MSM-d6): δ ppm 9.19/8.74 (brq+brd, 2H), 8.38/8.33 (s, 1H), 8.07/8.02 (dm, 1H), 7.66/7.65 (dm, 1H), 7.43/7.42 (m, 1H), 7.37-7.12 (m, 5H), 7.32 (m, 1H), 4.9 (brs, 1H), 4.21-2.62 (m, 12H), 3.87/3.86 (s, 3H), 1.95-0.64 (m, 6H).

$^{13}$C-NMR (125 MHz, MSM-d6) δ ppm 158, 152.7, 137.2, 122, 99.

Preparation R3dj: 3-[(4-hydroxy-1-{[(3R,4R)-3-phenylpiperidin-4-yl]carbonyl}piperidin-4-yl)methyl]-6,8-dimethylpyrimido[5,4-b]indolizin-4(3H)-one Using General Procedure 5 starting from Preparation R2dg as reagent, Preparation R3dj was obtained as HCl salt. HRMS calculated for $C_{29}H_{34}N_6O_3$: 514.2692; found 515.2757 [(M+H)$^+$ form].

¹H-NMR (500 MHz, MSM-d6): δ ppm 9.25/8.77 (brq+brd, 2H), 8.18/8.13 (s, 1H), 7.34-7.1 (m, 5H), 6.94/6.9 (s, 1H), 6.71/6.7 (q, 1H), 4.9 (brs, 1H), 4.13-2.6 (m, 12H), 2.47/2.45 (d, 3H), 2.45/2.44 (s, 3H), 1.95-0.62 (m, 6H).

¹³C-NMR (125 MHz, MSM-d6) δ ppm 159.3, 152.6, 140.4, 139, 127.9, 115.4, 108.8, 91.4.

Preparation R3dk: 6-chloro-3-[[4-hydroxy-1-[(3R,4R)-3-phenylpiperidine-4-carbonyl]-4-piperidyl]methyl]-7-phenyl-pyrrolo[2,3-d]pyrimidin-4-one Using General Procedure 5 starting from Preparation R2dh as reagent, Preparation R3dk was obtained as HCl salt. HRMS calculated for $C_{30}H_{32}ClN_5O_3$: 545.2194; found 546.2277 [(M+H)⁺ form].

¹H-NMR (500 MHz, MSM-d6) δ ppm 9.15/8.71 (brd+brq, 2H), 8.05/8 (s, 1H), 7.64-7.41 (m, 5H), 7.37-7.18 (m, 5H), 6.83/6.8 (s, 1H), 4.85 (s, 1H), 4.07-2.61 (m, 12H), 1.94-0.61 (m, 6H).

Preparation R3dl: 3-[[4-hydroxy-1-[(3R,4R)-3-phenylpiperidine-4-carbonyl]-4-piperidyl]methyl]-6-iodo-7-methyl-pyrrolo[2,3-d]pyrimidin-4-one Using General Procedure 5 starting from Preparation R2di as reagent, Preparation R3dl was obtained as HCl salt. HRMS calculated for $C_{25}H_{30}IN_5O_3$: 575.1393; found 576.1455 [(M+H)⁺ form].

¹H-NMR (500 MHz, MSM-d6) δ ppm 8.02/7.97 (s/s, 1H), 7.28-7.02 (m, 5H), 6.84/6.83 (s/s, 1H), 4.16-0.65 (m, 16H), 3.65/3.64 (s/s, 3H), 3.21/3.16 (m/m, 1H), 2.88 (m, 1H)

¹³C-NMR (125 MHz, MSM-d6) δ ppm 147.9/147.8, 111.7/111.6, 80.7/80.6, 46.2, 43.2/42.8, 33.1

Preparation R3dm: 3-[[3,3-difluoro-4-hydroxy-1-[trans-3-phenylpiperidine-4-carbonyl]-4-piperidyl]methyl]-7-phenyl-pyrrolo[2,3-d]pyrimidin-4-one Trimethyl-sulfoxonium iodide (1.11 g, 5 mmol) was dissolved in abs. MSM (10 ml) then sodium-hydride dispersion (60% in mineral oil, 200 mg, 5 mmol) was added sequentially and stirred for 20 minutes at r.t. tert-butyl 3,3-difluoro-4-oxo-piperidine-1-carboxylate (783 mg, 3.33 mmol) solution in MSM (5 ml, abs.) was added to the mixture and stirred for 15 hours at r.t. The reaction mixture was poured into ice-water mixture (40 ml) and extracted with DEE (4×15 ml). The combined organic layer was washed with water, brine, then dried over MgSO₄ and evaporated.

The raw epoxide product was reacted with Preparation R2bu according to General Procedure 5.

The resulted raw HCl salt was reacted with trans-1-tert-butoxycarbonyl-3-phenyl-piperidine-4-carboxylic acid using General Procedure 7.

The raw product was deprotected according to Step 2 of General Procedure 5 to give Preparation R3dm. HRMS calculated for $C_{30}H_{31}F_2N_5O_3$: 547.2394; found 548.2454 and 548.2490 (two diastereomers) [(M+H)⁺ form].

¹H NMR (500 MHz, MSM-d₆): δ ppm 9.24/8.82 (m+m, 2H), 8.19-8.09 (4*s, 1H), 7.71 (m, 2H), 7.6-7.5 (4*d, 1H), 7.56 (m, 2H), 7.42 (m, 1H), 7.34-7.16 (m, 5H), 6.79-6.67 (4*d, 1H), 6.08 (brs, 1H), 4.74-2.35 (m, 12H), 2.06-1.1 (m, 4H)

Preparation R3dn: 3-[[3,3-difluoro-4-hydroxy-1-[trans-3-phenylpiperidine-4-carbonyl]-4-piperidyl]methyl]-7-(4-methoxyphenyl)pyrrolo[2,3-d]pyrimidin-4-one Trimethyl-sulfoxonium iodide (1.11 g, 5 mmol) was dissolved in abs. MSM (10 ml) then sodium-hydride dispersion (60% in mineral oil, 200 mg, 5 mmol) was added sequentially and stirred for 20 minutes at r.t. tert-butyl 3,3-difluoro-4-oxo-piperidine-1-carboxylate (783 mg, 3.33 mmol) solution in MSM (5 ml, abs.) was added to the mixture and stirred for 15 hours at r.t. The reaction mixture was poured into ice-water mixture (40 ml) and extracted with DEE (4×15 ml). The combined organic layer was washed with water, brine, then dried over MgSO₄ and evaporated.

The raw epoxide product was reacted with Preparation R2ax according to General Procedure 5.

The resulted raw HCl salt was reacted with trans-1-tert-butoxycarbonyl-3-phenyl-piperidine-4-carboxylic acid according to General Procedure 7.

The raw product was deprotected according to Step 2 of General Procedure 5 to give Preparation R3dn. HRMS calculated for $C_{31}H_{33}F_2N_5O_4$: 577.2501; found 578.2547 and 578.2572 (two diastereomers) [(M+H)⁺ form].

¹H NMR (500 MHz, MSM-d₆): δ ppm 9.13/8.74 (m+m, 2H), 8.16-8.05 (4*s, 1H), 7.63-7.54 (m, 2H), 7.48-7.41 (4*d, 1H), 7.36-7.16 (m, 5H), 7.14-7.06 (m, 2H), 6.74-6.63 (4*d, 1H), 6.17-5.95 (brs, 1H), 4.69-2.77 (m, 12H), 3.82/3.81 (s, 3H), 2.05-1.15 (m, 4H)

EXAMPLES

The following Examples illustrate the invention but do not limit it in any way.

3-[(1-{[(3S,4S)-1-benzyl-3-phenylpiperidin-4-yl]carbonyl}-4-hydroxypiperidin-4-yl)methyl]-3,7-dihydro-4H-pyrrolo[2,3-d]pyrimidin-4-one (Example 1)

Using General Procedure 6 starting from 3-[(4-hydroxy-1-{[(3S,4S)-3-phenylpiperidin-4-yl]carbonyl}piperidin-4-yl)methyl]-3,7-dihydro-4H-pyrrolo[2,3-d]pyrimidin-4-one (which was obtained according to General Procedure 5 with tert-butyl (3S,4S)-4-(2-oxa-6-azaspiro[2.5]octane-6-carbonyl)-3-phenyl-piperidine-1-carboxylate and 3H,4H,7H-pyrrolo[2,3-d]pyrimidin-4-one) and benzyl bromide as reagents, EXAMPLE 1 was obtained. HRMS calculated for $C_{31}H_{35}N_5O_3$: 525.2739; found 526.2815 [(M+H)⁺ form].

7-(2-chlorobenzyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 2)

Using General Procedure 6 starting from Preparation R3aa and Preparation R1c as reagents, EXAMPLE 2 was obtained. HRMS calculated for $C_{41}H_{42}ClN_7O_3S$: 747.2758; found 374.6457 [(M+2H)²⁺ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one (Example 3)

Using General Procedure 6 starting from Preparation R3ac and Preparation R1c as reagents, EXAMPLE 3 was obtained. HRMS calculated for $C_{43}H_{47}N_7O_6S$: 789.3309; found 395.6734 [(M+2H)²⁺ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one (Example 4)

Using General Procedure 6 starting from Preparation R3ac and 5-(chloromethyl)-2-(6-methoxy-3-pyridyl)thiazole as reagents, EXAMPLE 4 was obtained. HRMS calculated for $C_{43}H_{47}N_7O_7S$: 805.3257; found 403.6694 [(M+2H)$^{2+}$ form].

7-(3,5-dichlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 5)

Using General Procedure 6 starting from Preparation R3ad and Preparation R1c as reagents, EXAMPLE 5 was obtained. HRMS calculated for $C_{40}H_{39}N_7O_3SCl_2$: 767.2212; found 768.2251 [(M+H)$^+$ form].

7-(3,5-dichlorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 6)

Using General Procedure 6 starting from Preparation R3ad and 5-(chloromethyl)-2-(6-methoxy-3-pyridyl)thiazole as reagents, EXAMPLE 6 was obtained. HRMS calculated for $C_{40}H_{39}N_7O_4SCl_2$: 783.2161; found 784.2235 [(M+H)$^+$ form].

7-(3-chloro-5-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 7)

Using General Procedure 6 starting from Preparation R3ae and Preparation R1c as reagents, EXAMPLE 7 was obtained. HRMS calculated for $C_{41}H_{42}ClN_7O_4S$: 763.2708; found 764.2766 [(M+H)$^+$ form].

7-(3-chloro-5-methoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 8)

Using General Procedure 6 starting from Preparation R3ae and 5-(chloromethyl)-2-(6-methoxy-3-pyridyl)thiazole as reagents, EXAMPLE 8 was obtained. HRMS calculated for $C_{41}H_{42}ClN_7O_5S$: 779.2657; found 780.2734 [(M+H)$^+$ form].

7-(3,5-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 9)

Using General Procedure 6 starting from Preparation R3af and Preparation R1c as reagents, EXAMPLE 9 was obtained. HRMS calculated for $C_{42}H_{45}N_7O_5S$: 759.3203; found 760.3244 [(M+H)$^+$ form].

7-(3,5-dimethoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 10)

Using General Procedure 6 starting from Preparation R3af and 5-(chloromethyl)-2-(6-methoxy-3-pyridyl)thiazole as reagents, EXAMPLE 10 was obtained. HRMS calculated for $C_{42}H_{45}N_7O_6S$: 775.3152; found 776.32 [(M+H)$^+$ form].

7-(4-chloro-3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 11)

Using General Procedure 6 starting from Preparation R3ah and Preparation R1c as reagents, EXAMPLE 11 was obtained. HRMS calculated for $C_{40}H_{39}ClFN_7O_3S$: 751.2508; found 752.2564 [(M+H)$^+$ form].

7-(4-chloro-3-fluorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 12)

Using General Procedure 6 starting from Preparation R3ah and 5-(chloromethyl)-2-(6-methoxy-3-pyridyl)thiazole as reagents, EXAMPLE 12 was obtained. HRMS calculated for $C_{40}H_{39}ClFN_7O_4S$: 767.2457; found 768.2552 [(M+H)$^+$ form].

7-(4-chloro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 13)

Using General Procedure 6 starting from Preparation R3ai and Preparation R1c as reagents, EXAMPLE 13 was obtained. HRMS calculated for $C_{41}H_{42}ClN_7O_4S$: 763.2708; found 764.2792 [(M+H)$^+$ form].

7-(4-chloro-3-methoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 14)

Using General Procedure 6 starting from Preparation R3ai and 5-(chloromethyl)-2-(6-methoxy-3-pyridyl)thiazole as reagents, EXAMPLE 14 was obtained. HRMS calculated for $C_{41}H_{42}ClN_7O_5S$: 779.2657; found 780.2729 [(M+H)$^+$ form].

7-(4-fluoro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 15)

Using General Procedure 6 starting from Preparation R3aj and Preparation R1c as reagents, EXAMPLE 15 was

7-(4-fluoro-3-methoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 16)

Using General Procedure 6 starting from Preparation R3aj and 5-(chloromethyl)-2-(6-methoxy-3-pyridyl)thiazole as reagents, EXAMPLE 16 was obtained. HRMS calculated for $C_{41}H_{42}FN_7O_5S$: 763.2952; found 764.3029 [(M+H)$^+$ form].

7-(3,4-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 17)

Using General Procedure 6 starting from Preparation R3ak and Preparation R1c as reagents, EXAMPLE 17 was obtained. HRMS calculated for $C_{42}H_{45}N_7O_5S$: 759.3203; found 380.6691 [(M+2H)$^{2+}$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-methylphenyl)-3,7-dihydro-4H-pyrrolo[2,3-d]pyrimidin-4-one (Example 18)

Using General Procedure 6 starting from Preparation R3am and 5-(chloromethyl)-2-(6-methoxy-3-pyridyl)thiazole as reagents, EXAMPLE 18 was obtained. HRMS calculated for $C_{41}H_{43}N_7O_4S$: 729.3096; found 730.3162 [(M+H)$^+$ form].

4-{3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-4-oxo-3,4-dihydro-7H-pyrrolo[2,3-d]pyrimidin-7-yl}benzonitrile (Example 19)

Using General Procedure 6 starting from Preparation R3an and Preparation R1c as reagents, EXAMPLE 19 was obtained. HRMS calculated for $C_{41}H_{40}N_8O_3S$: 724.2944; found 725.3009 [(M+H)$^+$ form].

4-{3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-4-oxo-3,4-dihydro-7H-pyrrolo[2,3-d]pyrimidin-7-yl}benzonitrile (Example 20)

Using General Procedure 6 starting from Preparation R3an and 5-(chloromethyl)-2-(6-methoxy-3-pyridyl)thiazole as reagents, EXAMPLE 20 was obtained. HRMS calculated for $C_{41}H_{40}N_8O_4S$: 740.2893; found 741.2984 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[4-(trifluoromethyl)phenyl]-3,7-dihydro-4H-pyrrolo[2,3-d]pyrimidin-4-one (Example 21)

Using General Procedure 6 starting from Preparation R3ao and Preparation R1c as reagents, EXAMPLE 21 was obtained. HRMS calculated for $C_{41}H_{40}N_7O_3F_3S$: 767.2866; found 768.2899 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[4-(trifluoromethyl)phenyl]-3,7-dihydro-4H-pyrrolo[2,3-d]pyrimidin-4-one (Example 22)

Using General Procedure 6 starting from Preparation R3ao and 5-(chloromethyl)-2-(6-methoxy-3-pyridyl)thiazole as reagents, EXAMPLE 22 was obtained. HRMS calculated for $C_{41}H_{40}F_3N_7O_4S$: 783.2814; found 784.2887 [(M+H)$^+$ form].

7-[4-(difluoromethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 23)

Using General Procedure 6 starting from Preparation R3ap and Preparation R1c as reagents, EXAMPLE 23 was obtained. HRMS calculated for $C_{41}H_{41}F_2N_7O_3S$: 749.2959; found 750.3017 [(M+H)$^+$ form].

7-[4-(difluoromethyl)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 24)

Using General Procedure 6 starting from Preparation R3ap and 5-(chloromethyl)-2-(6-methoxy-3-pyridyl)thiazole as reagents, EXAMPLE 24 was obtained. HRMS calculated for $C_{41}H_{41}F_2N_7O_4S$: 765.2909; found 766.297 [(M+H)$^+$ form].

7-[4-(hydroxymethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 25)

Using General Procedure 6 starting from Preparation R3aq and Preparation R1c as reagents, EXAMPLE 25 was obtained. HRMS calculated for $C_{41}H_{43}N_7O_4S$: 729.3097; found 730.3137 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one (Example 26)

Using General Procedure 6 starting from Preparation R3aq and 5-(chloromethyl)-2-(6-methoxy-3-pyridyl)thiazole as reagents, EXAMPLE 26 was obtained. HRMS calculated for $C_{41}H_{43}N_7O_5S$: 745.3046; found 746.3142 [(M+H)$^+$ form].

7-(4-chlorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 27)

Using General Procedure 6 starting from Preparation R3ar and 5-(chloromethyl)-2-(6-methoxy-3-pyridyl)thiazole as reagents, EXAMPLE 27 was obtained. HRMS calculated for $C_{40}H_{40}ClN_7O_4S$: 749.2551; found 750.2639 [(M+H)$^+$ form].

3-{1-({(3R,4R)-1-[(2-bromo-1,3-thiazol-5-yl)methyl]-3-phenylpiperidin-4-yl}carbonyl)-4-hydroxypiperidin-4-yl]methyl}-7-(4-chlorophenyl)-3,7-dihydro-4H-pyrrolo[2,3-d]pyrimidin-4-one (Example 28)

Using General Procedure 6 starting from Preparation R3ar and 2-bromo-5-(bromomethyl)thiazole as reagents, EXAMPLE 28 was obtained. HRMS calculated for $C_{34}H_{34}BrClN_6O_3S$: 720.1285; found 721.1355 [(M+H)$^+$ form].

7-(4-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 29)

Using General Procedure 6 starting from Preparation R3as and Preparation R1c as reagents, EXAMPLE 29 was obtained. HRMS calculated for $C_{40}H_{40}N_7O_3FS$: 717.2897; found 718.2982 [(M+H)$^+$ form].

7-(4-fluorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 30)

Using General Procedure 6 starting from Preparation R3as and 5-(chloromethyl)-2-(6-methoxy-3-pyridyl)thiazole as reagents, EXAMPLE 30 was obtained. HRMS calculated for $C_{40}H_{40}FN_7O_4S$: 733.2847; found 734.2907 [(M+H)$^+$ form].

3-{1-({(3R,4R)-1-[(2-bromo-1,3-thiazol-5-yl)methyl]-3-phenylpiperidin-4-yl}carbonyl)-4-hydroxypiperidin-4-yl]methyl}-7-(4-fluorophenyl)-3,7-dihydro-4H-pyrrolo[2,3-d]pyrimidin-4-one (Example 31)

Using General Procedure 6 starting from Preparation R3as and 2-bromo-5-(bromomethyl)thiazole as reagents, EXAMPLE 31 was obtained. HRMS calculated for $C_{34}H_{34}BrFN_6O_3S$: 704.1580; found 705.1642 [(M+H)$^+$ form].

7-[4-(dimethylamino)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 32)

Using General Procedure 6 starting from Preparation R3at and Preparation R1c as reagents, EXAMPLE 32 was obtained. HRMS calculated for $C_{42}H_{46}N_8O_3S$: 742.3414; found 743.3467 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 33)

Using General Procedure 6 starting from Preparation R3ax and 5-(chloromethyl)-2-(6-methoxy-3-pyridyl)thiazole as reagents, EXAMPLE 33 was obtained. HRMS calculated for $C_{41}H_{43}N_7O_5S$: 745.3047; found 746.3124 [(M+H)$^+$ form].

3-{1-({(3R,4R)-1-[(2-bromo-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 34)

Using General Procedure 6 starting from Preparation R3ax and 2-bromo-5-(bromomethyl)thiazole as reagents, EXAMPLE 34 was obtained. HRMS calculated for $C_{35}H_{37}BrN_6O_4S$: 716.1780396; found 717.1836 [(M+H)$^+$ form].

3-{[4-hydroxy-1-({(3R,4R)-1-[(1-methyl-1H-pyrazol-4-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 35)

Using General Procedure 6 starting from Preparation R3ax and 4-(chloromethyl)-1-methyl-pyrazole as reagents, EXAMPLE 35 was obtained. HRMS calculated for $C_{36}H_{41}N_7O_4$: 635.3220; found 636.3291 [(M+H)$^+$ form].

3-[(4-hydroxy-1-{[(3R,4R)-3-phenyl-1-(pyrazin-2-ylmethyl)piperidin-4-yl]carbonyl}piperidin-4-yl)methyl]-7-(4-methoxyphenyl)-3,7-dihydro-4H-pyrrolo[2,3-d]pyrimidin-4-one (Example 36)

Using General Procedure 6 starting from Preparation R3ax and 2-(chloromethyl)pyrazine hydrochloride as reagents, EXAMPLE 36 was obtained. HRMS calculated for $C_{36}H_{39}N_7O_4$: 633.3063; found 634.3114 [(M+H)$^+$ form].

3-{[4-hydroxy-1-({(3R,4R)-1-[(5-methyl-1,3-thiazol-2-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 37)

Using General Procedure 6 starting from Preparation R3ax and 2-(chloromethyl)-5-methyl-thiazole as reagents, EXAMPLE 37 was obtained. HRMS calculated for $C_{36}H_{40}N_6O_4S$: 652.2832031; found 653.2891 [(M+H)$^+$ form].

3-{1-({(3R,4R)-1-[(5-bromopyridin-3-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 38)

Using General Procedure 6 starting from Preparation R3ax and 3-bromo-5-(chloromethyl)pyridine as reagents, EXAMPLE 38 was obtained. HRMS calculated for $C_{37}H_{39}BrN_6O_4$: 710.2216; found 711.2297 [(M+H)$^+$ form].

3-[(4-hydroxy-1-{[(3R,4R)-3-phenyl-1-(pyridin-3-ylmethyl)piperidin-4-yl]carbonyl}piperidin-4-yl)methyl]-7-(4-methoxyphenyl)-3,7-dihydro-4H-pyrrolo[2,3-d]pyrimidin-4-one (Example 39)

Using General Procedure 6 starting from Preparation R3ax and 3-(chloromethyl)pyridine hydrochloride as

3-[(4-hydroxy-1-{[(3R,4R)-3-phenyl-1-(1,3-thiazol-5-ylmethyl)piperidin-4-yl]carbonyl}piperidin-4-yl)methyl]-7-(4-methoxyphenyl)-3,7-dihydro-4H-pyrrolo[2,3-d]pyrimidin-4-one (Example 40)

Using General Procedure 6 starting from Preparation R3ax and 5-(chloromethyl)thiazole as reagents, EXAMPLE 40 was obtained. HRMS calculated for $C_{35}H_{38}N_6O_4S$: 638.2675; found 639.2738 [(M+H)$^+$ form].

3-[(4-hydroxy-1-{[(3R,4R)-3-phenyl-1-(1,3-thiazol-2-ylmethyl)piperidin-4-yl]carbonyl}piperidin-4-yl)methyl]-7-(4-methoxyphenyl)-3,7-dihydro-4H-pyrrolo[2,3-d]pyrimidin-4-one (Example 41)

Using General Procedure 6 starting from Preparation R3ax and 2-(chloromethyl)thiazole as reagents, EXAMPLE 41 was obtained. HRMS calculated for $C_{35}H_{38}N_6O_4S$: 638.2675; found 639.2758 [(M+H)$^+$ form].

3-{[4-hydroxy-1-({(3R,4R)-1-[(4-methyl-1,3-thiazol-2-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 42)

Using General Procedure 6 starting from Preparation R3ax and 2-(chloromethyl)-4-methyl-thiazole as reagents, EXAMPLE 42 was obtained. HRMS calculated for $C_{36}H_{40}N_6O_4S$: 652.2832; found 653.2885 [(M+H)$^+$ form].

3-{[1-({(3R,4R)-1-[(4,5-dimethyl-1,3-thiazol-2-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 43)

Using General Procedure 6 starting from Preparation R3ax and 2-(chloromethyl)-4,5-dimethyl-thiazole as reagents, EXAMPLE 43 was obtained. HRMS calculated for $C_{37}H_{42}N_6O_4S$: 666.2988; found 667.3059 [(M+H)$^+$ form].

3-{[1-({(3R,4R)-1-[(2,4-dimethyl-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 44)

Using General Procedure 6 starting from Preparation R3ax and 5-(chloromethyl)-2,4-dimethyl-thiazole as reagents, EXAMPLE 44 was obtained. HRMS calculated for $C_{37}H_{42}N_6O_4S$: 666.2988; found 667.3047 [(M+H)$^+$ form].

3-{[4-hydroxy-1-({(3R,4R)-1-[(1-methyl-1H-pyrazol-5-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 45)

Using General Procedure 6 starting from Preparation R3ax and 5-(chloromethyl)-1-methyl-pyrazole as reagents, EXAMPLE 45 was obtained. HRMS calculated for $C_{36}H_{41}N_7O_4$: 635.3220; found 636.3288 [(M+H)$^+$ form].

3-{[1-({(3R,4R)-1-[(1,3-dimethyl-1H-pyrazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 46)

Using General Procedure 6 starting from Preparation R3ax and 5-(chloromethyl)-1,3-dimethyl-pyrazole as reagents, EXAMPLE 46 was obtained. HRMS calculated for $C_{37}H_{43}N_7O_4$: 649.3376; found 650.3455 [(M+H)$^+$ form].

4-({(3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)pyridine-2-carbonitrile (Example 47)

Using General Procedure 6 starting from Preparation R3ax and 4-(chloromethyl)pyridine-2-carbonitrile as reagents, EXAMPLE 47 was obtained. HRMS calculated for $C_{38}H_{39}N_7O_4$: 657.3063; found 658.3133 [(M+H)$^+$ form].

3-{[4-hydroxy-1-({(3R,4R)-1-[(6-methylpyridin-3-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 48)

Using General Procedure 6 starting from Preparation R3ax and 5-(bromomethyl)-2-methyl-pyridine hydrobromide as reagents, EXAMPLE 48 was obtained. HRMS calculated for $C_{38}H_{42}N_6O_4$: 646.3267; found 647.3343 [(M+H)$^+$ form].

5-({(3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)pyridine-2-carbonitrile (Example 49)

Using General Procedure 6 starting from Preparation R3ax and 5-(bromomethyl)pyridine-2-carbonitrile as reagents, EXAMPLE 49 was obtained. HRMS calculated for $C_{38}H_{39}N_7O_4$: 657.3063; found 658.3138 [(M+H)$^+$ form].

3-[(4-hydroxy-1-{[(3R,4R)-1-(1,3-oxazol-4-ylmethyl)-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 50)

Using General Procedure 6 starting from Preparation R3ax and 4-(chloromethyl)oxazole as reagents, EXAMPLE 50 was obtained. HRMS calculated for $C_{35}H_{38}N_6O_5$: 622.2903; found 623.2975 [(M+H)$^+$ form].

3-{[1-({(3R,4R)-1-[(1,5-dimethyl-1H-pyrazol-3-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one (Example 51)

Using General Procedure 6 starting from Preparation R3ax and 3-(chloromethyl)-1,5-dimethyl-pyrazole as reagents, EXAMPLE 51 was obtained. HRMS calculated for $C_{37}H_{43}N_7O_4$: 649.3376; found 650.3431 [(M+H)$^+$ form].

3-{[4-hydroxy-1-({(3R,4R)-1-[(5-methyl-1,3-ox-azol-2-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 52)

Using General Procedure 6 starting from Preparation R3ax and 2-(chloromethyl)-5-methyl-oxazole as reagents, EXAMPLE 52 was obtained. HRMS calculated for $C_{36}H_{40}N_6O_5$: 636.3060; found 637.3141 [(M+H)$^+$ form].

3-{[4-hydroxy-1-({(3R,4R)-1-[(2-methyl-1,3-thi-azol-4-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 53)

Using General Procedure 6 starting from Preparation R3ax and 4-(chloromethyl)-2-methyl-thiazole as reagents, EXAMPLE 53 was obtained. HRMS calculated for $C_{36}H_{40}N_6O_4S$: 652.2832; found 653.2896 [(M+H)$^+$ form].

3-{[4-hydroxy-1-({(3R,4R)-1-[(5-methyl-1,2-ox-azol-3-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 54)

Using General Procedure 6 starting from Preparation R3ax and 3-(chloromethyl)-5-methyl-isoxazole as reagents, EXAMPLE 54 was obtained. HRMS calculated for $C_{36}H_{40}N_6O_5$: 636.3060; found 637.3118 [(M+H)$^+$ form].

3-[(4-hydroxy-1-{[(3R,4R)-1-(1,2-oxazol-3-ylm-ethyl)-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 55)

Using General Procedure 6 starting from Preparation R3ax and 3-(chloromethyl)isoxazole as reagents, EXAMPLE 55 was obtained. HRMS calculated for $C_{35}H_{38}N_6O_5$: 622.2903; found 623.2961 [(M+H)$^+$ form].

3-{[4-hydroxy-1-({(3R,4R)-1-[(3-methyl-1,2-ox-azol-5-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 56)

Using General Procedure 6 starting from Preparation R3ax and 5-(chloromethyl)-3-methyl-isoxazole as reagents, EXAMPLE 56 was obtained. HRMS calculated for $C_{36}H_{40}N_6O_5$: 636.3060; found 637.3119 [(M+H)$^+$ form].

3-{[4-hydroxy-1-({(3R,4R)-1-[(5-methyl-1,2-ox-azol-4-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one (Example 57)

Using General Procedure 6 starting from Preparation R3ax and 4-(chloromethyl)-5-methyl-isoxazole as reagents, EXAMPLE 57 was obtained. HRMS calculated for $C_{36}H_{40}N_6O_5$: 636.3060; found 637.3139 [(M+H)$^+$ form].

3-[(4-hydroxy-1-{[(3R,4R)-3-phenyl-1-{[6-(trifluo-romethyl)pyridin-3-yl]methyl}piperidin-4-yl]carbonyl}piperidin-4-yl)methyl]-7-(4-methoxyphe-nyl)-3,7-dihydro-4H-pyrrolo[2,3-d]pyrimidin-4-one (Example 58)

Using General Procedure 6 starting from Preparation R3ax and 5-(bromomethyl)-2-(trifluoromethyl)pyridine as reagents, EXAMPLE 58 was obtained. HRMS calculated for $C_{38}H_{39}F_3N_6O_4$: 700.2985; found 701.3082 [(M+H)$^+$ form].

3-[(4-hydroxy-1-{[(3R,4R)-1-{[2-(6-methoxypyri-din-3-yl)-1,3-thiazol-5-yl]methyl}-3-phenylpiperi-din-4-yl]carbonyl}piperidin-4-yl)methyl]-7-[4-(trif-luoromethoxy)phenyl]-3,7-dihydro-4H-pyrrolo[2,3-d]pyrimidin-4-one (Example 59)

Using General Procedure 6 starting from Preparation R3ay and 5-(chloromethyl)-2-(6-methoxy-3-pyridyl)thiaz-ole as reagents, EXAMPLE 59 was obtained. HRMS calculated for $C_{41}H_{40}F_3N_7O_5S$: 799.2764; found 800.2855 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[4-(trifluo-romethoxy)phenyl]-3,7-dihydro-4H-pyrrolo[2,3-d]pyrimidin-4-one (Example 60)

Using General Procedure 6 starting from Preparation R3ay and Preparation R1c as reagents, EXAMPLE 60 was obtained. HRMS calculated for $C_{41}H_{40}F_3N_7O_4S$: 783.2814; found 784.2904 [(M+H)$^+$ form].

7-[4-(benzyloxy)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 61)

Using General Procedure 6 starting from Preparation R3az and Preparation R1c as reagents, EXAMPLE 61 was obtained. HRMS calculated for $C_{47}H_{47}N_7O_4S$: 805.3410; found 403.6767 [(M+2H)$^{2+}$ form].

7-[4-(benzyloxy)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 62)

Using General Procedure 5 starting from Preparation R3az and 5-(chloromethyl)-2-(6-methoxy-3-pyridyl)thiaz-ole as reagents, EXAMPLE 62 was obtained. HRMS calculated for $C_{47}H_{47}N_7O_5S$: 821.3359; found 822.3433 [(M+H)$^+$ form].

3-[(1-{[(3S,4S)-1-benzyl-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 63)

Using General Procedure 6 starting from 3-({4-hydroxy-1-[(3S,4S)-3-phenylpiperidine-4-carbonyl]piperidin-4-yl}methyl)-7-methyl-3H,4H,7H-pyrrolo[2,3-d]pyrimidin-4-one (which was obtained according to General Procedure 5 with tert-butyl (3S,4S)-4-(2-oxa-6-azaspiro[2.5]octane-6- carbonyl)-3-phenyl-piperidine-1-carboxylate and Preparation R2b) and benzyl bromide as reagents, EXAMPLE 63 was obtained. HRMS calculated for $C_{32}H_{37}N_5O_3$: 539.2896; found 540.2984 [(M+H)$^+$ form].

3-[(1-{[(3R,4R)-1-benzyl-3-phenylpiperidin-4-yl]
carbonyl}-4-hydroxypiperidin-4-yl)methyl]-7-
methyl-3,7-dihydro-4H-pyrrolo[2,3-d]pyrimidin-4-
one (Example 64)

Using General Procedure 6 starting from Preparation R3b and benzyl bromide as reagents, EXAMPLE 64 was obtained. HRMS calculated for $C_{32}H_{37}N_5O_3$: 539.2896; found 540.2977 [(M+H)$^+$ form].

3-[(1-{[(3R,4R)-1-(2-fluorobenzyl)-3-phenylpiperi-
din-4-yl]carbonyl}-4-hydroxypiperidin-4-yl)
methyl]-7-methyl-3,7-dihydro-4H-pyrrolo[2,3-d]
pyrimidin-4-one (Example 65)

Using General Procedure 6 starting from Preparation R3b and 1-(bromomethyl)-2-fluoro-benzene as reagents, EXAMPLE 65 was obtained. HRMS calculated for $C_{32}H_{36}FN_5O_3$: 557.2802; found 558.2879 [(M+H)$^+$ form].

3-[(1-{[(3R,4R)-1-(3-fluorobenzyl)-3-phenylpiperi-
din-4-yl]carbonyl}-4-hydroxypiperidin-4-yl)
methyl]-7-methyl-3,7-dihydro-4H-pyrrolo[2,3-d]
pyrimidin-4-one (Example 66)

Using General Procedure 6 starting from Preparation R3b and 1-(bromomethyl)-3-fluoro-benzene as reagents, EXAMPLE 66 was obtained. HRMS calculated for $C_{32}H_{36}FN_5O_3$: 557.2802; found 558.2902 [(M+H)$^+$ form].

3-[(4-hydroxy-1-{[(3R,4R)-1-(2-methylbenzyl)-3-
phenylpiperidin-4-yl]carbonyl}piperidin-4-yl)
methyl]-7-methyl-3,7-dihydro-4H-pyrrolo[2,3-d]
pyrimidin-4-one (Example 67)

Using General Procedure 6 starting from Preparation R3b and 1-(bromomethyl)-2-methyl-benzene as reagents, EXAMPLE 67 was obtained. HRMS calculated for $C_{33}H_{39}N_5O_3$: 553.3053; found 554.3138 [(M+H)$^+$ form].

3-[(4-hydroxy-1-{[(3R,4R)-1-(3-methylbenzyl)-3-
phenylpiperidin-4-yl]carbonyl}piperidin-4-yl)
methyl]-7-methyl-3,7-dihydro-4H-pyrrolo[2,3-d]
pyrimidin-4-one (Example 68)

Using General Procedure 6 starting from Preparation R3b and 1-(bromomethyl)-3-methyl-benzene as reagents, EXAMPLE 68 was obtained. HRMS calculated for $C_{33}H_{39}N_5O_3$: 553.3052; found 554.3090 [(M+H)$^+$ form].

3-[(1-{[(3R,4R)-1-(3-bromobenzyl)-3-phenylpiperi-
din-4-yl]carbonyl}-4-hydroxypiperidin-4-yl)
methyl]-7-methyl-3,7-dihydro-4H-pyrrolo[2,3-d]
pyrimidin-4-one (Example 69)

Using General Procedure 6 starting from Preparation R3b and 1-bromo-3-(bromomethyl)benzene as reagents, EXAMPLE 69 was obtained. HRMS calculated for $C_{32}H_{36}BrN_5O_3$: 617.2001; found 618.2094 [(M+H)$^+$ form].

6-{[(3R,4R)-4-({4-hydroxy-4-[(7-methyl-4-oxo-4,7-
dihydro-3H-pyrrolo[2,3-d]pyrimidin-3-yl)methyl]
piperidin-1-yl}carbonyl)-3-phenylpiperidin-1-yl]
methyl}-1-methyl-3,4-dihydroquinolin-2(1H)-one
(Example 70)

Using General Procedure 6 starting from Preparation R3b and 6-(chloromethyl)-1-methyl-3,4-dihydroquinolin-2-one as reagents, EXAMPLE 70 was obtained. HRMS calculated for $C_{36}H_{42}N_6O_4$: 622.3268; found 623.3354 [(M+H)$^+$ form].

3-[(1-{[(3R,4R)-1-(3-acetylbenzyl)-3-phenylpiperi-
din-4-yl]carbonyl}-4-hydroxypiperidin-4-yl)
methyl]-7-methyl-3,7-dihydro-4H-pyrrolo[2,3-d]
pyrimidin-4-one (Example 71)

Using General Procedure 6 starting from Preparation R3b and 1-[3-(chloromethyl)phenyl]ethanone as reagents, EXAMPLE 71 was obtained. HRMS calculated for $C_{34}H_{39}N_5O_4$: 581.3002; found 582.3054 [(M+H)$^+$ form].

3-[(4-hydroxy-1-{[(3R,4R)-1-{[2-(6-methylpyridin-
3-yl)-1,3-thiazol-5-yl]methyl}-3-phenylpiperidin-4-
yl]carbonyl}piperidin-4-yl)methyl]-7-(5-methylthio-
phen-2-yl)-3,7-dihydro-4H-pyrrolo[2,3-d]pyrimidin-
4-one (Example 72)

Using General Procedure 6 starting from Preparation R3ba and Preparation R1c as reagents, EXAMPLE 72 was obtained. HRMS calculated for $C_{39}H_{41}N_7O_3S_2$: 719.2712; found 720.2762 [(M+H)$^+$ form].

3-[(4-hydroxy-1-{[(3R,4R)-1-{[2-(6-methoxypyri-
din-3-yl)-1,3-thiazol-5-yl]methyl}-3-phenylpiperi-
din-4-yl]carbonyl}piperidin-4-yl)methyl]-7-(5-meth-
ylthiophen-2-yl)-3,7-dihydro-4H-pyrrolo[2,3-d]
pyrimidin-4-one (Example 73)

Using General Procedure 6 starting from Preparation R3ba and 5-(chloromethyl)-2-(6-methoxy-3-pyridyl)thiazole as reagents, EXAMPLE 73 was obtained. HRMS calculated for $C_{39}H_{41}N_7O_4S_2$: 735.2661; found 736.2727 [(M+H)$^+$ form].

7-(5-chlorothiophen-2-yl)-3-[(4-hydroxy-1-{[(3R,
4R)-1-{[2-(6-methoxypyridin-3-yl)-1,3-thiazol-5-yl]
methyl}-3-phenylpiperidin-4-yl]carbonyl}piperidin-
4-yl)methyl]-3,7-dihydro-4H-pyrrolo[2,3-d]
pyrimidin-4-one (Example 74)

Using General Procedure 6 starting from Preparation R3bb and 5-(chloromethyl)-2-(6-methoxy-3-pyridyl)thiazole as reagents, EXAMPLE 74 was obtained. HRMS calculated for $C_{38}H_{38}ClN_7O_4S_2$: 755.2115; found 756.219 [(M+H)$^+$ form].

7-(5-chlorothiophen-2-yl)-3-[(4-hydroxy-1-{[(3R,
4R)-1-{[2-(6-methylpyridin-3-yl)-1,3-thiazol-5-yl]
methyl}-3-phenylpiperidin-4-yl]carbonyl}piperidin-
4-yl)methyl]-3,7-dihydro-4H-pyrrolo[2,3-d]
pyrimidin-4-one (Example 75)

Using General Procedure 6 starting from Preparation R3bb and Preparation R1c as reagents, EXAMPLE 75 was

7-(2,3-dihydro-1,4-benzodioxin-6-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 76)

Using General Procedure 6 starting from Preparation R3bc and Preparation R1c as reagents, EXAMPLE 76 was obtained. HRMS calculated for $C_{42}H_{43}N_7O_5S$: 757.3046; found 758.3125 [(M+H)$^+$ form].

7-(2,3-dihydro-1,4-benzodioxin-6-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 77)

Using General Procedure 6 starting from Preparation R3bc and 5-(chloromethyl)-2-(6-methoxy-3-pyridyl)thiazole as reagents, EXAMPLE 77 was obtained. HRMS calculated for $C_{42}H_{43}N_7O_6S$: 773.2996; found 774.3038 [(M+H)$^+$ form].

7-(1,3-benzodioxol-5-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 78)

Using General Procedure 6 starting from Preparation R3bd and Preparation R1c as reagents, EXAMPLE 78 was obtained. HRMS calculated for $C_{41}H_{41}N_7O_5S$: 743.2890; found 372.6517 [(M+2H)$^{2+}$ form].

7-(1,3-benzodioxol-5-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 79)

Using General Procedure 6 starting from Preparation R3bd and 5-(chloromethyl)-2-(6-methoxy-3-pyridyl)thiazole as reagents, EXAMPLE 79 was obtained. HRMS calculated for $C_{41}H_{41}N_7O_6S$: 759.2838; found 380.6487 [(M+2H)$^{2+}$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one (Example 80)

Using General Procedure 6 starting from Preparation R3bf and 5-(chloromethyl)-2-(6-methoxy-3-pyridyl)thiazole as reagents, EXAMPLE 80 was obtained. HRMS calculated for $C_{41}H_{43}N_7O_4S$: 729.3097; found 730.3189 [(M+H)$^+$ form]. 3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one (Example 81)

Using General Procedure 6 starting from Preparation R3bg and Preparation R1c as reagents, EXAMPLE 81 was obtained. HRMS calculated for $C_{41}H_{40}F_3N_7O_3S$: 767.2865; found 768.2943 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one (Example 82)

Using General Procedure 6 starting from Preparation R3bg and 5-(chloromethyl)-2-(6-methoxy-3-pyridyl)thiazole as reagents, EXAMPLE 82 was obtained. HRMS calculated for $C_{41}H_{40}F_3N_7O_4S$: 783.2814; found 784.2897 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-{3-[(4-methylpiperazin-1-yl)methyl]phenyl}-3,7-dihydro-4H-pyrrolo[2,3-d]pyrimidin-4-one (Example 83)

Using General Procedure 6 starting from Preparation R3bh and Preparation R1c as reagents, EXAMPLE 83 was obtained. HRMS calculated for $C_{46}H_{53}N_9O_3S$: 811.3992; found 406.7081 [(M+2H)$^{2+}$ form].

7-[3-(hydroxymethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 84)

Using General Procedure 6 starting from Preparation R3bi and Preparation R1c as reagents, EXAMPLE 84 was obtained. HRMS calculated for $C_{41}H_{43}N_7O_4S$: 729.3098; found 730.3153 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one (Example 85)

Using General Procedure 6 starting from Preparation R3bi and 5-(chloromethyl)-2-(6-methoxy-3-pyridyl)thiazole as reagents, EXAMPLE 85 was obtained. HRMS calculated for $C_{41}H_{43}N_7O_5S$: 745.3046; found 746.313 [(M+H)$^+$ form].

7-(3-chlorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 86)

Using General Procedure 6 starting from Preparation R3bj and 5-(chloromethyl)-2-(6-methoxy-3-pyridyl)thiazole as reagents, EXAMPLE 86 was obtained. HRMS calculated for $C_{40}H_{40}N_7O_4SCl$: 749.2551; found 750.2624 [(M+H)$^+$ form].

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-(3-chlorophenyl)-3,7-dihydro-4H-pyrrolo[2,3-d]pyrimidin-4-one (Example 87)

Using General Procedure 6 starting from Preparation R3bj and 2-bromo-5-(bromomethyl)thiazole as reagents, EXAMPLE 87 was obtained. HRMS calculated for $C_{34}H_{34}BrClN_6O_3S$: 720.1284; found 721.1336 [(M+H)+ form].

7-(3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 88)

Using General Procedure 6 starting from Preparation R3bk and Preparation R1c as reagents, EXAMPLE 88 was obtained. HRMS calculated for $C_{40}H_{40}FN_7O_3S$: 717.2897; found 359.6513 [(M+2H)²⁺ form].

7-(3-fluorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 89)

Using General Procedure 6 starting from Preparation R3bk and 5-(chloromethyl)-2-(6-methoxy-3-pyridyl)thiazole as reagents, EXAMPLE 89 was obtained. HRMS calculated for $C_{40}H_{40}FN_7O_4S$: 733.2847; found 734.2893 [(M+H)+ form]. 7-[3-(dimethylamino)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 90)

Using General Procedure 6 starting from Preparation R3bl and Preparation R1c as reagents, EXAMPLE 90 was obtained. HRMS calculated for $C_{42}H_{46}N_8O_3S$: 742.3413; found 372.1784 [(M+2H)²⁺ form].

7-[3-(dimethylamino)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 91)

Using General Procedure 6 starting from Preparation R3bl and 5-(chloromethyl)-2-(6-methoxy-3-pyridyl)thiazole as reagents, EXAMPLE 91 was obtained. HRMS calculated for $C_{42}H_{46}N_8O_4S$: 758.3362; found 380.1752 [(M+2H)²⁺ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one (Example 92)

Using General Procedure 6 starting from Preparation R3bm and Preparation R1c as reagents, EXAMPLE 92 was obtained. HRMS calculated for $C_{44}H_{48}N_8O_4S$: 784.3519; found 785.3594 [(M+H)+ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one (Example 93)

Using General Procedure 6 starting from Preparation R3bm and 5-(chloromethyl)-2-(6-methoxy-3-pyridyl)thiazole as reagents, EXAMPLE 93 was obtained. HRMS calculated for $C_{44}H_{48}N_8O_5S$: 800.3468; found 801.3546 [(M+H)+ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 94)

Using General Procedure 6 starting from Preparation R3bo and 5-(chloromethyl)-2-(6-methoxy-3-pyridyl)thiazole as reagents, EXAMPLE 94 was obtained. HRMS calculated for $C_{41}H_{43}N_7O_5S$: 745.3046; found 746.3117 [(M+H)+ form].

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-(3-methoxyphenyl)-3,7-dihydro-4H-pyrrolo[2,3-d]pyrimidin-4-one (Example 95)

Using General Procedure 6 starting from Preparation R3bo and 2-bromo-5-(bromomethyl)thiazole as reagents, EXAMPLE 95 was obtained. HRMS calculated for $C_{35}H_{37}BrN_6O_4S$: 716.1780; found 717.1825 [(M+H)+ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(trifluoromethoxy)phenyl]-3,7-dihydro-4H-pyrrolo[2,3-d]pyrimidin-4-one (Example 96)

Using General Procedure 6 starting from Preparation R3bp and Preparation R1c as reagents, EXAMPLE 96 was obtained. HRMS calculated for $C_{41}H_{40}F_3N_7O_4S$: 783.2814; found 784.2878 [(M+H)+ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(trifluoromethoxy)phenyl]-3,7-dihydro-4H-pyrrolo[2,3-d]pyrimidin-4-one (Example 97)

Using General Procedure 6 starting from Preparation R3bp and 5-(chloromethyl)-2-(6-methoxy-3-pyridyl)thiazole as reagents, EXAMPLE 97 was obtained. HRMS calculated for $C_{41}H_{40}F_3N_7O_5S$: 799.2764; found 800.2856 [(M+H)+ form].

7-[3-(benzyloxy)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 98)

Using General Procedure 6 starting from Preparation R3bq and 5-(chloromethyl)-2-(6-methoxy-3-pyridyl)thiazole as reagents, EXAMPLE 98 was obtained. HRMS calculated for $C_{47}H_{47}N_7O_5S$: 821.3359; found 822.343 [(M+H)+ form].

7-[3-(benzyloxy)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 99)

Using General Procedure 6 starting from Preparation R3bq and Preparation R1c as reagents, EXAMPLE 99 was obtained. HRMS calculated for $C_{47}H_{47}N_7O_4S$: 805.3410; found 806.3484 (M+H)⁺ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(6-methoxy-pyridin-2-yl)-3,7-dihydro-4H-pyrrolo[2,3-d]pyrimidin-4-one (Example 100)

Using General Procedure 6 starting from Preparation R3bs and Preparation R1c as reagents, EXAMPLE 100 was obtained. HRMS calculated for $C_{40}H_{42}N_8O_4S$: 730.3049; found 731.3128 [(M+H)⁺ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(6-methoxypyridin-2-yl)-3,7-dihydro-4H-pyrrolo[2,3-d]pyrimidin-4-one (Example 101)

Using General Procedure 6 starting from Preparation R3bs and 5-(chloromethyl)-2-(6-methoxy-3-pyridyl)thiazole as reagents, EXAMPLE 101 was obtained. HRMS calculated for $C_{40}H_{42}N_8O_5S$: 746.2998; found 747.308 [(M+H)⁺ form].

3-[(1-{[(3R,4R)-1-benzyl-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 102)

Using General Procedure 6 starting from Preparation R3bu and benzyl bromide as reagents, EXAMPLE 102 was obtained. HRMS calculated for $C_{37}H_{39}N_5O_3$: 601.3053; found 602.3155 [(M+H)⁺ form].

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 103)

Using General Procedure 6 starting from Preparation R3bu and 2-bromo-5-(bromomethyl)thiazole as reagents, EXAMPLE 103 was obtained. HRMS calculated for $C_{34}H_{35}N_6O_3SBr$: 686.1675; found 687.1743 [(M+H)⁺ form].

3-{[1-({(3R,4R)-1-[(5-bromopyridin-3-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 104)

Using General Procedure 6 starting from Preparation R3bu and 3-bromo-5-(chloromethyl)pyridine as reagents, EXAMPLE 104 was obtained. HRMS calculated for $C_{36}H_{37}BrN_6O_3$: 680.2111; found 681.2179 [(M+H)⁺ form].

3-[(4-hydroxy-1-{[(3R,4R)-3-phenyl-1-(pyridin-4-ylmethyl)piperidin-4-yl]carbonyl}piperidin-4-yl)methyl]-7-phenyl-3,7-dihydro-4H-pyrrolo[2,3-d]pyrimidin-4-one (Example 105)

Using General Procedure 6 starting from Preparation R3bu and 4-(chloromethyl)pyridine as reagents, EXAMPLE 105 was obtained. HRMS calculated for $C_{36}H_{38}N_6O_3$: 602.3005; found 603.3085 [(M+H)⁺ form].

3-[(4-hydroxy-1-{[(3R,4R)-3-phenyl-1-(pyridin-3-ylmethyl)piperidin-4-yl]carbonyl}piperidin-4-yl)methyl]-7-phenyl-3,7-dihydro-4H-pyrrolo[2,3-d]pyrimidin-4-one (Example 106)

Using General Procedure 6 starting from Preparation R3bu and 3-(bromomethyl)pyridine hydrobromide as reagents, EXAMPLE 106 was obtained. HRMS calculated for $C_{36}H_{38}N_6O_3$: 602.3005; found 603.3062 [(M+H)⁺ form].

3-{[4-hydroxy-1-({(3R,4R)-1-[(1-methyl-1H-pyrazol-4-yl)methyl]-3-phenylpiperidin-4-yl}carbonyl)piperidin-4-yl]methyl}-7-phenyl-3,7-dihydro-4H-pyrrolo[2,3-d]pyrimidin-4-one (Example 107)

Using General Procedure 6 starting from Preparation R3bu and 4-(chloromethyl)-1-methyl-pyrazole as reagents, EXAMPLE 107 was obtained. HRMS calculated for $C_{35}H_{39}N_7O_3$: 605.3115; found 606.3188 [(M+H)⁺ form].

3-[(4-hydroxy-1-{[(3R,4R)-3-phenyl-1-(pyrazin-2-ylmethyl)piperidin-4-yl]carbonyl}piperidin-4-yl)methyl]-7-phenyl-3,7-dihydro-4H-pyrrolo[2,3-d]pyrimidin-4-one (Example 108)

Using General Procedure 6 starting from Preparation R3bu and 2-(chloromethyl)pyrazine hydrochloride as reagents, EXAMPLE 108 was obtained. HRMS calculated for $C_{35}H_{37}N_7O_3$: 603.2958; found 604.3021 [(M+H)⁺ form].

3-[(4-hydroxy-1-{[(3R,4R)-3-phenyl-1-(1,3-thiazol-5-ylmethyl)piperidin-4-yl]carbonyl}piperidin-4-yl)methyl]-7-phenyl-3,7-dihydro-4H-pyrrolo[2,3-d]pyrimidin-4-one (Example 109)

Using General Procedure 9 starting from EXAMPLE 103 and methyl 5-(4,4,5,5-tetramethyl-1,3,2-dioxaborolan-2-yl)pyridine-2-carboxylate as reagents, EXAMPLE 109 was obtained as a result of a dehalogenation during the Suzuki coupling. HRMS calculated for $C_{34}H_{36}N_6O_3S$: 608.2567; found 609.265 [(M+H)⁺ form].

3-{[4-hydroxy-1-({(3R,4R)-1-[(5-methyl-1,3-oxazol-2-yl)methyl]-3-phenylpiperidin-4-yl}carbonyl)piperidin-4-yl]methyl}-7-phenyl-3,7-dihydro-4H-pyrrolo[2,3-d]pyrimidin-4-one (Example 110)

Using General Procedure 6 starting from Preparation R3bu and 2-(chloromethyl)-5-methyl-oxazole as reagents, EXAMPLE 110 was obtained. HRMS calculated for $C_{35}H_{38}N_6O_4$: 606.2955; found 607.3016 [(M+H)⁺ form].

3-[(4-hydroxy-1-{[(3R,4R)-3-phenyl-1-(1,3-thiazol-2-ylmethyl)piperidin-4-yl]carbonyl}piperidin-4-yl)methyl]-7-phenyl-3,7-dihydro-4H-pyrrolo[2,3-d]pyrimidin-4-one (Example 111)

Using General Procedure 6 starting from Preparation R3bu and 2-(chloromethyl)thiazole as reagents, EXAMPLE 111 was obtained. HRMS calculated for $C_{34}H_{36}N_6O_3S$: 608.2567; found 609.2651 [(M+H)⁺ form].

3-{[4-hydroxy-1-({(3R,4R)-1-[(5-methyl-1,3-thi-
azol-2-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 112)

Using General Procedure 6 starting from Preparation R3bu and 2-(chloromethyl)-5-methyl-thiazole as reagents, EXAMPLE 112 was obtained. HRMS calculated for $C_{35}H_{38}N_6O_3S$: 622.2726; found 623.2783 [(M+H)$^+$ form].

3-[(4-hydroxy-1-{[(3R,4R)-1-(1,2-oxazol-3-ylm-
ethyl)-3-phenylpiperidin-4-yl]carbonyl}piperidin-4-
yl)methyl]-7-phenyl-3,7-dihydro-4H-pyrrolo[2,3-d]
pyrimidin-4-one (Example 113)

Using General Procedure 6 starting from Preparation R3bu and 3-(chloromethyl)isoxazole as reagents, EXAMPLE 113 was obtained. HRMS calculated for $C_{34}H_{36}N_6O_4$: 592.2798; found 593.2864 [(M+H)$^+$ form].

3-{[4-hydroxy-1-({(3R,4R)-1-[(3-methyl-1,2-ox-
azol-5-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 114)

Using General Procedure 6 starting from Preparation R3bu and 5-(chloromethyl)-3-methyl-isoxazole as reagents, EXAMPLE 114 was obtained. HRMS calculated for $C_{35}H_{38}N_6O_4$: 606.2955; found 607.3046 [(M+H)$^+$ form].

3-{[4-hydroxy-1-({(3R,4R)-1-[(4-methyl-1,3-thi-
azol-2-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 115)

Using General Procedure 6 starting from Preparation R3bu and 2-(chloromethyl)-4-methyl-thiazole as reagents, EXAMPLE 115 was obtained. HRMS calculated for $C_{35}H_{38}N_6O_3S$: 622.2726; found 623.2782 [(M+H)$^+$ form].

3-{[1-({(3R,4R)-1-[(2,4-dimethyl-1,3-thiazol-5-yl)
methyl]-3-phenylpiperidin-4-yl}carbonyl)-4-hy-
droxypiperidin-4-yl]methyl}-7-phenyl-3,7-dihydro-
4H-pyrrolo[2,3-d]pyrimidin-4-one (Example 116)

Using General Procedure 6 starting from Preparation R3bu and 5-(chloromethyl)-2,4-dimethyl-thiazole as reagents, EXAMPLE 116 was obtained. HRMS calculated for $C_{36}H_{40}N_6O_3S$: 636.2883; found 637.2942 [(M+H)$^+$ form].

3-{[1-({(3R,4R)-1-[(4,5-dimethyl-1,3-thiazol-2-yl)
methyl]-3-phenylpiperidin-4-yl}carbonyl)-4-hy-
droxypiperidin-4-yl]methyl}-7-phenyl-3,7-dihydro-
4H-pyrrolo[2,3-d]pyrimidin-4-one (Example 117)

Using General Procedure 6 starting from Preparation R3bu and 2-(chloromethyl)-4,5-dimethyl-thiazole as reagents, EXAMPLE 117 was obtained. HRMS calculated for $C_{36}H_{40}N_6O_3S$: 636.2883; found 637.2965 [(M+H)$^+$ form].

3-{[4-hydroxy-1-({(3R,4R)-1-[(5-methyl-1,2-ox-
azol-4-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 118)

Using General Procedure 6 starting from Preparation R3bu and 4-(chloromethyl)-5-methyl-isoxazole as reagents, EXAMPLE 118 was obtained. HRMS calculated for $C_{35}H_{38}N_6O_4$: 606.2955; found 607.3009 [(M+H)$^+$ form].

3-{[4-hydroxy-1-({(3R,4R)-1-[(1-methyl-1H-pyra-
zol-5-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 119)

Using General Procedure 6 starting from Preparation R3bu and 5-(chloromethyl)-1-methyl-pyrazole as reagents, EXAMPLE 119 was obtained. HRMS calculated for $C_{35}H_{39}N_7O_3$: 605.3115; found 606.3186 [(M+H)$^+$ form].

3-{[4-hydroxy-1-({(3R,4R)-1-[(5-methyl-1,2-ox-
azol-3-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 120)

Using General Procedure 6 starting from Preparation R3bu and 3-(chloromethyl)-5-methyl-isoxazole as reagents, EXAMPLE 120 was obtained. HRMS calculated for $C_{35}H_{38}N_6O_4$: 606.2955; found 607.3011 [(M+H)$^+$ form].

3-{[4-hydroxy-1-({(3R,4R)-1-[(2-methyl-1,3-thi-
azol-4-yl)methyl]-3-phenylpiperidin-4-yl}carbonyl)
piperidin-4-yl]methyl}-7-phenyl-3,7-dihydro-4H-
pyrrolo[2,3-d]pyrimidin-4-one (Example 121)

Using General Procedure 6 starting from Preparation R3bu and 4-(chloromethyl)-2-methyl-thiazole as reagents, EXAMPLE 121 was obtained. HRMS calculated for $C_{35}H_{38}N_6O_3S$: 622.2726; found 623.2799 [(M+H)$^+$ form].

4-{[(3R,4R)-4-({4-hydroxy-4-[(4-oxo-7-phenyl-4,7-
dihydro-3H-pyrrolo[2,3-d]pyrimidin-3-yl)methyl]
piperidin-1-yl}carbonyl)-3-phenylpiperidin-1-yl]
methyl}pyridine-2-carbonitrile (Example 122)

Using General Procedure 6 starting from Preparation R3bu and 4-(chloromethyl)pyridine-2-carbonitrile as reagents, EXAMPLE 122 was obtained. HRMS calculated for $C_{37}H_{37}N_7O_3$: 627.2958; found 628.3026 [(M+H)$^+$ form].

5-{[(3R,4R)-4-({4-hydroxy-4-[(4-oxo-7-phenyl-4,7-
dihydro-3H-pyrrolo[2,3-d]pyrimidin-3-yl)methyl]
piperidin-1-yl}carbonyl)-3-phenylpiperidin-1-yl]
methyl}pyridine-2-carbonitrile (Example 123)

Using General Procedure 6 starting from Preparation R3bu and 5-(bromomethyl)pyridine-2-carbonitrile as reagents, EXAMPLE 123 was obtained. HRMS calculated for $C_{37}H_{37}N_7O_3$: 627.2958; found 628.3025 [(M+H)$^+$ form].

3-[(4-hydroxy-1-{[(3R,4R)-1-(1,3-oxazol-4-ylm-
ethyl)-3-phenylpiperidin-4-yl]carbonyl}piperidin-4-
yl)methyl]-7-phenyl-3,7-dihydro-4H-pyrrolo[2,3-d]
pyrimidin-4-one (Example 124)

Using General Procedure 6 starting from Preparation R3bu and 4-(chloromethyl)oxazole as reagents, EXAMPLE 124 was obtained. HRMS calculated for $C_{34}H_{36}N_6O_4$: 592.2797852; found 593.2876 [(M+H)$^+$ form].

3-{[4-hydroxy-1-({(3R,4R)-1-[(6-methylpyridin-3-yl)methyl]-3-phenylpiperidin-4-yl}carbonyl)piperidin-4-yl]methyl}-7-phenyl-3,7-dihydro-4H-pyrrolo[2,3-d]pyrimidin-4-one (Example 125)

Using General Procedure 6 starting from Preparation R3bu and 5-(bromomethyl)-2-methyl-pyridine hydrobromide as reagents, EXAMPLE 125 was obtained. HRMS calculated for $C_{37}H_{40}N_6O_3$: 616.3162; found 617.3241 [(M+H)$^+$ form].

3-[(1-{[(3S,4S)-1-benzyl-3-phenylpiperidin-4-yl]carbonyl}-4-hydroxypiperidin-4-yl)methyl]-7-ethyl-3,7-dihydro-4H-pyrrolo[2,3-d]pyrimidin-4-one (Example 126)

Using General Procedure 6 starting from 7-ethyl-3-({4-hydroxy-1-[(3S,4S)-3-phenylpiperidine-4-carbonyl]piperidin-4-yl}methyl)-3H,4H,7H-pyrrolo[2,3-d]pyrimidin-4-one (which was obtained according to General Procedure 5 with tert-butyl (3S,4S)-4-(2-oxa-6-azaspiro[2.5]octane-6-carbonyl)-3-phenyl-piperidine-1-carboxylate and Preparation R2c) and benzyl bromide as reagents, EXAMPLE 126 was obtained. HRMS calculated for $C_{33}H_{39}N_5O_3$: 553.3053; found 554.312 [(M+H)$^+$ form].

3-[(1-{[(3R,4R)-1-benzyl-3-phenylpiperidin-4-yl]carbonyl}-4-hydroxypiperidin-4-yl)methyl]-7-ethyl-3,7-dihydro-4H-pyrrolo[2,3-d]pyrimidin-4-one (Example 127)

Using General Procedure 6 starting from Preparation R3c and benzyl bromide as reagents, EXAMPLE 127 was obtained. HRMS calculated for $C_{33}H_{39}N_5O_3$: 553.3053; found 554.3122 [(M+H)$^+$ form].

7-ethyl-3-[(1-{[(3R,4R)-1-(2-fluorobenzyl)-3-phenylpiperidin-4-yl]carbonyl}-4-hydroxypiperidin-4-yl)methyl]-3,7-dihydro-4H-pyrrolo[2,3-d]pyrimidin-4-one (Example 128)

Using General Procedure 6 starting from Preparation R3c and 1-(bromomethyl)-2-fluoro-benzene as reagents, EXAMPLE 128 was obtained. HRMS calculated for $C_{33}H_{38}FN_5O_3$: 571.2959; found 572.3022 [(M+H)$^+$ form].

7-ethyl-3-[(1-{[(3R,4R)-1-(3-fluorobenzyl)-3-phenylpiperidin-4-yl]carbonyl}-4-hydroxypiperidin-4-yl)methyl]-3,7-dihydro-4H-pyrrolo[2,3-d]pyrimidin-4-one (Example 129)

Using General Procedure 6 starting from Preparation R3c and 1-(bromomethyl)-3-fluoro-benzene as reagents, EXAMPLE 129 was obtained. HRMS calculated for $C_{33}H_{38}FN_5O_3$: 571.2959; found 572.3037 [(M+H)$^+$ form].

7-ethyl-3-[(4-hydroxy-1-{[(3R,4R)-1-(2-methylbenzyl)-3-phenylpiperidin-4-yl]carbonyl}piperidin-4-yl)methyl]-3,7-dihydro-4H-pyrrolo[2,3-d]pyrimidin-4-one (Example 130)

Using General Procedure 6 starting from Preparation R3c and 1-(bromomethyl)-2-methyl-benzene as reagents, EXAMPLE 130 was obtained. HRMS calculated for $C_{34}H_{41}N_5O_3$: 567.3209; found 568.327 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one (Example 131)

Using General Procedure 6 starting from Preparation R3cc and Preparation R1c as reagents, EXAMPLE 131 was obtained. HRMS calculated for $C_{38}H_{39}N_7O_3S_2$: 705.2556; found 706.262 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one (Example 132)

Using General Procedure 6 starting from Preparation R3cc and 5-(chloromethyl)-2-(6-methoxy-3-pyridyl)thiazole as reagents, EXAMPLE 132 was obtained. HRMS calculated for $C_{38}H_{39}N_7O_4S_2$: 721.2505; found 722.2596 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one (Example 133)

Using General Procedure 6 starting from Preparation R3cf and 5-(chloromethyl)-2-(6-methoxy-3-pyridyl)thiazole as reagents, EXAMPLE 133 was obtained. HRMS calculated for $C_{38}H_{39}N_7O_4S_2$: 721.2505; found 722.2570 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1-methyl-1H-imidazol-4-yl)-3,7-dihydro-4H-pyrrolo[2,3-d]pyrimidin-4-one (Example 134)

Using General Procedure 6 starting from Preparation R3cg and Preparation R1c as reagents, EXAMPLE 134 was obtained. HRMS calculated for $C_{38}H_{41}N_9O_3S$: 703.3053; found 352.6599 [(M+2H)$^{2+}$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(1-methyl-1H-imidazol-4-yl)-3,7-dihydro-4H-pyrrolo[2,3-d]pyrimidin-4-one (Example 135)

Using General Procedure 6 starting from Preparation R3cg and 5-(chloromethyl)-2-(6-methoxy-3-pyridyl)thiazole as reagents, EXAMPLE 135 was obtained. HRMS calculated for $C_{38}H_{41}N_9O_4S$: 719.3002; found 360.6580 [(M+2H)$^{2+}$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one (Example 136)

Using General Procedure 6 starting from Preparation R3ch and Preparation R1c as reagents, EXAMPLE 136 was obtained. HRMS calculated for $C_{38}H_{41}N_9O_3S$: 703.3053; found 704.3095 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one (Example 137)

Using General Procedure 6 starting from Preparation R3ch and 5-(chloromethyl)-2-(6-methoxy-3-pyridyl)thiazole as reagents, EXAMPLE 137 was obtained. HRMS calculated for $C_{38}H_{41}N_9O_4S$: 719.3002; found 720.3059 [(M+H)$^+$ form].

7-[1-(difluoromethyl)-1H-pyrazol-4-yl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 138)

Using General Procedure 6 starting from Preparation R3ci and Preparation R1c as reagents, EXAMPLE 138 was obtained. HRMS calculated for $C_{38}H_{39}F_2N_9O_3S$: 739.2864; found 740.2936 [(M+H)$^+$ form].

7-[1-(difluoromethyl)-1H-pyrazol-4-yl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 139)

Using General Procedure 6 starting from Preparation R3ci and 5-(chloromethyl)-2-(6-methoxy-3-pyridyl)thiazole as reagents, EXAMPLE 139 was obtained. HRMS calculated for $C_{38}H_{39}F_2N_9O_4S$: 755.2814; found 756.287 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1,3-thiazol-2-yl)-3,7-dihydro-4H-pyrrolo[2,3-d]pyrimidin-4-one (Example 140)

Using General Procedure 6 starting from Preparation R3ck and Preparation R1c as reagents, EXAMPLE 140 was obtained. HRMS calculated for $C_{37}H_{38}N_8O_3S_2$: 706.2509; found 707.257 [(M+H)$^+$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(1,3-thiazol-2-yl)-3,7-dihydro-4H-pyrrolo[2,3-d]pyrimidin-4-one (Example 141)

Using General Procedure 6 starting from Preparation R3ck and 5-(chloromethyl)-2-(6-methoxy-3-pyridyl)thiazole as reagents, EXAMPLE 141 was obtained. HRMS calculated for $C_{37}H_{38}N_8O_4S_2$: 722.2457; found 723.2535 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(prop-2-yn-1-yl)-3,7-dihydro-4H-pyrrolo[2,3-d]pyrimidin-4-one (Example 142)

Using General Procedure 6 starting from Preparation R3m and Preparation R1c as reagents, EXAMPLE 142 was obtained. HRMS calculated for $C_{37}H_{39}N_7O_3S$: 661.2835; found 662.2896 [(M+H)$^+$ form].

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-(2,2,2-trifluoroethyl)-3,7-dihydro-4H-pyrrolo[2,3-d]pyrimidin-4-one (Example 143)

Using General Procedure 6 starting from Preparation R3o and 2-bromo-5-(bromomethyl)thiazole as reagents, EXAMPLE 143 was obtained. HRMS calculated for $C_{30}H_{32}BrF_3N_6O_3S$: 692.1392; found 693.1452 [(M+H)$^+$ form].

7-(buta-2,3-dien-1-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 144)

Using General Procedure 6 starting from Preparation R3s and Preparation R1c as reagents, EXAMPLE 144 was obtained. HRMS calculated for $C_{38}H_{41}N_7O_3S$: 675.2991; found 676.3089 [(M+H)$^+$ form].

7-(4-chlorobenzyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 145)

Using General Procedure 6 starting from Preparation R3x and Preparation R1c as reagents, EXAMPLE 145 was obtained. HRMS calculated for $C_{41}H_{42}ClN_7O_3S$: 747.2758; found 374.6462 [(M+2H)$^{2+}$ form].

7-(3-chlorobenzyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 146)

Using General Procedure 6 starting from Preparation R3y and Preparation R1c as reagents, EXAMPLE 146 was obtained. HRMS calculated for $C_{41}H_{42}ClN_7O_3S$: 747.2758; found 374.645 [(M+2H)$^{2+}$ form].

7-benzyl-3-[(1-{[1-benzyl-3-phenylpiperidin-4-yl]carbonyl}-4-hydroxypiperidin-4-yl)methyl]-3,7-dihydro-4H-pyrrolo[2,3-d]pyrimidin-4-one (Example 147)

Using General Procedure 6 starting from racemic 7-benzyl-3-({4-hydroxy-1-[3-phenylpiperidine-4-carbonyl]piperidin-4-yl}methyl)-3H,4H,7H-pyrrolo[2,3-d]pyrimidin-4-one (which was obtained according to General Procedure 5 with racemic tert-butyl 4-(2-oxa-6-azaspiro[2.5]octane-6-carbonyl)-3-phenyl-piperidine-1-carboxylate and 7-benzyl-3H,4H,7H-pyrrolo[2,3-d]pyrimidin-4-one) and benzyl bromide as reagents, EXAMPLE 147 was obtained. HRMS calculated for $C_{38}H_{41}N_5O_3$: 615.3209; found 616.3308 [(M+H)$^+$ form].

7-benzyl-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 148)

Using General Procedure 6 starting from Preparation R3z and Preparation R1c as reagents, EXAMPLE 148 was obtained. HRMS calculated for $C_{41}H_{43}N_7O_3S$: 713.3148; found 357.6653 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one (Example 149)

Using General Procedure 7 starting from Preparation R3ac and Preparation R1d as reagents, EXAMPLE 149 was obtained. HRMS calculated for $C_{44}H_{47}N_7O_7s$: 817.3257; found 818.3322 [(M+H)$^+$ form].

7-(3,5-dichlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 150)

Using General Procedure 7 starting from Preparation R3ad and Preparation R1d as reagents, EXAMPLE 150 was obtained. HRMS calculated for $C_{41}H_{39}N_7O_4SCl_2$: 795.2161; found 796.225 [(M+H)$^+$ form].

7-(3-chloro-5-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 151)

Using General Procedure 7 starting from Preparation R3ae and Preparation R1d as reagents, EXAMPLE 151 was obtained. HRMS calculated for $C_{42}H_{42}N_7O_5SCl$: 791.2657; found 792.2736 [(M+H)$^+$ form].

7-(3,5-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 152)

Using General Procedure 7 starting from Preparation R3af and Preparation R1d as reagents, EXAMPLE 152 was obtained. HRMS calculated for $C_{43}H_{45}N_7O_6S$: 787.3152; found 788.3224 [(M+H)$^+$ form].

7-(3,4-dichlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 153)

Using General Procedure 7 starting from Preparation R3ag and Preparation R1d as reagents, EXAMPLE 153 was obtained. HRMS calculated for $C_{41}H_{39}Cl_2N_7O_4S$: 795.2161; found 796.2221 [(M+H)$^+$ form].

7-(4-chloro-3-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 154)

Using General Procedure 7 starting from Preparation R3ah and Preparation R1d as reagents, EXAMPLE 154 was obtained. HRMS calculated for $C_{41}H_{39}ClFN_7O_4S$: 779.2457; found 780.2528 [(M+H)$^+$ form].

7-(4-chloro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 155)

Using General Procedure 7 starting from Preparation R3ai and Preparation R1d as reagents, EXAMPLE 155 was obtained. HRMS calculated for $C_{42}H_{42}ClN_7O_5S$: 791.2657; found 792.2735 [(M+H)$^+$ form].

7-(4-fluoro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 156)

Using General Procedure 7 starting from Preparation R3aj and Preparation R1d as reagents, EXAMPLE 156 was obtained. HRMS calculated for $C_{42}H_{42}FN_7O_5S$: 775.2952; found 776.3023 [(M+H)$^+$ form].

7-(3,4-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 157)

Using General Procedure 7 starting from Preparation R3ak and Preparation R1d as reagents, EXAMPLE 157 was obtained. HRMS calculated for $C_{43}H_{45}N_7O_6S$: 787.3152; found 394.6638 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(trifluoromethyl)phenyl]-3,7-dihydro-4H-pyrrolo[2,3-d]pyrimidin-4-one (Example 158)

Using General Procedure 7 starting from Preparation R3ao and Preparation R1d as reagents, EXAMPLE 158 was obtained. HRMS calculated for $C_{42}H_{40}F_3N_7O_4S$: 795.2814; found 796.2886 [(M+H)$^+$ form].

7-[4-(difluoromethyl)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 159)

Using General Procedure 7 starting from Preparation R3ap and Preparation R1d as reagents, EXAMPLE 159 was obtained. HRMS calculated for $C_{42}H_{41}F_2N_7O_4S$: 777.2909; found 778.2984 [(M+H)$^+$ form].

7-[4-(benzyloxy)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 160)

Using General Procedure 7 starting from Preparation R3az and Preparation R1d as reagents, EXAMPLE 160 was obtained. HRMS calculated for $C_{48}H_{47}N_7O_5S$: 833.3359; found 834.3447 [(M+H)$^+$ form].

3-{[4-hydroxy-1-({(3R,4R)-1-[(4-methyl-2-phenyl-1,3-thiazol-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 161)

Using General Procedure 7 starting from Preparation R3b and 4-methyl-2-phenyl-thiazole-5-carboxylic acid as reagents, EXAMPLE 161 was obtained. HRMS calculated for $C_{36}H_{38}N_6O_4S$: 650.2675; found 651.2754 [(M+H)$^+$ form].

3-{[4-hydroxy-1-({(3R,4R)-1-[(3-methyl-1,2-thiazol-4-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 162)

Using General Procedure 7 starting from Preparation R3b and 3-methylisothiazole-4-carboxylic acid as reagents, EXAMPLE 162 was obtained. HRMS calculated for $C_{30}H_{34}N_6O_4S$: 574.2362; found 575.2434 [(M+H)$^+$ form].

3-{[4-hydroxy-1-({(3R,4R)-3-phenyl-1-[(2-phenyl-1,3-thiazol-5-yl)carbonyl]piperidin-4-yl}carbonyl)piperidin-4-yl]methyl}-7-methyl-3,7-dihydro-4H-pyrrolo[2,3-d]pyrimidin-4-one (Example 163)

Using General Procedure 7 starting from Preparation R3b and 2-phenylthiazole-5-carboxylic acid as reagents, EXAMPLE 163 was obtained. HRMS calculated for $C_{35}H_{36}N_6O_4S$: 636.2519; found 637.2593 [(M+H)$^+$ form].

3-{[4-hydroxy-1-({(3R,4R)-1-[(4-methyl-1,3-thiazol-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 164)

Using General Procedure 7 starting from Preparation R3b and 4-methylthiazole-5-carboxylic acid as reagents, EXAMPLE 164 was obtained. HRMS calculated for $C_{30}H_{34}N_6O_4S$: 574.2362; found 575.2437 [(M+H)$^+$ form].

3-{[1-({(3R,4R)-1-[(2-benzyl-4-methyl-1,3-thiazol-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 165)

Using General Procedure 7 starting from Preparation R3b and 2-benzyl-4-methyl-thiazole-5-carboxylic acid as reagents, EXAMPLE 165 was obtained. HRMS calculated for $C_{37}H_{40}N_6O_4S$: 664.2832; found 665.2897 [(M+H)$^+$ form].

3-[(4-hydroxy-1-{[(3R,4R)-1-(2-methylbenzoyl)-3-phenylpiperidin-4-yl]carbonyl}piperidin-4-yl)methyl]-7-methyl-3,7-dihydro-4H-pyrrolo[2,3-d]pyrimidin-4-one (Example 166)

Using General Procedure 7 starting from Preparation R3b and 2-methylbenzoic acid as reagents, EXAMPLE 166 was obtained. HRMS calculated for $C_{33}H_{37}N_5O_4$: 567.2846; found 568.2904 [(M+H)$^+$ form].

3-[(4-hydroxy-1-{[(3R,4R)-1-(3-methylbenzoyl)-3-phenylpiperidin-4-yl]carbonyl}piperidin-4-yl)methyl]-7-methyl-3,7-dihydro-4H-pyrrolo[2,3-d]pyrimidin-4-one (Example 167)

Using General Procedure 7 starting from Preparation R3b and 3-methylbenzoic acid as reagents, EXAMPLE 167 was obtained. HRMS calculated for $C_{33}H_{37}N_5O_4$: 567.2846; found 668.2916 [(M+H)$^+$ form].

3-[(4-hydroxy-1-{[(3R,4R)-1-(4-methylbenzoyl)-3-phenylpiperidin-4-yl]carbonyl}piperidin-4-yl)methyl]-7-methyl-3,7-dihydro-4H-pyrrolo[2,3-d]pyrimidin-4-one (Example 168)

Using General Procedure 7 starting from Preparation R3b and 4-methylbenzoic acid as reagents, EXAMPLE 168 was obtained. HRMS calculated for $C_{33}H_{37}N_5O_4$: 567.2846; found 568.2919 [(M+H)$^+$ form].

3-[(1-{[(3R,4R)-1-(2-fluorobenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 169)

Using General Procedure 7 starting from Preparation R3b and 2-fluorobenzoic acid as reagents, EXAMPLE 169 was obtained. HRMS calculated for $C_{32}H_{34}FN_5O_4$: 571.2595; found 572.266 [(M+H)$^+$ form].

3-[(1-{[(3R,4R)-1-(3-fluorobenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 170)

Using General Procedure 7 starting from Preparation R3b and 3-fluorobenzoic acid as reagents, EXAMPLE 170 was obtained. HRMS calculated for $C_{32}H_{34}FN_5O_4$: 571.2595; found 572.265 [(M+H)$^+$ form].

3-[(1-{[(3R,4R)-1-(4-fluorobenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 171)

Using General Procedure 7 starting from Preparation R3b and 4-fluorobenzoic acid as reagents, EXAMPLE 171 was obtained. HRMS calculated for $C_{32}H_{34}FN_5O_4$: 571.2595; found 572.267 [(M+H)$^+$ form].

3-[(4-hydroxy-1-{[(3R,4R)-1-{[4-methyl-2-(pyridin-4-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 172)

Using General Procedure 7 starting from Preparation R3b and 4-methyl-2-(4-pyridyl)thiazole-5-carboxylic acid as reagents, EXAMPLE 172 was obtained. HRMS calculated for $C_{35}H_{37}N_7O_4S$: 651.2628; found 652.27 [(M+H)$^+$ form].

3-[(4-hydroxy-1-{[(3R,4R)-3-phenyl-1-{[2-(pyridin-4-yl)-1,3-thiazol-5-yl]carbonyl}piperidin-4-yl]carbonyl}piperidin-4-yl)methyl]-7-methyl-3,7-dihydro-4H-pyrrolo[2,3-d]pyrimidin-4-one (Example 173)

Using General Procedure 7 starting from Preparation R3b and 2-(4-pyridyl)thiazole-5-carboxylic acid as reagents, EXAMPLE 173 was obtained. HRMS calculated for $C_{34}H_{35}N_7O_4S$: 637.2471; found 638.254 [(M+H)$^+$ form].

3-[(1-{[(3R,4R)-1-{[2-(2-fluorophenyl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 174)

Using General Procedure 7 starting from Preparation R3b and 2-(2-fluorophenyl)-4-methyl-thiazole-5-carboxylic acid as reagents, EXAMPLE 174 was obtained. HRMS calculated for $C_{36}H_{37}FN_6O_4S$: 668.2581; found 669.2668 [(M+H)$^+$ form].

3-[(4-hydroxy-1-{[(3R,4R)-1-{[4-methyl-2-(2-methylphenyl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 175)

Using General Procedure 7 starting from Preparation R3b and 4-methyl-2-(o-tolyl)thiazole-5-carboxylic acid as reagents, EXAMPLE 175 was obtained. HRMS calculated for $C_{37}H_{40}N_6O_4S$: 664.2832; found 665.2917 [(M+H)$^+$ form].

3-{[1-({(3R,4R)-1-[(5-bromothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 176)

Using General Procedure 7 starting from Preparation R3b and 5-bromothiophene-2-carboxylic acid as reagents, EXAMPLE 176 was obtained. HRMS calculated for $C_{30}H_{32}BrN_5O_4S$: 637.1358; found 638.1430 [(M+H)$^+$ form].

3-{[1-({(3R,4R)-1-[(1-benzyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 177)

Using General Procedure 7 starting from Preparation R3b and 1-benzylpyrrole-2-carboxylic acid as reagents, EXAMPLE 177 was obtained. HRMS calculated for $C_{37}H_{40}N_6O_4$: 632.3111; found 633.3184 [(M+H)$^+$ form].

3-{[4-hydroxy-1-({(3R,4R)-1-[(1-methyl-5-phenyl-1H-pyrrol-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 178)

Using General Procedure 7 starting from Preparation R3b and 1-methyl-5-phenyl-pyrrole-2-carboxylic acid as reagents, EXAMPLE 178 was obtained. HRMS calculated for $C_{37}H_{40}N_6O_4$: 632.3111; found 633.3183 [(M+H)$^+$ form].

3-[(4-hydroxy-1-{[(3R,4R)-3-phenyl-1-(1H-pyrrol-2-ylcarbonyl)piperidin-4-yl]carbonyl}piperidin-4-yl)methyl]-7-methyl-3,7-dihydro-4H-pyrrolo[2,3-d]pyrimidin-4-one (Example 179)

Using General Procedure 7 starting from Preparation R3b and 1H-pyrrole-2-carboxylic acid as reagents, EXAMPLE 179 was obtained. HRMS calculated for $C_{30}H_{34}N_6O_4$: 542.2642; found 543.2711 [(M+H)$^+$ form].

3-{[4-hydroxy-1-({(3R,4R)-1-[(1-methyl-1H-pyrrol-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 180)

Using General Procedure 7 starting from Preparation R3b and 1-methylpyrrole-2-carboxylic acid as reagents, EXAMPLE 180 was obtained. HRMS calculated for $C_{31}H_{36}N_6O_4$: 556.2798; found 557.2862 [(M+H)$^+$ form].

3-[(4-hydroxy-1-{[(3R,4R)-3-phenyl-1-{[1-(pyridin-3-ylmethyl)-1H-pyrrol-2-yl]carbonyl}piperidin-4-yl]carbonyl}piperidin-4-yl)methyl]-7-methyl-3,7-dihydro-4H-pyrrolo[2,3-d]pyrimidin-4-one (Example 181)

Using General Procedure 7 starting from Preparation R3b and 1-(3-pyridylmethyl)pyrrole-2-carboxylic acid as reagents, EXAMPLE 181 was obtained. HRMS calculated for $C_{36}H_{39}N_7O_4$: 633.3064; found 317.6602 [(M+2H)$^{2+}$ form].

3-[(1-{[(3R,4R)-1-{[5-(2-aminopyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 182)

Using General Procedure 7 starting from Preparation R3b and 5-(2-amino-4-pyridyl)thiophene-2-carboxylic acid as reagents, EXAMPLE 182 was obtained. HRMS calculated for $C_{35}H_{37}N_7O_4S$: 651.2628; found 326.638 [(M+2H)$^{2+}$ form].

3-[(4-hydroxy-1-{[(3R,4R)-1-{[4-methyl-5-(pyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 183)

Using General Procedure 7 starting from Preparation R3b and 4-methyl-5-(4-pyridyl)thiophene-2-carboxylic acid as reagents, EXAMPLE 183 was obtained. HRMS calculated for $C_{36}H_{38}N_6O_4S$: 650.2676; found 651.2752 [(M+H)$^+$ form].

3-[(4-hydroxy-1-{[(3S,4S)-3-phenyl-1-{[5-(pyridin-4-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 184)

Using General Procedure 7 starting from 3-({4-hydroxy-1-[(3S,4S)-3-phenylpiperidine-4-carbonyl]piperidin-4- yl}methyl)-7-methyl-3H,4H,7H-pyrrolo[2,3-d]pyrimidin-4-one (which was obtained according to General Procedure 5 with tert-butyl (3S,4S)-4-(2-oxa-6-azaspiro[2.5]octane-6-carbonyl)-3-phenyl-piperidine-1-carboxylate and Preparation R2b) and 5-(4-pyridyl)thiophene-2-carboxylic acid as reagents, EXAMPLE 184 was obtained. HRMS calculated for $C_{35}H_{36}N_6O_4S$: 636.2519; found 637.2591 [(M+H)$^+$ form].

3-[(4-hydroxy-1-{[(3R,4R)-1-{[4-nitro-5-(pyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 185)

Using General Procedure 7 starting from Preparation R3b and Preparation Rip as reagents, EXAMPLE 185 was obtained. HRMS calculated for $C_{35}H_{35}N_7O_6S$: 681.2369; found 682.2432 [(M+H)$^+$ form].

3-{[1-({(3R,4R)-1-[(1-ethenyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 186)

Using General Procedure 7 starting from Preparation R3b and 1-vinylpyrrole-2-carboxylic acid as reagents, EXAMPLE 186 was obtained. HRMS calculated for $C_{32}H_{36}N_6O_4$: 568.2798; found 569.2884 [(M+H)$^+$ form].

3-[(4-hydroxy-1-{[(3R,4R)-3-phenyl-1-{[1-(prop-2-en-1-yl)-1H-pyrrol-2-yl]carbonyl}piperidin-4-yl]carbonyl}piperidin-4-yl)methyl]-7-methyl-3,7-dihydro-4H-pyrrolo[2,3-d]pyrimidin-4-one (Example 187)

Using General Procedure 7 starting from Preparation R3b and 1-allylpyrrole-2-carboxylic acid as reagents, EXAMPLE 187 was obtained. HRMS calculated for $C_{33}H_{38}N_6O_4$: 582.2955; found 583.3039 [(M+H)$^+$ form].

3-{[4-hydroxy-1-({(3R,4R)-1-[(1-methyl-1H-indol-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 188)

Using General Procedure 7 starting from Preparation R3b and 1-methylindole-2-carboxylic acid as reagents, EXAMPLE 188 was obtained. HRMS calculated for $C_{35}H_{38}N_6O_4$: 606.2955; found 607.3033 [(M+H)$^+$ form].

3-{[1-({(3R,4R)-1-[(4-bromo-1-methyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 189)

Using General Procedure 7 starting from Preparation R3b and 4-bromo-1-methylpyrrole-2-carboxylic acid as reagents, EXAMPLE 189 was obtained. HRMS calculated for $C_{31}H_{35}BrN_6O_4$: 634.1903; found 635.1981 [(M+H)$^+$ form].

3-{[1-({(3R,4R)-1-[(2,2-difluoro-1,3-benzodioxol-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 190)

Using General Procedure 7 starting from Preparation R3b and 2,2-difluoro-1,3-benzodioxole-5-carboxylic acid as reagents, EXAMPLE 190 was obtained. HRMS calculated for $C_{33}H_{33}F_2N_5O_6$: 633.2399; found 634.2475 [(M+H)$^+$ form].

3-[(4-hydroxy-1-{[(3R,4R)-1-(1H-indol-5-ylcarbonyl)-3-phenylpiperidin-4-yl]carbonyl}piperidin-4-yl)methyl]-7-methyl-3,7-dihydro-4H-pyrrolo[2,3-d]pyrimidin-4-one (Example 191)

Using General Procedure 7 starting from Preparation R3b and 1H-indole-5-carboxylic acid as reagents, EXAMPLE 191 was obtained. HRMS calculated for $C_{34}H_{36}N_6O_4$: 592.2798; found 593.2881 [(M+H)$^+$ form].

tert-butyl 6-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3,4-dihydroisoquinoline-2(1H)-carboxylate (Example 192)

Using General Procedure 7 starting from Preparation R3b and 2-tert-butoxycarbonyl-3,4-dihydro-1H-isoquinoline-6-carboxylic acid as reagents, EXAMPLE 192 was obtained. HRMS calculated for $C_{40}H_{48}N_6O_6$: 708.3635; found 709.3717 [(M+H)$^+$ form].

3-{[1-({(3R,4R)-1-[(1-acetyl-1,2,3,4-tetrahydroquinolin-6-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 193)

Using General Procedure 7 starting from Preparation R3b and 1-acetyl-3,4-dihydro-2H-quinoline-6-carboxylic acid as reagents, EXAMPLE 193 was obtained. HRMS calculated for $C_{37}H_{42}N_6O_5$: 650.3217; found 651.3306 [(M+H)$^+$ form].

3-{[1-({(3R,4R)-1-[(4-bromopyridin-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 194)

Using General Procedure 7 starting from Preparation R3b and 4-bromopyridine-2-carboxylic acid as reagents, EXAMPLE 194 was obtained. HRMS calculated for $C_{31}H_{33}BrN_6O_4$: 632.1747; found 633.1821 [(M+H)$^+$ form].

3-{[1-({(3R,4R)-1-[(2-bromopyridin-4-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 195)

Using General Procedure 7 starting from Preparation R3b and 2-bromopyridine-4-carboxylic acid as reagents, EXAMPLE 195 was obtained. HRMS calculated for $C_{31}H_{33}BrN_6O_4$: 632.1747; found 633.1824 [(M+H)$^+$ form].

3-{[1-({(3R,4R)-1-[(5-bromopyridin-3-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 196)

Using General Procedure 7 starting from Preparation R3b and 5-bromopyridine-3-carboxylic acid as reagents, EXAMPLE 196 was obtained. HRMS calculated for $C_{31}H_{33}BrN_6O_4$: 632.1747; found 633.1827 [(M+H)$^+$ form].

3-{[1-({(3R,4R)-1-[(5-bromo-3-fluorothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 197)

Using General Procedure 7 starting from Preparation R3b and 5-bromo-3-fluoro-thiophene-2-carboxylic acid as reagents, EXAMPLE 197 was obtained. HRMS calculated for $C_{30}H_{31}BrFN_5O_4S$: 655.1264; found 656.1341 [(M+H)$^+$ form].

3-{[1-({(3R,4R)-1-[(6-bromopyridin-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 198)

Using General Procedure 7 starting from Preparation R3b and 6-bromopyridine-2-carboxylic acid as reagents, EXAMPLE 198 was obtained. HRMS calculated for $C_{31}H_{33}BrN_6O_4$: 632.1747; found 633.1822 [(M+H)$^+$ form].

3-[(1-{[(3R,4R)-1-(1H-benzotriazol-5-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 199)

Using General Procedure 7 starting from Preparation R3b and 1H-benzotriazole-5-carboxylic acid as reagents, EXAMPLE 199 was obtained. HRMS calculated for $C_{32}H_{34}N_8O_4$: 594.2703; found 595.2782 [(M+H)$^+$ form].

3-[(4-hydroxy-1-{[(3R,4R)-3-phenyl-1-{[trans-2-phenylcyclopropyl]carbonyl}piperidin-4-yl]carbonyl}piperidin-4-yl)methyl]-7-methyl-3,7-dihydro-4H-pyrrolo[2,3-d]pyrimidin-4-one, diastereoisomer 1 (Example 200)

Using General Procedure 7 starting from Preparation R3b and trans-2-phenyl-1-cyclopropanecarboxylic acid as reagents, EXAMPLE 200 was obtained as pure diastereoisomer after purification on preparative LC (C-18 Gemini-NX 5 µm column, 5 mM aqueous NH$_4$HCO$_3$-MCN, isocratic 37%). HRMS calculated for $C_{35}H_{39}N_5O_4$: 593.3002; found 594.3082 [(M+H)$^+$ form].

3-[(1-{[(3R,4R)-1-(3-bromobenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 201)

Using General Procedure 7 starting from Preparation R3b and 3-bromobenzoic acid as reagents, EXAMPLE 201 was obtained. HRMS calculated for $C_{32}H_{34}BrN_5O_4$: 631.1794; found 632.1873 [(M+H)$^+$ form].

3-[(4-hydroxy-1-{[(3R,4R)-3-phenyl-1-{[trans-2-phenylcyclopropyl]carbonyl}piperidin-4-yl]carbonyl}piperidin-4-yl)methyl]-7-methyl-3,7-dihydro-4H-pyrrolo[2,3-d]pyrimidin-4-one, diastereoisomer 2 (Example 202)

Using General Procedure 7 starting from Preparation R3b and trans-2-phenylcyclopropanecarboxylic acid as reagents, EXAMPLE 202 was obtained was obtained as pure diastereoisomer after purification on preparative LC (C-18 Gemini-NX 5 µm column, 5 mM aqueous NH$_4$HCO$_3$-MCN, isocratic 37%). HRMS calculated for $C_{35}H_{39}N_5O_4$: 593.3002; found 594.3084 [(M+H)$^+$ form].

3-[(4-hydroxy-1-{[(3R,4R)-1-(3-nitrobenzoyl)-3-phenylpiperidin-4-yl]carbonyl}piperidin-4-yl)methyl]-7-methyl-3,7-dihydro-4H-pyrrolo[2,3-d]pyrimidin-4-one (Example 203)

Using General Procedure 7 starting from Preparation R3b and 3-nitrobenzoic acid as reagents, EXAMPLE 203 was obtained. HRMS calculated for $C_{32}H_{34}N_6O_6$: 598.2539; found 599.2625 [(M+H)$^+$ form].

3-[(1-{[(3R,4R)-1-benzoyl-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 204)

Using General Procedure 7 starting from Preparation R3b and benzoic acid as reagents, EXAMPLE 204 was obtained. HRMS calculated for $C_{32}H_{35}N_5O_4$: 553.2689; found 554.2782 [(M+H)$^+$ form].

3-[(1-{[(3R,4R)-1-(3-ethynylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 205)

Using General Procedure 7 starting from Preparation R3b and 3-ethynylbenzoic acid as reagents, EXAMPLE 205 was obtained. HRMS calculated for $C_{34}H_{35}N_5O_4$: 577.2689; found 578.2776 [(M+H)$^+$ form].

methyl 3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 206)

Using General Procedure 7 starting from Preparation R3b and 3-methoxycarbonylbenzoic acid as reagents, EXAMPLE 206 was obtained. HRMS calculated for $C_{34}H_{37}N_5O_6$: 611.2744; found 612.2837 [(M+H)$^+$ form].

3-{[4-hydroxy-1-({(3R,4R)-3-phenyl-1-[3-(trifluoromethyl)benzoyl]piperidin-4-yl}carbonyl)piperidin-4-yl]methyl}-7-methyl-3,7-dihydro-4H-pyrrolo[2,3-d]pyrimidin-4-one (Example 207)

Using General Procedure 7 starting from Preparation R3b and 3-(trifluoromethyl)benzoic acid as reagents, EXAMPLE 207 was obtained. HRMS calculated for $C_{33}H_{34}F_3N_5O_4$: 621.2563; found 622.265 [(M+H)$^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzonitrile (Example 208)

Using General Procedure 7 starting from Preparation R3b and 3-cyanobenzoic acid as reagents, EXAMPLE 208 was obtained. HRMS calculated for $C_{33}H_{34}N_6O_4$: 578.2642; found 579.272 [(M+H)$^+$ form].

3-[(4-hydroxy-1-{[(3R,4R)-1-(3-methoxybenzoyl)-3-phenylpiperidin-4-yl]carbonyl}piperidin-4-yl)methyl]-7-methyl-3,7-dihydro-4H-pyrrolo[2,3-d]pyrimidin-4-one (Example 209)

Using General Procedure 7 starting from Preparation R3b and 3-methoxybenzoic acid as reagents, EXAMPLE 209 was obtained. HRMS calculated for $C_{33}H_{37}N_5O_5$: 583.2795; found 584.2889 [(M+H)$^+$ form].

3-[(4-hydroxy-1-{[(3R,4R)-1-(3-phenoxybenzoyl)-3-phenylpiperidin-4-yl]carbonyl}piperidin-4-yl)methyl]-7-methyl-3,7-dihydro-4H-pyrrolo[2,3-d]pyrimidin-4-one (Example 210)

Using General Procedure 7 starting from Preparation R3b and 3-phenoxybenzoic acid as reagents, EXAMPLE 210 was obtained. HRMS calculated for $C_{38}H_{39}N_5O_5$: 645.2951; found 646.3025 [(M+H)$^+$ form].

3-[(1-{[(3R,4R)-1-(3-tert-butylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 211)

Using General Procedure 7 starting from Preparation R3b and 3-tert-butylbenzoic acid as reagents, EXAMPLE 211 was obtained. HRMS calculated for $C_{36}H_{43}N_5O_4$: 609.3315; found 610.3382 [(M+H)$^+$ form].

5-bromo-2-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}thiophene-3-carbonitrile (Example 212)

Using General Procedure 7 starting from Preparation R3b and 5-bromo-3-cyano-thiophene-2-carboxylic acid as reagents, EXAMPLE 212 was obtained. HRMS calculated for $C_{31}H_{31}BrN_6O_4S$: 662.1311; found 663.1384 [(M+H)$^+$ form].

3-[(4-hydroxy-1-{[(3R,4R)-3-phenyl-1-(quinolin-6-ylcarbonyl)piperidin-4-yl]carbonyl}piperidin-4-yl)methyl]-7-methyl-3,7-dihydro-4H-pyrrolo[2,3-d]pyrimidin-4-one (Example 213)

Using General Procedure 7 starting from Preparation R3b and quinoline-6-carboxylic acid as reagents, EXAMPLE 213 was obtained. HRMS calculated for $C_{35}H_{36}N_6O_4$: 604.2798; found 605.2872 [(M+H)$^+$ form].

3-[(1-{[(3R,4R)-1-(2,3-dihydro-1,4-benzodioxin-6-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 214)

Using General Procedure 7 starting from Preparation R3b and 2,3-dihydro-1,4-benzodioxine-6-carboxylic acid as reagents, EXAMPLE 214 was obtained. HRMS calculated for $C_{34}H_{37}N_5O_6$: 611.2744; found 612.2822 [(M+H)$^+$ form].

3-[(1-{[(3R,4R)-1-(5,6-dihydro-4H-cyclopenta[b]thiophen-2-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 215)

Using General Procedure 7 starting from Preparation R3b and 5,6-dihydro-4H-cyclopenta[b]thiophene-2-carboxylic acid as reagents, EXAMPLE 215 was obtained. HRMS calculated for $C_{33}H_{37}N_5O_4S$: 599.2567; found 600.2645 [(M+H)$^+$ form].

3-[(4-hydroxy-1-{[(3R,4R)-3-phenyl-1-(4,5,6,7-tetrahydro-1-benzothiophen-2-ylcarbonyl)piperidin-4-yl]carbonyl}piperidin-4-yl)methyl]-7-methyl-3,7-dihydro-4H-pyrrolo[2,3-d]pyrimidin-4-one (Example 216)

Using General Procedure 7 starting from Preparation R3b and 4,5,6,7-tetrahydrobenzothiophene-2-carboxylic acid as reagents, EXAMPLE 216 was obtained. HRMS calculated for $C_{34}H_{39}N_5O_4S$: 613.2723; found 614.2805 [(M+H)$^+$ form].

3-{[1-({(3R,4R)-1-[(5-bromo-1-methyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 217)

Using General Procedure 7 starting from Preparation R3b and 5-bromo-1-methylpyrrole-2-carboxylic acid as reagents, EXAMPLE 217 was obtained. HRMS calculated for $C_{31}H_{35}N_6O_4Br$: 634.1903; found 637.1959 [(M+H)$^+$ form].

3-{[4-hydroxy-1-({(3R,4R)-3-phenyl-1-[(3-phenylcyclobutyl)carbonyl]piperidin-4-yl}carbonyl)piperidin-4-yl]methyl}-7-methyl-3,7-dihydro-4H-pyrrolo[2,3-d]pyrimidin-4-one (Example 218)

Using General Procedure 7 starting from Preparation R3b and 3-phenylcyclobutanecarboxylic acid as reagents, EXAMPLE 218 was obtained. HRMS calculated for $C_{36}H_{41}N_5O_4$: 607.3159; found 608.3236 [(M+H)$^+$ form].

3-[(1-{[(3R,4R)-1-(3-ethoxybenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 219)

Using General Procedure 7 starting from Preparation R3b and 3-ethoxybenzoic acid as reagents, EXAMPLE 219 was obtained. HRMS calculated for $C_{34}H_{39}N_5O_5$: 597.2951; found 598.3032 [(M+H)$^+$ form].

3-{[4-hydroxy-1-({(3R,4R)-1-[3-(4-methylpiperazin-1-yl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 220)

Using General Procedure 7 starting from Preparation R3b and 3-(4-methylpiperazin-1-yl)benzoic acid as reagents, EXAMPLE 220 was obtained. HRMS calculated for $C_{37}H_{45}N_7O_4$: 651.3533; found 652.3604 [(M+H)⁺ form].

3-{[4-hydroxy-1-({(3R,4R)-3-phenyl-1-[3-(propan-2-yl)benzoyl]piperidin-4-yl}carbonyl)piperidin-4-yl]methyl}-7-methyl-3,7-dihydro-4H-pyrrolo[2,3-d]pyrimidin-4-one (Example 221)

Using General Procedure 7 starting from Preparation R3b and 3-isopropylbenzoic acid as reagents, EXAMPLE 221 was obtained. HRMS calculated for $C_{35}H_{41}N_5O_4$: 595.3159; found 596.3251 [(M+H)⁺ form].

3-{[4-hydroxy-1-({(3R,4R)-3-phenyl-1-[3-(pyrrolidin-1-ylmethyl)benzoyl]piperidin-4-yl}carbonyl)piperidin-4-yl]methyl}-7-methyl-3,7-dihydro-4H-pyrrolo[2,3-d]pyrimidin-4-one (Example 222)

Using General Procedure 7 starting from Preparation R3b and 3-(pyrrolidin-1-ylmethyl)benzoic acid as reagents, EXAMPLE 222 was obtained. HRMS calculated for $C_{37}H_{44}N_6O_4$: 636.3424; found 637.3504 [(M+H)⁺ form].

3-{[1-({(3R,4R)-1-[3-(dimethylamino)benzoyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 223)

Using General Procedure 7 starting from Preparation R3b and 3-(dimethylamino)benzoic acid as reagents, EXAMPLE 223 was obtained. HRMS calculated for $C_{34}H_{40}N_6O_4$: 596.3111; found 597.3194 [(M+H)⁺ form].

3-{[4-hydroxy-1-({(3R,4R)-1-[3-(morpholin-4-yl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 224)

Using General Procedure 7 starting from Preparation R3b and 3-morpholinobenzoic acid as reagents, EXAMPLE 224 was obtained. HRMS calculated for $C_{36}H_{42}N_6O_5$: 638.3217; found 639.3282 [(M+H)⁺ form].

3-[(4-hydroxy-1-{[(3R,4R)-1-{[1-(methylsulfonyl)-1,2,3,4-tetrahydroquinolin-6-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 225)

Using General Procedure 7 starting from Preparation R3b and 1-methylsulfonyl-3,4-dihydro-2H-quinoline-6-carboxylic acid as reagents, EXAMPLE 225 was obtained. HRMS calculated for $C_{36}H_{42}N_6O_6S$: 686.2886; found 687.2962 [(M+H)⁺ form].

3-{[4-hydroxy-1-({(3R,4R)-3-phenyl-1-[3-(piperidin-1-yl)benzoyl]piperidin-4-yl}carbonyl)piperidin-4-yl]methyl}-7-methyl-3,7-dihydro-4H-pyrrolo[2,3-d]pyrimidin-4-one (Example 226)

Using General Procedure 7 starting from Preparation R3b and 3-(1-piperidyl)benzoic acid as reagents, EXAMPLE 226 was obtained. HRMS calculated for $C_{37}H_{44}N_6O_4$: 636.3424; found 637.3483 [(M+H)⁺ form].

6-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-1-methyl-3,4-dihydroquinolin-2(1H)-one (Example 227)

Using General Procedure 7 starting from Preparation R3b and 1-methyl-2-oxo-3,4-dihydroquinoline-6-carboxylic acid as reagents, EXAMPLE 227 was obtained. HRMS calculated for $C_{36}H_{40}N_6O_5$: 636.3060; found 637.3162 [(M+H)⁺ form].

3-[(1-{[(3R,4R)-1-{3-[(dimethylamino)methyl]benzoyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 228)

Using General Procedure 7 starting from Preparation R3b and 3-(dimethylaminomethyl)benzoic acid as reagents, EXAMPLE 228 was obtained. HRMS calculated for $C_{35}H_{42}N_6O_4$: 610.3268; found 611.335 [(M+H)⁺ form].

3-{[1-({(3R,4R)-1-[(1-ethenyl-1H-indol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 229)

Using General Procedure 7 starting from Preparation R3b and Preparation R1t as reagents, EXAMPLE 229 was obtained. HRMS calculated for $C_{36}H_{38}N_6O_4$: 618.2955; found 619.3002 [(M+H)⁺ form].

3-{[1-({(3R,4R)-1-[(5-bromo-1-ethenyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 230)

Using General Procedure 7 starting from Preparation R3b and Preparation R1u as reagents, EXAMPLE 230 was obtained. HRMS calculated for $C_{32}H_{35}BrN_6O_4$: 646.1903; found 647.1989 [(M+H)⁺ form].

3-[(1-{[(3R,4R)-1-(2-acetylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 231)

Using General Procedure 7 starting from Preparation R3b and 2-acetylbenzoic acid as reagents, EXAMPLE 231 was obtained. HRMS calculated for $C_{34}H_{37}N_5O_5$: 595.2795; found 596.2861 [(M+H)⁺ form].

3-{[1-({(3R,4R)-1-[(3-fluoro-4,5-diiodothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 232)

Using General Procedure 7 starting from Preparation R3b and Preparation R1h as reagents, EXAMPLE 232 was obtained. HRMS calculated for $C_{30}H_{30}FI_2N_5O_4S$: 829.0092; found 830.0159 [(M+H)⁺ form].

methyl 2-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 233)

Using General Procedure 7 starting from Preparation R3b and 2-methoxycarbonylbenzoic acid as reagents, EXAMPLE 233 was obtained. HRMS calculated for $C_{34}H_{37}N_5O_6$: 611.2744; found 612.2823 [(M+H)$^+$ form].

3-{[1-({(3R,4R)-1-[(3-fluoro-4-iodo-5-methylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 234)

Using General Procedure 7 starting from Preparation R3b and Preparation R1i as reagents, EXAMPLE 234 was obtained. HRMS calculated for $C_{31}H_{33}FIN_5O_4S$: 717.1282; found 718.1352 [(M+H)$^+$ form].

3-{[1-({(3R,4R)-1-[(4-bromo-1-ethenyl-1H-pyrrol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 235)

Using General Procedure 7 starting from Preparation R3b and Preparation R1v as reagents, EXAMPLE 235 was obtained. HRMS calculated for $C_{32}H_{35}BrN_6O_4$: 646.1903; found 647.198 [(M+H)$^+$ form].

3-{[1-({(3R,4R)-1-[(3-chloro-4-methylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 236)

Using General Procedure 7 starting from Preparation R3b and 3-chloro-4-methyl-thiophene-2-carboxylic acid as reagents, EXAMPLE 236 was obtained. HRMS calculated for $C_{31}H_{34}ClN_5O_4S$: 607.2020; found 608.2107 [(M+H)$^+$ form].

3-[(1-{[(3R,4R)-1-{[3-amino-4-(methylsulfonyl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 237)

Using General Procedure 7 starting from Preparation R3b and 3-amino-4-methylsulfonyl-thiophene-2-carboxylic acid as reagents, EXAMPLE 237 was obtained. HRMS calculated for $C_{31}H_{36}N_6O_6S_2$: 652.2137; found 653.2224 [(M+H)$^+$ form].

3-{[4-hydroxy-1-({(3R,4R)-1-[(3-iodo-4-methylthiophen-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 238)

Using General Procedure 7 starting from Preparation R3b and 3-iodo-4-methyl-thiophene-2-carboxylic acid as reagents, EXAMPLE 238 was obtained. HRMS calculated for $C_{31}H_{34}IN_5O_4S$: 699.1376; found 700.145 [(M+H)$^+$ form].

3-{[1-({(3R,4R)-1-[(5-bromo-3-chloro-4-methylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 239)

Using General Procedure 7 starting from Preparation R3b and 5-bromo-3-chloro-4-methyl-thiophene-2-carboxylic acid as reagents, EXAMPLE 239 was obtained. HRMS calculated for $C_{31}H_{33}BrClN_5O_4S$: 685.1125; found 686.1217 [(M+H)$^+$ form].

3-[(4-hydroxy-1-{[(3R,4R)-1-({1-[(methylsulfanyl)methyl]-1H-pyrrol-2-yl}carbonyl)-3-phenylpiperidin-4-yl]carbonyl}piperidin-4-yl)methyl]-7-methyl-3,7-dihydro-4H-pyrrolo[2,3-d]pyrimidin-4-one (Example 240)

Using General Procedure 7 starting from Preparation R3b and 1-(methylsulfanylmethyl)pyrrole-2-carboxylic acid as reagents, EXAMPLE 240 was obtained. HRMS calculated for $C_{32}H_{38}N_6O_4S$: 602.2675; found 603.2756 [(M+H)$^+$ form].

3-[(4-hydroxy-1-{[(3R,4R)-3-phenyl-1-(quinoxalin-6-ylcarbonyl)piperidin-4-yl]carbonyl}piperidin-4-yl)methyl]-7-methyl-3,7-dihydro-4H-pyrrolo[2,3-d]pyrimidin-4-one (Example 241)

Using General Procedure 7 starting from Preparation R3b and quinoxaline-6-carboxylic acid as reagents, EXAMPLE 241 was obtained. HRMS calculated for $C_{34}H_{35}N_7O_4$: 605.2750; found 606.2831 [(M+H)$^+$ form].

3-{[4-hydroxy-1-({(3R,4R)-1-[(1-methyl-1H-indol-6-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 242)

Using General Procedure 7 starting from Preparation R3b and 1-methylindole-6-carboxylic acid as reagents, EXAMPLE 242 was obtained. HRMS calculated for $C_{35}H_{38}N_6O_4$: 606.2955; found 607.3035 [(M+H)$^+$ form].

3-{[4-hydroxy-1-({(3R,4R)-1-[(5-oxo-1-phenylpyrrolidin-3-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 243)

Using General Procedure 7 starting from Preparation R3b and 5-oxo-1-phenyl-pyrrolidine-3-carboxylic acid as reagents, EXAMPLE 243 was obtained. HRMS calculated for $C_{36}H_{40}N_6O_5$: 636.3060; found 637.3129 [(M+H)$^+$ form].

tert-butyl 7-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3,4-dihydroquinoxaline-1(2H)-carboxylate (Example 244)

Using General Procedure 7 starting from Preparation R3b and 4-tert-butoxycarbonyl-2,3-dihydro-1H-quinoxaline-6-carboxylic acid as reagents, EXAMPLE 244 was obtained. HRMS calculated for $C_{39}H_{47}N_7O_6$: 709.3588; found 710.3667 [(M+H)$^+$ form].

tert-butyl 7-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3,4-dihydroquinoline-1(2H)-carboxylate (Example 245)

Using General Procedure 7 starting from Preparation R3b and 1-tert-butoxycarbonyl-3,4-dihydro-2H-quinoline-7-carboxylic acid as reagents, EXAMPLE 245 was obtained. HRMS calculated for $C_{40}H_{48}N_6O_6$: 708.3635; found 709.3715 [(M+H)$^+$ form].

3-{[4-hydroxy-1-({(3R,4R)-1-[3-(hydroxyacetyl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 246)

Using General Procedure 7 starting from Preparation R3b and 3-(2-chloroacetyl)benzoic acid as reagents, EXAMPLE 246 was obtained. HRMS calculated for $C_{34}H_{37}N_5O_6$: 611.2744; found 612.2817 [(M+H)$^+$ form].

3-{[1-({(3R,4R)-1-[(3-bromothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 247)

Using General Procedure 7 starting from Preparation R3b and 3-bromothiophene-2-carboxylic acid as reagents, EXAMPLE 247 was obtained. HRMS calculated for $C_{30}H_{32}BrN_5O_4S$: 637.1359; found 638.1428 [(M+H)$^+$ form].

3-{[1-({(3R,4R)-1-[(4-bromo-1,3-thiazol-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 248)

Using General Procedure 7 starting from Preparation R3b and 4-bromothiazole-2-carboxylic acid as reagents, EXAMPLE 248 was obtained. HRMS calculated for $C_{29}H_{31}BrN_6O_4S$: 638.1311; found 639.1389 [(M+H)$^+$ form].

3-{[1-({(3R,4R)-1-[(5-bromothiophen-3-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 249)

Using General Procedure 7 starting from Preparation R3b and 5-bromothiophene-3-carboxylic acid as reagents, EXAMPLE 249 was obtained. HRMS calculated for $C_{30}H_{32}BrN_5O_4S$: 637.1359; found 638.1438 [(M+H)$^+$ form].

3-{[1-({(3R,4R)-1-[(2-bromothiophen-3-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 250)

Using General Procedure 7 starting from Preparation R3b and 2-bromothiophene-3-carboxylic acid as reagents, EXAMPLE 250 was obtained. HRMS calculated for $C_{30}H_{32}BrN_5O_4S$: 637.1359; found 638.1443 [(M+H)$^+$ form].

3-ethoxy-N-(4-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzyl)propanamide (Example 251)

Using General Procedure 7 starting from Preparation R3b and 4-[(3-ethoxypropanoylamino)methyl]benzoic acid as reagents, EXAMPLE 251 was obtained. HRMS calculated for $C_{38}H_{46}N_6O_6$: 682.3479; found 683.3559 [(M+H)$^+$ form].

tert-butyl (4-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzyl)carbamate (Example 252)

Using General Procedure 7 starting from Preparation R3b and 4-[(tert-butoxycarbonylamino)methyl]benzoic acid as reagents, EXAMPLE 252 was obtained. HRMS calculated for $C_{38}H_{46}N_6O_6$: 682.3479; found 683.3567 [(M+H)$^+$ form].

3-{[1-({(3R,4R)-1-[(3-chloro-5-iodothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 253)

Using General Procedure 7 starting from Preparation R3b and Preparation R1j as reagents, EXAMPLE 253 was obtained. HRMS calculated for $C_{30}H_{31}ClIN_5O_4S$: 719.0830; found 720.0905 [(M+H)$^+$ form].

3-[(1-{[(3R,4R)-1-(3-acetylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 254)

Using General Procedure 7 starting from Preparation R3b and 3-acetylbenzoic acid as reagents, EXAMPLE 254 was obtained. HRMS calculated for $C_{34}H_{37}N_5O_5$: 595.2795; found 596.2875 [(M+H)$^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzaldehyde (Example 255)

Using General Procedure 7 starting from Preparation R3b and 3-formylbenzoic acid as reagents, EXAMPLE 255 was obtained. HRMS calculated for $C_{33}H_{35}N_5O_5$: 581.2638; found 582.271 [(M+H)$^+$ form].

3-[(1-{[(3R,4R)-1-(3-ethenylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 256)

Using General Procedure 7 starting from Preparation R3b and 3-vinylbenzoic acid as reagents, EXAMPLE 256 was obtained. HRMS calculated for $C_{34}H_{37}N_5O_4$: 579.2845; found 580.2931 [(M+H)$^+$ form].

3-[(1-{[(3R,4R)-1-(3-ethylbenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 257)

Using General Procedure 7 starting from Preparation R3b and 3-ethylbenzoic acid as reagents, EXAMPLE 257 was obtained. HRMS calculated for $C_{34}H_{39}N_5O_4$: 581.3002; found 582.3077 [(M+H)$^+$ form].

3-{[4-hydroxy-1-({(3R,4R)-1-[3-(methylsulfonyl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 258)

Using General Procedure 7 starting from Preparation R3b and 3-methylsulfonylbenzoic acid as reagents, EXAMPLE 258 was obtained. HRMS calculated for $C_{33}H_{37}N_5O_6S$: 631.2465; found 632.2549 [(M+H)$^+$ form].

3-{[1-({(3R,4R)-1-[(4,5-dichloro-3-fluorothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 259)

Using General Procedure 7 starting from Preparation R3b and Preparation R1w as reagents, EXAMPLE 259 was obtained. HRMS calculated for $C_{30}H_{30}Cl_2FN_5O_4S$: 645.1379; found 646.1449 [(M+H)$^+$ form].

tert-butyl 3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 260)

Using General Procedure 7 starting from Preparation R3b and 3-tert-butoxycarbonylbenzoic acid as reagents, EXAMPLE 260 was obtained. HRMS calculated for $C_{37}H_{43}N_5O_6$: 653.3214; found 654.3298 [(M+H)$^+$ form].

3-{1-({(3R,4R)-1-[(5-chloro-3-fluoro-4-methylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 261)

Using General Procedure 7 starting from Preparation R3b and Preparation R1l as reagents, EXAMPLE 261 was obtained. HRMS calculated for $C_{31}H_{33}ClFN_5O_4S$: 625.1926; found 626.1997 [(M+H)$^+$ form].

3-[(1-{[(3R,4R)-1-{[2,4-bis(6-methylpyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 262)

Using General Procedure 7 starting from Preparation R3b and 2,4-bis(6-methyl-3-pyridyl)thiazole-5-carboxylic acid as reagents, EXAMPLE 262 was obtained. HRMS calculated for $C_{41}H_{42}N_8O_4S$: 742.3049; found 743.3126 [(M+H)$^+$ form].

3-[(1-{[(3R,4R)-1-{[4-chloro-2-(6-methylpyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 263)

Using General Procedure 7 starting from Preparation R3b and 4-chloro-2-(6-methyl-3-pyridyl)thiazole-5-carboxylic acid as reagents, EXAMPLE 263 was obtained. HRMS calculated for $C_{35}H_{36}ClN_7O_4S$: 685.2238; found 686.2299 [(M+H)$^+$ form].

3-{[1-({(3R,4R)-1-[(4-chloro-2-methoxy-1,3-thiazol-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 264)

Using General Procedure 7 starting from Preparation R3b and 4-chloro-2-methoxy-thiazole-5-carboxylic acid as reagents, EXAMPLE 264 was obtained. HRMS calculated for $C_{30}H_{33}ClN_6O_5S$: 624.1921; found 625.2 [(M+H)$^+$ form].

3-{[1-({(3R,4R)-1-[(4-bromo-2-methoxy-1,3-thiazol-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 265)

Using General Procedure 7 starting from Preparation R3b and 4-bromo-2-methoxy-thiazole-5-carboxylic acid as reagents, EXAMPLE 265 was obtained. HRMS calculated for $C_{30}H_{33}BrN_6O_5S$: 668.1417; found 669.1494 [(M+H)$^+$ form].

6-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}quinazolin-4(3H)-one (Example 266)

Using General Procedure 7 starting from Preparation R3b and 4-oxo-3H-quinazoline-6-carboxylic acid as reagents, EXAMPLE 266 was obtained. HRMS calculated for $C_{34}H_{35}N_7O_5$: 621.2699; found 622.2775 [(M+H)$^+$ form].

3-[(4-hydroxy-1-{[(3R,4R)-3-phenyl-1-{[5-(pyridin-2-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 267)

Using General Procedure 7 starting from Preparation R3b and 5-(2-pyridyl)thiophene-2-carboxylic acid as reagents, EXAMPLE 267 was obtained. HRMS calculated for $C_{35}H_{36}N_6O_4S$: 636.2519; found 637.2603 [(M+H)$^+$ form].

7-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3,4-dihydroisoquinolin-1(2H)-one (Example 268)

Using General Procedure 7 starting from Preparation R3b and 1-oxo-3,4-dihydro-2H-isoquinoline-7-carboxylic acid as reagents, EXAMPLE 268 was obtained. HRMS calculated for $C_{35}H_{38}N_6O_5$: 622.2903; found 623.2977 [(M+H)$^+$ form].

3-{[1-({(3R,4R)-1-[(3-fluoro-5-iodothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 269)

Using General Procedure 7 starting from Preparation R3b and Preparation R1g as reagents, EXAMPLE 269 was obtained. HRMS calculated for $C_{30}H_{31}N_5O_4FSI$: 703.1125; found 704.1203 [(M+H)$^+$ form].

3-[(1-{[(3R,4R)-1-{[4-chloro-2-(2-oxopyridin-1(2H)-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 270)

Using General Procedure 7 starting from Preparation R3b and 4-chloro-2-(2-oxo-1-pyridyl)thiazole-5-carboxylic acid as reagents, EXAMPLE 270 was obtained. HRMS calculated for $C_{34}H_{34}ClN_7O_5S$: 687.2031; found 688.2081 [(M+H)$^+$ form].

3-[(4-hydroxy-1-{[(3R,4R)-1-{[4-methyl-2-(pyridin-2-ylmethyl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 271)

Using General Procedure 7 starting from Preparation R3b and 4-methyl-2-(2-pyridylmethyl)thiazole-5-carboxylic acid as reagents, EXAMPLE 271 was obtained. HRMS calculated for $C_{36}H_{39}N_7O_4S$: 665.2784; found 666.2862 [(M+H)$^+$ form].

5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-1H-indole-2,3-dione (Example 272)

Using General Procedure 7 starting from Preparation R3b and 2,3-dioxoindoline-5-carboxylic acid as reagents, EXAMPLE 272 was obtained. HRMS calculated for $C_{34}H_{34}N_6O_6$: 622.2539; found 623.2633 [(M+H)$^+$ form].

3-{[4-hydroxy-1-({(3R,4R)-1-[3-(hydroxymethyl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 273)

Using General Procedure 7 starting from Preparation R3b and 3-(hydroxymethyl)benzoic acid as reagents, EXAMPLE 273 was obtained. HRMS calculated for $C_{33}H_{37}N_5O_5$: 583.2795; found 584.2875 [(M+H)$^+$ form].

3-[(4-hydroxy-1-{[(3R,4R)-1-(2-hydroxybenzoyl)-3-phenylpiperidin-4-yl]carbonyl}piperidin-4-yl)methyl]-7-methyl-3,7-dihydro-4H-pyrrolo[2,3-d]pyrimidin-4-one (Example 274)

Using General Procedure 7 starting from Preparation R3b and 2-hydroxybenzoic acid as reagents, EXAMPLE 274 was obtained. HRMS calculated for $C_{32}H_{35}N_5O_5$: 569.2638; found 570.2727 [(M+H)$^+$ form].

3-[(1-{[(3R,4R)-1-{[5-chloro-4-(dimethylamino)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 275)

Using General Procedure 7 starting from Preparation R3b and 5-chloro-4-(dimethylamino)thiophene-2-carboxylic acid as reagents, EXAMPLE 275 was obtained. HRMS calculated for $C_{32}H_{37}ClN_6O_4S$: 636.2286; found 637.2358 [(M+H)$^+$ form].

3-{[1-({(3R,4R)-1-[(5-bromo-4-methoxythiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 276)

Using General Procedure 7 starting from Preparation R3b and 5-bromo-4-methoxy-thiophene-2-carboxylic acid as reagents, EXAMPLE 276 was obtained. HRMS calculated for $C_{31}H_{34}BrN_5O_5S$: 667.1464; found 668.153 [(M+H)$^+$ form].

3-{[1-({(3R,4R)-1-[(4,5-dibromothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 277)

Using General Procedure 7 starting from Preparation R3b and 4,5-dibromothiophene-2-carboxylic acid as reagents, EXAMPLE 277 was obtained. HRMS calculated for $C_{30}H_{31}Br_2N_5O_4S$: 715.0463; found 716.053 [(M+H)$^+$ form].

3-{[4-hydroxy-1-({(3R,4R)-1-[(3-oxo-2,3-dihydro-1H-inden-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 278)

Using General Procedure 7 starting from Preparation R3b and 3-oxoindane-5-carboxylic acid as reagents, EXAMPLE 278 was obtained. HRMS calculated for $C_{35}H_{37}N_5O_5$: 607.2795; found 608.2871 [(M+H)$^+$ form].

3-{[4-hydroxy-1-({(3R,4R)-1-[(3-oxo-2,3-dihydro-1H-isoindol-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 279)

Using General Procedure 7 starting from Preparation R3b and 3-oxoisoindoline-5-carboxylic acid as reagents, EXAMPLE 279 was obtained. HRMS calculated for $C_{34}H_{36}N_6O_5$: 608.2747; found 609.2814 [(M+H)$^+$ form].

3-[(1-{[(3R,4R)-1-{[4-chloro-2-(6-methoxypyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 280)

Using General Procedure 7 starting from Preparation R3b and 4-chloro-2-(6-methoxy-3-pyridyl)thiazole-5-carboxylic acid as reagents, EXAMPLE 280 was obtained. HRMS calculated for $C_{35}H_{36}N_7O_5SCl$: 701.2187; found 702.2257 [(M+H)$^+$ form].

methyl 5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}pyridine-3-carboxylate (Example 281)

Using General Procedure 7 starting from Preparation R3b and 5-methoxycarbonylpyridine-3-carboxylic acid as reagents, EXAMPLE 281 was obtained. HRMS calculated for $C_{33}H_{36}N_6O_6$: 612.2697; found 613.2776 [$(M+H)^+$ form].

3-{[4-hydroxy-1-({(3R,4R)-1-[3-(2-hydroxyethyl) benzoyl]-3-phenylpiperidin-4-yl}carbonyl)piperidin-4-yl]methyl}-7-methyl-3,7-dihydro-4H-pyrrolo[2,3-d]pyrimidin-4-one (Example 282)

Using General Procedure 7 starting from Preparation R3b and 3-(2-hydroxyethyl)benzoic acid as reagents, EXAMPLE 282 was obtained. HRMS calculated for $C_{34}H_{39}N_5O_5$: 597.2951; found 598.3031 [$(M+H)^+$ form].

3-{[4-hydroxy-1-({(3R,4R)-1-[3-(methylsulfanyl) benzoyl]-3-phenylpiperidin-4-yl}carbonyl)piperidin-4-yl]methyl}-7-methyl-3,7-dihydro-4H-pyrrolo[2,3-d]pyrimidin-4-one (Example 283)

Using General Procedure 7 starting from Preparation R3b and 3-methylsulfanylbenzoic acid as reagents, EXAMPLE 283 was obtained. HRMS calculated for $C_{33}H_{37}N_5O_4S$: 599.2567; found 600.2656 [$(M+H)^+$ form].

4-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}pyridine-2-carbonitrile (Example 284)

Using General Procedure 7 starting from Preparation R3b and 2-cyanopyridine-4-carboxylic acid as reagents, EXAMPLE 284 was obtained. HRMS calculated for $C_{32}H_{33}N_7O_4$: 579.2594; found 580.2682 [$(M+H)^+$ form].

methyl 3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-5-nitrobenzoate (Example 285)

Using General Procedure 7 starting from Preparation R3b and 3-methoxycarbonyl-5-nitro-benzoic acid as reagents, EXAMPLE 285 was obtained. HRMS calculated for $C_{34}H_{36}N_6O_8$: 656.2595; found 657.2679 [$(M+H)^+$ form].

dimethyl 5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzene-1,3-dicarboxylate (Example 286)

Using General Procedure 7 starting from Preparation R3b and 3,5-bis(methoxycarbonyl)benzoic acid as reagents, EXAMPLE 286 was obtained. HRMS calculated for $C_{36}H_{39}N_5O_8$: 669.2798; found 670.2847 [$(M+H)^+$ form].

methyl 3-bromo-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 287)

Using General Procedure 7 starting from Preparation R3b and 3-bromo-5-methoxycarbonyl-benzoic acid as reagents, EXAMPLE 287 was obtained. HRMS calculated for $C_{34}H_{36}BrN_5O_6$: 689.1849; found 690.1936 [$(M+H)^+$ form].

tert-butyl methyl 5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzene-1,3-dicarboxylate (Example 288)

Using General Procedure 7 starting from Preparation R3b and 3-tert-butoxycarbonyl-5-methoxycarbonyl-benzoic acid as reagents, EXAMPLE 288 was obtained. HRMS calculated for $C_{39}H_{45}N_5O_8$: 711.3268; found 712.3342 [$(M+H)^+$ form].

3-[(4-hydroxy-1-{[(3R,4R)-3-phenyl-1-{[5-(pyridin-4-yl)thiophen-2-yl]carbonyl}piperidin-4-yl] carbonyl}piperidin-4-yl)methyl]-7-methyl-3,7-dihydro-4H-pyrrolo[2,3-d]pyrimidin-4-one (Example 289)

Using General Procedure 7 starting from Preparation R3b and 5-(4-pyridyl)thiophene-2-carboxylic acid as reagents, EXAMPLE 289 was obtained. HRMS calculated for $C_{35}H_{36}N_6O_4S$: 636.2519; found 637.2597 [$(M+H)^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one (Example 290)

Using General Procedure 7 starting from Preparation R3ba and Preparation R1d as reagents, EXAMPLE 290 was obtained. HRMS calculated for $C_{40}H_{41}N_7O_4S_2$: 747.2662; found 748.2743 [$(M+H)^+$ form].

7-(5-chlorothiophen-2-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 291)

Using General Procedure 7 starting from Preparation R3bb and Preparation R1d as reagents, EXAMPLE 291 was obtained. HRMS calculated for $C_{39}H_{38}ClN_7O_4S_2$: 767.2115; found 768.2171 [$(M+H)^+$ form].

7-(2,3-dihydro-1,4-benzodioxin-6-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 292)

Using General Procedure 7 starting from Preparation R3bc and Preparation R1d as reagents, EXAMPLE 292 was obtained. HRMS calculated for $C_{43}H_{43}N_7O_6S$: 785.2996; found 786.307 [$(M+H)^+$ form].

7-(1,3-benzodioxol-5-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 293)

Using General Procedure 7 starting from Preparation R3bd and Preparation R1d as reagents, EXAMPLE 293 was obtained. HRMS calculated for $C_{42}H_{41}N_7O_6S$: 771.2839; found 772.2895 [$(M+H)^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one (Example 294)

Using General Procedure 7 starting from Preparation R3bg and Preparation R1d as reagents, EXAMPLE 294 was obtained. HRMS calculated for $C_{42}H_{40}F_3N_7O_4S$: 795.2814; found 796.2883 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one (Example 295)

Using General Procedure 7 starting from Preparation R3bi and Preparation R1d as reagents, EXAMPLE 295 was obtained. HRMS calculated for $C_{42}H_{43}N_7O_5S$: 757.3046; found 758.3124 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(trifluoromethoxy)phenyl]-3,7-dihydro-4H-pyrrolo[2,3-d]pyrimidin-4-one (Example 296)

Using General Procedure 7 starting from Preparation R3bp and Preparation R1d as reagents, EXAMPLE 296 was obtained. HRMS calculated for $C_{42}H_{40}N_7O_5F_3S$: 811.2764; found 812.2837 [(M+H)$^+$ form].

7-[3-(benzyloxy)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 297)

Using General Procedure 7 starting from Preparation R3bq and Preparation R1d as reagents, EXAMPLE 297 was obtained. HRMS calculated for $C_{48}H_{47}N_7O_5S$: 833.3359; found 834.3436 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(6-methylpyridin-2-yl)-3,7-dihydro-4H-pyrrolo[2,3-d]pyrimidin-4-one (Example 298)

Using General Procedure 7 starting from Preparation R3br and Preparation R1d as reagents, EXAMPLE 298 was obtained. HRMS calculated for $C_{41}H_{42}N_8O_4S$: 742.3049; found 743.313 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(6-methoxypyridin-2-yl)-3,7-dihydro-4H-pyrrolo[2,3-d]pyrimidin-4-one (Example 299)

Using General Procedure 7 starting from Preparation R3bs and Preparation R1d as reagents, EXAMPLE 299 was obtained. HRMS calculated for $C_{41}H_{42}N_8O_5S$: 758.2998; found 759.3062 [(M+H)$^+$ form].

3-[(1-{[(3R,4R)-1-{[4-chloro-2-(6-methoxypyridin-3-yl)-1,3-thiazol-5-yl]carbonyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 300)

Using General Procedure 7 starting from Preparation R3bu and 4-chloro-2-(6-methoxy-3-pyridyl)thiazole-5-carboxylic acid as reagents, EXAMPLE 300 was obtained. HRMS calculated for $C_{40}H_{38}N_7O_5SCl$: 763.2344; found 764.242 [(M+H)$^+$ form].

3-[(4-hydroxy-1-{[(3S,4S)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one (Example 301)

Using General Procedure 7 starting from 3-[(4-hydroxy-1-{[(3S,4S)-3-phenylpiperidin-4-yl]carbonyl}piperidin-4-yl)methyl]-7-phenyl-3,7-dihydro-4H-pyrrolo[2,3-d]pyrimidin-4-one (which was obtained according to General Procedure 5 with tert-butyl (3S,4S)-4-(2-oxa-6-azaspiro[2.5]octane-6-carbonyl)-3-phenyl-piperidine-1-carboxylate and Preparation R2bu) and Preparation R1d as reagents, EXAMPLE 301 was obtained. HRMS calculated for $C_{41}H_{41}N_7O_4S$: 727.2941; found 364.6536 [(M+2H)$^{2+}$ form].

3-{[1-({(3R,4R)-1-[(2-bromopyridin-4-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 302)

Using General Procedure 7 starting from Preparation R3bu and 2-bromopyridine-4-carboxylic acid as reagents, EXAMPLE 302 was obtained. HRMS calculated for $C_{36}H_{35}N_6O_4Br$: 694.1903; found 695.1969 [(M+H)$^+$ form].

3-{[1-({(3R,4R)-1-[(5-bromopyridin-3-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 303)

Using General Procedure 7 starting from Preparation R3bu and 5-bromopyridine-3-carboxylic acid as reagents, EXAMPLE 303 was obtained. HRMS calculated for $C_{36}H_{35}N_6O_4Br$: 694.1903; found 695.1974 [(M+H)$^+$ form].

3-[(4-hydroxy-1-{[(3R,4R)-3-phenyl-1-(1,3-thiazol-5-ylcarbonyl)piperidin-4-yl]carbonyl}piperidin-4-yl)methyl]-7-phenyl-3,7-dihydro-4H-pyrrolo[2,3-d]pyrimidin-4-one (Example 304)

Using General Procedure 7 starting from Preparation R3bu and thiazole-5-carboxylic acid as reagents, EXAMPLE 304 was obtained. HRMS calculated for $C_{34}H_{34}N_6O_4S$: 622.2362; found 623.2429 [(M+H)$^+$ form].

3-[(4-hydroxy-1-{[(3R,4R)-3-phenyl-1-(1,3-thiazol-4-ylcarbonyl)piperidin-4-yl]carbonyl}piperidin-4-yl)methyl]-7-phenyl-3,7-dihydro-4H-pyrrolo[2,3-d]pyrimidin-4-one (Example 305)

Using General Procedure 7 starting from Preparation R3bu and thiazole-4-carboxylic acid as reagents, EXAMPLE 305 was obtained. HRMS calculated for $C_{34}H_{34}N_6O_4S$: 622.2362; found 623.2434 [(M+H)+ form].

3-[(4-hydroxy-1-{[(3R,4R)-1-{[4-methyl-2-(morpholin-4-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one (Example 306)

Using General Procedure 7 starting from Preparation R3bu and 4-methyl-2-morpholino-thiazole-5-carboxylic acid as reagents, EXAMPLE 306 was obtained. HRMS calculated for $C_{39}H_{43}N_7O_5S$: 721.3046; found 722.311 [(M+H)+ form].

3-{[4-hydroxy-1-({(3R,4R)-1-[(4-methyl-1,3-thiazol-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 307)

Using General Procedure 7 starting from Preparation R3bu and 4-methylthiazole-5-carboxylic acid as reagents, EXAMPLE 307 was obtained. HRMS calculated for $C_{35}H_{36}N_6O_4S$: 636.2519; found 637.2595 [(M+H)+ form].

3-{[4-hydroxy-1-({(3R,4R)-1-[(2-methyl-1,3-thiazol-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 308)

Using General Procedure 7 starting from Preparation R3bu and 2-methylthiazole-5-carboxylic acid as reagents, EXAMPLE 308 was obtained. HRMS calculated for $C_{35}H_{36}N_6O_4S$: 636.2519; found 637.2582 [(M+H)+ form].

3-{[1-({(3R,4R)-1-[(2-chloro-1,3-thiazol-5-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 309)

Using General Procedure 7 starting from Preparation R3bu and 2-chlorothiazole-5-carboxylic acid as reagents, EXAMPLE 309 was obtained. HRMS calculated for $C_{34}H_{33}ClN_6O_4S$: 656.1973; found 657.2041 [(M+H)+ form].

3-{[4-hydroxy-1-({(3R,4R)-1-[(1-methyl-1H-indol-2-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 310)

Using General Procedure 7 starting from Preparation R3bu and 1-methylindole-2-carboxylic acid as reagents, EXAMPLE 310 was obtained. HRMS calculated for $C_{40}H_{40}N_6O_4$: 668.3111; found 669.3183 [(M+H)+ form].

3-{[4-hydroxy-1-({(3R,4R)-1-[(1-methyl-5-phenyl-1H-pyrrol-2-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 311)

Using General Procedure 7 starting from Preparation R3bu and 1-methyl-5-phenyl-pyrrole-2-carboxylic acid as reagents, EXAMPLE 311 was obtained. HRMS calculated for $C_{42}H_{42}N_6O_4$: 694.3268; found 695.3331 [(M+H)+ form].

methyl 3-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}benzoate (Example 312)

Using General Procedure 7 starting from Preparation R3bu and 3-methoxycarbonylbenzoic acid as reagents, EXAMPLE 312 was obtained. HRMS calculated for $C_{39}H_{39}N_5O_6$: 673.2900; found 674.2969 [(M+H)+ form].

methyl 5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}pyridine-3-carboxylate (Example 313)

Using General Procedure 7 starting from Preparation R3bu and 5-methoxycarbonylpyridine-3-carboxylic acid as reagents, EXAMPLE 313 was obtained. HRMS calculated for $C_{38}H_{38}N_6O_6$: 674.2853; found 675.291 [(M+H)+ form].

methyl 4-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}pyridine-2-carboxylate (Example 314)

Using General Procedure 7 starting from Preparation R3bu and 2-methoxycarbonylpyridine-4-carboxylic acid as reagents, EXAMPLE 314 was obtained. HRMS calculated for $C_{38}H_{38}N_6O_6$: 674.2853; found 675.2914 [(M+H)+ form].

7-ethyl-3-{[4-hydroxy-1-({(3R,4R)-1-[(4-methyl-2-phenyl-1,3-thiazol-5-yl)carbonyl]-3-phenylpiperidin-4-yl}carbonyl)piperidin-4-yl]methyl}-3,7-dihydro-4H-pyrrolo[2,3-d]pyrimidin-4-one (Example 315)

Using General Procedure 7 starting from Preparation R3c and 4-methyl-2-phenyl-thiazole-5-carboxylic acid as reagents, EXAMPLE 315 was obtained. HRMS calculated for $C_{37}H_{40}N_6O_4S$: 664.2832; found 665.2903 [(M+H)+ form].

7-ethyl-3-{[4-hydroxy-1-({(3R,4R)-1-[(3-methyl-1,2-thiazol-4-yl)carbonyl]-3-phenylpiperidin-4-yl}carbonyl)piperidin-4-yl]methyl}-3,7-dihydro-4H-pyrrolo[2,3-d]pyrimidin-4-one (Example 316)

Using General Procedure 7 starting from Preparation R3c and 3-methylisothiazole-4-carboxylic acid as reagents, EXAMPLE 316 was obtained. HRMS calculated for $C_{31}H_{36}N_6O_4S$: 588.2519; found 589.2601 [(M+H)+ form].

7-ethyl-3-{[4-hydroxy-1-({(3R,4R)-3-phenyl-1-[(2-phenyl-1,3-thiazol-5-yl)carbonyl]piperidin-4-yl}carbonyl)piperidin-4-yl]methyl}-3,7-dihydro-4H-pyrrolo[2,3-d]pyrimidin-4-one (Example 317)

Using General Procedure 7 starting from Preparation R3c and 2-phenylthiazole-5-carboxylic acid as reagents, EXAMPLE 317 was obtained. HRMS calculated for $C_{36}H_{38}N_6O_4S$: 650.2675; found 651.2749 [(M+H)$^+$ form].

7-ethyl-3-{[4-hydroxy-1-({(3R,4R)-1-[(4-methyl-1,3-thiazol-5-yl)carbonyl]-3-phenylpiperidin-4-yl}carbonyl)piperidin-4-yl]methyl}-3,7-dihydro-4H-pyrrolo[2,3-d]pyrimidin-4-one (Example 318)

Using General Procedure 7 starting from Preparation R3c and 4-methylthiazole-5-carboxylic acid as reagents, EXAMPLE 318 was obtained. HRMS calculated for $C_{31}H_{36}N_6O_4S$: 588.2519; found 589.259 [(M+H)$^+$ form].

3-{[1-({(3R,4R)-1-[(2-benzyl-4-methyl-1,3-thiazol-5-yl)carbonyl]-3-phenylpiperidin-4-yl}carbonyl)-4-hydroxypiperidin-4-yl]methyl}-7-ethyl-3,7-dihydro-4H-pyrrolo[2,3-d]pyrimidin-4-one (Example 319)

Using General Procedure 7 starting from Preparation R3c and 2-benzyl-4-methyl-thiazole-5-carboxylic acid as reagents, EXAMPLE 319 was obtained. HRMS calculated for $C_{38}H_{42}N_6O_4S$: 678.2988; found 679.3065 [(M+H)$^+$ form].

7-ethyl-3-[(4-hydroxy-1-{[(3R,4R)-1-(2-methylbenzoyl)-3-phenylpiperidin-4-yl]carbonyl}piperidin-4-yl)methyl]-3,7-dihydro-4H-pyrrolo[2,3-d]pyrimidin-4-one (Example 320)

Using General Procedure 6 starting from Preparation R3c and 2-methylbenzoic acid as reagents, EXAMPLE 320 was obtained. HRMS calculated for $C_{34}H_{39}N_5O_4$: 581.3002; found 582.3088 [(M+H)$^+$ form].

7-ethyl-3-[(4-hydroxy-1-{[(3R,4R)-1-(3-methylbenzoyl)-3-phenylpiperidin-4-yl]carbonyl}piperidin-4-yl)methyl]-3,7-dihydro-4H-pyrrolo[2,3-d]pyrimidin-4-one (Example 321)

Using General Procedure 7 starting from Preparation R3c and 3-methylbenzoic acid as reagents, EXAMPLE 321 was obtained. HRMS calculated for $C_{34}H_{39}N_5O_4$: 581.3002; found 582.3075 [(M+H)$^+$ form].

7-ethyl-3-[(4-hydroxy-1-{[(3R,4R)-1-(4-methylbenzoyl)-3-phenylpiperidin-4-yl]carbonyl}piperidin-4-yl)methyl]-3,7-dihydro-4H-pyrrolo[2,3-d]pyrimidin-4-one (Example 322)

Using General Procedure 7 starting from Preparation R3c and 4-methylbenzoic acid as reagents, EXAMPLE 322 was obtained. HRMS calculated for $C_{34}H_{39}N_5O_4$: 581.3002; found 582.3073 [(M+H)$^+$ form].

7-ethyl-3-[(1-{[(3R,4R)-1-(2-fluorobenzoyl)-3-phenylpiperidin-4-yl]carbonyl}-4-hydroxypiperidin-4-yl)methyl]-3,7-dihydro-4H-pyrrolo[2,3-d]pyrimidin-4-one (Example 323)

Using General Procedure 7 starting from Preparation R3c and 2-fluorobenzoic acid as reagents, EXAMPLE 323 was obtained. HRMS calculated for $C_{33}H_{36}FN_5O_4$: 585.2751; found 586.282 [(M+H)$^+$ form].

7-ethyl-3-[(1-{[(3R,4R)-1-(3-fluorobenzoyl)-3-phenylpiperidin-4-yl]carbonyl}-4-hydroxypiperidin-4-yl)methyl]-3,7-dihydro-4H-pyrrolo[2,3-d]pyrimidin-4-one (Example 324)

Using General Procedure 7 starting from Preparation R3c and 3-fluorobenzoic acid as reagents, EXAMPLE 324 was obtained. HRMS calculated for $C_{33}H_{36}FN_5O_4$: 585.2751; found 586.2827 [(M+H)$^+$ form].

7-ethyl-3-[(1-{[(3R,4R)-1-(4-fluorobenzoyl)-3-phenylpiperidin-4-yl]carbonyl}-4-hydroxypiperidin-4-yl)methyl]-3,7-dihydro-4H-pyrrolo[2,3-d]pyrimidin-4-one (Example 325)

Using General Procedure 7 starting from Preparation R3c and 4-fluorobenzoic acid as reagents, EXAMPLE 325 was obtained. HRMS calculated for $C_{33}H_{36}FN_5O_4$: 585.2751; found 586.2846 [(M+H)$^+$ form].

7-ethyl-3-[(1-{[(3R,4R)-1-{[2-(2-fluorobenzyl)-1,3-thiazol-5-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 326)

Using General Procedure 7 starting from Preparation R3c and 2-[(2-fluorophenyl)methyl]thiazole-5-carboxylic acid as reagents, EXAMPLE 326 was obtained. HRMS calculated for $C_{37}H_{39}FN_6O_4S$: 682.2738; found 683.2804 [(M+H)$^+$ form].

7-ethyl-3-[(4-hydroxy-1-{[(3R,4R)-1-{[4-methyl-2-(2-methylphenyl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 327)

Using General Procedure 7 starting from Preparation R3c and 4-methyl-2-(o-tolyl)thiazole-5-carboxylic acid as reagents, EXAMPLE 327 was obtained. HRMS calculated for $C_{38}H_{42}N_6O_4S$: 678.2988; found 679.3069 [(M+H)$^+$ form].

7-ethyl-3-[(4-hydroxy-1-{[(3R,4R)-3-phenyl-1-{[5-(pyridin-4-yl)thiophen-2-yl]carbonyl}piperidin-4-yl]carbonyl}piperidin-4-yl)methyl]-3,7-dihydro-4H-pyrrolo[2,3-d]pyrimidin-4-one (Example 328)

Using General Procedure 7 starting from Preparation R3c and 5-(4-pyridyl)thiophene-2-carboxylic acid as reagents, EXAMPLE 328 was obtained. HRMS calculated for $C_{36}H_{38}N_6O_4S$: 650.2675; found 651.2755 [(M+H)$^+$ form].

7-ethyl-3-[(4-hydroxy-1-{[(3R,4R)-1-{[4-methyl-2-(pyridin-4-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 329)

Using General Procedure 7 starting from Preparation R3c and 4-methyl-2-(4-pyridyl)thiazole-5-carboxylic acid as reagents, EXAMPLE 329 was obtained. HRMS calculated for $C_{36}H_{39}N_7O_4S$: 665.2784; found 666.2855 [(M+H)$^+$ form].

7-ethyl-3-[(4-hydroxy-1-{[(3R,4R)-3-phenyl-1-{[2-(pyridin-4-yl)-1,3-thiazol-5-yl]carbonyl}piperidin-4-yl]carbonyl}piperidin-4-yl)methyl]-3,7-dihydro-4H-pyrrolo[2,3-d]pyrimidin-4-one (Example 330)

Using General Procedure 7 starting from Preparation R3c and 2-(4-pyridyl)thiazole-5-carboxylic acid as reagents, EXAMPLE 330 was obtained. HRMS calculated for $C_{35}H_{37}N_7O_4S$: 651.2628; found 652.269 [(M+H)$^+$ form].

7-ethyl-3-[(1-{[(3R,4R)-1-{[2-(2-fluorophenyl)-4-methyl-1,3-thiazol-5-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 331)

Using General Procedure 7 starting from Preparation R3c and 2-(2-fluorophenyl)-4-methyl-thiazole-5-carboxylic acid as reagents, EXAMPLE 331 was obtained. HRMS calculated for $C_{37}H_{39}FN_6O_4S$: 682.2738; found 683.2823 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-2-yl)-3,7-dihydro-4H-pyrrolo[2,3-d]pyrimidin-4-one (Example 332)

Using General Procedure 7 starting from Preparation R3ca and Preparation R1d as reagents, EXAMPLE 332 was obtained. HRMS calculated for $C_{40}H_{40}N_8O_4S$: 728.2893; found 729.2970 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1-methyl-1H-imidazol-4-yl)-3,7-dihydro-4H-pyrrolo[2,3-d]pyrimidin-4-one (Example 333)

Using General Procedure 7 starting from Preparation R3cg and Preparation R1d as reagents, EXAMPLE 333 was obtained. HRMS calculated for $C_{39}H_{41}N_9O_4S$: 731.3002; found 732.3086 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one (Example 334)

Using General Procedure 7 starting from Preparation R3ch and Preparation R1d as reagents, EXAMPLE 334 was obtained. HRMS calculated for $C_{39}H_{41}N_9O_4S$: 731.3002; found 732.3083 [(M+H)$^+$ form].

7-[1-(difluoromethyl)-1H-pyrazol-4-yl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 335)

Using General Procedure 7 starting from Preparation R3ci and Preparation R1d as reagents, EXAMPLE 335 was obtained. HRMS calculated for $C_{39}H_{39}F_2N_9O_4S$: 767.2814; found 768.2908 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyrimidin-2-yl)-3,7-dihydro-4H-pyrrolo[2,3-d]pyrimidin-4-one (Example 336)

Using General Procedure 7 starting from Preparation R3cj and Preparation R1d as reagents, EXAMPLE 336 was obtained. HRMS calculated for $C_{39}H_{39}N_9O_4S$: 729.2845; found 730.2922 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1,3-thiazol-2-yl)-3,7-dihydro-4H-pyrrolo[2,3-d]pyrimidin-4-one (Example 337)

Using General Procedure 7 starting from Preparation R3ck and Preparation R1d as reagents, EXAMPLE 337 was obtained. HRMS calculated for $C_{38}H_{38}N_8O_4S_2$: 734.2457; found 735.2523 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1-methylpiperidin-4-yl)-3,7-dihydro-4H-pyrrolo[2,3-d]pyrimidin-4-one (Example 338)

Using General Procedure 7 starting from Preparation R3k and Preparation R1d as reagents, EXAMPLE 338 was obtained. HRMS calculated for $C_{41}H_{48}N_8O_4S$: 748.3519; found 375.1823 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(prop-2-yn-1-yl)-3,7-dihydro-4H-pyrrolo[2,3-d]pyrimidin-4-one (Example 339)

Using General Procedure 7 starting from Preparation R3m and Preparation R1d as reagents, EXAMPLE 339 was obtained. HRMS calculated for $C_{38}H_{39}N_7O_4S$: 689.2784; found 690.2847 [(M+H)$^+$ form].

3-{[1-({(3R,4R)-1-[(3-fluoro-5-iodothiophen-2-yl)carbonyl]-3-phenylpiperidin-4-yl}carbonyl)-4-hydroxypiperidin-4-yl]methyl}-7-(2,2,2-trifluoroethyl)-3,7-dihydro-4H-pyrrolo[2,3-d]pyrimidin-4-one (Example 340)

Using General Procedure 7 starting from Preparation R3o and Preparation R1g as reagents, EXAMPLE 340 was obtained. HRMS calculated for $C_{31}H_{30}F_4IN_5O_4S$: 771.0999; found 772.1074 [(M+H)$^+$ form].

7-(buta-2,3-dien-1-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 341)

Using General Procedure 7 starting from Preparation R3s and Preparation R1d as reagents, EXAMPLE 341 was obtained. HRMS calculated for $C_{39}H_{41}N_7O_4S$: 703.2941; found 704.3008 [(M+H)$^+$ form].

3-{1-({(3R,4R)-1-[(5-bromothiophen-2-yl)sulfonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 342)

Using General Procedure 8 starting from Preparation R3b and 5-bromothiophene-2-sulfonyl chloride as reagents, EXAMPLE 342 was obtained. HRMS calculated for $C_{29}H_{32}BrN_5O_5S_2$: 673.1028; found 674.1114 [(M+H)$^+$ form].

3-{[1-({(3R,4R)-1-[(3-bromophenyl)sulfonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 343)

Using General Procedure 8 starting from Preparation R3b and 3-bromobenzenesulfonyl chloride as reagents, EXAMPLE 343 was obtained. HRMS calculated for $C_{31}H_{34}BrN_5O_5S$: 667.1464; found 668.153 [(M+H)$^+$ form].

3-[(4-hydroxy-1-{[(3R,4R)-3-phenyl-1-(phenylsulfonyl)piperidin-4-yl]carbonyl}piperidin-4-yl)methyl]-7-phenyl-3,7-dihydro-4H-pyrrolo[2,3-d]pyrimidin-4-one (Example 344)

Using General Procedure 8 starting from Preparation R3bu and benzenesulfonyl chloride as reagents, EXAMPLE 344 was obtained. HRMS calculated for $C_{36}H_{37}N_5O_5S$: 651.2515; found 652.2577 [(M+H)$^+$ form].

7-(3,4-dichlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 345)

Using General Procedure 6 starting from Preparation R3ag and Preparation R1c as reagents, EXAMPLE 345 was obtained. HRMS calculated for $C_{40}H_{39}Cl_2N_7O_3S$: 767.2212; found 768.2266 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methylphenyl)-3,7-dihydro-4H-pyrrolo[2,3-d]pyrimidin-4-one (Example 346)

Using General Procedure 6 starting from Preparation R3am and Preparation R1c as reagents, EXAMPLE 346 was obtained. HRMS calculated for $C_{41}H_{43}N_7O_3S$: 713.3148; found 714.3224 [(M+H)$^+$ form].

7-(4-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 347)

Using General Procedure 7 starting from Preparation R3ar and Preparation R1d as reagents, EXAMPLE 347 was obtained. HRMS calculated for $C_{41}H_{40}N_7O_4SCl$: 761.2551; found 762.2622 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 348)

Using General Procedure 7 starting from Preparation R3ax and Preparation R1d as reagents, EXAMPLE 348 was obtained. HRMS calculated for $C_{42}H_{43}N_7O_5S$: 757.3046; found 758.3117 [(M+H)$^+$ form].

3-{[1-({(3R,4R)-1-[(2-bromo-4-methyl-1,3-thiazol-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 349)

Using General Procedure 7 starting from Preparation R3b and 2-bromo-4-methyl-thiazole-5-carboxylic acid as reagents, EXAMPLE 349 was obtained. HRMS calculated for $C_{30}H_{33}BrN_6O_4S$: 652.1467; found 653.1548 [(M+H)$^+$ form].

3-{[4-hydroxy-1-({(3R,4R)-1-[(4-methyl-2-phenyl-1,3-thiazol-5-yl)sulfonyl]-3-phenylpiperidin-4-yl}carbonyl)piperidin-4-yl]methyl}-7-methyl-3,7-dihydro-4H-pyrrolo[2,3-d]pyrimidin-4-one (Example 350)

Using General Procedure 8 starting from Preparation R3b and 2-bromo-4-methyl-1,3-thiazole-5-sulfonyl chloride acid as reagents, the resulted crude bromo-compound was reacted with phenylboronic acid according to General procedure 9, to give EXAMPLE 350. HRMS calculated for $C_{35}H_{38}N_6O_5S_2$: 686.2345; found 687.2389 [(M+H) form].

3-[(4-hydroxy-1-{[(3R,4R)-1-{[4-methyl-2-(pyridin-4-yl)-1,3-thiazol-5-yl]sulfonyl}-3-phenylpiperidin-4-yl]carbonyl}piperidin-4-yl)methyl]-7-methyl-3,7-dihydro-4H-pyrrolo[2,3-d]pyrimidin-4-one (Example 351)

Using General Procedure 8 starting from Preparation R3b and 2-bromo-4-methyl-1,3-thiazole-5-sulfonyl chloride acid as reagents, the resulted crude bromo-compound was reacted with 4-(4,4,5,5-tetramethyl-1,3,2-dioxaborolan-2-yl)pyridine according to General Procedure 9, to give EXAMPLE 351. HRMS calculated for $C_{34}H_{37}N_7O_5S_2$: 687.2298; found 344.6232 [(M+2H)$^{2+}$ form].

3-[(4-hydroxy-1-{[(3R,4R)-1-{[4-methyl-2-(pyrimidin-5-yl)-1,3-thiazol-5-yl]sulfonyl}-3-phenylpiperidin-4-yl]carbonyl}piperidin-4-yl)methyl]-7-methyl-3,7-dihydro-4H-pyrrolo[2,3-d]pyrimidin-4-one (Example 352)

Using General Procedure 8 starting from Preparation R3b and 2-bromo-4-methyl-1,3-thiazole-5-sulfonyl chloride acid as reagents, the resulted crude bromo-compound was reacted with pyrimidin-5-ylboronic acid according to General Procedure 9, to give EXAMPLE 352. HRMS calculated for $C_{33}H_{36}N_8O_5S_2$: 688.2250; found 689.2304 [(M+H)$^+$ form].

3-[(4-hydroxy-1-{[(3R,4R)-1-{[4-methyl-2-(1-methyl-1H-pyrazol-5-yl)-1,3-thiazol-5-yl]sulfonyl}-3-phenylpiperidin-4-yl]carbonyl}piperidin-4-yl)methyl]-7-methyl-3,7-dihydro-4H-pyrrolo[2,3-d]pyrimidin-4-one (Example 353)

Using General Procedure 8 starting from Preparation R3b and 2-bromo-4-methyl-1,3-thiazole-5-sulfonyl chloride acid as reagents, the resulted crude bromo-compound was reacted with 1-methyl-5-(4,4,5,5-tetramethyl-1,3,2-dioxaborolan-2-yl)pyrazole according to General Procedure 9, to give EXAMPLE 353. HRMS calculated for $C_{33}H_{38}N_8O_5S_2$: 690.2407; found 691.2481 [(M+H)$^+$ form].

3-[(4-hydroxy-1-{[(3R,4R)-3-phenyl-1-{[5-(pyrimidin-5-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 354)

Using General Procedure 7 starting from Preparation R3b and 5-bromothiazole-2-carboxylic acid as reagents, the resulted crude bromo-compound was reacted with pyrimidin-5-ylboronic acid according to General Procedure 9, to give EXAMPLE 354. HRMS calculated for $C_{33}H_{34}N_8O_4S$: 638.2424; found 639.25 [(M+H)$^+$ form].

3-[(4-hydroxy-1-{[(3R,4R)-3-phenyl-1-{[5-(pyridin-3-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 355)

Using General Procedure 7 starting from Preparation R3b and 5-bromothiazole-2-carboxylic acid as reagents, the resulted crude bromo-compound was reacted with 3-pyridylboronic acid according to General Procedure 9, to give EXAMPLE 355. HRMS calculated for $C_{34}H_{35}N_7O_4S$: 637.2471; found 638.254 [(M+H)$^+$ form].

3-[(4-hydroxy-1-{[(3R,4R)-3-phenyl-1-{[5-(pyridin-4-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 356)

Using General Procedure 7 starting from Preparation R3b and 5-bromothiazole-2-carboxylic acid as reagents, the resulted crude bromo-compound was reacted with 4-(4,4,5,5-tetramethyl-1,3,2-dioxaborolan-2-yl)pyridine according to General Procedure 9, to give EXAMPLE 356. HRMS calculated for $C_{34}H_{35}N_7O_4S$: 637.2471; found 638.252 [(M+H)$^+$ form].

3-[(4-hydroxy-1-{[(3R,4R)-1-{[5-(1-methyl-1H-pyrazol-5-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 357)

Using General Procedure 7 starting from Preparation R3b and 5-bromothiazole-2-carboxylic acid as reagents, the resulted crude bromo-compound was reacted with 1-methyl-5-(4,4,5,5-tetramethyl-1,3,2-dioxaborolan-2-yl)pyrazole according to General Procedure 9, to give EXAMPLE 357. HRMS calculated for $C_{33}H_{36}N_8O_4S$: 640.2580; found 641.268 [(M+H)$^+$ form].

3-[(4-hydroxy-1-{[(3R,4R)-3-phenyl-1-{[5-(pyridin-3-yl)thiophen-2-yl]methyl}piperidin-4-yl]carbonyl}piperidin-4-yl)methyl]-7-methyl-3,7-dihydro-4H-pyrrolo[2,3-d]pyrimidin-4-one (Example 358)

Using General Procedure 6 starting from Preparation R3b and 2-bromo-5-(chloromethyl)thiophene as reagents, the resulted crude bromo-compound was reacted with 3-pyridylboronic acid according to General Procedure 9, to give EXAMPLE 358. HRMS calculated for $C_{35}H_{38}N_6O_3S$: 622.2726; found 623.2807 [(M+H)$^+$ form].

3-[(4-hydroxy-1-{[(3R,4R)-3-phenyl-1-{[5-(pyridin-4-yl)thiophen-2-yl]methyl}piperidin-4-yl]carbonyl}piperidin-4-yl)methyl]-7-methyl-3,7-dihydro-4H-pyrrolo[2,3-d]pyrimidin-4-one (Example 359)

Using General Procedure 6 starting from Preparation R3b and 2-bromo-5-(chloromethyl)thiophene as reagents, the resulted crude bromo-compound was reacted with 4-(4,4,5,5-tetramethyl-1,3,2-dioxaborolan-2-yl)pyridine according to General Procedure 9, to give EXAMPLE 359. HRMS calculated for $C_{35}H_{38}N_6O_3S$: 622.2726; found 623.2807 [(M+H)$^+$ form].

3-{[4-hydroxy-1-({(3R,4R)-3-phenyl-1-[(5-phenylthiophen-2-yl)methyl]piperidin-4-yl}carbonyl)piperidin-4-yl]methyl}-7-methyl-3,7-dihydro-4H-pyrrolo[2,3-d]pyrimidin-4-one (Example 360)

Using General Procedure 6 starting from Preparation R3b and 2-bromo-5-(chloromethyl)thiophene as reagents, the resulted crude bromo-compound was reacted with phenylboronic acid according to General Procedure 9, to give EXAMPLE 360. HRMS calculated for $C_{36}H_{39}N_5O_3S$: 621.2773; found 622.2859 [(M+H)$^+$ form].

3-[(4-hydroxy-1-{[(3R,4R)-1-{[5-(1-methyl-1H-pyrazol-5-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 361)

Using General Procedure 6 starting from Preparation R3b and 2-bromo-5-(chloromethyl)thiophene as reagents, the resulted crude bromo-compound was reacted with 1-methyl-5-(4,4,5,5-tetramethyl-1,3,2-dioxaborolan-2-yl)pyrazole according to General Procedure 9, to give EXAMPLE 361. HRMS calculated for $C_{34}H_{36}N_7O_3S$: 625.2835; found 626.2919 [(M+H)$^+$ form].

3-{[4-hydroxy-1-({(3R,4R)-3-phenyl-1-[(5-phenyl-1,3-thiazol-2-yl)carbonyl]piperidin-4-yl}carbonyl)piperidin-4-yl]methyl}-7-methyl-3,7-dihydro-4H-pyrrolo[2,3-d]pyrimidin-4-one (Example 362)

Using General Procedure 7 starting from Preparation R3b and 5-bromothiazole-2-carboxylic acid as reagents, the resulted crude bromo-compound was reacted with phenylboronic acid according to General Procedure 9, to give EXAMPLE 362. HRMS calculated for $C_{35}H_{36}N_6O_4S$: 636.2519; found 637.2592 [(M+H)$^+$ form].

3-[(4-hydroxy-1-{[(3R,4R)-3-phenyl-1-{[5-(pyrimidin-5-yl)thiophen-2-yl]methyl}piperidin-4-yl]carbonyl}piperidin-4-yl)methyl]-7-methyl-3,7-dihydro-4H-pyrrolo[2,3-d]pyrimidin-4-one (Example 363)

Using General Procedure 6 starting from Preparation R3b and 2-bromo-5-(chloromethyl)thiophene as reagents, the resulted crude bromo-compound was reacted with pyrimidin-5-ylboronic acid according to General Procedure 9, to give EXAMPLE 363. HRMS calculated for $C_{34}H_{37}N_7O_3S$: 623.2679; found 624.2761 [(M+H)$^+$ form].

3-[(4-hydroxy-1-{[(3R,4R)-1-{[4-methyl-5-(1-methyl-1H-pyrazol-5-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 364)

Using General Procedure 7 starting from Preparation R3b and 5-bromo-4-methyl-thiazole-2-carboxylic acid as reagents, the resulted crude bromo-compound was reacted with 1-methyl-5-(4,4,5,5-tetramethyl-1,3,2-dioxaborolan-2-yl)pyrazole according to General Procedure 9, to give EXAMPLE 364. HRMS calculated for $C_{34}H_{38}N_8O_4S$: 654.2737; found 655.2814 [(M+H)$^+$ form].

3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 365)

Using General Procedure 6 starting from Preparation R3b and 2-bromo-5-(bromomethyl)thiazole as reagents, the resulted crude bromo-compound was reacted with 1-methyl-5-(4,4,5,5-tetramethyl-1,3,2-dioxaborolan-2-yl)pyrazole according to General Procedure 9, to give EXAMPLE 365. HRMS calculated for $C_{33}H_{38}N_8O_3S$: 626.2787; found 627.2871 [(M+H)$^+$ form].

3-{[4-hydroxy-1-({(3R,4R)-1-[(4-methyl-5-phenyl-1,3-thiazol-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 366)

Using General Procedure 7 starting from Preparation R3b and 5-bromo-4-methyl-thiazole-2-carboxylic acid as reagents, the resulted crude bromo-compound was reacted with phenylboronic acid according to General Procedure 9, to give EXAMPLE 366. HRMS calculated for $C_{36}H_{38}N_6O_4S$: 650.2675; found 651.2756 [(M+H)$^+$ form].

3-{[4-hydroxy-1-({(3R,4R)-3-phenyl-1-[(2-phenyl-1,3-thiazol-5-yl)methyl]piperidin-4-yl}carbonyl)piperidin-4-yl]methyl}-7-methyl-3,7-dihydro-4H-pyrrolo[2,3-d]pyrimidin-4-one (Example 367)

Using General Procedure 6 starting from Preparation R3b and 2-bromo-5-(bromomethyl)thiazole as reagents, the resulted crude bromo-compound was reacted with phenylboronic acid according to General Procedure 9, to give EXAMPLE 367. HRMS calculated for $C_{35}H_{38}N_6O_3S$: 622.2726; found 623.2794 [(M+H)$^+$ form].

3-[(4-hydroxy-1-{[(3R,4R)-1-{[4-methyl-5-(pyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 368)

Using General Procedure 7 starting from Preparation R3b and 5-bromo-4-methyl-thiazole-2-carboxylic acid as reagents, the resulted crude bromo-compound was reacted with 4-(4,4,5,5-tetramethyl-1,3,2-dioxaborolan-2-yl)pyridine according to General Procedure 9, to give EXAMPLE 368. HRMS calculated for $C_{35}H_{37}N_7O_4S$: 651.2628; found 652.2727 [(M+H)$^+$ form].

3-[(4-hydroxy-1-{[(3R,4R)-3-phenyl-1-{[2-(pyridin-4-yl)-1,3-thiazol-5-yl]methyl}piperidin-4-yl]carbonyl}piperidin-4-yl)methyl]-7-methyl-3,7-dihydro-4H-pyrrolo[2,3-d]pyrimidin-4-one (Example 369)

Using General Procedure 6 starting from Preparation R3b and 2-bromo-5-(bromomethyl)thiazole as reagents, the resulted crude bromo-compound was reacted with 4-(4,4,5,5-tetramethyl-1,3,2-dioxaborolan-2-yl)pyridine according to General Procedure 9, to give EXAMPLE 369. HRMS calculated for $C_{34}H_{37}N_7O_3S$: 623.2679; found 624.274 [(M+H)$^+$ form].

3-[(4-hydroxy-1-{[(3R,4R)-1-{[4-methyl-5-(pyrimidin-5-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 370)

Using General Procedure 7 starting from Preparation R3b and 5-bromo-4-methyl-thiazole-2-carboxylic acid as reagents, the resulted crude bromo-compound was reacted with pyrimidin-5-ylboronic acid according to General Procedure 9, to give EXAMPLE 370. HRMS calculated for $C_{34}H_{36}N_8O_4S$: 652.2580; found 653.2632 [(M+H)$^+$ form].

3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-methyl-3,7-dihydro-4H-pyrrolo[2,3-d]pyrimidin-4-one (Example 371)

Using General Procedure 6 starting from Preparation R3b and 2-bromo-5-(bromomethyl)thiazole as reagents, the resulted crude bromo-compound was reacted with pyrimidin-5-ylboronic acid according to General Procedure 9, to give EXAMPLE 371. HRMS calculated for $C_{33}H_{36}N_8O_3S$: 624.2631; found 625.2706 [(M+H)$^+$ form].

3-[(4-hydroxy-1-{[(3R,4R)-1-{[4-methyl-5-(pyridin-3-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 372)

Using General Procedure 7 starting from Preparation R3b and 5-bromo-4-methyl-thiazole-2-carboxylic acid as reagents, the resulted crude bromo-compound was reacted with 3-pyridylboronic acid according to General Procedure 9, to give EXAMPLE 372. HRMS calculated for $C_{35}H_{37}N_7O_4S$: 651.2628; found 652.2723 [(M+H)$^+$ form].

3-[(4-hydroxy-1-{[(3R,4R)-3-phenyl-1-{[2-(pyridin-3-yl)-1,3-thiazol-5-yl]methyl}piperidin-4-yl]carbonyl}piperidin-4-yl)methyl]-7-methyl-3,7-dihydro-4H-pyrrolo[2,3-d]pyrimidin-4-one (Example 373)

Using General Procedure 6 starting from Preparation R3b and 2-bromo-5-(bromomethyl)thiazole as reagents, the resulted crude bromo-compound was reacted with 3-pyridylboronic according to General Procedure 9, to give EXAMPLE 373. HRMS calculated for $C_{34}H_{37}N_7O_3S$: 623.2679; found 624.2747 [(M+H)$^+$ form].

3-[(1-{[(3R,4R)-1-{[5-chloro-3-fluoro-4-(2-methyl-pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 374)

Using General Procedure 7 starting from Preparation R3b and Preparation R1k as reagents, the resulted crude product was reacted with 2-methyl-4-(4,4,5,5-tetramethyl-1,3,2-dioxaborolan-2-yl)pyridine according to General Procedure 9, to give EXAMPLE 374. HRMS calculated for $C_{36}H_{36}ClFN_6O_4S$: 702.2191; found 703.2273 [(M+H)$^+$ form].

3-[(1-{[(3R,4R)-1-{[3-fluoro-5-methyl-4-(2-methyl-pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 375)

Using General Procedure 7 starting from Preparation R3b and Preparation R1i as reagents, the resulted crude product was reacted with 2-methyl-4-(4,4,5,5-tetramethyl-1,3,2-dioxaborolan-2-yl)pyridine according to General Procedure 9, to give EXAMPLE 375. HRMS calculated for $C_{37}H_{39}FN_6O_4S$: 682.2737; found 683.28 [(M+H)$^+$ form].

3-[(4-hydroxy-1-{[(3R,4R)-3-phenyl-1-{[5-(pyridin-3-yl)-1,3-thiazol-2-yl]methyl}piperidin-4-yl]carbonyl}piperidin-4-yl)methyl]-7-methyl-3,7-dihydro-4H-pyrrolo[2,3-d]pyrimidin-4-one (Example 376)

Using General Procedure 6 starting from Preparation R3b and 5-bromo-2-(bromomethyl)thiazole as reagents, the resulted crude product was reacted with 3-pyridylboronic acid according to General Procedure 9, to give EXAMPLE 376. HRMS calculated for $C_{34}H_{37}N_7O_3S$: 623.2679; found 624.2737 [(M+H)$^+$ form].

3-[(4-hydroxy-1-{[(3R,4R)-3-phenyl-1-{[5-(pyrimidin-5-yl)-1,3-thiazol-2-yl]methyl}piperidin-4-yl]carbonyl}piperidin-4-yl)methyl]-7-methyl-3,7-dihydro-4H-pyrrolo[2,3-d]pyrimidin-4-one (Example 377)

Using General Procedure 6 starting from Preparation R3b and 5-bromo-2-(bromomethyl)thiazole as reagents, the resulted crude product was reacted with pyrimidin-5-ylboronic acid according to General Procedure 9, to give EXAMPLE 377. HRMS calculated for $C_{33}H_{36}N_8O_3S$: 624.2631; found 625.2697 [(M+H)$^+$ form].

3-[(4-hydroxy-1-{[(3R,4R)-3-phenyl-1-{[5-(pyridin-4-yl)-1,3-thiazol-2-yl]methyl}piperidin-4-yl]carbonyl}piperidin-4-yl)methyl]-7-methyl-3,7-dihydro-4H-pyrrolo[2,3-d]pyrimidin-4-one (Example 378)

Using General Procedure 6 starting from Preparation R3b and 5-bromo-2-(bromomethyl)thiazole as reagents, the resulted crude product was reacted with 4-(4,4,5,5-tetramethyl-1,3,2-dioxaborolan-2-yl)pyridine according to General Procedure 9, to give EXAMPLE 378. HRMS calculated for $C_{34}H_{37}N_7O_3S$: 623.2679; found 624.274 [(M+H)$^+$ form].

3-{[4-hydroxy-1-({(3R,4R)-3-phenyl-1-[(5-phenyl-1,3-thiazol-2-yl)methyl]piperidin-4-yl}carbonyl)piperidin-4-yl]methyl}-7-methyl-3,7-dihydro-4H-pyrrolo[2,3-d]pyrimidin-4-one (Example 379)

Using General Procedure 6 starting from Preparation R3b and 5-bromo-2-(bromomethyl)thiazole as reagents, the resulted crude product was reacted with phenylboronic acid according to General Procedure 9, to give EXAMPLE 379. HRMS calculated for $C_{35}H_{38}N_6O_3S$: 622.2726; found 623.2816 [(M+H)$^+$ form].

3-[(4-hydroxy-1-{[(3R,4R)-1-{[5-(1-methyl-1H-pyrazol-5-yl)-1,3-thiazol-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 380)

Using General Procedure 6 starting from Preparation R3b and 5-bromo-2-(bromomethyl)thiazole as reagents, the resulted crude product was reacted with 1-methyl-5-(4,4,5,5-tetramethyl-1,3,2-dioxaborolan-2-yl)pyrazole according to General Procedure 9, to give EXAMPLE 380. HRMS calculated for $C_{33}H_{38}N_8O_3S$: 626.2787; found 627.2861 [(M+H)$^+$ form].

3-[(4-hydroxy-1-{[(3R,4R)-1-{[5-(2-methylpyridin-4-yl)-1,3-thiazol-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 381)

Using General Procedure 6 starting from Preparation R3b and 5-bromo-2-(bromomethyl)thiazole as reagents, the resulted crude product was reacted with 2-methyl-4-(4,4,5,5-tetramethyl-1,3,2-dioxaborolan-2-yl)pyridine according to General Procedure 9, to give EXAMPLE 381. HRMS calculated for $C_{35}H_{39}N_7O_3S$: 637.2835; found 638.2912 [(M+H)$^+$ form].

3-[(4-hydroxy-1-{[(3R,4R)-1-{[2-(2-methoxy-6-methylpyridin-4-yl)-1,3-thiazol-5-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 382)

Using General Procedure 6 starting from Preparation R3b and 2-bromo-5-(bromomethyl)thiazole as reagents, the resulted crude product was reacted with 2-methoxy-6-methyl-4-(4,4,5,5-tetramethyl-1,3,2-dioxaborolan-2-yl)pyridine according to General Procedure 9, to give EXAMPLE 382. HRMS calculated for $C_{36}H_{41}N_7O_4S$: 667.2940; found 668.3009 [(M+H)$^+$ form].

3-[(4-hydroxy-1-{[(3R,4R)-1-{[3-methyl-5-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 383)

Using General Procedure 7 starting from Preparation R3b and 5-bromo-3-methyl-thiophene-2-carboxylic acid as reagents, the resulted crude product was reacted with 2-methyl-4-(4,4,5,5-tetramethyl-1,3,2-dioxaborolan-2-yl)pyridine according to General Procedure 9, to give EXAMPLE 383. HRMS calculated for $C_{37}H_{40}N_6O_4S$: 664.2832; found 665.291 [(M+H)$^+$ form].

3-[(4-hydroxy-1-{[(3R,4R)-1-{[5-(2-methoxypyridin-4-yl)-3-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 384)

Using General Procedure 7 starting from Preparation R3b and 5-bromo-3-methyl-thiophene-2-carboxylic acid as reagents, the resulted crude product was reacted with (2-methoxy-4-pyridyl)boronic acid according to General Procedure 9, to give EXAMPLE 384. HRMS calculated for $C_{37}H_{40}N_6O_5S$: 680.2781; found 681.2864 [(M+H)$^+$ form].

3-[(4-hydroxy-1-{[(3R,4R)-1-{[5-(3-methoxypyridin-4-yl)-3-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 385)

Using General Procedure 7 starting from Preparation R3b and 5-bromo-3-methyl-thiophene-2-carboxylic acid as reagents, the resulted crude product was reacted with (3-methoxy-4-pyridyl)boronic acid according to General Procedure 9, to give EXAMPLE 385. HRMS calculated for $C_{37}H_{40}N_6O_5S$: 680.2781; found 681.286 [(M+H)$^+$ form].

3-[(4-hydroxy-1-{[(3R,4R)-1-{[3-methyl-5-(pyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 386)

Using General Procedure 7 starting from Preparation R3b and 5-bromo-3-methyl-thiophene-2-carboxylic acid as reagents, the resulted crude product was reacted with 3-pyridylboronic acid according to General Procedure 9, to give EXAMPLE 386. HRMS calculated for $C_{36}H_{38}N_6O_4S$: 650.2675; found 651.2762 [(M+H)$^+$ form].

3-[(4-hydroxy-1-{[(3R,4R)-1-{[5-(2-methylpyridin-4-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 387)

Using General Procedure 6 starting from Preparation R3b and 2-bromo-5-(chloromethyl)thiophene as reagents, the resulted crude product was reacted with 2-methyl-4-(4,4,5,5-tetramethyl-1,3,2-dioxaborolan-2-yl)pyridine according to General Procedure 9, to give EXAMPLE 387. HRMS calculated for $C_{36}H_{40}N_6O_3S$: 636.2883; found 637.2976 [(M+H)$^+$ form].

3-[(4-hydroxy-1-{[(3R,4R)-1-{[5-(2-methoxypyridin-4-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 388)

Using General Procedure 6 starting from Preparation R3b and 2-bromo-5-(chloromethyl)thiophene as reagents, the resulted crude product was reacted with (2-methoxy-4-pyridyl)boronic acid according to General Procedure 9, to give EXAMPLE 388. HRMS calculated for $C_{36}H_{40}N_6O_4S$: 652.2832; found 327.1501 [(M+2H)$^{2+}$ form].

3-[(1-{[(3R,4R)-1-(2,3'-bithiophen-5-ylmethyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 389)

Using General Procedure 6 starting from Preparation R3b and 2-bromo-5-(chloromethyl)thiophene as reagents, the resulted crude product was reacted with 4,4,5,5-tetramethyl-2-(3-thienyl)-1,3,2-dioxaborolane according to General Procedure 9, to give EXAMPLE 389. HRMS calculated for $C_{34}H_{37}N_5O_3S_2$: 627.2338; found 628.2426 [(M+H)$^+$ form].

3-[(4-hydroxy-1-{[(3R,4R)-1-{[5-(6-methylpyridin-3-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 390)

Using General Procedure 6 starting from Preparation R3b and 2-bromo-5-(chloromethyl)thiophene as reagents, the resulted crude product was reacted with (6-methyl-3-pyridyl)boronic acid according to General Procedure 9, to give EXAMPLE 390. HRMS calculated for $C_{36}H_{40}N_6O_3S$: 636.2883; found 637.2964 [(M+H)$^+$ form].

3-[(4-hydroxy-1-{[(3R,4R)-1-{[5-(3-methoxypyridin-4-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 391)

Using General Procedure 6 starting from Preparation R3b and 2-bromo-5-(chloromethyl)thiophene as reagents, the resulted crude product was reacted with (3-methoxy-4-pyridyl)boronic acid according to General Procedure 9, to give EXAMPLE 391. HRMS calculated for $C_{36}H_{40}N_6O_4S$: 652.2832; found 653.2935 [(M+H)$^+$ form].

tert-butyl [4-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]methyl}thiophen-2-yl)pyridin-2-yl]carbamate (Example 392)

Using General Procedure 6 starting from Preparation R3b and 2-bromo-5-(chloromethyl)thiophene as reagents, the resulted crude product was reacted with tert-butyl N-[4-(4,4,5,5-tetramethyl-1,3,2-dioxaborolan-2-yl)-2-pyridyl]carbamate according to General Procedure 9, to give EXAMPLE 392. HRMS calculated for $C_{40}H_{47}N_7O_5S$: 737.3359; found 738.3434 [(M+H)$^+$ form].

3-[(1-{[(3R,4R)-1-{[5-(6-aminopyridin-3-yl)thiophen-2-yl]methyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 393)

Using General Procedure 6 starting from Preparation R3b and 2-bromo-5-(chloromethyl)thiophene as reagents, the resulted crude product was reacted 5-(4,4,5,5-tetramethyl-1,3,2-dioxaborolan-2-yl)pyridin-2-amine according to General Procedure 9, to give EXAMPLE 393. HRMS calculated for $C_{35}H_{39}N_7O_3S$: 637.2835; found 638.2918 [(M+H)$^+$ form].

3-[(4-hydroxy-1-{[(3R,4R)-1-{[5-(2-methoxy-6-methylpyridin-4-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 394)

Using General Procedure 6 starting from Preparation R3b and 2-bromo-5-(chloromethyl)thiophene as reagents, the resulted crude product was reacted 2-methoxy-6-methyl-4-(4,4,5,5-tetramethyl-1,3,2-dioxaborolan-2-yl)pyridine according to General Procedure 9, to give EXAMPLE 394. HRMS calculated for $C_{37}H_{42}N_6O_4S$: 666.2988; found 667.3071 [(M+H)$^+$ form].

3-[(4-hydroxy-1-{[(3R,4R)-1-{[5-(6-methoxypyridin-3-yl)thiophen-2-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 395)

Using General Procedure 6 starting from Preparation R3b and 2-bromo-5-(chloromethyl)thiophene as reagents, the resulted crude product was reacted (6-methoxy-3-pyridyl)boronic acid according to General Procedure 9, to give EXAMPLE 395. HRMS calculated for $C_{36}H_{40}N_6O_4S$: 652.2832; found 653.2910 [(M+H)$^+$ form].

3-{[4-hydroxy-1-({(3R,4R)-1-[(4-methyl-2,3'-bithiophen-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 396)

Using General Procedure 7 starting from Preparation R3b and 5-bromo-3-methyl-thiophene-2-carboxylic acid as reagents, the resulted crude product was reacted with 4,4,5,5-tetramethyl-2-(3-thienyl)-1,3,2-dioxaborolane according to General Procedure 9, to give to give EXAMPLE 396. HRMS calculated for $C_{35}H_{37}N_5O_4S_2$: 655.2287; found 656.2362 [(M+H)$^+$ form].

3-{[4-hydroxy-1-({(3R,4R)-1-[(3-methyl-5-phenylthiophen-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 397)

Using General Procedure 7 starting from Preparation R3b and 5-bromo-3-methyl-thiophene-2-carboxylic acid as reagents, the resulted crude product was reacted with phenylboronic acid according to General Procedure 9, to give EXAMPLE 397. HRMS calculated for $C_{37}H_{39}N_5O_4S$: 649.2723; found 650.2806 [(M+H)$^+$ form].

tert-butyl [4-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3-methylthiophen-2-yl)pyridin-2-yl]carbamate (Example 398)

Using General Procedure 7 starting from Preparation R3b and 5-bromo-4-methyl-thiophene-2-carboxylic acid as reagents, the resulted crude product was reacted with tert-butyl N-[4-(4,4,5,5-tetramethyl-1,3,2-dioxaborolan-2-yl)-2-pyridyl]carbamate according to General Procedure 9, to give EXAMPLE 398. HRMS calculated for $C_{41}H_{47}N_7O_6S$: 765.3309; found 766.3374 [(M+H)$^+$ form].

3-[(4-hydroxy-1-{[(3R,4R)-1-{[4-methyl-5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 399)

Using General Procedure 7 starting from Preparation R3b and 5-bromo-4-methyl-thiophene-2-carboxylic acid as reagents, the resulted crude product was reacted with (6-methyl-3-pyridyl)boronic acid according to General Procedure 9, to give EXAMPLE 399. HRMS calculated for $C_{37}H_{40}N_6O_4S$: 664.2832; found 665.2922 [(M+H)$^+$ form].

3-[(4-hydroxy-1-{[(3R,4R)-1-{[5-(6-methoxypyridin-3-yl)-4-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 400)

Using General Procedure 7 starting from Preparation R3b and 5-bromo-4-methyl-thiophene-2-carboxylic acid as reagents, the resulted crude product was reacted with (6-methoxy-3-pyridyl)boronic acid according to General Procedure 9, as reagents, to give EXAMPLE 400. HRMS calculated for $C_{37}H_{40}N_6O_5S$: 680.2781; found 681.2854 [(M+H)$^+$ form].

3-[(1-{[(3R,4R)-1-{[5-(6-aminopyridin-3-yl)-4-methylthiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 401)

Using General Procedure 7 starting from Preparation R3b and 5-bromo-4-methyl-thiophene-2-carboxylic acid as reagents, the resulted crude product was reacted with 5-(4,4,5,5-tetramethyl-1,3,2-dioxaborolan-2-yl)pyridin-2-amine according to General Procedure 9, to give EXAMPLE 401. HRMS calculated for $C_{36}H_{39}N_7O_4S$: 665.2784; found 333.6475 [(M+2H)$^{2+}$ form].

tert-butyl [4-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-4-methylthiophen-2-yl)pyridin-2-yl]carbamate (Example 402)

Using General Procedure 7 starting from Preparation R3b and 5-bromo-3-methyl-thiophene-2-carboxylic acid as reagents, the resulted crude product was reacted with tert-butyl N-[4-(4,4,5,5-tetramethyl-1,3,2-dioxaborolan-2-yl)-2-pyridyl]carbamate according to General Procedure 9, to give EXAMPLE 402. HRMS calculated for $C_{41}H_{47}N_7O_6S$: 765.3309; found 766.3381 [(M+H)$^+$ form].

3-[(4-hydroxy-1-{[(3R,4R)-1-{[5-(2-methoxypyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 403)

Using General Procedure 7 starting from Preparation R3b and 5-bromothiazole-2-carboxylic acid as reagents, the resulted crude product was reacted with (2-methoxy-4-pyridyl)boronic acid according to General Procedure 9, to give EXAMPLE 403. HRMS calculated for $C_{35}H_{37}N_7O_5S$: 667.2577; found 668.2654 [(M+H)$^+$ form].

3-[(4-hydroxy-1-{[(3R,4R)-1-{[5-(3-methoxypyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 404)

Using General Procedure 7 starting from Preparation R3b and 5-bromothiazole-2-carboxylic acid as reagents, the resulted crude product was reacted with (3-methoxy-4-pyridyl)boronic acid according to General Procedure 9, to give EXAMPLE 404. HRMS calculated for $C_{35}H_{37}N_7O_5S$: 667.2577; found 668.2651 [(M+H)$^+$ form].

3-[(4-hydroxy-1-{[(3R,4R)-1-{[5-(6-methoxypyridin-3-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 405)

Using General Procedure 7 starting from Preparation R3b and 5-bromothiazole-2-carboxylic acid as reagents, the resulted crude product was reacted with (6-methoxy-3-pyridyl)boronic acid according to General Procedure 9, to give EXAMPLE 405. HRMS calculated for $C_{35}H_{37}N_7O_5S$: 667.2577; found 668.2649 [(M+H)$^+$ form].

3-[(4-hydroxy-1-{[(3R,4R)-1-{[5-(6-methylpyridin-3-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 406)

Using General Procedure 7 starting from Preparation R3b and 5-bromothiazole-2-carboxylic acid as reagents, the resulted crude product was reacted with (6-methyl-3-pyridyl)boronic acid according to General Procedure 9, to give EXAMPLE 406. HRMS calculated for $C_{35}H_{37}N_7O_4S$: 651.2628; found 652.2702 [(M+H)$^+$ form].

3-{[1-({(3R,4R)-1-[(3-fluoro-5-phenylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 407)

Using General Procedure 7 starting from Preparation R3b and Preparation R1g as reagents, the resulted crude product was reacted with phenylboronic acid according to General Procedure 9, to give EXAMPLE 407. HRMS calculated for $C_{36}H_{36}FN_5O_4S$: 653.2472; found 654.2545 [(M+H)$^+$ form].

3-[(4-hydroxy-1-{[(3R,4R)-1-({3-methyl-5-[2-(trifluoromethyl)pyridin-4-yl]thiophen-2-yl}carbonyl)-3-phenylpiperidin-4-yl]carbonyl}piperidin-4-yl)methyl]-7-methyl-3,7-dihydro-4H-pyrrolo[2,3-d]pyrimidin-4-one (Example 408)

Using General Procedure 7 starting from Preparation R3b and 5-bromo-3-methyl-thiophene-2-carboxylic acid as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 408. HRMS calculated for $C_{37}H_{37}F_3N_6O_4S$: 718.2549; found 719.2627 [(M+H)$^+$ form].

3-{[4-hydroxy-1-({(3R,4R)-1-[(4-methyl-5-phenyl-thiophen-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 409)

Using General Procedure 7 starting from Preparation R3b and 5-bromo-4-methyl-thiophene-2-carboxylic acid as reagents, the resulted crude product was reacted with phenylboronic acid according to General Procedure 9, to give EXAMPLE 409. HRMS calculated for $C_{37}H_{39}N_5O_4S$: 649.2723; found 650.2803 [(M+H)$^+$ form].

3-[(4-hydroxy-1-{[(3R,4R)-3-phenyl-1-{[5-(thiophen-3-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 410)

Using General Procedure 7 starting from Preparation R3b and 5-bromothiazole-2-carboxylic acid as reagents, the resulted crude product was reacted with 4,4,5,5-tetramethyl-2-(3-thienyl)-1,3,2-dioxaborolane according to General Procedure 9, to give EXAMPLE 410. HRMS calculated for $C_{33}H_{34}N_6O_4S_2$: 642.2083; found 643.2166 [(M+H)$^+$ form].

3-[(4-hydroxy-1-{[(3R,4R)-3-phenyl-1-({5-[2-(trifluoromethyl)pyridin-4-yl]-1,3-thiazol-2-yl}carbonyl)piperidin-4-yl]carbonyl}piperidin-4-yl)methyl]-7-methyl-3,7-dihydro-4H-pyrrolo[2,3-d]pyrimidin-4-one (Example 411)

Using General Procedure 7 starting from Preparation R3b and 5-bromothiazole-2-carboxylic acid as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 411. HRMS calculated for $C_{35}H_{34}N_7O_4F_3S$: 705.2345; found 706.2421 [(M+H)$^+$ form].

3-[(4-hydroxy-1-{[(3R,4R)-1-({4-methyl-5-[2-(trifluoromethyl)pyridin-4-yl]thiophen-2-yl}carbonyl)-3-phenylpiperidin-4-yl]carbonyl}piperidin-4-yl)methyl]-7-methyl-3,7-dihydro-4H-pyrrolo[2,3-d]pyrimidin-4-one (Example 412)

Using General Procedure 7 starting from Preparation R3b and 5-bromo-4-methyl-thiophene-2-carboxylic acid as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 412. HRMS calculated for $C_{37}H_{37}N_6O_4F_3S$: 718.2549; found 719.2622 [(M+H)$^+$ form].

3-[(4-hydroxy-1-{[(3R,4R)-3-phenyl-1-({5-[2-(trifluoromethyl)pyridin-4-yl]thiophen-2-yl}methyl)piperidin-4-yl]carbonyl}piperidin-4-yl)methyl]-7-methyl-3,7-dihydro-4H-pyrrolo[2,3-d]pyrimidin-4-one (Example 413)

Using General Procedure 6 starting from Preparation R3b and 2-bromo-5-(chloromethyl)thiophene as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 413. HRMS calculated for $C_{36}H_{37}F_3N_6O_3S$: 690.2600; found 691.2681 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 414)

Using General Procedure 6 starting from Preparation R3b and 2-bromo-5-(bromomethyl)thiazole as reagents, the resulted crude product was reacted with (6-methyl-3-pyridyl)boronic acid according to General Procedure 9, to give EXAMPLE 414. HRMS calculated for $C_{35}H_{39}N_7O_3S$: 637.2835; found 638.2893 [(M+H)$^+$ form].

3-[(4-hydroxy-1-{[(3R,4R)-3-phenyl-1-({2-[6-(trifluoromethyl)pyridin-3-yl]-1,3-thiazol-5-yl}methyl)piperidin-4-yl]carbonyl}piperidin-4-yl)methyl]-7-methyl-3,7-dihydro-4H-pyrrolo[2,3-d]pyrimidin-4-one (Example 415)

Using General Procedure 6 starting from Preparation R3b and 2-bromo-5-(bromomethyl)thiazole as reagents, the resulted crude product was reacted with [2-(trifluoromethyl)-4-pyridyl]boronic acid according to General Procedure 9, to give EXAMPLE 415. HRMS calculated for $C_{35}H_{36}F_3N_7O_3S$: 691.2552; found 692.2610 [(M+H)$^+$ form].

3-[(4-hydroxy-1-{[(3R,4R)-1-{[2-(2-methylpyridin-4-yl)-1,3-thiazol-5-yl]methyl}-3-phenylpiperidin-4-yl]carbonyl}piperidin-4-yl)methyl]-7-methyl-3,7-dihydro-4H-pyrrolo[2,3-d]pyrimidin-4-one (Example 416)

Using General Procedure 6 starting from Preparation R3b and 2-bromo-5-(bromomethyl)thiazole as reagents, the resulted crude product was reacted with 2-methyl-4-(4,4,5,5-tetramethyl-1,3,2-dioxaborolan-2-yl)pyridine according to General Procedure 9, to give EXAMPLE 416. HRMS calculated for $C_{35}H_{39}N_7O_3S$: 637.2835; found 638.2889 [(M+H)$^+$ form].

3-[(1-{[(3R,4R)-1-{[3-fluoro-4,5-bis(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 417)

and

3-[(1-{[(3R,4R)-1-{[5-chloro-3-fluoro-4-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 418)

Using General Procedure 7 starting from Preparation R3b and Preparation R1k as reagents, the resulted crude product was reacted with (6-methyl-3-pyridyl)boronic acid according to General Procedure 9, to give EXAMPLE 417 and EXAMPLE 418 which were separated by chromatography.

Example 417

HRMS calculated for $C_{42}H_{42}FN_7O_4S$: 759.3003; found 760.3079 [(M+H)$^+$ form].

Example 418

HRMS calculated for $C_{36}H_{36}ClFN_6O_4S$: 702.2191; found 703.227 [(M+H)$^+$ form].

3-[(1-{[(3R,4R)-1-{[3-fluoro-4,5-di(pyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 419) and

3-[(1-{[(3R,4R)-1-{[5-chloro-3-fluoro-4-(pyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 420)

Using General Procedure 7 starting from Preparation R3b and Preparation R1k as reagents, the resulted crude product was reacted with 3-pyridylboronic acid according to General Procedure 9, to give EXAMPLE 419 and EXAMPLE 420 which were separated by chromatography.

Example 419

HRMS calculated for $C_{40}H_{38}FN_7O_4S$: 731.2690; found 732.275 [(M+H)$^+$ form].

Example 420

HRMS calculated for $C_{35}H_{34}ClFN_6O_4S$: 688.2035; found 689.212 [(M+H)$^+$ form].

3-[(4-hydroxy-1-{[(3R,4R)-3-phenyl-1-{[4-(pyridin-4-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 421)

Using General Procedure 7 starting from Preparation R3b and 4-bromothiophene-2-carboxylic acid as reagents, the resulted crude product was reacted with 4-(4,4,5,5-tetramethyl-1,3,2-dioxaborolan-2-yl)pyridine according to General Procedure 9, to give EXAMPLE 421. HRMS calculated for $C_{35}H_{36}N_6O_4S$: 636.2519; found 637.2608 (M+H)$^+$ form].

3-[(4-hydroxy-1-{[(3R,4R)-1-{[4-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 422)

Using General Procedure 7 starting from Preparation R3b and 4-bromothiophene-2-carboxylic acid as reagents, the resulted crude product was reacted with (6-methyl-3-pyridyl)boronic acid according to General Procedure 9, to give EXAMPLE 422. HRMS calculated for $C_{36}H_{38}N_6O_4S$: 650.2675; found 651.2778 [(M+H)$^+$ form].

3-[(4-hydroxy-1-{[(3R,4R)-3-phenyl-1-{[4-(pyridin-3-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 423)

Using General Procedure 7 starting from Preparation R3b and 4-bromothiophene-2-carboxylic acid as reagents, the resulted crude product was reacted with 3-pyridylboronic acid according to General Procedure 9, to give EXAMPLE 423. HRMS calculated for $C_{35}H_{36}N_6O_4S$: 636.2519; found 637.2606 [(M+H)$^+$ form].

3-[(4-hydroxy-1-{[(3R,4R)-1-{[4-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 424)

Using General Procedure 7 starting from Preparation R3b and 4-bromothiophene-2-carboxylic acid as reagents, the resulted crude product was reacted with 2-methyl-4-(4,4,5,5-tetramethyl-1,3,2-dioxaborolan-2-yl)pyridine according to General Procedure 9, to give EXAMPLE 424. HRMS calculated for $C_{36}H_{38}N_6O_4S$: 650.2675; found 651.2763 [(M+H)$^+$ form].

3-[(4-hydroxy-1-{[(3R,4R)-1-{[7-(6-methylpyridin-3-yl)-2,3-dihydrothieno[3,4-b][1,4]dioxin-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 425)

Using General Procedure 7 starting from Preparation R3b and 5-bromo-2,3-dihydrothieno[3,4-b][1,4]dioxine-7-carboxylic acid as reagents, the resulted crude product was reacted with (6-methyl-3-pyridyl)boronic acid according to General Procedure 9, to give EXAMPLE 425. HRMS calculated for $C_{38}H_{40}N_6O_6S$: 708.2730; found 709.2799 [(M+H)$^+$ form].

5-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carbonitrile (Example 426)

Using General Procedure 6 starting from Preparation R3b and 2-bromo-5-(chloromethyl)thiazole as reagents, the resulted crude product was reacted with 5-(4,4,5,5-tetramethyl-1,3,2-dioxaborolan-2-yl)pyridine-2-carbonitrile according to General Procedure 9, to give EXAMPLE 426. HRMS calculated for $C_{35}H_{36}N_8O_3S$: 648.2631; found 649.2731 [(M+H)$^+$ form].

3-[(1-{[(3R,4R)-1-({2-[6-(cyclopropylmethoxy)pyridin-3-yl]-1,3-thiazol-5-yl}methyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 427)

Using General Procedure 6 starting from Preparation R3b and 2-bromo-5-(chloromethyl)thiazole as reagents, the resulted crude product was reacted with 2-(cyclopropylmethoxy)-5-(4,4,5,5-tetramethyl-1,3,2-dioxaborolan-2-yl)pyridine according to General Procedure 9, to give EXAMPLE 427. HRMS calculated for $C_{38}H_{43}N_7O_4S$: 693.3098; found 347.6613 [(M+2H)$^{2+}$ form].

3-[(4-hydroxy-1-{[(3R,4R)-1-{[4-(methoxymethyl)-5-(6-methoxypyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 428)

Using General Procedure 7 starting from Preparation R3b and 5-bromo-4-(methoxymethyl)thiophene-2-carboxylic acid as reagents, the resulted crude product was reacted with (6-methoxy-3-pyridyl)boronic acid according to General Procedure 9, to give EXAMPLE 428. HRMS calculated for $C_{38}H_{42}N_6O_6S$: 710.2886; found 711.2966 [(M+H)$^+$ form].

3-[(1-{[(3R,4R)-1-{[5-(6-aminopyridin-3-yl)-4-(methoxymethyl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 429)

Using General Procedure 7 starting from Preparation R3b and 5-bromo-4-(methoxymethyl)thiophene-2-carboxylic acid as reagents, the resulted crude product was reacted with 5-(4,4,5,5-tetramethyl-1,3,2-dioxaborolan-2-yl)pyridin-2-amine according to General Procedure 9, to give EXAMPLE 429. HRMS calculated for $C_{37}H_{41}N_7O_5S$: 695.2890; found 696.2961 [M+H)$^+$ form].

3-[(4-hydroxy-1-{[(3R,4R)-1-{[4-(methylamino)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 430) and

3-[(4-hydroxy-1-{[(3R,4R)-1-{[4-(methylamino)-5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 431)

Using General Procedure 7 starting from Preparation R3b and 5-chloro-3-(methylamino)thiophene-2-carboxylic acid as reagents, the resulted crude product was reacted with (6-methyl-3-pyridyl)boronic acid according to General Procedure 9, to give EXAMPLE 430 (dehalogenated byproduct) and EXAMPLE 431 which were separated by chromatography.

Example 430

HRMS calculated for $C_{31}H_{36}N_6O_4S$: 588.2519; found 589.2593 [(M+H)$^+$ form].

Example 431

HRMS calculated for $C_{37}H_{41}N_7O_4S$: 679.2941; found 680.3015 [(M+H)$^+$ form].

3-[(1-{[(3R,4R)-1-({2-[6-(dimethylamino)pyridin-3-yl]-1,3-thiazol-5-yl}methyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 432)

Using General Procedure 6 starting from Preparation R3b and 2-bromo-5-(chloromethyl)thiazole as reagents, the resulted crude product was reacted with 6-(dimethylamino)-3-pyridyl]boronic acid according to General Procedure 9, to give EXAMPLE 432. HRMS calculated for $C_{36}H_{42}N_8O_3S$: 666.3101; found 667.3171 [(M+H)$^+$ form].

3-[(4-hydroxy-1-{[(3R,4R)-1-{[3-(6-methylpyridin-3-yl)-4,5,6,7-tetrahydro-2-benzothiophen-1-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 433)

Using General Procedure 7 starting from Preparation R3b and 3-iodo-4,5,6,7-tetrahydro-2-benzothiophene-1-carboxylic acid as reagents, the resulted crude product was reacted with (6-methyl-3-pyridyl)boronic acid according to General Procedure 9, to give EXAMPLE 433. HRMS calculated for $C_{40}H_{44}N_6O_4S$: 704.3145; found 705.3219 [(M+H)$^+$ form].

3-[(1-{[(3R,4R)-1-{[4-amino-5-(2-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 434)

4-Amino-5-bromo-2-thiophenecarboxylic acid (500 mg, 2.25 mmol) was dissolved in PDO (2 ml) and water (2 ml) then sodium-hydroxide (194 mg, 4.86 mmol) was added to the stirred mixture at 0° C., then Boc$_2$O (1768 mg, 8.1 mmol) was added. The reaction mixture was stirred for 116 hours while the reaction mixture warmed up to r.t. Aqueous HCl solution (1 N, 4 ml) was added to the mixture, the precipitate was filtered off, washed with water and dried.

The resulted 4-(tert-butoxycarbonylamino)-5-methyl-thiophene-2-carboxylic acid (316 mg, 0.93 mmol) and Preparation R3b (488 mg, 0.93 mmol, as bis HCl salt) were coupled using General Procedure 7.

The resulted product (320 mg, 0.42 mmol) was stirred in PDO (3 ml) and aqueous HCl solution (12.2 M, 103 µl, 1.26 mmol) at 50° C. for 20 hours. The reaction mixture was purified by preparative LC (on C-18 Gemini-NX 5 µm column, 5 mM aqueous NH$_4$HCO$_3$-MeCN, gradient).

Using General Procedure 9 starting from the resulted amino-compound and 2-methyl-4-(4,4,5,5-tetramethyl-1,3,2-dioxaborolan-2-yl)pyridine as reagents, EXAMPLE 434 was obtained. HRMS calculated for $C_{36}H_{39}N_7O_4S$: 665.2784; found 333.648 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(naphthalen-2-yl)-3,7-dihydro-4H-pyrrolo[2,3-d]pyrimidin-4-one (Example 435)

Using General Procedure 7 starting from Preparation R3be and 2-bromo-4-methyl-thiazole-5-carboxylic acid as reagents, the resulted crude product was reacted with (6-methyl-3-pyridyl)boronic acid according to General Procedure 9, to give EXAMPLE 435. HRMS calculated for $C_{45}H_{43}N_7O_4S$: 777.3098; found 778.3185 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one (Example 436)

Using General Procedure 6 starting from Preparation R3bf and 2-bromo-5-(bromomethyl)thiazole as reagents, the resulted crude product was reacted with (6-methyl-3-pyridyl)boronic acid according to General Procedure 9, to give EXAMPLE 436. HRMS calculated for $C_{41}H_{43}N_7O_3S$: 713.3148; found 714.3205 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(naphthalen-1-yl)-3,7-dihydro-4H-pyrrolo[2,3-d]pyrimidin-4-one (Example 437)

Using General Procedure 7 starting from Preparation R3bt and 2-bromo-4-methyl-thiazole-5-carboxylic acid as reagents, the resulted crude product was reacted with (6-methyl-3-pyridyl)boronic acid according to General Procedure 9, to give EXAMPLE 437. HRMS calculated for $C_{45}H_{43}N_7O_4S$: 777.3098; found 778.3177 [(M+H)$^+$ form].

7-ethyl-3-[(1-{[(3R,4R)-1-{[3-fluoro-5-(pyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 438)

Using General Procedure 7 starting from Preparation R3c and Preparation R1g as reagents, the resulted crude product was reacted with 3-pyridylboronic acid according to General Procedure 9, to give EXAMPLE 438. HRMS calculated for $C_{36}H_{37}FN_6O_4S$: 668.2581; found 669.2654 [(M+H)$^+$ form].

7-ethyl-3-[(1-{[(3R,4R)-1-{[3-fluoro-5-(pyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 439)

Using General Procedure 7 starting from Preparation R3c and Preparation R1g as reagents, the resulted crude product was reacted with 4-(4,4,5,5-tetramethyl-1,3,2-dioxaborolan-2-yl)pyridine according to General Procedure 9, to give EXAMPLE 439. HRMS calculated for $C_{36}H_{37}FN_6O_4S$: 668.2581; found 669.2661 [(M+H)$^+$ form].

7-ethyl-3-[(1-{[(3R,4R)-1-{[3-fluoro-5-(2-methylpyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 440)

Using General Procedure 7 starting from Preparation R3c and Preparation R1g as reagents, the resulted crude product was reacted with 2-methyl-4-(4,4,5,5-tetramethyl-1,3,2-dioxaborolan-2-yl)pyridine according to General Procedure 9, to give EXAMPLE 440. HRMS calculated for $C_{37}H_{39}FN_6O_4S$: 682.2737; found 683.2819 [(M+H)$^+$ form].

7-ethyl-3-{[1-({(3R,4R)-1-[(4-fluoro-2,3'-bithiophen-5-yl)carbonyl]-3-phenylpiperidin-4-yl}carbonyl)-4-hydroxypiperidin-4-yl]methyl}-3,7-dihydro-4H-pyrrolo[2,3-d]pyrimidin-4-one (Example 441)

Using General Procedure 7 starting from Preparation R3c and Preparation R1g as reagents, the resulted crude product was reacted with 4,4,5,5-tetramethyl-2-(3-thienyl)-1,3,2-dioxaborolane according to General Procedure 9, to give EXAMPLE 441. HRMS calculated for $C_{35}H_{36}FN_5O_4S_2$: 673.2193; found 674.2272 [(M+H)$^+$ form].

7-ethyl-3-{[1-({(3R,4R)-1-[(3-fluoro-5-phenylthiophen-2-yl)carbonyl]-3-phenylpiperidin-4-yl}carbonyl)-4-hydroxypiperidin-4-yl]methyl}-3,7-dihydro-4H-pyrrolo[2,3-d]pyrimidin-4-one (Example 442)

Using General Procedure 7 starting from Preparation R3c and Preparation R1g as reagents, the resulted crude product was reacted with phenylboronic acid according to General Procedure 9, to give EXAMPLE 442. HRMS calculated for $C_{37}H_{38}FN_5O_4S$: 667.2629; found 668.2702 [(M+H)$^+$ form].

7-ethyl-3-[(1-{[(3R,4R)-1-({3-fluoro-5-[2-(trifluoromethyl)pyridin-4-yl]thiophen-2-yl}carbonyl)-3-phenylpiperidin-4-yl]carbonyl}-4-hydroxypiperidin-4-yl)methyl]-3,7-dihydro-4H-pyrrolo[2,3-d]pyrimidin-4-one (Example 443)

Using General Procedure 7 starting from Preparation R3c and Preparation R1g as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 443. HRMS calculated for $C_{37}H_{36}F_4N_6O_4S$: 736.2455; found 737.2524 (M+H)$^+$ form].

7-ethyl-3-[(1-{[(3R,4R)-1-{[3-fluoro-5-(2-methoxy-6-methylpyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 444)

Using General Procedure 7 starting from Preparation R3c and Preparation R1g as reagents, the resulted crude product was reacted with 2-methoxy-6-methyl-4-(4,4,5,5-tetramethyl-1,3,2-dioxaborolan-2-yl)pyridine according to General Procedure 9, to give EXAMPLE 444. HRMS calculated for $C_{38}H_{41}FN_6O_5S$: 712.2843; found 713.2916 (M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(pyridin-2-yl)-3,7-dihydro-4H-pyrrolo[2,3-d]pyrimidin-4-one (Example 445)

Using General Procedure 6 starting from Preparation R3ca and 2-bromo-5-(bromomethyl)thiazole as reagents, the resulted crude product was reacted with (6-methyl-3-pyridyl)boronic acid according to General Procedure 9, to give EXAMPLE 445. HRMS calculated for $C_{39}H_{40}N_8O_3S$: 700.2944; found 701.2986 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one (Example 446)

Using General Procedure 7 starting from Preparation R3cb and 2-bromo-4-methyl-thiazole-5-carboxylic acid as reagents, the resulted crude product was reacted with (6-methyl-3-pyridyl)boronic acid according to General Procedure 9, to give EXAMPLE 446. HRMS calculated for $C_{40}H_{40}N_8O_4S$: 728.2893; found 729.2968 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one (Example 447)

Using General Procedure 6 starting from Preparation R3cb and 2-bromo-5-(bromomethyl)thiazole as reagents, the resulted crude product was reacted with (6-methyl-3-pyridyl)boronic acid according to General Procedure 9, to give EXAMPLE 447. HRMS calculated for $C_{39}H_{40}N_8O_3S$: 700.2944; found 701.2985 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one (Example 448)

Using General Procedure 7 starting from Preparation R3cf and 2-bromo-4-methyl-thiazole-5-carboxylic acid as reagents, the resulted crude product was reacted with (6-methyl-3-pyridyl)boronic acid according to General Procedure 9, to give EXAMPLE 448. HRMS calculated for $C_{39}H_{39}N_7O_4S_2$: 733.2505; found 734.2596 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one (Example 449)

Using General Procedure 6 starting from Preparation R3cf and 2-bromo-5-(bromomethyl)thiazole as reagents, the resulted crude product was reacted with (6-methyl-3-pyridyl)boronic acid according to General Procedure 9, to give EXAMPLE 449. HRMS calculated for $C_{38}H_{39}N_7O_3S_2$: 705.2556; found 706.2666 [(M+H)$^+$ form].

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-(propan-2-yl)-3,7-dihydro-4H-pyrrolo[2,3-d]pyrimidin-4-one (Example 450)

Using General Procedure 7 starting from Preparation R3d and Preparation R1g as reagents, the resulted crude product was reacted with (6-methyl-3-pyridyl)boronic acid according to General Procedure 9, to give EXAMPLE 450. HRMS calculated for $C_{38}H_{41}FN_6O_4S$: 696.2894; found 697.2968 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(propan-2-yl)-3,7-dihydro-4H-pyrrolo[2,3-d]pyrimidin-4-one (Example 451)

Using General Procedure 6 starting from Preparation R3d and 2-bromo-5-(bromomethyl)thiazole as reagents, the resulted crude product was reacted with (6-methyl-3-pyridyl)boronic acid according to General Procedure 9, to give EXAMPLE 451. HRMS calculated for $C_{37}H_{43}N_7O_3S$: 665.3148; found 333.6636 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(propan-2-yl)-3,7-dihydro-4H-pyrrolo[2,3-d]pyrimidin-4-one (Example 452)

Using General Procedure 7 starting from Preparation R3d and 2-bromo-4-methyl-thiazole-5-carboxylic acid as reactants, the resulted crude product was reacted with (6-methyl-3-pyridyl)boronic acid according to General Procedure 9, to give EXAMPLE 452. HRMS calculated for $C_{38}H_{43}N_7O_4S$: 693.3098; found 694.3173 [(M+H)$^+$ form].

7-cyclopropyl-3-{[1-({(3R,4R)-1-[(3-fluoro-5-phenylthiophen-2-yl)carbonyl]-3-phenylpiperidin-4-yl}carbonyl)-4-hydroxypiperidin-4-yl]methyl}-3,7-dihydro-4H-pyrrolo[2,3-d]pyrimidin-4-one (Example 453)

Using General Procedure 7 starting from Preparation R3g and Preparation R1g as reagents, the resulted crude product was reacted with phenylboronic acid according to General Procedure 9, to give EXAMPLE 453. HRMS calculated for $C_{38}H_{38}FN_5O_4S$: 679.2629; found 680.2696 [(M+H)$^+$ form].

7-cyclopropyl-3-[(1-{[(3R,4R)-1-{[3-fluoro-5-(2-methylpyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 454)

Using General Procedure 7 starting from Preparation R3g and Preparation R1g as reagents, the resulted crude product was reacted with 2-methyl-4-(4,4,5,5-tetramethyl-1,3,2-dioxaborolan-2-yl)pyridine according to General Procedure 9, to give EXAMPLE 454. HRMS calculated for $C_{38}H_{39}FN_6O_4S$: 694.2737; found 695.2808 [(M+H)$^+$ form].

7-cyclopropyl-3-[(1-{[(3R,4R)-1-{[3-fluoro-5-(pyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 455)

Using General Procedure 7 starting from Preparation R3g and Preparation R1g as reagents, the resulted crude product was reacted with 4-(4,4,5,5-tetramethyl-1,3,2-dioxaborolan-2-yl)pyridine according to General Procedure 9, to give EXAMPLE 455. HRMS calculated for $C_{37}H_{37}FN_6O_4S$: 680.2581; found 681.2645 [(M+H)$^+$ form].

7-cyclopropyl-3-[(1-{[(3R,4R)-1-{[3-fluoro-5-(pyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 456)

Using General Procedure 7 starting from Preparation R3g and Preparation R1g as reagents, the resulted crude product was reacted with 3-pyridylboronic acid according to General Procedure 9, to give EXAMPLE 456. HRMS calculated for $C_{37}H_{37}FN_6O_4S$: 680.2581; found 681.2648 [(M+H)$^+$ form].

7-cyclopropyl-3-{[1-({(3R,4R)-1-[(4-fluoro-2,3'-bithiophen-5-yl)carbonyl]-3-phenylpiperidin-4-yl}carbonyl)-4-hydroxypiperidin-4-yl]methyl}-3,7-dihydro-4H-pyrrolo[2,3-d]pyrimidin-4-one (Example 457)

Using General Procedure 7 starting from Preparation R3g and Preparation R1g as reagents, the resulted crude product was reacted with 4,4,5,5-tetramethyl-2-(3-thienyl)-1,3,2-dioxaborolane according to General Procedure 9, to give EXAMPLE 457. HRMS calculated for $C_{36}H_{36}FN_5O_4S_2$: 685.2193; found 686.2269 [(M+H)$^+$ form].

7-cyclopropyl-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 458)

Using General Procedure 7 starting from Preparation R3g and Preparation R1g as reagents, the resulted crude product was reacted with (6-methyl-3-pyridyl)boronic acid according to General Procedure 9, to give EXAMPLE 458. HRMS calculated for $C_{38}H_{39}FN_6O_4S$: 694.2737; found 695.2812 [(M+H)$^+$ form].

7-cyclopropyl-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 459)

Using General Procedure 7 starting from Preparation R3g and 2-bromo-4-methyl-thiazole-5-carboxylic acid as reagents, the resulted crude product was reacted with (6-methyl-3-pyridyl)boronic acid according to General Procedure 9, to give EXAMPLE 459. HRMS calculated for $C_{38}H_{41}N_7O_4S$: 691.2941; found 692.3024 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1-methylpiperidin-4-yl)-3,7-dihydro-4H-pyrrolo[2,3-d]pyrimidin-4-one (Example 460)

Using General Procedure 6 starting from Preparation R3k and 2-bromo-5-(bromomethyl)thiazole as reagents, the resulted crude product was reacted with (6-methyl-3-pyridyl)boronic acid according to General Procedure 9, to give EXAMPLE 460. HRMS calculated for $C_{40}H_{48}N_8O_3S$: 720.3570; found 361.1855 [(M+2H)$^{2+}$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(2-methylpropyl)-3,7-dihydro-4H-pyrrolo[2,3-d]pyrimidin-4-one (Example 461)

Using General Procedure 6 starting from Preparation R3n and 2-bromo-5-(bromomethyl)thiazole as reagents, the resulted crude product was reacted with (6-methyl-3-pyridyl)boronic acid according to General Procedure 9, to give EXAMPLE 461. HRMS calculated for $C_{38}H_{45}N_7O_3S$: 679.3304; found 340.6733 [(M+2H)$^{2+}$ form].

7-(2,2-difluoroethyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 462)

Using General Procedure 6 starting from Preparation R3p and 2-bromo-5-(bromomethyl)thiazole as reagents, the resulted crude product was reacted with (6-methyl-3-pyridyl)boronic acid according to General Procedure 9, to give EXAMPLE 462. HRMS calculated for $C_{36}H_{39}F_2N_7O_3S$: 687.2803; found 344.6487 [(M+2H)$^{2+}$ form].

7-(2,2-difluoroethyl)-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 463)

Using General Procedure 7 starting from Preparation R3p and Preparation R1g as reagents, the resulted crude product was reacted with (6-methyl-3-pyridyl)boronic acid according to General Procedure 9, to give EXAMPLE 463. HRMS calculated for $C_{37}H_{37}N_6O_4F_3S$: 718.2549; found 719.2625 [(M+H)$^+$ form].

7-(cyclopropylmethyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 464)

Using General Procedure 6 starting from Preparation R3q and 2-bromo-5-(bromomethyl)thiazole as reagents, the resulted crude product was reacted with (6-methyl-3-pyridyl)boronic acid according to General Procedure 9, to give EXAMPLE 464. HRMS calculated for $C_{38}H_{43}N_7O_3S$: 677.3149; found 339.6648 [(M+2H)$^{2+}$ form].

7-(cyclopropylmethyl)-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 465)

Using General Procedure 7 starting from Preparation R3q and Preparation R1g as reagents, the resulted crude product was reacted with (6-methyl-3-pyridyl)boronic acid according to General Procedure 9, to give EXAMPLE 465. HRMS calculated for $C_{39}H_{41}N_6O_4FS$: 708.2894; found 709.2973 [(M+H)$^+$ form].

7-(cyclobutylmethyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 466)

Using General Procedure 7 starting from Preparation R3r and 2-bromo-4-methyl-thiazole-5-carboxylic acid as reagents, the resulted crude product was reacted with (6-methyl-3-pyridyl)boronic acid according to General Procedure 9, to give EXAMPLE 466. HRMS calculated for $C_{40}H_{45}N_7O_4S$: 719.3254; found 720.3333 [(M+H)$^+$ form].

7-(cyclobutylmethyl)-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 467)

Using General Procedure 7 starting from Preparation R3r and Preparation R1g as reagents, the resulted crude product was reacted with (6-methyl-3-pyridyl)boronic acid according to General Procedure 9, to give EXAMPLE 467. HRMS calculated for $C_{40}H_{43}FN_6O_4S$: 722.3051; found 723.3125 [(M+H)$^+$ form].

7-(cyclobutylmethyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 468)

Using General Procedure 6 starting from Preparation R3r and 2-bromo-5-(bromomethyl)thiazole as reagents, the resulted crude product was reacted with (6-methyl-3-pyridyl)boronic acid according to General Procedure 9, to give EXAMPLE 468. HRMS calculated for C39H45N7O3S: 691.3304; found 692.3396 [(M+H)$^+$ form].

7-(2-fluoroethyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 469)

Using General Procedure 6 starting from Preparation R3u and 2-bromo-5-(bromomethyl)thiazole as reagents, the resulted crude product was reacted with (6-methyl-3-pyridyl)boronic acid according to General Procedure 9, to give EXAMPLE 469. HRMS calculated for $C_{36}H_{40}FN_7O_3S$: 669.2897; found 335.6529 [(M+2H)$^{2+}$ form].

7-(2-fluoroethyl)-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 470)

Using General Procedure 7 starting from Preparation R3u and Preparation R1g as reagents, the resulted crude product was reacted with (6-methyl-3-pyridyl)boronic acid according to General Procedure 9, to give EXAMPLE 470. HRMS calculated for $C_{37}H_{38}N_6O_4F_2S$: 700.2643; found 701.2725 [(M+H)$^+$ form].

7-(2-hydroxyethyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 471)

Using General Procedure 6 starting from Preparation R3w and 2-bromo-5-(bromomethyl)thiazole as reagents, the resulted crude product was reacted with (6-methyl-3-pyridyl)boronic acid according to General Procedure 9, to give EXAMPLE 471. HRMS calculated for $C_{36}H_{41}N_7O_4S$: 667.2941; found 334.6543 [(M+2H)$^{2+}$ form].

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-(2-hydroxyethyl)-3,7-dihydro-4H-pyrrolo[2,3-d]pyrimidin-4-one (Example 472)

Using General Procedure 7 starting from Preparation R3w and Preparation R1g as reagents, the resulted crude product was reacted with (6-methyl-3-pyridyl)boronic acid according to General Procedure 9, to give EXAMPLE 472. HRMS calculated for $C_{37}H_{39}N_6O_5FS$: 698.2687; found 699.2757 [(M+H)$^+$ form].

3-[(1-{[(3R,4R)-1-(3-fluorobenzyl)-3-phenylpiperidin-4-yl]carbonyl}-4-hydroxypiperidin-4-yl)methyl]-3,7-dihydro-4H-pyrrolo[2,3-d]pyrimidin-4-one (Example 473)

Using General Procedure 6 starting from Preparation R1n and 1-(bromomethyl)-3-fluoro-benzene as reagents, the resulted crude product (35 mg, 0.052 mmol) was reacted with TBAF (1 M in THF, 0.16 ml, 0.156 mmol) in THF (2 ml) at 75° C. for 4 days. The reaction mixture was purified by preparative LC (on C-18 Gemini-NX 5 μm column, 5 mM aqueous NH$_4$HCO$_3$-MeCN, gradient) to give EXAMPLE 473. HRMS calculated for $C_{31}H_{34}FN_5O_3$: 543.2646; found 544.272 [(M+H)$^+$ form].

3-[(1-{[(3R,4R)-1-(2-fluorobenzyl)-3-phenylpiperidin-4-yl]carbonyl}-4-hydroxypiperidin-4-yl)methyl]-3,7-dihydro-4H-pyrrolo[2,3-d]pyrimidin-4-one (Example 474)

Using General Procedure 6 starting from Preparation R1n and 1-(bromomethyl)-2-fluoro-benzene as reagents, the resulted crude product (80 mg, 0.12 mmol) was reacted with TBAF (1 M in THF, 0.24 ml, 0.24 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 474. HRMS calculated for $C_{31}H_{34}FN_5O_3$: 543.2646; found 544.274 [(M+H)$^+$ form].

3-[(4-hydroxy-1-{[(3R,4R)-1-(3-methylbenzyl)-3-phenylpiperidin-4-yl]carbonyl}piperidin-4-yl)methyl]-3,7-dihydro-4H-pyrrolo[2,3-d]pyrimidin-4-one (Example 475)

Using General Procedure 6 starting from Preparation R1n and 1-(bromomethyl)-3-methyl-benzene as reagents, the resulted crude product (74 mg, 0.11 mmol) was reacted with TBAF (1 M in THF, 0.22 ml, 0.22 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 475. HRMS calculated for $C_{32}H_{37}N_5O_3$: 539.2896; found 540.2940 [(M+H)$^+$ form].

3-[(4-hydroxy-1-{[(3R,4R)-1-(2-methylbenzyl)-3-phenylpiperidin-4-yl]carbonyl}piperidin-4-yl)methyl]-3,7-dihydro-4H-pyrrolo[2,3-d]pyrimidin-4-one (Example 476)

Using General Procedure 6 starting from Preparation R1n and 1-(bromomethyl)-2-methyl-benzene as reagents, the resulted crude product (88 mg, 0.13 mmol) was reacted with TBAF (1 M in THF, 0.26 ml, 0.26 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 476. HRMS calculated for $C_{32}H_{37}N_5O_3$: 539.2896; found 540.295 [(M+H)$^+$ form].

3-[(1-{[(3R,4R)-1-(1-benzofuran-2-ylmethyl)-3-phenylpiperidin-4-yl]carbonyl}-4-hydroxypiperidin-4-yl)methyl]-3,7-dihydro-4H-pyrrolo[2,3-d]pyrimidin-4-one (Example 477)

Using General Procedure 6 starting from Preparation R1n and 2-(chloromethyl)benzofurane as reagents, the resulted crude product (32 mg, 0.046 mmol) was reacted with TBAF (1 M in THF, 0.09 ml, 0.09 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 477. HRMS calculated for $C_{33}H_{35}N_5O_4$: 565.2689; found 566.2772 [(M+H)$^+$ form].

3-{[4-hydroxy-1-({(3R,4R)-1-[(4-methyl-1,3-thiazol-5-yl)carbonyl]-3-phenylpiperidin-4-yl}carbonyl)piperidin-4-yl]methyl}-3,7-dihydro-4H-pyrrolo[2,3-d]pyrimidin-4-one (Example 478)

Using General Procedure 7 starting from Preparation R1n and 4-methylthiazole-5-carboxylic acid as reagents, the resulted crude product (87 mg, 0.126 mmol) was reacted with TBAF (1 M in THF, 0.315 ml, 0.315 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 478. HRMS calculated for $C_{29}H_{32}N_6O_4S$: 560.2206; found 561.228 [(M+H)$^+$ form].

3-{[4-hydroxy-1-({(3R,4R)-3-phenyl-1-[(2-phenyl-1,3-thiazol-5-yl)carbonyl]piperidin-4-yl}carbonyl)piperidin-4-yl]methyl}-3,7-dihydro-4H-pyrrolo[2,3-d]pyrimidin-4-one (Example 479)

Using General Procedure 7 starting from Preparation R1n and 2-phenylthiazole-5-carboxylic acid as reagents, the resulted crude product (86 mg, 0.11 mmol) was reacted with TBAF (1 M in THF, 0.285 ml, 0.285 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 479. HRMS calculated for $C_{34}H_{34}N_6O_4S$: 622.2362; found 623.2442 [(M+H)$^+$ form].

3-{[4-hydroxy-1-({(3R,4R)-1-[(4-methyl-2-phenyl-1,3-thiazol-5-yl)carbonyl]-3-phenylpiperidin-4-yl}carbonyl)piperidin-4-yl]methyl}-3,7-dihydro-4H-pyrrolo[2,3-d]pyrimidin-4-one (Example 480)

Using General Procedure 7 starting from Preparation R1n and 4-methyl-2-phenylthiazole-5-carboxylic acid as reagents, the resulted crude product (90 mg, 0.117 mmol) was reacted with TBAF (1 M in THF, 0.293 ml, 0.293 mmol) in THF (3 ml) at 75° C. for 1 day. The reaction mixture was purified by preparative LC (on C-18 Gemini-NX 5 μm column, 5 mM aqueous NH$_4$HCO$_3$-MeCN, gradient) then with flash chromatography (MeOH-DCM gradient) to give EXAMPLE 480. HRMS calculated for C$_{35}$H$_{36}$N$_6$O$_4$S: 636.2519; found 637.2601 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(2-oxopyrrolidin-1-yl)-3,7-dihydro-4H-pyrrolo[2,3-d]pyrimidin-4-one (Example 481)

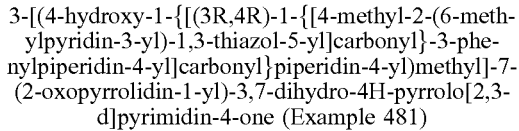

Using General Procedure 11 starting from Preparation R2ab and Preparation R1m as reagents, EXAMPLE 481 was obtained. HRMS calculated for C$_{39}$H$_{42}$N$_8$O$_5$S: 734.2999; found 735.3045 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methylphenyl)-3,7-dihydro-4H-pyrrolo[2,3-d]pyrimidin-4-one (Example 482)

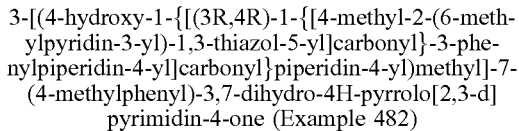

Using General Procedure 11 starting from Preparation R2am and Preparation R1m as reagents, EXAMPLE 482 was obtained. HRMS calculated for C$_{42}$H$_{43}$N$_7$O$_4$S: 741.3098; found 742.3167 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one (Example 483)

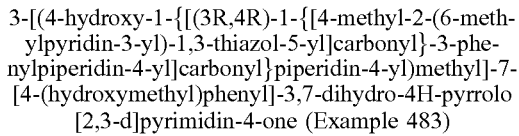

Using General Procedure 11 starting from Preparation R2aq and Preparation R1m as reagents, EXAMPLE 483 was obtained. HRMS calculated for C$_{42}$H$_{43}$N$_7$O$_5$S: 757.3046; found 758.3122 [(M+H)$^+$ form].

7-(4-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 484)

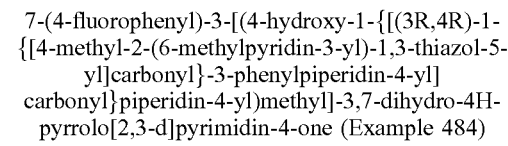

Using General Procedure 11 starting from Preparation R2as and Preparation R1m as reagents, EXAMPLE 484 was obtained. HRMS calculated for C$_{41}$H$_{40}$FN$_7$O$_4$S: 745.2847; found 373.6485 [(M+2H)$^{2+}$ form].

7-[4-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 485)

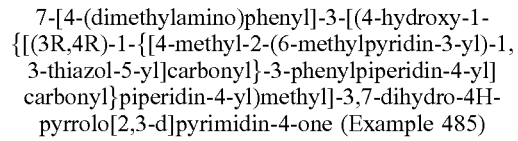

Using General Procedure 11 starting from Preparation R2at and Preparation R1m as reagents, EXAMPLE 485 was obtained. HRMS calculated for C$_{43}$H$_{46}$N$_8$O$_4$S: 770.3362; found 771.3439 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(4-methylpiperazin-1-yl)phenyl]-3,7-dihydro-4H-pyrrolo[2,3-d]pyrimidin-4-one (Example 486)

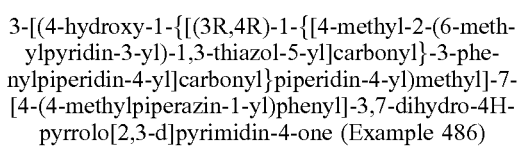

Using General Procedure 11 starting from Preparation R2au and Preparation R1m as reagents, EXAMPLE 486 was obtained. HRMS calculated for C$_{46}$H$_{51}$N$_9$O$_4$S: 825.3785; found 413.6974 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(morpholin-4-yl)phenyl]-3,7-dihydro-4H-pyrrolo[2,3-d]pyrimidin-4-one (Example 487)

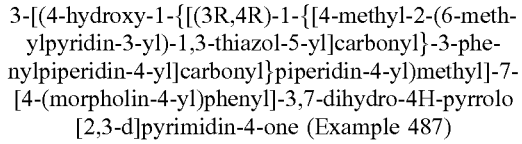

Using General Procedure 11 starting from Preparation R2av and Preparation R1m as reagents, EXAMPLE 487 was obtained. HRMS calculated for C$_{45}$H$_{48}$N$_8$O$_5$S: 812.3469; found 813.3555 [(M+H)$^+$ form].

Preparation of 3-[(4-hydroxy-1-{[(3R,4R)-1-{[5-(2-methylpyrimidin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 488)

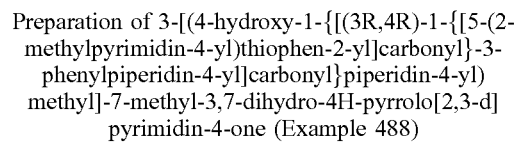

Using General Procedure 7 starting from Preparation R3b and 5-(4,4,5,5-tetramethyl-1,3,2-dioxaborolan-2-yl)thiophene-2-carboxylic acid as reagents, the resulted crude boronic acid was reacted with 4-bromo-2-methyl-pyrimidine as halo compound according to General Procedure 9, to give EXAMPLE 488. HRMS calculated for C$_{35}$H$_{37}$N$_7$O$_4$S: 651.2628; found 652.2698 [(M+H)$^+$ form].

3-[(4-hydroxy-1-{[(3R,4R)-1-{[5-(5-methylpyrazin-2-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 489)

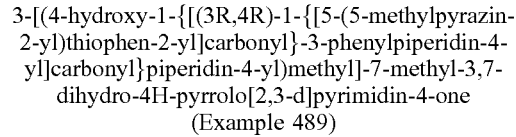

Using General Procedure 7 starting from Preparation R3b and 5-(4,4,5,5-tetramethyl-1,3,2-dioxaborolan-2-yl)thiophene-2-carboxylic acid as reagents, the resulted crude boronic acid was reacted with 2-bromo-5-methyl-pyrazine as halo compound according to General Procedure 9, to give EXAMPLE 489. HRMS calculated for C$_{35}$H$_{37}$N$_7$O$_4$S: 651.2628; found 652.2703 [(M+H)$^+$ form].

3-[(4-hydroxy-1-{[(3R,4R)-3-phenyl-1-{[5-(pyrazin-2-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 490)

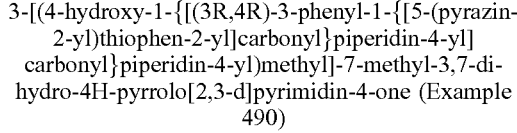

Using General Procedure 7 starting from Preparation R3b and 5-(4,4,5,5-tetramethyl-1,3,2-dioxaborolan-2-yl)thiophene-2-carboxylic acid as reagents, the resulted crude boronic acid was reacted with 2-chloropyrazine as halo compound according to General Procedure 9, to give EXAMPLE 490. HRMS calculated for C$_{34}$H$_{35}$N$_7$O$_4$S: 637.2471; found 638.2547 [(M+H)$^+$ form].

3-[(4-hydroxy-1-{[(3R,4R)-1-{[5-(6-methylpyridazin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 491)

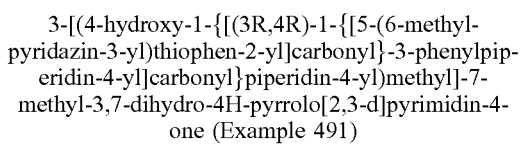

Using General Procedure 7 starting from Preparation R3b and 5-(4,4,5,5-tetramethyl-1,3,2-dioxaborolan-2-yl)thiophene-2-carboxylic acid as reagents, the resulted crude boronic acid was reacted with 3-chloro-6-methyl-pyridazine as halo compound according to General Procedure 9, to give EXAMPLE 491. HRMS calculated for $C_{35}H_{37}N_7O_4S$: 651.2628; found 652.2709 [(M+H)$^+$ form].

3-[(4-hydroxy-1-{[(3R,4R)-1-{[5-(6-methylpyrazin-2-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 492)

Using General Procedure 7 starting from Preparation R3b and 5-(4,4,5,5-tetramethyl-1,3,2-dioxaborolan-2-yl)thiophene-2-carboxylic acid as reagents, the resulted crude boronic acid was reacted with 2-chloro-6-methyl-pyrazine as halo compound according to General Procedure 9, to give EXAMPLE 492. HRMS calculated for $C_{35}H_{37}N_7O_4S$: 651.2628; found 652.2699 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methylphenyl)-3,7-dihydro-4H-pyrrolo[2,3-d]pyrimidin-4-one (Example 493)

Using General Procedure 11 starting from Preparation R2bf and Preparation R1m as reagents, EXAMPLE 493 was obtained. HRMS calculated for $C_{42}H_{43}N_7O_4S$: 741.3098; found 742.3171 [(M+H)$^+$ form].

7-(3-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 494)

Using General Procedure 11 starting from Preparation R3bj and Preparation R1m as reagents, EXAMPLE 494 was obtained. HRMS calculated for $C_{41}H_{40}N_7O_4SCl$: 761.2551; found 762.2622 [(M+H)$^+$ form].

7-(3-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 495)

Using General Procedure 11 starting from Preparation R2bk and Preparation R1m as reagents, EXAMPLE 495 was obtained. HRMS calculated for $C_{41}H_{40}FN_7O_4S$: 745.2847; found 373.6504 [(M+2H)$^{2+}$ form].

7-[3-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 496)

Using General Procedure 11 starting from Preparation R2bl and Preparation R1m as reagents, EXAMPLE 496 was obtained. HRMS calculated for $C_{43}H_{46}N_8O_4S$: 770.3362; found 771.3436 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one (Example 497)

Using General Procedure 11 starting from Preparation R2bm and Preparation R1m as reagents, EXAMPLE 497 was obtained. HRMS calculated for $C_{45}H_{48}N_8O_5S$: 812.3469; found 813.3544 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one (Example 498)

Using General Procedure 10 starting from EXAMPLE 297 and boron-tribromide as reagents, EXAMPLE 498 was obtained. HRMS calculated for $C_{41}H_{41}N_7O_5S$: 743.2890; found 744.2956 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 499)

Using General Procedure 11 starting from Preparation R2bo and Preparation R1m as reagents, EXAMPLE 499 was obtained. HRMS calculated for $C_{42}H_{43}N_7O_5S$: 757.3046; found 379.6582 [(M+2H)$^{2+}$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(2-methylphenyl)-3,7-dihydro-4H-pyrrolo[2,3-d]pyrimidin-4-one (Example 500)

Using General Procedure 11 starting from Preparation R2bv and Preparation R1m as reagents, EXAMPLE 500 was obtained. HRMS calculated for $C_{42}H_{43}N_7O_4S$: 741.3098; found 742.3169 [(M+H)$^+$ form].

7-(2-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 501)

Using General Procedure 11 starting from Preparation R2bw and Preparation R1m as reagents, EXAMPLE 501 was obtained. HRMS calculated for $C_{41}H_{40}ClN_7O_4S$: 761.2551; found 762.2633 [(M+H)$^+$ form].

7-(2-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 502)

Using General Procedure 11 starting from Preparation R2bx and Preparation R1m as reagents, EXAMPLE 502 was obtained. HRMS calculated for $C_{41}H_{40}N_7O_4FS$: 745.2847; found 746.2924 [(M+H)$^+$ form].

7-[2-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 503)

Using General Procedure 11 starting from Preparation R2by and Preparation R1m as reagents, EXAMPLE 503 was obtained. HRMS calculated for $C_{43}H_{46}N_8O_4S$: 770.3362; found 771.3447 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(2-methoxyphenyl)-3,7-dihydro-4H-pyrrolo[2,3-d]pyrimidin-4-one (Example 504)

Using General Procedure 11 starting from Preparation R2bz and Preparation R1m as reagents, EXAMPLE 504 was obtained. HRMS calculated for $C_{42}H_{43}N_7O_5S$: 757.3046; found 758.3114 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one (Example 505)

Using General Procedure 11 starting from Preparation R2cc and Preparation R1m as reagents, EXAMPLE 505 was obtained. HRMS calculated for $C_{39}H_{39}N_7O_4S_2$: 733.2505; found 734.2591 [(M+H)$^+$ form].

7-(furan-3-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 506)

Using General Procedure 11 starting from Preparation R2ce and Preparation R1m as reagents, EXAMPLE 506 was obtained. HRMS calculated for $C_{39}H_{39}N_7O_5S$: 717.2733; found 718.2818 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1H-indol-1-yl)-3,7-dihydro-4H-pyrrolo[2,3-d]pyrimidin-4-one (Example 507)

Using General Procedure 11 starting from Preparation R2cl and Preparation R1m as reagents, EXAMPLE 507 was obtained. HRMS calculated for $C_{43}H_{42}N_8O_4S$: 766.3050; found 767.312 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1H-pyrrol-1-yl)-3,7-dihydro-4H-pyrrolo[2,3-d]pyrimidin-4-one (Example 508)

Using General Procedure 11 starting from Preparation R2cm and Preparation R1m as reagents, EXAMPLE 508 was obtained. HRMS calculated for $C_{39}H_{40}N_8O_4S$: 716.2893; found 717.2976 [(M+H)$^+$ form].

7-cyclopentyl-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 509)

Using General Procedure 11 starting from Preparation R2i and Preparation R1m as reagents, EXAMPLE 509 was obtained. HRMS calculated for $C_{40}H_{45}N_7O_4S$: 719.3254; found 718.3195 [(M–H)$^-$ form].

7-cyclohexyl-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 510)

Using General Procedure 11 starting from Preparation R2j and Preparation R1m as reagents, EXAMPLE 510 was obtained. HRMS calculated for $C_{41}H_{47}N_7O_4S$: 733.3410; found 732.3356 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(tetrahydro-2H-pyran-4-yl)-3,7-dihydro-4H-pyrrolo[2,3-d]pyrimidin-4-one (Example 511)

Using General Procedure 11 starting from Preparation R2l and Preparation R1m as reagents, EXAMPLE 511 was obtained. HRMS calculated for $C_{40}H_{45}N_7O_5S$: 735.3203; found 734.3166 [(M–H)$^-$ form].

3-[(1-{[(3R,4R)-1-(3-aminobenzoyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 512)

Using General Procedure 12 starting from EXAMPLE 203 and as starting material, EXAMPLE 512 was obtained. HRMS calculated for $C_{32}H_{36}N_6O_4$: 568.2798; found 569.2855 [(M+H)$^+$ form].

3-{[4-hydroxy-1-({(3R,4R)-1-[3-(methylamino)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 513)

Using General Procedure 13 starting from EXAMPLE 512 as amino reagent, EXAMPLE 513 was obtained. HRMS calculated for $C_{33}H_{38}N_6O_4$: 582.2955; found 583.3036 [(M+H)$^+$ form].

tert-butyl 4-acetyl-7-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-3,4-dihydroquinoxaline-1(2H)-carboxylate (Example 514)

Using General Procedure 7 starting from EXAMPLE 244 and acetic acid as reagents, EXAMPLE 514 was obtained. HRMS calculated for $C_{41}H_{49}N_7O_7$: 751.3693; found 752.3755 [(M+H)$^+$ form].

7-{4-[6-(dimethylamino)pyridin-3-yl]phenyl}-3-[(1-
{[(3R,4R)-1-({2-[6-(dimethylamino)pyridin-3-yl]-1,
3-thiazol-5-yl}methyl)-3-phenylpiperidin-4-yl]car-
bonyl}-4-hydroxypiperidin-4-yl)methyl]-3,7-
dihydro-4H-pyrrolo[2,3-d]pyrimidin-4-one
(Example 515)

and 7-(4-chlorophenyl)-3-[(1-{[(3R,4R)-1-({2-[6-(dim-
ethylamino)pyridin-3-yl]-1,3-thiazol-5-yl}methyl)-3-
phenylpiperidin-4-yl]carbonyl}-4-hydroxypiperidin-
4-yl)methyl]-3,7-dihydro-4H-pyrrolo[2,3-d]
pyrimidin-4-one (Example 516)

Using General Procedure 9 starting from EXAMPLE 28 and [6-(dimethylamino)-3-pyridyl]boronic acid as reagents, EXAMPLE 515 and EXAMPLE 516 were obtained and separated by chromatography.

Example 515

HRMS calculated for $C_{48}H_{52}N_{10}O_3S$: 848.3945; found 425.2060 [(M+2H)$^{2+}$ form].

Example 516

HRMS calculated for $C_{41}H_{43}ClN_8O_3S$: 762.2867; found 382.1494 [(M+2H)$^{2+}$ form].

5-[5-({(3R,4R)-4-[(4-{[7-(4-chlorophenyl)-4-oxo-4,
7-dihydro-3H-pyrrolo[2,3-d]pyrimidin-3-yl]methyl}-
4-hydroxypiperidin-1-yl)carbonyl]-3-phenylpiperi-
din-1-yl}methyl)-1,3-thiazol-2-yl]pyridine-2-
carbonitrile (Example 517)

Using General Procedure 9 starting from EXAMPLE 28 and 5-(4,4,5,5-tetramethyl-1,3,2-dioxaborolan-2-yl)pyridine-2-carbonitrile as reagents, EXAMPLE 517 was obtained. HRMS calculated for $C_{40}H_{37}ClN_8O_3S$: 744.2398; found 745.2471 [M+H]$^+$ form].

7-(4-chlorophenyl)-3-[(4-hydroxy-1-{[(3R,4R)-1-
{[2-(6-methylpyridin-3-yl)-1,3-thiazol-5-yl]methyl}-
3-phenylpiperidin-4-yl]carbonyl}piperidin-4-yl)
methyl]-3,7-dihydro-4H-pyrrolo[2,3-d]pyrimidin-4-
one (Example 518)

Using General Procedure 9 starting from EXAMPLE 28 and (6-methyl-3-pyridyl)boronic acid as reagents, EXAMPLE 518 was obtained. HRMS calculated for $C_{40}H_{40}ClN_7O_3S$: 733.2602; found 367.6385 [(M+2H)$^{2+}$ form].

5-[5-({(3R,4R)-4-[(4-{[7-(4-fluorophenyl)-4-oxo-4,
7-dihydro-3H-pyrrolo[2,3-d]pyrimidin-3-yl]methyl}-
4-hydroxypiperidin-1-yl)carbonyl]-3-phenylpiperi-
din-1-yl}methyl)-1,3-thiazol-2-yl]pyridine-2-
carbonitrile (Example 519)

Using General Procedure 9 starting from EXAMPLE 31 and 5-(4,4,5,5-tetramethyl-1,3,2-dioxaborolan-2-yl)pyridine-2-carbonitrile as reagents, EXAMPLE 519 was obtained. HRMS calculated for $C_{40}H_{37}FN_8O_3S$: 728.2693; found 729.2757 (M+H)$^+$ form].

3-[(4-hydroxy-1-{[(3R,4R)-3-phenyl-1-{[2-(thio-
phen-2-yl)-1,3-thiazol-5-yl]methyl}piperidin-4-yl]
carbonyl}piperidin-4-yl)methyl]-7-(4-methoxyphe-
nyl)-3,7-dihydro-4H-pyrrolo[2,3-d]pyrimidin-4-one
(Example 520)

Using General Procedure 9 starting from EXAMPLE 34 and 2-thienylboronic acid as reagents, EXAMPLE 520 was obtained. HRMS calculated for $C_{39}H_{40}N_6O_4S_2$: 720.2552; found 721.2612 [(M+H)$^+$ form].

3-[(1-{[(3R,4R)-1-({2-[6-(dimethylamino)pyridin-3-
yl]-1,3-thiazol-5-yl}methyl)-3-phenylpiperidin-4-yl]
carbonyl}-4-hydroxypiperidin-4-yl)methyl]-7-(4-
methoxyphenyl)-3,7-dihydro-4H-pyrrolo[2,3-d]
pyrimidin-4-one (Example 521)

Using General Procedure 9 starting from EXAMPLE 34 and [6-(dimethylamino)-3-pyridyl]boronic acid as reagents, EXAMPLE 521 was obtained. HRMS calculated for $C_{42}H_{46}N_8O_4S$: 758.3362; found 380.1763 [M+2H]$^{2+}$ form].

3-[(4-hydroxy-1-{[(3R,4R)-3-phenyl-1-({2-[6-(trif-
luoromethyl)pyridin-3-yl]-1,3-thiazol-5-yl}methyl)
piperidin-4-yl]carbonyl}piperidin-4-yl)methyl]-7-(4-
methoxyphenyl)-3,7-dihydro-4H-pyrrolo[2,3-d]
pyrimidin-4-one (Example 522)

Using General Procedure 9 starting from EXAMPLE 34 and [6-(trifluoromethyl)-3-pyridyl]boronic acid as reagents, EXAMPLE 522 was obtained. HRMS calculated for $C_{41}H_{40}F_3N_7O_4S$: 783.2814; found 784.2893 [(M+H)$^+$ form].

3-[(4-hydroxy-1-{[(3R,4R)-3-phenyl-1-{[2-(pyrimi-
din-5-yl)-1,3-thiazol-5-yl]methyl}piperidin-4-yl]
carbonyl}piperidin-4-yl)methyl]-7-(4-methoxyphe-
nyl)-3,7-dihydro-4H-pyrrolo[2,3-d]pyrimidin-4-one
(Example 523)

Using General Procedure 9 starting from EXAMPLE 34 and pyrimidin-5-ylboronic acid as reagents, EXAMPLE 523 was obtained. HRMS calculated for $C_{39}H_{40}N_8O_4S$: 716.2893; found 717.2999 [(M+H)$^+$ form].

3-[(4-hydroxy-1-{[(3R,4R)-1-{[2-(1-methyl-1H-
pyrazol-5-yl)-1,3-thiazol-5-yl]methyl}-3-phenylpip-
eridin-4-yl]carbonyl}piperidin-4-yl)methyl]-7-(4-
methoxyphenyl)-3,7-dihydro-4H-pyrrolo[2,3-d]
pyrimidin-4-one (Example 524)

Using General Procedure 9 starting from EXAMPLE 34 and 1-methyl-5-(4,4,5,5-tetramethyl-1,3,2-dioxaborolan-2-yl)pyrazole as reagents, EXAMPLE 524 was obtained. HRMS calculated for $C_{39}H_{42}N_8O_4S$: 718.3050; found 719.3108 [(M+H)$^+$ form].

3-[(4-hydroxy-1-{[(3R,4R)-1-{[2-(1-methyl-1H-
pyrazol-4-yl)-1,3-thiazol-5-yl]methyl}-3-phenylpip-
eridin-4-yl]carbonyl}piperidin-4-yl)methyl]-7-(4-
methoxyphenyl)-3,7-dihydro-4H-pyrrolo[2,3-d]
pyrimidin-4-one (Example 525)

Using General Procedure 9 starting from EXAMPLE 34 and 1-methyl-4-(4,4,5,5-tetramethyl-1,3,2-dioxaborolan-2- yl)pyrazole as reagents, EXAMPLE 525 was obtained. HRMS calculated for $C_{39}H_{42}N_8O_4S$: 718.3050; found 719.3131 [(M+H)⁺ form].

3-[(4-hydroxy-1-{[(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 526)

Using General Procedure 9 starting from EXAMPLE 34 and 1-methyl-3-(4,4,5,5-tetramethyl-1,3,2-dioxaborolan-2-yl)pyrrole as reagents, EXAMPLE 526 was obtained. HRMS calculated for $C_{40}H_{43}N_7O_4S$: 717.3098; found 718.3145 [(M+H)⁺ form].

3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one (Example 527)

Using General Procedure 9 starting from EXAMPLE 34 and 4,4,5,5-tetramethyl-2-(3-thienyl)-1,3,2-dioxaborolane as reagents, EXAMPLE 527 was obtained. HRMS calculated for $C_{39}H_{40}N_6O_4S_2$: 720.2552; found 721.2649 [(M+H)⁺ form].

3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one (Example 528)

Using General Procedure 9 starting from EXAMPLE 34 and 2-(3-furyl)-4,4,5,5-tetramethyl-1,3,2-dioxaborolane as reagents, EXAMPLE 528 was obtained. HRMS calculated for $C_{39}H_{40}N_6O_5S$: 704.2781; found 705.2852 [(M+H)⁺ form].

3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one (Example 529)

Using General Procedure 9 starting from EXAMPLE 34 and 2-furylboronic acid as reagents, EXAMPLE 529 was obtained. HRMS calculated for $C_{39}H_{40}N_6O_5S$: 704.2781; found 705.2837 [(M+H)⁺ form].

5-[5-({(3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile (Example 530)

Using General Procedure 9 starting from EXAMPLE 34 and 5-(4,4,5,5-tetramethyl-1,3,2-dioxaborolan-2-yl)pyridine-2-carbonitrile as reagents, EXAMPLE 530 was obtained. HRMS calculated for $C_{41}H_{40}N_8O_4S$: 740.2893; found 741.2956 [M+H)⁺ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one (Example 531)

Using General Procedure 9 starting from EXAMPLE 34 and (6-methyl-3-pyridyl)boronic acid as reagents, EXAMPLE 531 was obtained. HRMS calculated for $C_{41}H_{43}N_7O_4S$: 729.3098; found 365.6619 [(M+2H)²⁺ form].

3-[(1-{[(3R,4R)-1-{[5-(furan-2-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 532)

Using General Procedure 9 starting from EXAMPLE 176 and 2-furylboronic acid as reagents, EXAMPLE 532 was obtained. HRMS calculated for $C_{34}H_{35}N_5O_5S$: 625.2359; found 626.2436 [(M+H)⁺ form].

3-[(4-hydroxy-1-{[(3R,4R)-1-{[5-(1-methyl-1H-pyrazol-5-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 533)

Using General Procedure 9 starting from EXAMPLE 176 and 1-methyl-5-(4,4,5,5-tetramethyl-1,3,2-dioxaborolan-2-yl)pyrazole as reagents, EXAMPLE 533 was obtained. HRMS calculated for $C_{34}H_{37}N_7O_4S$: 639.2628; found 640.2696 [(M+H)⁺ form].

3-[(4-hydroxy-1-{[(3R,4R)-3-phenyl-1-{[5-(pyridin-3-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 534)

Using General Procedure 9 starting from EXAMPLE 176 and 3-pyridylboronic acid as reagents, EXAMPLE 534 was obtained. HRMS calculated for $C_{35}H_{36}N_6O_4S$: 636.2519; found 637.2582 [(M+H)⁺ form].

3-[(4-hydroxy-1-{[(3R,4R)-1-{[5-(1-methyl-1H-pyrrol-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 535)

Using General Procedure 9 starting from EXAMPLE 176 and 1-methyl-3-(4,4,5,5-tetramethyl-1,3,2-dioxaborolan-2-yl)pyrrole as reagents, EXAMPLE 535 was obtained. HRMS calculated for $C_{35}H_{38}N_6O_4S$: 638.2675; found 639.2750 [M+H)⁺ form].

3-[(1-{[(3R,4R)-1-{[5-(4-fluorophenyl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 536)

Using General Procedure 9 starting from EXAMPLE 176 and (4-fluorophenyl)boronic acid as reagents, EXAMPLE 536 was obtained. HRMS calculated for $C_{36}H_{36}FN_5O_4S$: 653.2472; found 654.254 [(M+H)⁺ form].

3-[(1-{[(3R,4R)-1-{[5-(3-fluorophenyl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 537)

Using General Procedure 9 starting from EXAMPLE 176 and (3-fluorophenyl)boronic acid as reagents, EXAMPLE 537 was obtained. HRMS calculated for $C_{36}H_{36}FN_5O_4S$: 653.2472; found 654.2552 [(M+H)$^+$ form].

3-[(4-hydroxy-1-{[(3R,4R)-1-{[5-(3-methylphenyl) thiophen-2-yl]carbonyl}-3-phenylpiperidin-4-yl] carbonyl}piperidin-4-yl)methyl]-7-methyl-3,7-dihydro-4H-pyrrolo[2,3-d]pyrimidin-4-one (Example 538)

Using General Procedure 9 starting from EXAMPLE 176 and m-tolylboronic acid as reagents, EXAMPLE 538 was obtained. HRMS calculated for $C_{37}H_{39}N_5O_4S$: 649.2723; found 650.2793 [(M+H)$^+$ form].

3-[(4-hydroxy-1-{[(3R,4R)-1-{[5-(2-methylphenyl) thiophen-2-yl]carbonyl}-3-phenylpiperidin-4-yl] carbonyl}piperidin-4-yl)methyl]-7-methyl-3,7-dihydro-4H-pyrrolo[2,3-d]pyrimidin-4-one (Example 539)

Using General Procedure 9 starting from EXAMPLE 176 and o-tolylboronic acid as reagents, EXAMPLE 539 was obtained. HRMS calculated for $C_{37}H_{39}N_5O_4S$: 649.2723; found 650.2793 [(M+H)$^+$ form].

3-[(4-hydroxy-1-{[(3R,4R)-1-{[5-(4-methylphenyl) thiophen-2-yl]carbonyl}-3-phenylpiperidin-4-yl] carbonyl}piperidin-4-yl)methyl]-7-methyl-3,7-dihydro-4H-pyrrolo[2,3-d]pyrimidin-4-one (Example 540)

Using General Procedure 9 starting from EXAMPLE 176 and p-tolylboronic acid as reagents, EXAMPLE 540 was obtained. HRMS calculated for $C_{37}H_{39}N_5O_4S$: 649.2723; found 650.2792 [(M+H)$^+$ form].

3-[(1-{[(3R,4R)-1-{[5-(furan-3-yl)thiophen-2-yl] carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 541)

Using General Procedure 9 starting from EXAMPLE 176 and 2-(3-furyl)-4,4,5,5-tetramethyl-1,3,2-dioxaborolane as reagents, EXAMPLE 541 was obtained. HRMS calculated for: 625.2359; found $C_{34}H_{35}N_5O_5S$ 626.2425 [(M+H)$^+$ form].

3-[(4-hydroxy-1-{[(3R,4R)-3-phenyl-1-{[5-(pyrimidin-5-yl)thiophen-2-yl]carbonyl}piperidin-4-yl] carbonyl}piperidin-4-yl)methyl]-7-methyl-3,7-dihydro-4H-pyrrolo[2,3-d]pyrimidin-4-one (Example 542)

Using General Procedure 9 starting from EXAMPLE 176 and pyrimidin-5-ylboronic acid as reagents, EXAMPLE 542 was obtained. HRMS calculated for $C_{34}H_{35}N_7O_4S$: 637.2471; found 638.2544 [(M+H)$^+$ form].

3-[(1-{[(3R,4R)-1-{[2-(furan-2-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 543)

Using General Procedure 9 starting from EXAMPLE 349 and 2-furylboronic acid as reagents, EXAMPLE 543 was obtained. HRMS calculated for $C_{34}H_{36}N_6O_5S$: 640.2468; found 641.2544 [(M+H)$^+$ form].

3-[(4-hydroxy-1-{[(3R,4R)-1-{[4-methyl-2-(pyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 544)

Using General Procedure 9 starting from EXAMPLE 349 and 3-pyridylboronic acid as reagents, EXAMPLE 544 was obtained. HRMS calculated for $C_{35}H_{37}N_7O_4S$: 651.2628; found 652.2697 [(M+H)$^+$ form].

3-[(4-hydroxy-1-{[(3R,4R)-1-{[4-methyl-2-(1-methyl-1H-pyrazol-5-yl)-1,3-thiazol-5-yl]carbonyl}-3-phenylpiperidin-4-yl]carbonyl}piperidin-4-yl) methyl]-7-methyl-3,7-dihydro-4H-pyrrolo[2,3-d] pyrimidin-4-one (Example 545)

Using General Procedure 9 starting from EXAMPLE 349 and 1-methyl-5-(4,4,5,5-tetramethyl-1,3,2-dioxaborolan-2-yl)pyrazole as reagents, EXAMPLE 545 was obtained. HRMS calculated for $C_{34}H_{38}N_8O_4S$: 654.2737; found 655.2823 [(M+H)$^+$ form].

3-[(4-hydroxy-1-{[(3R,4R)-1-{[4-methyl-2-(1-methyl-1H-pyrrol-3-yl)-1,3-thiazol-5-yl]carbonyl}-3-phenylpiperidin-4-yl]carbonyl}piperidin-4-yl) methyl]-7-methyl-3,7-dihydro-4H-pyrrolo[2,3-d] pyrimidin-4-one (Example 546)

Using General Procedure 9 starting from EXAMPLE 349 and 1-methyl-3-(4,4,5,5-tetramethyl-1,3,2-dioxaborolan-2-yl)pyrrole as reagents, EXAMPLE 546 was obtained. HRMS calculated for $C_{35}H_{39}N_7O_4S$: 653.2784; found 654.2848 [(M+H)$^+$ form].

3-[(4-hydroxy-1-{[(3R,4R)-1-{[4-methyl-2-(1-methyl-1H-pyrazol-4-yl)-1,3-thiazol-5-yl]carbonyl}-3-phenylpiperidin-4-yl]carbonyl}piperidin-4-yl) methyl]-7-methyl-3,7-dihydro-4H-pyrrolo[2,3-d] pyrimidin-4-one (Example 547)

Using General Procedure 9 starting from EXAMPLE 349 and 1-methyl-4-(4,4,5,5-tetramethyl-1,3,2-dioxaborolan-2-yl)pyrazole as reagents, EXAMPLE 547 was obtained. HRMS calculated for $C_{34}H_{38}N_8O_4S$: 654.2737; found 655.2817 [(M+H)$^+$ form].

3-[(1-{[(3R,4R)-1-{[2-(furan-3-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 548)

Using General Procedure 9 starting from EXAMPLE 349 and 2-furylboronic acid as reagents, EXAMPLE 548 was obtained. HRMS calculated for $C_{34}H_{36}N_6O_5S$: 640.2468; found 641.2541 [(M+H)$^+$ form].

3-[(4-hydroxy-1-{[(3R,4R)-1-{[4-methyl-2-(pyrimidin-5-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 549)

Using General Procedure 9 starting from EXAMPLE 349 and pyrimidin-5-ylboronic acid as reagents, EXAMPLE 549

3-[(4-hydroxy-1-{[(3R,4R)-1-{[4-methyl-2-(3-methylphenyl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 550)

Using General Procedure 9 starting from EXAMPLE 349 and m-tolylboronic acid as reagents, EXAMPLE 550 was obtained. HRMS calculated for $C_{37}H_{40}N_6O_4S$: 664.2832; found 665.2893 [(M+H)$^+$ form].

3-[(4-hydroxy-1-{[(3R,4R)-1-{[4-methyl-2-(thiophen-2-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 551)

Using General Procedure 9 starting from EXAMPLE 349 and 2-thienylboronic acid as reagents, EXAMPLE 551 was obtained. HRMS calculated for $C_{34}H_{36}N_6O_4S_2$: 656.2239; found 657.2318 [(M+H)$^+$ form].

3-[(4-hydroxy-1-{[(3R,4R)-1-{[4-methyl-2-(4-methylphenyl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 552)

Using General Procedure 9 starting from EXAMPLE 349 and p-tolylboronic acid as reagents, EXAMPLE 552 was obtained. HRMS calculated for $C_{37}H_{40}N_6O_4S$: 664.2832; found 665.2908 [(M+H)$^+$ form].

3-[(1-{[(3R,4R)-1-{[2-(4-fluorophenyl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 553)

Using General Procedure 9 starting from EXAMPLE 349 and (4-fluorophenyl)boronic acid as reagents, EXAMPLE 553 was obtained. HRMS calculated for $C_{36}H_{37}FN_6O_4S$: 668.2581; found 669.2656 [(M+H)$^+$ form].

3-[(1-{[(3R,4R)-1-{[2-(3-fluorophenyl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 554)

Using General Procedure 9 starting from EXAMPLE 349 and (3-fluorophenyl)boronic acid as reagents, EXAMPLE 554 was obtained. HRMS calculated for $C_{36}H_{37}FN_6O_4S$: 668.2581; found 669.2659 [(M+H)$^+$ form].

3-[(4-hydroxy-1-{[(3R,4R)-1-{[4-methyl-2-(thiophen-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 555)

Using General Procedure 9 starting from EXAMPLE 349 and 4,4,5,5-tetramethyl-2-(3-thienyl)-1,3,2-dioxaborolane as reagents, EXAMPLE 555 was obtained. HRMS calculated for $C_{34}H_{36}N_6O_4S_2$: 656.2239; found 657.2300 [(M+H)$^+$ form].

3-[(1-{[(3R,4R)-1-{[5-(3-fluoropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 556)

Using General Procedure 9 starting from EXAMPLE 176 and (3-fluoro-4-pyridyl)boronic acid as reagents, EXAMPLE 556 was obtained. HRMS calculated for $C_{35}H_{35}FN_6O_4S$: 654.2425; found 655.2499 [(M+H)$^+$ form].

3-[(1-{[(3R,4R)-1-(2,2'-bithiophen-5-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 557)

Using General Procedure 9 starting from EXAMPLE 176 and 2-thienylboronic acid as reagents, EXAMPLE 557 was obtained. HRMS calculated for $C_{34}H_{35}N_5O_4S_2$: 641.2130; found 642.2219 [(M+H)$^+$ form].

3-[(1-{[(3R,4R)-1-(2,3'-bithiophen-5-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 558)

Using General Procedure 9 starting from EXAMPLE 176 and 4,4,5,5-tetramethyl-2-(3-thienyl)-1,3,2-dioxaborolane as reagents, EXAMPLE 558 was obtained. HRMS calculated for $C_{34}H_{35}N_5O_4S_2$: 641.2131; found (642.2210 [(M+H)$^+$ form].

3-[(1-{[(3R,4R)-1-{[5-(2-fluorophenyl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 559)

Using General Procedure 9 starting from EXAMPLE 176 and (2-fluorophenyl)boronic acid as reagents, EXAMPLE 559 was obtained. HRMS calculated for $C_{36}H_{36}FN_5O_4S$: 653.2472; found 654.2541 [(M+H)$^+$ form].

3-{[4-hydroxy-1-({(3R,4R)-3-phenyl-1-[(5-phenylthiophen-2-yl)carbonyl]piperidin-4-yl}carbonyl)piperidin-4-yl]methyl}-7-methyl-3,7-dihydro-4H-pyrrolo[2,3-d]pyrimidin-4-one (Example 560)

Using General Procedure 9 starting from EXAMPLE 176 and phenylboronic acid as reagents, EXAMPLE 560 was obtained. HRMS calculated for $C_{36}H_{37}N_5O_4S$: 635.2566; found 636.264 [(M+H)$^+$ form].

3-[(4-hydroxy-1-{[(3R,4R)-1-{[5-(1-methyl-1H-pyrazol-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 561)

Using General Procedure 9 starting from EXAMPLE 176 and 1-methyl-4-(4,4,5,5-tetramethyl-1,3,2-dioxaborolan-2- yl)pyrazole as reagents, EXAMPLE 561 was obtained. HRMS calculated for $C_{34}H_{37}N_7O_4S$: 639.2628; found 640.2695 [(M+H)$^+$ form].

3-[(1-{[(3R,4R)-1-{[5-(2-chloropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 562)

Using General Procedure 9 starting from EXAMPLE 176 and (2-chloro-4-pyridyl)boronic acid as reagents, EXAMPLE 562 was obtained. HRMS calculated for $C_{35}H_{35}ClN_6O_4S$: 670.2129; found 671.2194 [(M+H)$^+$ form].

3-[(1-{[(3R,4R)-1-{[5-(3-chloropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 563)

Using General Procedure 9 starting from EXAMPLE 176 and (3-chloro-4-pyridyl)boronic acid as reagents, EXAMPLE 563 was obtained. HRMS calculated for $C_{35}H_{35}ClN_6O_4S$: 670.2129; found 671.2188 [(M+H)$^+$ form].

3-[(4-hydroxy-1-{[(3R,4R)-1-{[5-(3-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 564)

Using General Procedure 9 starting from EXAMPLE 176 and (3-methyl-4-pyridyl)boronic acid as reagents, EXAMPLE 564 was obtained. HRMS calculated for $C_{36}H_{38}N_6O_4S$: 650.2675; found 651.2742 [(M+H)$^+$ form].

3-[(4-hydroxy-1-{[(3R,4R)-1-{[5-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 565)

Using General Procedure 9 starting from EXAMPLE 176 and (2-methyl-4-pyridyl)boronic acid as reagents, EXAMPLE 565 was obtained. HRMS calculated for $C_{36}H_{38}N_6O_4S$: 650.2675; found 651.2724 [(M+H)$^+$ form].

3-[(1-{[(3R,4R)-1-{[5-(5-chloro-2-fluoropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 566)

Using General Procedure 9 starting from EXAMPLE 176 and (5-chloro-2-fluoro-4-pyridyl)boronic acid as reagents, EXAMPLE 566 was obtained. HRMS calculated for $C_{35}H_{34}ClFN_6O_4S$: 688.2035; found 689.2135 [(M+H)+ form].

3-[(1-{[(3R,4R)-1-{[5-(2,5-dichloropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 567)

Using General Procedure 9 starting from EXAMPLE 176 and 2,5-dichloro-4-(4,4,5,5-tetramethyl-1,3,2-dioxaborolan-2-yl)pyridine as reagents, EXAMPLE 567 was obtained. HRMS calculated for $C_{35}H_{34}N_6O_4SCl_2$: 704.1740; found 705.1819 [(M+H)$^+$ form].

3-[(1-{[(3R,4R)-1-{[5-(2-fluoropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 568)

Using General Procedure 9 starting from EXAMPLE 176 and (2-fluoro-4-pyridyl)boronic acid as reagents, EXAMPLE 568 was obtained. HRMS calculated for $C_{35}H_{35}N_6O_4S$: 654.2425; found 655.251 [(M+H)$^+$ form].

3-{[4-hydroxy-1-({(3R,4R)-3-phenyl-1-[(5-phenylthiophen-2-yl)sulfonyl]piperidin-4-yl}carbonyl)piperidin-4-yl]methyl}-7-methyl-3,7-dihydro-4H-pyrrolo[2,3-d]pyrimidin-4-one (Example 569)

Using General Procedure 9 starting from EXAMPLE 342 and phenylboronic acid as reagents, EXAMPLE 569 was obtained. HRMS calculated for $C_{35}H_{37}N_5O_5S_2$: 671.2236; found 672.2297 [(M+H)$^+$ form].

3-[(4-hydroxy-1-{[(3R,4R)-3-phenyl-1-{[5-(pyridin-4-yl)thiophen-2-yl]sulfonyl}piperidin-4-yl]carbonyl}piperidin-4-yl)methyl]-7-methyl-3,7-dihydro-4H-pyrrolo[2,3-d]pyrimidin-4-one (Example 570)

Using General Procedure 9 starting from EXAMPLE 342 and 4-(4,4,5,5-tetramethyl-1,3,2-dioxaborolan-2-yl)pyridine as reagents, EXAMPLE 570 was obtained. HRMS calculated for $C_{34}H_{36}N_6O_5S_2$: 672.2189; found 337.1169 [(M+2H)$^{2+}$ form].

3-[(4-hydroxy-1-{[(3R,4R)-3-phenyl-1-{[5-(pyrimidin-5-yl)thiophen-2-yl]sulfonyl}piperidin-4-yl]carbonyl}piperidin-4-yl)methyl]-7-methyl-3,7-dihydro-4H-pyrrolo[2,3-d]pyrimidin-4-one (Example 571)

Using General Procedure 9 starting from EXAMPLE 342 and pyrimidin-5-ylboronic acid as reagents, EXAMPLE 571 was obtained. HRMS calculated for $C_{33}H_{35}N_7O_5S_2$: 673.2141; found 674.221 [(M+H)$^+$ form].

3-{[4-hydroxy-1-({(3R,4R)-1-[3-(1-methyl-1H-pyrazol-5-yl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 572)

Using General Procedure 9 starting from EXAMPLE 201 and 1-methyl-5-(4,4,5,5-tetramethyl-1,3,2-dioxaborolan-2-yl)pyrazole as reagents, EXAMPLE 572 was obtained. HRMS calculated for $C_{36}H_{39}N_7O_4$: 633.3063; found 634.3140 [(M+H)$^+$ form].

3-{[4-hydroxy-1-({(3R,4R)-3-phenyl-1-[3-(pyrimidin-5-yl)benzoyl]piperidin-4-yl}carbonyl)piperidin-4-yl]methyl}-7-methyl-3,7-dihydro-4H-pyrrolo[2,3-d]pyrimidin-4-one (Example 573)

Using General Procedure 9 starting from EXAMPLE 201 and pyrimidin-5-ylboronic acid as reagents, EXAMPLE 573 was obtained. HRMS calculated for $C_{36}H_{37}N_7O_4$: 631.2907; found 632.2982 [(M+H)$^+$ form].

3-{[4-hydroxy-1-({(3R,4R)-3-phenyl-1-[3-(pyridin-4-yl)benzoyl]piperidin-4-yl}carbonyl)piperidin-4-yl]methyl}-7-methyl-3,7-dihydro-4H-pyrrolo[2,3-d]pyrimidin-4-one (Example 574)

Using General Procedure 9 starting from EXAMPLE 201 and 4-(4,4,5,5-tetramethyl-1,3,2-dioxaborolan-2-yl)pyridine as reagents, EXAMPLE 574 was obtained. HRMS calculated for $C_{37}H_{38}N_6O_4$: 630.2955; found 316.1552 [(M+2H)$^{2+}$ form].

3-{[4-hydroxy-1-({(3R,4R)-3-phenyl-1-[3-(pyridin-3-yl)benzoyl]piperidin-4-yl}carbonyl)piperidin-4-yl]methyl}-7-methyl-3,7-dihydro-4H-pyrrolo[2,3-d]pyrimidin-4-one (Example 575)

Using General Procedure 9 starting from EXAMPLE 201 and 3-pyridylboronic acid as reagents, EXAMPLE 575 was obtained. HRMS calculated for $C_{37}H_{38}N_6O_4$: 630.2955; found 631.3037 [(M+H)$^+$ form].

3-[(4-hydroxy-1-{[(3R,4R)-1-{[4-(1-methyl-1H-pyrazol-5-yl)pyridin-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 576)

Using General Procedure 9 starting from EXAMPLE 194 and 1-methyl-5-(4,4,5,5-tetramethyl-1,3,2-dioxaborolan-2-yl)pyrazole as reagents, EXAMPLE 576 was obtained. HRMS calculated for $C_{35}H_{38}N_8O_4$: 634.3016; found 635.3092 [(M+H)$^+$ form].

3-[(1-{[(3R,4R)-1-(4,4'-bipyridin-2-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 577)

Using General Procedure 9 starting from EXAMPLE 194 and 4-(4,4,5,5-tetramethyl-1,3,2-dioxaborolan-2-yl)pyridine as reagents, EXAMPLE 577 was obtained. HRMS calculated for $C_{36}H_{37}N_7O_4$: 631.2907; found 632.2978 [(M+H)+ form].

3-[(4-hydroxy-1-{[(3R,4R)-1-{[5-(1-methyl-1H-pyrazol-5-yl)thiophen-2-yl]sulfonyl}-3-phenylpiperidin-4-yl]carbonyl}piperidin-4-yl)methyl]-7-methyl-3,7-dihydro-4H-pyrrolo[2,3-d]pyrimidin-4-one (Example 578)

Using General Procedure 9 starting from EXAMPLE 342 and 1-methyl-5-(4,4,5,5-tetramethyl-1,3,2-dioxaborolan-2-yl)pyrazole as reagents, EXAMPLE 578 was obtained. HRMS calculated for $C_{33}H_{37}N_7O_5S_2$: 675.2297; found 676.2372 [(M+H)+ form].

3-{[4-hydroxy-1-({(3R,4R)-3-phenyl-1-[3-(pyrimidin-5-yl)benzyl]piperidin-4-yl}carbonyl)piperidin-4-yl]methyl}-7-methyl-3,7-dihydro-4H-pyrrolo[2,3-d]pyrimidin-4-one (Example 579)

Using General Procedure 9 starting from EXAMPLE 69 and pyrimidin-5-ylboronic acid as reagents, EXAMPLE 579 was obtained. HRMS calculated for $C_{36}H_{39}N_7O_3$: 617.3115; found 618.3169 [(M+H)$^+$ form].

3-[(4-hydroxy-1-{[(3R,4R)-3-phenyl-1-{[3-(pyrimidin-5-yl)phenyl]sulfonyl}piperidin-4-yl]carbonyl}piperidin-4-yl)methyl]-7-methyl-3,7-dihydro-4H-pyrrolo[2,3-d]pyrimidin-4-one (Example 580)

Using General Procedure 9 starting from EXAMPLE 343 and pyrimidin-5-ylboronic acid as reagents, EXAMPLE 580 was obtained. HRMS calculated for $C_{35}H_{37}N_7O_5S$: 667.2577; found 668.2657 [(M+H)$^+$ form].

3-[(1-{[(3R,4R)-1-(biphenyl-3-ylmethyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 581)

Using General Procedure 9 starting from EXAMPLE 69 and phenylboronic acid as reagents, EXAMPLE 581 was obtained. HRMS calculated for $C_{38}H_{41}N_5O_3$: 615.3209; found 616.3306 [(M+H)$^+$ form].

3-[(1-{[(3R,4R)-1-(biphenyl-3-ylsulfonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 582)

Using General Procedure 9 starting from EXAMPLE 343 and phenylboronic acid as reagents, EXAMPLE 582 was obtained. HRMS calculated for $C_{37}H_{39}N_5O_5S$: 665.2672; found 666.2747 [(M+H)$^+$ form].

3-{[4-hydroxy-1-({(3R,4R)-3-phenyl-1-[3-(pyridin-4-yl)benzyl]piperidin-4-yl}carbonyl)piperidin-4-yl]methyl}-7-methyl-3,7-dihydro-4H-pyrrolo[2,3-d]pyrimidin-4-one (Example 583)

Using General Procedure 9 starting from EXAMPLE 69 and 4-(4,4,5,5-tetramethyl-1,3,2-dioxaborolan-2-yl)pyridine as reagents, EXAMPLE 583 was obtained. HRMS calculated for $C_{37}H_{40}N_6O_3$: 616.3162; found 309.1648 [(M+2H)$^{2+}$ form].

3-[(1-{[(3R,4R)-1-{[3-fluoro-5-(pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 584)

Using General Procedure 9 starting from EXAMPLE 197 and 4-(4,4,5,5-tetramethyl-1,3,2-dioxaborolan-2-yl)pyridine as reagents, EXAMPLE 584 was obtained. HRMS calculated for $C_{35}H_{35}FN_6O_4S$: 654.2425; found (655.2508 [(M+H)$^+$ form].

3-[(4-hydroxy-1-{[(3R,4R)-1-{[2-(1-methyl-1H-pyrazol-5-yl)pyridin-4-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 585)

Using General Procedure 9 starting from EXAMPLE 195 and 1-methyl-5-(4,4,5,5-tetramethyl-1,3,2-dioxaborolan-2- yl)pyrazole as reagents, EXAMPLE 585 was obtained. HRMS calculated for $C_{35}H_{38}N_8O_4$: 634.3016; found 635.3109 [(M+H)$^+$ form].

3-[(1-{[(3R,4R)-1-(2,4'-bipyridin-4-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 586)

Using General Procedure 9 starting from EXAMPLE 195 and 4-(4,4,5,5-tetramethyl-1,3,2-dioxaborolan-2-yl)pyridine as reagents, EXAMPLE 586 was obtained. HRMS calculated for $C_{36}H_{37}N_7O_4$: 631.2907; found 632.2999 [(M+H)$^+$ form].

3-[(4-hydroxy-1-{[(3R,4R)-1-{[5-(1-methyl-1H-pyrazol-5-yl)pyridin-3-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 587)

Using General Procedure 9 starting from EXAMPLE 196 and 1-methyl-5-(4,4,5,5-tetramethyl-1,3,2-dioxaborolan-2-yl)pyrazole as reagents, EXAMPLE 587 was obtained. HRMS calculated for $C_{35}H_{38}N_8O_4$: 634.3016; found 635.3091 [(M+H)$^+$ form].

3-[(1-{[(3R,4R)-1-(3,4'-bipyridin-5-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 588)

Using General Procedure 9 starting from EXAMPLE 196 and 4-(4,4,5,5-tetramethyl-1,3,2-dioxaborolan-2-yl)pyridine as reagents, EXAMPLE 588 was obtained. HRMS calculated for $C_{36}H_{37}N_7O_4$: 631.2907; found 632.2985 [(M+H)$^+$ form].

3-[(4-hydroxy-1-{[(3R,4R)-1-{[6-(1-methyl-1H-pyrazol-5-yl)pyridin-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 589)

Using General Procedure 9 starting from EXAMPLE 198 and 1-methyl-5-(4,4,5,5-tetramethyl-1,3,2-dioxaborolan-2-yl)pyrazole as reagents, EXAMPLE 589 was obtained. HRMS calculated for $C_{35}H_{38}N_8O_4$: 634.3016; found 635.3110 [(M+H)$^+$ form].

3-[(1-{[(3R,4R)-1-(2,4'-bipyridin-6-ylcarbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 590)

Using General Procedure 9 starting from EXAMPLE 198 and 4-(4,4,5,5-tetramethyl-1,3,2-dioxaborolan-2-yl)pyridine as reagents, EXAMPLE 590 was obtained. HRMS calculated for $C_{36}H_{37}N_7O_4$: 631.2907; found 632.2996 [(M+H)$^+$ form].

3-[(4-hydroxy-1-{[(3R,4R)-3-phenyl-1-{[3-(pyridin-4-yl)phenyl]sulfonyl}piperidin-4-yl]carbonyl}piperidin-4-yl)methyl]-7-methyl-3,7-dihydro-4H-pyrrolo[2,3-d]pyrimidin-4-one (Example 591)

Using General Procedure 9 starting from EXAMPLE 343 and 4-(4,4,5,5-tetramethyl-1,3,2-dioxaborolan-2-yl)pyridine as reagents, EXAMPLE 591 was obtained. HRMS calculated for $C_{36}H_{38}N_6O_5S$: 666.2625; found 667.2711 [(M+H)$^+$ form].

3-{[4-hydroxy-1-({(3R,4R)-1-[(1-methyl-4-phenyl-1H-pyrrol-2-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 592)

Using General Procedure 9 starting from EXAMPLE 189 and phenylboronic acid as reagents, EXAMPLE 592 was obtained. HRMS calculated for $C_{37}H_{40}N_6O_4$: 632.3111; found 633.3178 [(M+H)$^+$ form].

3-{[4-hydroxy-1-({(3R,4R)-1-[3-(1-methyl-1H-pyrazol-5-yl)benzyl]-3-phenylpiperidin-4-yl}carbonyl)piperidin-4-yl]methyl}-7-methyl-3,7-dihydro-4H-pyrrolo[2,3-d]pyrimidin-4-one (Example 593)

Using General Procedure 9 starting from EXAMPLE 69 and 1-methyl-5-(4,4,5,5-tetramethyl-1,3,2-dioxaborolan-2-yl)pyrazole as reagents, EXAMPLE 593 was obtained. HRMS calculated for $C_{36}H_{41}N_7O_3$: 619.3271; found 620.3359 [(M+H)$^+$ form].

3-[(4-hydroxy-1-{[(3R,4R)-1-{[3-(1-methyl-1H-pyrazol-5-yl)phenyl]sulfonyl}-3-phenylpiperidin-4-yl]carbonyl}piperidin-4-yl)methyl]-7-methyl-3,7-dihydro-4H-pyrrolo[2,3-d]pyrimidin-4-one (Example 594)

Using General Procedure 9 starting from EXAMPLE 343 and 1-methyl-5-(4,4,5,5-tetramethyl-1,3,2-dioxaborolan-2-yl)pyrazole as reagents, EXAMPLE 594 was obtained. HRMS calculated for $C_{35}H_{39}N_7O_5S$: 669.2733; found 670.2827 [(M+H)$^+$ form].

3-[(1-{[(3R,4R)-1-{[5-(2,3-dichloropyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 595)

Using General Procedure 9 starting from EXAMPLE 176 and 2,3-dichloro-4-(4,4,5,5-tetramethyl-1,3,2-dioxaborolan-2-yl)pyridine as reagents, EXAMPLE 595 was obtained. HRMS calculated for $C_{35}H_{34}N_6O_4SCl_2$: 704.1740; found 705.1807 [(M+H)$^+$ form].

3-[(4-hydroxy-1-{[(3R,4R)-1-{[5-(2-methoxypyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 596)

Using General Procedure 9 starting from EXAMPLE 176 and (2-methoxy-4-pyridyl)boronic acid as reagents, EXAMPLE 596 was obtained. HRMS calculated for $C_{36}H_{38}N_6O_5S$: 666.2625; found 667.2699 [(M+H)$^+$ form].

3-[(4-hydroxy-1-{[(3R,4R)-1-{[5-(3-methoxypyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 597)

Using General Procedure 9 starting from EXAMPLE 176 and (3-methoxy-4-pyridyl)boronic acid as reagents, EXAMPLE 597 was obtained. HRMS calculated for $C_{36}H_{38}N_6O_5S$: 666.2625; found 667.2702 [(M+H)$^+$ form].

2-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-5-(pyridin-4-yl)thiophene-3-carbonitrile (Example 598)

Using General Procedure 9 starting from EXAMPLE 212 and 4-(4,4,5,5-tetramethyl-1,3,2-dioxaborolan-2-yl)pyridine as reagents, EXAMPLE 598 was obtained. HRMS calculated for $C_{36}H_{35}N_7O_4S$: 661.2471; found 662.2543 [(M+H)$^+$ form].

3-[(1-{[(3R,4R)-1-{[3-fluoro-5-(2-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 599)

Using General Procedure 9 starting from EXAMPLE 197 and (2-methyl-4-pyridyl)boronic acid as reagents, EXAMPLE 599 was obtained. HRMS calculated for $C_{36}H_{37}N_6O_4FS$: 668.2581; found 669.2662 [(M+H)$^+$ form].

3-[(4-hydroxy-1-{[(3R,4R)-1-{[5-(4-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 600)

Using General Procedure 9 starting from EXAMPLE 176 and (4-methyl-3-pyridyl)boronic acid as reagents, EXAMPLE 600 was obtained. HRMS calculated for $C_{36}H_{38}N_6O_4S$: 650.2675; found 651.2756 [(M+H)$^+$ form].

3-[(4-hydroxy-1-{[(3R,4R)-1-{[5-(5-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 601)

Using General Procedure 9 starting from EXAMPLE 176 and (5-methyl-3-pyridyl)boronic acid as reagents, EXAMPLE 601 was obtained. HRMS calculated for $C_{36}H_{38}N_6O_4S$: 650.2675; found 651.2774 [(M+H)$^+$ form].

3-[(4-hydroxy-1-{[(3R,4R)-1-{[5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 602)

Using General Procedure 9 starting from EXAMPLE 176 and (6-methyl-3-pyridyl)boronic acid as reagents, EXAMPLE 602 was obtained. HRMS calculated for $C_{36}H_{38}N_6O_4S$: 650.2675; found 651.2757 [(M+H)$^+$ form].

3-[(4-hydroxy-1-{[(3R,4R)-1-{[5-(2-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 603)

Using General Procedure 9 starting from EXAMPLE 176 and 2-methyl-3-(4,4,5,5-tetramethyl-1,3,2-dioxaborolan-2-yl)pyridine as reagents, EXAMPLE 603 was obtained. HRMS calculated for $C_{36}H_{38}N_6O_4S$: 650.2675; found 651.2768 [(M+H)$^+$ form].

3-[(1-{[(3R,4R)-1-{[5-(6-aminopyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 604)

Using General Procedure 9 starting from EXAMPLE 176 and 5-(4,4,5,5-tetramethyl-1,3,2-dioxaborolan-2-yl)pyridin-2-amine as reagents, EXAMPLE 604 was obtained. HRMS calculated for $C_{35}H_{37}N_7O_4S$: 651.2628; found 651.2710 [(M+H)$^+$ form].

3-[(4-hydroxy-1-{[(3R,4R)-1-{[5-(6-methoxypyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 605)

Using General Procedure 9 starting from EXAMPLE 176 and (6-methoxy-3-pyridyl)boronic acid as reagents, EXAMPLE 605 was obtained. HRMS calculated for $C_{36}H_{38}N_6O_5S$: 666.2625; found 667.2700 [(M+H)$^+$ form].

3-[(1-{[(3R,4R)-1-{[5-(4-chloropyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 606)

Using General Procedure 9 starting from EXAMPLE 176 and 4-chloro-3-(4,4,5,5-tetramethyl-1,3,2-dioxaborolan-2-yl)pyridine as reagents, EXAMPLE 606 was obtained. HRMS calculated for $C_{35}H_{35}ClN_6O_4S$: 670.2129; found 671.2207 (M+H)$^+$ form].

3-[(4-hydroxy-1-{[(3R,4R)-1-{[4-methyl-2-(4-methylpyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 607)

Using General Procedure 9 starting from EXAMPLE 349 and (4-methyl-3-pyridyl)boronic acid as reagents, EXAMPLE 607 was obtained. HRMS calculated for $C_{36}H_{39}N_7O_4S$: 665.2784; found 666.2838 [(M+H)$^+$ form].

3-[(4-hydroxy-1-{[(3R,4R)-1-{[4-methyl-2-(5-methylpyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 608)

Using General Procedure 9 starting from EXAMPLE 349 and (5-methyl-3-pyridyl)boronic acid as reagents, EXAMPLE 608 was obtained. HRMS calculated for $C_{36}H_{39}N_7O_4S$: 665.2784; found 666.2845 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 609)

Using General Procedure 9 starting from EXAMPLE 349 and (6-methyl-3-pyridyl)boronic acid as reagents, EXAMPLE 609 was obtained. HRMS calculated for C$_{36}$H$_{39}$N$_7$O$_4$S: 665.2784; found 666.2829 [(M+H)$^+$ form].

3-[(4-hydroxy-1-{[(3R,4R)-1-{[4-methyl-2-(2-methylpyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 610)

Using General Procedure 9 starting from EXAMPLE 349 and 2-methyl-3-(4,4,5,5-tetramethyl-1,3,2-dioxaborolan-2-yl)pyridine as reagents, EXAMPLE 610 was obtained. HRMS calculated for C$_{36}$H$_{39}$N$_7$O$_4$S: 665.2784; found 666.2825 (M+H)$^+$ form].

3-[(1-{[(3R,4R)-1-{[2-(6-aminopyridin-3-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 611)

Using General Procedure 9 starting from EXAMPLE 349 and 5-(4,4,5,5-tetramethyl-1,3,2-dioxaborolan-2-yl)pyridin-2-amine as reagents, EXAMPLE 611 was obtained. HRMS calculated for C$_{35}$H$_{38}$N$_8$O$_4$S: 666.2737; found 667.2802 [(M+H)$^+$ form].

3-[(4-hydroxy-1-{[(3R,4R)-1-{[2-(6-methoxypyridin-3-yl)-4-methyl-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 612)

Using General Procedure 9 starting from EXAMPLE 349 and (6-methoxy-3-pyridyl)boronic acid as reagents, EXAMPLE 612 was obtained. HRMS calculated for C$_{36}$H$_{39}$N$_7$O$_5$S: 681.2733; found 682.2797 [(M+H)$^+$ form].

3-[(4-hydroxy-1-{[(3R,4R)-1-{[1-methyl-5-(2-methylpyridin-4-yl)-1H-pyrrol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 613)

Using General Procedure 9 starting from EXAMPLE 217 and (2-methyl-4-pyridyl)boronic acid as reagents, EXAMPLE 613 was obtained. HRMS calculated for C$_{37}$H$_{41}$N$_7$O$_4$: 647.3220; found 648.3316 [(M+H)$^+$ form].

3-[(4-hydroxy-1-{[(3R,4R)-1-{[1-methyl-5-(pyridin-3-yl)-1H-pyrrol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 614)

Using General Procedure 9 starting from EXAMPLE 217 and 3-pyridylboronic acid as reagents, EXAMPLE 614 was obtained. HRMS calculated for C$_{36}$H$_{39}$N$_7$O$_4$: 633.3063; found 634.3138 [(M+H)$^+$ form].

3-[(4-hydroxy-1-{[(3R,4R)-1-{[1-methyl-5-(pyrimidin-5-yl)-1H-pyrrol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 615)

Using General Procedure 9 starting from EXAMPLE 217 and pyrimidin-5-ylboronic acid as reagents, EXAMPLE 615 was obtained. HRMS calculated for C$_{35}$H$_{38}$N$_8$O$_4$: 634.3016; found 635.3092 [(M+H)$^+$ form].

3-[(1-{[(3R,4R)-1-{[2-(5-chloropyridin-3-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 616)

Using General Procedure 9 starting from EXAMPLE 349 and 3-chloro-5-(4,4,5,5-tetramethyl-1,3,2-dioxaborolan-2-yl)pyridine as reagents, EXAMPLE 616 was obtained. HRMS calculated for C$_{35}$H$_{36}$ClN$_7$O$_4$S: 685.2238; found 686.2306 [(M+H)$^+$ form].

3-[(4-hydroxy-1-{[(3R,4R)-1-{[1-methyl-5-(1-methyl-1H-pyrazol-5-yl)-1H-pyrrol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 617)

Using General Procedure 9 starting from EXAMPLE 217 and 1-methyl-5-(4,4,5,5-tetramethyl-1,3,2-dioxaborolan-2-yl)pyrazole as reagents, EXAMPLE 617 was obtained. HRMS calculated for C$_{35}$H$_{40}$N$_8$O$_4$: 636.3173; found 637.3251 [(M+H)$^+$ form].

3-[(4-hydroxy-1-{[(3R,4R)-1-{[1-methyl-5-(pyridin-4-yl)-1H-pyrrol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 618)

Using General Procedure 9 starting from EXAMPLE 217 and 4-(4,4,5,5-tetramethyl-1,3,2-dioxaborolan-2-yl)pyridine as reagents, EXAMPLE 618 was obtained. HRMS calculated for C$_{36}$H$_{39}$N$_7$O$_4$: 633.3063; found 634.3128 [(M+H)$^+$ form].

3-[(1-{[(3R,4R)-1-{[3-fluoro-5-(2-methoxypyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 619)

Using General Procedure 9 starting from EXAMPLE 197 and (2-methoxy-4-pyridyl)boronic acid as reagents, EXAMPLE 619 was obtained. HRMS calculated for C$_{36}$H$_{37}$FN$_6$O$_5$S: 684.2530; found 685.2594 [(M+H)$^+$ form].

3-[(4-hydroxy-1-{[(3R,4R)-1-{[2-(3-methoxypyridin-4-yl)-4-methyl-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 620)

Using General Procedure 9 starting from EXAMPLE 349 and (3-methoxy-4-pyridyl)boronic acid as reagents, EXAMPLE 620 was obtained. HRMS calculated for C$_{36}$H$_{39}$N$_7$O$_5$S: 681.2733; found 682.2827 [(M+H)$^+$ form].

3-[(1-{[(3R,4R)-1-{[5-(5-chloropyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 621)

Using General Procedure 9 starting from EXAMPLE 176 and 3-chloro-5-(4,4,5,5-tetramethyl-1,3,2-dioxaborolan-2- yl)pyridine as reagents, EXAMPLE 621 was obtained. HRMS calculated for $C_{35}H_{35}ClN_6O_4S$: 670.2129; found 671.2200 [(M+H)⁺ form].

3-[(4-hydroxy-1-{[(3R,4R)-1-{[4-methyl-5-(2-methylpyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 622)

Using General Procedure 7 starting from Preparation R3b and 5-bromo-4-methyl-thiazole-2-carboxylic acid as reagents, the resulted crude product was reacted with (2-methyl-4-pyridyl)boronic acid according to General Procedure 9, to give EXAMPLE 622. HRMS calculated for $C_{36}H_{39}N_7O_4S$: 665.2784; found 666.2863 [(M+H)⁺ form].

3-[(4-hydroxy-1-{[(3R,4R)-1-{[2-(2-methoxypyridin-4-yl)-4-methyl-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 623)

Using General Procedure 9 starting from EXAMPLE 349 and (2-methoxy-4-pyridyl)boronic acid as reagents, EXAMPLE 623 was obtained. HRMS calculated for $C_{36}H_{39}N_7O_5S$: 681.2733; found 682.2807 [(M+H)⁺ form].

3-[(1-{[(3R,4R)-1-{[3-fluoro-5-(2-methoxy-6-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 624)

Using General Procedure 9 starting from EXAMPLE 269 and 2-methoxy-6-methyl-4-(4,4,5,5-tetramethyl-1,3,2-dioxaborolan-2-yl)pyridine as reagents, EXAMPLE 624 was obtained. HRMS calculated for $C_{37}H_{39}FN_6O_5S$: 698.2687; found 699.2764 [(M+H)⁺ form].

3-[(4-hydroxy-1-{[(3R,4R)-1-{[4-methyl-2-(2-methylpyridin-4-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 625)

Using General Procedure 9 starting from EXAMPLE 349 and (2-methyl-4-pyridyl)boronic acid as reagents, EXAMPLE 625 was obtained. HRMS calculated for $C_{36}H_{39}N_7O_4S$: 665.2784; found 666.287 [(M+H)⁺ form].

3-[(1-{[(3R,4R)-1-{[3-fluoro-5-(pyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 626)

Using General Procedure 9 starting from EXAMPLE 269 and 3-pyridylboronic acid as reagents, EXAMPLE 626 was obtained. HRMS calculated for $C_{35}H_{35}FN_6O_4S$: 654.2424; found 655.2505 [(M+H)⁺ form].

3-[(1-{[(3R,4R)-1-{[3-fluoro-5-(3-methoxypyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 627)

Using General Procedure 9 starting from EXAMPLE 269 and (3-methoxy-4-pyridyl)boronic acid as reagents, EXAMPLE 627 was obtained. HRMS calculated for $C_{36}H_{37}FN_6O_5S$: 684.2530; found 685.2598 [(M+H)⁺ form].

tert-butyl [4-(4-fluoro-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}thiophen-2-yl)pyridin-2-yl]carbamate (Example 628)

Using General Procedure 9 starting from EXAMPLE 269 and tert-butyl N-[4-(4,4,5,5-tetramethyl-1,3,2-dioxaborolan-2-yl)-2-pyridyl]carbamate as reagents, EXAMPLE 628 was obtained. HRMS calculated for $C_{40}H_{44}FN_7O_6S$: 769.3058; found 770.3118 [(M+H)⁺ form].

3-[(4-hydroxy-1-{[(3R,4R)-1-{[3-methyl-5-(pyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 629)

Using General Procedure 7 starting from Preparation R3b and 5-bromo-3-methyl-thiophene-2-carboxylic acid as reagents, the resulted crude product was reacted with 4-(4,4,5,5-tetramethyl-1,3,2-dioxaborolan-2-yl)pyridine according to General Procedure 9, to give EXAMPLE 629. HRMS calculated for $C_{36}H_{38}N_6O_4S$: found 651.2752 [(M+H)⁺ form].

3-[(1-{[(3R,4R)-1-{[3-fluoro-5-(6-methoxypyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 630)

Using General Procedure 9 starting from EXAMPLE 269 and (6-methoxy-3-pyridyl)boronic acid as reagents, EXAMPLE 630 was obtained. HRMS calculated for $C_{36}H_{37}FN_6O_5S$: 684.253; found 685.2619 [(M+H)⁺ form].

3-[(4-hydroxy-1-{[(3R,4R)-1-{[5-(6-methoxypyridin-3-yl)-3-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 631)

Using General Procedure 7 starting from Preparation R3b and 5-bromo-3-methyl-thiophene-2-carboxylic acid as reagents, the resulted crude product was reacted with (6-methoxy-3-pyridyl)boronic acid according to General Procedure 9, to give EXAMPLE 631. HRMS calculated for $C_{37}H_{40}N_6O_5S$: 680.2781; found 681.2868 [(M+H)⁺ form].

3-[(1-{[(3R,4R)-1-{[5-(6-aminopyridin-3-yl)-3-fluorothiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 632)

Using General Procedure 9 starting from EXAMPLE 269 and 5-(4,4,5,5-tetramethyl-1,3,2-dioxaborolan-2-yl)pyridin-2-amine as reagents, EXAMPLE 632 was obtained. HRMS calculated for $C_{35}H_{36}FN_7O_4S$: 669.2534; found 335.6352 $(M+2H)^{2+}$ form].

3-[(1-{[(3R,4R)-1-{[5-(6-aminopyridin-3-yl)-3-methylthiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 633)

Using General Procedure 7 starting from Preparation R3b and 5-bromo-3-methyl-thiophene-2-carboxylic acid as reagents, the resulted crude product was reacted with 5-(4,4,5,5-tetramethyl-1,3,2-dioxaborolan-2-yl)pyridin-2-amine according to General Procedure 9, to give EXAMPLE 633. HRMS calculated for $C_{36}H_{39}N_7O_4S$: 665.2784; found 333.647 [(M+2H)$^{2+}$ form].

3-[(4-hydroxy-1-{[(3R,4R)-1-{[3-methyl-5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 634)

Using General Procedure 7 starting from Preparation R3b and 5-bromo-3-methyl-thiophene-2-carboxylic acid as reagents, the resulted crude product was reacted with (6-methyl-3-pyridyl)boronic acid according to General Procedure 9, to give EXAMPLE 634. HRMS calculated for $C_{37}H_{40}N_6O_4S$: 664.2832; found 665.2914 [(M+H)$^+$ form].

3-{[4-hydroxy-1-({(3R,4R)-1-[(3-methyl-2,3'-bithiophen-5-yl)carbonyl]-3-phenylpiperidin-4-yl}carbonyl)piperidin-4-yl]methyl}-7-methyl-3,7-dihydro-4H-pyrrolo[2,3-d]pyrimidin-4-one (Example 635)

Using General Procedure 7 starting from Preparation R3b and 5-bromo-4-methyl-thiophene-2-carboxylic acid as reagents, the resulted crude product was reacted with 4,4,5,5-tetramethyl-2-(3-thienyl)-1,3,2-dioxaborolane according to General Procedure 9, to give EXAMPLE 635. HRMS calculated for $C_{35}H_{37}N_5O_4S_2$: 655.2287; found 656.2362 [(M+H)$^+$ form].

3-[(4-hydroxy-1-{[(3R,4R)-1-{[4-methyl-5-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 636)

Using General Procedure 7 starting from Preparation R3b and 5-bromo-4-methyl-thiophene-2-carboxylic acid as reagents, the resulted crude product was reacted with (2-methyl-4-pyridyl)boronic acid according to General Procedure 9, to give EXAMPLE 636. HRMS calculated for $C_{37}H_{40}N_6O_4S$: 664.2832; found 665.2913 [(M+H)$^+$ form].

3-[(4-hydroxy-1-{[(3R,4R)-1-{[5-(2-methoxypyridin-4-yl)-4-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 637)

Using General Procedure 7 starting from Preparation R3b and 5-bromo-4-methyl-thiophene-2-carboxylic acid as reagents, the resulted crude product was reacted with (2-methoxy-4-pyridyl)boronic acid according to General Procedure 9, to give EXAMPLE 637. HRMS calculated for $C_{37}H_{40}N_6O_5S$: 680.2781; found [(681.2854 (M+H)$^+$ form].

3-[(4-hydroxy-1-{[(3R,4R)-1-{[4-methyl-5-(pyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 638)

Using General Procedure 7 starting from Preparation R3b and 5-bromo-4-methyl-thiophene-2-carboxylic acid as reagents, the resulted crude product was reacted with 3-pyridylboronic acid according to General Procedure 9, to give EXAMPLE 638. HRMS calculated for $C_{36}H_{38}N_6O_4S$: 650.2675; found 651.2737 [(M+H)$^+$ form].

3-[(4-hydroxy-1-{[(3R,4R)-1-{[5-(3-methoxypyridin-4-yl)-4-methylthiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 639)

Using General Procedure 7 starting from Preparation R3b and 5-bromo-4-methyl-thiophene-2-carboxylic acid as reagents, the resulted crude product was reacted with (3-methoxy-4-pyridyl)boronic acid according to General Procedure 9, to give EXAMPLE 639. HRMS calculated for $C_{37}H_{40}N_6O_5S$: 680.2781; found 681.2859 [(M+H)$^+$ form].

3-[(4-hydroxy-1-{[(3R,4R)-1-({4-methyl-2-[2-(trifluoromethyl)pyridin-4-yl]-1,3-thiazol-5-yl}carbonyl)-3-phenylpiperidin-4-yl]carbonyl}piperidin-4-yl)methyl]-7-methyl-3,7-dihydro-4H-pyrrolo[2,3-d]pyrimidin-4-one (Example 640)

Using General Procedure 9 starting from EXAMPLE 349 and 4-(4,4,5,5-tetramethyl-1,3,2-dioxaborolan-2-yl)-2-(trifluoromethyl)pyridine as reagents, EXAMPLE 640 was obtained. HRMS calculated for $C_{36}H_{36}F_3N_7O_4S$: 719.2502; found 720.2566 [(M+H)$^+$ form].

3-[(1-{[(3R,4R)-1-({3-fluoro-5-[2-(trifluoromethyl)pyridin-4-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 641)

Using General Procedure 9 starting from EXAMPLE 269 and 4-(4,4,5,5-tetramethyl-1,3,2-dioxaborolan-2-yl)-2-(trifluoromethyl)pyridine as reagents, EXAMPLE 641 was obtained. HRMS calculated for $C_{36}H_{34}F_4N_6O_4S$: 722.2299; found 723.2378 [(M+H)$^+$ form].

3-{[1-({(3R,4R)-1-[(4-fluoro-2,3'-bithiophen-5-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 642)

Using General Procedure 9 starting from EXAMPLE 269 and 4,4,5,5-tetramethyl-2-(3-thienyl)-1,3,2-dioxaborolane as reagents, EXAMPLE 642 was obtained. HRMS calculated for $C_{34}H_{34}FN_5O_4S_2$: 659.2036; found 660.2108 [(M+H)$^+$ form].

3-[(4-hydroxy-1-{[(3R,4R)-1-{[5-(2-methylpyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 643)

Using General Procedure 7 starting from Preparation R3b and 5-bromothiazole-2-carboxylic acid as reagents, the resulted crude product was reacted with (2-methyl-4-pyridyl)boronic acid according to General Procedure 9, to give EXAMPLE 643. HRMS calculated for $C_{35}H_{37}N_7O_4S$: 651.26276; found 652.2709 [(M+H)$^+$ form].

tert-butyl [4-(2-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-1,3-thiazol-5-yl)pyridin-2-yl]carbamate (Example 644)

Using General Procedure 7 starting from Preparation R3b and 5-bromothiazole-2-carboxylic acid as reagents, the resulted crude product was reacted with tert-butyl N-[4-(4,4,5,5-tetramethyl-1,3,2-dioxaborolan-2-yl)-2-pyridyl]carbamate according to General Procedure 9, to give EXAMPLE 644. HRMS calculated for $C_{39}H_{44}N_8O_6S$: 752.3104; found 753.318 [(M+H)$^+$ form].

tert-butyl [4-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-4-methyl-1,3-thiazol-2-yl)pyridin-2-yl]carbamate (Example 645)

Using General Procedure 9 starting from EXAMPLE 349 and tert-butyl N-[4-(4,4,5,5-tetramethyl-1,3,2-dioxaborolan-2-yl)-2-pyridyl]carbamate as reagents, EXAMPLE 645 was obtained. HRMS calculated for $C_{40}H_{46}N_8O_6S$: 766.3261; found 767.3336 [(M+H)$^+$ form].

3-[(4-hydroxy-1-{[(3R,4R)-1-{[4-methyl-3,5-bis(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 646) and 3-[(1-{[(3R,4R)-1-{[3-chloro-4-methyl-5-(2-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 647)

Using General Procedure 9 starting from EXAMPLE 239 and (2-methyl-4-pyridyl)boronic acid as reagents, EXAMPLE 646 and EXAMPLE 647 were obtained and separated by chromatography.

Example 646

HRMS calculated for $C_{43}H_{45}N_7O_4S$: 755.3254; found 756.3331 [(M+H)$^+$ form].

Example 647

HRMS calculated for $C_{37}H_{39}ClN_6O_4S$: 698.2442; found 699.253 [(M+H)$^+$ form].

3-{[1-({(3R,4R)-1-[(3-chloro-4-methyl-5-phenylthiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 648)

Using General Procedure 9 starting from EXAMPLE 239 and phenylboronic acid as reagents, EXAMPLE 648 was obtained. HRMS calculated for $C_{37}H_{38}ClN_5O_4S$: 683.2333; found 684.241 [(M+H)$^+$ form].

3-[(1-{[(3R,4R)-1-{[3-chloro-4-methyl-5-(pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 649)

Using General Procedure 9 starting from EXAMPLE 239 and 4-(4,4,5,5-tetramethyl-1,3,2-dioxaborolan-2-yl)pyridine as reagents, EXAMPLE 649 was obtained. HRMS calculated for $C_{36}H_{37}ClN_6O_4S$: 684.2286; found 685.2365 [(M+H)$^+$ form].

3-[(4-hydroxy-1-{[(3R,4R)-1-({4-methyl-2-[6-(trifluoromethyl)pyridin-3-yl]-1,3-thiazol-5-yl}carbonyl)-3-phenylpiperidin-4-yl]carbonyl}piperidin-4-yl)methyl]-7-methyl-3,7-dihydro-4H-pyrrolo[2,3-d]pyrimidin-4-one (Example 650)

Using General Procedure 9 starting from EXAMPLE 349 and [6-(trifluoromethyl)-3-pyridyl]boronic acid as reagents, EXAMPLE 650 was obtained. HRMS calculated for $C_{36}H_{36}F_3N_7O_4S$: 719.2502; found 720.2575 [(M+H)$^+$ form].

3-[(1-{[(3R,4R)-1-{[2-(2,6-difluoropyridin-3-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 651)

Using General Procedure 9 starting from EXAMPLE 349 and (2,6-difluoro-3-pyridyl)boronic acid as reagents, EXAMPLE 651 was obtained. HRMS calculated for $C_{35}H_{35}F_2N_7O_4S$: 687.2440; found 688.2516 [(M+H)$^+$ form].

3-[(1-{[(3R,4R)-1-{[2-(6-fluoropyridin-3-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 652)

Using General Procedure 9 starting from EXAMPLE 349 and (6-fluoro-3-pyridyl)boronic acid as reagents, EXAMPLE 652 was obtained. HRMS calculated for $C_{35}H_{36}FN_7O_4S$: 669.25336; found 670.2603 [(M+H)$^+$ form].

3-[(1-{[(3R,4R)-1-{[3-fluoro-4-(pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 653)

and

3-[(1-{[(3R,4R)-1-{[3-fluoro-4,5-di(pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 654)

Using General Procedure 9 starting from EXAMPLE 232 and 4-(4,4,5,5-tetramethyl-1,3,2-dioxaborolan-2-yl)pyridine as reagents, EXAMPLE 653 (dehalogenated byproduct) and EXAMPLE 654 were obtained and separated by chromatography.

Example 653

HRMS calculated for $C_{35}H_{35}FN_6O_4S$: 654.2424; found 655.2502 [(M+H)$^+$ form].

Example 654

HRMS calculated for $C_{40}H_{38}FN_7O_4S$: 731.2690; found 732.2764 [(M+H)$^+$ form].

3-[(1-{[(3R,4R)-1-{[3-chloro-4-methyl-5-(6-methyl-pyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 655)

Using General Procedure 9 starting from EXAMPLE 239 and (6-methyl-3-pyridyl)boronic acid as reagents, EXAMPLE 655 was obtained. HRMS calculated for $C_{37}H_{39}ClN_6O_4S$: 698.2442; found 699.2514 [(M+H)$^+$ form].

3-[(1-{[(3R,4R)-1-({3-chloro-4-methyl-5-[2-(trifluoromethyl)pyridin-4-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 656)

Using General Procedure 9 starting from EXAMPLE 239 and 4-(4,4,5,5-tetramethyl-1,3,2-dioxaborolan-2-yl)-2-(trifluoromethyl)pyridine as reagents, EXAMPLE 656 was obtained. HRMS calculated for $C_{37}H_{36}ClF_3N_6O_4S$: 752.2159; found 753.2258 [(M+H)$^+$ form].

tert-butyl [4-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-1,3-thiazol-2-yl)pyridin-2-yl]carbamate (Example 657)

Using General Procedure 7 starting from Preparation R3b and 2-bromothiazole-5-carboxylic acid as reagents, the resulted crude product was reacted with tert-butyl N-[4-(4,4,5,5-tetramethyl-1,3,2-dioxaborolan-2-yl)-2-pyridyl]carbamate according to General Procedure 9, to give EXAMPLE 657. HRMS calculated for $C_{39}H_{44}N_8O_6S$: 752.3104; found 753.3187 [(M+H)$^+$ form].

3-[(4-hydroxy-1-{[(3R,4R)-1-{[3-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 658)

Using General Procedure 9 starting from EXAMPLE 247 and (2-methyl-4-pyridyl)boronic acid as reagents, EXAMPLE 658 was obtained. HRMS calculated for $C_{36}H_{38}N_6O_4S$: 650.2675; found 651.2767 [(M+H)$^+$ form].

3-[(4-hydroxy-1-{[(3R,4R)-3-phenyl-1-{[3-(pyridin-4-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 659)

Using General Procedure 9 starting from EXAMPLE 247 and 4-(4,4,5,5-tetramethyl-1,3,2-dioxaborolan-2-yl)pyridine as reagents, EXAMPLE 659 was obtained. HRMS calculated for $C_{35}H_{36}N_6O_4S$: 636.2519; found 637.2606 [(M+H)$^+$ form].

3-[(4-hydroxy-1-{[(3R,4R)-1-{[3-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 660)

Using General Procedure 9 starting from EXAMPLE 247 and (6-methyl-3-pyridyl)boronic acid as reagents, EXAMPLE 660 was obtained. HRMS calculated for $C_{36}H_{38}N_6O_4S$: 650.2675; found 651.2762 [(M+H)$^+$ form].

3-[(4-hydroxy-1-{[(3R,4R)-3-phenyl-1-{[3-(pyridin-3-yl)thiophen-2-yl]carbonyl}piperidin-4-yl]carbonyl}piperidin-4-yl)methyl]-7-methyl-3,7-dihydro-4H-pyrrolo[2,3-d]pyrimidin-4-one (Example 661)

Using General Procedure 9 starting from EXAMPLE 247 and 3-pyridylboronic acid as reagents, EXAMPLE 661 was obtained. HRMS calculated for $C_{35}H_{36}N_6O_4S$: 636.2519; found 637.2617 [(M+H)$^+$ form].

3-[(4-hydroxy-1-{[(3R,4R)-3-phenyl-1-{[4-(pyridin-4-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 662)

Using General Procedure 9 starting from EXAMPLE 248 and 4-(4,4,5,5-tetramethyl-1,3,2-dioxaborolan-2-yl)pyridine as reagents, EXAMPLE 662 was obtained. HRMS calculated for $C_{34}H_{35}N_7O_4S$: 637.2471; found 638.2564 [(M+H)$^+$ form].

3-[(4-hydroxy-1-{[(3R,4R)-1-{[4-(6-methylpyridin-3-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 663)

Using General Procedure 9 starting from EXAMPLE 248 and (6-methyl-3-pyridyl)boronic acid as reagents, EXAMPLE 663 was obtained. HRMS calculated for $C_{35}H_{37}N_7O_4S$: 651.26276; found 652.272 [(M+H)$^+$ form].

3-[(4-hydroxy-1-{[(3R,4R)-3-phenyl-1-{[4-(pyridin-3-yl)-1,3-thiazol-2-yl]carbonyl}piperidin-4-yl]carbonyl}piperidin-4-yl)methyl]-7-methyl-3,7-dihydro-4H-pyrrolo[2,3-d]pyrimidin-4-one (Example 664)

Using General Procedure 9 starting from EXAMPLE 248 and 3-pyridylboronic acid as reagents, EXAMPLE 664 was obtained. HRMS calculated for $C_{34}H_{35}N_7O_4S$: 637.2471; found 638.256 [(M+H)⁺ form].

3-[(4-hydroxy-1-{[(3R,4R)-1-{[4-(2-methylpyridin-4-yl)-1,3-thiazol-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 665)

Using General Procedure 9 starting from EXAMPLE 248 and (2-methyl-4-pyridyl)boronic acid as reagents, EXAMPLE 665 was obtained. HRMS calculated for $C_{35}H_{37}N_7O_4S$: 651.2628; found 652.2727 [(M+H)⁺ form].

3-[(4-hydroxy-1-{[(3R,4R)-3-phenyl-1-{[5-(pyridin-4-yl)thiophen-3-yl]carbonyl}piperidin-4-yl]carbonyl}piperidin-4-yl)methyl]-7-methyl-3,7-dihydro-4H-pyrrolo[2,3-d]pyrimidin-4-one (Example 666)

Using General Procedure 9 starting from EXAMPLE 249 and 4-(4,4,5,5-tetramethyl-1,3,2-dioxaborolan-2-yl)pyridine as reagents, EXAMPLE 666 was obtained. HRMS calculated for $C_{35}H_{36}N_6O_4S$: 636.2519; found 637.2601 [(M+H)⁺ form].

3-[(4-hydroxy-1-{[(3R,4R)-1-{[5-(6-methylpyridin-3-yl)thiophen-3-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 667)

Using General Procedure 9 starting from EXAMPLE 249 and (6-methyl-3-pyridyl)boronic acid as reagents, EXAMPLE 667 was obtained. HRMS calculated for $C_{36}H_{38}N_6O_4S$: 650.2675; found 651.2766 [(M+H)⁺ form].

3-[(4-hydroxy-1-{[(3R,4R)-3-phenyl-1-{[5-(pyridin-3-yl)thiophen-3-yl]carbonyl}piperidin-4-yl]carbonyl}piperidin-4-yl)methyl]-7-methyl-3,7-dihydro-4H-pyrrolo[2,3-d]pyrimidin-4-one (Example 668)

Using General Procedure 9 starting from EXAMPLE 249 and 3-pyridylboronic acid as reagents, EXAMPLE 668 was obtained. HRMS calculated for $C_{35}H_{36}N_6O_4S$: 636.2519; found 637.26 [(M+H)⁺ form].

3-[(4-hydroxy-1-{[(3R,4R)-1-{[5-(2-methylpyridin-4-yl)thiophen-3-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 669)

Using General Procedure 9 starting from EXAMPLE 249 and (2-methyl-4-pyridyl)boronic acid as reagents, EXAMPLE 669 was obtained. HRMS calculated for $C_{36}H_{38}N_6O_4S$: 650.2675; found 651.2756 [(M+H)⁺ form].

3-[(4-hydroxy-1-{[(3R,4R)-3-phenyl-1-{[2-(pyridin-4-yl)thiophen-3-yl]carbonyl}piperidin-4-yl]carbonyl}piperidin-4-yl)methyl]-7-methyl-3,7-dihydro-4H-pyrrolo[2,3-d]pyrimidin-4-one (Example 670)

Using General Procedure 9 starting from EXAMPLE 250 and 4-(4,4,5,5-tetramethyl-1,3,2-dioxaborolan-2-yl)pyridine as reagents, EXAMPLE 670 was obtained. HRMS calculated for $C_{35}H_{36}N_6O_4S$: 636.2519; found 637.2615 [(M+H)⁺ form].

3-[(4-hydroxy-1-{[(3R,4R)-3-phenyl-1-{[2-(pyridin-3-yl)-1,3-thiazol-5-yl]carbonyl}piperidin-4-yl]carbonyl}piperidin-4-yl)methyl]-7-methyl-3,7-dihydro-4H-pyrrolo[2,3-d]pyrimidin-4-one (Example 671)

Using General Procedure 7 starting from Preparation R3b and 2-bromothiazole-5-carboxylic acid as reagents, the resulted crude product was reacted with 3-pyridylboronic acid according to General Procedure 9, to give EXAMPLE 671. HRMS calculated for $C_{34}H_{35}N_7O_4S$: 637.2471; found 638.2542 [(M+H)⁺ form].

3-[(4-hydroxy-1-{[(3R,4R)-1-{[2-(2-methylpyridin-4-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 672)

Using General Procedure 7 starting from Preparation R3b and 2-bromothiazole-5-carboxylic acid as reagents, the resulted crude product was reacted with (2-methyl-4-pyridyl)boronic acid according to General Procedure 9, to give EXAMPLE 672. HRMS calculated for $C_{35}H_{37}N_7O_4S$: 651.2628; found 652.2702 [(M+H)⁺ form].

3-[(4-hydroxy-1-{[(3R,4R)-1-{[2-(6-methoxypyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 673)

Using General Procedure 7 starting from Preparation R3b and 2-bromothiazole-5-carboxylic acid as reagents, the resulted crude product was reacted with (6-methoxy-3-pyridyl)boronic acid according to General Procedure 9, to give EXAMPLE 673. HRMS calculated for $C_{35}H_{37}N_7O_5S$: 667.2577; found 668.2648 [(M+H)⁺ form].

3-[(1-{[(3R,4R)-1-{[2-(6-aminopyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 674)

Using General Procedure 7 starting from Preparation R3b and 2-bromothiazole-5-carboxylic acid as reagents, the resulted crude product was reacted with 5-(4,4,5,5-tetramethyl-1,3,2-dioxaborolan-2-yl)pyridin-2-amine according to General Procedure 9, to give EXAMPLE 674. HRMS calculated for $C_{34}H_{36}N_8O_4S$: 652.2580; found 327.1370 [(M+2H)²⁺ form].

3-[(4-hydroxy-1-{[(3R,4R)-3-phenyl-1-({2-[2-(trifluoromethyl)pyridin-4-yl]-1,3-thiazol-5-yl}carbonyl)piperidin-4-yl]carbonyl}piperidin-4-yl)methyl]-7-methyl-3,7-dihydro-4H-pyrrolo[2,3-d]pyrimidin-4-one (Example 675)

Using General Procedure 7 starting from Preparation R3b and 2-bromothiazole-5-carboxylic acid as reagents, the resulted crude product was reacted with 4-(4,4,5,5-tetramethyl-1,3,2-dioxaborolan-2-yl)-2-(trifluoromethyl)pyridine according to General Procedure 9, to give EXAMPLE 675. HRMS calculated for $C_{35}H_{34}F_3N_7O_4S$: 705.2345; found 706.2403 [(M+H)$^+$ form].

3-[(4-hydroxy-1-{[(3R,4R)-1-{[2-(3-methoxypyridin-4-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 676)

Using General Procedure 7 starting from Preparation R3b and 2-bromothiazole-5-carboxylic acid as reagents, the resulted crude product was reacted with (3-methoxy-4-pyridyl)boronic acid according to General Procedure 9, to give EXAMPLE 676. HRMS calculated for $C_{35}H_{37}N_7O_5S$: 667.2577; found 668.2638 [(M+H)$^+$ form].

3-[(4-hydroxy-1-{[(3R,4R)-3-phenyl-1-{[2-(thiophen-3-yl)-1,3-thiazol-5-yl]carbonyl}piperidin-4-yl]carbonyl}piperidin-4-yl)methyl]-7-methyl-3,7-dihydro-4H-pyrrolo[2,3-d]pyrimidin-4-one (Example 677)

Using General Procedure 7 starting from Preparation R3b and 2-bromothiazole-5-carboxylic acid as reagents, the resulted crude product was reacted with 4,4,5,5-tetramethyl-2-(3-thienyl)-1,3,2-dioxaborolane according to General Procedure 9, to give EXAMPLE 677. HRMS calculated for $C_{33}H_{34}N_6O_4S_2$: 642.2083; found 643.2151 [(M+H)$^+$ form].

3-[(4-hydroxy-1-{[(3R,4R)-1-{[2-(6-methylpyridin-3-yl)-1,3-thiazol-5-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 678)

Using General Procedure 7 starting from Preparation R3b and 2-bromothiazole-5-carboxylic acid as reagents, the resulted crude product was reacted with (6-methyl-3-pyridyl)boronic acid according to General Procedure 9, to give EXAMPLE 678. HRMS calculated for $C_{35}H_{37}N_7O_4S$: 651.2628; found 652.2696 [(M+H)$^+$ form].

3-[(4-hydroxy-1-{[(3R,4R)-1-{[2-(6-methylpyridin-3-yl)thiophen-3-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 679)

Using General Procedure 9 starting from EXAMPLE 250 and (6-methyl-3-pyridyl)boronic acid as reagents, EXAMPLE 679 was obtained. HRMS calculated for $C_{36}H_{38}N_6O_4S$: 650.2675; found 651.277 [(M+H)$^+$ form].

3-[(4-hydroxy-1-{[(3R,4R)-3-phenyl-1-{[2-(pyridin-3-yl)thiophen-3-yl]carbonyl}piperidin-4-yl]carbonyl}piperidin-4-yl)methyl]-7-methyl-3,7-dihydro-4H-pyrrolo[2,3-d]pyrimidin-4-one (Example 680)

Using General Procedure 9 starting from EXAMPLE 250 and 3-pyridylboronic acid as reagents, EXAMPLE 680 was obtained. HRMS calculated for $C_{35}H_{36}N_6O_4S$: 636.2519; found 637.2603 [(M+H)$^+$ form].

3-[(4-hydroxy-1-{[(3R,4R)-1-{[2-(2-methylpyridin-4-yl)thiophen-3-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 681)

Using General Procedure 9 starting from EXAMPLE 250 and (2-methyl-4-pyridyl)boronic acid as reagents, EXAMPLE 681 was obtained. HRMS calculated for $C_{36}H_{38}N_6O_4S$: 650.2675; found 651.2761 [(M+H)$^+$ form].

3-[(1-{[(3R,4R)-1-{[3-chloro-5-(pyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 682)

Using General Procedure 9 starting from EXAMPLE 253 and 3-pyridylboronic acid as reagents, EXAMPLE 682 was obtained. HRMS calculated for $C_{35}H_{35}ClN_6O_4S$: 670.2129; found 671.2205 [(M+H)$^+$ form].

3-[(1-{[(3R,4R)-1-{[3-chloro-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 683)

Using General Procedure 9 starting from EXAMPLE 253 and (6-methyl-3-pyridyl)boronic acid as reagents, EXAMPLE 683 was obtained. HRMS calculated for $C_{36}H_{37}ClN_6O_4S$: 684.2286; found 685.2368 [(M+H)$^+$ form].

3-[(1-{[(3R,4R)-1-({3-chloro-5-[6-(trifluoromethyl)pyridin-3-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 684)

Using General Procedure 9 starting from EXAMPLE 253 and [6-(trifluoromethyl)-3-pyridyl]boronic acid as reagents, EXAMPLE 684 was obtained. HRMS calculated for $C_{36}H_{34}ClF_3N_6O_4S$: 738.2003; found 739.2071 [(M+H)$^+$ form].

3-[(1-{[(3R,4R)-1-({5-[6-(dimethylamino)pyridin-3-yl]-3-fluorothiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 685)

Using General Procedure 9 starting from EXAMPLE 269 and [6-(dimethylamino)-3-pyridyl]boronic acid as reagents, EXAMPLE 685 was obtained. HRMS calculated for $C_{37}H_{40}FN_7O_4S$: 697.2847; found 349.6491 [(M+2H)$^{2+}$ form].

3-{[1-({(3R,4R)-1-[(4-chloro-3-fluorothiophen-2-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 686)

Using General Procedure 9 starting from EXAMPLE 259 and (6-methyl-3-pyridyl)boronic acid as reagents, EXAMPLE 686 was obtained as dehalogenated byproduct. HRMS calculated for $C_{30}H_{31}ClFN_5O_4S$: 611.1769; found 612.1852 [(M+H)$^+$ form].

3-[(1-{[(3R,4R)-1-({5-[6-(cyclopropylmethoxy)pyridin-3-yl]-3-fluorothiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 687)

Using General Procedure 9 starting from EXAMPLE 269 and 2-(cyclopropylmethoxy)-5-(4,4,5,5-tetramethyl-1,3,2-dioxaborolan-2-yl)pyridine as reagents, EXAMPLE 687 was obtained. HRMS calculated for $C_{39}H_{41}FN_6O_5S$: 724.2843; found 363.1484 [(M+2H)$^{2+}$ form].

3-[(1-{[(3R,4R)-1-{[5-(6-ethoxypyridin-3-yl)-3-fluorothiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 688)

Using General Procedure 9 starting from EXAMPLE 269 and (6-ethoxy-3-pyridyl)boronic acid as reagents, EXAMPLE 688 was obtained. HRMS calculated for $C_{37}H_{39}FN_6O_5S$: 698.2687; found 350.1408 [(M+2H)$^{2+}$ form].

3-[(1-{[(3R,4R)-1-{[4-chloro-3-fluoro-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 689)

Using General Procedure 9 starting from EXAMPLE 259 and (6-methyl-3-pyridyl)boronic acid as reagents, EXAMPLE 689 was obtained. HRMS calculated for $C_{36}H_{36}ClFN_6O_4S$: 702.2191; found 703.2265 [(M+H)$^+$ form].

5-(4-fluoro-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}thiophen-2-yl)pyridine-2-carbonitrile (Example 690)

Using General Procedure 9 starting from EXAMPLE 269 and (6-cyano-3-pyridyl)boronic acid as reagents, EXAMPLE 690 was obtained. HRMS calculated for $C_{36}H_{34}FN_7O_4S$: 679.2377; found 680.2461 [(M+H)$^+$ form].

3-[(1-{[(3R,4R)-1-{[3-chloro-5-(2-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 691)

Using General Procedure 9 starting from EXAMPLE 253 and (2-methyl-4-pyridyl)boronic acid as reagents, EXAMPLE 691 was obtained. HRMS calculated for $C_{36}H_{37}ClN_6O_4S$: 684.2286; found 685.2357 [(M+H)$^+$ form].

3-[(1-{[(3R,4R)-1-{[3-fluoro-4-methyl-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 692)

Using General Procedure 9 starting from EXAMPLE 261 and (6-methyl-3-pyridyl)boronic acid as reagents, EXAMPLE 692 was obtained. HRMS calculated for $C_{37}H_{39}FN_6O_4S$: 682.2737; found 683.2826 [(M+H)$^+$ form].

3-[(1-{[(3R,4R)-1-{[3-fluoro-4-methyl-5-(2-methylpyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 693)

Using General Procedure 9 starting from EXAMPLE 261 and (2-methyl-4-pyridyl)boronic acid as reagents, EXAMPLE 693 was obtained. HRMS calculated for $C_{37}H_{39}FN_6O_4S$: 682.2737; found 683.2816 [(M+H)$^+$ form].

3-[(1-{[(3R,4R)-1-{[4-cyclopropyl-2-(6-methylpyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 694)

Using General Procedure 9 starting from EXAMPLE 263 and cyclopropyl boronic acid as reagents, EXAMPLE 694 was obtained. HRMS calculated for $C_{38}H_{41}N_7O_4S$: 691.2941; found 692.3038 [(M+H)$^+$ form].

3-[(1-{[(3R,4R)-1-{[3-fluoro-5-(6-methoxypyridin-3-yl)-4-methylthiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 695)

Using General Procedure 9 starting from EXAMPLE 261 and (6-methoxy-3-pyridyl)boronic acid as reagents, EXAMPLE 695 was obtained. HRMS calculated for $C_{37}H_{39}FN_6O_5S$: 698.2687; found 350.1423 [(M+2H)$^{2+}$ form].

3-[(1-{[(3R,4R)-1-({3-fluoro-4-methyl-5-[6-(trifluoromethyl)pyridin-3-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 696)

Using General Procedure 9 starting from EXAMPLE 261 and [6-(trifluoromethyl)-3-pyridyl]boronic acid as reagents, EXAMPLE 696 was obtained. HRMS calculated for $C_{37}H_{36}F_4N_6O_4S$: 736.2455; found 737.2549 [(M+H)$^+$ form].

3-[(1-{[(3R,4R)-1-{[3-fluoro-5-(imidazo[1,2-a]pyridin-7-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 697)

Using General Procedure 9 starting from EXAMPLE 269 and imidazo[1,2-a]pyridin-7-ylboronic acid as reagents, EXAMPLE 697 was obtained. HRMS calculated for $C_{37}H_{36}FN_7O_4S$: 693.2534; found 694.2616 [(M+H)$^+$ form].

3-[(1-{[(3R,4R)-1-({2-[6-(dimethylamino)pyridin-3-yl]-4-methyl-1,3-thiazol-5-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 698)

Using General Procedure 9 starting from EXAMPLE 349 and [6-(dimethylamino)-3-pyridyl]boronic acid as reagents, EXAMPLE 698 was obtained. HRMS calculated for $C_{37}H_{42}N_8O_4S$: 694.3050; found 695.3133 [(M+H)$^+$ form].

3-[(1-{[(3R,4R)-1-({3-fluoro-5-[6-(piperazin-1-yl)pyridin-3-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 699)

Using General Procedure 9 starting from EXAMPLE 269 and 1-[5-(4,4,5,5-tetramethyl-1,3,2-dioxaborolan-2-yl)-2-pyridyl]piperazine as reagents, EXAMPLE 699 was obtained. HRMS calculated for $C_{39}H_{43}FN_8O_4S$: 738.3112; found 739.3183 [(M+H)$^+$ form].

3-[(1-{[(3R,4R)-1-({2-[6-(cyclopropylmethoxy)pyridin-3-yl]-4-methyl-1,3-thiazol-5-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 700)

Using General Procedure 9 starting from EXAMPLE 349 and 2-(cyclopropylmethoxy)-5-(4,4,5,5-tetramethyl-1,3,2-dioxaborolan-2-yl)pyridine as reagents, EXAMPLE 700 was obtained. HRMS calculated for $C_{39}H_{43}N_7O_5S$: 721.3046; found 722.3118 [(M+H)$^+$ form].

5-(5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-4-methyl-1,3-thiazol-2-yl)pyridine-2-carbonitrile (Example 701)

Using General Procedure 9 starting from EXAMPLE 349 and (6-cyano-3-pyridyl)boronic acid as reagents, EXAMPLE 701 was obtained. HRMS calculated for $C_{36}H_{36}N_8O_4S$: 676.2580; found 677.2649 [(M+H)$^+$ form].

3-[(4-hydroxy-1-{[(3R,4R)-1-{[4-(methoxymethyl)-5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 702)

Using General Procedure 7 starting from Preparation R3b and 5-bromo-4-(methoxymethyl)thiophene-2-carboxylic acid as reagents, the resulted crude product was reacted with (6-methyl-3-pyridyl)boronic acid according to General Procedure 9, to give EXAMPLE 702. HRMS calculated for $C_{38}H_{42}N_6O_5S$: 694.2938; found 695.302 [(M+H)$^+$ form].

3-[(4-hydroxy-1-{[(3R,4R)-1-{[4-(methoxymethyl)-5-(2-methylpyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 703)

Using General Procedure 7 starting from Preparation R3b and 5-bromo-4-(methoxymethyl)thiophene-2-carboxylic acid as reagents. The resulted crude product was reacted with (2-methyl-4-pyridyl)boronic acid according to General Procedure 9, to give EXAMPLE 703. HRMS calculated for $C_{38}H_{42}N_6O_5S$: 694.2938; found 695.3030 [(M+H)$^+$ form].

3-[(1-{[(3R,4R)-1-({3-fluoro-5-[6-(2,2,2-trifluoroethoxy)pyridin-3-yl]thiophen-2-yl}carbonyl)-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 704)

Using General Procedure 9 starting from EXAMPLE 269 and [6-(2,2,2-trifluoroethoxy)-3-pyridyl]boronic acid as reagents, EXAMPLE 704 was obtained. HRMS calculated for $C_{37}H_{36}F_4N_6O_5S$: 752.2404; found 753.2476 [(M+H)$^+$ form].

3-[(1-{[(3R,4R)-1-{[3-fluoro-5-(3-methyl-3H-imidazo[4,5-b]pyridin-6-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 705)

Using General Procedure 9 starting from EXAMPLE 269 and 3-methyl-6-(4,4,5,5-tetramethyl-1,3,2-dioxaborolan-2-yl)imidazo[4,5-b]pyridine as reagents, EXAMPLE 705 was obtained. HRMS calculated for $C_{37}H_{37}FN_8O_4S$: 708.2642; found 709.2708 [(M+H)$^+$ form].

3-[(1-{[(3R,4R)-1-{[4-ethyl-2-(6-methylpyridin-3-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 706)

Using General Procedure 9 starting from EXAMPLE 263 and potassium ethyltrifluoroborate as reagents, EXAMPLE 706 was obtained. HRMS calculated for $C_{37}H_{41}N_7O_4S$: 679.2941; found 680.3022 [(M+H)$^+$ form].

3-[(1-{[(3R,4R)-1-{[4-(dimethylamino)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 707)

and

3-[(1-{[(3R,4R)-1-{[4-(dimethylamino)-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 708)

Using General Procedure 9 starting from EXAMPLE 275 and (6-methyl-3-pyridyl)boronic acid as reagents, EXAMPLE 707 (dehalogenated byproduct) and EXAMPLE 708 were obtained and separated by chromatography.

Example 707

HRMS calculated for $C_{32}H_{38}N_6O_4S$: 602.2675; found 603.2751 [(M+H)$^+$ form].

Example 708

HRMS calculated for $C_{38}H_{43}N_7O_4S$: 693.3098; found 694.3175 [(M+H)$^+$ form].

3-[(4-hydroxy-1-{[(3R,4R)-1-{[4-methoxy-5-(6-methylpyridin-3-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one (Example 709)

Using General Procedure 9 starting from EXAMPLE 276 and (6-methyl-3-pyridyl)boronic acid as reagents, EXAMPLE 709 was obtained. HRMS calculated for $C_{37}H_{40}N_6O_5S$: 680.2781; found 681.2860 [(M+H)$^+$ form].

3-[(1-{[(3R,4R)-1-{[4-bromo-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 710)

and

3-[(1-{[(3R,4R)-1-{[4,5-bis(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 711)

Using General Procedure 9 starting from EXAMPLE 277 and (6-methyl-3-pyridyl)boronic acid as reagents, EXAMPLE 710 and EXAMPLE 711 were obtained and separated by chromatography.

Example 710

HRMS calculated for $C_{36}H_{37}N_6O_4SBr$: 728.1780; found 729.1856 [(M+H)$^+$ form].

Example 711

HRMS calculated for $C_{42}H_{43}N_7O_4S$: 741.3098; found 742.3166 [(M+H)$^+$ form].

methyl 3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-5-(6-methylpyridin-3-yl)benzoate (Example 712)

Using General Procedure 9 starting from EXAMPLE 287 and (6-methyl-3-pyridyl)boronic acid as reagents, EXAMPLE 712 was obtained. HRMS calculated for $C_{40}H_{42}N_6O_6$: 702.3166; found 703.323 [(M+H)$^+$ form].
3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 713)

Using General Procedure 9 starting from EXAMPLE 269 and (6-methyl-3-pyridyl)boronic acid as reagents, EXAMPLE 713 was obtained. HRMS calculated for $C_{36}H_{37}FN_6O_4S$: 668.2581; found 669.2661 [(M+H)$^+$ form].

5-[5-({(3R,4R)-4-[(4-{[7-(3-chlorophenyl)-4-oxo-4,7-dihydro-3H-pyrrolo[2,3-d]pyrimidin-3-yl]methyl}-4-hydroxypiperidin-1-yl)carbonyl]-3-phenylpiperidin-1-yl}methyl)-1,3-thiazol-2-yl]pyridine-2-carbonitrile (Example 714)

Using General Procedure 9 starting from EXAMPLE 87 and (6-cyano-3-pyridyl)boronic acid as reagents, EXAMPLE 714 was obtained. HRMS calculated for $C_{40}H_{37}ClN_8O_3S$: 744.2398; found 745.2479 [(M+H)$^+$ form].

7-(3-chlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 715)

Using General Procedure 9 starting from EXAMPLE 87 and (6-methyl-3-pyridyl)boronic acid as reagents, EXAMPLE 715 was obtained. HRMS calculated for $C_{40}H_{40}ClN_7O_3S$: 733.2602; found 734.2693 [(M+H)$^+$ form].

3-[(4-hydroxy-1-{[(3R,4R)-3-phenyl-1-{[2-(thiophen-2-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one (Example 716)

Using General Procedure 9 starting from EXAMPLE 95 and 2-thienylboronic acid as reagents, EXAMPLE 716 was obtained. HRMS calculated for $C_{39}H_{40}N_6O_4S_2$: 720.2552; found 721.2616 [(M+H)$^+$ form].

3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one (Example 717)

Using General Procedure 9 starting from EXAMPLE 95 and pyrimidin-5-ylboronic acid as reagents, EXAMPLE 717 was obtained. HRMS calculated for $C_{39}H_{40}N_8O_4S$: 716.2893; found 717.2989 [(M+H)$^+$ form].

3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 718)

Using General Procedure 9 starting from EXAMPLE 95 and 1-methyl-5-(4,4,5,5-tetramethyl-1,3,2-dioxaborolan-2-yl)pyrazole as reagents, EXAMPLE 718 was obtained. HRMS calculated for $C_{39}H_{42}N_8O_4S$: 718.3050; found 719.3109 [(M+H)$^+$ form].

3-[(4-hydroxy-1-{[(3R,4R)-1-{[2-(1-methyl-1H-pyrazol-4-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 719)

Using General Procedure 9 starting from EXAMPLE 95 and 1-methyl-4-(4,4,5,5-tetramethyl-1,3,2-dioxaborolan-2-yl)pyrazole as reagents, EXAMPLE 719 was obtained. HRMS calculated for $C_{39}H_{42}N_8O_4S$: 718.3050; found 719.3087 [(M+H)$^+$ form].

3-[(4-hydroxy-1-{[(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 720)

Using General Procedure 9 starting from EXAMPLE 95 and 1-methyl-3-(4,4,5,5-tetramethyl-1,3,2-dioxaborolan-2- yl)pyrrole as reagents, EXAMPLE 720 was obtained. HRMS calculated for $C_{40}H_{43}N_7O_4S$: 717.3098; found 718.3169 [(M+H)$^+$ form].

3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one (Example 721)

Using General Procedure 9 starting from EXAMPLE 95 and 4,4,5,5-tetramethyl-2-(3-thienyl)-1,3,2-dioxaborolane as reagents, EXAMPLE 721 was obtained. HRMS calculated for $C_{39}H_{40}N_6O_4S_2$: 720.2552; found 721.2639 [(M+H)$^+$ form].

3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one (Example 722)

Using General Procedure 9 starting from EXAMPLE 95 and 2-(3-furyl)-4,4,5,5-tetramethyl-1,3,2-dioxaborolane as reagents, EXAMPLE 722 was obtained. HRMS calculated for $C_{39}H_{40}N_6O_5S$: 704.2781; found 705.2823 [(M+H)$^+$ form].

3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one (Example 723)

Using General Procedure 9 starting from EXAMPLE 95 and 2-furylboronic acid as reagents, EXAMPLE 723 was obtained. HRMS calculated for $C_{39}H_{40}N_6O_5S$: 704.2781; found 705.2846 [(M+H)$^+$ form].

5-[5-({(3R,4R)-4-[(4-hydroxy-4-{[7-(3-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile (Example 724)

Using General Procedure 9 starting from EXAMPLE 95 and (6-cyano-3-pyridyl)boronic acid as reagents, EXAMPLE 724 was obtained. HRMS calculated for $C_{41}H_{40}N_8O_4S$: 740.2893; found 741.2958 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one (Example 725)

Using General Procedure 9 starting from EXAMPLE 95 and (6-methyl-3-pyridyl)boronic acid as reagents, EXAMPLE 725 was obtained. HRMS calculated for $C_{41}H_{43}N_7O_4S$: 729.3098; found 365.6635 [(M+2H)$^{2+}$ form].

3-{[4-hydroxy-1-({(3R,4R)-1-[(6'-methyl-3,3'-bipyridin-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 726)

Using General Procedure 9 starting from EXAMPLE 303 and (6-methyl-3-pyridyl)boronic acid as reagents, EXAMPLE 726 was obtained. HRMS calculated for $C_{42}H_{41}N_7O_4$: 707.3220; found 708.329 [(M+H)$^+$ form].

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 727)

Using General Procedure 7 starting from Preparation R3bu and Preparation R1g as reagents, the resulted crude product was reacted with (6-methyl-3-pyridyl)boronic acid according to General Procedure 9, to give EXAMPLE 727. HRMS calculated for $C_{41}H_{39}FN_6O_4S$: 730.2737; found 731.2812 [(M+H)$^+$ form].

3-{[1-({(3R,4R)-1-[(2-bromo-4-methyl-1,3-thiazol-5-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one (Example 728)

Using General Procedure 7 starting from Preparation R3bu and 2-bromo-4-methyl-thiazole-5-carboxylic acid as reagents, EXAMPLE 728 was obtained. HRMS calculated for $C_{35}H_{35}N_6O_4SBr$: 714.1624; found 715.1701 [(M+H)$^+$ form].

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}-4-methyl-1,3-thiazol-2-yl)pyridine-2-carbonitrile (Example 729)

Using General Procedure 9 starting from EXAMPLE 728 and (6-cyano-3-pyridyl)boronic acid as reagents, EXAMPLE 729 was obtained. HRMS calculated for $C_{41}H_{38}N_8O_4S$: 738.2737; found 739.2816 [(M+H)$^+$ form].

3-[(1-{[(3R,4R)-1-({2-[6-(dimethylamino)pyridin-3-yl]-4-methyl-1,3-thiazol-5-yl}carbonyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 730)

Using General Procedure 9 starting from EXAMPLE 728 and [6-(dimethylamino)-3-pyridyl]boronic acid as reagents, EXAMPLE 730 was obtained. HRMS calculated for $C_{42}H_{44}N_8O_4S$: 756.3206; found 757.3285 [(M+H)$^+$ form].

3-[(4-hydroxy-1-{[(3R,4R)-1-({4-methyl-2-[6-(trifluoromethyl)pyridin-3-yl]-1,3-thiazol-5-yl}carbonyl)-3-phenylpiperidin-4-yl]carbonyl}piperidin-4-yl)methyl]-7-phenyl-3,7-dihydro-4H-pyrrolo[2,3-d]pyrimidin-4-one (Example 731)

Using General Procedure 9 starting from EXAMPLE 728 and [6-(trifluoromethyl)-3-pyridyl]boronic acid as reagents, EXAMPLE 731 was obtained. HRMS calculated for $C_{41}H_{38}F_3N_7O_4S$: 781.2658; found 782.2735 [(M+H)$^+$ form].

3-[(1-{[(3R,4R)-1-({2-[6-(dimethylamino)pyridin-3-yl]-1,3-thiazol-5-yl}methyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 732)

Using General Procedure 9 starting from EXAMPLE 103 and [6-(dimethylamino)-3-pyridyl]boronic acid as reagents, EXAMPLE 732 was obtained. HRMS calculated for C$_{41}$H$_{44}$N$_8$O$_3$S: 728.3257; found 365.1688 [(M+2H)$^{2+}$ form].

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one (Example 733)

Using General Procedure 9 starting from EXAMPLE 103 and (6-methoxy-3-pyridyl)boronic acid as reagents, EXAMPLE 733 was obtained. HRMS calculated for C$_{40}$H$_{41}$N$_7$O$_4$S: 715.2941; found 358.6536 [(M+2H)$^{2+}$ form].

3-[(4-hydroxy-1-{[(3R,4R)-1-{[2-(6-methoxypyridin-3-yl)-4-methyl-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one (Example 734)

Using General Procedure 9 starting from EXAMPLE 728 and (6-methoxy-3-pyridyl)boronic acid as reagents, EXAMPLE 734 was obtained. HRMS calculated for C$_{41}$H$_{41}$N$_7$O$_5$S: 743.2890; found 744.2969 [(M+H)$^+$ form].

3-[(4-hydroxy-1-{[(3R,4R)-1-({2-[6-(morpholin-4-yl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one (Example 735)

Using General Procedure 9 starting from EXAMPLE 103 and (6-morpholino-3-pyridyl)boronic acid as reagents, EXAMPLE 735 was obtained. HRMS calculated for C$_{43}$H$_{46}$N$_8$O$_4$S: 770.3362; found 386.1758 [(M+2H)$^{2+}$ form].

3-[(4-hydroxy-1-{[(3R,4R)-3-phenyl-1-({2-[6-(trifluoromethyl)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one (Example 736)

Using General Procedure 9 starting from EXAMPLE 103 and [6-(trifluoromethyl)-3-pyridyl]boronic acid as reagents, EXAMPLE 736 was obtained. HRMS calculated for C$_{40}$H$_{38}$F$_3$N$_7$O$_3$S: 753.2709; found 754.2786 [(M+H)$^+$ form].

3-[(4-hydroxy-1-{[(3R,4R)-3-phenyl-1-({2-[6-(piperazin-1-yl)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one (Example 737)

Using General Procedure 9 starting from EXAMPLE 103 and 1-[5-(4,4,5,5-tetramethyl-1,3,2-dioxaborolan-2-yl)-2-pyridyl]piperazine as reagents, EXAMPLE 737 was obtained. HRMS calculated for C$_{43}$H$_{47}$N$_9$O$_3$S: 769.3522; found 770.3601 [(M+H)$^+$ form].

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carbonitrile (Example 738)

Using General Procedure 9 starting from EXAMPLE 103 and (6-cyano-3-pyridyl)boronic acid as reagents, EXAMPLE 738 was obtained. HRMS calculated for C$_{40}$H$_{38}$N$_8$O$_3$S: 710.2787; found 711.2881 [(M+H)$^+$ form].

3-[(4-hydroxy-1-{[(3R,4R)-1-({2-[6-(hydroxymethyl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one (Example 739)

Using General Procedure 9 starting from EXAMPLE 103 and [6-(hydroxymethyl)-3-pyridyl]boronic acid as reagents, EXAMPLE 739 was obtained. HRMS calculated for C$_{40}$H$_{41}$N$_7$O$_4$S: 715.2941; found 716.3019 [(M+H)$^+$ form].

3-[(4-hydroxy-1-{[(3R,4R)-1-{[2-(3-methyl-3H-imidazo[4,5-b]pyridin-6-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one (Example 740)

Using General Procedure 9 starting from EXAMPLE 103 and 3-methyl-6-(4,4,5,5-tetramethyl-1,3,2-dioxaborolan-2-yl)imidazo[4,5-b]pyridine as reagents, EXAMPLE 740 was obtained. HRMS calculated for C$_{41}$H$_{41}$N$_9$O$_3$S: 739.3053; found 370.6594 [(M+2H)$^{2+}$ form].

3-[(1-{[(3R,4R)-1-{[2-(5-fluoro-6-hydroxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 741)

Using General Procedure 9 starting from EXAMPLE 103 and (5-fluoro-6-hydroxy-3-pyridyl)boronic acid as reagents, EXAMPLE 741 was obtained. HRMS calculated for C$_{39}$H$_{38}$FN$_7$O$_4$S: 719.2690; found 720.2742 [(M+H)$^+$ form].

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-3-carboxamide (Example 742)

Using General Procedure 9 starting from EXAMPLE 103 and 5-(4,4,5,5-tetramethyl-1,3,2-dioxaborolan-2-yl)pyridine-3-carboxamide as reagents, EXAMPLE 742 was obtained. HRMS calculated for C$_{40}$H$_{40}$N$_8$O$_4$S: 728.2893; found 729.296 [(M+H)$^+$ form].

3-[(4-hydroxy-1-{[(3R,4R)-1-({2-[5-(hydroxymethyl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one (Example 743)

Using General Procedure 9 starting from EXAMPLE 103 and [5-(4,4,5,5-tetramethyl-1,3,2-dioxaborolan-2-yl)-3-pyridyl]methanol as reagents, EXAMPLE 743 was obtained. HRMS calculated for C$_{40}$H$_{41}$N$_7$O$_4$S: 715.2941; found 358.6526 [(M+2H)$^{2+}$ form].

3-[(4-hydroxy-1-{[(3R,4R)-3-phenyl-1-({2-[6-(tetrahydro-2H-pyran-4-yloxy)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one (Example 744)

Using General Procedure 9 starting from EXAMPLE 103 and 2-tetrahydropyran-4-yloxy-5-(4,4,5,5-tetramethyl-1,3, 2-dioxaborolan-2-yl)pyridine as reagents, EXAMPLE 744 was obtained. HRMS calculated for $C_{44}H_{47}N_7O_5S$: 785.3359; found 393.6745 [(M+2H)$^{2+}$ form].

3-[(1-{[(3R,4R)-1-{[2-(5-amino-6-methoxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one (Example 745)

Using General Procedure 9 starting from EXAMPLE 103 and 2-methoxy-5-(4,4,5,5-tetramethyl-1,3,2-dioxaborolan-2-yl)pyridin-3-amine as reagents, EXAMPLE 745 was obtained. HRMS calculated for $C_{40}H_{42}N_8O_4S$: 730.3050; found 366.1585 [(M+2H)$^{2+}$ form].

methyl 5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carboxylate (Example 746)

Using General Procedure 9 starting from EXAMPLE 103 and methyl 5-(4,4,5,5-tetramethyl-1,3,2-dioxaborolan-2-yl)pyridine-2-carboxylate as reagents, EXAMPLE 746 was obtained. HRMS calculated for $C_{41}H_{41}N_7O_5S$: 743.2890; found 744.2954 [(M+H)$^+$ form].

3-[(4-hydroxy-1-{[(3R,4R)-1-({2-[6-(2-methoxyethoxy)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one (Example 747)

Using General Procedure 9 starting from EXAMPLE 103 and 2-(2-methoxyethoxy)-5-(4,4,5,5-tetramethyl-1,3,2-dioxaborolan-2-yl)pyridine as reagents, EXAMPLE 747 was obtained. HRMS calculated for $C_{42}H_{45}N_7O_5S$: 759.3203; found 760.3268 [(M+H)$^+$ form].

3-{[4-hydroxy-1-({(3R,4R)-1-[2-{6-[(2-methoxyethyl)amino]pyridin-3-yl}-1,3-thiazol-5-yl)methyl]-3-phenylpiperidin-4-yl}carbonyl)piperidin-4-yl]methyl}-7-phenyl-3,7-dihydro-4H-pyrrolo[2,3-d]pyrimidin-4-one (Example 748)

Using General Procedure 9 starting from EXAMPLE 103 and N-(2-methoxyethyl)-5-(4,4,5,5-tetramethyl-1,3,2-dioxaborolan-2-yl)pyridin-2-amine as reagents, EXAMPLE 748 was obtained. HRMS calculated for $C_{42}H_{46}N_8O_4S$: 758.3362; found 380.1717 [(M+2H)$^{2+}$ form].

3-{[4-hydroxy-1-({(3R,4R)-1-[(6'-methyl-2,3'-bipyridin-4-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one (Example 749)

Using General Procedure 9 starting from EXAMPLE 302 and (6-methyl-3-pyridyl)boronic acid as reagents, EXAMPLE 749 was obtained. HRMS calculated for $C_{42}H_{41}N_7O_4$: 707.3220; found 708.3294 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one (Example 750)

Using General Procedure 9 starting from EXAMPLE 728 and (6-methyl-3-pyridyl)boronic acid as reagents, EXAMPLE 750 was obtained. HRMS calculated for $C_{41}H_{41}N_7O_4S$: 727.2941; found 728.3013 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one (Example 751)

Using General Procedure 9 starting from EXAMPLE 103 and (6-methyl-3-pyridyl)boronic acid as reagents, EXAMPLE 751 was obtained. HRMS calculated for $C_{40}H_{41}N_7O_3S$: 699.2991; found 350.6573 [(M+2H)$^{2+}$ form].

7-ethyl-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 752)

Using General Procedure 7 starting from Preparation R3c and 2-bromo-4-methyl-thiazole-5-carboxylic acid as reagents, the resulted crude product was reacted with (6-methyl-3-pyridyl)boronic acid according to General Procedure 9, to give EXAMPLE 752. HRMS calculated for $C_{37}H_{41}N_7O_4S$: 679.2941; found 680.3014 [(M+H)$^+$ form].

3-[(1-{[(3R,4R)-1-{[2-(6-aminopyridin-3-yl)-4-methyl-1,3-thiazol-5-yl]carbonyl}-3-phenylpiperidin-4-yl]carbonyl}-4-hydroxypiperidin-4-yl)methyl]-7-ethyl-3,7-dihydro-4H-pyrrolo[2,3-d]pyrimidin-4-one (Example 753)

Using General Procedure 7 starting from Preparation R3c and 2-bromo-4-methyl-thiazole-5-carboxylic acid as reagents, the resulted crude product was reacted with 5-(4,4,5,5-tetramethyl-1,3,2-dioxaborolan-2-yl)pyridin-2-amine according to General Procedure 9, to give EXAMPLE 753. HRMS calculated for $C_{36}H_{40}N_8O_4S$: 680.2893; found 341.1534 [(M+2H)$^{2+}$ form].

7-ethyl-3-[(4-hydroxy-1-{[(3R,4R)-1-({4-methyl-2-[6-(trifluoromethyl)pyridin-3-yl]-1,3-thiazol-5-yl}carbonyl)-3-phenylpiperidin-4-yl]carbonyl}piperidin-4-yl)methyl]-3,7-dihydro-4H-pyrrolo[2,3-d]pyrimidin-4-one (Example 754)

Using General Procedure 7 starting from Preparation R3c and 2-bromo-4-methyl-thiazole-5-carboxylic acid as reagents, the resulted crude product was reacted with [6-(trifluoromethyl)-3-pyridyl]boronic acid according to General Procedure 9, to give EXAMPLE 754. HRMS calculated for $C_{37}H_{38}N_7O_4F_3S$: 733.2658; found 734.2738 [(M+H)$^+$ form].

7-ethyl-3-[(4-hydroxy-1-{[(3R,4R)-1-{[2-(6-methoxypyridin-3-yl)-4-methyl-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 755)

Using General Procedure 7 starting from Preparation R3c and 2-bromo-4-methyl-thiazole-5-carboxylic acid as reagents, the resulted crude product was reacted with (6-methoxy-3-pyridyl)boronic acid according to General Procedure 9, to give EXAMPLE 755. HRMS calculated for $C_{37}H_{41}N_7O_5S$: 695.2890; found 696.2959 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-4-yl)-3,7-dihydro-4H-pyrrolo[2,3-d]pyrimidin-4-one (Example 756)

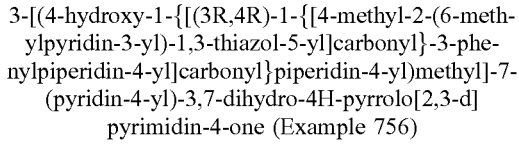

Using General Procedure 7 starting from Preparation R3cd and 2-bromo-4-methyl-thiazole-5-carboxylic acid as reagents, the resulted crude product was reacted with (6-methyl-3-pyridyl)boronic acid according to General Procedure 9, to give EXAMPLE 756. HRMS calculated for $C_{40}H_{40}N_8O_4S$: 728.2893; found 729.2971 [(M+H) form].

7-cyclopropyl-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 757)

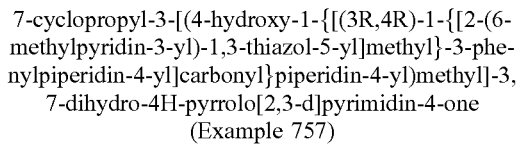

Using General Procedure 6 starting from Preparation R3g and 2-bromo-5-(bromomethyl)thiazole as reagents, the resulted crude product was reacted with (6-methyl-3-pyridyl)boronic acid according to General Procedure 9, to give EXAMPLE 757. HRMS calculated for $C_{37}H_{41}N_7O_3S$: 663.2991; found 332.6581 [(M+2H)$^{2+}$ form].

7-cyclopropyl-3-[(1-{[(3R,4R)-1-({3-fluoro-5-[6-(2,2,2-trifluoroethoxy)pyridin-3-yl]thiophen-2-yl}carbonyl)-3-phenylpiperidin-4-yl]carbonyl}-4-hydroxypiperidin-4-yl)methyl]-3,7-dihydro-4H-pyrrolo[2,3-d]pyrimidin-4-one (Example 758)

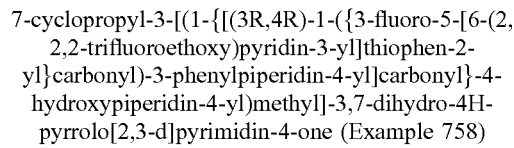

Using General Procedure 7 starting from Preparation R3g and Preparation R1g as reagents, the resulted crude product was reacted with [6-(2,2,2-trifluoroethoxy)-3-pyridyl]boronic acid according to General Procedure 9, to give EXAMPLE 758. HRMS calculated for $C_{39}H_{38}F_4N_6O_5S$: 778.256; found 779.2595 [(M+H)$^+$ form].

7-cyclobutyl-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 759)

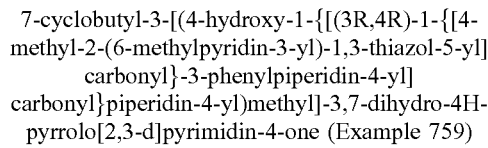

Using General Procedure 7 starting from Preparation R3h and Preparation R1g as reagents, the resulted crude product was reacted with (6-methyl-3-pyridyl)boronic acid according to General Procedure 9, to give EXAMPLE 759. HRMS calculated for $C_{39}H_{43}N_7O_4S$: 705.3098; found 706.3173 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(2-methylpropyl)-3,7-dihydro-4H-pyrrolo[2,3-d]pyrimidin-4-one (Example 760)

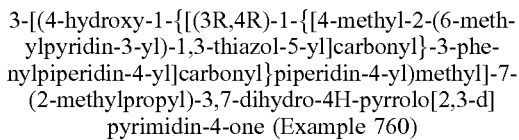

Using General Procedure 6 starting from Preparation R3n and 2-bromo-5-(bromomethyl)thiazole as reagents, the resulted crude product was reacted with (6-methyl-3-pyridyl)boronic acid according to General Procedure 9, to give EXAMPLE 760. HRMS calculated for $C_{39}H_{45}N_7O_4S$: 707.3254; found 708.3342 [(M+H)$^+$ form].

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-(2-methylpropyl)-3,7-dihydro-4H-pyrrolo[2,3-d]pyrimidin-4-one (Example 761)

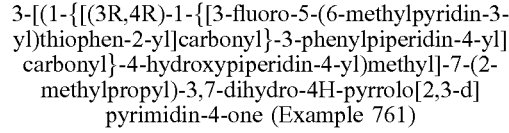

Using General Procedure 7 starting from Preparation R3n and Preparation R1g as reagents, the resulted crude product was reacted with (6-methyl-3-pyridyl)boronic acid according to General Procedure 9, to give EXAMPLE 761. HRMS calculated for $C_{39}H_{43}FN_6O_4S$: 710.3051; found 711.3123 [(M+H)$^+$ form].

3-{[1-({(3R,4R)-1-[(2-bromo-4-methyl-1,3-thiazol-5-yl)carbonyl]-3-phenylpiperidin-4-yl}carbonyl)-4-hydroxypiperidin-4-yl]methyl}-7-(2,2,2-trifluoroethyl)-3,7-dihydro-4H-pyrrolo[2,3-d]pyrimidin-4-one (Example 762)

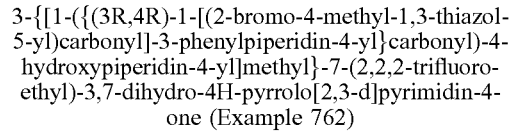

Using General Procedure 7 starting from Preparation R3o and 2-bromo-4-methyl-thiazole-5-carboxylic acid as reagents, EXAMPLE 762 was obtained. HRMS calculated for $C_{31}H_{32}BrF_3N_6O_4S$: 720.1341; found 721.1421 [(M+H)$^+$ form].

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-(2,2,2-trifluoroethyl)-3,7-dihydro-4H-pyrrolo[2,3-d]pyrimidin-4-one (Example 763)

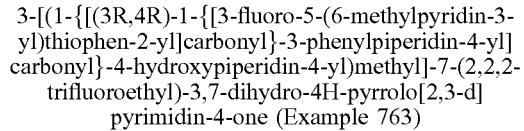

Using General Procedure 9 starting from EXAMPLE 340 and (6-methyl-3-pyridyl)boronic acid as reagents, EXAMPLE 763 was obtained. HRMS calculated for $C_{37}H_{36}F_4N_6O_4S$: 736.2455; found 737.253 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(2,2,2-trifluoroethyl)-3,7-dihydro-4H-pyrrolo[2,3-d]pyrimidin-4-one (Example 764)

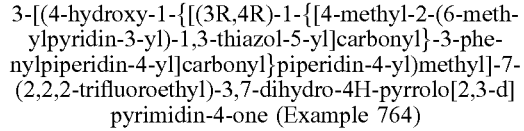

Using General Procedure 9 starting from EXAMPLE 762 and (6-methyl-3-pyridyl)boronic acid as reagents, EXAMPLE 764 was obtained. HRMS calculated for $C_{37}H_{38}F_3N_7O_4S$: 733.2658; found 734.274 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(2,2,2-trifluoroethyl)-3,7-dihydro-4H-pyrrolo[2,3-d]pyrimidin-4-one (Example 765)

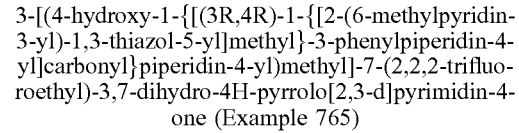

Using General Procedure 9 starting from EXAMPLE 143 and (6-methyl-3-pyridyl)boronic acid as reagents, EXAMPLE 765 was obtained. HRMS calculated for $C_{36}H_{38}N_7O_3F_3S$: 705.2709; found 706.2759 [(M+H)$^+$ form].

7-(2,2-difluoroethyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 766)

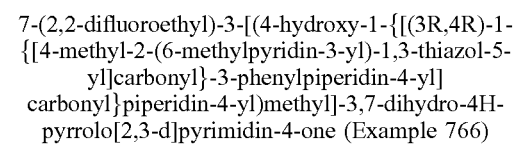

Using General Procedure 7 starting from Preparation R3p and 2-bromo-4-methyl-thiazole-5-carboxylic acid as reagents, the resulted crude product was reacted with (6-methyl-3-pyridyl)boronic acid according to General Procedure 9, to give EXAMPLE 766. HRMS calculated for $C_{37}H_{39}F_2N_7O_4S$: 715.2752; found 716.2836 [(M+H)$^+$ form].

7-(cyclopropylmethyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 767)

Using General Procedure 7 starting from Preparation R3q and 2-bromo-4-methyl-thiazole-5-carboxylic acid as reagents, the resulted crude product was reacted with (6-methyl-3-pyridyl)boronic acid according to General Procedure 9, to give EXAMPLE 767. HRMS calculated for $C_{39}H_{43}N_7O_4S$: 705.3098; found 353.6637 [(M+2H)$^{2+}$ form].

7-[3-(dimethylamino)propyl]-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 768)

Using General Procedure 7 starting from Preparation R3t and Preparation R1g as reagents, the resulted crude product was reacted with (6-methyl-3-pyridyl)boronic acid according to General Procedure 9, to give EXAMPLE 768. HRMS calculated for $C_{40}H_{46}FN_7O_4S$: 739.3316; found 370.6742 [(M+2H)$^{2+}$ form].

7-(2-fluoroethyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 769)

Using General Procedure 7 starting from Preparation R3u and 2-bromo-4-methyl-thiazole-5-carboxylic acid as reagents, the resulted crude product was reacted with (6-methyl-3-pyridyl)boronic acid according to General Procedure 9, to give EXAMPLE 769. HRMS calculated for $C_{37}H_{40}FN_7O_4S$: 697.2847; found 698.2920 [(M+H)$^+$ form].

7-[2-(dimethylamino)ethyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 770)

Using General Procedure 7 starting from Preparation R3v and 2-bromo-4-methyl-thiazole-5-carboxylic acid as reagents, the resulted crude product was reacted with (6-methyl-3-pyridyl)boronic acid according to General Procedure 9, to give EXAMPLE 770. HRMS calculated for $C_{39}H_{46}N_8O_4S$: 722.3362; found 362.1756 [(M+2H)$^{2+}$ form].

7-[2-(dimethylamino)ethyl]-3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one (Example 771)

Using General Procedure 7 starting from Preparation R3v and Preparation R1g as reagents, the resulted crude product was reacted with (6-methyl-3-pyridyl)boronic acid according to General Procedure 9, to give EXAMPLE 771. HRMS calculated for $C_{39}H_{44}FN_7O_4S$: 725.3160; found 363.6647 [(M+2H)$^{2+}$ form].

7-[2-(dimethylamino)ethyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 772)

Using General Procedure 6 starting from Preparation R3v and 2-bromo-5-(bromomethyl)thiazole as reagents, the resulted crude product was reacted with (6-methyl-3-pyridyl)boronic acid General Procedure 9, to give EXAMPLE 772. HRMS calculated for $C_{38}H_{46}N_8O_3S$: 694.3414; found 348.1773 [(M+2H)$^{2+}$ form].

7-(2-hydroxyethyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one (Example 773)

Using General Procedure 7 starting from Preparation R3w and 2-bromo-4-methyl-thiazole-5-carboxylic acid as reagents, the resulted crude product was reacted with (6-methyl-3-pyridyl)boronic acid according to General Procedure 9, to give EXAMPLE 773. HRMS calculated for $C_{37}H_{41}N_7O_5S$: 695.2890; found 696.2960 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one (Example 774)

Using General Procedure 10 starting from EXAMPLE 160 and boron-tribromide as reagents, EXAMPLE 774 was obtained. HRMS calculated for $C_{41}H_{41}N_7O_5S$: 743.2890; found 744.2970 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one (Example 775)

Using General Procedure 10 starting from EXAMPLE 61 and boron-tribromide as reagents, EXAMPLE 775 was obtained. HRMS calculated for $C_{40}H_{41}N_7O_4S$: 715.2941; found 358.6539 [(M+2H)$^{2+}$ form].

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one (Example 776)

and

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one (Example 777)

Using General Procedure 10 starting from EXAMPLE 62 and boron-tribromide as reagents, EXAMPLE 776 and EXAMPLE 777 were obtained and separated by chromatography.

Example 776

HRMS calculated for $C_{39}H_{39}N_7O_5S$: 717.2733; found 718.2818 [(M+H)$^+$ form].

Example 777

HRMS calculated for $C_{40}H_{41}N_7O_5S$: 731.2890; found 732.2963 [(M+H)$^+$ form].

3-[(1-{[(3R,4R)-1-{[5-(2-aminopyridin-4-yl)-3-methylthiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 778)

Using General Procedure 14 starting from EXAMPLE 402 as reactant, EXAMPLE 778 was obtained. HRMS calculated for $C_{36}H_{39}N_7O_4S$: 665.2784; found 333.6468 [(M+2H)$^{2+}$ form].

3-[(1-{[(3R,4R)-1-{[4-amino-5-(pyridin-4-yl)thiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 779)

Using General Procedure 12 starting from EXAMPLE 185 as reactant, EXAMPLE 779 was obtained. HRMS calculated for $C_{35}H_{37}N_7O_4S$: 651.2628; found 326.6382 [(M+2H)$^{2+}$ form].

3-[(4-hydroxy-1-{[(3R,4R)-3-phenyl-1-(1,2,3,4-tetrahydroisoquinolin-6-ylcarbonyl)piperidin-4-yl]carbonyl}piperidin-4-yl)methyl]-7-methyl-3,7-dihydro-4H-pyrrolo[2,3-d]pyrimidin-4-one (Example 780)

Using General Procedure 14 starting from EXAMPLE 192 as reactant, EXAMPLE 780 was obtained. HRMS calculated for $C_{35}H_{40}N_6O_4$: 608.3111; found 305.1639 [(M+2H)$^{2+}$ form].

N-(3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}phenyl)acetamide (Example 781)

Using General Procedure 7 starting from EXAMPLE 512 and acetic acid as reagents, EXAMPLE 781 was obtained. HRMS calculated for $C_{34}H_{38}N_6O_5$: 610.2903; found 611.2989 [(M+H)$^+$ form].

N-(3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}phenyl)benzamide (Example 782)

Using General Procedure 7 starting from EXAMPLE 512 and benzoic acid as reagents, EXAMPLE 782 was obtained. HRMS calculated for $C_{39}H_{40}N_6O_5$: 672.30603; found 673.3148 [(M+H)$^+$ form].

tert-butyl (2-bromo-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}thiophen-3-yl)carbamate (Example 783)

Using General Procedure 7 starting from Preparation R3b and Preparation R1o as reagents, EXAMPLE 783 was obtained. HRMS calculated for $C_{35}H_{41}BrN_6O_6S$: 752.1992; found 753.2074 [(M+H)$^+$ form].

2-chloro-N-(3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}phenyl)acetamide (Example 784)

EXAMPLE 512 (100 mg, 0.176 mmol), and chloroacetyl chloride (17 µl, 24 mg, 0.21 mmol) and potassium-carbonate (73 mg, 0.527 mmol) were stirred in DMF (2 ml) at r.t. for 3 hours. The reaction mixture was purified by preparative LC (on C-18 Gemini-NX 5 µm column, 5 mM aqueous NH$_4$HCO$_3$-MeCN, gradient) to give EXAMPLE 784. HRMS calculated for $C_{34}H_{37}ClN_6O_5$: 644.2514; found 645.2606 [(M+H)$^+$ form].

N-(3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}phenyl)prop-2-enamide (Example 785)

Using General Procedure 7 starting from EXAMPLE 512 and acrylic acid as reagents, EXAMPLE 785 was obtained. HRMS calculated for $C_{35}H_{38}N_6O_5$: 622.2903; found 623.2988 [(M+H)$^+$ form].

3-[(1-{[(3R,4R)-1-{[5-(2-aminopyridin-4-yl)-3-fluorothiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 786)

Using General Procedure 14 starting from EXAMPLE 628 as reactant, EXAMPLE 786 was obtained. HRMS calculated for $C_{35}H_{36}FN_7O_4S$: 669.2534; found 335.6337 [(M+2H)$^{2+}$ form].

3-[(1-{[(3R,4R)-1-{[5-(2-aminopyridin-4-yl)thiophen-2-yl]methyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 787)

Using General Procedure 14 starting from EXAMPLE 392 as reactant, EXAMPLE 787 was obtained. HRMS calculated for $C_{35}H_{39}N_7O_3S$: 637.2835; found 319.6503 [$(M+2H)^{2+}$ form].

3-[(4-hydroxy-1-{[(3R,4R)-3-phenyl-1-(1,2,3,4-tetrahydroquinolin-7-ylcarbonyl)piperidin-4-yl]carbonyl}piperidin-4-yl)methyl]-7-methyl-3,7-dihydro-4H-pyrrolo[2,3-d]pyrimidin-4-one (Example 788)

Using General Procedure 14 starting from EXAMPLE 245 as reactant, EXAMPLE 788 was obtained. HRMS calculated for $C_{35}H_{40}N_6O_4$: 608.3111; found 609.3200 [$(M+H)^+$ form].

3-[(1-{[(3R,4R)-1-{[5-(2-aminopyridin-4-yl)-1,3-thiazol-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 789)

Using General Procedure 14 starting from EXAMPLE 644 as reactant, EXAMPLE 789 was obtained. HRMS calculated for $C_{34}H_{36}N_8O_4S$: 652.2580; found 327.137 [$(M+2H)^{2+}$ form].

3-[(1-{[(3R,4R)-1-{[2-(2-aminopyridin-4-yl)-4-methyl-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 790)

Using General Procedure 14 starting from EXAMPLE 645 as reactant, EXAMPLE 790 was obtained. HRMS calculated for $C_{35}H_{38}N_8O_4S$: 666.2737; found 334.1454 [$(M+2H)^{2+}$ form].

3-[(1-{[(3R,4R)-1-{[5-(2-aminopyridin-4-yl)-4-methylthiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 791)

Using General Procedure 14 starting from EXAMPLE 398 as reactant, EXAMPLE 791 was obtained. HRMS calculated for $C_{36}H_{39}N_7O_4S$: 665.2784; found 333.6473 [$(M+2H)^{2+}$ form].

3-[(1-{[(3R,4R)-1-{[2-(2-aminopyridin-4-yl)-1,3-thiazol-5-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one (Example 792)

Using General Procedure 14 starting from EXAMPLE 657 as reactant, EXAMPLE 792 was obtained. HRMS calculated for $C_{34}H_{36}N_8O_4S$: 652.2580; found 653.2646 [$(M+H)^+$ form].

3-{[1-({(3R,4R)-1-[4-(aminomethyl)benzoyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 793)

Using General Procedure 14 starting from EXAMPLE 252 as reactant, EXAMPLE 793 was obtained. HRMS calculated for $C_{33}H_{38}N_6O_4$: 582.2955; found 292.1560 [$(M+2H)^{2+}$ form].

N-(4-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzyl)prop-2-enamide (Example 794)

Using General Procedure 7 starting from EXAMPLE 793 and acrylic acid as reagents, EXAMPLE 794 was obtained. HRMS calculated for $C_{36}H_{40}N_6O_5$: 636.3060; found 637.3134 [$(M+H)^+$ form].

3-{[1-({(3R,4R)-1-[(1-acryloyl-1,2,3,4-tetrahydroquinolin-7-yl)carbonyl]-3-phenylpiperidin-4-yl}carbonyl)-4-hydroxypiperidin-4-yl]methyl}-7-methyl-3,7-dihydro-4H-pyrrolo[2,3-d]pyrimidin-4-one (Example 795)

Using General Procedure 7 starting from EXAMPLE 788 and acrylic acid as reagents, EXAMPLE 795 was obtained. HRMS calculated for $C_{38}H_{42}N_6O_5$: 662.3217; found 663.3297 [$(M+H)^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzamide (Example 796)

The mixture of EXAMPLE 208 (0.23 mmol), acetaldoxime (141 μl, 137 mg, 2.3 mmol, 10 eq.), and copper(II)-chloride-treated molecular sieve (4 Å, 50 mg) was stirred in MeOH (2 ml) for 5 hours at 60° C. The reaction mixture was filtered, the filtrate was purified by preparative LC (on C-18 Gemini-NX 5 μm column, 5 mM aqueous $NH_4HCO_3$-MeCN, gradient) to give EXAMPLE 796. HRMS calculated for $C_{33}H_{36}N_6O_5$: 596.2747; found 597.283 [$(M+H)^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoic acid (Example 797)

The mixture of EXAMPLE 260 (0.66 mmol), hydrochloric acid (aq. 1 N, 1.33 ml, 2 eq.) in MeCN (2 ml) was stirred at 80° C. for 4 hours. The reaction mixture was injected to preparative LC (on C-18 Gemini-NX 5 μm column, 5 mM aqueous $NH_4HCO_3$-MeCN, gradient) to give EXAMPLE 797. HRMS calculated for $C_{33}H_{35}N_5O_6$: 597.2587; found 598.2659 [$(M+H)^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-N-methylbenzamide (Example 798)

Using General Procedure 7 starting from EXAMPLE 797 as carboxylic acid reactant and methylamine hydrochloride as amine reactant, EXAMPLE 798 was obtained. HRMS calculated for $C_{34}H_{38}N_6O_5$: 610.2903; found 611.2978 [(M+H)$^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-N,N-dimethylbenzamide (Example 799)

Using General Procedure 7 starting from EXAMPLE 797 as carboxylic acid reactant and dimethylamine hydrochloride as amine reactant, EXAMPLE 799 was obtained. HRMS calculated for $C_{35}H_{40}N_6O_5$: 624.3060; found 625.3139 [(M+H)$^+$ form].

3-{[4-hydroxy-1-({(3R,4R)-1-[3-(morpholin-4-ylcarbonyl)benzoyl]-3-phenylpiperidin-4-yl}carbonyl)piperidin-4-yl]methyl}-7-methyl-3,7-dihydro-4H-pyrrolo[2,3-d]pyrimidin-4-one (Example 800)

Using General Procedure 7 starting from EXAMPLE 797 as carboxylic acid reactant and morpholine as amine reactant, EXAMPLE 800 was obtained. HRMS calculated for $C_{37}H_{42}N_6O_6$: 666.3166; found 334.1668 [(M+2H)$^{2+}$ form].

5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-2-(6-methylpyridin-3-yl)-1,3-thiazole-4-carbonitrile (Example 801)

Mixture of EXAMPLE 263 (0.15 mmol) and copper(I)-cyanide (156 mg, 1.74 mmol, 12 eq.) in NMP (5 ml) was microwave irradiated for 4 hours at 200° C. The reaction mixture was purified by preparative LC (on C-18 Gemini-NX 5 µm column, 5 mM aqueous formic acid —MeCN, then 5 mM aqueous $NH_4HCO_3$-MeCN, gradient) to give EXAMPLE 801. HRMS calculated for $C_{36}H_{36}N_8O_4S$: 676.2580; found 677.266 [(M+H)$^+$ form].

(3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}phenyl)(methyl)sulfoniumolate (Example 802)

The mixture of EXAMPLE 283 (0.267 mmol) and Oxone® (164 mg, 0.267 mmol, 1 eq) in MeOH (5 ml), water (5 ml) and MeCN (5 ml) was stirred at r.t. for 10 hours. Water (30 ml) and MSM (3 ml) was added to the reaction mixture and evaporated. To the residue brine (30 ml) was added and extracted with DCM (4×50 ml), the combined organic layers were dried over $MgSO_4$ and evaporated. The residue was purified by preparative LC (on C-18 Gemini-NX 5 µm column, 5 mM aqueous $NH_4HCO_3$-MeCN, gradient) to give EXAMPLE 802. HRMS calculated for $C_{33}H_{37}N_5O_5S$: 615.2515; found 616.2622 [(M+H)$^+$ form].

methyl 3-amino-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 803)

Using General Procedure 12 starting from EXAMPLE 285 as reactant, EXAMPLE 803 was obtained. HRMS calculated for $C_{34}H_{38}N_6O_6$: 626.2853; found 627.295 [(M+H)$^+$ form].

3-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}-N-methoxy-N-methylbenzamide (Example 804)

Using General Procedure 7 starting from EXAMPLE 797 as carboxylic acid reactant and N,O-dimethylhydroxylamine hydrochloride as amine reactant, EXAMPLE 804 was obtained. HRMS calculated for $C_{35}H_{40}N_6O_6$: 640.3009; found 641.3089 [(M+H)$^+$ form].

methyl 3-(acetylamino)-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 805)

Using General Procedure 7 starting from EXAMPLE 803 and acetic acid as reactants, EXAMPLE 805 was obtained. HRMS calculated for $C_{36}H_{40}N_6O_7$: 668.2958; found 669.3036 [(M+H)$^+$ form].

methyl 3-(benzoylamino)-5-{[(3R,4R)-4-({4-hydroxy-4-[(7-methyl-4-oxo-4,7-dihydro-3H-pyrrolo[2,3-d]pyrimidin-3-yl)methyl]piperidin-1-yl}carbonyl)-3-phenylpiperidin-1-yl]carbonyl}benzoate (Example 806)

Using General Procedure 7 starting from EXAMPLE 803 and benzoic acid as reagents, EXAMPLE 806 was obtained. HRMS calculated for $C_{41}H_{42}N_6O_7$: 730.3115; found 731.3194 [(M+H)$^+$ form].

7-(3-chlorophenyl)-3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one (Example 807)

Using General Procedure 10 starting from EXAMPLE 86 as reactant, EXAMPLE 807 was obtained. HRMS calculated for $C_{39}H_{38}N_7O_4SCl$: 735.2394; found 736.2464 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one (Example 808)

Using General Procedure 10 starting from EXAMPLE 99 as reactant, EXAMPLE 808 was obtained. HRMS calculated for $C_{40}H_{41}N_7O_4S$: 715.2941; found 716.3012 [(M+H)$^+$ form].

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one (Example 809)

Using General Procedure 10 starting from EXAMPLE 94 as reactant, EXAMPLE 809 was obtained. HRMS calculated for $C_{39}H_{39}N_7O_5S$: 717.2733; found 718.2805 [(M+H)$^+$ form].

3-[(4-hydroxy-1-{[(3R,4R)-1-{[2-(6-oxo-1,6-dihydropyridin-3-yl)-1,3-thiazol-5-yl]methyl}-3-phenylpiperidin-4-yl]carbonyl}piperidin-4-yl)methyl]-7-(6-methoxypyridin-2-yl)-3,7-dihydro-4H-pyrrolo[2,3-d]pyrimidin-4-one (Example 810)

Using General Procedure 15 starting from EXAMPLE 101 as reactant, EXAMPLE 810 was obtained. HRMS calculated for $C_{39}H_{40}N_8O_5S$: 732.2842; found 733.2893 [(M+H)$^+$ form].

3-[(4-hydroxy-1-{[(3R,4R)-1-{[4-methyl-2-(6-methyl-1-oxidopyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one (Example 811)

The mixture of EXAMPLE 750 (0.137 mmol), mCPBA (24 mg, 0.137 mmol, 1 eq.) in DCM (1 ml) was stirred at r.t. for 25 hours. The reaction mixture was evaporated, purified by preparative LC (on C-18 Gemini-NX 5 μm column, 5 mM aqueous NH$_4$HCO$_3$-MeCN, gradient) to give EXAMPLE 811. HRMS calculated for $C_{41}H_{41}N_7O_5S$: 743.2890; found 744.2959 [(M+H)$^+$ form].

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one (Example 812)

Using General Procedure 10 starting from EXAMPLE 733 as reactant, EXAMPLE 812 was obtained. HRMS calculated for $C_{39}H_{39}N_7O_4S$: 701.2784; found 702.2841 [(M+H)$^+$ form].

3-[(4-hydroxy-1-{[(3R,4R)-1-{[2-(4-methylpiperazin-1-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one (Example 813)

The mixture of EXAMPLE 103 (0.391 mmol) and N-methylpiperazine (96 μl, 87 mg, 0.872 mmol, 3 eq.) and PDO (5 ml) was microwave irradiated for altogether 9 hours at 150° C. The reaction mixture was purified by preparative LC (on C-18 Gemini-NX 5 μm column, 5 mM aqueous NH$_4$HCO$_3$-MeCN, gradient) to give EXAMPLE 813. HRMS calculated for $C_{39}H_{46}N_8O_3S$: 706.3414; found 707.3487 [(M+H)$^+$ form].

5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carboxylic acid (Example 814)

Using General Procedure 9 starting from EXAMPLE 103 and methyl 5-(4,4,5,5-tetramethyl-1,3,2-dioxaborolan-2-yl)pyridine-2-carboxylate as reagents, the crude product was dissolved in MeOH (5 ml) and water (5 ml), lithium-hydroxide monohydrate (74 mg, 1.76 mmol) was added and the mixture was stirred for 2 hours at r.t. The reaction mixture was evaporated to water, neutralized with HCl solution (aq., 1 N), purified by preparative LC (on C-18 Gemini-NX 5 μm column, 5 mM aqueous NH$_4$HCO$_3$-MeCN, gradient) to give EXAMPLE 814. HRMS calculated for $C_{40}H_{39}N_7O_5S$: 729.2733; found 730.278 [(M+H)$^+$ form].

3-[(4-hydroxy-1-{[(3R,4R)-1-{[2-(6-oxo-1,6-dihydropyridin-3-yl)-1,3-thiazol-5-yl]methyl}-3-phenylpiperidin-4-yl]carbonyl}piperidin-4-yl)methyl]-7-(6-oxo-1,6-dihydropyridin-2-yl)-3,7-dihydro-4H-pyrrolo[2,3-d]pyrimidin-4-one (Example 815)

Using General Procedure 15 starting from EXAMPLE 101 as reactant, EXAMPLE 815 was obtained. HRMS calculated for $C_{38}H_{38}N_8O_5S$: 718.2686; found 719.2756 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(6-oxo-1,6-dihydropyridin-2-yl)-3,7-dihydro-4H-pyrrolo[2,3-d]pyrimidin-4-one (Example 816)

Using General Procedure 15 starting from EXAMPLE 100 as reactant, EXAMPLE 816 was obtained. HRMS calculated for $C_{39}H_{40}N_8O_4S$: 716.2893; found 717.2966 [(M+H)$^+$ form].

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1-methyl-6-oxo-1,6-dihydropyridin-2-yl)-3,7-dihydro-4H-pyrrolo[2,3-d]pyrimidin-4-one (Example 817)

Using General Procedure 13 starting from EXAMPLE 816 as reactant and iodomethane as reagent, EXAMPLE 817 was obtained. HRMS calculated for $C_{40}H_{42}N_8O_4S$: 730.3050; found 731.3121 [(M+H)$^+$ form].

3-[[1-[(3S,4S)-1-benzyl-3-phenyl-piperidine-4-carbonyl]-4-hydroxy-4-piperidyl]methyl]thieno[2,3-d]pyrimidin-4-one (Example 818)

Using General Procedure 6 starting from 3-[[4-hydroxy-1-[(3S,4S)-3-phenylpiperidine-4-carbonyl]-4-piperidyl]methyl]thieno[2,3-d]pyrimidin-4-one (which was obtained according to General Procedure 5 with tert-butyl (3S,4S)-4-(2-oxa-6-azaspiro[2.5]octane-6-carbonyl)-3-phenyl-piperidine-1-carboxylate and 3H-thieno[2,3-d]pyrimidin-4-one) and benzyl bromide as reagents, EXAMPLE 818 was obtained. HRMS calculated for $C_{31}H_{34}N_4O_3S$: 542.2352; found 543.2419 [(M+H)$^+$ form].

3-[[1-[(3R,4R)-1-benzyl-3-phenyl-piperidine-4-carbonyl]-4-hydroxy-4-piperidyl]methyl]thieno[2,3-d]pyrimidin-4-one (Example 819)

Using General Procedure 6 starting from Preparation R3cp and benzyl bromide as reagents, EXAMPLE 819 was obtained. HRMS calculated for $C_{31}H_{34}N_4O_3S$: 543.2352; found 543.2401 [(M+H)$^+$ form].

3-[[1-[(3S,4S)-1-benzyl-3-phenyl-piperidine-4-carbonyl]-4-hydroxy-4-piperidyl]methyl]pyrido[3,2-d]pyrimidin-4-one (Example 820)

Using General Procedure 6 starting from Preparation R3cn and benzyl bromide as reagents, EXAMPLE 820 was

3-[[1-[(3R,4R)-1-benzyl-3-phenyl-piperidine-4-carbonyl]-4-hydroxy-4-piperidyl]methyl]pyrido[3,2-d]pyrimidin-4-one (Example 821)

Using General Procedure 6 starting from Preparation R3co and benzyl bromide as reagents, EXAMPLE 821 was obtained. HRMS calculated for $C_{32}H_{35}N_5O_4$: 537.2740; found 538.2809 [(M+H)$^+$ form].

3-[[1-[(3R,4S)-1-benzyl-3-(2-thienyl)piperidine-4-carbonyl]-4-hydroxy-4-piperidyl]methyl]pyrido[3,2-d]pyrimidin-4-one (Example 822)

Using General Procedure 5, starting from 3H-pyrido[3,2-d]pyrimidin-4-one and Preparation R1e as reactants, the resulted crude piperidine product was reacted with Preparation R1q-(3R,4S) according to General Procedure 7, to give EXAMPLE 822. HRMS calculated for $C_{30}H_{33}N_5O_3S$: 544.2304; found 544.2381 [(M+H)$^+$ form].

3-[[1-[(3S,4R)-1-benzyl-3-(2-thienyl)piperidine-4-carbonyl]-4-hydroxy-4-piperidyl]methyl]pyrido[3,2-d]pyrimidin-4-one (Example 823)

Using General Procedure 5, starting from 3H-pyrido[3,2-d]pyrimidin-4-one and Preparation R1e as reactants, the resulted crude piperidine product was reacted with Preparation R1q-(3S,4R) according to General Procedure 7, to give EXAMPLE 823. HRMS calculated for $C_{30}H_{33}N_5O_3S$: 544.2304; found 544.2394 [(M+H)$^+$ form].

3-[[1-[(3R,4R)-1-[(2-fluorophenyl)methyl]-3-phenyl-piperidine-4-carbonyl]-4-hydroxy-4-piperidyl]methyl]thieno[2,3-d]pyrimidin-4-one (Example 824)

Using General Procedure 6 starting from Preparation R3cp and 1-(bromomethyl)-2-fluoro-benzene as reagents, EXAMPLE 824 was obtained. HRMS calculated for $C_{31}H_{33}FN_4O_3S$: 560.2257; found 561.2301 [(M+H)$^+$ form].

3-[[1-[(3R,4R)-1-[(3-fluorophenyl)methyl]-3-phenyl-piperidine-4-carbonyl]-4-hydroxy-4-piperidyl]methyl]thieno[2,3-d]pyrimidin-4-one (Example 825)

Using General Procedure 6 starting from Preparation R3cp and 1-(bromomethyl)-3-fluoro-benzene as reagents, EXAMPLE 825 was obtained. HRMS calculated for $C_{31}H_{33}FN_4O_3S$: 560.2257; found 561.2331 [(M+H)$^+$ form].

3-[[4-hydroxy-1-[(3R,4R)-1-(o-tolylmethyl)-3-phenyl-piperidine-4-carbonyl]-4-piperidyl]methyl]thieno[2,3-d]pyrimidin-4-one (Example 826)

Using General Procedure 6 starting from Preparation R3cp and 1-(bromomethyl)-2-methyl-benzene as reagents, EXAMPLE 826 was obtained. HRMS calculated for $C_{32}H_{36}N_4O_3S$: 556.2508; found 557.2565 [(M+H)$^+$ form].

3-[[4-hydroxy-1-[(3R,4R)-1-(m-tolylmethyl)-3-phenyl-piperidine-4-carbonyl]-4-piperidyl]methyl]thieno[2,3-d]pyrimidin-4-one (Example 827)

Using General Procedure 6 starting from Preparation R3cp and 1-(bromomethyl)-3-methyl-benzene as reagents, EXAMPLE 827 was obtained. HRMS calculated for $C_{32}H_{36}N_4O_3S$: 556.2508; found 557.2597 [(M+H)$^+$ form].

3-[[4-hydroxy-1-[(3R,4R)-1-(4-methyl-2-phenyl-thiazole-5-carbonyl)-3-phenyl-piperidine-4-carbonyl]-4-piperidyl]methyl]pyrido[3,2-d]pyrimidin-4-one (Example 828)

Using General Procedure 7 starting from Preparation R3co and 4-methyl-2-phenyl-thiazole-5-carboxylic acid as reagents, EXAMPLE 828 was obtained. HRMS calculated for $C_{36}H_{36}N_6O_4S$: 648.2519; found 649.2583 [(M+H)$^+$ form].

3-[[4-hydroxy-1-[(3R,4R)-3-phenyl-1-(2-phenylthiazole-5-carbonyl)piperidine-4-carbonyl]-4-piperidyl]methyl]pyrido[3,2-d]pyrimidin-4-one (Example 829)

Using General Procedure 7 starting from Preparation R3co and 2-phenylthiazole-5-carboxylic acid as reagents, EXAMPLE 829 was obtained. HRMS calculated for $C_{35}H_{34}N_6O_4S$: 634.2362; found 635.2429 [(M+H)$^+$ form].

3-[[1-[(3R,4R)-1-benzyl-3-phenyl-piperidine-4-carbonyl]-4-hydroxy-4-piperidyl]methyl]-6-chloro-pyrido[3,2-d]pyrimidin-4-one (Example 830)

Using General Procedure 6 starting from Preparation R3cq and benzyl bromide as reagents, EXAMPLE 830 was obtained. HRMS calculated for $C_{32}H_{34}ClN_5O_3$: 571.235; found 572.2416 [(M+H)$^+$ form].

3-[[1-[(3R,4R)-1-benzyl-3-phenyl-piperidine-4-carbonyl]-4-hydroxy-4-piperidyl]methyl]-6-methoxy-pyrido[3,2-d]pyrimidin-4-one (Example 831)

Using General Procedure 6 starting from Preparation R3cr and benzyl bromide as reagents, EXAMPLE 831 was obtained. HRMS calculated for $C_{33}H_{37}N_5O_4$: 567.2846; found 568.2902 [(M+H)$^+$ form].

3-[[1-[(3R,4R)-1-benzyl-3-phenyl-piperidine-4-carbonyl]-4-hydroxy-4-piperidyl]methyl]-5H-pyrido[3,2-d]pyrimidine-4,6-dione (Example 832)

Using General Procedure 6 starting from Preparation R3cs and benzyl bromide as reagents, EXAMPLE 832 was obtained. HRMS calculated for $C_{32}H_{35}N_5O_4$: 553.2689; found 554.2762 [(M+H)$^+$ form].

3-[[4-hydroxy-1-[(3R,4R)-1-(3-methylisothiazole-4-carbonyl)-3-phenyl-piperidine-4-carbonyl]-4-piperidyl]methyl]pyrido[3,2-d]pyrimidin-4-one (Example 833)

Using General Procedure 7 starting from Preparation R3co and 3-methylisothiazole-4-carboxylic acid as reagents, EXAMPLE 833 was obtained. HRMS calculated for $C_{30}H_{32}N_6O_4S$: 572.2206; found 573.2285 [(M+H)$^+$ form].

3-[[1-[(3R,4R)-1-[(2-fluorophenyl)methyl]-3-phenyl-piperidine-4-carbonyl]-4-hydroxy-4-piperidyl]methyl]pyrido[3,2-d]pyrimidin-4-one (Example 834)

Using General Procedure 6 starting from Preparation R3co and 1-(bromomethyl)-2-fluoro-benzene as reagents,

--- obtained. HRMS calculated for $C_{32}H_{35}N_5O_3$: 537.274; found 538.2837 [(M+H)$^+$ form].

EXAMPLE 834 was obtained. HRMS calculated for $C_{32}H_{34}FN_5O_3$: 555.2646; found 556.2701 [(M+H)$^+$ form].

3-[[1-[(3R,4R)-1-[(3-fluorophenyl)methyl]-3-phenyl-piperidine-4-carbonyl]-4-hydroxy-4-piperidyl]methyl]pyrido[3,2-d]pyrimidin-4-one (Example 835)

Using General Procedure 6 starting from Preparation R3co and 1-(bromomethyl)-3-fluoro-benzene as reagents, EXAMPLE 835 was obtained. HRMS calculated for $C_{32}H_{34}FN_5O_4$: 555.2647; found 556.2702 [(M+H)$^+$ form].

3-[[4-hydroxy-1-[(3R,4R)-1-(o-tolylmethyl)-3-phenyl-piperidine-4-carbonyl]-4-piperidyl]methyl]pyrido[3,2-d]pyrimidin-4-one (Example 836)

Using General Procedure 6 starting from Preparation R3co and 1-(bromomethyl)-2-methyl-benzene as reagents, EXAMPLE 836 was obtained. HRMS calculated for $C_{33}H_{37}N_5O_3$: 551.2896; found 552.2943 [(M+H)$^+$ form].

3-[[4-hydroxy-1-[(3R,4R)-1-(m-tolylmethyl)-3-phenyl-piperidine-4-carbonyl]-4-piperidyl]methyl]pyrido[3,2-d]pyrimidin-4-one (Example 837)

Using General Procedure 6 starting from Preparation R3co and 1-(bromomethyl)-3-methyl-benzene as reagents, EXAMPLE 837 was obtained. HRMS calculated for $C_{33}H_{37}N_5O_4$: 551.2897; found 552.2990 [(M+H)$^+$ form].

3-[[4-hydroxy-1-[(3R,4R)-1-(4-methyl-2-phenyl-thiazole-5-carbonyl)-3-phenyl-piperidine-4-carbonyl]-4-piperidyl]methyl]thieno[2,3-d]pyrimidin-4-one (Example 838)

Using General Procedure 7 starting from Preparation R3cp and 4-methyl-2-phenyl-thiazole-5-carboxylic acid as reagents, EXAMPLE 838 was obtained. HRMS calculated for $C_{35}H_{35}N_5O_4S_2$: 653.2130; found 654.2212 [(M+H)$^+$ form].

3-[[1-[(3R,4R)-1-(2-benzyl-4-methyl-thiazole-5-carbonyl)-3-phenyl-piperidine-4-carbonyl]-4-hydroxy-4-piperidyl]methyl]thieno[2,3-d]pyrimidin-4-one (Example 839)

Using General Procedure 7 starting from Preparation R3cp and 2-benzyl-4-methyl-thiazole-5-carboxylic acid as reagents, EXAMPLE 839 was obtained. HRMS calculated for $C_{36}H_{37}N_5O_4S_2$: 667.2287; found 668.2371 [(M+H)$^+$ form].

3-[[4-hydroxy-1-[(3R,4R)-1-(3-methylisothiazole-4-carbonyl)-3-phenyl-piperidine-4-carbonyl]-4-piperidyl]methyl]thieno[2,3-d]pyrimidin-4-one (Example 840)

Using General Procedure 7 starting from Preparation R3cp and 3-methylisothiazole-4-carboxylic acid as reagents, EXAMPLE 840 was obtained. HRMS calculated for $C_{29}H_{31}N_5O_4S_2$: 577.1817; found 578.1901 [(M+H)$^+$ form].

3-[[1-[(3R,4R)-1-(benzofuran-2-ylmethyl)-3-phenyl-piperidine-4-carbonyl]-4-hydroxy-4-piperidyl]methyl]thieno[2,3-d]pyrimidin-4-one (Example 841)

Using General Procedure 6 starting from Preparation R3cp and 2-(chloromethyl)benzofurane as reagents, EXAMPLE 841 was obtained. HRMS calculated for $C_{33}H_{34}N_4O_4S$: 582.2301; found 583.2376 [(M+H)$^+$ form].

3-[(3R,4R)-4-[4-hydroxy-4-[(4-oxothieno[2,3-d]pyrimidin-3-yl)methyl]piperidine-1-carbonyl]-3-phenyl-piperidine-1-carbonyl]-1H-indazole-5-carbonitrile (Example 842)

Using General Procedure 7 starting from Preparation R3cp and 5-cyano-1H-indazole-3-carboxylic acid as reagents, EXAMPLE 842 was obtained. HRMS calculated for $C_{33}H_{31}N_7O_4S$: 621.2158; found 622.2229 [(M+H)$^+$ form].

3-[[1-[(3R,4R)-1-(2-benzyl-4-methyl-thiazole-5-carbonyl)-3-phenyl-piperidine-4-carbonyl]-4-hydroxy-4-piperidyl]methyl]pyrido[3,2-d]pyrimidin-4-one (Example 843)

Using General Procedure 7 starting from Preparation R3co and 2-benzyl-4-methyl-thiazole-5-carboxylic acid as reagents, EXAMPLE 843 was obtained. HRMS calculated for $C_{37}H_{38}N_6O_4S$: 662.2675; found 663.2743 [(M+H)$^+$ form].

3-[[1-[(3R,4R)-1-[2-(2-fluorophenyl)-4-methyl-thiazole-5-carbonyl]-3-phenyl-piperidine-4-carbonyl]-4-hydroxy-4-piperidyl]methyl]pyrido[3,2-d]pyrimidin-4-one (Example 844)

Using General Procedure 7 starting from Preparation R3co and 2-(2-fluorophenyl)-4-methyl-thiazole-5-carboxylic acid as reagents, EXAMPLE 844 was obtained. HRMS calculated for $C_{36}H_{35}FN_6O_4S$: 666.2425; found 667.2498 [(M+H)$^+$ form].

3-[[4-hydroxy-1-[(3R,4R)-1-[4-methyl-2-(o-tolyl)thiazole-5-carbonyl]-3-phenyl-piperidine-4-carbonyl]-4-piperidyl]methyl]pyrido[3,2-d]pyrimidin-4-one (Example 845)

Using General Procedure 7 starting from Preparation R3co and 4-methyl-2-(o-tolyl)thiazole-5-carboxylic acid as reagents, EXAMPLE 845 was obtained. HRMS calculated for $C_{37}H_{38}N_6O_4S$: 662.2675; found 663.2751 [(M+H)$^+$ form].

3-[[4-hydroxy-1-[(3R,4R)-3-phenyl-1-[2-(4-pyridyl)thiazole-5-carbonyl]piperidine-4-carbonyl]-4-piperidyl]methyl]pyrido[3,2-d]pyrimidin-4-one (Example 846)

Using General Procedure 7 starting from Preparation R3co and 2-(4-pyridyl)thiazole-5-carboxylic acid as reagents, EXAMPLE 846 was obtained. HRMS calculated for $C_{34}H_{33}N_7O_4S$: 635.2314; found 636.2401 [(M+H)$^+$ form].

3-[[4-hydroxy-1-[(3S,4S)-3-phenyl-1-[2-(4-pyridyl)thiazole-5-carbonyl]piperidine-4-carbonyl]-4-piperidyl]methyl]pyrido[3,2-d]pyrimidin-4-one (Example 847)

Using General Procedure 7 starting from Preparation R3cn and 2-(4-pyridyl)thiazole-5-carboxylic acid as reagents, EXAMPLE 847 was obtained. HRMS calculated for $C_{34}H_{33}N_7O_4S$: 635.2315; found 318.6241 [$(M+2H)^{2+}$ form].

3-[[1-[(3R,4R)-1-[2-[(2-fluorophenyl)methyl]thiazole-5-carbonyl]-3-phenyl-piperidine-4-carbonyl]-4-hydroxy-4-piperidyl]methyl]pyrido[3,2-d]pyrimidin-4-one (Example 848)

Using General Procedure 7 starting from Preparation R3co and 2-[(2-fluorophenyl)methyl]thiazole-5-carboxylic acid as reagents, EXAMPLE 848 was obtained. HRMS calculated for $C_{36}H_{35}FN_6O_4S$: 666.2425; found 667.2498 [$(M+H)^+$ form].

6-(benzylamino)-3-[[1-[(3R,4R)-1-benzyl-3-phenyl-piperidine-4-carbonyl]-4-hydroxy-4-piperidyl]methyl]pyrido[3,2-d]pyrimidin-4-one (Example 849)

Using General Procedure 6 starting from Preparation R3ct and benzyl bromide as reagents, EXAMPLE 849 was obtained. HRMS calculated for $C_{39}H_{42}N_6O_3$: 642.3318; found 322.1727 [$(M+2H)^{2+}$ form].

3-[[4-hydroxy-1-[(3R,4R)-3-phenyl-1-[5-(4-pyridyl)thiophene-2-carbonyl]piperidine-4-carbonyl]-4-piperidyl]methyl]pyrido[3,2-d]pyrimidin-4-one (Example 850)

Using General Procedure 7 starting from Preparation R3co and 5-(4-pyridyl)thiophene-2-carboxylic acid as reagents, EXAMPLE 850 was obtained. HRMS calculated for $C_{35}H_{34}N_6O_4S$: 634.2362; found 635.2439 [$(M+H)^+$ form].

3-[[4-hydroxy-1-[(3R,4R)-1-[4-methyl-2-(4-pyridyl)thiazole-5-carbonyl]-3-phenyl-piperidine-4-carbonyl]-4-piperidyl]methyl]pyrido[3,2-d]pyrimidin-4-one (Example 851)

Using General Procedure 7 starting from Preparation R3co and 4-methyl-2-(4-pyridyl)thiazole-5-carboxylic acid as reagents, EXAMPLE 851 was obtained. HRMS calculated for $C_{35}H_{35}N_7O_4S$: 649.2471; found 650.2547 [$(M+H)^+$ form].

3-[[1-[(3R,4R)-1-[(2-fluorophenyl)methyl]-3-phenyl-piperidine-4-carbonyl]-4-hydroxy-4-piperidyl]methyl]-6-[(4-methoxyphenyl)methylamino]pyrido[3,2-d]pyrimidin-4-one (Example 852)

Using General Procedure 6 starting from Preparation R3cu and 1-(bromomethyl)-2-fluoro-benzene as reagents, EXAMPLE 852 was obtained. HRMS calculated for $C_{40}H_{43}FN_6O_4$: 690.333; found 346.1732 [$(M+2H)^{2+}$ form].

6-chloro-3-[[4-hydroxy-1-[(3R,4R)-1-(4-methyl-2-phenyl-thiazole-5-carbonyl)-3-phenyl-piperidine-4-carbonyl]-4-piperidyl]methyl]pyrido[3,2-d]pyrimidin-4-one (Example 853)

Using General Procedure 5 Step 1, starting from 6-chloro-3H-pyrido[3,2-d]pyrimidin-4-one and Preparation R1s as epoxide compound, EXAMPLE 853 was obtained. HRMS calculated for $C_{36}H_{35}ClN_6O_4S$: 682.2129; found 683.2201 [$(M+H)^+$ form].

3-[[4-hydroxy-1-[(3R,4R)-3-phenyl-1-(5-pyrimidin-5-ylthiophene-2-carbonyl)piperidine-4-carbonyl]-4-piperidyl]methyl]thieno[2,3-d]pyrimidin-4-one (Example 854)

Using General Procedure 7 starting from Preparation R3cp and 5-bromothiophene-2-carboxylic acid as reagents, the resulted crude bromo compound was reacted according to General Procedure 9 with pyrimidin-5-ylboronic acid to give EXAMPLE 854. HRMS calculated for $C_{33}H_{32}N_6O_4S_2$: 640.1926; found 641.1995 [$(M+H)^+$ form].

3-[[4-hydroxy-1-[(3R,4R)-1-(4-methyl-2-pyrimidin-5-yl-thiazole-5-carbonyl)-3-phenyl-piperidine-4-carbonyl]-4-piperidyl]methyl]thieno[2,3-d]pyrimidin-4-one (Example 855)

Using General Procedure 7 starting from Preparation R3cp and 2-bromo-4-methyl-thiazole-5-carboxylic acid as reagents, the resulted crude bromo compound was reacted according to General Procedure 9 with pyrimidin-5-ylboronic acid to give EXAMPLE 855. HRMS calculated for $C_{33}H_{33}N_7O_4S_2$: 655.2035; found 656.2132 [$(M+H)^+$ form].

3-[[4-hydroxy-1-[(3R,4R)-3-phenyl-1-(5-pyrimidin-5-ylthiophene-2-carbonyl)piperidine-4-carbonyl]-4-piperidyl]methyl]pyrido[3,2-d]pyrimidin-4-one (Example 856)

Using General Procedure 7 starting from Preparation R3co and 5-bromothiophene-2-carboxylic acid as reagents, the resulted crude bromo compound was reacted according to General Procedure 9 with pyrimidin-5-ylboronic acid to give EXAMPLE 856. HRMS calculated for $C_{34}H_{33}N_7O_4S$: 635.2315; found 636.2387 [$(M+H)^+$ form].

3-[[4-hydroxy-1-[(3R,4R)-1-[5-(2-methylpyrazol-3-yl)thiophene-2-carbonyl]-3-phenyl-piperidine-4-carbonyl]-4-piperidyl]methyl]thieno[2,3-d]pyrimidin-4-one (Example 857)

Using General Procedure 7 starting from Preparation R3cp and 5-bromothiophene-2-carboxylic acid as reagents, the resulted crude bromo compound was reacted according to General Procedure 9 with 1-methyl-5-(4,4,5,5-tetramethyl-1,3,2-dioxaborolan-2-yl)pyrazole to give EXAMPLE 857. HRMS calculated for $C_{33}H_{34}N_6O_4S_2$: 642.2083; found 643.2163 [$(M+H)^+$ form].

3-[[4-hydroxy-1-[(3R,4R)-1-[4-methyl-2-(2-methylpyrazol-3-yl)thiazole-5-carbonyl]-3-phenyl-piperidine-4-carbonyl]-4-piperidyl]methyl]thieno[2,3-d]pyrimidin-4-one (Example 858)

Using General Procedure 7 starting from Preparation R3cp and 2-bromo-4-methyl-thiazole-5-carboxylic acid as reagents, the resulted crude bromo compound was reacted according to General Procedure 9 with 1-methyl-5-(4,4,5,5-tetramethyl-1,3,2-dioxaborolan-2-yl)pyrazole to give EXAMPLE 858. HRMS calculated for $C_{33}H_{35}N_7O_4S_2$: 657.2192; found 658.2279 [$(M+H)^+$ form].

3-[[4-hydroxy-1-[(3R,4R)-1-[5-(2-methylpyrazol-3-yl)thiophene-2-carbonyl]-3-phenyl-piperidine-4-carbonyl]-4-piperidyl]methyl]pyrido[3,2-d]pyrimidin-4-one (Example 859)

Using General Procedure 7 starting from Preparation R3co and 5-bromothiophene-2-carboxylic acid as reagents, the resulted crude bromo compound was reacted according to General Procedure 9 with 1-methyl-5-(4,4,5,5-tetramethyl-1,3,2-dioxaborolan-2-yl)pyrazole to give EXAMPLE 859. HRMS calculated for $C_{34}H_{35}N_7O_4S$: 637.2471; found 638.2525 [(M+H)⁺ form].

3-[[4-hydroxy-1-[(3R,4R)-1-[2-(6-methoxy-3-pyridyl)-4-methyl-thiazole-5-carbonyl]-3-phenyl-piperidine-4-carbonyl]-4-piperidyl]methyl]thieno[2,3-d]pyrimidin-4-one (Example 860)

Using General Procedure 7 starting from Preparation R3cp and 2-bromo-4-methyl-thiazole-5-carboxylic acid as reagents, the resulted crude bromo compound was reacted according to General Procedure 9 with (6-methoxy-3-pyridyl)boronic acid to give EXAMPLE 860. HRMS calculated for $C_{35}H_{36}N_6O_5S_2$: 684.2189; found 685.2269 [(M+H)+ form].

3-[[1-[(3R,4R)-1-[2-(6-amino-3-pyridyl)-4-methyl-thiazole-5-carbonyl]-3-phenyl-piperidine-4-carbonyl]-4-hydroxy-4-piperidyl]methyl]thieno[2,3-d]pyrimidin-4-one (Example 861)

Using General Procedure 7 starting from Preparation R3cp and 2-bromo-4-methyl-thiazole-5-carboxylic acid as reagents, the resulted crude bromo compound was reacted according to General Procedure 9 with 5-(4,4,5,5-tetramethyl-1,3,2-dioxaborolan-2-yl)pyridin-2-amine to give EXAMPLE 861 was obtained. HRMS calculated for $C_{34}H_{35}N_7O_4S_2$: 669.2192; found 670.2245 [(M+H)⁺ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]thieno[2,3-d]pyrimidin-4-one (Example 862)

Using General Procedure 7 starting from Preparation R3cp and 2-bromo-4-methyl-thiazole-5-carboxylic acid as reagents, the resulted crude bromo compound was reacted according to General Procedure 9 with (6-methyl-3-pyridyl)boronic acid to give EXAMPLE 862. HRMS calculated for $C_{35}H_{36}N_6O_4S_2$: 668.2239; found 669.2306 [(M+H)⁺ form].

3-[[1-[(3R,4R)-1-[3-fluoro-5-(6-methyl-3-pyridyl)thiophene-2-carbonyl]-3-phenyl-piperidine-4-carbonyl]-4-hydroxy-4-piperidyl]methyl]thieno[2,3-d]pyrimidin-4-one (Example 863)

Using General Procedure 7 starting from Preparation R3cp and Preparation R1g as reagents, the resulted crude iodo compound was reacted according to General Procedure 9 with (6-methyl-3-pyridyl)boronic acid to give EXAMPLE 863. HRMS calculated for $C_{35}H_{34}FN_5O_4S_2$: 671.2036; found 336.6092 [(M+2H)²⁺ form].

3-[[1-[(3R,4R)-1-[5-(6-amino-3-pyridyl)-3-fluoro-thiophene-2-carbonyl]-3-phenyl-piperidine-4-carbonyl]-4-hydroxy-4-piperidyl]methyl]thieno[2,3-d]pyrimidin-4-one (Example 864)

Using General Procedure 7 starting from Preparation R3cp and Preparation R1g as reagents, the resulted crude iodo compound was reacted according to General Procedure 9 with 5-(4,4,5,5-tetramethyl-1,3,2-dioxaborolan-2-yl)pyridin-2-amine to give EXAMPLE 864. HRMS calculated for $C_{34}H_{33}FN_6O_4S_2$: 672.1989; found 671.1926 [(M−H)⁻ form].

3-[[1-[(3R,4R)-1-[3-fluoro-5-(6-piperazin-1-yl-3-pyridyl)thiophene-2-carbonyl]-3-phenyl-piperidine-4-carbonyl]-4-hydroxy-4-piperidyl]methyl]thieno[2,3-d]pyrimidin-4-one (Example 865)

Using General Procedure 7 starting from Preparation R3cp and Preparation R1g as reagents, the resulted crude iodo compound was reacted according to General Procedure 9 with 1-[5-(4,4,5,5-tetramethyl-1,3,2-dioxaborolan-2-yl)-2-pyridyl]piperazine to give EXAMPLE 865. HRMS calculated for $C_{38}H_{40}FN_7O_4S_2$: 741.2567; found 740.2504 [(M−H)⁻ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]thieno[2,3-d]pyrimidin-4-one (Example 866)

Using General Procedure 6 starting from Preparation R3cp and Preparation R1c as reagents, EXAMPLE 866 was obtained. HRMS calculated for $C_{34}H_{36}N_6O_3S_2$: 640.2290; found 641.2336 [(M+H)⁺ form].

3-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]thieno[2,3-d]pyrimidin-4-one (Example 867)

Using General Procedure 6 starting from Preparation R3cp and 5-(chloromethyl)-2-(6-methoxy-3-pyridyl)thiazole as reagents, EXAMPLE 867 was obtained. HRMS calculated for $C_{34}H_{36}N_6O_4S_2$: 656.2239; found 657.2343 [(M+H)⁺ form].

3-[[4-hydroxy-1-[(3R,4R)-3-phenyl-1-[[2-(6-piperazin-1-yl-3-pyridyl)thiazol-5-yl]methyl]piperidine-4-carbonyl]-4-piperidyl]methyl]thieno[2,3-d]pyrimidin-4-one (Example 868)

Using General Procedure 6 starting from Preparation R3cp and 2-bromo-5-(bromomethyl)thiazole as reagents, the resulted crude bromo compound was reacted according to General Procedure 9 with 1-[5-(4,4,5,5-tetramethyl-1,3,2-dioxaborolan-2-yl)-2-pyridyl]piperazine to give EXAMPLE 868. HRMS calculated for $C_{37}H_{42}N_8O_3S_2$: 710.2821; found 356.1477 [(M+2H)²⁺ form].

3-[[1-[(3R,4R)-1-[[2-(6-amino-3-pyridyl)thiazol-5-yl]methyl]-3-phenyl-piperidine-4-carbonyl]-4-hydroxy-4-piperidyl]methyl]thieno[2,3-d]pyrimidin-4-one (Example 869)

Using General Procedure 6 starting from Preparation R3cp and 2-bromo-5-(bromomethyl)thiazole as reagents, the resulted crude bromo compound was reacted according to General Procedure 9 with 5-(4,4,5,5-tetramethyl-1,3,2-dioxaborolan-2-yl)pyridin-2-amine to give EXAMPLE 869. HRMS calculated for $C_{33}H_{35}N_7O_3S_2$: 641.2243; found 642.2342 [(M+H)⁺ form].

3-[[4-hydroxy-1-[(3R,4R)-1-[[2-(3-methylimidazo[4,5-b]pyridin-6-yl)thiazol-5-yl]methyl]-3-phenyl-piperidine-4-carbonyl]-4-piperidyl]methyl]thieno[2,3-d]pyrimidin-4-one (Example 870)

Using General Procedure 6 starting from Preparation R3cp and 2-bromo-5-(bromomethyl)thiazole as reagents, the resulted crude bromo compound was reacted according to General Procedure 9 with 3-methyl-6-(4,4,5,5-tetramethyl-1,3,2-dioxaborolan-2-yl)imidazo[4,5-b]pyridine to give EXAMPLE 870. HRMS calculated for $C_{35}H_{36}N_8O_3S_2$: 680.2352; found 341.1257 [(M+2H)$^{2+}$ form].

3-[[4-hydroxy-1-[(3R,4R)-1-[(2-imidazo[1,2-a]pyridin-7-yl)thiazol-5-yl)methyl]-3-phenyl-piperidine-4-carbonyl]-4-piperidyl]methyl]thieno[2,3-d]pyrimidin-4-one (Example 871)

Using General Procedure 6 starting from Preparation R3cp and 2-bromo-5-(bromomethyl)thiazole as reagents, the resulted crude bromo compound was reacted according to General Procedure 9 with imidazo[1,2-a]pyridin-7-ylboronic acid to give EXAMPLE 871. HRMS calculated for $C_{35}H_{35}N_7O_3S_2$: 665.2243; found 333.6191 [(M+2H)$^{2+}$ form].

6-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-3-phenyl-triazolo[4,5-d]pyrimidin-7-one (Example 872)

Using General Procedure 7 starting from Preparation R3cv and Preparation R1d as reagents, EXAMPLE 872 was obtained. HRMS calculated for $C_{39}H_{39}N_9O_4S$: 729.2845; found 730.2937 [(M+H)$^+$ form].

1-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-9-phenyl-purin-6-one (Example 873)

Using General Procedure 7 starting from Preparation R3cw and Preparation R1d as reagents, EXAMPLE 873 was obtained. HRMS calculated for $C_{40}H_{40}N_8O_4$: 728.2893; found 727.2866 [(M+H)$^+$ form].

5-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-1-phenyl-pyrazolo[3,4-d]pyrimidin-4-one (Example 874)

Using General Procedure 6 starting from Preparation R3cx and Preparation R1c as reagents, EXAMPLE 874 was obtained. HRMS calculated for $C_{39}H_{40}N_8O_3S$: 700.2944; found 701.3000 [(M+H)$^+$ form].

1-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-9-phenyl-purin-6-one (Example 875)

Using General Procedure 6 starting from Preparation R3cw and Preparation R1c as reagents, EXAMPLE 875 was obtained. HRMS calculated for $C_{39}H_{40}N_8O_3S$: 700.2944; found 351.1551 [(M+2H)$^{2+}$ form].

1-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]-9-phenyl-purin-6-one (Example 876)

Using General Procedure 6 starting from Preparation R3cw and 5-(chloromethyl)-2-(6-methoxy-3-pyridyl)thiazole as reagents, EXAMPLE 876 was obtained. HRMS calculated for $C_{39}H_{40}N_8O_4S$: 716.2893; found 359.1535 [(M+2H)$^{2+}$ form].

5-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]-1-phenyl-pyrazolo[3,4-d]pyrimidin-4-one (Example 877)

Using General Procedure 6 starting from Preparation R3cx and 5-(chloromethyl)-2-(6-methoxy-3-pyridyl)thiazole as reagents, EXAMPLE 877 was obtained. HRMS calculated for $C_{39}H_{40}N_8O_4S$: 716.2893; found 717.2979 [(M+H)$^+$ form].

5-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-1-phenyl-pyrazolo[3,4-d]pyrimidin-4-one (Example 878)

Using General Procedure 7 starting from Preparation R3cx and Preparation R1d as reagents, EXAMPLE 878 was obtained. HRMS calculated for $C_{40}H_{40}N_8O_4S$: 728.2893; found 729.2961 [(M+H)$^+$ form].

7-bromo-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrrolo[2,1-f][1,2,4]triazin-4-one (Example 879)

Using General Procedure 6 starting from Preparation R3cy and Preparation R1c as reagents, EXAMPLE 879 was obtained. HRMS calculated for $C_{34}H_{36}BrN_7O_3S$: 701.1783; found 702.1856 [(M+H)$^+$ form].

6-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-3-phenyl-isothiazolo[4,5-d]pyrimidin-7-one (Example 880)

Using General Procedure 6 starting from Preparation R3cz and Preparation R1c as reagents, EXAMPLE 880 was obtained. HRMS calculated for $C_{39}H_{39}N_7O_3S_2$: 717.2556; found 718.2602 [(M+H)$^+$ form].

6-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-3-phenyl-isothiazolo[4,5-d]pyrimidin-7-one (Example 881)

Using General Procedure 7 starting from Preparation R3cz and Preparation R1d as reagents, EXAMPLE 881 was obtained. HRMS calculated for $C_{40}H_{39}N_7O_4S_2$: 745.2505; found 746.2575 [(M+H)$^+$ form].

7-bromo-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]pyrrolo[2,1-f][1,2,4]triazin-4-one (Example 882)

Using General Procedure 7 starting from Preparation R3cy and Preparation R1d as reagents, EXAMPLE 882 was obtained. HRMS calculated for $C_{35}H_{36}BrN_7O_4S$: 729.1733; found 730.1797 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-phenyl-thieno[3,4-d]pyrimidin-4-one (Example 883)

Using General Procedure 7 starting from Preparation R3da and Preparation R1d as reagents, EXAMPLE 883 was obtained. HRMS calculated for $C_{41}H_{40}N_6O_4S_2$: 744.2552; found 745.2617 [(M+H)⁺ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-phenyl-thieno[3,4-d]pyrimidin-4-one (Example 884)

Using General Procedure 6 starting from Preparation R3da and Preparation R1c as reagents, EXAMPLE 884 was obtained. HRMS calculated for $C_{40}H_{40}N_6O_3S_2$: 716.2603; found 717.2680 [(M+H)⁺ form].

3-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]-7-phenyl-thieno[3,4-d]pyrimidin-4-one (Example 885)

Using General Procedure 6 starting from Preparation R3da and 5-(chloromethyl)-2-(6-methoxy-3-pyridyl)thiazole as reagents, EXAMPLE 885 was obtained. HRMS calculated for $C_{40}H_{40}N_6O_4S_2$: 732.2552; found 733.2628 [(M+H)⁺ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-phenyl-5H-pyrrolo[3,2-d]pyrimidin-4-one (Example 886)

Using General Procedure 7 starting from Preparation R3db and Preparation R1d as reagents, EXAMPLE 886 was obtained. HRMS calculated for $C_{41}H_{41}N_7O_4S$: 727.2941; found 728.3012 [(M+H)⁺ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-phenyl-5H-pyrrolo[3,2-d]pyrimidin-4-one (Example 887)

Using General Procedure 6 starting from Preparation R3db and Preparation R1c as reagents, EXAMPLE 887 was obtained. HRMS calculated for $C_{40}H_{41}N_7O_3S$: 699.2991; found 700.3065 [(M+H)⁺ form].

3-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]-7-phenyl-5H-pyrrolo[3,2-d]pyrimidin-4-one (Example 888)

Using General Procedure 6 starting from Preparation R3db and 5-(chloromethyl)-2-(6-methoxy-3-pyridyl)thiazole as reagents, EXAMPLE 888 was obtained. HRMS calculated for $C_{40}H_{41}N_7O_4S$: 715.2941; found 716.3013 [(M+H)⁺ form].

7-chloro-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]thieno[3,4-d]pyrimidin-4-one (Example 889)

Using General Procedure 7 starting from Preparation R3dc and Preparation R1d as reagents, EXAMPLE 889 was obtained. HRMS calculated for $C_{35}H_{35}N_6O_4S_2Cl$: 702.185; found 703.1921 [(M+H)⁺ form].

7-chloro-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]thieno[3,4-d]pyrimidin-4-one (Example 890)

Using General Procedure 6 starting from Preparation R3dc and Preparation R1c as reagents, EXAMPLE 890 was obtained. HRMS calculated for $C_{34}H_{35}ClN_6O_3S_2$: 674.1901; found 675.1992 [(M+H)⁺ form].

6-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-3-phenyl-isoxazolo[4,5-d]pyrimidin-7-one (Example 891)

Using General Procedure 7 starting from Preparation R3dd and Preparation R1d as reagents, EXAMPLE 891 was obtained. HRMS calculated for $C_{40}H_{39}N_7O_5S$: 729.2733; found 730.2806 [(M+H)⁺ form].

6-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-3-phenyl-isoxazolo[4,5-d]pyrimidin-7-one (Example 892)

Using General Procedure 6 starting from Preparation R3dd and Preparation R1c as reagents, EXAMPLE 892 was obtained. HRMS calculated for $C_{39}H_{39}N_7O_4S$: 701.2784; found 702.2878 [(M+H)⁺ form].

5-[[1-[(3R,4R)-1-[(2-bromothiazol-5-yl)methyl]-3-phenyl-piperidine-4-carbonyl]-4-hydroxy-4-piperidyl]methyl]-1-(4-methoxyphenyl)pyrazolo[3,4-d]pyrimidin-4-one (Example 893)

Using General Procedure 6 starting from Preparation R3de and 2-bromo-5-(bromomethyl)thiazole as reagents, EXAMPLE 893 was obtained. HRMS calculated for $C_{34}H_{36}BrN_7O_4S$: 717.1733; found 718.1792 [(M+H)⁺ form].

5-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-1-(4-methoxyphenyl)pyrazolo[3,4-d]pyrimidin-4-one (Example 894)

Using General Procedure 6 starting from Preparation R3de and Preparation R1c as reagents, EXAMPLE 894 was obtained. HRMS calculated for $C_{40}H_{42}N_8O_4S$: 730.305; found 731.3146 [(M+H)⁺ form].

5-[[4-hydroxy-1-[(3R,4R)-1-[[2-(6-methoxy-3-pyridyl)thiazol-5-yl]methyl]-3-phenyl-piperidine-4-carbonyl]-4-piperidyl]methyl]-1-(4-methoxyphenyl)pyrazolo[3,4-d]pyrimidin-4-one (Example 895)

Using General Procedure 6 starting from Preparation R3de and 5-(chloromethyl)-2-(6-methoxy-3-pyridyl)thiazole as reagents, EXAMPLE 895 was obtained. HRMS calculated for $C_{40}H_{42}N_8O_5S$: 746.2999; found 747.3071 [(M+H)⁺ form].

5-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-1-(4-methoxyphenyl)pyrazolo[3,4-d]pyrimidin-4-one (Example 896)

Using General Procedure 7 starting from Preparation R3de and Preparation R1d as reagents, EXAMPLE 896 was obtained. HRMS calculated for $C_{41}H_{42}N_8O_5S$: 758.2999; found 759.3064 [(M+H)$^+$ form].

1-(2,3-dihydro-1,4-benzodioxin-6-yl)-5-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]pyrazolo[3,4-d]pyrimidin-4-one (Example 897)

Using General Procedure 7 starting from Preparation R3df and Preparation R1d as reagents, EXAMPLE 897 was obtained. HRMS calculated for $C_{42}H_{42}N_8O_6S$: 786.2948; found 787.3016 [(M+H)$^+$ form].

1-(2,3-dihydro-1,4-benzodioxin-6-yl)-5-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrazolo[3,4-d]pyrimidin-4-one (Example 898)

Using General Procedure 6 starting from Preparation R3df and Preparation R1c as reagents, EXAMPLE 898 was obtained. HRMS calculated for $C_{41}H_{42}N_8O_5S$: 758.2999; found 759.3077 [(M+H)$^+$ form].

6-amino-3-[[1-[(3R,4R)-1-benzyl-3-phenyl-piperidine-4-carbonyl]-4-hydroxy-4-piperidyl]methyl]pyrido[3,2-d]pyrimidin-4-one (Example 899)

EXAMPLE 830 (8 mg, 0.013 mmol), benzophenone imine (18 mg, 0.1 mmol), cesium-carbonate (11.1 mg, 0.033 mmol), 4,5-bis(diphenylphosphino)-9,9-dimethylxanthene (1.3 mg, 0.002 mmol), tris(dibenzylideneacetone)dipalladium(0) (1.1 mg, 0.001 mmol) were stirred in abs. toluene (3 ml) at 110° C. for 5 hours. The reaction mixture was evaporated, to the residue aqueous HCl solution (1 N, 2 ml) and PDO (1 ml) were added and the mixture was stirred at r.t. for 3 hours. The reaction mixture was purified by preparative LC (on C-18 Gemini-NX 5 μm column, 5 mM aqueous NH$_4$HCO$_3$-MeCN, gradient) to give EXAMPLE 899. HRMS calculated for $C_{32}H_{36}N_6O_3$: 552.2849; found 551.2818 [(M+H)$^+$ form].

6-amino-3-[[1-[(3R,4R)-1-[(2-fluorophenyl)methyl]-3-phenyl-piperidine-4-carbonyl]-4-hydroxy-4-piperidyl]methyl]pyrido[3,2-d]pyrimidin-4-one (Example 900)

The solution of EXAMPLE 852 (110 mg, 0.159 mmol) in TFA (3 ml) was stirred at 70° C. for 90 minutes, then evaporated. The residue was purified by preparative LC (on C-18 Gemini-NX 5 μm column, 5 mM aqueous NH$_4$HCO$_3$-MeCN, gradient) to give EXAMPLE 900. HRMS calculated for $C_{32}H_{35}FN_6O_3$: 570.2755; found 286.1457 [(M+2H)$^{2+}$ form].

N-[3-[[1-[(3R,4R)-1-[(2-fluorophenyl)methyl]-3-phenyl-piperidine-4-carbonyl]-4-hydroxy-4-piperidyl]methyl]-4-oxo-pyrido[3,2-d]pyrimidin-6-yl]-2-(2-oxoindolin-6-yl)acetamide (Example 901)

Using General Procedure 7 starting from EXAMPLE 900 as amine component and 2-(2-oxoindolin-6-yl)acetic acid as carboxylic acid reactant, EXAMPLE 901 was obtained. HRMS calculated for $C_{42}H_{42}FN_7O_5$: 743.3231; found 372.6692 [(M+2H)$^{2+}$ form].

N-[3-[[1-[(3R,4R)-1-[(2-fluorophenyl)methyl]-3-phenyl-piperidine-4-carbonyl]-4-hydroxy-4-piperidyl]methyl]-4-oxo-pyrido[3,2-d]pyrimidin-6-yl]-2-(3-hydroxyphenyl)acetamide (Example 902)

Using General Procedure 7 starting from EXAMPLE 900 as amine component and 3-hydroxyphenylacetic acid as carboxylic acid reactant, EXAMPLE 902 was obtained. HRMS calculated for $C_{40}H_{41}FN_6O_5$: 704.3122; found 353.1636 [(M+2H)$^{2+}$ form].

3-[[4-hydroxy-1-[(3R,4R)-1-(4-methyl-2-phenyl-thiazole-5-carbonyl)-3-phenyl-piperidine-4-carbonyl]-4-piperidyl]methyl]-6-[(4-methoxyphenyl)methylamino]pyrido[3,2-d]pyrimidin-4-one (Example 903)

EXAMPLE 853 (320 mg, 0.468 mmol) was stirred in 4-methoxybenzylamine (7 ml) at 100° C. for 4 hours. The reaction mixture was purified by preparative LC (on C-18 Gemini-NX 5 μm column, 5 mM aqueous NH$_4$HCO$_3$-MeCN, gradient) to give EXAMPLE 903. HRMS calculated for $C_{44}H_{45}N_7O_5S$: 783.3203; found 784.326 [(M+H)$^+$ form].

6-amino-3-[[4-hydroxy-1-[(3R,4R)-1-(4-methyl-2-phenyl-thiazole-5-carbonyl)-3-phenyl-piperidine-4-carbonyl]-4-piperidyl]methyl]pyrido[3,2-d]pyrimidin-4-one (Example 904)

The solution of EXAMPLE 903 (159 mg, 0.203 mmol) in TFA (3 ml) was stirred at 70° C. for 120 minutes, then evaporated. The residue was purified by preparative LC (on C-18 Gemini-NX 5 μm column, 5 mM aqueous NH$_4$HCO$_3$-MeCN, gradient) to give EXAMPLE 904. HRMS calculated for $C_{36}H_{37}N_7O_4S$: 663.2628; found 332.6401 [(M+2H)$^{2+}$ form].

N-[3-[[4-hydroxy-1-[(3R,4R)-1-(4-methyl-2-phenyl-thiazole-5-carbonyl)-3-phenyl-piperidine-4-carbonyl]-4-piperidyl]methyl]-4-oxo-pyrido[3,2-d]pyrimidin-6-yl]-2-(2-oxoindolin-6-yl)acetamide (Example 905)

Using General Procedure 7 starting from EXAMPLE 904 as amine component and 2-(2-oxoindolin-6-yl)acetic acid as carboxylic acid reactant, EXAMPLE 905 was obtained. HRMS calculated for $C_{46}H_{44}N_8O_6S$: 836.3105; found 837.3173 [(M+H)$^+$ form].

N-[3-[[4-hydroxy-1-[(3R,4R)-1-(4-methyl-2-phenyl-thiazole-5-carbonyl)-3-phenyl-piperidine-4-carbonyl]-4-piperidyl]methyl]-4-oxo-pyrido[3,2-d]pyrimidin-6-yl]-2-(3-hydroxyphenyl)acetamide (Example 906)

Using General Procedure 7 starting from EXAMPLE 904 as amine component and 3-hydroxyphenylacetic acid as carboxylic acid reactant, EXAMPLE 906 was obtained. HRMS calculated for $C_{44}H_{43}N_7O_6S$: 797.2996; found 798.3073 [(M+H)$^+$ form].

N-[3-[[4-hydroxy-1-[(3R,4R)-1-(4-methyl-2-phenyl-thiazole-5-carbonyl)-3-phenyl-piperidine-4-carbonyl]-4-piperidyl]methyl]-4-oxo-pyrido[3,2-d]pyrimidin-6-yl]-2-phenyl-acetamide (Example 907)

Using General Procedure 7 starting from EXAMPLE 904 as amine component and phenylacetic acid as carboxylic acid reactant, EXAMPLE 907 was obtained. HRMS calculated for $C_{44}H_{43}N_7O_5S$: 781.3046; found 782.3136 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-phenyl-pyrrolo[2,1-f][1,2,4]triazin-4-one (Example 908)

Using General Procedure 9 starting from EXAMPLE 879 as reactant and phenylboronic acid as reagent, EXAMPLE 908 was obtained. HRMS calculated for $C_{40}H_{41}N_7O_3S$: 699.2991; found 700.3034 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-phenyl-pyrrolo[2,1-f][1,2,4]triazin-4-one (Example 909)

Using General Procedure 9 starting from EXAMPLE 882 as reactant and phenylboronic acid as reagents, EXAMPLE 909 was obtained. HRMS calculated for $C_{41}H_{41}N_7O_4S$: 727.2941; found 728.3013 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-5-methyl-7-phenyl-pyrrolo[3,2-d]pyrimidin-4-one (Example 910)

The suspension of EXAMPLE 886 (0.052 mmol), iodomethane (6.5 µl, 0.104 mmol) and $K_2CO_3$ (14.4 mg, 0.104 mmol) in DMF (1 ml) was stirred at r.t. overnight. The reaction mixture was filtered through syringe filter and purified by preparative LC (on C-18 Gemini-NX 5 µm column, 5 mM aqueous $NH_4HCO_3$-MeCN, gradient) to give EXAMPLE 910. HRMS calculated for $C_{42}H_{43}N_7O_4S$: 741.3098; found 742.3171 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-(1-methylpyrrol-3-yl)thieno[3,4-d]pyrimidin-4-one (Example 911)

Using General Procedure 9 starting from EXAMPLE 890 and 1-methyl-3-(4,4,5,5-tetramethyl-1,3,2-dioxaborolan-2-yl)pyrrole as reagents, EXAMPLE 911 was obtained. HRMS calculated for $C_{39}H_{41}N_7O_3S_2$: 719.2712; found 718.2672 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-(1-methylpyrazol-4-yl)thieno[3,4-d]pyrimidin-4-one (Example 912)

Using General Procedure 9 starting from EXAMPLE 890 and 1-methyl-4-(4,4,5,5-tetramethyl-1,3,2-dioxaborolan-2-yl)pyrazole as reagents, EXAMPLE 912 was obtained. HRMS calculated for $C_{38}H_{40}N_8O_3S_2$: 720.2665; found 721.2703 [(M+H)$^+$ form].

7-(3-furyl)-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]thieno[3,4-d]pyrimidin-4-one (Example 913)

Using General Procedure 9 starting from EXAMPLE 890 and 2-(3-furyl)-4,4,5,5-tetramethyl-1,3,2-dioxaborolane as reagents, EXAMPLE 913 was obtained. HRMS calculated for $C_{38}H_{38}N_6O_4S_2$: 706.2396; found 707.2448 [(M+H)$^+$ form].

7-[4-(hydroxymethyl)phenyl]-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]thieno[3,4-d]pyrimidin-4-one (Example 914)

Using General Procedure 9 starting from EXAMPLE 890 and [4-(hydroxymethyl)phenyl]boronic acid as reagents, EXAMPLE 914 was obtained. HRMS calculated for $C_{41}H_{42}N_6O_4S_2$: 746.2709; found 747.2782 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-(1-methylpyrrol-3-yl)pyrrolo[2,1-f][1,2,4]triazin-4-one (Example 915)

Using General Procedure 9 starting from EXAMPLE 879 as reactant and 1-methyl-3-(4,4,5,5-tetramethyl-1,3,2-dioxaborolan-2-yl)pyrrole as reagent, EXAMPLE 915 was obtained. HRMS calculated for $C_{39}H_{42}N_8O_3S$: 702.3101; found 703.3187 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-7-(1-methylpyrazol-4-yl)pyrrolo[2,1-f][1,2,4]triazin-4-one (Example 916)

Using General Procedure 9 starting from EXAMPLE 879 as reactant and 1-methyl-4-(4,4,5,5-tetramethyl-1,3,2-dioxaborolan-2-yl)pyrazole as boron reagent, EXAMPLE 916 was obtained. HRMS calculated for $C_{38}H_{41}N_9O_3S$: 703.3053; found 704.3159 [(M+H)$^+$ form].

7-(3-furyl)-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrrolo[2,1-f][1,2,4]triazin-4-one (Example 917)

Using General Procedure 9 starting from EXAMPLE 879 as reactant and 2-(3-furyl)-4,4,5,5-tetramethyl-1,3,2-dioxaborolane as boron reagent, EXAMPLE 917 was obtained. HRMS calculated for $C_{38}H_{39}N_7O_4S$: 689.2784; found 690.2875 [(M+H)$^+$ form].

7-(2-furyl)-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrrolo[2,1-f][1,2,4]triazin-4-one (Example 918)

Using General Procedure 9 starting from EXAMPLE 879 as reactant and 2-furylboronic acid as boron reagent, EXAMPLE 918 was obtained. HRMS calculated for $C_{38}H_{39}N_7O_4S$: 689.2784; found 690.2865 [(M+H)$^+$ form].

7-[4-(hydroxymethyl)phenyl]-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrrolo[2,1-f][1,2,4]triazin-4-one (Example 919)

Using General Procedure 9 starting from EXAMPLE 879 as reactant and [4-(hydroxymethyl)phenyl]boronic acid as boron reagent, EXAMPLE 919 was obtained. HRMS calculated for $C_{41}H_{43}N_7O_4S$: 729.3098; found 730.3161 [(M+H)$^+$ form].

6-chloro-7-(4-chloro-3-fluoro-phenyl)-3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]pyrrolo[2,3-d]pyrimidin-4-one (Example 920)

Using General Procedure 6 starting from Preparation R3dg and Preparation R1c as reagents, EXAMPLE 920 was obtained. HRMS calculated for $C_{40}H_{38}Cl_2FN_7O_3S$: 785.2118; found 786.2163 [(M+H)$^+$ form].

3-[[4-hydroxy-1-[(3R,4R)-1-[[2-(6-methyl-3-pyridyl)thiazol-5-yl]methyl]-3-phenyl-piperidine-4-carbonyl]-4-piperidyl]methyl]-6-methyl-7-phenyl-pyrrolo[2,3-d]pyrimidin-4-one (Example 921)

Using General Procedure 6 starting from Preparation R3dh and Preparation R1c as reagents, EXAMPLE 921 was obtained. HRMS calculated for $C_{41}H_{43}N_7O_3S$: 713.3148; found 714.3208 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-9-methyl-pyrimido[4,5-b]indol-4-one (Example 922)

Using General Procedure 7 starting from Preparation R3di and Preparation R1d as reagents, EXAMPLE 922 was obtained. HRMS calculated for $C_{40}H_{41}N_7O_4$: 715.2941; found 716.3047 [(M+H)$^+$ form].

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-6,8-dimethylpyrimido[5',4':4,5]pyrrolo[1,2-b]pyridazin-4(3H)-one (Example 923)

Using General Procedure 7 starting from Preparation R3dj and Preparation R1d as reagents, EXAMPLE 923 was obtained. HRMS calculated for $C_{40}H_{42}N_8O_4$: 730.305; found 731.3134 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-6-methyl-7-phenyl-pyrrolo[2,3-d]pyrimidin-4-one (Example 924)

Using General Procedure 7 starting from Preparation R3dh and Preparation R1d as reagents, EXAMPLE 924 was obtained. HRMS calculated for $C_{42}H_{43}N_7O_4$: 741.3098; found 742.3179 [(M+H)$^+$ form].

6-chloro-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-phenyl-pyrrolo[2,3-d]pyrimidin-4-one (Example 925)

Using General Procedure 7 starting from Preparation R3dk and Preparation R1d as reagents, EXAMPLE 925 was obtained. HRMS calculated for $C_{41}H_{40}ClN_7O_4S$: 761.2551; found 762.2633 [(M+H)$^+$ form].

3-[[1-[(3R,4R)-1-[3-fluoro-5-(2-methyl-4-pyridyl)thiophene-2-carbonyl]-3-phenyl-piperidine-4-carbonyl]-4-hydroxy-4-piperidyl]methyl]-7-methyl-6-(2-thienyl)pyrrolo[2,3-d]pyrimidin-4-one (Example 926)

Using General Procedure 9 starting from Preparation R3dl as halogenated reactant and 2-thienylboronic acid as boronic acid reagent, 3-[(4-hydroxy-1-{[(3R,4R)-3-phenylpiperidin-4-yl]carbonyl}piperidin-4-yl)methyl]-7-methyl-6-(thiophen-2-yl)-3,7-dihydro-4H-pyrrolo[2,3-d]pyrimidin-4-one was obtained. This intermediate was reacted with Preparation R1g according to General Procedure 7, and the crude iodo compound was reacted according to General Procedure 9 with (2-methyl-4-pyridyl)boronic acid to give EXAMPLE 926. HRMS calculated for $C_{40}H_{39}FN_6O_4S_2$: 750.2458; found 751.2537 [(M+H)$^+$ form].

N-[[3-[[1-[(3R,4R)-1-[(3-fluorophenyl)methyl]-3-phenyl-piperidine-4-carbonyl]-4-hydroxy-4-piperidyl]methyl]-4-oxo-7H-pyrrolo[2,3-d]pyrimidin-6-yl]methyl]acetamide (Example 927)

2-[(4-chloropyrrolo[2,3-d]pyrimidin-7-yl)methoxy]ethyl-trimethyl-silane (3.5 g, 12.3 mmol) was dissolved in abs. THF (55 ml) and cooled to −78° C., then LDA (2.0 M, 6.8 ml, 13.6 mmol) was added to the mixture and stirred at −78° C. for 40 minutes, then iodine (3.13 g, 12.3 mmol) was added to the mixture, continued stirring at −78° C. for 3 hours. Water (25 ml) was added to the reaction mixture and extracted with EEO (2×30 ml). The combined organic layers were evaporated to Celite and purified by flash chromatography (heptane-EEO, gradient).

A part of the crude product (2.38 g, 5.81 mmol) and lithium-hydroxide hydrate (2.44 g, 58.1 mmol) were dissolved in PDO and water mixture (30 ml, v/v=1:1) and stirred at 100° C. for 70 hours. The reaction mixture was acidified with 1 N aqueous HCl solution. The resulted solid compound was filtered off, washed with water and dried.

The pyrimidone product was reacted using General Procedure 5 with Preparation R1e as epoxide component.

The crude product (3.5 g, 5.79 mmol), copper(I)-cyanide (2.18 g, 24.32 mmol), tetraethylammonium-cyanide (950 mg, 6.08 mmol), tris (dibenzylideneacetone)dipalladium(0) (531 mg, 0.58 mmol), and 1,1'-bis(diphenylphosphino)ferrocene (1.29 g, 2.32 mmol) were dissolved in abs. PDO (45 ml) and the mixture was stirred at 110° C. for 2.3 hours. The reaction mixture was filtered, the filtrate was evaporated, the residue was diluted with MeOH (15 ml) then filtered again. The filtrate was evaporated to Celite and purified by flash chromatography (DCM-MeOH, gradient).

The resulted Boc-protected cyano-product (2.42 g, 4.81 mmol) was deprotected by stirring in mixture of TFA (1.11 ml, 14.47 mmol), formic acid (6.29 ml, 166.6 mmol) and DCM (60 ml) at r.t. for 52 hours. To the reaction mixture $K_2CO_3$ (25 g) and DCM (180 ml) was added and extracted with water (2×160 ml). The organic layer was evaporated.

The crude piperidine product was reacted with (3R,4R)-1-tert-butoxycarbonyl-3-phenyl-piperidine-4-carboxylic acid using General Procedure 7.

The resulted Boc-protected product (798 mg, 1.16 mmol) was deprotected by stirring in mixture of TFA (266 µl, 3.48 mmol), formic acid (503 µl, 13.3 mmol) and DCM (15 ml)

at r.t. for 164 hours. To the reaction mixture K$_2$CO$_3$ (2.8 g) was added and extracted with water (2×75 ml). The organic layer was evaporated.

The crude piperidine product was reacted with 3-fluorobenzylchloride according to General Procedure 6.

The resulted crude product (534 mg, 0.76 mmol) and Raney-nickel (240 mg) were stirred in ammonia solution in methanol (7 M, 15 ml) under hydrogen atmosphere (2 bar) for 68 hours. The reaction mixture was filtered, the filtrate was evaporated.

The crude aminomethyl product was reacted with acetic acid according to General Procedure 7.

The resulted product (85.7 mg, 0.115 mmol) was stirred in TBAF solution (1 M in THF, 223 µl, 0.223 mmol) and THF (0.5 ml) at 75° C. for 65 hours. The reaction mixture was purified by preparative LC (on C-18 Gemini-NX 10 µm column, 5 mM aqueous NH$_4$HCO$_3$-MeCN, gradient) to give EXAMPLE 927. HRMS calculated for C$_{34}$H$_{39}$FN$_6$O$_4$: 614.3017; found 615.3082 [(M+H)$^+$ form].

3-[[4-hydroxy-1-[(3R,4R)-3-phenyl-1-(p-tolylmethyl)piperidine-4-carbonyl]-4-piperidyl]methyl]-6-(2-thienyl)-7H-pyrrolo[2,3-d]pyrimidin-4-one (Example 928)

2-[(4-chloropyrrolo[2,3-d]pyrimidin-7-yl)methoxy]ethyl-trimethyl-silane (3.5 g, 12.3 mmol) was dissolved in THF (abs., 55 ml) and cooled to −78° C., then LDA (2.0 M, 6.8 ml, 13.6 mmol) was added to the mixture and stirred at −78° C. for 40 minutes, then iodine (3.13 g, 12.3 mmol) was added to the mixture, continued stirring at −78° C. for 3 hours. Water (25 ml) was added to the reaction mixture and extracted with EEO (2×30 ml). The combined organic layers were evaporated to Celite and purified by flash chromatography (heptane-EEO gradient).

A part of the crude product (2.0 g, 4.88 mmol) and lithium-hydroxide hydrate (2.05 g, 48.8 mmol) were dissolved in PDO and water mixture (30 ml, v/v=1:1) and stirred at 100° C. for 65 hours. The reaction mixture was acidified with 1 N aqueous HCl solution. The resulted solid compound was filtered off, washed with water and dried.

The pyrimidone product was reacted using General Procedure 5 with Preparation R1e as epoxide component.

The resulted Boc-protected product (930 mg, 1.54 mmol) was deprotected by stirring in mixture of TFA (363 µl, 4.74 mmol), formic acid (2.06 ml, 54.6 mmol) and DCM (18.6 ml) at r.t. for 46 hours. To the reaction mixture K$_2$CO$_3$ (6.5 g) was added and extracted with water (2×80 ml). The organic layers were evaporated and the residue was triturated with water (5 ml) to give a solid compound which was filtered off and dried.

The crude piperidine product was reacted with (3R,4R)-1-tert-butoxycarbonyl-3-phenyl-piperidine-4-carboxylic acid using General Procedure 7.

The crude Boc-protected product (647 mg, 0.82 mmol) was deprotected by stirring in mixture of TFA (188 µl, 2.46 mmol), formic acid (356 µl, 9.43 mmol) and DCM (13 ml) at r.t. for 214 hours. To the reaction mixture, K$_2$CO$_3$ (1.99 g) was added. The solution was extracted with water (2×70 ml) and the organic layer was evaporated.

The crude product was N-alkylated with 4-methyl-benzylchloride according to General Procedure 6.

The crude alkylated compound (165 mg, 0.21 mmol), 2-thienylboronic acid (41 mg, 0.32 mmol), lithium-chloride (27 mg, 0.63 mmol) and [1,1'-bis(diphenylphosphino)ferrocene]dichloropalladium(II) (15 mg, 0.021 mmol) were dissolved in aqueous Na$_2$CO$_3$ solution (2 M, 265 µl, 0.53 mmol), toluene (4 ml) and EtOH (4 ml) and stirred at 80° C. for 23 hours. The insoluble part was filtered off, the filtrate was evaporated and the residue was purified by preparative LC (on C-18 Gemini-NX 10 µm column, 25 mM aqueous NH$_4$HCO$_3$-MeCN, gradient).

The resulted product (72 mg, 0.096 mmol) was stirred in TBAF solution (1 M in THF, 144 µl, 0.144 mmol) and THF (0.5 ml) at 75° C. for 65 hours. The reaction mixture was purified by preparative LC (on C-18 Gemini-NX 10 µm column, 5 mM aqueous NH$_4$HCO$_3$-MeCN, gradient) to give EXAMPLE 928. HRMS calculated for C$_{36}$H$_{39}$N$_5$O$_3$S: 621.2773; found 622.2846 [(M+H)$^+$ form].

3-[[4-hydroxy-1-[(3R,4R)-3-phenyl-1-(p-tolylmethyl)piperidine-4-carbonyl]-4-piperidyl]methyl]-6-(3-thienyl)-7H-pyrrolo[2,3-d]pyrimidin-4-one (Example 929)

2-[(4-chloropyrrolo[2,3-d]pyrimidin-7-yl)methoxy]ethyl-trimethyl-silane (3.5 g, 12.3 mmol) was dissolved in THF (abs., 55 ml) and cooled to −78° C., then LDA (2.0 M, 6.8 ml, 13.6 mmol) was added to the mixture and stirred at −78° C. for 40 minutes, then iodine (3.13 g, 12.3 mmol) was added to the mixture, continued stirring at −78° C. for 3 hours. Water (25 ml) was added to the reaction mixture and extracted with EEO (2×30 ml). The combined organic layers were evaporated to Celite and purified by flash chromatography (heptane-EEO gradient).

A part of the crude product (2.0 g, 4.88 mmol) and lithium-hydroxide hydrate (2.05 g, 48.8 mmol) were dissolved in PDO and water mixture (30 ml, v/v=1:1) and stirred at 100° C. for 65 hours. The reaction mixture was acidified with 1 N aqueous HCl solution. The resulted solid compound was filtered off, washed with water and dried.

The pyrimidone product was reacted using General Procedure 5 with Preparation R1e as epoxide component.

The resulted Boc-protected product (930 mg, 1.54 mmol) was deprotected by stirring in mixture of TFA (363 µl, 4.74 mmol), formic acid (2.06 ml, 54.6 mmol) and DCM (18.6 ml) at r.t. for 46 hours. To the reaction mixture K$_2$CO$_3$ (6.5 g) was added and extracted with water (2×80 ml). The organic layers were evaporated and the residue was triturated with water (5 ml) to give a solid compound which was filtered off and dried.

The crude piperidine product was reacted with (3R,4R)-1-tert-butoxycarbonyl-3-phenyl-piperidine-4-carboxylic acid using General Procedure 7.

The crude Boc-protected product (647 mg, 0.82 mmol) was deprotected by stirring in mixture of TFA (188 µl, 2.46 mmol), formic acid (356 µl, 9.43 mmol) and DCM (13 ml) at r.t. for 214 hours. To the reaction mixture, K$_2$CO$_3$ (1.99 g) was added. The solution was extracted with water (2×70 ml) and the organic layer was evaporated.

The crude product was N-alkylated with 4-methyl-benzylchloride according to General Procedure 6.

The crude alkylated compound (170 mg, 0.21 mmol), 4,4,5,5-tetramethyl-2-(3-thienyl)-1,3,2-dioxaborolane (67 mg, 0.32 mmol), lithium-chloride (27 mg, 0.63 mmol) and [1,1'-bis(diphenylphosphino)ferrocene]dichloropalladium (II) (15 mg, 0.021 mmol) were dissolved in aqueous Na$_2$CO$_3$ solution (2 M, 265 µl, 0.53 mmol), toluene (4 ml) and EtOH (4 ml) and stirred at 80° C. for 23 hours. The insoluble part was filtered off, the filtrate was evaporated and the residue was purified by preparative LC (on C-18 Gemini-NX 5 µm column, 5 mM aqueous NH$_4$HCO$_3$-MeCN, gradient).

The resulted product (72 mg, 0.096 mmol) was stirred in TBAF solution (1 M in THF, 144 μl, 0.144 mmol) and THF (0.5 ml) at 75° C. for 60 hours. The reaction mixture was purified by preparative LC (on C-18 Gemini-NX 10 μm column, 5 mM aqueous $NH_4HCO_3$-MeCN, gradient) to give EXAMPLE 929. HRMS calculated for $C_{36}H_{39}N_5O_3S$: 621.2773; found 622.2834 [$(M+H)^+$ form].

6-(2-fluorophenyl)-3-[[4-hydroxy-1-[(3R,4R)-3-phenyl-1-(p-tolylmethyl)piperidine-4-carbonyl]-4-piperidyl]methyl]-7H-pyrrolo[2,3-d]pyrimidin-4-one (Example 930)

2-[(4-chloropyrrolo[2,3-d]pyrimidin-7-yl)methoxy]ethyl-trimethyl-silane (3.5 g, 12.3 mmol) was dissolved in THF (abs., 55 ml) and cooled to −78° C., then LDA (2.0 M, 6.8 ml, 13.6 mmol) was added to the mixture and stirred at −78° C. for 40 minutes, then iodine (3.13 g, 12.3 mmol) was added to the mixture, continued stirring at −78° C. for 3 hours. Water (25 ml) was added to the reaction mixture and extracted with EEO (2×30 ml). The combined organic layers were evaporated to Celite and purified by flash chromatography (heptane-EEO gradient).

A part of the crude product (2.0 g, 4.88 mmol) and lithium-hydroxide hydrate (2.05 g, 48.8 mmol) were dissolved in PDO and water mixture (30 ml, v/v=1:1) and stirred at 100° C. for 65 hours. The reaction mixture was acidified with 1 N aqueous HCl solution. The resulted solid compound was filtered off, washed with water and dried.

The pyrimidone product was reacted using General Procedure 5 with Preparation R1e as epoxide component.

The resulted Boc-protected product (930 mg, 1.54 mmol) was deprotected by stirring in mixture of TFA (363 μl, 4.74 mmol), formic acid (2.06 ml, 54.6 mmol) and DCM (18.6 ml) at r.t. for 46 hours. To the reaction mixture $K_2CO_3$ (6.5 g) was added and extracted with water (2×80 ml). The organic layers were evaporated and the residue was triturated with water (5 ml) to give a solid compound which was filtered off and dried.

The crude piperidine product was reacted with (3R,4R)-1-tert-butoxycarbonyl-3-phenyl-piperidine-4-carboxylic acid using General Procedure 7.

The crude Boc-protected product (647 mg, 0.82 mmol) was deprotected by stirring in mixture of TFA (188 μl, 2.46 mmol), formic acid (356 μl, 9.43 mmol) and DCM (13 ml) at r.t. for 214 hours. To the reaction mixture, $K_2CO_3$ (1.99 g) was added. The solution was extracted with water (2×70 ml) and the organic layer was evaporated.

The crude product was N-alkylated with 4-methyl-benzylchloride according to General Procedure 6.

The crude alkylated compound (170 mg, 0.21 mmol), 2-fluorophenylboronic acid (44 mg, 0.32 mmol), lithium-chloride (27 mg, 0.63 mmol) and [1,1'-bis(diphenylphosphino)ferrocene]dichloropalladium(II) (15 mg, 0.021 mmol) were dissolved in aqueous $Na_2CO_3$ solution (2 M, 265 μl, 0.53 mmol), toluene (4 ml) and EtOH (4 ml) and stirred at 80° C. for 22 hours. The insoluble part was filtered off, the filtrate was evaporated and the residue was purified by preparative LC (on C-18 Gemini-NX 5 μm column, 5 mM aqueous $NH_4HCO_3$-MeCN, gradient).

The resulted product (70 mg, 0.09 mmol) was stirred in TBAF solution (1 M in THF, 138 μl, 0.138 mmol) and THF (0.5 ml) at 75° C. for 60 hours. The reaction mixture was purified by preparative LC (on C-18 Gemini-NX 10 μm column, 5 mM aqueous $NH_4HCO_3$-MeCN, gradient) to give EXAMPLE 930. HRMS calculated for $C_{38}H_{40}FN_5O_3$: 633.3115; found 634.3194 [$(M+H)^+$ form].

5-fluoro-3-[[4-hydroxy-1-[(3R,4R)-1-(4-methyl-2-phenyl-thiazole-5-carbonyl)-3-phenyl-piperidine-4-carbonyl]-4-piperidyl]methyl]-7-methyl-pyrrolo[2,3-d]pyrimidin-4-one (Example 931)

Using General Procedure 11 starting from Preparation R2dj and (4-methyl-2-phenyl-1,3-thiazol-5-yl) [(3R,4R)-4-(1-oxa-6-azaspiro[2.5]oct-6-ylcarbonyl)-3-phenylpiperidin-1-yl]methanone as reagents, EXAMPLE 931 was obtained. HRMS calculated for $C_{36}H_{37}FN_6O_4S$: 668.2581; found 669.2649 [$(M+H)^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7,8-dihydro-6H-pyrimido[5,4-b]pyrrolizin-4-one (Example 932)

Using General Procedure 11 starting from Preparation R2dk and Preparation R1m as reagents, EXAMPLE 932 was obtained. HRMS calculated for $C_{38}H_{41}N_7O_4S$: 691.2941; found 346.6539 [$M+2H)^{2+}$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-6,7,8,9-tetrahydro-pyrimido[5,4-b]indolizin-4-one (Example 933)

Using General Procedure 11 starting from Preparation R2dl and Preparation R1m as reagents, EXAMPLE 933 was obtained. HRMS calculated for $C_{39}H_{43}N_7O_4S$: 705.3098; found 706.3172 [$(M+H)^+$ form].

3-[[1-[(3R,4S)-1-benzyl-3-(2-thienyl)piperidine-4-carbonyl]-4-hydroxy-4-piperidyl]methyl]-7H-pyrrolo[2,3-d]pyrimidin-4-one (Example 934)

Using General Procedure 5 starting from 3H,4H,7H-pyrrolo[2,3-d]pyrimidin-4-one and Preparation R1e as epoxide component, the crude product was reacted with Preparation R1q-(3R,4S) according to General Procedure 7 to give EXAMPLE 934. HRMS calculated for $C_{29}H_{33}N_5O_3S$: 531.2304; found 532.2388 [$(M+H)^+$ form].

3-[[1-[(3S,4R)-1-benzyl-3-(2-thienyl)piperidine-4-carbonyl]-4-hydroxy-4-piperidyl]methyl]-7H-pyrrolo[2,3-d]pyrimidin-4-one (Example 935)

Using General Procedure 5 starting from 3H,4H,7H-pyrrolo[2,3-d]pyrimidin-4-one and Preparation R1e as epoxide component, the crude product was reacted with Preparation R1q-(3S,4R) according to General Procedure 7 to give EXAMPLE 935. HRMS calculated for $C_{29}H_{33}N_5O_3S$: 531.2304; found 532.2388 [$(M+H)^+$ form].

3-[[1-[(3R,4S)-1-benzyl-3-(2-thienyl)piperidine-4-carbonyl]-4-hydroxy-4-piperidyl]methyl]-6-methyl-7H-pyrrolo[2,3-d]pyrimidin-4-one (Example 936)

2-[(4-chloropyrrolo[2,3-d]pyrimidin-7-yl)methoxy]ethyl-trimethyl-silane (600 mg, 2.11 mmol) was dissolved in abs. THF (12 ml) and cooled to −78° C., then LDA solution (2.0 M, 1.2 ml, 2.4 mmol) was added to the mixture and stirred at −78° C. for 1 hour, then iodomethane (158 μl, 2.53 mmol) was added to the mixture, continued stirring at −78° C. for 3 hours. Water (10 ml) was added to the reaction mixture and extracted with EEO (2×20 ml). The combined organic layers were evaporated and purified by preparative LC (on C-18 Gemini-NX 5 μm column, 5 mM aqueous $NH_4HCO_3$-MeCN, gradient).

A part of the crude product (300 mg, 1.01 mmol) and lithium-hydroxide hydrate (423 mg, 10.1 mmol) were dissolved in PDO and water mixture (4 ml, v/v=1:1) and stirred at 100° C. for 142 hours. The reaction mixture was acidified with aqueous HCl solution (1 N, 9.5 ml). The resulted solid compound was filtered off, washed with water and dried.

Using General Procedure 5 starting from the crude product and Preparation R1e as epoxide component, the resulted product (140 mg, 0.28 mmol) was then stirred in TBAF solution (1 M in THF, 1.4 ml, 1.4 mmol) at 90° C. for 24 hours. Water (5 ml) was added to the reaction mixture and extracted with EEO (2×10 ml). The combined organic layers were extracted with water (2×10 ml), dried over $MgSO_4$ and evaporated. The residue was purified by preparative LC (on C-18 Gemini-NX 10 μm column, 25 mM aqueous $NH_4HCO_3$-MeCN, ISO39).

The resulted desilylated product (23.5 mg, 0.065 mmol) was stirred in mixture of aqueous HCl solution (0.65 ml) and PDO (0.5 ml) at 60° C. for 4 hours. The reaction mixture was evaporated.

The crude product was reacted with Preparation R1q-(3R, 4S) according to General Procedure 7 to give EXAMPLE 936. HRMS calculated for $C_{30}H_{35}N_5O_3S$: 545.2460; found 546.2546 [(M+H)+ form].

3-[[1-[(3S,4R)-1-benzyl-3-(2-thienyl)piperidine-4-carbonyl]-4-hydroxy-4-piperidyl]methyl]-6-methyl-7H-pyrrolo[2,3-d]pyrimidin-4-one (Example 937)

2-[(4-chloropyrrolo[2,3-d]pyrimidin-7-yl)methoxy]ethyl-trimethyl-silane (600 mg, 2.11 mmol) was dissolved in abs. THF (12 ml) and cooled to −78° C., then LDA (2.0 M, 1.2 ml, 2.4 mmol) was added to the mixture and stirred at −78° C. for 1 hour, then iodomethane (158 μl, 2.53 mmol) was added to the mixture, continued stirring at −78° C. for 3 hours. Water (10 ml) was added to the reaction mixture and extracted with EEO (2×20 ml). The combined organic layers were evaporated and purified by preparative LC (on C-18 Gemini-NX 5 μm column, 5 mM aqueous $NH_4HCO_3$-MeCN, gradient).

A part of the crude product (300 mg, 1.01 mmol) and lithium-hydroxide hydrate (423 mg, 10.1 mmol) were dissolved in PDO and water mixture (4 ml, v/v=1:1) and stirred at 100° C. for 142 hours. The reaction mixture was acidified with aqueous HCl solution (1 N, 9.5 ml) The resulted solid compound was filtered off, washed with water and dried.

Using General Procedure 5 starting from the crude product and Preparation R1e as epoxide component, the resulted product (140 mg, 0.28 mmol) was then stirred in TBAF solution (1 M in THF, 1.4 ml, 1.4 mmol) at 90° C. for 24 hours. Water (5 ml) was added to the reaction mixture and extracted with EEO (2×10 ml). The combined organic layers were extracted with water (2×10 ml), dried over $MgSO_4$ and evaporated. The residue was purified by preparative LC (on C-18 Gemini-NX 10 μm column, 25 mM aqueous $NH_4HCO_3$-MeCN, ISO39).

The resulted desilylated product (23.5 mg, 0.065 mmol) was stirred in mixture of aqueous HCl solution (0.65 ml) and PDO (0.5 ml) at 60° C. for 4 hours. The reaction mixture was evaporated.

The crude product was reacted with Preparation R1q-(3S, 4R) according to General Procedure 7 to give EXAMPLE 937. HRMS calculated for $C_{30}H_{35}N_5O_3S$: 545.246; found 546.2527 [(M+H)+ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-(1-methylpyrazol-4-yl)pyrrolo[2,1-f][1,2,4]triazin-4-one (Example 938)

Using General Procedure 7 starting from Preparation R3cy and Preparation R1d as reagents, the resulted crude product was reacted with 1-methyl-4-(4,4,5,5-tetramethyl-1,3,2-dioxaborolan-2-yl)pyrazole according to General Procedure 9, to give EXAMPLE 938. HRMS calculated for $C_{39}H_{41}N_9O_4S$: 731.3002; found 732.3057 [(M+H)+ form].

7-(3-furyl)-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]pyrrolo[2,1-f][1,2,4]triazin-4-one (Example 939)

Using General Procedure 7 starting from Preparation R3cy and Preparation R1d as reagents, the resulted crude product was reacted with 2-(3-furyl)-4,4,5,5-tetramethyl-1,3,2-dioxaborolane according to General Procedure 9, to give EXAMPLE 939. HRMS calculated for $C_{39}H_{39}N_7O_5S$: 717.2734; found 718.2804 [(M+H)+ form].

7-(3-furyl)-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]thieno[3,4-d]pyrimidin-4-one (Example 940)

Using General Procedure 7 starting from Preparation R3dc and Preparation R1d as reagents, the resulted crude product was reacted with 2-(3-furyl)-4,4,5,5-tetramethyl-1,3,2-dioxaborolane according to General Procedure 9, to give EXAMPLE 940. HRMS calculated for $C_{39}H_{38}N_6O_5S_2$: 734.2345; found 735.2417 [(M+H)+ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-(1-methylpyrazol-4-yl)thieno[3,4-d]pyrimidin-4-one (Example 941)

Using General Procedure 7 starting from Preparation R3dc and Preparation R1d as reagents, the resulted crude product was reacted with 1-methyl-4-(4,4,5,5-tetramethyl-1,3,2-dioxaborolan-2-yl)pyrazole according to General Procedure 9, to give EXAMPLE 941. HRMS calculated for $C_{39}H_{40}N_8O_4S_2$: 748.2614; found 749.2704 [(M+H)+ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-[4-(hydroxymethyl)phenyl]pyrrolo[2,1-f][1,2,4]triazin-4-one (Example 942)

Using General Procedure 7 starting from R3cy and R1d as reagents, the resulted crude product was reacted with [4-(hydroxymethyl)phenyl]boronic acid according to General Procedure 9, to give EXAMPLE 942. HRMS calculated for $C_{42}H_{43}N_7O_5S$: 757.3046; found 758.3135 [(M+H)+ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-[4-(hydroxymethyl)phenyl]thieno[3,4-d]pyrimidin-4-one (Example 943)

Using General Procedure 7 starting from Preparation R3dc and Preparation R1d as reagents, the resulted crude product was reacted with [4-(hydroxymethyl)phenyl]boronic acid according to General Procedure 9, to give EXAMPLE 943. HRMS calculated for $C_{42}H_{42}N_6O_5S_2$: 774.2658; found 775.2733 [(M+H)$^+$ form].

3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]-7-phenyl-pyrrolo[2,3-d]pyrimidin-4-one (Example 944)

Using General Procedure 7 starting from Preparation R3bu and Preparation R1x as reagents, EXAMPLE 944 was obtained. HRMS calculated for $C_{40}H_{39}N_7O_4S$: 713.2784; found 714.2859 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-(1-methylpyrrol-3-yl)pyrrolo[2,1-f][1,2,4]triazin-4-one (Example 945)

Using General Procedure 7 starting from Preparation R3cy and Preparation R1d as reagents, the resulted crude product was reacted with 1-methyl-3-(4,4,5,5-tetramethyl-1,3,2-dioxaborolan-2-yl)pyrrole according to General Procedure 9, to give EXAMPLE 945. HRMS calculated for $C_{40}H_{42}N_8O_4S$: 730.3050; found 731.3113 [(M+H) form].

7-(3-chlorophenyl)-3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]pyrrolo[2,3-d]pyrimidin-4-one (Example 946)

Using General Procedure 7 starting from Preparation R3ar and Preparation R1x as reagents, EXAMPLE 946 was obtained. HRMS calculated for $C_{40}H_{38}N_7O_4SCl$: 747.2395; found 748.2461 [(M+H)$^+$ form].

3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]-7-(3-methoxyphenyl)pyrrolo[2,3-d]pyrimidin-4-one (Example 947)

Using General Procedure 7 starting from Preparation R3bo and Preparation R1x as reagents, EXAMPLE 947 was obtained. HRMS calculated for $C_{41}H_{41}N_7O_5S$: 743.2890; found 744.2968 [(M+H)$^+$ form].

7-(4-fluorophenyl)-3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]pyrrolo[2,3-d]pyrimidin-4-one (Example 948)

Using General Procedure 7 starting from Preparation R3as and Preparation R1x as reagents, EXAMPLE 948 was obtained. HRMS calculated for $C_{40}H_{38}N_7O_4FS$: 731.2690; found 732.2765 [(M+H)$^+$ form].

3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]-7-(4-methoxyphenyl)pyrrolo[2,3-d]pyrimidin-4-one (Example 949)

Using General Procedure 7 starting from Preparation R3ax and Preparation R1x as reagents, EXAMPLE 949 was obtained. HRMS calculated for $C_{41}H_{41}N_7O_5S$: 743.2890; found 744.2951 [(M+H)$^+$ form].

3-[[4-hydroxy-1-[(3R,4R)-1-[2-(6-methoxy-3-pyridyl)thiazole-5-carbonyl]-3-phenyl-piperidine-4-carbonyl]-4-piperidyl]methyl]-7-(4-methoxyphenyl)pyrrolo[2,3-d]pyrimidin-4-one (Example 950)

Ethyl 2-(6-methoxy-3-pyridyl)thiazole-5-carboxylate (0.75 mmol) was stirred with lithium-hydroxide hydrate (3 mmol) in mixture of water (2 ml) and methanol (2 ml) at 40° C. for 4 hours. The reaction mixture was neutralized with aqueous 1N HCl solution (3 ml), then evaporated. The resulted crude 2-(6-methoxy-3-pyridyl)thiazole-5-carboxylic acid was reacted with R3ax according to General Procedure 7 to give EXAMPLE 950. HRMS calculated for $C_{41}H_{41}N_7O_6S$: 759.2839; found 760.2908 [(M+H)$^+$ form].

7-(2-furyl)-3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]pyrrolo[2,1-f][1,2,4]triazin-4-one (Example 951)

Using General Procedure 7 starting from Preparation R3cy and Preparation R1d as reagents, the resulted crude product was reacted with 2-furylboronic acid according to General Procedure 9, to give EXAMPLE 951. HRMS calculated for $C_{39}H_{39}N_7O_5S$: 717.2734; found 718.2801 [(M+H)$^+$ form].

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-(1-methylpyrrol-3-yl)thieno[3,4-d]pyrimidin-4-one (Example 952)

Using General Procedure 7 starting from Preparation R3dc and Preparation R1d as reagents, the resulted crude product was reacted with 1-methyl-3-(4,4,5,5-tetramethyl-1,3,2-dioxaborolan-2-yl)pyrrole according to General Procedure 9, to give EXAMPLE 952. HRMS calculated for $C_{40}H_{41}N_7O_4S_2$: 747.2661; found 748.2722 [(M+H)$^+$ form].

3-[[3,3-difluoro-4-hydroxy-1-[trans-1-[4-methyl-2-(6-methyl-3-pyridyl)thiazole-5-carbonyl]-3-phenyl-piperidine-4-carbonyl]-4-piperidyl]methyl]-7-phenyl-pyrrolo [2,3-d]pyrimidin-4-one, enantiomer 1 (Example 953)

and

3-[[3,3-difluoro-4-hydroxy-1-[trans-1-[4-methyl-2-(6-methyl-3-pyridyl)thiazole-5-carbonyl]-3-phenyl-piperidine-4-carbonyl]-4-piperidyl]methyl]-7-phenyl-pyrrolo [2,3-d]pyrimidin-4-one, enantiomer 2 (Example 954)

Using General Procedure 7 starting from Preparation R3dm and Preparation R1d as reagents, EXAMPLE 953 and EXAMPLE 954 were obtained and separated by liquid chromatography.

Example 953

HRMS calculated for $C_{41}H_{39}N_7O_4F_2S$: 763.2752; found 382.6463 [(M+2H)$^{2+}$ form].

Example 954

HRMS calculated for $C_{41}H_{39}N_7O_4F_2S$: 763.2752; found 382.6463 [(M+2H)$^{2+}$ form].

3-[[3,3-difluoro-4-hydroxy-1-[trans-1-[4-methyl-2-(6-methyl-3-pyridyl)thiazole-5-carbonyl]-3-phenyl-piperidine-4-carbonyl]-4-piperidyl]methyl]-7-(4-methoxyphenyl)pyrrolo[2,3-d]pyrimidin-4-one, enantiomer 1 (Example 955)

and

3-[[3,3-difluoro-4-hydroxy-1-[trans-1-[4-methyl-2-(6-methyl-3-pyridyl)thiazole-5-carbonyl]-3-phenyl-piperidine-4-carbonyl]-4-piperidyl]methyl]-7-(4-methoxyphenyl)pyrrolo[2,3-d]pyrimidin-4-one, enantiomer 2 (Example 956)

Using General Procedure 7 starting from Preparation R3dn and Preparation R1d as reagents, EXAMPLE 955 and EXAMPLE 956 were obtained and separated by liquid chromatography.

Example 955

HRMS calculated for $C_{42}H_{41}N_7O_5F_2S$: 793.2858; found 794.2910 [(M+H)$^+$ form].

Example 956

HRMS calculated for $C_{42}H_{41}N_7O_5F_2S$: 793.2858; found 794.2960 [(M+H)$^+$ form].

3-[[4-hydroxy-1-[(3R,4R)-1-[[4-methyl-2-(6-methyl-3-pyridyl)thiazol-5-yl]methyl]-3-phenyl-piperidine-4-carbonyl]-4-piperidyl]methyl]-7-phenyl-pyrrolo[2,3-d]pyrimidin-4-one (Example 957)

Using General Procedure 6 starting from Preparation R3bu and 5-(chloromethyl)-4-methyl-2-(6-methyl-3-pyridyl)thiazole as reagents, EXAMPLE 957 was obtained. HRMS calculated for $C_{41}H_{43}N_7O_3S$: 713.3148; found 714.3215 [(M+H)$^+$ form].

3-[[4-hydroxy-1-[(3R,4R)-1-[[4-methyl-2-(6-methyl-3-pyridyl)thiazol-5-yl]methyl]-3-phenyl-piperidine-4-carbonyl]-4-piperidyl]methyl]-7-(4-methoxyphenyl)pyrrolo [2,3-d]pyrimidin-4-one (Example 958)

Using General Procedure 6 starting from Preparation R3ax and 5-(chloromethyl)-4-methyl-2-(6-methyl-3-pyridyl)thiazole as reagents, EXAMPLE 958 was obtained. HRMS calculated for $C_{42}H_{45}N_7O_4S$: 743.3254; found 744.3323 [(M+H)$^+$ form].

7-(3,5-dimethoxyphenyl)-3-[[4-hydroxy-1-[(3S,4S)-1-[4-methyl-2-(6-methyl-3-pyridyl)thiazole-5-carbonyl]-3-phenyl-piperidine-4-carbonyl]-4-piperidyl]methyl]pyrrolo[2,3-d]pyrimidin-4-one (Example 959)

Using General Procedure 7 starting from Preparation R3af and Preparation R1d as reagents, EXAMPLE 959 was obtained. HRMS calculated for $C_{43}H_{45}N_7O_6S$: 787.3152; found 788.3226 [(M+H)$^+$ form].

3-[[4-hydroxy-1-[(3R,4R)-3-phenyl-1-(pyrimidin-4-ylmethyl)piperidine-4-carbonyl]-4-piperidyl]methyl]-7-phenyl-pyrrolo[2,3-d]pyrimidin-4-one (Example 960)

Using General Procedure 6 starting from Preparation R3bu and 4-(chloromethyl)pyrimidine as reagents, EXAMPLE 960 was obtained. HRMS calculated for $C_{35}H_{37}N_7O_3$: 603.2958; found 604.2303 [(M+H)$^+$ form].

3-[[4-hydroxy-1-[(3R,4R)-3-phenyl-1-(pyrimidin-4-ylmethyl)piperidine-4-carbonyl]-4-piperidyl]methyl]-7-(4-methoxyphenyl)pyrrolo[2,3-d]pyrimidin-4-one (Example 961)

Using General Procedure 6 starting from Preparation R3ax and 4-(chloromethyl)pyrimidine as reagents, EXAMPLE 961 was obtained. HRMS calculated for $C_{36}H_{39}N_7O_4$: 633.3064; found 634.3140 [(M+H)$^+$ form].

3-[[4-hydroxy-1-[(3R,4R)-1-[(2-methoxypyrimidin-4-yl)methyl]-3-phenyl-piperidine-4-carbonyl]-4-piperidyl]methyl]-7-phenyl-pyrrolo[2,3-d]pyrimidin-4-one (Example 962)

Using General Procedure 6 starting from Preparation R3bu and 4-(chloromethyl)-2-methoxy-pyrimidine as reagents, EXAMPLE 962 was obtained. HRMS calculated for $C_{36}H_{39}N_7O_4$: 633.3064; found 634.3126 [(M+H)$^+$ form].

3-[[4-hydroxy-1-[(3R,4R)-1-[(2-methoxypyrimidin-4-yl)methyl]-3-phenyl-piperidine-4-carbonyl]-4-piperidyl]methyl]-7-(4-methoxyphenyl)pyrrolo[2,3-d]pyrimidin-4-one (Example 963)

Using General Procedure 6 starting from Preparation R3ax and 4-(chloromethyl)-2-methoxy-pyrimidine as reagents, EXAMPLE 963 was obtained. HRMS calculated for $C_{37}H_{41}N_7O_5$: 663.3169; found 664.3251 [(M+H)$^+$ form].

3-[[1-[(3R,4R)-1-(3-fluorophenyl)sulfonyl-3-phenyl-piperidine-4-carbonyl]-4-hydroxy-4-piperidyl]methyl]-7-phenyl-pyrrolo[2,3-d]pyrimidin-4-one (Example 964)

Using General Procedure 8 starting from Preparation R3bu and 3-fluorobenzenesulfonyl chloride as reagents, EXAMPLE 964 was obtained. HRMS calculated for $C_{36}H_{36}N_5O_5FS$: 669.2421; found 670.2489 [(M+H)$^+$ form].

3-[[1-[(3R,4R)-1-(3-fluorophenyl)sulfonyl-3-phenyl-piperidine-4-carbonyl]-4-hydroxy-4-piperidyl]methyl]-7-(4-methoxyphenyl)pyrrolo[2,3-d]pyrimidin-4-one (Example 965)

Using General Procedure 8 starting from Preparation R3ax and 3-fluorobenzenesulfonyl chloride as reagents, EXAMPLE 965 was obtained. HRMS calculated for $C_{37}H_{38}N_5O_6FS$: 699.2527; found 700.2596 [(M+H)$^+$ form].

3-[[1-[(3R,4R)-1-(2-fluorophenyl)sulfonyl-3-phenyl-piperidine-4-carbonyl]-4-hydroxy-4-piperidyl]methyl]-7-phenyl-pyrrolo[2,3-d]pyrimidin-4-one (Example 966)

Using General Procedure 8 starting from Preparation R3bu and 2-fluorobenzenesulfonyl chloride as reagents, EXAMPLE 966 was obtained. HRMS calculated for $C_{36}H_{36}N_5O_5FS$: 669.2421; found 670.2492 [(M+H)$^+$ form].

3-[[1-[(3R,4R)-1-(2-fluorophenyl)sulfonyl-3-phenyl-piperidine-4-carbonyl]-4-hydroxy-4-piperidyl]methyl]-7-(4-methoxyphenyl)pyrrolo[2,3-d]pyrimidin-4-one (Example 967)

Using General Procedure 8 starting from Preparation R3ax and 2-fluorobenzenesulfonyl chloride as reagents, EXAMPLE 967 was obtained. HRMS calculated for $C_{37}H_{38}N_5O_6FS$: 699.2527; found 700.2598 [(M+H)$^+$ form].

3-[[1-[(3R,4R)-1-(4-fluorophenyl)sulfonyl-3-phenyl-piperidine-4-carbonyl]-4-hydroxy-4-piperidyl]methyl]-7-phenyl-pyrrolo[2,3-d]pyrimidin-4-one (Example 968)

Using General Procedure 8 starting from Preparation R3bu and 4-fluorobenzenesulfonyl chloride as reagents, EXAMPLE 968 was obtained. HRMS calculated for $C_{36}H_{36}N_5O_5FS$: 669.2421; found 670.2494 [(M+H)$^+$ form].

3-[[1-[(3R,4R)-1-(4-fluorophenyl)sulfonyl-3-phenyl-piperidine-4-carbonyl]-4-hydroxy-4-piperidyl]methyl]-7-(4-methoxyphenyl)pyrrolo[2,3-d]pyrimidin-4-one (Example 969)

Using General Procedure 8 starting from Preparation R3ax and 4-fluorobenzenesulfonyl chloride as reagents, EXAMPLE 969 was obtained. HRMS calculated for $C_{37}H_{38}N_5O_6FS$: 699.2527; found 700.2598 [(M+H)$^+$ form].

7-bromo-3-[[4-hydroxy-1-[(3R,4R)-3-phenyl-1-(pyrazin-2-ylmethyl)piperidine-4-carbonyl]-4-piperidyl]methyl]pyrrolo[2,1-f][1,2,4]triazin-4-one (Example 970)

Using General Procedure 6 starting from Preparation R3cy and 2-(chloromethyl)pyrazine as reagents, EXAMPLE 970 was obtained. HRMS calculated for $C_{29}H_{32}N_7O_3Br$: 605.1750; found 606.1826 [(M+H)$^+$ form].

7-chloro-3-[[4-hydroxy-1-[(3R,4R)-3-phenyl-1-(pyrazin-2-ylmethyl)piperidine-4-carbonyl]-4-piperidyl]methyl]thieno[3,4-d]pyrimidin-4-one (Example 971)

Using General Procedure 6 starting from Preparation R3dc and 2-(chloromethyl)pyrazine as reagents, EXAMPLE 971 was obtained. HRMS calculated for $C_{29}H_{31}N_6O_3SCl$: 578.1867; found 579.1947 [(M+H)$^+$ form].

3-[[4-hydroxy-1-[(3R,4R)-3-phenyl-1-(pyrazine-2-carbonyl)piperidine-4-carbonyl]-4-piperidyl]methyl]-7-phenyl-pyrrolo[2,3-d]pyrimidin-4-one (Example 972)

Using General Procedure 7 starting from Preparation R3bu and pyrazine-2-carboxylic acid as reagents, EXAMPLE 972 was obtained. HRMS calculated for $C_{35}H_{35}N_7O_4$: 617.2751; found 618.2826 [(M+H)$^+$ form].

3-[[4-hydroxy-1-[(3R,4R)-3-phenyl-1-(pyrazine-2-carbonyl)piperidine-4-carbonyl]-4-piperidyl]methyl]-7-(4-methoxyphenyl)pyrrolo[2,3-d]pyrimidin-4-one (Example 973)

Using General Procedure 7 starting from Preparation R3ax and pyrazine-2-carboxylic acid as reagents, EXAMPLE 973 was obtained. HRMS calculated for $C_{36}H_{37}N_7O_5$: 647.2856; found 648.2931 [(M+H)$^+$ form].

3-[[4-hydroxy-1-[(3R,4R)-1-[(6-methylpyrazin-2-yl)methyl]-3-phenyl-piperidine-4-carbonyl]-4-piperidyl]methyl]-7-phenyl-pyrrolo[2,3-d]pyrimidin-4-one (Example 974)

Using General Procedure 6 starting from Preparation R3bu and 2-(chloromethyl)-6-methyl-pyrazine as reagents, EXAMPLE 974 was obtained. HRMS calculated for $C_{36}H_{39}N_7O_3$: 617.3114; found 618.3178 [(M+H)$^+$ form].

3-[[4-hydroxy-1-[(3R,4R)-1-[(6-methylpyrazin-2-yl)methyl]-3-phenyl-piperidine-4-carbonyl]-4-piperidyl]methyl]-7-(4-methoxyphenyl)pyrrolo[2,3-d]pyrimidin-4-one (Example 975)

Using General Procedure 6 starting from Preparation R3ax and 2-(chloromethyl)-6-methyl-pyrazine as reagents, EXAMPLE 975 was obtained. HRMS calculated for $C_{37}H_{41}N_7O_4$: 647.3220; found 648.3285 [(M+H)$^+$ form].

3-[[1-[(3R,4R)-1-[(4,6-dimethylpyrimidin-2-yl)methyl]-3-phenyl-piperidine-4-carbonyl]-4-hydroxy-4-piperidyl]methyl]-7-phenyl-pyrrolo[2,3-d]pyrimidin-4-one (Example 976)

Using General Procedure 6 starting from Preparation R3bu and 2-(chloromethyl)-4,6-dimethyl-pyrimidine as reagents, EXAMPLE 976 was obtained. HRMS calculated for $C_{37}H_{41}N_7O_3$: 631.3271; found 632.3338 [(M+H)$^+$ form].

3-[[1-[(3R,4R)-1-[(4,6-dimethylpyrimidin-2-yl)methyl]-3-phenyl-piperidine-4-carbonyl]-4-hydroxy-4-piperidyl]methyl]-7-(4-methoxyphenyl)pyrrolo[2,3-d]pyrimidin-4-one (Example 977)

Using General Procedure 6 starting from Preparation R3ax and 2-(chloromethyl)-4,6-dimethyl-pyrimidine as reagents, EXAMPLE 977 was obtained. HRMS calculated for $C_{38}H_{43}N_7O_4$: 661.3377; found 662.3424 [(M+H)$^+$ form].

3-[[4-hydroxy-1-[(3R,4R)-3-phenyl-1-(pyrazin-2-ylmethyl)piperidine-4-carbonyl]-4-piperidyl]methyl]-7-phenyl-pyrrolo[2,1-f][1,2,4]triazin-4-one (Example 978)

Using General Procedure 9 starting from EXAMPLE 970 and phenylboronic acid as reagents, EXAMPLE 978 was obtained. HRMS calculated for $C_{35}H_{37}N_7O_3$: 603.2958; found 604.3022 [(M+H)$^+$ form].

3-[[4-hydroxy-1-[(3R,4R)-3-phenyl-1-(pyrazin-2-ylmethyl)piperidine-4-carbonyl]-4-piperidyl]methyl]-7-(4-methoxyphenyl)pyrrolo[2,1-f][1,2,4]triazin-4-one (Example 979)

Using General Procedure 9 starting from EXAMPLE 970 and (4-methoxyphenyl)boronic acid as reagents, EXAMPLE 979 was obtained. HRMS calculated for $C_{36}H_{39}N_7O_4$: 633.3064; found 634.3127 [(M+H)$^+$ form].

3-[[4-hydroxy-1-[(3R,4R)-3-phenyl-1-(pyrazin-2-ylmethyl)piperidine-4-carbonyl]-4-piperidyl]methyl]-7-phenyl-thieno[3,4-d]pyrimidin-4-one (Example 980)

Using General Procedure 9 starting from EXAMPLE 971 and phenylboronic acid as reagents, EXAMPLE 980 was obtained. HRMS calculated for $C_{35}H_{36}N_6O_3S$: 620.2570; found 621.2627 [(M+H)$^+$ form].

3-[[4-hydroxy-1-[(3R,4R)-3-phenyl-1-(pyrazin-2-ylmethyl)piperidine-4-carbonyl]-4-piperidyl]methyl]-7-(4-methoxyphenyl)thieno[3,4-d]pyrimidin-4-one (Example 981)

Using General Procedure 9 starting from EXAMPLE 971 and (4-methoxyphenyl)boronic acid as reagents, EXAMPLE 981 was obtained. HRMS calculated for $C_{36}H_{38}N_6O_4S$: 650.2676; found 651.2745 [(M+H)$^+$ form].

3-[[4-hydroxy-1-[(3R,4R)-3-phenyl-1-(pyridazin-3-ylmethyl)piperidine-4-carbonyl]-4-piperidyl]methyl]-7-phenyl-pyrrolo[2,3-d]pyrimidin-4-one (Example 982)

Using General Procedure 6 starting from Preparation R3bu and 3-(bromomethyl)pyridazine as reagents, EXAMPLE 982 was obtained. HRMS calculated for $C_{35}H_{37}N_7O_3$: 603.2958; found 604.3017 [(M+H)$^+$ form].

3-[[4-hydroxy-1-[(3R,4R)-3-phenyl-1-(pyridazin-3-ylmethyl)piperidine-4-carbonyl]-4-piperidyl]methyl]-7-(4-methoxyphenyl)pyrrolo[2,3-d]pyrimidin-4-one (Example 983)

Using General Procedure 6 starting from Preparation R3ax and 3-(bromomethyl)pyridazine as reagents, EXAMPLE 983 was obtained. HRMS calculated for $C_{36}H_{39}N_7O_4$: 633.3064; found 634.3139 [(M+H)$^+$ form].

3-[[4-hydroxy-1-[(3R,4R)-1-[(5-methylpyrazin-2-yl)methyl]-3-phenyl-piperidine-4-carbonyl]-4-piperidyl]methyl]-7-phenyl-pyrrolo[2,3-d]pyrimidin-4-one (Example 984)

Using General Procedure 6 starting from Preparation R3bu and 2-(chloromethyl)-5-methyl-pyrazine as reagents, EXAMPLE 984 was obtained. HRMS calculated for $C_{36}H_{39}N_7O_3$: 617.3114; found 618.3172 [(M+H)$^+$ form].

3-[[4-hydroxy-1-[(3R,4R)-1-[(5-methylpyrazin-2-yl)methyl]-3-phenyl-piperidine-4-carbonyl]-4-piperidyl]methyl]-7-(4-methoxyphenyl)pyrrolo[2,3-d]pyrimidin-4-one (Example 985)

Using General Procedure 6 starting from Preparation R3ax and 2-(chloromethyl)-5-methyl-pyrazine as reagents, EXAMPLE 985 was obtained. HRMS calculated for $C_{37}H_{41}N_7O_4$: 647.3220; found 648.3314 [(M+H)$^+$ form].

3-[[4-hydroxy-1-[(3R,4R)-3-phenyl-1-(pyrimidin-2-ylmethyl)piperidine-4-carbonyl]-4-piperidyl]methyl]-7-phenyl-pyrrolo[2,3-d]pyrimidin-4-one (Example 986)

Using General Procedure 6 starting from Preparation R3bu and 2-(chloromethyl)pyrimidine as reagents, EXAMPLE 986 was obtained. HRMS calculated for $C_{35}H_{37}N_7O_3$: 603.2958; found 604.3022 [(M+H)$^+$ form].

3-[[4-hydroxy-1-[(3R,4R)-3-phenyl-1-(pyrimidin-2-ylmethyl)piperidine-4-carbonyl]-4-piperidyl]methyl]-7-(4-methoxyphenyl)pyrrolo[2,3-d]pyrimidin-4-one (Example 987)

Using General Procedure 6 starting from Preparation R3ax and 2-(chloromethyl)pyrimidine as reagents, EXAMPLE 987 was obtained. HRMS calculated for $C_{36}H_{39}N_7O_4$: 633.3064; found 634.3128 [(M+H)$^+$ form].

3-[[4-hydroxy-1-[(3R,4R)-1-[(4-methylpyrimidin-2-yl)methyl]-3-phenyl-piperidine-4-carbonyl]-4-piperidyl]methyl]-7-phenyl-pyrrolo[2,3-d]pyrimidin-4-one (Example 988)

Using General Procedure 6 starting from Preparation R3bu and 2-(chloromethyl)-4-methyl-pyrimidine as reagents, EXAMPLE 988 was obtained. HRMS calculated for $C_{36}H_{39}N_7O_3$: 617.3114; found 618.3158 [(M+H)$^+$ form].

3-[[4-hydroxy-1-[(3R,4R)-1-[(4-methylpyrimidin-2-yl)methyl]-3-phenyl-piperidine-4-carbonyl]-4-piperidyl]methyl]-7-(4-methoxyphenyl)pyrrolo[2,3-d]pyrimidin-4-one (Example 989)

Using General Procedure 6 starting from Preparation R3ax and 2-(chloromethyl)-4-methyl-pyrimidine as reagents, EXAMPLE 989 was obtained. HRMS calculated for $C_{37}H_{41}N_7O_4$: 647.3220; found 648.3298 [(M+H)$^+$ form].

3-[[4-hydroxy-1-[(3R,4R)-1-[(2-methylpyrimidin-4-yl)methyl]-3-phenyl-piperidine-4-carbonyl]-4-piperidyl]methyl]-7-phenyl-pyrrolo[2,3-d]pyrimidin-4-one (Example 990)

Using General Procedure 6 starting from Preparation R3bu and 4-(chloromethyl)-2-methyl-pyrimidine as reagents, EXAMPLE 990 was obtained. HRMS calculated for $C_{36}H_{39}N_7O_3$: 617.3114; found 618.3179 [(M+H)$^+$ form].

3-[[4-hydroxy-1-[(3R,4R)-1-[(2-methylpyrimidin-4-yl)methyl]-3-phenyl-piperidine-4-carbonyl]-4-piperidyl]methyl]-7-(4-methoxyphenyl)pyrrolo[2,3-d]pyrimidin-4-one (Example 991)

Using General Procedure 6 starting from Preparation R3ax and 4-(chloromethyl)-2-methyl-pyrimidine as reagents, EXAMPLE 991 was obtained. HRMS calculated for $C_{37}H_{41}N_7O_4$: 647.3220; found 648.3282 [(M+H)$^+$ form].

3-[[4-hydroxy-1-[(3R,4R)-1-[(6-methoxypyridazin-3-yl)methyl]-3-phenyl-piperidine-4-carbonyl]-4-piperidyl]methyl]-7-phenyl-pyrrolo[2,3-d]pyrimidin-4-one (Example 992)

Using General Procedure 6 starting from Preparation R3bu and 3-(chloromethyl)-6-methoxy-pyridazine as reagents, EXAMPLE 992 was obtained. HRMS calculated for $C_{36}H_{39}N_7O_4$: 633.3064; found 634.3129 [(M+H)$^+$ form].

3-[[4-hydroxy-1-[(3R,4R)-1-[(6-methoxypyridazin-3-yl)methyl]-3-phenyl-piperidine-4-carbonyl]-4-piperidyl]methyl]-7-(4-methoxyphenyl)pyrrolo[2,3-d]pyrimidin-4-one (Example 993)

Using General Procedure 6 starting from Preparation R3ax and 3-(chloromethyl)-6-methoxy-pyridazine as reagents, EXAMPLE 993 was obtained. HRMS calculated for $C_{37}H_{41}N_7O_5$: 663.3169; found 664.3223 [(M+H)$^+$ form].

3-[[4-hydroxy-1-[(3R,4R)-1-[(3-methoxypyrazin-2-yl)methyl]-3-phenyl-piperidine-4-carbonyl]-4-piperidyl]methyl]-7-phenyl-pyrrolo[2,3-d]pyrimidin-4-one (Example 994)

Using General Procedure 6 starting from Preparation R3bu and 2-(chloromethyl)-3-methoxy-pyrazine as reagents, EXAMPLE 994 was obtained. HRMS calculated for $C_{36}H_{39}N_7O_4$: 633.3064; found 634.3142 [(M+H)$^+$ form].

3-[[4-hydroxy-1-[(3R,4R)-1-[(3-methylpyrazin-2-yl)methyl]-3-phenyl-piperidine-4-carbonyl]-4-piperidyl]methyl]-7-phenyl-pyrrolo[2,3-d]pyrimidin-4-one (Example 995)

Using General Procedure 6 starting from Preparation R3bu and 2-(chloromethyl)-3-methyl-pyrazine as reagents, EXAMPLE 995 was obtained. HRMS calculated for $C_{36}H_{39}N_7O_3$: 617.3114; found 618.3214 [(M+H)$^+$ form].

3-[[4-hydroxy-1-[(3R,4R)-1-[(3-methylpyrazin-2-yl)methyl]-3-phenyl-piperidine-4-carbonyl]-4-piperidyl]methyl]-7-(4-methoxyphenyl)pyrrolo[2,3-d]pyrimidin-4-one (Example 996)

Using General Procedure 6 starting from Preparation R3ax and 2-(chloromethyl)-3-methyl-pyrazine as reagents, EXAMPLE 996 was obtained. HRMS calculated for $C_{37}H_{41}N_7O_4$: 647.3220; found 648.3265 [(M+H)$^+$ form].

3-[[4-hydroxy-1-[(3R,4R)-1-[(3-methoxypyrazin-2-yl)methyl]-3-phenyl-piperidine-4-carbonyl]-4-piperidyl]methyl]-7-(4-methoxyphenyl)pyrrolo[2,3-d]pyrimidin-4-one (Example 997)

Using General Procedure 6 starting from Preparation R3ax and 2-(chloromethyl)-3-methoxy-pyrazine as reagents, EXAMPLE 997 was obtained. HRMS calculated for $C_{37}H_{41}N_7O_5$: 663.3169; found 664.3211 [(M+H)$^+$ form].

4-[[(3R,4R)-4-[4-hydroxy-4-[[4-oxo-7-(2-pyridyl)pyrrolo[2,3-d]pyrimidin-3-yl]methyl]piperidine-1-carbonyl]-3-phenyl-1-piperidyl]methyl]pyridine-2-carbonitrile (Example 998)

Using General Procedure 6 starting from Preparation R3ca and 4-(chloromethyl)pyridine-2-carbonitrile as reagents, EXAMPLE 998 was obtained. HRMS calculated for $C_{36}H_{36}N_8O_3$: 628.2910; found 629.2987 [(M+H)$^+$ form].

5-[[(3R,4R)-4-[4-hydroxy-4-[[7-(1-methylpyrazol-4-yl)-4-oxo-pyrrolo[2,3-d]pyrimidin-3-yl]methyl]piperidine-1-carbonyl]-3-phenyl-1-piperidyl]methyl]pyridine-2-carbonitrile (Example 999)

Using General Procedure 6 starting from Preparation R3ch and 4-(bromomethyl)pyridine-2-carbonitrile as reagents, EXAMPLE 999 was obtained. HRMS calculated for $C_{35}H_{37}N_9O_3$: 631.3019; found 632.3066 [(M+H)$^+$ form].

5-[[(3R,4R)-4-[4-hydroxy-4-[[4-oxo-7-(2-pyridyl)pyrrolo[2,3-d]pyrimidin-3-yl]methyl]piperidine-1-carbonyl]-3-phenyl-1-piperidyl]methyl]pyridine-2-carbonitrile (Example 1000)

Using General Procedure 6 starting from Preparation R3ca and 4-(bromomethyl)pyridine-2-carbonitrile as reagents, EXAMPLE 1000 was obtained. HRMS calculated for $C_{36}H_{36}N_8O_3$: 628.2910; found 629.2976 [(M+H)$^+$ form].

5-[[(3R,4R)-4-[4-hydroxy-4-[[7-(1-methylpyrazol-4-yl)-4-oxo-pyrrolo[2,1-f][1,2,4]triazin-3-yl]methyl]piperidine-1-carbonyl]-3-phenyl-1-piperidyl]methyl]pyridine-2-carbonitrile (Example 1001)

Using General Procedure 6 starting from Preparation R3cy and 5-(bromomethyl)pyridine-2-carbonitrile as reagents, the resulted crude product was reacted with 1-methyl-4-(4,4,5,5-tetramethyl-1,3,2-dioxaborolan-2-yl)pyrazole according to General Procedure 9, to give EXAMPLE 1001. HRMS calculated for $C_{35}H_{37}N_9O_3$: 631.3019; found 632.3068 [(M+H)$^+$ form].

4-[[(3R,4R)-4-[4-hydroxy-4-[[7-(1-methylpyrazol-4-yl)-4-oxo-pyrrolo[2,1-f][1,2,4]triazin-3-yl]methyl]piperidine-1-carbonyl]-3-phenyl-1-piperidyl]methyl]pyridine-2-carbonitrile (Example 1002)

Using General Procedure 6 starting from Preparation R3cy and 4-(chloromethyl)pyridine-2-carbonitrile as reagents, the resulted crude product was reacted with 1-methyl-4-(4,4,5,5-tetramethyl-1,3,2-dioxaborolan-2-yl)pyrazole according to General Procedure 9, to give EXAMPLE 1002. HRMS calculated for $C_{35}H_{37}N_9O_3$: 631.3019; found 632.3071 [(M+H)$^+$ form].

4-[[(3R,4R)-4-[4-hydroxy-4-[[7-(1-methylpyrazol-4-yl)-4-oxo-thieno[3,4-d]pyrimidin-3-yl]methyl]piperidine-1-carbonyl]-3-phenyl-1-piperidyl]methyl]pyridine-2-carbonitrile (Example 1003)

Using General Procedure 6 starting from Preparation R3dc and 4-(chloromethyl)pyridine-2-carbonitrile as reagents, the resulted crude product was reacted with 1-methyl-4-(4,4,5,5-tetramethyl-1,3,2-dioxaborolan-2-yl)pyrazole according to General Procedure 9, to give EXAMPLE 1003. HRMS calculated for $C_{35}H_{36}N_8O_3S$: 648.2631; found 649.2693 [(M+H)$^+$ form].

3-[[4-hydroxy-1-[(3R,4R)-1-[(5-methylpyrazin-2-yl)methyl]-3-phenyl-piperidine-4-carbonyl]-4-piperidyl]methyl]-7-phenyl-thieno[3,4-d]pyrimidin-4-one (Example 1004)

Using General Procedure 6 starting from Preparation R3da and 2-(chloromethyl)-5-methyl-pyrazine as reagents, EXAMPLE 1004 was obtained. HRMS calculated for $C_{36}H_{38}N_6O_3S$: 634.2726; found 635.2793 [(M+H)$^+$ form].

3-[[4-hydroxy-1-[(3R,4R)-3-phenyl-1-(pyrimidin-2-ylmethyl)piperidine-4-carbonyl]-4-piperidyl]methyl]-7-phenyl-thieno[3,4-d]pyrimidin-4-one (Example 1005)

Using General Procedure 6 starting from Preparation R3da and 2-(chloromethyl)pyrimidine as reagents, EXAMPLE 1005 was obtained. HRMS calculated for $C_{35}H_{36}N_6O_3S$: 620.2570; found 621.2619 [(M+H)$^+$ form].

3-[[4-hydroxy-1-[(3R,4R)-1-[(4-methylpyrimidin-2-yl)methyl]-3-phenyl-piperidine-4-carbonyl]-4-piperidyl]methyl]-7-phenyl-thieno[3,4-d]pyrimidin-4-one (Example 1006)

Using General Procedure 6 starting from Preparation R3da and 2-(chloromethyl)-4-methyl-pyrimidine as reagents, EXAMPLE 1006 was obtained. HRMS calculated for $C_{36}H_{38}N_6O_3S$: 634.2726; found 635.2791 [(M+H)$^+$ form].

3-[[4-hydroxy-1-[(3R,4R)-3-phenyl-1-(pyrimidin-4-ylmethyl)piperidine-4-carbonyl]-4-piperidyl]methyl]-7-phenyl-thieno[3,4-d]pyrimidin-4-one (Example 1007)

Using General Procedure 6 starting from Preparation R3da and 4-(chloromethyl)pyrimidine as reagents, EXAMPLE 1007 was obtained. HRMS calculated for $C_{35}H_{36}N_6O_3S$: 620.2570; found 621.2656 [(M+H)$^+$ form].

3-[[1-[(3R,4R)-1-[(4,6-dimethylpyrimidin-2-yl)methyl]-3-phenyl-piperidine-4-carbonyl]-4-hydroxy-4-piperidyl]methyl]-7-phenyl-thieno[3,4-d]pyrimidin-4-one (Example 1008)

Using General Procedure 6 starting from Preparation R3da and 2-(chloromethyl)-4,6-dimethyl-pyrimidine as reagents, EXAMPLE 1008 was obtained. HRMS calculated for $C_{37}H_{40}N_6O_3S$: 648.2883; found 649.2952 [(M+H)$^+$ form].

3-[[4-hydroxy-1-[(3R,4R)-1-[(2-methoxypyrimidin-4-yl)methyl]-3-phenyl-piperidine-4-carbonyl]-4-piperidyl]methyl]-7-phenyl-thieno[3,4-d]pyrimidin-4-one (Example 1009)

Using General Procedure 6 starting from Preparation R3da and 4-(chloromethyl)-2-methoxy-pyrimidine as reagents, EXAMPLE 1009 was obtained. HRMS calculated for $C_{36}H_{38}N_6O_4S$: 650.2675; found 651.2744 [(M+H)$^+$ form].

3-[[4-hydroxy-1-[(3R,4R)-1-[(2-methylpyrimidin-4-yl)methyl]-3-phenyl-piperidine-4-carbonyl]-4-piperidyl]methyl]-7-phenyl-thieno[3,4-d]pyrimidin-4-one (Example 1010)

Using General Procedure 6 starting from Preparation R3da and 4-(chloromethyl)-2-methyl-pyrimidine as reagents, EXAMPLE 1010 was obtained. HRMS calculated for $C_{36}H_{38}N_6O_3S$: 634.2726; found 635.2805 [(M+H)$^+$ form].

3-[[4-hydroxy-1-[(3R,4R)-1-[(6-methylpyrazin-2-yl)methyl]-3-phenyl-piperidine-4-carbonyl]-4-piperidyl]methyl]-7-phenyl-thieno[3,4-d]pyrimidin-4-one (Example 1011)

Using General Procedure 6 starting from Preparation R3da and 2-(chloromethyl)-6-methyl-pyrazine as reagents, EXAMPLE 1011 was obtained. HRMS calculated for $C_{36}H_{38}N_6O_3S$: 634.2726; found 635.2792 [(M+H)$^+$ form].

3-[[4-hydroxy-1-[(3R,4R)-1-[(3-methylpyrazin-2-yl)methyl]-3-phenyl-piperidine-4-carbonyl]-4-piperidyl]methyl]-7-phenyl-thieno[3,4-d]pyrimidin-4-one (Example 1012)

Using General Procedure 6 starting from Preparation R3da and 2-(chloromethyl)-3-methyl-pyrazine as reagents, EXAMPLE 1012 was obtained. HRMS calculated for $C_{36}H_{38}N_6O_3S$: 634.2726; found 635.2782 [(M+H)$^+$ form].

3-[[4-hydroxy-1-[(3R,4R)-1-[(3-methoxypyrazin-2-yl)methyl]-3-phenyl-piperidine-4-carbonyl]-4-piperidyl]methyl]-7-phenyl-thieno[3,4-d]pyrimidin-4-one (Example 1013)

Using General Procedure 6 starting from Preparation R3da and 2-(chloromethyl)-3-methoxy-pyrazine as reagents, EXAMPLE 1013 was obtained. HRMS calculated for $C_{36}H_{38}N_6O_4S$: 650.2675; found 651.2764 [(M+H)$^+$ form].

PHARMACOLOGICAL STUDY

Example A: Evaluation of the Inhibition of USP7 by the Fluorescence Intensity (FLINT) Readings USP7 activity was measured using Rhodamine-110 c-terminal labelled Ubiquitin as a substrate (Viva Biosciences). Incubation with USP7 results in the release of Rhodamine-110 leading to an increase in fluorescence which can be used in the continuous measurement of USP7 activity.

The USP7 reactions were performed in a 50 μL volume, in 384 well black solid low binding plates (Corning #3575). The reaction buffer consisted of 100 mM Bicine pH 8.0, 0.01% TritonX100, 1 mM TCEP, and 10% DMSO.

0.25 nM His-His-USP7 (aa208-560, [C315A]) was incubated with compound (final concentration 10% DMSO) for 60 minutes at 30° C. The reaction was then initiated by the addition of 500 nM Ubiquitin-Rhodamine-110 substrate and the plate read every 3 minutes for 21 minutes to measure the release of Rhodamine-110. Fluorescence Intensity (FLINT) readings were measured using a Biomek Neo plate reader (Ex.485 nm, Em.535 nm).

The inhibition of increasing doses of compound was expressed as a percentage reduction in kinetic rate compared to the kinetic rates established between 'DMSO only' and 'total inhibition' controls (no USP7). The inhibitory concentrations that gave a 50% reduction in kinetic rate ($IC_{50}$) were determined, from 11-point dose response curves, in XL-Fit using a 4-Parameter Logistic Model (Sigmoidal Dose-Response Model).

The results presented in Table 1 below show that compounds of the invention inhibit interaction between USP7 protein and the fluorescent peptide described hereinbefore.

Example B: In Vitro Cytotoxicity

The cytotoxicity studies were evaluated by MTT assay and carried out on MM1S multiple myeloma or Z138 mantle cell lymphoma tumour cell lines. The cells are distributed onto microplates and exposed to the test compounds for 96 hours. The cell viability is then quantified by a colorimetric assay, the Microculture Tetrazolium Assay (Carmichael et al., *Cancer Res.* 1987, 47, 936-942). The results are expressed in $IC_{50}$ (the concentration of compound that inhibits cell viability by 50%) and are presented in Table 1 below.

The results show that the compounds of the invention are cytotoxic.

TABLE 1

$IC_{50}$ of USP7 inhibition and of cytotoxicity for MM1S or Z138 cells
Note: $IC_{50}$ of cytotoxicity for Z138 tumour cell line are underlined.

| EXAMPLE | $IC_{50}$ (M) USP7 FLINT | $IC_{50}$ (M) MTT |
|---|---|---|
| 1 | 1.4E−07 | 2.8E−06 |
| 2 | 7.9E−08 | NT |
| 3 | 4.9E−09 | 3.3E−09 |
| 4 | 3.3E−09 | 3.4E−09 |
| 5 | 5.2E−08 | 2.1E−08 |
| 6 | 1.2E−07 | NT |
| 7 | 2.8E−08 | 5.0E−09 |
| 8 | 7.3E−08 | NT |
| 9 | 1.2E−08 | 4.3E−09 |
| 10 | 1.5E−08 | 1.1E−08 |
| 11 | 1.6E−08 | 7.6E−09 |
| 12 | 3.2E−08 | 1.6E−08 |
| 13 | 5.9E−09 | 6.1E−08 |
| 14 | 1.6E−08 | 1.5E−08 |
| 15 | 6.2E−09 | 2.4E−09 |
| 16 | 1.3E−08 | 7.1E−09 |
| 17 | 2.7E−08 | 5.9E−09 |
| 18 | 2.9E−08 | 4.6E−09 |
| 19 | 1.2E−08 | 2.4E−09 |
| 20 | 9.3E−09 | NT |
| 21 | 5.1E−08 | 1.9E−08 |
| 22 | 7.3E−08 | NT |
| 23 | 7.5E−09 | 4.8E−09 |
| 24 | 2.3E−08 | 7.4E−09 |
| 25 | 6.8E−09 | 1.1E−08 |
| 26 | 1.5E−08 | 2.7E−09 |
| 27 | 1.5E−08 | 9.1E−09 |
| 28 | 1.6E−08 | 1.1E−08 |
| 29 | 1.2E−08 | 2.8E−09 |
| 30 | 1.1E−08 | 6.5E−09 |
| 31 | 1.4E−08 | 1.7E−08 |
| 32 | 9.4E−09 | 1.5E−08 |
| 33 | 9.1E−09 | 2.4E−09 |
| 34 | 7.7E−09 | 9.1E−09 |
| 35 | 2.5E−08 | 7.6E−09 |
| 36 | 1.6E−08 | 2.6E−09 |
| 37 | 2.2E−08 | 7.7E−09 |
| 38 | 1.7E−08 | 5.1E−09 |
| 39 | 1.8E−08 | NT |
| 40 | 9.9E−09 | 4.23E−09 |
| 41 | 2.5E−08 | NT |
| 42 | 3.2E−08 | NT |
| 43 | 6.6E−08 | NT |
| 44 | 4.3E−08 | 5.2E−09 |
| 45 | 1.0E−07 | NT |
| 46 | 2.2E−08 | NT |
| 47 | 1.1E−08 | 2.56E−09 |
| 48 | 2.0E−08 | NT |
| 49 | 2.2E−08 | NT |
| 50 | 2.9E−08 | 7.3E−09 |
| 51 | 3.3E−08 | 1.0E−08 |
| 52 | 2.2E−08 | 9.7E−09 |
| 53 | 2.3E−08 | NT |
| 54 | 2.7E−08 | 5.48E−09 |
| 55 | 3.3E−08 | 1.0E−08 |
| 56 | 1.7E−08 | NT |
| 57 | 2.3E−08 | 7.84E−09 |
| 58 | 7.0E−08 | 1.42E−08 |
| 59 | 5.9E−08 | NT |
| 60 | 4.3E−08 | NT |
| 61 | 9.3E−09 | NT |
| 62 | 3.7E−08 | NT |
| 63 | 8.4E−05 | NT |
| 64 | 1.0E−07 | 7.7E−07 |
| 65 | 7.0E−08 | NT |
| 66 | 1.4E−07 | NT |
| 67 | 1.1E−07 | NT |
| 68 | 1.1E−07 | NT |
| 69 | 3.6E−08 | 2.1E−07 |
| 70 | 1.3E−07 | NT |
| 71 | 9.1E−08 | NT |
| 72 | 1.6E−08 | 4.0E−09 |
| 73 | 2.0E−08 | 7.6E−09 |
| 74 | 3.4E−08 | 1.7E−08 |
| 75 | 1.2E−08 | 6.4E−09 |
| 76 | 7.0E−09 | 2.8E−09 |
| 77 | 1.1E−08 | 4.1E−09 |
| 78 | 4.3E−09 | 2.4E−09 |
| 79 | 1.2E−08 | 5.0E−09 |
| 80 | 2.0E−08 | 8.3E−09 |
| 81 | 2.0E−08 | 9.5E−09 |
| 82 | 3.8E−08 | 1.6E−08 |
| 83 | 1.7E−09 | 4.7E−08 |
| 84 | 4.6E−09 | 2.5E−09 |
| 85 | 8.2E−09 | 9.6E−09 |
| 86 | 1.7E−08 | 2.1E−08 |
| 87 | 2.4E−08 | 3.8E−08 |
| 88 | 1.2E−08 | 6.1E−09 |
| 89 | 6.7E−09 | 1.9E−08 |
| 90 | 8.3E−09 | 6.6E−09 |
| 91 | 1.1E−08 | 2.0E−08 |
| 92 | 5.0E−09 | 5.3E−09 |
| 93 | 3.8E−09 | 7.0E−09 |
| 94 | 9.4E−09 | 6.3E−09 |
| 95 | 1.5E−08 | 3.2E−08 |
| 96 | 3.2E−08 | 1.5E−08 |
| 97 | 7.3E−08 | NT |
| 98 | 7.9E−08 | NT |
| 99 | 3.4E−08 | 1.7E−08 |
| 100 | 4.7E−08 | 1.7E−08 |
| 101 | 1.0E−07 | 2.4E−08 |
| 102 | 5.8E−08 | 1.2E−08 |
| 103 | 1.1E−08 | 6.2E−09 |
| 104 | 7.9E−09 | 7.2E−09 |
| 105 | 1.7E−08 | 3.6E−09 |
| 106 | 9.9E−09 | 9.2E−09 |
| 107 | 2.5E−08 | 2.1E−08 |
| 108 | 2.5E−08 | 4.3E−09 |
| 109 | 1.9E−08 | 7.4E−09 |
| 110 | 3.9E−08 | 1.3E−08 |
| 111 | 1.2E−08 | 1.6E−08 |
| 112 | 2.0E−08 | 9.0E−09 |
| 113 | 3.9E−08 | 1.7E−08 |
| 114 | 5.8E−08 | 9.3E−09 |
| 115 | 3.6E−08 | 1.4E−08 |
| 116 | 3.2E−08 | 1.0E−08 |
| 117 | 2.9E−08 | 1.3E−08 |
| 118 | 4.2E−08 | 2.6E−08 |
| 119 | 3.4E−08 | 3.8E−08 |
| 120 | 5.8E−08 | 1.1E−08 |
| 121 | 4.8E−08 | 1.8E−08 |
| 122 | 5.1E−09 | 7.67E−09 |
| 123 | 2.5E−08 | 5.2E−09 |
| 124 | 6.3E−08 | NT |
| 125 | 5.2E−08 | 1.17E−08/1.93E−08 |
| 126 | 5.5E−05 | NT |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
| --- | --- | --- |
| 127 | 1.1E−07 | NT |
| 128 | 6.4E−08 | NT |
| 129 | 1.3E−07 | NT |
| 130 | 1.5E−07 | NT |
| 131 | 1.0E−08 | 8.2E−09 |
| 132 | 1.2E−08 | 8.7E−09 |
| 133 | 1.6E−08 | 6.9E−09 |
| 134 | 1.7E−08 | 4.1E−08 |
| 135 | 1.9E−08 | 4.8E−08 |
| 136 | 1.1E−08 | 4.9E−09 |
| 137 | 6.7E−09 | 4.8E−09 |
| 138 | 1.2E−08 | 8.3E−09 |
| 139 | 1.2E−08 | 1.2E−08 |
| 140 | 1.7E−08 | 9.9E−08 |
| 141 | 4.6E−08 | NT |
| 142 | 2.4E−08 | 4.5E−08 |
| 143 | 8.1E−07 | NT |
| 144 | 3.2E−08 | 5.3E−08 |
| 145 | 8.9E−08 | NT |
| 146 | 1.0E−07 | NT |
| 147 | 4.2E−07 | 3.5E−06 |
| 148 | 6.2E−08 | 2.9E−07 |
| 149 | 4.4E−09 | 2.4E−09 |
| 150 | 2.2E−08 | 1.4E−08 |
| 151 | 1.7E−08 | 3.1E−09 |
| 152 | 9.1E−09 | 2.3E−09 |
| 153 | 4.7E−08 | 8.8E−09 |
| 154 | 2.0E−08 | 3.7E−09 |
| 155 | 1.4E−08 | 5.5E−09 |
| 156 | 6.7E−09 | 2.0E−09 |
| 157 | 2.1E−08 | 5.2E−09 |
| 158 | 5.2E−08 | 1.4E−08 |
| 159 | 6.4E−09 | 3.3E−09 |
| 160 | 1.6E−08 | NT |
| 161 | 1.5E−08 | 7.1E−08 |
| 162 | 7.4E−08 | NT |
| 163 | 3.2E−08 | NT |
| 164 | 6.1E−08 | NT |
| 165 | 3.6E−08 | NT |
| 166 | 9.3E−08 | NT |
| 167 | 3.7E−08 | 3.2E−07 |
| 168 | 9.1E−08 | NT |
| 169 | 2.4E−07 | NT |
| 170 | 5.7E−08 | NT |
| 171 | 9.7E−08 | NT |
| 172 | 1.6E−08 | 3.9E−08 |
| 173 | 2.5E−08 | 6.4E−08 |
| 174 | 2.3E−08 | NT |
| 175 | 4.1E−08 | NT |
| 176 | 8.4E−08 | NT |
| 177 | 5.8E−07 | NT |
| 178 | 2.7E−08 | 1.2E−07 |
| 179 | 3.8E−07 | NT |
| 180 | 9.9E−08 | NT |
| 181 | 5.9E−07 | NT |
| 182 | 1.1E−08 | 5.3E−08 |
| 183 | 1.0E−08 | 3.6E−08 |
| 184 | 1.5E−05 | 1.3E−05 |
| 185 | 1.6E−08 | 5.7E−08 |
| 186 | 9.0E−08 | NT |
| 187 | 1.8E−07 | NT |
| 188 | 2.3E−08 | NT |
| 189 | 1.7E−08 | 1.2E−07 |
| 190 | 1.9E−08 | 1.7E−07 |
| 191 | 6.4E−08 | NT |
| 192 | 9.5E−08 | NT |
| 193 | 1.1E−07 | 6.2E−07 |
| 194 | 1.7E−07 | NT |
| 195 | 7.3E−08 | NT |
| 196 | 4.6E−08 | NT |
| 197 | 1.9E−08 | 1.3E−07 |
| 198 | 1.4E−07 | NT |
| 199 | 1.1E−07 | NT |
| 200 | 2.4E−07 | NT |
| 201 | 2.8E−08 | NT |
| 202 | 7.5E−07 | NT |
| 203 | 2.6E−08 | 6.9E−08 |
| 204 | 1.5E−07 | NT |
| 205 | 7.2E−08 | 1.2E−07 |
| 206 | 4.1E−08 | 4.4E−08 |
| 207 | 1.5E−07 | NT |
| 208 | 6.5E−08 | NT |
| 209 | 1.2E−07 | NT |
| 210 | 1.3E−07 | NT |
| 211 | 4.7E−07 | NT |
| 212 | 4.5E−08 | NT |
| 213 | 2.7E−08 | 1.1E−07 |
| 214 | 4.1E−08 | 1.7E−07 |
| 215 | 8.3E−08 | NT |
| 216 | 1.2E−07 | NT |
| 217 | 2.7E−08 | 1.4E−07 |
| 218 | 1.4E−07 | NT |
| 219 | 5.2E−08 | 1.6E−07 |
| 220 | 4.5E−08 | 3.8E−07 |
| 221 | 6.8E−08 | NT |
| 222 | 1.9E−07 | NT |
| 223 | 1.4E−07 | NT |
| 224 | 1.5E−07 | NT |
| 225 | 6.0E−08 | NT |
| 226 | 3.1E−07 | NT |
| 227 | 4.7E−08 | NT |
| 228 | 9.7E−08 | NT |
| 229 | 3.4E−07 | 1.6E−07 |
| 230 | 3.4E−07 | NT |
| 231 | 9.3E−07 | NT |
| 232 | 2.2E−07 | NT |
| 233 | 1.2E−06 | NT |
| 234 | 6.3E−07 | NT |
| 235 | 3.5E−08 | 4.1E−08 |
| 236 | 9.3E−08 | NT |
| 237 | 1.1E−07 | NT |
| 238 | 1.6E−07 | NT |
| 239 | 4.2E−08 | 1.0E−07 |
| 240 | 1.1E−06 | NT |
| 241 | 8.4E−08 | NT |
| 242 | 1.8E−07 | NT |
| 243 | 1.4E−06 | NT |
| 244 | 2.8E−07 | NT |
| 245 | 2.2E−07 | NT |
| 246 | 1.8E−08 | 4.6E−08 |
| 247 | 8.2E−08 | NT |
| 248 | 3.4E−07 | NT |
| 249 | 1.2E−07 | NT |
| 250 | 1.8E−07 | NT |
| 251 | 4.3E−07 | NT |
| 252 | 1.6E−07 | NT |
| 253 | 4.6E−08 | 1.5E−07 |
| 254 | 2.3E−08 | 1.2E−07 |
| 255 | 2.9E−08 | 1.8E−07 |
| 256 | 5.5E−08 | 1.0E−07 |
| 257 | 8.0E−08 | NT |
| 258 | 9.7E−08 | NT |
| 259 | 3.1E−08 | 1.7E−07 |
| 260 | 2.2E−08 | 7.4E−08 |
| 261 | 3.6E−08 | 1.3E−07 |
| 262 | 1.0E−07 | NT |
| 263 | 2.1E−08 | 2.8E−08 |
| 264 | 9.6E−08 | NT |
| 265 | 1.3E−07 | NT |
| 266 | 3.0E−08 | 3.8E−07 |
| 267 | 4.7E−08 | 6.5E−08 |
| 268 | 7.4E−08 | NT |
| 269 | 4.4E−08 | 1.7E−07 |
| 270 | 4.4E−08 | 4.5E−08 |
| 271 | 1.5E−07 | NT |
| 272 | 2.6E−08 | 3.8E−07 |
| 273 | 1.0E−07 | NT |
| 274 | 8.2E−07 | NT |
| 275 | 3.3E−07 | NT |
| 276 | 8.7E−08 | NT |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
|---|---|---|
| 277 | 8.6E−08 | NT |
| 278 | 5.4E−08 | NT |
| 279 | 1.2E−07 | NT |
| 280 | 5.5E−08 | NT |
| 281 | 2.6E−08 | 1.8E−07 |
| 282 | 1.2E−07 | NT |
| 283 | 1.0E−07 | NT |
| 284 | 4.1E−08 | NT |
| 285 | 1.6E−08 | NT |
| 286 | 1.5E−08 | NT |
| 287 | 2.5E−08 | NT |
| 288 | 6.0E−09 | 2.3E−08 |
| 289 | 1.2E−08 | 5.4E−08 |
| 290 | 7.4E−09 | 2.0E−09 |
| 291 | 8.4E−09 | 2.5E−09 |
| 292 | 5.8E−09 | 2.0E−09 |
| 293 | 4.0E−09 | 2.2E−09 |
| 294 | 9.8E−09 | 5.6E−09 |
| 295 | 8.0E−09 | 5.3E−09 |
| 296 | 2.3E−08 | 1.1E−08 |
| 297 | 1.4E−08 | NT |
| 298 | 1.4E−08 | 1.1E−08 |
| 299 | 3.9E−08 | 1.3E−08 |
| 300 | 2.5E−08 | NT |
| 301 | 1.3E−06 | 5.5E−07 |
| 302 | 1.6E−08 | 7.1E−09 |
| 303 | 1.5E−08 | 4.0E−09 |
| 304 | 5.7E−09 | 1.5E−08 |
| 305 | 1.8E−08 | 3.4E−08 |
| 306 | 1.1E−08 | 7.3E−09 |
| 307 | 1.4E−08 | 5.4E−09 |
| 308 | 1.2E−08 | 5.4E−09 |
| 309 | 1.1E−08 | 9.1E−09 |
| 310 | 3.6E−08 | 1.5E−08 |
| 311 | 1.2E−08 | 1.4E−08 |
| 312 | 5.5E−09 | 9.6E−09 |
| 313 | 8.2E−09 | 8.2E−09 |
| 314 | 2.1E−08 | 3.4E−08 |
| 315 | 4.9E−08 | NT |
| 316 | 1.2E−07 | NT |
| 317 | 5.3E−08 | NT |
| 318 | 8.7E−08 | NT |
| 319 | 6.4E−08 | NT |
| 320 | 1.6E−07 | NT |
| 321 | 1.0E−07 | NT |
| 322 | 1.4E−07 | NT |
| 323 | 2.3E−07 | NT |
| 324 | 7.2E−08 | NT |
| 325 | 8.6E−08 | NT |
| 326 | 7.9E−08 | NT |
| 327 | 3.9E−08 | 9.8E−08 |
| 328 | 2.0E−08 | NT |
| 329 | 1.8E−08 | 5.0E−08 |
| 330 | 2.0E−08 | 7.6E−08 |
| 331 | 4.4E−08 | NT |
| 332 | 3.2E−08 | 8.3E−09 |
| 333 | 1.9E−08 | 3.3E−08 |
| 334 | 7.1E−09 | 5.1E−09 |
| 335 | 1.1E−08 | 8.9E−09 |
| 336 | 2.4E−08 | 7.2E−08 |
| 337 | 2.1E−08 | 1.1E−07 |
| 338 | 1.4E−08 | 1.2E−06 |
| 339 | 2.5E−08 | 2.1E−08 |
| 340 | 5.0E−07 | NT |
| 341 | 2.6E−08 | 6.4E−08 |
| 342 | 2.3E−07 | NT |
| 343 | 3.3E−08 | NT |
| 344 | 9.6E−09 | 1.1E−08 |
| 345 | 1.1E−07 | NT |
| 346 | 2.1E−08 | 2.2E−09 |
| 347 | 1.5E−08 | 1.6E−09 |
| 348 | 1.2E−08 | 1.6E−09 |
| 349 | 7.6E−08 | NT |
| 350 | 3.5E−07 | NT |
| 351 | 5.7E−07 | NT |
| 352 | 3.9E−07 | NT |
| 353 | 1.2E−07 | NT |
| 354 | 3.9E−08 | 2.7E−07 |
| 355 | 4.1E−08 | NT |
| 356 | 1.4E−08 | 3.3E−08 |
| 357 | 6.4E−08 | NT |
| 358 | 4.5E−08 | NT |
| 359 | 4.1E−08 | NT |
| 360 | 1.1E−07 | NT |
| 361 | 7.2E−08 | NT |
| 362 | 2.9E−08 | 1.9E−07 |
| 363 | 2.8E−08 | 7.0E−08 |
| 364 | 3.5E−08 | 2.8E−07 |
| 365 | 4.2E−08 | 1.2E−07 |
| 366 | 3.8E−08 | 2.3E−07 |
| 367 | 2.0E−08 | 1.4E−07 |
| 368 | 2.7E−08 | 1.2E−07 |
| 369 | 2.6E−08 | 3.8E−08 |
| 370 | 1.0E−07 | NT |
| 371 | 5.4E−08 | NT |
| 372 | 9.4E−08 | NT |
| 373 | 3.4E−08 | 4.9E−08 |
| 374 | 2.8E−08 | 4.5E−08 |
| 375 | 4.4E−08 | 4.0E−08 |
| 376 | 3.1E−08 | 5.2E−08 |
| 377 | 3.7E−08 | 8.6E−08 |
| 378 | 3.1E−08 | 5.6E−08 |
| 379 | 9.2E−08 | NT |
| 380 | 9.8E−08 | NT |
| 381 | 4.3E−08 | NT |
| 382 | 2.1E−08 | 3.2E−08 |
| 383 | 1.9E−08 | 1.6E−08 |
| 384 | 1.6E−08 | 2.5E−08 |
| 385 | 2.5E−08 | 2.8E−08 |
| 386 | 2.1E−08 | 2.2E−08 |
| 387 | 1.5E−08 | 2.4E−08 |
| 388 | 5.4E−08 | 4.3E−08 |
| 389 | 1.7E−07 | NT |
| 390 | 3.9E−08 | NT |
| 391 | 6.0E−08 | 6.9E−08 |
| 392 | 8.0E−08 | NT |
| 393 | 6.2E−08 | NT |
| 394 | 6.0E−08 | NT |
| 395 | 6.6E−08 | NT |
| 396 | 1.7E−08 | 4.5E−08 |
| 397 | 2.8E−08 | 9.4E−08 |
| 398 | 3.3E−08 | 6.0E−08 |
| 399 | 3.6E−08 | 2.5E−08 |
| 400 | 4.8E−08 | NT |
| 401 | 2.9E−08 | 9.3E−08 |
| 402 | 2.7E−08 | 3.7E−08 |
| 403 | 1.4E−08 | 8.8E−08 |
| 404 | 1.9E−08 | 1.2E−07 |
| 405 | 3.5E−08 | NT |
| 406 | 2.3E−08 | 9.8E−08 |
| 407 | 2.4E−08 | 9.0E−08 |
| 408 | 2.1E−08 | 4.5E−08 |
| 409 | 5.2E−08 | NT |
| 410 | 4.0E−08 | 1.5E−07 |
| 411 | 4.8E−08 | NT |
| 412 | 2.4E−08 | 1.1E−07 |
| 413 | 3.5E−08 | NT |
| 414 | 1.3E−08 | NT |
| 415 | 2.0E−08 | 3.0E−08 |
| 416 | 1.9E−08 | 2.6E−08 |
| 417 | 2.5E−08 | 5.7E−08 |
| 418 | 3.0E−08 | 4.7E−08 |
| 419 | 2.3E−08 | 1.2E−07 |
| 420 | 2.3E−08 | 6.9E−08 |
| 421 | 2.6E−08 | 1.0E−07 |
| 422 | 2.8E−08 | 9.2E−08 |
| 423 | 2.8E−08 | 8.3E−08 |
| 424 | 3.1E−08 | 1.4E−07 |
| 425 | 8.0E−09 | 4.5E−08 |
| 426 | 1.9E−08 | 1.1E−07 |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
|---|---|---|
| 427 | 1.9E−08 | 6.4E−08 |
| 428 | 4.2E−08 | 2.5E−07 |
| 429 | 7.3E−08 | NT |
| 430 | 4.2E−07 | NT |
| 431 | 1.1E−07 | NT |
| 432 | 3.8E−08 | 2.9E−08 |
| 433 | 1.5E−08 | 2.0E−08 |
| 434 | 6.5E−08 | 2.5E−07 |
| 435 | 1.6E−08 | 5.7E−09 |
| 436 | 1.4E−08 | 2.7E−09 |
| 437 | 6.7E−08 | 1.3E−08 |
| 438 | 1.3E−08 | 1.5E−08 |
| 439 | 2.3E−08 | 1.5E−08 |
| 440 | 1.0E−08 | 1.7E−08 |
| 441 | 4.1E−08 | NT |
| 442 | 3.6E−08 | 7.9E−08 |
| 443 | 4.2E−08 | NT |
| 444 | 1.0E−07 | NT |
| 445 | 1.7E−08 | 1.1E−08 |
| 446 | 1.6E−08 | 4.0E−09 |
| 447 | 7.1E−09 | 4.9E−09 |
| 448 | 9.4E−09 | 1.7E−09 |
| 449 | 1.8E−08 | 3.4E−09 |
| 450 | 1.5E−08 | 1.8E−08 |
| 451 | 3.7E−08 | 5.0E−08 |
| 452 | 2.5E−08 | 2.2E−08 |
| 453 | 2.7E−08 | 6.4E−08 |
| 454 | 1.1E−08 | 1.5E−08 |
| 455 | 1.1E−08 | 8.4E−09 |
| 456 | 8.6E−09 | 1.3E−08 |
| 457 | 1.7E−08 | 2.8E−08 |
| 458 | 1.5E−08 | 1.2E−08 |
| 459 | 8.7E−09 | 1.8E−08 |
| 460 | 6.1E−09 | NT |
| 461 | 1.9E−07 | NT |
| 462 | 9.9E−08 | NT |
| 463 | 7.6E−08 | NT |
| 464 | 4.0E−08 | 4.3E−08 |
| 465 | 2.1E−08 | 3.3E−08 |
| 466 | 3.9E−08 | 3.7E−08 |
| 467 | 7.0E−08 | NT |
| 468 | 9.8E−08 | NT |
| 469 | 5.0E−08 | NT |
| 470 | 2.6E−08 | 2.4E−08 |
| 471 | 2.7E−08 | 2.5E−07 |
| 472 | 2.5E−08 | 1.3E−07 |
| 473 | 1.2E−07 | NT |
| 474 | 4.7E−08 | NT |
| 475 | 1.1E−07 | NT |
| 476 | 7.8E−08 | NT |
| 477 | 8.0E−08 | NT |
| 478 | 6.1E−08 | NT |
| 479 | 2.8E−08 | NT |
| 480 | 1.9E−08 | 7.6E−08 |
| 481 | 8.2E−08 | NT |
| 482 | 1.1E−08 | 1.9E−09 |
| 483 | 1.5E−08 | 5.6E−09 |
| 484 | 1.5E−08 | 2.0E−09 |
| 485 | 4.6E−08 | 2.6E−09 |
| 486 | 5.5E−09 | 7.1E−09 |
| 487 | 6.1E−09 | 8.4E−09 |
| 488 | 8.2E−08 | NT |
| 489 | 2.6E−08 | 6.0E−08 |
| 490 | 3.1E−08 | 5.4E−08 |
| 491 | 4.8E−08 | 7.0E−08 |
| 492 | 7.1E−08 | NT |
| 493 | 1.4E−08 | 2.6E−09 |
| 494 | 1.9E−08 | 4.2E−09 |
| 495 | 1.3E−08 | 2.7E−09 |
| 496 | 5.0E−08 | 2.6E−09 |
| 497 | 1.8E−08 | 2.7E−09 |
| 498 | 4.3E−09 | 6.0E−09 |
| 499 | 1.2E−08 | 2.0E−09 |
| 500 | 1.5E−07 | NT |
| 501 | 7.2E−08 | 8.8E−09 |
| 502 | 5.1E−08 | 7.2E−09 |
| 503 | 4.3E−07 | NT |
| 504 | 2.0E−07 | 1.4E−08 |
| 505 | 5.9E−09 | 2.9E−09 |
| 506 | 5.6E−09 | 2.1E−09 |
| 507 | 1.2E−07 | NT |
| 508 | 1.9E−08 | 6.9E−09 |
| 509 | 3.1E−08 | 1.5E−08 |
| 510 | 3.3E−08 | 2.0E−08 |
| 511 | 4.6E−08 | 7.8E−08 |
| 512 | 2.0E−07 | NT |
| 513 | 1.5E−07 | NT |
| 514 | 1.1E−07 | NT |
| 515 | 1.5E−07 | NT |
| 516 | 4.9E−08 | 6.5E−09 |
| 517 | 9.9E−09 | 6.2E−09 |
| 518 | 2.6E−08 | 3.5E−09 |
| 519 | 4.9E−09 | 4.0E−09 |
| 520 | 9.7E−09 | 5.6E−09 |
| 521 | 3.4E−08 | 3.1E−09 |
| 522 | 4.3E−08 | 9.8E−09 |
| 523 | 4.7E−09 | 1.9E−09 |
| 524 | 5.5E−09 | 2.8E−09 |
| 525 | 8.8E−09 | 3.5E−09 |
| 526 | 1.8E−08 | 8.6E−09 |
| 527 | 1.6E−08 | 9.8E−09 |
| 528 | 6.6E−09 | 3.5E−09 |
| 529 | 6.7E−09 | 3.0E−09 |
| 530 | 2.2E−08 | 3.1E−09 |
| 531 | 5.5E−09 | 2.1E−09 |
| 532 | 2.7E−08 | 1.1E−07 |
| 533 | 1.3E−08 | 8.1E−08 |
| 534 | 2.1E−08 | 5.0E−08 |
| 535 | 9.0E−08 | NT |
| 536 | 2.9E−08 | NT |
| 537 | 4.0E−08 | NT |
| 538 | 5.3E−08 | NT |
| 539 | 4.5E−08 | NT |
| 540 | 2.0E−08 | NT |
| 541 | 2.0E−08 | 1.0E−07 |
| 542 | 1.4E−08 | 7.9E−08 |
| 543 | 1.6E−08 | 6.2E−08 |
| 544 | 1.4E−08 | 4.9E−08 |
| 545 | 1.4E−08 | 1.3E−07 |
| 546 | 3.5E−08 | 8.9E−08 |
| 547 | 1.7E−08 | 1.4E−07 |
| 548 | 1.2E−08 | 9.4E−08 |
| 549 | 1.9E−08 | 6.5E−08 |
| 550 | 2.9E−08 | NT |
| 551 | 1.7E−08 | 4.2E−08 |
| 552 | 1.8E−08 | NT |
| 553 | 1.3E−08 | 8.1E−08 |
| 554 | 1.9E−08 | 4.5E−08 |
| 555 | 3.2E−08 | 4.2E−08 |
| 556 | 1.1E−08 | 2.0E−07 |
| 557 | 2.4E−08 | NT |
| 558 | 1.8E−08 | 6.7E−08 |
| 559 | 2.5E−08 | NT |
| 560 | 2.4E−08 | 1.4E−07 |
| 561 | 2.4E−08 | NT |
| 562 | 9.6E−09 | 5.6E−08 |
| 563 | 1.1E−08 | 8.6E−08 |
| 564 | 1.1E−08 | 7.1E−08 |
| 565 | 9.6E−09 | 4.5E−08 |
| 566 | 3.3E−08 | NT |
| 567 | 2.3E−08 | NT |
| 568 | 1.4E−08 | 5.4E−08 |
| 569 | 3.4E−07 | NT |
| 570 | 5.0E−07 | NT |
| 571 | 4.3E−07 | NT |
| 572 | 2.9E−08 | 2.8E−07 |
| 573 | 2.1E−08 | 2.1E−07 |
| 574 | 4.8E−08 | 1.5E−07 |
| 575 | 6.1E−08 | 1.2E−07 |
| 576 | 2.2E−07 | NT |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
|---|---|---|
| 577 | 1.2E−07 | NT |
| 578 | 1.3E−07 | NT |
| 579 | 5.2E−08 | NT |
| 580 | 1.3E−07 | NT |
| 581 | 4.5E−08 | NT |
| 582 | 4.1E−08 | NT |
| 583 | 2.4E−08 | NT |
| 584 | 1.2E−08 | 1.4E−08 |
| 585 | 1.2E−07 | NT |
| 586 | 5.4E−08 | NT |
| 587 | 8.0E−08 | NT |
| 588 | 5.4E−08 | NT |
| 589 | 3.6E−07 | NT |
| 590 | 2.0E−07 | NT |
| 591 | 1.1E−07 | NT |
| 592 | 9.0E−08 | NT |
| 593 | 8.9E−08 | NT |
| 594 | 1.8E−07 | NT |
| 595 | 1.7E−08 | 1.1E−07 |
| 596 | 1.6E−08 | 4.9E−08 |
| 597 | 1.8E−08 | 5.6E−08 |
| 598 | 2.5E−08 | 8.5E−08 |
| 599 | 6.7E−09 | 4.0E−08 |
| 600 | 3.3E−08 | 7.3E−08 |
| 601 | 3.1E−08 | 4.8E−08 |
| 602 | 7.7E−09 | 4.0E−08 |
| 603 | 3.6E−08 | 7.6E−08 |
| 604 | 2.0E−08 | 4.2E−08 |
| 605 | 2.4E−08 | 4.7E−08 |
| 606 | 4.1E−08 | 9.6E−08 |
| 607 | 4.4E−08 | NT |
| 608 | 3.1E−08 | 3.6E−08 |
| 609 | 1.4E−08 | 2.7E−08 |
| 610 | 3.8E−08 | 8.6E−08 |
| 611 | 2.1E−08 | 5.5E−08 |
| 612 | 6.0E−08 | 3.6E−08 |
| 613 | 3.2E−08 | 6.4E−08 |
| 614 | 5.6E−08 | NT |
| 615 | 6.9E−08 | NT |
| 616 | 6.1E−08 | 6.2E−08 |
| 617 | 3.5E−08 | 8.9E−08 |
| 618 | 2.0E−08 | 3.4E−08 |
| 619 | 3.8E−08 | 3.0E−08 |
| 620 | 3.0E−08 | 5.0E−08 |
| 621 | 4.1E−08 | NT |
| 622 | 5.7E−08 | NT |
| 623 | 2.7E−08 | 3.5E−08 |
| 624 | 6.2E−08 | NT |
| 625 | 3.1E−08 | 4.0E−08 |
| 626 | 1.2E−08 | 1.2E−08 |
| 627 | 2.0E−08 | 1.8E−08 |
| 628 | 4.1E−08 | NT |
| 629 | 1.2E−08 | 9.2E−09 |
| 630 | 2.5E−08 | 2.6E−08 |
| 631 | 3.1E−08 | 3.4E−08 |
| 632 | 1.0E−08 | 9.4E−09 |
| 633 | 1.9E−08 | 1.4E−08 |
| 634 | 1.7E−08 | 1.4E−08 |
| 635 | 4.0E−08 | 8.3E−08 |
| 636 | 2.7E−08 | 2.8E−08 |
| 637 | 3.3E−08 | 5.4E−08 |
| 638 | 3.8E−08 | 7.9E−08 |
| 639 | 9.0E−08 | NT |
| 640 | 3.0E−08 | 5.4E−08 |
| 641 | 2.5E−08 | 5.0E−08 |
| 642 | 2.0E−08 | 5.4E−08 |
| 643 | 3.2E−08 | 5.4E−08 |
| 644 | 6.2E−08 | NT |
| 645 | 2.2E−08 | NT |
| 646 | 7.0E−08 | NT |
| 647 | 3.2E−08 | 2.6E−08 |
| 648 | 6.9E−08 | NT |
| 649 | 1.5E−08 | 2.7E−08 |
| 650 | 1.9E−08 | 3.8E−08 |
| 651 | 2.8E−08 | 8.9E−08 |
| 652 | 1.4E−08 | 8.2E−08 |
| 653 | 2.4E−08 | 1.1E−07 |
| 654 | 1.9E−08 | 8.9E−08 |
| 655 | 2.7E−08 | 4.7E−08 |
| 656 | 2.7E−08 | 8.6E−08 |
| 657 | 6.2E−08 | NT |
| 658 | 6.2E−07 | NT |
| 659 | 5.7E−07 | NT |
| 660 | 7.7E−07 | NT |
| 661 | 3.8E−07 | NT |
| 662 | 2.6E−07 | NT |
| 663 | 1.6E−07 | NT |
| 664 | 2.2E−07 | NT |
| 665 | 2.3E−07 | NT |
| 666 | 3.4E−08 | 9.7E−08 |
| 667 | 3.2E−08 | 8.7E−08 |
| 668 | 3.1E−08 | 1.1E−07 |
| 669 | 2.7E−08 | 1.1E−07 |
| 670 | 6.7E−07 | NT |
| 671 | 3.0E−08 | 5.9E−08 |
| 672 | 2.8E−08 | 6.3E−08 |
| 673 | 1.6E−08 | 2.8E−08 |
| 674 | 2.6E−08 | 1.2E−07 |
| 675 | 2.7E−08 | 6.3E−08 |
| 676 | 2.9E−08 | 5.6E−08 |
| 677 | 4.2E−08 | NT |
| 678 | 1.9E−08 | 4.1E−08 |
| 679 | 5.8E−07 | NT |
| 680 | 5.8E−07 | NT |
| 681 | 5.9E−07 | NT |
| 682 | 1.3E−08 | 1.5E−08 |
| 683 | 1.8E−08 | 1.4E−08 |
| 684 | 1.2E−08 | 4.7E−08 |
| 685 | 7.8E−09 | 2.1E−08 |
| 686 | 2.3E−07 | NT |
| 687 | 1.6E−08 | 3.3E−08 |
| 688 | 1.5E−08 | 3.2E−08 |
| 689 | 1.7E−08 | 2.2E−08 |
| 690 | 1.0E−08 | 1.6E−08 |
| 691 | 1.2E−08 | 1.9E−08 |
| 692 | 2.0E−08 | 2.0E−08 |
| 693 | 3.2E−08 | 2.6E−08 |
| 694 | 1.9E−08 | 4.1E−08 |
| 695 | 2.0E−08 | 4.9E−08 |
| 696 | 2.1E−08 | 4.5E−08 |
| 697 | 1.4E−08 | 1.4E−08 |
| 698 | 2.0E−08 | 1.9E−08 |
| 699 | 8.0E−09 | 1.2E−08 |
| 700 | 2.4E−08 | 3.9E−08 |
| 701 | 2.2E−08 | 3.4E−08 |
| 702 | 2.4E−08 | 1.8E−07 |
| 703 | 2.6E−08 | 1.6E−07 |
| 704 | 2.9E−08 | 5.6E−08 |
| 705 | 7.7E−09 | 1.1E−08 |
| 706 | 1.1E−07 | NT |
| 707 | 2.9E−07 | NT |
| 708 | 9.9E−08 | NT |
| 709 | 1.6E−08 | 2.0E−08 |
| 710 | 2.9E−08 | 4.3E−08 |
| 711 | 3.6E−08 | NT |
| 712 | 2.2E−08 | NT |
| 713 | 7.9E−09 | 1.7E−08 |
| 714 | 1.1E−08 | 1.6E−08 |
| 715 | 1.0E−08 | 4.1E−09 |
| 716 | 1.3E−08 | 5.8E−09 |
| 717 | 7.1E−09 | 3.1E−09 |
| 718 | 7.3E−09 | 2.8E−09 |
| 719 | 9.4E−09 | 1.5E−09 |
| 720 | 8.6E−09 | 5.0E−09 |
| 721 | 1.8E−08 | 7.8E−09 |
| 722 | 2.2E−08 | 2.4E−09 |
| 723 | 1.2E−08 | 6.5E−09 |
| 724 | 5.1E−09 | 3.6E−09 |
| 725 | 4.4E−08 | 4.7E−09 |
| 726 | 3.4E−09 | 3.9E−09 |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
| --- | --- | --- |
| 727 | 1.7E−08 | 1.4E−09 |
| 728 | 4.0E−08 | 6.4E−09 |
| 729 | 2.6E−08 | 2.7E−09 |
| 730 | 5.0E−08 | 2.4E−09 |
| 731 | 6.9E−08 | 4.0E−09 |
| 732 | 1.7E−08 | 4.3E−09 |
| 733 | 2.3E−08 | 5.7E−09 |
| 734 | 1.5E−08 | 3.1E−09 |
| 735 | 1.6E−08 | 2.3E−09 |
| 736 | 1.5E−08 | 1.2E−08 |
| 737 | 2.0E−09 | 3.3E−09 |
| 738 | 2.1E−08 | 2.8E−09 |
| 739 | 6.5E−09 | 1.7E−09 |
| 740 | 4.3E−09 | 1.5E−09 |
| 741 | 4.5E−09 | 7.1E−09 |
| 742 | 2.9E−09 | 6.8E−09 |
| 743 | 4.9E−09 | 4.2E−09 |
| 744 | 1.0E−08 | 2.9E−09 |
| 745 | 9.2E−09 | 3.0E−09 |
| 746 | 5.1E−09 | 1.5E−08 |
| 747 | 5.2E−09 | 3.7E−09 |
| 748 | 4.8E−09 | 5.8E−09 |
| 749 | 1.3E−08 | 7.04E−09 |
| 750 | 7.7E−09 | 2.3E−09 |
| 751 | 1.3E−08 | 1.6E−09 |
| 752 | 2.3E−08 | 4.2E−08 |
| 753 | 2.6E−08 | 1.0E−07 |
| 754 | 2.4E−08 | 4.4E−08 |
| 755 | 2.8E−08 | 3.8E−08 |
| 756 | 1.1E−08 | 1.4E−08 |
| 757 | 1.9E−08 | 3.5E−08 |
| 758 | 1.8E−08 | 6.9E−08 |
| 759 | 2.3E−08 | NT |
| 760 | 8.3E−08 | NT |
| 761 | 5.1E−08 | NT |
| 762 | 5.3E−07 | NT |
| 763 | 2.6E−08 | 3.0E−07 |
| 764 | 5.4E−08 | NT |
| 765 | 7.6E−08 | NT |
| 766 | 8.5E−08 | NT |
| 767 | 3.5E−08 | 2.4E−08 |
| 768 | 5.1E−09 | 6.6E−08 |
| 769 | 2.1E−08 | 5.2E−08 |
| 770 | 1.1E−08 | 3.8E−07 |
| 771 | 8.5E−09 | 1.6E−07 |
| 772 | 3.0E−08 | 3.8E−07 |
| 773 | 4.8E−08 | NT |
| 774 | 1.5E−09 | 4.1E−09 |
| 775 | 4.8E−09 | 4.0E−09 |
| 776 | 1.8E−09 | 2.3E−09 |
| 777 | 5.3E−09 | 1.1E−08 |
| 778 | 1.0E−08 | 1.7E−08 |
| 779 | 5.5E−08 | NT |
| 780 | 1.2E−07 | NT |
| 781 | 2.0E−07 | NT |
| 782 | 6.5E−08 | NT |
| 783 | 1.7E−07 | NT |
| 784 | 7.5E−08 | NT |
| 785 | 1.7E−07 | NT |
| 786 | 1.2E−08 | 4.0E−08 |
| 787 | 3.9E−08 | 4.6E−08 |
| 788 | 1.4E−07 | NT |
| 789 | 2.4E−08 | 1.0E−07 |
| 790 | 2.0E−08 | 2.3E−07 |
| 791 | 1.5E−08 | 9.5E−08 |
| 792 | 2.2E−08 | 9.9E−08 |
| 793 | 1.2E−07 | NT |
| 794 | 2.6E−07 | NT |
| 795 | 1.4E−07 | NT |
| 796 | 7.2E−08 | NT |
| 797 | 5.7E−07 | NT |
| 798 | 9.8E−08 | NT |
| 799 | 2.0E−07 | NT |
| 800 | 5.1E−07 | NT |
| 801 | 4.9E−08 | NT |
| 802 | 1.3E−07 | NT |
| 803 | 3.6E−08 | NT |
| 804 | 1.5E−07 | NT |
| 805 | 3.1E−08 | 8.9E−06 |
| 806 | 1.8E−08 | 1.4E−07 |
| 807 | 1.3E−08 | 6.7E−09 |
| 808 | 9.6E−09 | 2.5E−09 |
| 809 | 3.3E−09 | 5.6E−09 |
| 810 | 1.6E−08 | 1.1E−08 |
| 811 | 7.1E−09 | 4.2E−09 |
| 812 | 4.9E−09 | 4.1E−09 |
| 813 | 1.0E−08 | 5.2E−09 |
| 814 | 1.4E−08 | NT |
| 815 | 3.6E−08 | 1.6E−07 |
| 816 | 3.6E−08 | 2.3E−08 |
| 817 | 3.0E−08 | 1.6E−08 |
| 818 | 48.2% @400 μM<br>52.4% @400 μM | NT |
| 819 | 2.2E−07 | NT |
| 820 | 58.5% @400 μM<br>60.9% @400 μM | NT |
| 821 | 1.8E−07 | NT |
| 822 | 68.6% @400 μM<br>66.3% @400 μM | NT |
| 823 | 1.1E−07 | NT |
| 824 | 1.8E−07 | NT |
| 825 | 1.2E−07 | NT |
| 826 | 4.3E−07 | NT |
| 827 | 2.4E−07 | NT |
| 828 | 4.2E−08 | 4.3E−07 |
| 829 | 5.7E−08 | NT |
| 830 | 3.4E−07 | NT |
| 831 | 3.1E−06 | NT |
| 832 | 1.7E−06 | NT |
| 833 | 3.2E−07 | NT |
| 834 | 8.6E−08 | NT |
| 835 | 1.7E−07 | NT |
| 836 | 2.6E−07 | NT |
| 837 | 3.6E−07 | NT |
| 838 | 7.9E−08 | NT |
| 839 | 1.2E−07 | NT |
| 840 | 4.7E−07 | NT |
| 841 | 3.2E−07 | NT |
| 842 | 5.6E−07 | NT |
| 843 | 7.4E−07 | NT |
| 844 | 3.7E−08 | 2.8E−07 |
| 845 | 6.5E−08 | NT |
| 846 | 1.9E−08 | 1.3E−06 |
| 847 | 8.3E−06 | NT |
| 848 | 1.5E−07 | NT |
| 849 | 2.9E−07 | NT |
| 850 | 2.1E−08 | NT |
| 851 | 2.4E−08 | NT |
| 852 | 1.0E−07 | NT |
| 853 | 1.3E−07 | NT |
| 854 | 7.5E−08 | NT |
| 855 | 8.5E−08 | NT |
| 856 | 3.9E−08 | 3.8E−07 |
| 857 | 8.6E−08 | NT |
| 858 | 1.1E−07 | NT |
| 859 | 6.5E−08 | NT |
| 860 | 8.2E−08 | NT |
| 861 | 5.6E−08 | 4.1E−07 |
| 862 | 7.3E−08 | 1.6E−07 |
| 863 | 2.9E−08 | 1.1E−07 |
| 864 | 3.1E−08 | 1.0E−07 |
| 865 | 1.5E−08 | 6.4E−08 |
| 866 | 8.8E−08 | NT |
| 867 | 1.5E−07 | NT |
| 868 | 2.5E−07 | 1.6E−07 |
| 869 | 7.3E−08 | NT |
| 870 | 4.5E−08 | NT |
| 871 | 5.8E−08 | NT |
| 872 | 3.1E−08 | 3.1E−08 |
| 873 | 8.6E−09 | 3.2E−08 |

TABLE 1-continued

IC$_{50}$ of USP7 inhibition and of cytotoxicity for MM1S or Z138 cells
Note: IC$_{50}$ of cytotoxicity for Z138 tumour cell line are underlined.

| EXAMPLE | IC$_{50}$ (M) USP7 FLINT | IC$_{50}$ (M) MTT |
|---|---|---|
| 874 | 1.5E−08 | 6.4E−09 |
| 875 | 2.2E−08 | 1.8E−08 |
| 876 | 2.7E−08 | 2.3E−08 |
| 877 | 1.7E−08 | 1.5E−08 |
| 878 | 5.2E−09 | 4.4E−09 |
| 879 | 1.6E−08 | NT |
| 880 | 3.9E−08 | 5.5E−08 |
| 881 | 3.9E−08 | 6.6E−08 |
| 882 | 4.6E−09 | 8.2E−09 |
| 883 | 5.3E−09 | 3.7E−09 |
| 884 | 9.8E−09 | 3.1E−09 |
| 885 | 3.6E−08 | 1.2E−08 |
| 886 | 9.1E−09 | 1.6E−09 |
| 887 | 9.8E−09 | 2.8E−09 |
| 888 | 1.1E−08 | 5.6E−09 |
| 889 | 3.0E−09 | 1.3E−08 |
| 890 | 2.6E−08 | NT |
| 891 | 1.6E−08 | _3.77E−08_ |
| 892 | 2.6E−08 | _7.7E−08_ |
| 893 | 8.6E−09 | 2.3E−08 |
| 894 | 4.8E−09 | 6.4E−09 |
| 895 | 6.3E−09 | 4.7E−09 |
| 896 | 4.1E−09 | 3.1E−09 |
| 897 | 3.2E−09 | 2.0E−09 |
| 898 | 6.4E−09 | 2.2E−09 |
| 899 | 5.3E−07 | NT |
| 900 | 1.4E−07 | NT |
| 901 | 1.5E−08 | NT |
| 902 | 2.9E−08 | NT |
| 903 | 1.4E−07 | NT |
| 904 | 5.5E−08 | NT |
| 905 | 1.2E−08 | NT |
| 906 | 2.2E−08 | NT |
| 907 | 3.8E−08 | NT |
| 908 | 3.7E−08 | 5.8E−09 |
| 909 | 2.4E−08 | 2.8E−09 |
| 910 | 4.1E−07 | NT |
| 911 | 2.3E−08 | NT |
| 912 | 1.1E−08 | 1.06E−08/_2.01E−08_ |
| 913 | 2.2E−08 | _2.94E−08_ |
| 914 | 7.9E−09 | _6.41E−09_ |
| 915 | 3.5E−08 | 1.69E−08/_2.29E−08_ |
| 916 | 2.5E−08 | _3.79E−08_ |
| 917 | 2.8E−08 | _9.48E−08_ |
| 918 | 1.2E−07 | NT |
| 919 | 3.3E−08 | _2.86E−09_ |
| 920 | 2.7E−08 | 2.1E−08 |
| 921 | 9.7E−09 | _4.2E−09_ |
| 922 | 8.1E−07 | NT |
| 923 | 2.6E−08 | 7.5E−09 |
| 924 | 1.2E−08 | _2.11E−09_ |
| 925 | 5.6E−09 | _4.6E−09_ |
| 926 | 1.4E−08 | _5.3E−08_ |
| 927 | 2.8E−07 | NT |
| 928 | 6.4E−08 | NT |
| 929 | 1.5E−07 | NT |
| 930 | 4.1E−07 | NT |
| 931 | 1.2E−07 | NT |
| 932 | 1.7E−08 | 5.7E−08 |
| 933 | 1.1E−08 | 4.1E−08 |
| 934 | 2.3E−05 | NT |
| 935 | 1.7E−07 | 7.9E−07 |
| 936 | 2.0E−05 | NT |
| 937 | 2.6E−07 | NT |
| 938 | 2.58E−08 | 1.78E−08 |
| 939 | 2.91E−08 | 3.25E−08 |
| 940 | 1.25E−08 | 7.48E−09 |
| 941 | 1.43E−08 | 3.99E−09 |
| 942 | 1.02E−08 | 1.56E−09 |
| 943 | 6.62E−09 | 1.48E−09 |
| 944 | 1.01E−08 | 3.19E−09 |
| 945 | 5.28E−08 | 6.32E−09 |
| 946 | 1.80E−08 | 6.08E−09 |
| 947 | 1.44E−08 | 1.96E−09 |
| 948 | 8.13E−09 | 2.73E−09 |
| 949 | 7.34E−09 | 2.01E−09 |
| 950 | 1.22E−08 | 3.36E−09 |
| 951 | 3.19E−08 | 4.66E−08 |
| 952 | 1.73E−07 | NT |
| 953 | 2.14E−08 | 1.51E−09 |
| 954 | 1.92E−07 | NT |
| 955 | 1.31E−08 | 1.18E−09 |
| 956 | 1.36E−07 | NT |
| 957 | 1.52E−08 | 2.75E−09 |
| 958 | 1.74E−08 | 2.40E−09 |
| 959 | 1.19E−06 | 1.24E−06 |
| 960 | 5.19E−08 | 2.81E−09 |
| 961 | 3.58E−08 | 2.10E−09 |
| 962 | 3.78E−08 | 1.90E−09 |
| 963 | 3.78E−08 | 1.49E−09 |
| 964 | 8.61E−08 | NT |
| 965 | 9.40E−08 | NT |
| 966 | 4.73E−08 | 4.11E−09 |
| 967 | 4.23E−08 | 2.21E−09 |
| 968 | 1.74E−07 | NT |
| 969 | 1.53E−07 | NT |
| 970 | 3.07E−08 | 9.92E−08 |
| 971 | 3.35E−08 | 2.86E−07 |
| 972 | 6.09E−08 | NT |
| 973 | 5.19E−08 | 9.67E−09 |
| 974 | 2.79E−08 | 3.66E−09 |
| 975 | 2.44E−08 | 2.92E−09 |
| 976 | 5.76E−08 | 6.67E−09 |
| 977 | 4.70E−08 | 3.95E−09 |
| 978 | 5.93E−08 | 1.20E−08 |
| 979 | 4.58E−08 | 7.15E−09 |
| 980 | 4.44E−08 | 9.71E−09 |
| 981 | 4.79E−08 | 8.68E−09 |
| 982 | 6.77E−08 | 1.23E−08 |
| 983 | 7.25E−08 | 2.92E−09 |
| 984 | 3.11E−08 | 1.34E−09 |
| 985 | 3.25E−08 | 1.35E−09 |
| 986 | 4.56E−08 | 2.08E−09 |
| 987 | 5.15E−08 | 1.92E−09 |
| 988 | 6.09E−08 | 6.05E−09 |
| 989 | 7.86E−08 | 3.50E−09 |
| 990 | 4.69E−08 | 1.99E−09 |
| 991 | 4.60E−08 | 8.32E−10 |
| 992 | 6.29E−08 | 3.03E−09 |
| 993 | 6.43E−08 | 1.52E−09 |
| 994 | 6.35E−08 | 9.57E−09 |
| 995 | 8.82E−08 | 7.82E−09 |
| 996 | 5.29E−08 | 2.81E−09 |
| 997 | 3.16E−08 | 4.21E−09 |
| 998 | 6.01E−08 | 4.48E−08 |
| 999 | 3.40E−08 | 1.62E−08 |
| 1000 | 7.97E−08 | 4.13E−08 |
| 1001 | 1.09E−07 | NT |
| 1002 | 8.61E−08 | 1.25E−07 |
| 1003 | 3.90E−08 | 4.07E−08 |
| 1004 | 1.81E−08 | 6.77E−09 |
| 1005 | 4.52E−08 | 8.38E−09 |
| 1006 | 5.27E−08 | 1.16E−08 |
| 1007 | 2.43E−08 | 1.32E−08 |
| 1008 | 4.65E−08 | 1.21E−08 |
| 1009 | 2.40E−08 | 7.61E−09 |
| 1010 | 2.84E−08 | 6.27E−09 |
| 1011 | 2.71E−08 | 1.09E−08 |
| 1012 | 2.75E−08 | 1.92E−08 |
| 1013 | 4.76E−08 | 2.14E−08 |

NT: not tested

For partial inhibitors, the percentage fluorescence intensity for a given concentration of the test compound is indicated. Accordingly, 48.2% @400 μM means that 48.2% fluorescence intensity is observed for a concentration of test compound equal to 400 μM.

Example C: Anti-Tumor Activity In Vivo

The anti-tumour activity of the compounds of the invention is evaluated in a xenograft model of multiple myeloma and/or acute lymphoblastic leukaemia cells.

Human tumour cells are grafted subcutaneously into immunosuppressed mice.

When the tumour volume (TV) reaches about 200 mm³, the mice are treated per os with the various compounds once a day for 5 days on/2 days off during 3 weeks. The tumour mass is measured twice weekly from the start of treatment.

The compounds of the invention display anti-tumour activities represented by the TGI (tumor growth inhibition) at the end of the treatment period ranging from 40 to 133.4%. The TGI is defined as follows:

$$TGI = \left(1 - \frac{\text{Median }(DTV \text{ at } Dx \text{ in treated group})}{\text{Median }(DTV \text{ at } Dx \text{ in control group})}\right) \times 100,$$

with:

DTV (delta tumoral volume) at Dx=(TV at Dx)−(TV at randomization for each animal).

Example D: Pharmaceutical Composition: Tablets 1000 tablets containing a dose of 5 mg of a compound selected from

| | |
|---|---|
| Examples 1 to 1013 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound of formula (I):

wherein:
- $R_1$ represents an aryl group or a heteroaryl group,
- $R_2$ represents a hydrogen atom or a halogen atom,
- n is an integer equal to 0, 1 or 2,
- J represents a —C(O)— group, a —CH($R_3$)— group, or an —SO$_2$— group,
- $R_3$ represents a hydrogen atom or a linear or branched ($C_1$-$C_6$)alkyl group,
- K represents a bond or a -$Cy_1$- group,
- L represents a -$Cy_2$ group or a —CH$_2$-$Cy_2$ group,
- W represents the group wherein
- A represents a heteroaryl ring,
- X represents a carbon atom or a nitrogen atom,
- $R_4$ represents a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a —$Y_1$—NR$_6$R$_7$ group, a —$Y_1$—OR$_6$ group, a linear or branched halo($C_1$-$C_6$)alkyl group, an oxo group, a —$Y_1$-Cy$_3$ group, a -Cy$_3$-R$_7$ group, a -Cy$_3$-OR$_7$ group, or a —$Y_1$—NR$_6$—C(O)—R$_7$ group,
- $R_5$ represents a hydrogen atom, a halogen atom, or a linear or branched ($C_1$-$C_6$)alkyl group,
- $R_6$ represents a hydrogen atom or a linear or branched ($C_1$-$C_6$)alkyl group,
- $R_7$ represents a hydrogen atom, a linear or branched ($C_1$-$C_6$)alkyl group, or a —$Y_2$-Cy$_4$ group,
- $Y_1$ and $Y_2$ independently of one another represent a bond or a linear or branched ($C_1$-$C_4$)alkylene group,
- Cy$_1$ represents a cycloalkyl group, a heterocycloalkyl group, an aryl group, or a heteroaryl group, which is linked to the group J and to the group L,
- Cy$_2$, Cy$_3$ and Cy$_4$ independently of one another, represent a cycloalkyl group, a heterocycloalkyl group, an aryl group, or a heteroaryl group, wherein
"aryl" means a phenyl, naphthyl, or indanyl group,
"heteroaryl" means any mono- or fused bi-cyclic group composed of from 5 to 10 ring members, having at least one aromatic moiety and having from 1 to 3 heteroatoms selected from oxygen, sulphur and nitrogen,
"cycloalkyl" means any mono- or fused bi-cyclic non-aromatic carbocyclic group having from 3 to 7 ring members,
"heterocycloalkyl" means any non-aromatic mono- or fused bi-cyclic group having from 3 to 10 ring members, and having from 1 to 3 heteroatoms selected from oxygen, sulphur and nitrogen,
wherein the aryl, heteroaryl, cycloalkyl and heterocycloalkyl groups so defined may be substituted by from 1 to 4 groups selected from linear or branched ($C_1$-$C_6$) alkyl, linear or branched ($C_2$-$C_6$)alkenyl, linear or branched ($C_2$-$C_6$)alkynyl, linear or branched halo($C_1$-$C_6$)alkyl, —$Y_1$—OR', —$Y_1$—NR'R", —$Y_1$—S(O)$_m$—R', oxo (or N-oxide where appropriate), nitro, cyano, —C(O)—R', —C(O)—OR', —O—C(O)—R', —C(O)—NR'R", —$Y_1$—NR'—C(O)—R", —$Y_1$—NR'—C(O)—OR", halogen, cyclopropyl, and pyridinyl which may be substituted by a linear or branched ($C_1$-$C_6$)alkyl group,
wherein R' and R", independently of one another, represent a hydrogen atom, a linear or branched ($C_1$-$C_6$) alkyl group, a linear or branched ($C_2$-$C_6$)alkenyl group, a linear or branched ($C_1$-$C_6$)alkoxy group, a linear or branched halo($C_1$-$C_6$)alkyl, a linear or branched hydroxy($C_1$-$C_6$)alkyl group, a linear or branched ($C_1$-

C$_6$)alkoxy(C$_1$-C$_6$)alkyl group, a phenyl group, a cyclopropylmethyl group, or a tetrahydropyranyl group,
or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by from 1 to 2 groups selected from a hydrogen atom and a linear or branched (C$_1$-C$_6$)alkyl group,
and wherein m is an integer equal to 0, 1 or 2,
its enantiomers, diastereoisomers and addition salts thereof with a pharmaceutically acceptable acid or base.

2. A compound of the following formula

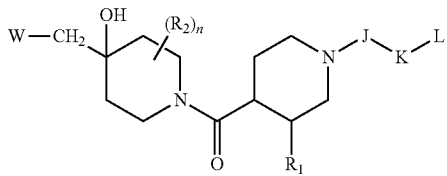

wherein:
R$_1$ represents an aryl group or a heteroaryl group,
R$_2$ represents a hydrogen atom or a halogen atom,
n is an integer equal to 0, 1 or 2,
J represents a —C(O)— group, a —CH(R$_3$)— group, or an —SO$_2$— group,
R$_3$ represents a hydrogen atom or a linear or branched (C$_1$-C$_6$)alkyl group,
K represents a -Cy$_1$- group,
L represents a -Cy$_2$ group or a —CH$_2$-Cy$_2$ group,
W represents the group

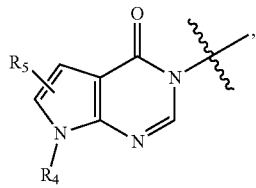

wherein:
R$_4$ represents a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a —Y$_1$—NR$_6$R$_7$ group, a —Y$_1$—OR$_6$ group, a linear or branched halo(C$_1$-C$_6$)alkyl group, an oxo group, a —Y$_1$-Cy$_3$ group, a -Cy$_3$-R$_7$ group, a -Cy$_3$-OR$_7$ group, or a —Y$_1$—NR$_6$—C(O)—R$_7$ group,
R$_5$ represents a hydrogen atom, a halogen atom, or a linear or branched (C$_1$-C$_6$)alkyl group,
R$_6$ represents a hydrogen atom or a linear or branched (C$_1$-C$_6$)alkyl group,
R$_7$ represents a hydrogen atom, a linear or branched (C$_1$-C$_6$)alkyl group, or a —Y$_2$-Cy$_4$ group,
Y$_1$ and Y$_2$ independently of one another represent a bond or a linear or branched (C$_1$-C$_4$)alkylene group,
Cy$_1$ represents a cycloalkyl group, a heterocycloalkyl group, an aryl group, or a heteroaryl group, which is linked to the group J and to the group L,
Cy$_2$ represents a heteroaryl group,
Cy$_3$ and Cy$_4$ independently of one another, represent a cycloalkyl group, a heterocycloalkyl group, an aryl group, or a heteroaryl group,
wherein
"aryl" means a phenyl, naphthyl, or indanyl group,
"heteroaryl" means any mono- or fused bi-cyclic group composed of from 5 to 10 ring members, having at least one aromatic moiety and having from 1 to 3 heteroatoms selected from oxygen, sulphur and nitrogen,
"cycloalkyl" means any mono- or fused bi-cyclic non-aromatic carbocyclic group having from 3 to 7 ring members,
"heterocycloalkyl" means any non-aromatic mono- or fused bi-cyclic group having from 3 to 10 ring members, and having from 1 to 3 heteroatoms selected from oxygen, sulphur and nitrogen,
wherein the aryl, heteroaryl, cycloalkyl and heterocycloalkyl groups so defined may be substituted by from 1 to 4 groups selected from linear or branched (C$_1$-C$_6$) alkyl, linear or branched (C$_2$-C$_6$)alkenyl, linear or branched (C$_2$-C$_6$)alkynyl, linear or branched halo(C$_1$-C$_6$)alkyl, —Y$_1$—OR', —Y$_1$—NR'R", —Y$_1$—S(O)$_m$—R', oxo (or N-oxide where appropriate), nitro, cyano, —C(O)—R', —C(O)—OR', —O—C(O)—R', —C(O)—NR'R", —Y$_1$—NR'—C(O)—R", —Y$_1$—NR'—C(O)—OR", halogen, cyclopropyl, and pyridinyl which may be substituted by a linear or branched (C$_1$-C$_6$)alkyl group,
wherein R' and R", independently of one another, represent a hydrogen atom, a linear or branched (C$_1$-C$_6$) alkyl group, a linear or branched (C$_2$-C$_6$)alkenyl group, a linear or branched (C$_1$-C$_6$)alkoxy group, a linear or branched halo(C$_1$-C$_6$)alkyl, a linear or branched hydroxy(C$_1$-C$_6$)alkyl group, a linear or branched (C$_1$-C$_6$)alkoxy(C$_1$-C$_6$)alkyl group, a phenyl group, a cyclopropylmethyl group, or a tetrahydropyranyl group,
or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by from 1 to 2 groups selected from a hydrogen atom and a linear or branched (C$_1$-C$_6$)alkyl group,
and wherein m is an integer equal to 0, 1 or 2,
its enantiomers, diastereoisomers and addition salts thereof with a pharmaceutically acceptable acid or base.

3. The compound according to claim 2, wherein K represents a phenyl group, a pyrrolyl group, a thienyl group, a thiazolyl group, a pyridinyl group, a tetrahydrobenzothienyl group, a dihydrothienodioxinyl group, a cyclopropyl group, a cyclobutyl group, or a pyrrolidinyl group.

4. The compound according to claim 2, wherein L represents a -Cy$_2$ group.

5. The compound according to claim 2, wherein Cy$_t$ represents a heteroaryl group substituted by 1 or 2 groups selected from linear or branched (C$_1$-C$_6$)alkyl, linear or branched halo(C$_1$-C$_6$)alkyl, —Y$_1$—OR', —Y$_1$—NR'R", N-oxide, cyano, —C(O)—OR', —C(O)—NR'R", halogen, wherein R' and R", independently of one another, represent a hydrogen atom, a linear or branched (C$_1$-C$_6$)alkyl group, a linear or branched (C$_1$-C$_6$)alkoxy group, or a tetrahydropyranyl group, or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by a linear or branched (C$_1$-C$_6$)alkyl group.

6. The compound according to claim 2, wherein K represents a thienyl group, a thiazolyl group or a pyridinyl group and L represents a pyrrolyl group, a furyl group, a thienyl group, a pyrazolyl group, a pyridinyl group, a pyrimidinyl group, or an imidazopyridinyl group, wherein each heteroaryl group may be substituted by 1 or 2 groups selected from linear or branched (C$_1$-C$_6$)alkyl, linear or branched halo(C$_1$-C$_6$)alkyl, —Y$_1$—OR', —Y$_1$—NR'R", N-oxide, cyano, —C(O)—NR'R", and halogen, wherein R' and R", independently of one another, represent a hydrogen atom, a linear or branched (C$_1$-C$_6$)alkyl group, a linear or branched (C$_1$-C$_6$)alkoxy group, a linear or branched (C$_1$-C$_6$)alkoxy(C$_1$-C$_6$)alkyl group, or a tetrahydropyranyl group, or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen.

7. The compound according to claim 2, which is selected from the group consisting of:

3-[(4-hydroxy-1-{[(3R,4R)-1-{[3-methyl-5-(pyridin-4-yl)thiophen-2-yl]carbonyl}-3-phenylpiperidin-4-yl]carbonyl}piperidin-4-yl)methyl]-7-methyl-3,7-dihydro-4H-pyrrolo[2,3-d]pyrimidin-4-one;

3-[(1-{[(3R,4R)-1-{[5-(6-aminopyridin-3-yl)-3-fluorothiophen-2-yl]carbonyl}-3-phenylpiperidin-4-yl]carbonyl}-4-hydroxypiperidin-4-yl)methyl]-7-methyl-3,7-dihydro-4H-pyrrolo[2,3-d]pyrimidin-4-one;

7-cyclopropyl-3-[1-{[(3R,4R)-1-{[3-fluoro-5-(pyridin-4-yl)thiophen-2-yl]carbonyl}-3-phenylpiperidin-4-yl]carbonyl}-4-hydroxypiperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;

3-[(1-{[(3R,4R)-1-{[3-fluoro-5-(6-methylpyridin-3-yl)thiophen-2-yl]carbonyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(naphthalen-2-yl)-3,7-dihydro-4H-pyrrolo[2,3-d]pyrimidin-4-one;

7-(4-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-methylphenyl)-3,7-dihydro-4H-pyrrolo[2,3-d]pyrimidin-4-one;

7-(3-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(furan-3-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(2-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(2-chlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-[4-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(4-methylpiperazin-1-yl)phenyl]-3,7-dihydro-4H-pyrrolo[2,3-d]pyrimidin-4-one;

7-[3-(dimethylamino)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1H-pyrrol-1-yl)-3,7-dihydro-4H-pyrrolo[2,3-d]pyrimidin-4-one;

5-(5-{[(3R,4R)-4-[(4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}-4-methyl-1,3-thiazol-2-yl)pyridine-2-carbonitrile;

3-[(1-{[(3R,4R)-1-({2-[6-(dimethylamino)pyridin-3-yl]-4-methyl-1,3-thiazol-5-yl}carbonyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(4-hydroxy-1-{[(3R,4R)-1-({4-methyl-2-[6-(trifluoromethyl)pyridin-3-yl]-1,3-thiazol-5-yl}carbonyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methoxypyridin-3-yl)-4-methyl-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

7-(3-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

3-[(1-{[(3R,4R)-1-{[2-[6-(dimethylamino)pyridin-3-yl]-1,3-thiazol-5-yl]methyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;

7-(4-fluorophenyl)-3-[(4-hydroxy-1-{R3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;

3-[(4-hydroxy-1-{[(3R,4R)-1-({2-[6-(morpholin-4-yl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methylphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(1-{[(3R,4R)-1-{[2-[6-(dimethylamino)pyridin-3-yl]-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

7-(4-chlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(1-{[(3R,4R)-1-{[2-[6-(dimethylamino)pyridin-3-yl]-1,3-thiazol-5-yl]methyl}-3-phenylpiperidin-4-yl]carbonyl}-4-hydroxypiperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-6,8-dimethylpyrimido[5',4':4,5]pyrrolo[1,2-b]pyridazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(morpholin-4-yl)phenyl]-3,7-dihydro-4H-pyrrolo[2,3-d]pyrimidin-4-one;

7-(3-chlorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methyl-1-oxidopyridin-3-yl)-1,3-thiazol-5-yl]carbonyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-({2-[6-(piperazin-1-yl)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-({2-[6-(trifluoromethyl)pyridin-3-yl]-1,3-thiazol-5-yl}methyl)piperidin-4-yl]carbonyl}piperidin-4-yl)methyl]-7-(4-methoxyphenyl)-3,7-dihydro-4H-pyrrolo[2,3-d]pyrimidin-4-one;

7-(3,4-dichlorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

5-(5-{[(3R,4R)-4-[(4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-2-carbonitrile;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(pyridin-2-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

7-(3,4-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3,4-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(pyridin-3-yl)-3,7-dihydro-4H-pyrrolo[2,3-d]pyrimidin-4-one;

5-[(4-hydroxy-1-1 [(3R,4R)-1-{[2-(6-methylpyridin-3-yl)-1,3-thiazol-5-yl]methyl}-3-phenylpiperidin-4-yl]carbonyl}piperidin-4-yl)methyl]-1-phenyl-1,5-dihydro-4H-pyrazolo[3,4-d]pyrimidin-4-one;

7-(3,5-dimethoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3,5-dimethoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

4-{3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-4-oxo-3,4-dihydro-7H-pyrrolo[2,3-d]pyrimidin-7-yl}benzonitrile;

3-[(4-hydroxy-1-1 [(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1-1 [(3R,4R)-1-{[2-(6-methylpyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one;

7-[3-(hydroxymethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-fluorophenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

5-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-1-phenyl-1,5-dihydro-4H-pyrazolo [3,4-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(1-methyl-1H-pyrazol-4-yl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(hydroxymethyl)phenyl]-3,7-dihydro-4H-pyrrolo[2,3-d]pyrimidin-4-one;

7-(4-fluorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(3-chloro-5-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(3-chloro-5-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chloro-3-methoxyphenyl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(4-chloro-3-methoxyphenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(5-chlorothiophen-2-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(5-chlorothiophen-2-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-bromo-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]pyrrolo[2,1-f][1,2,4]triazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(5-methylthiophen-2-yl)-3,7-dihydro-4H-pyrrolo[2,3-d]pyrimidin-4-one;

7-[4-(hydroxymethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[4-(hydroxymethyl)phenyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenylpyrrolo[2,1-f][1,2,4]triazin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenylpyrrolo[2,1-f][1,2,4]triazin-4(3H)-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(thiophen-2-yl)-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenylthieno[3,4-d]pyrimidin-4(3H)-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenylthieno[3,4-d]pyrimidin-4(3H)-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-phenyl-3,5-dihydro-4H-pyrrolo[3,2-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3-methylphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-methylphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(thiophen-3-yl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-[3-(morpholin-4-yl)phenyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-(4-hydroxyphenyl)-3,7-dihydro-4H-pyrrolo[2,3-d]pyrimidin-4-one;

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-[6-(hydroxymethyl)pyridin-3-yl]-1,3-thiazol-5-yl]methyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-[3-(trifluoromethyl)phenyl]-3,7-dihydro-4H-pyrrolo[2,3-d]pyrimidin-4-one;

7-[4-(difluoromethyl)phenyl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-[4-(difluoromethyl)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-[4-(difluoromethyl)phenyl]-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-[1-(difluoromethyl)-1H-pyrazol-4-yl]-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-[1-(difluoromethyl)-1H-pyrazol-4-yl]-3-[(4-hydroxy-1-{[(3R,4R)-1-{[2-(6-methylpyridin-3-yl)-1,3-thiazol-5-yl]methyl}-3-phenylpiperidin-4-yl]

- carbonyl}piperidin-4-yl)methyl]-3,7-dihydro-4H-pyrrolo[2,3-d]pyrimidin-4-one;
- 3-[(4-hydroxy-1-{[(3R,4R)-1-{[2-(3-methyl-3H-imidazo[4,5-b]pyridin-6-yl)-1,3-thiazol-5-yl]methyl}-3-phenylpiperidin-4-yl]carbonyl}piperidin-4-yl)methyl]-7-phenyl-3,7-dihydro-4H-pyrrolo[2,3-d]pyrimidin-4-one;
- 3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;
- 7-[3-(dimethylamino)phenyl]-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;
- 7-(3-fluorophenyl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;
- 3-[(1-{[(3R,4R)-1-{[2-(5-fluoro-6-hydroxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;
- 5-(5-{[(3R,4R)-4-({4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}-1,3-thiazol-2-yl)pyridine-3-carboxamide;
- 3-[(4-hydroxy-1-{[(3R,4R)-1-{2-[5-(hydroxymethyl)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one;
- 3-[(4-hydroxy-1-{[(3R,4R)-3-phenyl-1-({2-[6-(tetrahydro-2H-pyran-4-yloxy)pyridin-3-yl]-1,3-thiazol-5-yl}methyl)piperidin-4-yl]carbonyl}piperidin-4-yl)methyl]-7-phenyl-3,7-dihydro-4H-pyrrolo[2,3-d]pyrimidin-4-one;
- 3-[(1-{[(3R,4R)-1-{[2-(5-amino-6-methoxypyridin-3-yl)-1,3-thiazol-5-yl]methyl}-3-phenylpiperidin-4-yl]carbonyl}-4-hydroxypiperidin-4-yl)methyl]-7-phenyl-3,7-dihydro-4H-pyrrolo[2,3-d]pyrimidin-4-one;
- 3-[(4-hydroxy-1-{[(3R,4R)-3-phenyl-1-{[2-(thiophen-2-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;
- 3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;
- 3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;
- 3-[(4-hydroxy-1-1 [(3R,4R)-1-{[2-(1-methyl-1H-pyrazol-4-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;
- 3-[(4-hydroxy-1-1 [(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

- 3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(4-methoxyphenyl)-3,7-dihydro-4H-pyrrolo[2,3-d]pyrimidin-4-one;
- 7-(2,3-dihydro-1,4-benzodioxin-6-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;
- 7-(2,3-dihydro-1,4-benzodioxin-6-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;
- 3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one;
- 7-(3-chlorophenyl)-3-[(4-hydroxy-1-1 [(3R,4R)-1-{[2-(6-hydroxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;
- 3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;
- 3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;
- 3-[(4-hydroxy-1-{[(3R,4R)-3-phenyl-1-{[2-(thiophen-2-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-3-phenyl-1-{[2-(pyrimidin-5-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-1-{[2-(1-methyl-1H-pyrazol-5-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-1-{[2-(1-methyl-1H-pyrazol-4-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-1-{[2-(1-methyl-1H-pyrrol-3-yl)-1,3-thiazol-5-yl]methyl}-3-phenylpiperidin-4-yl]carbonyl}piperidin-4-yl)methyl]-7-(3-methoxyphenyl)-3,7-dihydro-4H-pyrrolo[2,3-d]pyrimidin-4-one;
- 3-[(4-hydroxy-1-{[(3R,4R)-3-phenyl-1-{[2-(thiophen-3-yl)-1,3-thiazol-5-yl]methyl}piperidin-4-yl]carbonyl}piperidin-4-yl)methyl]-7-(3-methoxyphenyl)-3,7-dihydro-4H-pyrrolo[2,3-d]pyrimidin-4-one;
- 3-[(1-{[(3R,4R)-1-{[2-(furan-3-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;
- 3-[(1-{[(3R,4R)-1-{[2-(furan-2-yl)-1,3-thiazol-5-yl]methyl}-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;
- 7-(2,3-dihydro-1,4-benzodioxin-6-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

7-(1,3-benzodioxol-5-yl)-3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-3,7-dihydro-4H-pyrrolo[2,3-d]pyrimidin-4-one;

7-(1,3-benzodioxol-5-yl)-3-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

7-(1,3-benzodioxol-5-yl)-3-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3,4,5-trimethoxyphenyl)-3,7-dihydro-4H-pyrrolo[2,3-d]pyrimidin-4-one;

3-{[4-hydroxy-1-{[(3R,4R)-1-[(6'-methyl-3,3*-bipyridin-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one;

3-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one;

5-[5-({(3R,4R)-4-[(4-hydroxy-4-{[7-(3-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile;

5-[5-({(3R,4R)-4-[(4-{[7-(4-chlorophenyl)-4-oxo-4,7-dihydro-3H-pyrrolo[2,3-d]pyrimidin-3-yl]methyl}-4-hydroxypiperidin-1-yl)carbonyl]-3-phenylpiperidin-1-yl}methyl)-1,3-thiazol-2-yl]pyridine-2-carbonitrile;

5-[5-({(3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidin-1-yl}methyl)-1,3-thiazol-2-yl]pyridine-2-carbonitrile;

3-[(4-hydroxy-1-{[(3R,4R)-1-({2-[6-(2-methoxyethoxy)pyridin-3-yl]-1,3-thiazol-5-yl}methyl)-3-phenylpiperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-1-{[2-(6-hydroxypyridin-3-yl)-1,3-thiazol-5-yl]methyl}-3-phenylpiperidin-4-yl]carbonyl}piperidin-4-yl)methyl]-7-(3-hydroxyphenyl)-3,7-dihydro-4H-pyrrolo[2,3-d]pyrimidin-4-one;

5-[5-({(3R,4R)-4-[(4-{[7-(4-fluorophenyl)-4-oxo-4,7-dihydro-3H-pyrrolo[2,3-d]pyrimidin-3-yl]methyl}-4-hydroxypiperidin-1-yl)carbonyl]-3-phenylpiperidin-1-yl}methyl)-1,3-thiazol-2-yl]pyridine-2-carbonitrile;

5-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-1-(4-methoxyphenyl)-1,5-dihydro-4H-pyrazolo[3,4-d]pyrimidin-4-one;

5-[(4-hydroxy-1-{[(3R,4R)-1-{[2-(6-methoxypyridin-3-yl)-1,3-thiazol-5-yl]methyl}-3-phenylpiperidin-4-yl]carbonyl}piperidin-4-yl)methyl]-1-(4-methoxyphenyl)-1,5-dihydro-4H-pyrazolo[3,4-d]pyrimidin-4-one;

5-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-1-(4-methoxyphenyl)-1,5-dihydro-4H-pyrazolo[3,4-d]pyrimidin-4-one;

3-{[4-hydroxy-1-({(3R,4R)-1-[(2-{6-[(2-methoxyethyl)amino]pyridin-3-yl}-1,3-thiazol-5-yl)methyl]-3-phenylpiperidin-4-yl}carbonyl)piperidin-4-yl]methyl}-7-phenyl-3,7-dihydro-4H-pyrrolo[2,3-d]pyrimidin-4-one;

1-(2,3-dihydro-1,4-benzodioxin-6-yl)-5-[(4-hydroxy-1-{[(3R,4R)-1-{[4-methyl-2-(6-methylpyridin-3-yl)-1,3-thiazol-5-yl]carbonyl}-3-phenylpiperidin-4-yl]carbonyl}piperidin-4-yl)methyl]-1,5-dihydro-4H-pyrazolo[3,4-d]pyrimidin-4-one;

1-(2,3-dihydro-1,4-benzodioxin-6-yl)-5-[(4-hydroxy-1-{[(3R,4R)-1-{[2-(6-methylpyridin-3-yl)-1,3-thiazol-5-yl]methyl}-3-phenylpiperidin-4-yl]carbonyl}piperidin-4-yl)methyl]-1,5-dihydro-4H-pyrazolo[3,4-d]pyrimidin-4-one;

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-[4-(hydroxymethyl)phenyl]pyrrolo[2,1-f][1,2,4]triazin-4-one;

3-[[4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-[4-(hydroxymethyl)phenyl]thieno[3,4-d]pyrimidin-4-one;

3-[[4-hydroxy-1-[(3R,4R)-1-[2-(6-methyl-3-pyridyl)thiazole-5-carbonyl]-3-phenyl-piperidine-4-carbonyl]-4-piperidyl]methyl]-7-(3-methoxyphenyl)pyrrolo[2,3-d]pyrimidin-4-one;

3-[[3,3-difluoro-4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-phenyl-pyrrolo[2,3-d]pyrimidin-4-one; and 3-[[3,3-difluoro-4-hydroxy-1-[(3R,4R)-1-[4-methyl-2-(6-methyl-3-pyridyl)thiazole-5-carbonyl]-3-phenyl-piperidine-4-carbonyl]-4-piperidyl]methyl]-7-(4-methoxyphenyl)pyrrolo[2,3-d]pyrimidin-4-one.

8. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the compound according to claim 1, alone or in combination with one or more pharmaceutically acceptable excipients.

9. A combination of the compound according to claim 1 with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies.

10. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the combination according to claim 9, alone or in combination with one or more pharmaceutically acceptable excipients.

11. A pharmaceutical composition comprising the compound according to claim 2, or an addition salt thereof with a pharmaceutically acceptable acid or base, in combination with one or more pharmaceutically acceptable excipients.

12. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the compound according to claim 2, alone or in combination with one or more pharmaceutically acceptable excipients.

13. A combination of the compound according to claim 2 with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies.

14. A pharmaceutical composition comprising the combination according to claim 13, in combination with one or more pharmaceutically acceptable excipients.

15. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the combination according to claim 13, alone or in combination with one or more pharmaceutically acceptable excipients.

16. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the compound according to claim 2, alone or in combination with one or more pharmaceutically acceptable excipients, in combination with radiotherapy.

17. A compound of the following formula

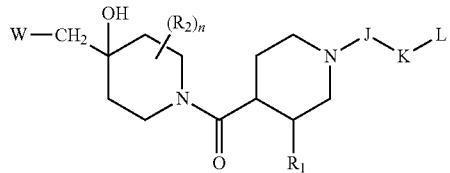

wherein:
$R_1$ represents an aryl group or a heteroaryl group,
$R_2$ represents a hydrogen atom or a halogen atom,
n is an integer equal to 0, 1 or 2,
J represents a —C(O)— group, a —CH($R_3$)— group, or an —SO$_2$— group,
$R_3$ represents a hydrogen atom or a linear or branched ($C_1$-$C_6$)alkyl group,
K represents a bond,
L represents a -Cy$_2$ group or a —CH$_2$-Cy$_2$ group,
W represents the group

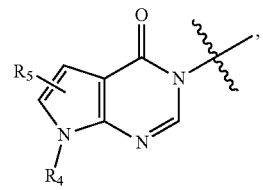

wherein:
$R_4$ represents a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a —$Y_1$—NR$_6$R$_7$ group, a —$Y_1$—OR$_6$ group, a linear or branched halo($C_1$-$C_6$)alkyl group, an oxo group, a —$Y_1$-Cy$_3$ group, a -Cy$_3$-R$_7$ group, a -Cy$_3$-OR$_7$ group, or a —$Y_1$—NR$_6$—C(O)—R$_7$ group,
$R_5$ represents a hydrogen atom, a halogen atom, or a linear or branched ($C_1$-$C_6$)alkyl group,
$R_6$ represents a hydrogen atom or a linear or branched ($C_1$-$C_6$)alkyl group,
$R_7$ represents a hydrogen atom, a linear or branched ($C_1$-$C_6$)alkyl group, or a —$Y_2$-Cy$_4$ group,
$Y_1$ and $Y_2$ independently of one another represent a bond or a linear or branched ($C_1$-$C_4$)alkylene group,
Cy$_2$, Cy$_3$ and Cy$_4$ independently of one another, represent a cycloalkyl group, a heterocycloalkyl group, an aryl group, or a heteroaryl group,
wherein
"aryl" means a phenyl, naphthyl, or indanyl group,
"heteroaryl" means any mono- or fused bi-cyclic group composed of from 5 to 10 ring members, having at least one aromatic moiety and having from 1 to 3 heteroatoms selected from oxygen, sulphur and nitrogen,
"cycloalkyl" means any mono- or fused bi-cyclic non-aromatic carbocyclic group having from 3 to 7 ring members,
"heterocycloalkyl" means any non-aromatic mono- or fused bi-cyclic group having from 3 to 10 ring members, and having from 1 to 3 heteroatoms selected from oxygen, sulphur and nitrogen,
wherein the aryl, heteroaryl, cycloalkyl and heterocycloalkyl groups so defined may be substituted by from 1 to 4 groups selected from linear or branched ($C_1$-$C_6$) alkyl, linear or branched ($C_2$-$C_6$)alkenyl, linear or branched ($C_2$-$C_6$)alkynyl, linear or branched halo($C_1$-$C_6$)alkyl, —$Y_1$—OR', —$Y_1$—NR'R'', —$Y_1$—S(O)$_m$— R', oxo (or N-oxide where appropriate), nitro, cyano, —C(O)—R', —C(O)—OR', —O—C(O)—R', —C(O)—NR'R'', —$Y_1$—NR'—C(O)—R'', —$Y_1$— NR'—C(O)—OR'', halogen, cyclopropyl, and pyridinyl which may be substituted by a linear or branched ($C_1$-$C_6$)alkyl group,
wherein R' and R'', independently of one another, represent a hydrogen atom, a linear or branched ($C_1$-$C_6$)

alkyl group, a linear or branched (C$_2$-C$_6$)alkenyl group, a linear or branched (C$_1$-C$_6$)alkoxy group, a linear or branched halo(C$_1$-C$_6$)alkyl, a linear or branched hydroxy(C$_1$-C$_6$)alkyl group, a linear or branched (C$_1$-C$_6$)alkoxy(C$_1$-C$_6$)alkyl group, a phenyl group, a cyclopropylmethyl group, or a tetrahydropyranyl group, or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by from 1 to 2 groups selected from a hydrogen atom and a linear or branched (C$_1$-C$_6$)alkyl group, and wherein m is an integer equal to 0, 1 or 2, its enantiomers, diastereoisomers and addition salts thereof with a pharmaceutically acceptable acid or base.

18. The compound according to claim 17, wherein L represents a -Cy$_2$ group.

19. The compound according to claim 17, wherein L represents a phenyl group, thiazolyl group, an oxazolyl group, an isoxazolyl group, a pyrazolyl group, a pyridinyl group, a pyrazinyl group, a pyridazinyl group or a pyrimidinyl group, wherein each heteroaryl group may be substituted by 1 or 2 groups selected from linear or branched (C$_1$-C$_6$)alkyl, —Y$_1$—OR', —Y$_1$—NR'R", cyano, —C(O)—OR', and halogen, wherein R' and R", independently of one another, represent a hydrogen atom, a linear or branched (C$_1$-C$_6$)alkyl group, or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by from 1 to 2 groups selected from a hydrogen atom and a linear or branched (C$_1$-C$_6$)alkyl group.

20. The compound according to claim 17, which is selected from the group consisting of:

3-{[1-({(3R,4R)-1-[(2-bromo-4-methyl-1,3-thiazol-5-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-{[1-({(3R,4R)-1-[(2-bromo-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one;

3-{1-({(3R,4R)-1-[(2-bromopyridin-4-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-{1-({(3R,4R)-1-[(5-bromopyridin-3-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-{1-({(3R,4R)-1-[(5-bromopyridin-3-yl)methyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-[(4-hydroxy-1-1 [(3R,4R)-3-phenyl-1-(pyridin-4-ylmethyl)piperidin-4-yl]carbonyl}piperidin-4-yl)methyl]-7-phenyl-3,7-dihydro-4H-pyrrolo[2,3-d]pyrimidin-4-one;

3-{[4-hydroxy-1-([(3R,4R)-1-[(4-methyl-1,3-thiazol-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one;

3-{[4-hydroxy-1-([(3R,4R)-1-[(2-methyl-1,3-thiazol-5-yl)carbonyl]-3-phenylpiperidin-4-yl}carbonyl)piperidin-4-yl]methyl}-7-phenyl-3,7-dihydro-4H-pyrrolo[2,3-d]pyrimidin-4-one;

3-{[1-({(3R,4R)-1-[(2-chloro-1,3-thiazol-5-yl)carbonyl]-3-phenylpiperidin-4-yl}carbonyl)-4-hydroxypiperidin-4-yl]methyl}-7-phenyl-3,7-dihydro-4H-pyrrolo[2,3-d]pyrimidin-4-one;

3-[(4-hydroxy-1-{[(3R,4R)-3-phenyl-1-(pyrazin-2-ylmethyl)piperidin-4-yl]carbonyl}piperidin-4-yl)methyl]-7-phenyl-3,7-dihydro-4H-pyrrolo[2,3-d]pyrimidin-4-one;

3-[(4-hydroxy-1-{[(3R,4R)-3-phenyl-1-(1,3-thiazol-5-ylmethyl)piperidin-4-yl]carbonyl}piperidin-4-yl)methyl]-7-phenyl-3,7-dihydro-4H-pyrrolo[2,3-d]pyrimidin-4-one;

methyl 3-{[(3R,4R)-4-[(4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}benzoate;

3-{[4-hydroxy-1-([(3R,4R)-1-[(1-methyl-1H-pyrazol-4-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one;

3-[(4-hydroxy-1-{[(3R,4R)-3-phenyl-1-(pyrazin-2-ylmethyl)piperidin-4-yl]carbonyl}piperidin-4-yl)methyl]-7-(4-methoxyphenyl)-3,7-dihydro-4H-pyrrolo[2,3-d]pyrimidin-4-one;

3-{[4-hydroxy-1-([(3R,4R)-1-[(5-methyl-1,3-thiazol-2-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one;

3-{1-({(3R,4R)-1-[(5-bromopyridin-3-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one;

methyl 5-{[(3R,4R)-4-[(4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]carbonyl}pyridine-3-carboxylate;

3-{[4-hydroxy-1-([(3R,4R)-1-[(5-methyl-1,3-thiazol-2-yl)methyl]-3-phenylpiperidin-4-yl}carbonyl)piperidin-4-yl]methyl}-7-phenyl-3,7-dihydro-4H-pyrrolo[2,3-d]pyrimidin-4-one;

3-{[4-hydroxy-1-([(3R,4R)-1-[(3-methyl-1,2-oxazol-5-yl)methyl]-3-phenylpiperidin-4-yl}carbonyl)piperidin-4-yl]methyl}-7-phenyl-3,7-dihydro-4H-pyrrolo[2,3-d]pyrimidin-4-one;

3-[(4-hydroxy-1-{[(3R,4R)-3-phenyl-1-[(2,4-dimethyl-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4H-pyrrolo[2,3-d]pyrimidin-4-one;

3-[(4-hydroxy-1-{[(3R,4R)-3-phenyl-1-(1,3-oxazol-4-ylmethyl)-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-{[4-hydroxy-1-([(3R,4R)-1-[(5-methyl-1,3-oxazol-2-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one;

5-{[(3R,4R)-4-([4-hydroxy-4-[(4-oxo-7-phenyl-4,7-dihydro-3H-pyrrolo[2,3-d]pyrimidin-3-yl)methyl]piperidin-1-yl}carbonyl)-3-phenylpiperidin-1-yl]methyl}pyridine-2-carbonitrile;
3-[[4-hydroxy-1-[(3R,4R)-1-[(2-methoxypyrimidin-4-yl)methyl]-3-phenyl-piperidine-4-carbonyl]-4-piperidyl]methyl]-7-phenyl-pyrrolo[2,3-d]pyrimidin-4-one;
3-[[4-hydroxy-1-[(3R,4R)-1-[(2-methoxypyrimidin-4-yl)methyl]-3-phenyl-piperidine-4-carbonyl]-4-piperidyl]methyl]-7-(4-methoxyphenyl)pyrrolo[2,3-d]pyrimidin-4-one;
3-[[4-hydroxy-1-[(3R,4R)-1-[(5-methylpyrazin-2-yl)methyl]-3-phenyl-piperidine-4-carbonyl]-4-piperidyl]methyl]-7-phenyl-pyrrolo[2,3-d]pyrimidin-4-one;
3-[[4-hydroxy-1-[(3R,4R)-1-[(5-methylpyrazin-2-yl)methyl]-3-phenyl-piperidine-4-carbonyl]-4-piperidyl]methyl]-7-(4-methoxyphenyl)pyrrolo[2,3-d]pyrimidin-4-one;
3-[[4-hydroxy-1-[(3R,4R)-3-phenyl-1-(pyrimidin-2-ylmethyl)piperidine-4-carbonyl]-4-piperidyl]methyl]-7-phenyl-pyrrolo[2,3-d]pyrimidin-4-one;
3-[[4-hydroxy-1-[(3R,4R)-3-phenyl-1-(pyrimidin-2-ylmethyl)piperidine-4-carbonyl]-4-piperidyl]methyl]-7-(4-methoxyphenyl)pyrrolo[2,3-d]pyrimidin-4-one;
3-[[4-hydroxy-1-[(3R,4R)-1-[(2-methylpyrimidin-4-yl)methyl]-3-phenyl-piperidine-4-carbonyl]-4-piperidyl]methyl]-7-phenyl-pyrrolo[2,3-d]pyrimidin-4-one;
3-[[4-hydroxy-1-R3R,4R)-1-[(2-methylpyrimidin-4-yl)methyl]-3-phenyl-piperidine-4-carbonyl]-4-piperidyl]methyl]-7-(4-methoxyphenyl)pyrrolo[2,3-d]pyrimidin-4-one;
3-[[4-hydroxy-1-R3R,4R)-1-[(6-methoxypyridazin-3-yl)methyl]-3-phenyl-piperidine-4-carbonyl]-4-piperidyl]methyl]-7-(4-methoxyphenyl)pyrrolo[2,3-d]pyrimidin-4-one;
3-[[4-hydroxy-1-R3R,4R)-1-[(5-methylpyrazin-2-yl)methyl]-3-phenyl-piperidine-4-carbonyl]-4-piperidyl]methyl]-7-phenyl-thieno[3,4-d]pyrimidin-4-one; and
3-[[4-hydroxy-1-R3R,4R)-1-[(2-methylpyrimidin-4-yl)methyl]-3-phenyl-piperidine-4-carbonyl]-4-piperidyl]methyl]-7-phenyl-thieno[3,4-d]pyrimidin-4-one;
3-{[4-hydroxy-1-([(3R,4R)-1-[(1-methyl-1H-pyrazol-4-yl)methyl]-3-phenylpiperidin-4-yl}carbonyl)piperidin-4-yl]methyl}-7-(4-methoxyphenyl)-3,7-dihydro-4H-pyrrolo[2,3-d]pyrimidin-4-one; and
3-[(4-hydroxy-1-{[(3R,4R)-3-phenyl-1-(pyridin-3-ylmethyl)piperidin-4-yl]carbonyl}piperidin-4-yl)methyl]-7-phenyl-3,7-dihydro-4H-pyrrolo[2,3-d]pyrimidin-4-one.

21. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the compound according to claim 17, alone or in combination with one or more pharmaceutically acceptable excipients.

22. A combination of the compound according to claim 17 with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies.

23. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the combination according to claim 22, alone or in combination with one or more pharmaceutically acceptable excipients.

24. A compound of the following formula

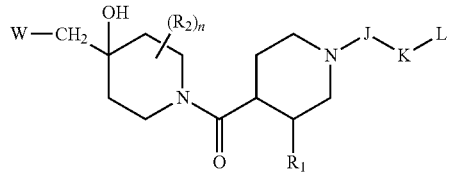

wherein:
$R_1$ represents an aryl group or a heteroaryl group,
$R_2$ represents a hydrogen atom or a halogen atom,
n is an integer equal to 0, 1 or 2,
J represents a —C(O)— group, a —CH($R_3$)— group, or an —$SO_2$— group,
$R_3$ represents a hydrogen atom or a linear or branched ($C_1$-$C_6$)alkyl group,
K represents a -$Cy_1$- group,
L represents a -$Cy_2$ group or a —$CH_2$-$Cy_2$ group,
W represents the group

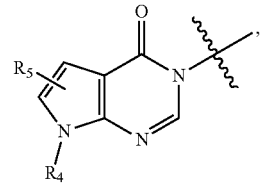

wherein:
$R_4$ represents a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a —$Y_1$—$NR_6R_7$ group, a —$Y_1$—$OR_6$ group, a linear or branched halo($C_1$-$C_6$)alkyl group, an oxo group, a —$Y_1$-$Cy_3$ group, a -$Cy_3$-$R_7$ group, a -$Cy_3$-$OR_7$ group, or a —$Y_1$—$NR_6$—C(O)—$R_7$ group,
$R_5$ represents a hydrogen atom, a halogen atom, or a linear or branched ($C_1$-$C_6$)alkyl group,
$R_6$ represents a hydrogen atom or a linear or branched ($C_1$-$C_6$)alkyl group,
$R_7$ represents a hydrogen atom, a linear or branched ($C_1$-$C_6$)alkyl group, or a —$Y_2$-$Cy_4$ group,
$Y_1$ and $Y_2$ independently of one another represent a bond or a linear or branched ($C_1$-$C_4$)alkylene group,
$Cy_1$ represents a cycloalkyl group, a heterocycloalkyl group, an aryl group, or a heteroaryl group, which is linked to the group J and to the group L,
$Cy_2$ represents a cycloalkyl group, a heterocycloalkyl group, or an aryl group,
$Cy_3$ and $Cy_4$ independently of one another, represent a cycloalkyl group, a heterocycloalkyl group, an aryl group, or a heteroaryl group, wherein
"aryl" means a phenyl, naphthyl, or indanyl group,
"heteroaryl" means any mono- or fused bi-cyclic group composed of from 5 to 10 ring members, having at least one aromatic moiety and having from 1 to 3 heteroatoms selected from oxygen, sulphur and nitrogen,
"cycloalkyl" means any mono- or fused bi-cyclic non-aromatic carbocyclic group having from 3 to 7 ring members,
"heterocycloalkyl" means any non-aromatic mono- or fused bi-cyclic group having from 3 to 10 ring members, and having from 1 to 3 heteroatoms selected from oxygen, sulphur and nitrogen,
wherein the aryl, heteroaryl, cycloalkyl and heterocycloalkyl groups so defined may be substituted by from 1 to 4 groups selected from linear or branched ($C_1$-$C_6$) alkyl, linear or branched ($C_2$-$C_6$)alkenyl, linear or branched ($C_2$-$C_6$)alkynyl, linear or branched halo($C_1$-$C_6$)alkyl, —$Y_1$—OR', —$Y_1$—NR'R", —$Y_1$—S(O)$_m$—R', oxo (or N-oxide where appropriate), nitro, cyano, —C(O)—R', —C(O)—OR', —O—C(O)—R', —C(O)—NR'R", —$Y_1$—NR'—C(O)—R", —$Y_1$—NR'—C(O)—OR", halogen, cyclopropyl, and pyridinyl which may be substituted by a linear or branched ($C_1$-$C_6$)alkyl group,
wherein R' and R", independently of one another, represent a hydrogen atom, a linear or branched ($C_1$-$C_6$) alkyl group, a linear or branched ($C_2$-$C_6$)alkenyl group, a linear or branched ($C_1$-$C_6$)alkoxy group, a linear or branched halo($C_1$-$C_6$)alkyl, a linear or branched hydroxy($C_1$-$C_6$)alkyl group, a linear or branched ($C_1$-$C_6$)alkoxy($C_1$-$C_6$)alkyl group, a phenyl group, a cyclopropylmethyl group, or a tetrahydropyranyl group,
or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by from 1 to 2 groups selected from a hydrogen atom and a linear or branched ($C_1$-$C_6$)alkyl group,
and wherein m is an integer equal to 0, 1 or 2,
its enantiomers, diastereoisomers and addition salts thereof with a pharmaceutically acceptable acid or base.

25. The compound according to claim 24, wherein K represents a phenyl group, a pyrrolyl group, a thienyl group, a thiazolyl group, a pyridinyl group, a tetrahydrobenzothienyl group, a dihydrothienodioxinyl group, a cyclopropyl group, a cyclobutyl group, or a pyrrolidinyl group.

26. The compound according to claim 24, wherein L represents a -Cy$_2$ group.

27. The compound according to claim 24, wherein Cy$_t$ represents a cycloalkyl group, a heterocycloalkyl group, or an aryl group which groups are substituted by 1 or 2 groups selected from linear or branched ($C_1$-$C_6$)alkyl, linear or branched halo($C_1$-$C_6$)alkyl, —$Y_1$—OR', —$Y_1$—NR'R", N-oxide, cyano, —C(O)—OR', —C(O)—NR'R", halogen, wherein R' and R", independently of one another, represent a hydrogen atom, a linear or branched ($C_1$-$C_6$)alkyl group, a linear or branched ($C_1$-$C_6$)alkoxy group, or a tetrahydropyranyl group, or the substituents of the pair (R', R"), together with the nitrogen atom carrying them, form a non-aromatic ring composed of from 5 to 7 ring members, which may have, in addition to the nitrogen, a second heteroatom selected from oxygen and nitrogen, wherein the second nitrogen in question may be substituted by a linear or branched ($C_1$-$C_6$)alkyl group.

28. The compound according to claim 24, which is selected from the group consisting of:
3-[(4-hydroxy-1-1[(3R,4R)-1-{[4-methyl-2-(morpholin-4-yl)-1,3-thiazol-5-yl]carbonyl}-3-phenylpiperidin-4-yl}carbonyl}piperidin-4-yl)methyl]-7-phenyl-3,7-dihydro-4H-pyrrolo[2,3-d]pyrimidin-4-one; and
3-[(4-hydroxy-1-{[(3R,4R)-1-{[2-(4-methylpiperazin-1-yl)-1,3-thiazol-5-yl]methyl}-3-phenylpiperidin-4-yl}carbonyl}piperidin-4-yl)methyl]-7-phenyl-3,7-dihydro-4H-pyrrolo[2,3-d]pyrimidin-4-one.

29. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the compound according to claim 24, alone or in combination with one or more pharmaceutically acceptable excipients.

30. A combination of the compound according to claim 24 with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies.

31. A method of treating cancer in a subject in need thereof, wherein the cancer is selected from the group consisting of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer, comprising administration of an effective amount of the combination according to claim 30, alone or in combination with one or more pharmaceutically acceptable excipients.

* * * * *

UNITED STATES PATENT AND TRADEMARK OFFICE
CERTIFICATE OF CORRECTION

PATENT NO. : 10,654,849 B2
APPLICATION NO. : 16/306941
DATED : May 19, 2020
INVENTOR(S) : András Kotschy et al.

It is certified that error appears in the above-identified patent and that said Letters Patent is hereby corrected as shown below:

On the Title Page

Inventor(s),
The fifth inventor should read Árpád Kiss.

In the Claims

Column 303,
Line 64: Claim 20, hydroxy-1-[ should read hydroxy-1-{.

Column 304,
Line 25: Claim 20, hydroxy-1-([ should read hydroxy-1-({.
Line 33: Claim 20, hydroxy-1-([ should read hydroxy-1-({.
Line 41: Claim 20, 4-[(4-hydroxy should read 4-({4-hydroxy.
Line 45: Claim 20, hydroxy-1-([( should read hydroxy-1-({(.
Line 49: Claim 20, hydroxy-1-([( should read hydroxy-1-({(.
Lines 53-57: Claim 20, Replace these lines with
3-{[1-({(3$R$,4$R$)-1-[(2,4-dimethyl-1,3-thiazol-5-yl)methyl]-3-phenylpiperidin-4-yl}carbonyl)-4-hydroxypiperidin-4-yl]methyl}-7-(4-methoxyphenyl)-3,7-dihydro-4$H$-pyrrolo[2,3-$d$]pyrimidin-4-one;.
Line 62: Claim 20, hydroxy-1-([( should read hydroxy-1-({(.
Line 66: Claim 20, -4-([4-hydroxy should read -4-({4-hydroxy.

Column 305,
Line 37: Claim 20, 1-R3R should read 1-[(3R.
Line 40: Claim 20, hydroxy-1-([( should read hydroxy-1-({(.

Column 307,
Line 54: Claim 27, Cy should read $Cy_2$.

Signed and Sealed this
Eighteenth Day of August, 2020

Andrei Iancu
*Director of the United States Patent and Trademark Office*

Column 308,
Line 18: Claim 28, hydroxy-1-1[( should read hydroxy-1-{[(.